(12) United States Patent
Zhou et al.

(10) Patent No.: US 11,913,012 B2
(45) Date of Patent: *Feb. 27, 2024

(54) CARDIAC CELL REPROGRAMMING WITH MYOCARDIN AND ASCL1

(71) Applicant: Tenaya Therapeutics, Inc., South San Francisco, CA (US)

(72) Inventors: Huanyu Zhou, South San Francisco, CA (US); Laura Lombardi, Redwood City, CA (US)

(73) Assignee: Tenaya Therapeutics, Inc., South San Francisco, CA (US)

( * ) Notice: Subject to any disclaimer, the term of this patent is extended or adjusted under 35 U.S.C. 154(b) by 192 days.

This patent is subject to a terminal disclaimer.

(21) Appl. No.: 17/211,559

(22) Filed: Mar. 24, 2021

(65) Prior Publication Data

US 2021/0207170 A1 Jul. 8, 2021

Related U.S. Application Data

(63) Continuation of application No. 17/028,881, filed on Sep. 22, 2020, now Pat. No. 11,015,211, which is a continuation of application No. PCT/US2019/049150, filed on Aug. 30, 2019.

(60) Provisional application No. 62/852,746, filed on May 24, 2019, provisional application No. 62/788,479, filed on Jan. 4, 2019, provisional application No. 62/725,168, filed on Aug. 30, 2018.

(51) Int. Cl.
| | |
|---|---|
| C12N 15/86 | (2006.01) |
| A61K 38/17 | (2006.01) |
| A61K 48/00 | (2006.01) |
| C12N 7/00 | (2006.01) |

(52) U.S. Cl.
CPC .......... *C12N 15/86* (2013.01); *A61K 38/1719* (2013.01); *A61K 48/005* (2013.01); *C12N 7/00* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 4,797,368 A | 1/1989 | Carter et al. | |
| 4,962,091 A | 10/1990 | Eppstein et al. | |
| 5,139,941 A | 8/1992 | Muzyczka et al. | |
| 5,384,253 A | 1/1995 | Krzyzek et al. | |
| 5,449,614 A | 9/1995 | Danos et al. | |
| 5,543,158 A | 8/1996 | Gref et al. | |
| 5,580,859 A | 12/1996 | Felgner et al. | |
| 5,589,466 A | 12/1996 | Felgner et al. | |
| 5,591,624 A | 1/1997 | Barber et al. | |
| 5,656,610 A | 8/1997 | Shuler et al. | |
| 5,702,932 A | 12/1997 | Hoy et al. | |
| 5,736,524 A | 4/1998 | Content et al. | |
| 5,780,448 A | 7/1998 | Davis | |
| 5,789,215 A | 8/1998 | Berns et al. | |
| 5,817,491 A | 10/1998 | Yee et al. | |
| 5,834,256 A | 11/1998 | Finer et al. | |
| 5,925,565 A | 7/1999 | Berlioz et al. | |
| 5,928,906 A | 7/1999 | Koster et al. | |
| 5,935,819 A | 8/1999 | Eichner et al. | |
| 5,945,100 A | 8/1999 | Fick | |
| 5,981,274 A | 11/1999 | Tyrrell et al. | |
| 5,994,136 A | 11/1999 | Naldini et al. | |
| 5,994,624 A | 11/1999 | Trolinder et al. | |
| 6,007,845 A | 12/1999 | Domb et al. | |
| 6,013,516 A | 1/2000 | Verma et al. | |
| 6,156,303 A | 12/2000 | Russell et al. | |
| 6,254,890 B1 | 7/2001 | Hirosue et al. | |
| 6,306,434 B1 | 10/2001 | Hong et al. | |
| 6,872,528 B2 | 3/2005 | Klatzmann et al. | |
| 6,910,434 B2 | 6/2005 | Lundgren | |
| 6,962,815 B2 | 11/2005 | Bartlett | |
| 6,984,517 B1 | 1/2006 | Chiorini et al. | |
| 6,995,009 B1 | 2/2006 | Kitamura et al. | |
| 6,998,115 B2 | 2/2006 | Langer et al. | |
| 7,070,994 B2 | 7/2006 | Barber et al. | |

(Continued)

FOREIGN PATENT DOCUMENTS

| | | |
|---|---|---|
| WO | WO 93/03769 A1 | 3/1993 |
| WO | WO 93/09239 A1 | 5/1993 |

(Continued)

OTHER PUBLICATIONS

U.S. Appl. No. 15/433,322, filed Feb. 15, 2017, Wilson et al.

(Continued)

*Primary Examiner* — Michael D Burkhart
(74) *Attorney, Agent, or Firm* — COOLEY LLP

(57) ABSTRACT

The present disclosure provides methods for generating induced cardiomyocytes and/or inducing a cardiomyocyte phenotype in cells in vivo or in vitro, such as by expression of ASCL1 or MYF6 and MYOCD. The present disclosure further provides gene-delivery vectors comprising one or more polynucleotides selected from ASCL1, MYF6, MYOCD, MEF2C, and TBX5. It further provides compositions comprising induced cardiomyocytes and provides methods of treating a heart condition, such as myocardial infarction. The disclosure also provides engineered myocardin proteins with an internal deletion, vectors encoding such engineered mycocardins, and methods of use thereof.

25 Claims, 36 Drawing Sheets

Specification includes a Sequence Listing.

(56) References Cited

U.S. PATENT DOCUMENTS

| | | |
|---|---|---|
| 7,105,345 B2 | 9/2006 | Wilson et al. |
| 7,198,951 B2 | 4/2007 | Gao et al. |
| 7,259,151 B2 | 8/2007 | Arbetman et al. |
| 7,427,394 B2 | 9/2008 | Anderson et al. |
| 7,718,424 B2 | 5/2010 | Chiorini et al. |
| 7,727,969 B2 | 6/2010 | Farokhzad et al. |
| 7,790,449 B2 | 9/2010 | Gao et al. |
| 7,867,484 B2 | 1/2011 | Samulski et al. |
| 7,906,111 B2 | 3/2011 | Wilson et al. |
| 7,968,698 B2 | 6/2011 | Kadonaga et al. |
| 8,071,082 B2 | 12/2011 | Zugates et al. |
| 8,105,652 B2 | 1/2012 | Wood et al. |
| 8,119,119 B2 | 2/2012 | Mallet et al. |
| 8,193,224 B2 | 6/2012 | Ihara et al. |
| 8,193,334 B2 | 6/2012 | Radovic-Moreno et al. |
| 8,323,698 B2 | 12/2012 | Gu et al. |
| 8,450,298 B2 | 5/2013 | Mahon et al. |
| 8,524,446 B2 | 9/2013 | Gao et al. |
| 8,784,799 B2 | 7/2014 | Samulski et al. |
| 8,935,819 B1 | 1/2015 | Hartley |
| 8,999,678 B2 | 4/2015 | Vandenberghe et al. |
| 9,169,494 B2 | 10/2015 | Hewitt et al. |
| 9,217,115 B2 | 12/2015 | Lange et al. |
| 9,233,131 B2 | 1/2016 | Schaffer et al. |
| 9,434,928 B2 | 9/2016 | Mendell et al. |
| 9,447,433 B2 | 9/2016 | Hirsch et al. |
| 9,517,250 B2 | 12/2016 | Srivastava et al. |
| 9,517,251 B2 | 12/2016 | Srivastava et al. |
| 9,523,079 B2 | 12/2016 | Nam et al. |
| 9,556,438 B2 | 1/2017 | Naldini et al. |
| 9,572,896 B2 | 2/2017 | Bancel et al. |
| 9,596,835 B2 | 3/2017 | Gao et al. |
| 9,737,618 B2 | 8/2017 | Wilson et al. |
| 9,783,824 B2 | 10/2017 | Kay et al. |
| 9,828,585 B2 | 11/2017 | Srivastava |
| 9,868,937 B2 | 1/2018 | Regnier et al. |
| 9,885,018 B1 | 2/2018 | Song et al. |
| 10,000,757 B2 | 6/2018 | Naldini et al. |
| 10,046,016 B2 | 8/2018 | Schaffer et al. |
| 10,166,297 B2 | 1/2019 | Gao et al. |
| 10,300,146 B2 | 5/2019 | Gao et al. |
| 10,479,821 B2 | 11/2019 | Chamberlain et al. |
| 11,015,211 B2 | 5/2021 | Zhou et al. |
| 2002/0164735 A1 | 11/2002 | Olsen et al. |
| 2003/0108890 A1* | 6/2003 | Baranova .............. G16B 20/00 435/6.14 |
| 2004/0265955 A1 | 12/2004 | Fang et al. |
| 2008/0268063 A1 | 10/2008 | Jon et al. |
| 2009/0298710 A1 | 12/2009 | Farokhzad et al. |
| 2010/0303723 A1 | 12/2010 | Farokhzad et al. |
| 2011/0009641 A1 | 1/2011 | Anderson et al. |
| 2011/0027172 A1 | 2/2011 | Wang et al. |
| 2011/0065807 A1 | 3/2011 | Radovic-Moreno et al. |
| 2012/0156135 A1 | 6/2012 | Farokhzad et al. |
| 2012/0213738 A1 | 8/2012 | Nam et al. |
| 2012/0251560 A1 | 10/2012 | Dahlman et al. |
| 2013/0158021 A1 | 6/2013 | Dong et al. |
| 2013/0216503 A1 | 8/2013 | Srivastava et al. |
| 2014/0093575 A1 | 4/2014 | Hammond et al. |
| 2014/0235526 A1 | 8/2014 | Srivastava et al. |
| 2014/0301991 A1 | 10/2014 | Srivastava et al. |
| 2015/0307847 A1 | 10/2015 | Nam et al. |
| 2016/0153000 A1 | 6/2016 | Glorioso et al. |
| 2016/0340393 A1 | 11/2016 | Schaffer et al. |
| 2018/0066285 A1 | 3/2018 | Ojala et al. |
| 2020/0405824 A1 | 12/2020 | Odom et al. |
| 2021/0180023 A1 | 6/2021 | Olson et al. |
| 2023/0103731 A1 | 4/2023 | Lombardi et al. |
| 2023/0137971 A1 | 5/2023 | Zhou et al. |

FOREIGN PATENT DOCUMENTS

| | | |
|---|---|---|
| WO | WO 93/19191 A1 | 9/1993 |
| WO | WO 94/07529 A1 | 4/1994 |
| WO | WO 94/12649 A2 | 6/1994 |
| WO | WO 94/28938 A1 | 12/1994 |
| WO | WO 95/00655 A1 | 1/1995 |
| WO | WO 95/11984 A2 | 5/1995 |
| WO | WO 01/83692 A2 | 11/2001 |
| WO | WO-02060946 A2 | 8/2002 |
| WO | WO-2007070483 A2 | 6/2007 |
| WO | WO-2009018492 A2 | 2/2009 |
| WO | WO-2009105759 A2 | 8/2009 |
| WO | WO 2011/159726 A2 | 12/2011 |
| WO | WO-2012006577 A2 | 1/2012 |
| WO | WO 2012/019168 A2 | 2/2012 |
| WO | WO 2012/045075 A1 | 4/2012 |
| WO | WO 2012/045082 A2 | 4/2012 |
| WO | WO 2013/052523 A1 | 4/2013 |
| WO | WO 2013/090648 A1 | 6/2013 |
| WO | WO 2013/090861 A1 | 6/2013 |
| WO | WO 2014/081507 A1 | 5/2014 |
| WO | WO 2015/061568 A1 | 4/2015 |
| WO | WO 2016/133917 A1 | 8/2016 |
| WO | WO 2017/173137 A1 | 10/2017 |
| WO | WO 2018/222503 A1 | 12/2018 |
| WO | WO 2019/036086 A1 | 2/2019 |
| WO | WO 2019/060454 A2 | 3/2019 |
| WO | WO 2020/047467 A1 | 3/2020 |
| WO | WO-2021007515 A1 | 1/2021 |
| WO | WO-2021178246 A1 | 9/2021 |

OTHER PUBLICATIONS

U.S. Appl. No. 15/782,980, filed Oct. 13, 2017, Gao et al.
International Search Report and Written Opinion dated Jan. 27, 2020 for International Application No. PCT/US2019/049150, 15 pages.
Aasen, T. et al., "Efficient and rapid generation of induced pluripotent stem cells from human keratinocytes," Nature Biotechnology, 26(11):1276-1284 (2008).
Addis, R. C. et al., "Optimization of direct fibroblast reprogramming to cardiomyocytes using calcium activity as a functional measure of success," Journal of Molecular and Cellular Cardiology, 60:97-106 (2013).
Ali, R. R. et al., "Gene transfer into the mouse retina mediated by an adeno-associated viral vector," Human Molecular Genetics, 5(5):591-594 (1996).
Ali, R. R. et al., "Adeno-Associated Virus Gene Transfer to Mouse Retina," Human Gene Therapy, 9:81-86 (1998).
Anderson, C. M. et al., "Cooperative activation of cardiac transcription through myocardin bridging of paired MEF2 sites," Development, 144:1235-1241 (2017).
Aoi, T. et al., "Generation of Pluripotent Stem Cells from Adult Mouse Liver and Stomach Cells," Science, 321:699-702 (2008), and Erratum, 2 pages.
Asokan, A. & Samulski, R. J., "An Emerging Adeno-Associated Viral Vector Pipeline for Cardiac Gene Therapy," Human Gene Therapy, 24:906-913 (2013).
Balaji, S. et al., "Pseudotyped adeno-associated viral vectors for gene transfer in dermal fibroblasts: implications for wound-healing applications," Journal of Surgical Research, 184:691-698 (2013).
Belian, E. et al., "Forward Programming of Cardiac Stem Cells by Homogeneous Transduction with MYOCD plus TBX5," PLoS One, 10(6):e0125384 (2015), 29 pages; doi:10.1371/journal.pone.0125384.
Bennett, J. et al., "Real-Time, Noninvasive In Vivo Assessment of Adeno-Associated Virus-Mediated Retinal Transduction," Investigative Ophthalmology & Visual Science, 38(13):2857-2863 (1997).
Bevis, B. J. & Glick, B. S., "Rapidly maturing variants of the Discosoma red fluorescent protein (DsRed)," Nature Biotechnology, 20:83-87 (2002).
Bitter, G. A. et al., "Expression and Secretion Vectors for Yeast," Methods in Enzymology, 153:516-544 (1987).
Blömer, U. et al., "Highly Efficient and Sustained Gene Transfer in Adult Neurons with a Lentivirus Vector," Journal of Virology, 71(9):6641-6649 (1997).

(56) References Cited

OTHER PUBLICATIONS

Borges, M. et al., "An achaete-scute homologue essential for neuroendocrine differentiation in the lung," Nature, 386:852-855 (1997).
Borrás, T. et al., "Adenoviral reporter gene transfer to the human trabecular meshwork does not alter aqueous humor outflow. Relevance for potential gene therapy of glaucoma," Gene Therapy, 6:515-524 (1999).
Braunwald, E., "The war against heart failure: the Lancet lecture," The Lancet, 385:812-824 (2015).
Cao, D. et al., "Modulation of Smooth Muscle Gene Expression by Association of Histone Acetyltransferases and Deacetylases with Myocardin," Molecular and Cellular Biology, 25(1):364-376 (2005).
Cao, D. et al., "Acetylation of Myocardin Is Required for the Activation of Cardiac and Smooth Muscle Genes," The Journal of Biological Chemistry, 287(46):38495-38504 (2012).
Chen, J.-F. et al., "Myocardin Marks the Earliest Cardiac Gene Expression and Plays an Important Role in Heart Development," Anat Rec (Hoboken), 291(10):1200-1211 (2008).
Chen, C. & Okayama, H., "High-Efficiency Transformation of Mammalian Cells by Plasmid DNA," Molecular and Cellular Biology, 7(8):2745-2752 (1987).
Choi, S. H. et al., Establishment of Isolation and Expansion Protocols for Human Cardiac C-kit-Positive Progenitor Cells for Stem Cell Therapy, Transplant Proc. 45(1):420-426 (2013).
Christoforou, N. et al., "Transcription Factors MYOCD, SRF, Mesp1 and SMARCD3 Enhance the Cardio-Inducing Effect Of GATA4, TBX5, and MEF2C During Direct Cellular Reprogramming," PLoS One, 8(5):e63577 (2013), 19 pages; doi:10.1371/journal.pone.0063577.
Chuang, W. et al., "Partial Reprogramming of Pluripotent Stem Cell-Derived Cardiomyocytes into Neurons," Scientific Reports, 7:44840 (2017), 10 pages; doi: 10.1038/srep44840.
Cotton, M. et al., "High-efficiency receptor-mediated delivery of small and large (48 kilobase gene constructs using the endosome-disruption activity of defective or chemically inactivated adenovirus particles," Proc. Natl. Acad. Sci. USA, 89:6094-6098 (1992).
Creemers, E. E. et al., "Myocardin is a direct transcriptional target of Mef2, Tead and Foxo proteins during cardiovascular development," Development, 133:4245-4256 (2006).
Creemers, E. E. et al., "Coactivation of MEF2 by the SAP Domain Proteins Myocardin and MASTR," Molecular Cell, 23:83-96 (2006).
Curiel, D. T., "High-Efficiency Gene Transfer Employing Adenovirus-Polylysine-DNA Complexes," Nat Immun, 13:141-164 (1994).
De, B. P. et al., "High Levels of Persistent Expression of α1-Antitrypsin Mediated by the Nonhuman Primate Serotype rh.10 Adeno-associated Virus Despite Preexisting Immunity to Common Human Adeno-associated Viruses," Molecular Therapy, 13(1):67-76 (2006).
"Developing Gene Therapy for Direct Cardiac Reprogramming," Tenaya Therapeutics, ISSCR Annual Meeting, Jun. 25, 2020, 12 pages.
Di Stefano, B. et al., "Efficient Genetic Reprogramming of Unmodified Somatic Neural Progenitors Uncovers the Essential Requirement of Oct4 and Klf4," Stem Cells and Development, 18(5):707-715 (2009).
Donnelly, M. L. L. et al., "Analysis of the aphthovirus 2A/2B polyprotein 'cleavage' mechanism indicates not a proteolytic reaction, but a novel translational effect : a putative ribosomal 'skip'," Journal of General Virology, 82:1013-1025 (2001).
Donnelly, M. L. L. et al., "The 'cleavage' activities of foot-and-mouth disease virus 2A site-directed mutants and naturally occurring '2A-like' sequences," Journal of General Virology, 82:1027-1041 (2001).
Dull, T. et al., "A Third-Generation Lentivirus Vector with a Conditional Packaging System," Journal of Virology, 72(11):8463-8471 (1998).
Dunbar, C. E. et al., "Gene Therapy Comes of Age," Science, Science 359, eaan4672 (2018), 12 pages; doi:10.1126/science.aan4672.

Eminli, S. et al., "Reprogramming of Neural Progenitor Cells into Induced Pluripotent Stem Cells in the Absence of Exogenous Sox2 Expression," Cells, 26:2467-2474 (2008).
Fechheimer, M. et al., "Transfection of mammalian cells with plasmid DNA by scrape loading and sonication loading," Proc. Natl. Acad. Sci., 84:8463-8467 (1987).
Felgner, P. L. et al., "Lipofection: A highly efficient, lipid-mediated DNA-transfection procedure," Proc. Natl. Acad. Sci. USA, 84:7413-7417 (1987).
Flannery, J. G. et al., "Efficient photoreceptor-targeted gene expression in vivo by recombinant adeno-associated virus," Proc. Natl. Acad. Sci. USA, 94:6916-6921 (1997).
Flotte, T. R. et al., "Stable in vivo expression of the cystic fibrosis transmembrane conductance regulator with an adeno-associated virus vector," Proc. Natl. Acad. Sci. USA, 90:10613-10617 (1993).
Fonoudi, H. et al., "A Universal and Robust Integrated Platform for the Scalable Production of Human Cardiomyocytes From Pluripotent Stem Cells," Stem Cells Translational Medicine, 4:1482-1494 (2015).
Fu, J.-D. et al., "Direct Reprogramming of Human Fibroblasts Toward a Cardiomyocyte-Like State," Stem Cell Reports, 1(3):235-247 (2013).
Fu, X. et al., "Specialized fibroblast differentiated states underlie scar formation in the infarcted mouse heart," J Clin Invest., 128(5):2127-2143 (2018); https://doi.org/10.1172/JCI98215.
Gao, X.-M. et al., "Serial echocardiographic assessment of left ventricular dimensions and function after myocardial infarction in mice," Cardiovascular Research, 45:330-338 (2000).
Gao, G. et al., "Clades of Adeno-Associated Viruses Are Widely Disseminated in Human Tissues," Journal of Virology, 78(12):6381-6388 (2004).
GenBank Accession No. AF085716.1, Feb. 9, 1999, 3 pages.
GenBank Accession No. AX753246.1, Jun. 23, 2003, 3 pages.
GenBank Accession No. AX753249.1, Jun. 23, 2003, 2 pages.
GenBank Accession No. NC_001401.2, Aug. 13, 2018, 6 pages.
GenBank Accession No. NC_001829.1, Aug. 13, 2018, 7 pages.
GenBank Accession No. NC_002077_1, Aug. 13, 2018, 3 pages.
GenBank Accession No. NC_001829.1, Aug. 13, 2018, 3 pages.
Gopal, T. V., "Gene Transfer Method for Transient Gene Expression, Stable Transformation, and Cotransformation of Suspension Cell Cultures," Molecular and Cellular Biology, 5(5): 1188-1190 (1985).
Graham, F. L. & Van Der Eb, A. J., "A New Technique for the Assay of Infectivity of Human Adenovirus 5 DNA," Virology, 52:456-467 (1973).
Grunhaus, A. et al., "Association of Vaccinia Virus-Expressed Adenovirus E3-19K Glycoprotein with Class I MHC and Its Effects on Virulence in a Murine Pneumonia Model," Virology, 200:535-546 (1994).
Hashimoto, M. et al., "Induction of Cardiac Cell Types by Direct Reprogramming," Circulation Research, e168 (2016), 1 paqe.
Hashimoto, H. et al., "Synergistic activation of the cardiac enhancer landscape during reprogramming," ESC Congress 2019 together with World Congress of Cardiology, Aug. 31-Sep. 4, 2019, Paris—France, 1 page.
Hashimoto, H. et al., "Cardiac Reprogramming Factors Synergistically Activate Genome-wide Cardiogenic Stage-Specific Enhancers," Cell Stem Cell, 25:69-86 (2019), and Methods, 5 pages.
Hanna, J. et al., "Direct Reprogramming of Terminally Differentiated Mature B Lymphocytes to Pluripotency," Cell, 133:250-264 (2008).
Harland, R. & Weintraub, H., "Translation of Is Specifically mRNA Injected into Xenopus Inhibited by Antisense RNA Oocytes," The Journal of Cell Biology, 101:1094-1099 (1985).
Hirai, H. et al., "Accelerated direct reprogramming of fibroblasts into cardiomyocyte-like cells with theMyoD transactivation domain," Cardiovascular Research, 100:105-113 (2013).
Hoey, T., Developing Gene Therapy for Direct Cardiac Reprogramming, Tenaya Therapeutics; ISSCR Annual Meeting: 12 pages. (Jun. 25, 2020).
Hoofnagle, M. H. et al., "Myocardin is differentially required for the development of smooth muscle cells and cardiomyocytes," Am J Physiol Heart Cir Physiol 300:H1707-H1721 (2011).

(56) References Cited

OTHER PUBLICATIONS

Hu, S. et al., "MicroRNA-302 Increases Reprogramming Efficiency via Repression of NR2F2," Stem Cells, 31:259-268 (2013).
Huang, J. et al., "Myocardin is required for cardiomyocyte survival and maintenance of heart function," PNAS, 106(44):18734-18739 (2009).
Hunter, J. J. et al., "Targeting Gene Expression to Specific Cardiovascular Cell Types in Transgenic Mice," Hypertension, 22:608-617 (1993).
Ieda et al., "Direct Reprogramming of Fibroblasts into Functional Cardiomyocytes by Defined Factors," Cell, 142(3):375-386 (2010).
Ieda, M. et al., "Cardiac fibroblasts regulate myocardial proliferation through β1 integrin signaling," Dev Cell, 16(2):233-44 (2009).
Illies, C. et al., "Requirement of Inositol Pyrophosphates for Full Exocytotic Capacity in Pancreatic β Cells," Science, 318:1299-1302 (2007).
Jayawardena, T. M. et al., "MicroRNA-Mediated In Vitro and In Vivo Direct Reprogramming of Cardiac Fibroblasts to Cardiomyocytes," Circ Res. 110(11):1465-73 (2012).
Jomary, C. et al., "Rescue of photoreceptor function by AAV-mediated gene transfer in a mouse model of inherited retinal degeneration," Gene Therapy, 4:683-690 (1997).
Kanasty, R. et al., "Delivery materials for siRNA therapeutics," Nature Materials, 12:967-977 (2013).
Kaneda, Y. et al., "Increased Expression of DNA Cointroduced with Nuclear Protein in Adult Rat Liver," Science, 243:375-378 (1989).
Kanegae, Y. et al., "Efficient gene activation in mammalian cells by using recombinant adenovirus expressing site-specific Cre recombinase," Nucleic Acids Research, 23(19):3816-3821 (1995).
Kato, K. et al., "Expression of Hepatitis B Virus Surface Antigen in Adult Rat Liver," The Journal of Biological Chemistry, 266(6):3361-3364 (1991).
Kelleher, Z. T. & Vos, J.-M. H., "Long-Term Episomal Gene Delivery in Human Lymphoid Cells Using Human and Avian Adenoviral-Assisted Transfection," BioTechniques, 17(6):1110-1117 (1994).
Kim, J. et al., "Direct reprogramming of mouse fibroblasts to neural progenitors," PNAS, 108(19):7838-7843 (2011).
Kim, J. H. et al, "High Cleavage Efficiency of a 2A Peptide Derived from Porcine Teschovirus-1 in Human Cell Lines, Zebrafish and Mice," PLoS One, 6(4):e18556 (2011), 8 pages; doi:10.1371/journal.pone.0018556.
Kitamura, T. et al., "Retrovirus-mediated gene transfer and expression cloning: Powerful tools in functional genomics," Experimental Hematology, 31:1007-1014 (2003).
Kotterman, M. A. & Schaffer, D. V., "Engineering adeno-associated viruses for clinical gene therapy," Nature Reviews Genetics, 15:445-451 (2014).
Li, T. et al., "In Vivo Transfer of a Reporter Gene to the Retina Mediated by an Adenoviral Vector," Invest Ophthalmol Vis Sci., 35:2543-2549 (1994).
Li, T. & Davidson, B. L., "Phenotype correction in retinal pigment epithelium in murine mucopolysaccharidosis VII by adenovirus-mediated gene transfer," Proc. Natl. Acad. Sci. USA, 92:7700-7704 (1995).
Lian, X. et al., "Directed cardiomyocyte differentiation from human pluripotent stem cells by modulating Wnt/β-catenin signaling under fully defined conditions," Nature Protocols, 8(1):162-175 (2013).
Linn, S. C. et al., "Conservation of an AE3 CI-/HCO3-Exchanger Cardiac-Specific Exon and Promoter Region and AE3 mRNA Expression Patterns in Murine and Human Hearts," Circulation Research, 76:584-591 (1995); Originally published Apr. 1, 1995; https://doi.org/10.1161/01.RES.76.4.584.
Litwin, S. E. et al., "Serial Echocardiographic Assessment of Left Ventricular Geometry and Function After Large Myocardial Infarction in the Rat," Circulation, 89:345-354 (1994).
Liu, Z. et al., "Systematic comparison of 2A peptides for cloning multi-genes in a polycistronic vector," Scientific Reports, 7:2193 (2017), 9 pages; doi:10.1038/s41598-017-02460-2.

Lowry, W. E. et al., "Generation of human induced pluripotent stem cells from dermal fibroblasts," PNAS, 105(8):2883-2888 (2008).
Macejak, D. G. & Sarnow, P., "Internal initiation of translation mediated by the 5' leader of a cellular mRNA," Nature, 353:90-94 (1991).
Mann, R. et al., "Construction of a Retrovirus Packaging Mutant and Its Use to Produce Helper-Free Defective Retrovirus," Cell, 33:153-159 (1983).
Mao, Z. & Nadal-Ginard, B., "Functional and Physical Interactions between Mammalian Achaete-Scute Homolog 1 and Myocyte Enhancer Factor 2A," The Journal of Biological Chemistry, 271(24):14371-14375 (1996).
Marsic, D. et al., "Vector Design Tour de Force: Integrating Combinatorial and Rational Approaches to Derive Novel Adeno-associated Virus Variants," Molecular Therapy, 22(11):1900-1909 (2014).
Mauritz, C. et al., "Generation of Functional Murine Cardiac Myocytes from Induced Pluripotent Stem Cells," Circulation, 118(5):507-517 (2008).
McClements, M. E. & MacLaren, R. E., "Adeno-associated Virus (AAV) Dual Vector Strategies for Gene Therapy Encoding Large Transgenes," Yale Journal of Biology and Medicine, 90:611-623 (2017).
Mendelson, E. et al., "Expression and Rescue of a Nonselected Marker from an Integrated AAV Vector," Virology, 166:154-165 (1988).
Miller, P. R. et al., "Radiation Resistance in a Doxorubicin-Resistant Human Fibrosarcoma Cell Line," Am J Clin Oncol (CCT), 15(3):216-221 (1992).
Min, J.-Y. et al., "Significant Improvement of Heart Function by Cotransplantation of Human Mesenchymal Stem Cells and Fetal Cardiomyocytes in Postinfarcted Pigs," Ann Thorac Surg, 74:1568-1575 (2002).
Miyoshi, H. et al., "Stable and efficient gene transfer into the retina using an HIV-based lentiviral vector," Proc. Natl. Acad. Sci. USA, 94:10319-10323 (1997).
Miyoshi, H. et al., "Development of a Self-Inactivating Lentivirus Vector," Journal of Virology, 72(10):8150-8157 (1998).
Mohamed, T. M. A. et al., "Chemical Enhancement of In Vitro and In Vivo Direct Cardiac Reprogramming," Circulation, 135:978-995 (2017).
Morgenstern, J. P. & Land, H., "Advanced mammalian gene transfer: high titre retroviral vectors with multiple drug selection markers and a complementary helper-free packaging cell line," Nucleic Acids Research, 18(12):3587-3596 (1990).
Morita, S. et al., "Plat-E: an efficient and stable system for transient packaging of retroviruses," Gene Therapy, 7:1063-1066 (2000).
Muehlich, S. et al., "Serum-Induced Phosphorylation of the Serum Response Factor Coactivator MKL1 by the Extracellular Signal-Regulated Kinase 1/2 Pathway Inhibits Its Nuclear Localization," Molecular and Cellular Biology, 28(20):6302-6313 (2008).
Muller, C. A. et al., "Bucindolol, a Beta Blocker, Decreased Ventricular Fibrillation and Maintained Mechanical Function in a Pig Model of Acute Myocardial Ischemia," Cardiovascular Drugs and Therapy, 6:233-237 (1992).
Muzyczka, N., "Use of Adeno-Associated Virus as a General Transduction Vector for Mammalian Cells," Current Topics in Microbiology and Immunology, 158:97-129 (1992).
Nabel, G. & Baltimore, D., "An inducible transcription factor activates expression of human immunodeficiency virus in T cells," Nature, 326:711-713 (1987).
Naldini, L. et al., "In Vivo Gene Delivery and Stable Transduction of Nondividing Cells by a Lentiviral Vector," Science, 272:263-267 (1996).
Naldini, L., "Lentiviruses as gene transfer agents for delivery to non-dividing cells," Current Opinion in Biotechnology, 9:457-463 (1998).
Nam, Y. et al., "Reprogramming of human fibroblasts toward a cardiac fate," Proc Natl Acad Sci USA, 110(14):5588-93 (2013).
Nicolas, J.-F. & Rubenstein, J. L. R., "Retroviral Vectors," In: Vectors: A Survey of Molecular Cloning Vectors and Their Uses, David T. Denhardt, Raymond L. Rodriguez (Eds.), pp. 493-513 (1988).

(56) References Cited

OTHER PUBLICATIONS

Nicolau, C. & Sene, C., "Liposome-Mediated DNA Transfer in Eukaryotic Cells," Biochimica et Biophysica Acta, 721:185-190 (1982).
Nicolau, C. et al., "Liposomes as Carriers for in Vivo Gene Transfer and Expression," Methods in Enzymology, 149:157-176 (1987).
Oh, J. et al., "Target Gene-Specific Modulation of Myocardin Activity by GATA Transcription Factors," Molecular and Cellular Biology, 24(19):8519-8528 (2004).
Onishi, M. et al., "Applications of retrovirus-mediated expression cloning," Experimental Hematology, 24:324-329 (1996).
Parmacek, M. S. et al., "A Novel Myogenic Regulatory Circuit Controls Slow/Cardiac Troponin C Gene Transcription in Skeletal Muscle," Molecular and Cellular Biology, 14(3): 1870-1885 (1994).
Paskind, M. P. et al., "Dependence of Moloney Murine Leukemia Virus Production on Cell Growth," Virology, 67:242-248 (1975).
Pelletier, J. & Sonenberg, N., "Internal initiation of translation of eukaryotic mRNA directed by a sequence derived from poliovirus RNA," Nature, 334:320-325 (1988).
Piras, B. A. et al., "Systemic injection of AAV9 carrying a periostin promoter targets gene expression to a myofibroblast-like lineage in mouse hearts after reperfused myocardial infarction," Gene Therapy, 23:469-478 (2016).
Potter, H. et al., "Enhancer-dependent expression of human Kc immunoglobulin genes introduced into mouse pre-B lymphocytes by electroporation," Proc. Natl. Acad. Sci. USA, 81:7161-7165 (1984).
Pozsgai, E. R. et al., "Systemic AAV-Mediated b-Sarcoglycan Delivery Targeting Cardiac and Skeletal Muscle Ameliorates Histological and Functional Deficits in LGMD2E Mice," Molecular Therapy, 24(4):855-869 (2017).
Protze, S. et al., "A new approach to transcription factor screening for reprogramming of fibroblasts to cardiomyocyte-like cells," J Mol Cell Cardiol., 53(3):323-32 (2012) Epub Apr. 28, 2012.
Qian, L. et al., "In vivo reprogramming of murine cardiac fibroblasts into induced cardiomyocytes," Nature, 485(7400):593-598 (2012).
Qin, D. et al., "Mouse Meningiocytes Express Sox2 and Yield High Efficiency of Chimeras after Nuclear Reprogramming with Exogenous Factors," The Journal of Biological Chemistry, 283(48):33730-33735 (2008), with Supplementary Table 1, 2 pages.
Rippe, R. A. et al., "DNA-Mediated Gene Transfer into Adult Rat Hepatocytes in Primary Culture," Molecular and Cellular Biology, 10(2):689-695 (1990).
Riviére, I. et al., "Effects of retroviral vector design on expression of human adenosine deaminase in murine bone marrow transplant recipients engrafted with genetically modified cells," Proc. Natl. Acad. Sci., 92:6733-6737 (1995).
Robbins, J. et al., "In Vivo Definition of a Cardiac Specific Promoter and Its Potential Utility in Remodeling the Heart," Annals New York Academy of Sciences, 752:492-505 (1995).
Rolling, F. et al., "Evaluation of Adeno-Associated Virus-Mediated Gene Transfer into the Rat Retina by Clinical Fluorescence Photography," Human Gene Therapy, 10:641-648 (1999).
Sakamoto, T. et al., "A vitrectomy improves the transfection efficiency of adenoviral vector-mediated gene transfer to Müller cells," Gene Therapy, 5:1088-1097 (1998).
Samulski, R. J. et al., "Helper-Free Stocks of Recombinant Adeno-Associated Viruses: Normal Integration Does Not Require Viral Gene Expression," Journal of Virology, 63(9):3822-3828 (1989).
Sartorelli, V. et al., "Myocardial activation of the human cardiac a-actin promoter by helix-loop-helix proteins," Proc. Natl. Acad. Sci. USA, 89:4047-4051 (1992).
Senyo, S. E. et al., "Cardiac regeneration based on mechanisms of cardiomyocyte proliferation and differentiation," Stem Cell Res., vol. 13, Issue 3, Part B, pp. 532-541 (2014); https://doi.org/10.1016/j.scr.2014.09.003.
Sheehy, S. P. et al., "Quality Metrics for Stem Cell-Derived Cardiac Myocytes," Stem Cell Reports, 2:282-294 (2014).
Small, E. M. et al., "Myocardin is sufficient and necessary for cardiac gene expression in Xenopus," Development, 132:987-997 (2004).
Srivastava, A. et al., "Nucleotide Sequence and Organization of the Adeno-Associated Virus 2 Genome," Journal of Virology, 45(2):555-564 (1983).
Srivastava, D. & DeWitt, N., "In Vivo Cellular Reprogramming: The Next Generation," Cell, 166:1386-1396 (2016).
Stadtfeld, M. & Hochedlinger, K., "Without a trace? PiggyBac-ing toward pluripotency," Nature Methods, 6(5):329-330 (2009).
Stadtfeld, M. et al., "Defining Molecular Cornerstones during Fibroblast to iPS Cell Reprogramming in Mouse," Cell Stem Cell, 2:230-240 (2008).
Szymczak-Workman, A. L. et al., "Design and Construction of 2A Peptide-Linked Multicistronic Vectors," Cold Spring Harbor Protoc, 2:199-204 (2012); doi:10.1101/pdb.ip067876.
Takahashi, M. et al., "Rescue from Photoreceptor Degeneration in the rd Mouse by Human Immunodeficiency Virus Vector-Mediated Gene Transfer," Journal of Virology, 73(9):7812-7816 (1999).
Takahashi, K. & Yamanaka, S., "Induction of pluripotent stem cells from mouse embryonic and adult fibroblast cultures by defined factors," Cell, 126:663-676 (2006).
Tang, J. et al., "Cardiac cell-integrated microneedle patch for treating myocardial infarction," Sci. Adv., 4:eaat9365 (2018), 12 pages; doi: 10.1126/sciadv.aat9365.
Temin, H. M., "Retrovirus Vectors for Gene Transfer: Efficient Integration into and Expression of Exogenous DNA in Vertebrate Cell Genomes," Gene Transfer, R. Kucherlapati (ed.), pp. 149-187 (1986).
Ueyama, T. et al., "Myocardin Expression Is Regulated by Nkx2.5, and Its Function Is Required for Cardiomyogenesis," Molecular and Cellular Biology, 23(24):9222-9232 (2003).
Van Tuyn, J. "Cellular and genetic approaches to myocardial regeneration," *Gildeprint BV, Enschede* (2007), 176 pages.
Vierbuchen, T. et al., "Direct conversion of fibroblasts to functional neurons by defined factors," Nature, 463(7284):1035-1041 (2010).
Wada, R. et al., "Induction of human cardiomyocyte-like cells from fibroblasts by defined factors," Proc Natl Acad Sci USA, 110(31):12667-12672 (2013).
Wang, Y. et al., "2A self-cleaving peptide-based multi-gene expression system in the silkworm *Bombyx mori*," Scientific Reports, 5:16273 (2015), 10 pages; doi: 10.1038/srep16273.
Wang, D.-Z. et al., "Activation of Cardiac Gene Expression by Myocardin, a Transcriptional Cofactor for Serum Response Factor," Cell, 105:851-862 (2001).
Wang, Z. et al., "Myocardin is a master regulator of smooth muscle gene expression," PNAS, 100(2):7129-7134 (2003).
Wang, Z. et al., "Myocardin and ternary complex factors compete for SRF to control smooth muscle gene expression," Nature, 428:185-189 (2004).
Wang, C. et al., "Synergistic Activation of Cardiac Genes by Myocardin and Tbx5," PLoS One, 6(8):e24242 (2011), 9 pages; doi:10.1371/journal.pone.0024242.
Yazawa, K. et al., "Current Progress in Suicide Gene Therapy for Cancer," World J. Surg., 26:783-789 (2002).
Yee, J.-K. et al., "Generation of High-Titer Pseudotyped Retroviral Vectors with Very Broad Host Range," Methods in Cell Biology, 43:99-112 (1994).
Yoshida, T. et al., "Myocardin Is a Key Regulator of CArG-Dependent Transcription of Multiple Smooth Muscle Marker Genes," Circ Res., 92:856-864 (2003).
Yusa, K. et al., "Generation of transgene-free induced pluripotent mouse stem cells by the piggyBac transposon," Nature Methods, 6(5):363-369 (2009), and Online Methods, 2 pages.
Zangi, L. et al., "Modified mRNA directs the fate of heart progenitor cells and induces vascular regeneration after myocardial infarction," Nature Biotechnology, 31:898-907 (2013); doi:10.1038/nbt.2682, and Corrigendum, 1 page.
Zhang, J. et al., "Overexpression of myocardin induces partial transdifferentiation of human-induced pluripotent stem cell-derived mesenchymal stem cells into cardiomyocytes," Physiol. Rep, 2(2):e00237 (2014), 14 pages; doi: 10.1002/phy2.237.

(56) References Cited

OTHER PUBLICATIONS

Zhou, L. et al., "Cardiac Gene Activation Analysis in Mammalian Non-Myoblasic Cells by Nkx2-5, Tbx5, Gata4 and Myocd," PLoS One, 7(10):e48028 (2012); doi: 10.1371/journal.pone.0048028.

Zhou, H. et al., "ZNF281 enhances cardiac reprogramming by modulating cardiac and inflammatory gene expression," Genes and Development, 31:1770-1783 (2017).

Zhou, H., "Molecular Regulation of Direct Cardiac Reprogramming," Dissertation, The University of Texas Southwestern Medical Center at Dallas, Dallas, Texas, Aug. 2017, 97 pages.

Zufferey, R. et al., "Multiply attenuated lentiviral vector achieves efficient gene delivery in vivo," Nature Biotechnology, 15:871-875 (1997).

Zufferey, R. et al., "Self-Inactivating Lentivirus Vector for Safe and Efficient In Vivo Gene Delivery," Journal of Virology, 72(12):9873-9880 (1998).

Adra, C. N., et al., "Cloning and expression of the mouse pgk-1 gene and the nucleotide sequence of its promoter," Gene 60 (1987), pp. 65-74.

Benoist, C., et al., "In vivo sequence requirements of the SV40 early promoter region," Nature vol. 290, Mar. 26, 1981, pp. 304-310.

Brown, B.D. et al., "Endogenous microRNA can be broadly exploited to regulate transgene expression according to tissue, lineage and differentiation state", Nature Biotechnology, vol. 25:1457-1467 (2007).

Cawood, R. et al., "Use of tissue-specific microRNA to control pathology of wild-type adenovirus without attenuation of its ability to kill cancer cells," PLOS Pathogens, vol. 5 (5): e1000440: (2009) (10 total pages).

Chanda, S., et al., "Generation of Induced Neuronal Cells by the Single Reprogramming Factor ASCL1," Stem Cell Reports, vol. 3, pp. 282-296, Aug. 12, 2014, http://dx.doi.org/10.1016/j.stemcr.2014.05.020.

Chen, J.-F., et al., "The role of microRNA-1 and micro-RNA-133 in skeletal muscle proliferation and differentiation," Nature Genetics, vol. 38, No. 2, Feb. 2006, pp. 228-233.

Du, K. L., et al., "Myocardin is a Critical Serum Response Factor Cofactor in the Transcriptional Program Regulating Smooth Muscle Cell Differentiation," Molecular and Cellular Biology, Apr. 2003, vol. 23, No. 7, pp. 2425-2437, DOI: 10.1128/MCB.23.7.2425-2437.2003.

Extended European Search Report for Application No. EP20190853735, dated Jul. 29, 2022, 11 pages.

Fraley, R. T., et al., "Entrapment of a bacterial plasmid in phospholipid vesicles: Potential for gene transfer," Proc. Natl. Acad. Sci. USA, vol. 76, No. 7, pp. 3348-3352, Jul. 1979.

Frangiogianis N.G. (2015). Pathophysiology of Myocardial Infarction. Comprehensive Physiology, vol. 5, Oct. 2015, pp. 1841-1875, DOI: 10.1002/cphy.c150006.

Franz, W-M., et al., "Analysis of tissue-specific gene delivery by recombinant adenoviruses containing cardiac=specific promoters," Cardiovascular Research 35 (1997), 560-566.

Fu, X. et al., "Specialized fibroblast differentiated states underlie scar formation in the infarcted mouse heart," Journal of Clinical Investigation 2018, 128(5):2127-2143, including Supplemental Material, https://doi.org/10.1172/JCI98215.

Gagan, J., et al., "MicroRNA-378 Targets the Myogenic Repressor MyoR during Myoblast Differentiation," Journal of Biological Chemistry 2-15, Jun. 3, 2011, vol. 286, No. 22, pp. 19431-19438.

Gao, P., et al., "Possible absence of critical thickness and size effect in ultrathin perovskite ferroelectric films," Nature Communications, 2017, 8:15549, DOI: 10.1038/ncomms15549, published Jun. 6, 2017.

GenBank Accession No. NC-001862.1, Jan. 12, 2004, 3 pages.

Goncalves et al., "Transcription Factor Rational Design Improves Directed Differentiation of Human Mesenchymal Stem Cells into Skeletal Myocytes," Molecular Therapy, vol. 19, No. 7, pp. 1331-1341 (Jul. 2011).

Gordan, J. W., "Regulation of cardiac myocyte cell death and differentiation by myocardin," Molecular and Cellular Biochemistry, vol. 437, No. 1, pp. 119-131, doi: 10.1007/S11010-017-3100-3 (Jun. 2017).

Ma, G., et al., "MiR-206, a Key Modulator of Skeletal Muscle Development and Disease," International Journal of Biological Sciences, 2015, vol. 11(3), 345-352, doi: 10.7150/ijbs.10921, published Feb. 5, 2015.

Gray, S. J., et al., "Optimizing Promoters for Recombinant Adeno-Associated Virus-Mediated Gene Expression in the Peripheral and Central Nervous System Using Self-Complementary Vectors," Human Gene Therapy 22: 1143-1153, Sep. 2011, DOI: 10.1089/hum.2010.245 (25 total pages).

Hemmings, KE, et al., "A Transgenic Approach to Study the Effect of Cardiac Fibroblast-Specific Ablation of IL-1 Signaling on Myocardial Remodeling," Heart, Dec. 2014, vol. 100, Supp 4, doi: 10.1136/heartjnl-2014-306916.58.

Hon, L., et al., "The roles of binding site arrangement and combinatorial targeting in microRNA repression of gene expression," Genome Biology, 2007, 8:R166, doi:10.1186/gb-2007-8-8-r166.

International Preliminary Report on Patentability for International Application No. PCT/US2021/020032, dated Sep. 15, 2022, 9 pages.

International Preliminary Report on Patentability, dated Mar. 2, 2021, for International Application No. PCT/US2019/049150 (11 total pages).

International Preliminary Report on Patentability, dated Jan. 20, 2022, for International Application No. PCT/US2020/041602 (9 total pages).

International Search Report and Written Opinion, dated Jul. 23, 2021, for International Application No. PCT/US2021/020032 (12 total pages).

International Search Report and Written Opinion, dated Oct. 14, 2020, for International Application No. PCT/US2020/041602 (12 total pages).

Invitation to Pay Additional Fees, and Where Applicable, Protest Fee, dated Oct. 30, 2019, for International Application No. PCT/US2019/049150 (2 total pages).

Kakimoto, Y., et al., "MicroRNA deep sequencing reveals chamber-specific miR-208 family expression patterns in the human heart," International Journal of Cardiology 211 (2016) 43-48, http://dx.doi.org/10.1016/j.ijcard.2016.02.145.

Kamps, J.A., "Micromanaging Cardiac Regeneration: Targeted Delivery of microRNAs for Cardiac Repair and Regeneration," World Journal of Cardiology, Feb. 26, 2016, vol. 8(2), pp. 163-179.

Khalil, H., et al., "Fibroblast-specific TGF-β-Smad2/3 signaling underlies cardiac fibrosis," The Journal of Clinical Investigation, vol. 127, No. 10, Oct. 2017, pp. 3770-3783.

Kim, E. et al., "Direct reprogramming and biomaterials for controlling cell fate," Biomaterials Research, vol. 20, No. 39, Dec. 2016, https://doi.org/10.1186/s40824-016-0086-y.

Kita-Matsuo, H., et al., "Lentiviral Vectors and Protocols for Creation of Stable hESC Lines for Fluorescent Tracking and Drug Resistance Selection of Cardiomyocytes," PLOS ONE, Apr. 2009, vol. 4, Issue 4, e5046, 15 pages.

Krist, B., et al., "The Role of miR-378a in Metabolism, Angiogenesis, and Muscle Biology," International Journal of Endocrinology 2015, vol. 2015, Article ID 281756, 13 pages, http://dx.doi.org/10.1155/2015/281756.

Li, Y., et al., "Cardiac Fibroblast-Specific Activating Transcription Factor 3 Protects Against Heart Failure by Suppressing MAP2K3-p38 Signaling," Circulation 2017; 135:2041-2057, DOI: 10.1161/CIRCULATIONAHA.116.024599.

Liu, Y., et al., "More complexity to the Bloom's syndrome complex," Genes & Development 2008, 22:2737-2742, http://www.genesdev.org/cgi/doi/10.1101/gad.1732808.

Lombardi, L. M. et al., "Cardiac Direct Reprogramming Gene Therapy for Ischemic Injury," 2020 American Society of Gene & Cell Therapy 23rd Annual Meeting, May 12, 2020 (1 total page).

Mallat, Y., et al., "Proteome Modulation in H9c2 Cardiac Cells by microRNAs miR-378 and miR-378*," Molecular & Cellular Proteomics, 13.1, pp. 18-29, Jan. 2014, DOI: 10.1074/mcp.M113.030569.

(56) References Cited

OTHER PUBLICATIONS

Malo, N., et al., "Statistical practice in high-throughput screening data analysis," Nature Biotechnology, vol. 24, No. 2, Feb. 2006, pp. 167-175, DOI:10.1038/nbt1186.

Mizushima, S., et al., "pEF-BOS, a powerful mammalian expression vector," Nucleic Acids Research, vol. 18, No. 17, 5322 (1990), 1 page.

Mori, S., et al., "Two novel adeno-associated viruses from cynomolgus monkey: pseudotyping characterization of capsid protein," Virology 330 (2004) 375-383, DOI: 10.1016/j.virol.2004.10.012.

Muraoka, N., et al., "MiR-133 promotes cardiac reprogramming by directly repressing Snai1 and silencing fibroblast signatures," The EMBO Journal, 2014, vol. 33, No. 14, pp. 1565-1581, DOI 10.15252/embj.201387605, Published online Jun. 11, 2014.

Nam, Y. et al., "Reprogramming of human fibroblasts toward a cardiac fate," Proc Natl Acad Sci USA, Apr. 2, 2013, vol. 110, No. 14, pp. 5588-5593, including Supporting Information, doi: 10.1073/pnas.1301019110, 14 total pages.

Niwa, H. et al., "Efficient selection for high-expression transfectants with a novel eukaryotic vector," Gene 108 (1991), pp. 193-200.

Non-Final Office Action, dated Dec. 20, 2020, for U.S. Appl. No. 17/028,881 (7 pages).

Qiao, C., et al., "Liver-specific microRNA-122 target sequences incorporated in AAV vectors efficiently inhibits transgene expression in the liver," Gene Therapy (2011) 18, 403-410; doi:10.1038/gt.2010.157; published online Dec. 9, 2010.

Qin, J. Y., et al., "Systematic Comparison of Constitutive Promoters and the Doxycycline-Inducible Promoter," PLOS ONE, May 2010, vol. 5, Issue 5, e10611, doi:10.1371/journal.pone.0010611, 4 pages.

Reid, C.A., et al., "miRNA-mediated post-transcriptional silencing of transgenes leads to increased adeno-associated viral vector yield and targeting specificity," Gene Therapy, 2017, 24, pp. 462-469, DOI: 10.1038/gt.2017.50.

Sanjana, N. E., et al., "Improved vectors and genome-wide libraries for CRISP screening," Nature Methods, vol. 11, No. 8, Aug. 2014, pp. 783-784.

Schorpp, M., et al., "The human ubiquitin C promoter directs high ubiquitous expression of transgenes in mice," Nucleic Acids Research, 1996, vol. 24, No. 9, pp. 1787-1788.

Song, K. et al., "Heart repair by reprogramming non-myocytes with cardiac transcription factors." Nature 485(7400): 599-604 (2012).

Srinath, C., et al., "Developing an Optimized Cardiac Reprogramming Cocktail for Gene Therapy in Humans," 2020 American Society of Gene & Cell Therapy 23rd Annual Meeting, May 12, 2020 (1 total page).

Takahashi, K., et al., "Induction of Pluripotent Stem Cells from Adult Human Fibroblasts by Defined Factors," Cell 131, Nov. 30, 2007, pp. 861-872.

Tang, C., et al., "MicroRNA-145 performs as a tumor suppressor in human esophageal squamous cell carcinoma by targeting phospholipase C epsilon 1," Journal of Cellular Biochemistry 2019, 120:10678-10687, DOI: 10.1002/jcb.28358.

Tian, J., et al., "Myocardial fibrosis in congenital and pediatric heart disease (Review)," Experimental and Therapeutic Medicine, 2017, 13: 1660-1664, DOI: 10.3892/etm.2017.4224.

Tsai, Y-C., et al., "The Interaction of miR-378i-Skp2 Regulates Cell Senescence in Diabetic Nephropathy," Journal of Clinical Medicine 2018, 7, 468, doi:10.3390/jcm7120468, 21 pages.

Tur-Kaspa, R., et al., "Use of Electroporation to Introduce Biologically Active Foreign Genes into Primary Rat Hepatocytes," Molecular and Cellular Biology 1986, 6:2, 716-718, DOI: 10.1128/mcb.6.2.716-718.1986.

Van Rooij, E., et al., "A Family of microRNAs Encoded by Myosin Genes Governs Myosin Expression and Muscle Performance," Developmental Cell 17, 662-673, Nov. 17, 2009, DOI 10.1016/j.devcel.2009.10.013.

Van Rooij, E., et al. "A signature pattern of stress-responsive microRNAs that can evoke cardiac hypertrophy and heart failure," PNAS, Nov. 28, 2006, vol. 103, No. 48, pp. 18255-18260.

Van Rooij, E., et al., "Control of Stress-Dependent Cardiac Growth and Gene Expression by a MicroRNA," Apr. 27, 2007, vol. 316 (5824), pp. 575-579.

Vivas, E. L. et al., "MicroRNA Regulation of Stem Cell Fate and Reprogramming," MicroRNAs in Medicine, First Edition, Edited by Charles H Lawrie, 2014, pp. 27-40 (22 total pages).

Wang, H. et al., "Direct cell reprogramming: approaches, mechanisms and progress", Nat. Rev. Mol. Cell Biol., vol. 22, No. 6, pp. 410-424 (Feb. 2021).

Wang, L., et al., "Stoichiometry of Gata4, Mef2c, and Tbx5 Influences the Efficiency and Quality of Induced Cardiac Myocyte Reprogramming," Circulation Research, 116, 237-244, Jan. 16, 2015, DOI: 10.1161/CIRCRESAHA.116.305547.

Wang, Z-Y., et al., "Acute promyelocytic leukemia: from highly fatal to highly curable," Blood, Mar. 1, 2008, vol. 111, No. 5, pp. 2505-2515.

Wapinski, O. L., et al., "Hierarchical Mechanisms for Direct Reprogramming of Fibroblasts to Neurons," Cell 155, 621-635, Oct. 24, 2013.

Wapinski, O. L., et al., "Rapid Chromatin Switch in the Direct Reprogramming of Fibroblasts to Neurons," Cell Reports 20, 3236-3247, Sep. 26, 2017, http://dx.doi.org/10.1016/j.celrep.2017.09.011.

Warren, L., et al., "Highly Efficient Reprogramming to Pluripotency and Directed Differentiation of Human Cells with Synthetic Modified mRNA," Cell Stem Cell 7, 618-630, Nov. 5, 2010.

Werner, J. H., et al, "Molecular discoveries and treatment strategies by direct reprogramming in cardiac regeneration", Translational Research, vol. 203, pp. 73-87 (Jan. 2019).

Wilson, J. M., et al., "Implantation of Vascular Grafts Lined with Genetically Modified Endothelial Cells," Science, Jun. 16, 1989, vol. 244, pp. 1344-1346.

Woltjen, K., et al., "piggyBac transposition reprograms fibroblasts to induced pluripotent stem cells," Nature, vol. 458, Apr. 9, 2009, pp. 766-770, including METHODS, 1 page, DOI: 10.1038/nature07863.

Wong, T.-K., et al., "Appearance of β-lactamase activity in animal cells upon liposome-mediated gene transfer," Gene 10, (1980), pp. 87-94.

Wright, G. W., et al., "A random variance model for detection of differential gene expression in small microarray experiments," Bioinformatics, 2003, vol. 19, No. 18, pp. 2448-2455, DOI: 10.1093/bioinformatics/btg345.

Wu, G. Y., et al., "Evidence for Targeted Gene Delivery to Hep G2 Hepatoma Cells in Vitro," Biochemistry 1988, 27, 887-892.

Wu, G. Y., et al., "Receptor-mediated in Vitro Gene Transformation by a Soluble DNA Carrier System," The Journal of Biological Chemistry, vol. 262, No. 10, Issue of Apr. 5, 1987, pp. 4429-4432.

Wystub, K., et al., "miR-1/133a Clusters Cooperatively Specify the Cardiomyogenic Lineage by Adjustment of Myocardin Levels During Embryonic Heart Development," PLoS Genetics, 2013, vol. 9(9), pp. e1003793, 17 total pages.

Yang, J., et al., "Efficacy of Cardiac Reprogramming via Gene Therapy in Rat with Chronic Heart Failure," 2020 American Society of Gene & Cell Therapy 23rd Annual Meeting, May 12, 2020 (1 total page).

Yu, H., et al., "microRNA-133: Expression, Function and Therapeutic Potential in Muscle Diseases and Cancer," Current Drug Targets, 2014, 15, 817-828.

Zhang, W., et al., "The emerging role of oxidative stress in regulating autophagy: applications of cancer therapy," Cellular and Molecular Biology, Cellular and Molecular Biology 2017, vol. 63, Issue 4, pp. 67-76, Doi: http://dx.doi.org/10.14715/cmb/2017.63.4.11.

Zhao et al. (2007). "Dysregulation of Cardiogenesis, Cardiac Conduction, and Cell Cycle in Mice Lacking miRNA-1-2," Cell 129, 303-317, Apr. 20, 2007, DOI 10.1016/j.cell.2007.03.030.

Zhao, Z., et al., "Pressure induced metallization with absence of structural transition in layered molybdenum diselenide," Nature Communications 2015, 6:7312, DOI: 10.1038/ncomms8312, Published Jun. 19, 2015, 8 pages.

(56) References Cited

OTHER PUBLICATIONS

Zhou, H., et al., Abstract 543: "Clinical Development of Cardiac Reprogramming Gene Therapy," Circulation Research 2020, 127:A543, https://doi.org/10.1161/res.127.suppl_1.543, 1 page.

Zhou, H., et al., "Akt1/protein kinase B enhances transcriptional programming of fibroblasts to functional cardiomyocytes," PNAS, Sep. 22, 2015, vol. 112, No. 38, pp. 11864-11869, www.pnas.org/cgi/doi/10.1073/pnas.1516237112.

Zhou, H. et al., "ZNF281 enhances cardiac reprogramming by modulating cardiac and inflammatory gene expression," Genes and Development 2017, 31:1770-1783, including Supplementary Material, doi: 10.1101/gad.305482.117, 28 pages.

* cited by examiner

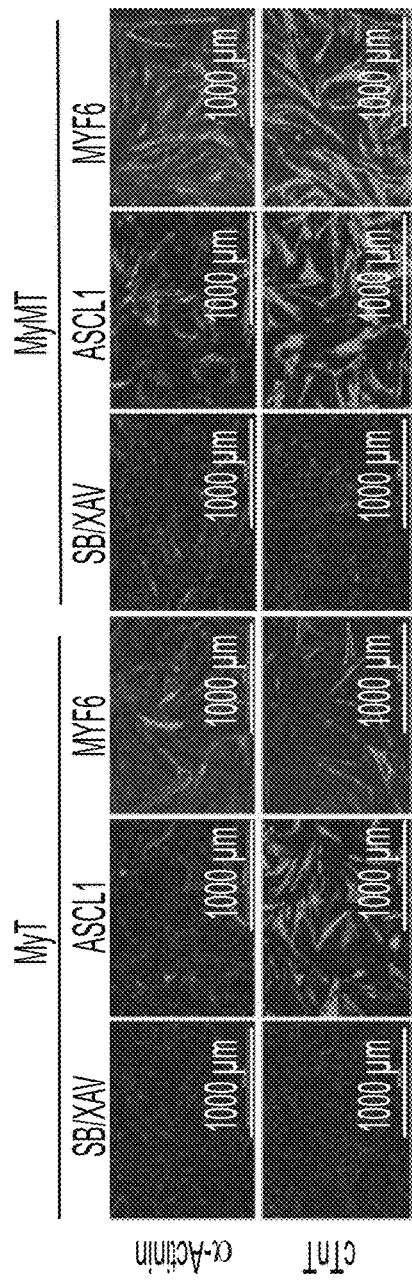
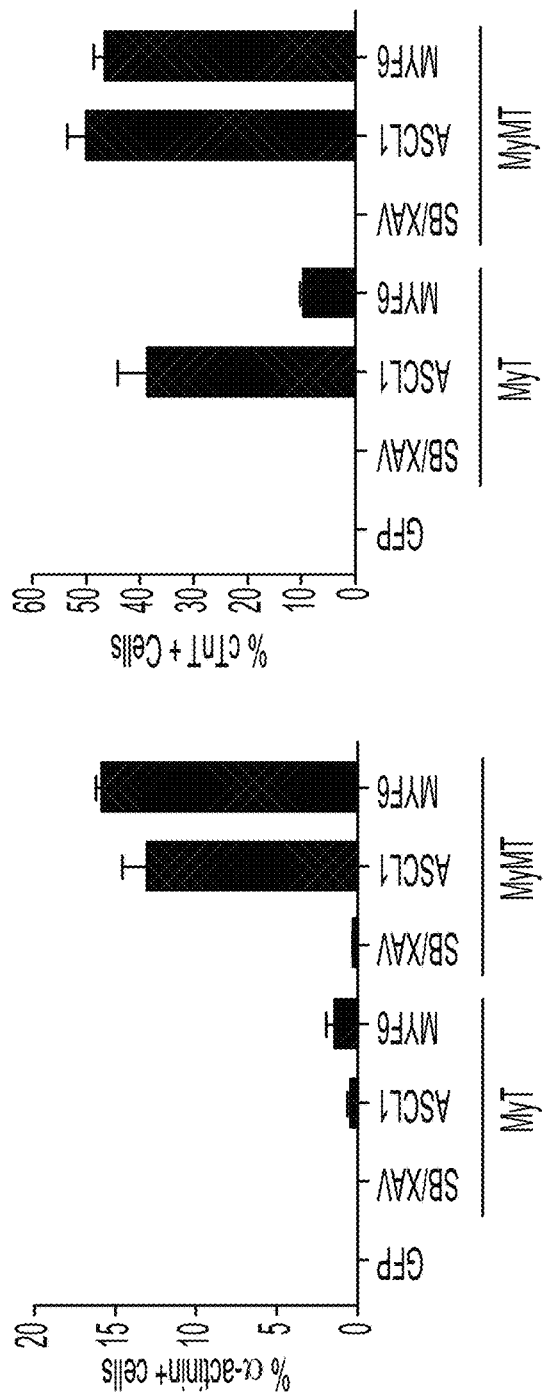
FIG. 2A
FIG. 2B

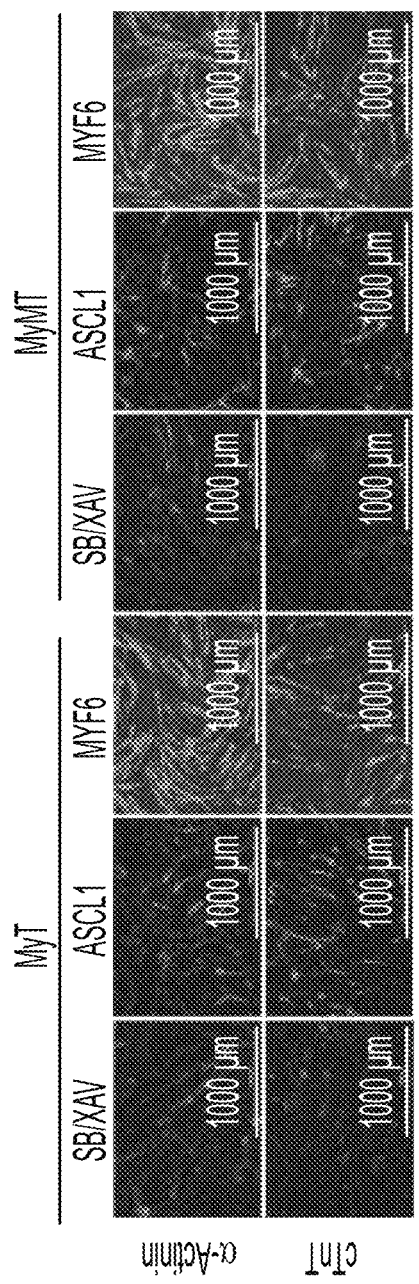
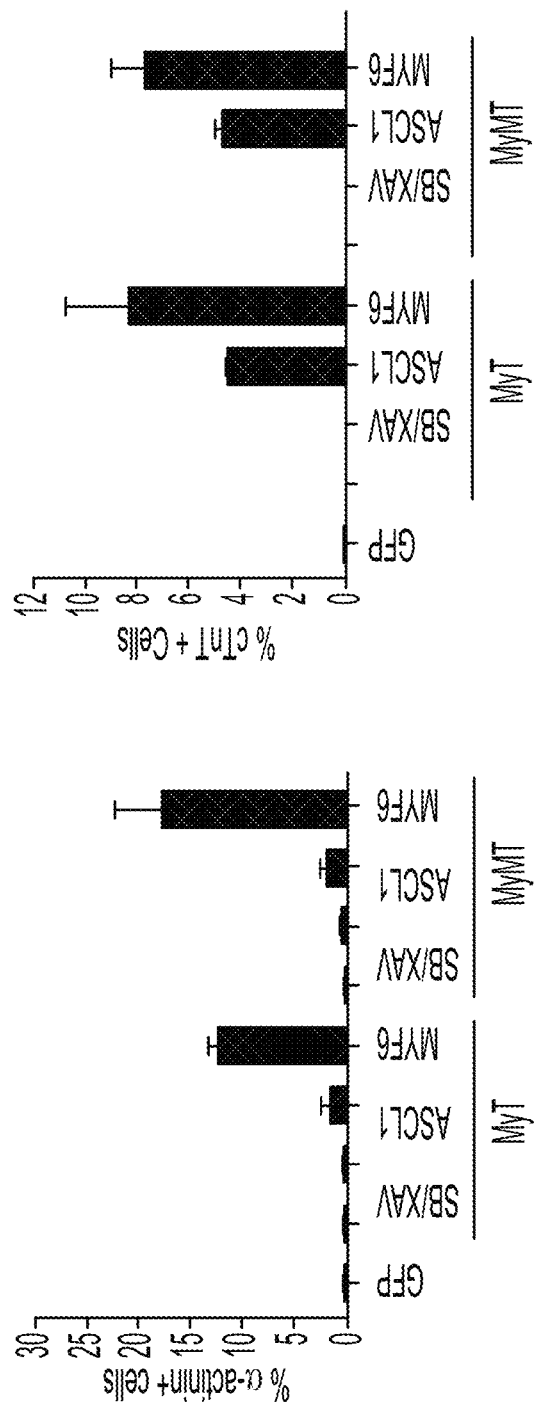
FIG. 2C
FIG. 2D

CARDIAC CELL REPROGRAMMING WITH MYOCARDIN AND ASCL1

RELATED APPLICATIONS

This application is a continuation of U.S. application Ser. No. 17/028,881, filed Sep. 22, 2020, which is continuation of International PCT Application No. PCT/US2019/049150, filed Aug. 30, 2019, which claims the benefit of priority to U.S. Provisional Patent Appl. No. 62/852,746, filed May 24, 2019; U.S. Provisional Patent Appl. No. 62/788,479, filed Jan. 4, 2019; and U.S. Provisional Patent Appl. No. 62/725,168, filed Aug. 30, 2018, each of which is incorporated herein by reference in its entirety.

FIELD OF THE INVENTION

The present disclosure relates generally to the fields of gene therapy, cellular reprogramming, and cellular therapy for diseases or disorders of the heart.

REFERENCE TO SEQUENCE LISTING

This application is being filed electronically via EFS-Web and includes an electronically submitted sequence listing in .txt format. The .txt file contains a sequence listing entitled "TENA_007_03US_SeqList_ST25.txt" created on Mar. 23, 2021 and having a size of ~277 kilobytes. The sequence listing contained in this .txt file is part of the specification and is incorporated herein by reference in its entirety.

BACKGROUND

Heart failure is a major cause of death worldwide. *Braunwald's Heart Disease*, 11$^{th}$ ed. (2015). It has an estimated prevalence of 38 million patients worldwide, a number that is increasing with the ageing of the population. Braunwald, E. The War against Heart Failure. *Lancet* 385:812-824 (2015). The prognosis of heart failure is worse than that of most cancers. Various treatments for heart failure have been proposed, including: (1) enhancing myofilament sensitivity to $Ca^{2+}$, e.g. transfer of the gene for SERCA2a (the protein that pumps calcium into the sarcoplasmic reticulum of the cardiomyocyte); (2) gene therapy to correct abnormal calcium-handling proteins; (3) treatment with antagomirs to block the function of selected microRNAs; (4) cell therapy, e.g., with bone marrow-derived mononuclear cells or mesenchymal cells; and (5) long-term ventricular assistance devices, in some cases leading to myocardial recovery and explanation of the device.

An alternative approach is cell-based therapy with induced cardiomyocytes (iCM). Cardiomyocytes have an extremely limited capacity for cell division, thus limiting the capacity of the heart to regenerate new muscle and repair itself. One strategy for generating cardiomyocytes is ex vivo induction of fibroblast cells to form induced pluripotent stem cells (iPSCs) and then subsequent differentiation of iPSCs into iCMs. For example, the factors OCT4, SOX2, KLF4, and c-MYC generate iPSCs (Takahasi et al. *Cell.* 2006; 126:663-76), which can be differentiated into iCMs with various method including modified temporal modulation of TGF-beta signaling and Wnt signaling using various cytokines and small molecule inhibitors (Lian et al. *Nat. Protoc.* 8:162-75 (2013); Fonoudi et al. *Stem Cells Transl. Med.* 4:1482-94 (2015)).

Direct cardiac reprogramming has emerged as a strategy to create new cardiomyocytes, leading to improved heart function following injury to the heart, such as from myocardial infarction (MI). Srivastava and DeWitt. *Cell* 166: 1386-96 (2016). Direct cardiac reprogramming involves conversion of cells into cardiomyocytes without induction of a pluripotent phenotype. In one application of direct cardiac reprogramming, resident support cells within damaged organs are converted into the desired cell type in situ. For example, a combination of three cardiac developmental transcription factors—GATA4, MEF2C, and TBX5 (GMT)—can be used to reprogram dermal or cardiac fibroblasts to iCM-like cells in mice. Ieda et al. *Cell.* 142:375-86 (2010).

Various other combinations of genetic, as well as chemical approaches, to convert fibroblasts to cardiac progenitor or cardiomyocyte state have been proposed. HAND2, NKX2.5, JAK or TGF-β enhance such reprogramming. GATA4, MEF2C, TBX5, MESP1, and MYOCD (GMTMM) when expressed together as a cocktail of factors change cell morphology from a spindle-like shape to a rod-like shape and causes cells to exhibit spontaneous $Ca^{2+}$ oscillation. In humans, supplementation of GMT with ETS2 and MESP1 induces cardiac-specific gene expression and sarcomere formation. Other combinations of factors for direct reprogramming are known.

SUMMARY OF THE DISCLOSURE

There remains a long-felt and unmet need for compositions and methods for generating induced cardiomyocyte cells and for the treatment of heart conditions (including heart injury, such as MI, congenic heart disease, heart disease associated with aging, and other heart failure). The present disclosure provides such compositions and methods, and more. Reprogramming factor cocktails for generating cardiomyocytes generally require the use of at least three reprogramming factors. The inventors have surprisingly found that MYOCD and either one of the factors ASCL1 and MYF6 achieve, in human cells, direct reprogramming of non-cardiomyocytes into cardiomyocytes. Embodiments of the disclosure include compositions and methods that use MYOCD and ASCL1 and/or MYF6, optionally with other factors, to directly reprogram non-cardiomyocytes (e.g., human cardiac fibroblasts) into cardiomyocytes. Advantageously, fewer than five factors are used to reprogram human cardiac fibroblasts into cardiomyocytes. Yet more advantageously, only two factors are used to reprogram human cardiac fibroblasts into cardiomyocytes.

The disclosure provides vectors comprising combinations of a MYOCD polynucleotide; an ASCL1 polynucleotide and/or a MYF6 polynucleotide; and, optionally, a MEF2C polynucleotide and/or a TBX5 polynucleotide. These protein-coding polynucleotides can be arranged in the vector in any 5' to 3' order and on the same or different polynucleotide strands within the vector. The disclosure further provides vector systems made up of more than one vector. Some vectors are polycistronic vectors—for example, 2A-linked polycistronic vectors, such as, without limitation, vectors comprising MYOCD-2A-ASCL1, ASCL1-2A-MYOCD, MYOCD-2A-MYF6, or MYF6-2A-MYOCD polynucleotides. In some cases, vector systems include a first polycistronic vector selected from the foregoing and a complementary second polycistronic vector providing MEF2C and TBX5 polynucleotides.

The vectors include viral and non-viral vectors, such as, without limitation, a lipid nanoparticle, a transposon, an adeno-associated virus (AAV) vector, an adenovirus, a retrovirus, an integrating lentiviral vector (LVV), and a non-integrating LVV. Each of the polynucleotides optionally share sequence identity to a native, human polynucleotide sequence for the corresponding gene, or have a heterologous sequence encoding a protein identical to or sharing sequence identity to the corresponding native, human protein. In some embodiments, the MYOCD encoded by the MYOCD polynucleotide is an engineered myocardin. For example, myocardin may be engineered to include an internal deletion that reduces its size but preserves its function.

The disclosure further provides methods of using the foregoing vectors and vector systems. Methods of use include methods of inducing a cardiomyocyte phenotype in differentiated cells (in vivo or in vitro) and methods of treating a heart condition in a subject suffering from, or at risk for, a heart condition. In some embodiments, the method of inducing a cardiomyocyte phenotype converts a non-cardiomyocyte cell into an induced cardiomyocyte cell. The methods of the disclosure further include methods of converting a non-cardiomyocyte cell into an induced cardiomyocyte cell. In some embodiments, the non-cardiomyocyte cell is a differentiated non-cardiomyocyte cell. In some embodiments, the non-cardiomyocyte cell is a non-cardiomyocyte cardiac cell, or cardiac fibrolast cell. Cardiomyocyte phenotype may be defined by increased expression of cTnT and/or α-actinin, or by expression of other markers for cardiomycote phenotype known in the art or prospectively indentified. The disclosure further provides kits comprising vectors and vector systems with instructions for use in treating a heart condition.

In an aspect, the disclosure provides a vector, comprising a MYOCD polynucleotide and either or both of an ASCL1 polynucleotide or a MYF6 polynucleotide; each polynucleotide operatively linked to at least one promoter. In some embodiments, vector comprises a MYOCD polynucleotide and an ASCL1 polynucleotide. In some embodiments, the vector comprises a MYOCD polynucleotide and a MYF6 polynucleotide. In some embodiments, the vector comprises a MYOCD polynucleotide; either or both of a MEF2C polynucleotide and a TBX5 polynucleotide; and either or both of an ASCL1 polynucleotide and a MYF6 polynucleotide. In some embodiments, the vector comprises a MYOCD polynucleotide, an ASCL1 polynucleotide, a MEF2C polynucleotide, and a TBX5 polynucleotide. In some embodiments, the vector comprises a MYOCD polynucleotide, a MYF6 polynucleotide, a MEF2C polynucleotide, and a TBX5 polynucleotide. In some embodiments, the MYOCD is an engineered myocardin. In some embodiments, the vector comprises no reprogramming factor polynucleotide other than a MYOCD polynucleotide, an ASCL1 polynucleotide, a MYF6 polynucleotide, a MEF2C polynucleotide, or a TBX5 polynucleotide. In some embodiments, the vector comprises no other other protein-coding gene. In some embodiments, the vector is a polycistronic vector. In some embodiments, the vector is a viral vector. In some embodiments, the vector is an AAV vector. In some embodiments, n the vector is lentiviral vector. In some embodiments, the ASCL1 polynucleotide, if present, or the MYF6 polynucleotide, if present, and the MYOCD polynucleotide are operatively linked to the same promoter and are co-translationally expressed. In some embodiments, the vector comprises a MYOCD-2A-ASCL1 polynucleotide or an ASCL1-2A-MYOCD polynucleotide, operatively linked to a single promoter. In some embodiments, the vector comprises a MYOCD-2A-MYF6 polynucleotide or an ASCL1-2A-MYF6 polynucleotide, operatively linked to a single promoter.

In some embodiments, the MYOCD polynucleotide comprises the nucleotide sequence of human MYOCD (SEQ ID NO: 4) or a codon variant thereof. In some embodiments, the MYOCD polynucleotide shares at least 90%, 95%, 96%, 97%, 98%, 99%, or 100% identity to the nucleotide sequence of human MYOCD (SEQ ID NO: 4). In some embodiments, the MYOCD polynucleotide encodes human MYOCD (SEQ ID NO: 3) or a functional variant thereof. In some embodiments, the MYOCD polynucleotide encodes a polypeptide that shares at least 90%, 95%, 96%, 97%, 98%, 99%, or 100% identity to human MYOCD (SEQ ID NO: 3). In some embodiments, the MYOCD polynucleotide comprises the nucleotide sequence of MyΔ3 (SEQ ID NO: 72) or a codon variant thereof. In some embodiments, the MYOCD polynucleotide shares at least 90%, 95%, 96%, 97%, 98%, 99%, or 100% identity to the nucleotide sequence of MyΔ3 (SEQ ID NO: 72). In some embodiments, the MYOCD polynucleotide encodes MyΔ3 (SEQ ID NO: 16) or a functional variant thereof. In some embodiments, the MYOCD polynucleotide encodes a polypeptide that shares at least 90%, 95%, 96%, 97%, 98%, 99%, or 100% identity to MyΔ3 (SEQ ID NO: 16) or a codon variant thereof. In some embodiments, the ASCL1 polynucleotide comprises the nucleotide sequence of human ASCL1 (SEQ ID NO: 2) or a codon variant thereof. In some embodiments, the ASCL1 polynucleotide shares at least 90%, 95%, 96%, 97%, 98%, 99%, or 100% identity to the nucleotide sequence of human ASCL1 (SEQ ID NO: 2) or a codon variant thereof. In some embodiments, the ASCL1 polynucleotide encodes a polypeptide that shares at least 90%, 95%, 96%, 97%, 98%, 99%, or 100% identity to human ASCL1 (SEQ ID NO: 1). In some embodiments, the ASCL1 polynucleotide encodes human ASCL1 (SEQ ID NO: 1). In some embodiments, the MYF6 polynucleotide shares at least 90%, 95%, 96%, 97%, 98%, 99%, or 100% identity to the nucleotide sequence of human MYF6 (SEQ ID NO: 56).

In some embodiments, the vector comprises an expression cassette, the expression cassette comprising: the MYOCD polynucleotide, wherein the MYOCD polynucleotide comprises MyΔ3 (SEQ ID NO: 72) or a codon variant thereof, and/or encodes MyΔ3 (SEQ ID NO: 16) or a functional variant thereof, the MYOCD polynucleotide operatively linked to a first promoter; and the ASCL1 polynucleotide, wherein the ASCL1 polynucleotide comprises ASCL1 (SEQ ID NO: 2) or a codon variant thereof, and/or encodes ASCL1 (SEQ ID NO: 1) or a functional variant thereof, the ASCL1 polynucleotide operatively linked to a second promoter.

In some embodiments, the first promoter shares at least 90%, 95%, 96%, 97%, 98%, 99%, or 100% identity to a CAG promoter (SEQ ID NO: 67) and/or the second promoter shares at least 90%, 95%, 96%, 97%, 98%, 99%, or 100% identity to a SCP promoter (SEQ ID NO: 68).

In some embodiments, the vector comprises an expression cassette, the expression cassette comprising a MYOCD-2A-ASCL1 polynucleotide, operatively linked to a single promoter.

In some embodiments, the MYOCD-2A-ASCL1 polynucleotide comprises SEQ ID NO: 37 or a codon variant thereof. In some embodiments, the MYOCD-2A-ASCL1 polynucleotide shares at least 90%, 95%, 96%, 97%, 98%, 99%, or 100% identity to SEQ ID NO: 37.

In some embodiments, the MYOCD-2A-ASCL1 polynucleotide encodes SEQ ID NO: 59 or a functional variant thereof. In some embodiments, the MYOCD-2A-ASCL1 polynucleotide encodes a polypeptide that shares at least 90%, 95%, 96%, 97%, 98%, 99%, or 100% identity to SEQ ID NO: 59. In some embodiments, the expression cassette comprises one or more of an SV40 intron (SEQ ID NO: 73), a short polyA signal (SEQ ID NO: 74) and a WPRE (SEQ ID NO: 75).

In some embodiments, the expression cassette is flanked by inverted terminal repeats, optionally AAV2 ITRs (SEQ ID NO: 76). In some embodiments, the vector comprises an AAV5 capsid protein, optionally comprising SEQ ID NO: 71 or a functional variant thereof. In some embodiments, the vector is capable of reprogramming differentiated cells into induced cardiomyocyte (iCM) cells. In some embodiments, at least 2.5%, at least 5%, at least 10%, at least 15%, or at least 20% of iCM cells are α-actinin positive. In some embodiments, at least 2%, at least 5%, or at least 8% of iCM cells are cTnT positive.

In another aspect, the disclosure provides a vector system, comprising a first vector encoding a MYOCD polynucleotide and either or both of an ASCL1 polynucleotide or a MYF6 polynucleotide; and a second vector comprising a MEF2C polynucleotide and a TBX5 polynucleotide. In some embodiments, the first vector comprises a MYOCD-2A-ASCL1 polynucleotide or an ASCL1-2A-MYOCD polynucleotide. In some embodiments, the first vector comprises a MYOCD-2A-MYF6 polynucleotide or an ASCL1-2A-MYF6 polynucleotide. In some embodiments, vector system the vector system comprises a first vector encoding a MYOCD polynucleotide and a second vector encoding an ASCL1 polynucleotide or a MYF6 polynucleotide.

In some embodiments, the first vector and the second vector are each independently selected from a lipid nanoparticle, a transposon, an adeno-associated virus (AAV) vector, an adenovirus, a retrovirus, an integrating lentiviral vector (LVV), and a non-integrating LVV.

In some embodiments, the ASCL1 polynucleotide shares at least 90%, 95%, 96%, 97%, 98%, 99%, or 100% identity to the nucleotide sequence of human ASCL1 (SEQ ID NO: 2).

In some embodiments, the MYOCD polynucleotide encodes human MYOCD (SEQ ID NO: 3) or a functional variant thereof or MyΔ3 (SEQ ID NO: 16) or a functional variant thereof.

In another aspect, the disclosure provides method of inducing a cardiomyocyte phenotype in differentiated cells, comprising contacting the differentiated cells with a vector or vector system of the disclosure. In some embodiments, the differentiated cells are cardiac fibroblast cells. In some embodiments, the differentiated cells are in vitro cells during the contacting step. In some embodiments, the differentiated cells are in vivo cells in a subject suffering from or at risk for a heart condition.

In another aspect, the disclosure provides a method of treating a heart condition in a subject suffering from or at risk for the heart condition, comprising contacting the differentiated cells in vitro with a vector or vector system to generate iCM cells, and administering the iCM cells to the subject. In some embodiments, the heart condition is dilated cardiomyopathy.

In another aspect, the disclosure provides a method of treating a heart condition in a subject suffering from or at risk for a heart condition, comprising administering the a vector or vector system of the disclosure to the subject. In some embodiments, the heart condition is a myocardiac infarction. In some embodiments, the heart condition is an acute myocardiac infarction.

In some embodiments the heart condition is a heart failure. In some embodiments, the heart condition is a chronic ischemic heart failure.

In another aspect, the disclosure provides a kit comprising a vector or vector system of the disclosure, and instructions for use in treating a heart condition.

In another aspect, the disclosure provides a method of converting a differentiated non-cardiomycyte cell into a cardiomyocyte, comprising comprising contacting the differentiated cells with a vector or vector system of the disclosure. In some embodiments, the differentiated non-cardiomycyte cell is a differentiated non-cardiomycyte cell. In some embodiments, the differentiated non-cardiomycyte cell is a human differentiated non-cardiomycyte cell. In some embodiments, the differentiated non-cardiomycyte cell is an in vivo differentiated non-cardiomycyte cell. In some embodiments, the differentiated non-cardiomycyte cell is an in vitro differentiated non-cardiomycyte cell. In some embodiments, the differentiated non-cardiomycyte cell is a cardiac cell.

Furthermore, there also remains a long-felt and unmet need for compositions and methods for generating induced cardiomyocyte cells and for the treatment of heart injury, such as MI. The present disclosure provides such compositions and methods, and more.

Myocardin has the domain architecture depicted in FIG. 9A. The present inventors have discovered that the myocardin protein retains its function when an internal deletion is made, such as an internal deletion between the SAP domain and the TAD domain. The second Gata4 interaction domain is dispensable for function in some cases. The leucine zipper (LZ) domain within the second Gata4 internation domain is deleted in some embodiments, although some embodiments retain this LZ domain. Moreover, the present inventors have discovered that some embodiments of mycocardin with an internal deletion have increased potency compared to full-length myocardin.

Various embodiments of the functional engineered myocardin proteins are depicted in FIGS. 9B-9D. This disclosure provides these engineered myocardin proteins and others, isolated polynucleotides encoding such engineered myocardin proteins and others, vectors for delivering such polynucleotides alone or in combination with other nucleic acids, and methods of using such polynucleotides and vectors for gene therapy, cellular reprogramming, and other uses. Also provided are kits, pharmaceutical compositions, compositions for use, and other useful embodiments of the present invention.

In one aspect, the disclosure provides an isolated polynucleotide, comprising an engineered MYOCD polynucleotide encoding an engineered myocardin protein having a length of at most 850 amino acids, wherein the engineered myocardin protein comprises an SRF interaction domain, an SAP domain, and a TAD domain.

In some embodiments, the engineered myocardin protein comprises an Mef2c interaction domain. In some embodiments, the Mef2c interaction domain shares at least 85% identity to SEQ ID NO: 17, the SRF domain shares at least 85% identity to SEQ ID NO: 18, the SAP domain shares at least 85% identity to SEQ ID NO: 19, and the TAD domain shares at least 85% identity to SEQ ID NO: 11. In some embodiments, the engineered myocardin protein comprises an LZ domain. In some embodiments, the LZ domain shares at least 85% identity to SEQ ID NO: 20.

In some embodiments, the engineered myocardin protein comprises a first polypeptide that shares at least 85% identity to residues 5-413 of human myocardin (SEQ ID NO: 10), and second polypeptide that shares at least 85% identity to residues 764-986 of human myocardin (SEQ ID NO: 11), wherein the first polypeptide and the second polypeptide are linked by a linker comprising a peptide bond or a polypeptide linker of 1-50 amino acid residues.

In some embodiments, the engineered myocardin protein comprises a first polypeptide that shares at least 85% identity to residues 5-438 of human myocardin (SEQ ID NO: 12), and second polypeptide that shares at least 85% identity to residues 764-938 of human myocardin (SEQ ID NO: 11), wherein the first polypeptide and the second polypeptide are linked by a linker comprising a peptide bond or a polypeptide linker of 1-50 amino acid residues.

In some embodiments, the engineered myocardin protein comprises a first polypeptide that shares at least 85% identity to residues 5-559 of human myocardin (SEQ ID NO: 13), and second polypeptide that shares at least 85% identity to residues 764-938 of human myocardin (SEQ ID NO: 11), wherein the first polypeptide and the second polypeptide are linked by a linker comprising a peptide bond or a polypeptide linker of 1-50 amino acid residues.

In some embodiments, the linker consists of a peptide bond. In some embodiments, the linker is a polypeptide selected from G, GG, GGG, GSG, GSS, GGS, GGSGGS (SEQ ID NO: 30), GSSGGS (SEQ ID NO: 31), GGSGSS (SEQ ID NO: 32), GGSGGSGGS (SEQ ID NO: 33), GGSGGSGGSGGS (SEQ ID NO: 34).

In some embodiments, the engineered myocardin protein comprises a sequence selected from SEQ ID NOs: 14-16.

In another aspect, the disclosure provides an isolated polynucleotide, comprising an engineered MYOCD polynucleotide encoding an engineered myocardin protein, wherein the engineered myocardin protein comprises a deletion of at least 50 amino acids in the region corresponding to amino acids 414-764 of the native mycocardin (SEQ ID NO: 3).

In some embodiments, the engineered myocardin protein comprises a deletion of amino acids from about 414 to about 763 of the native mycocardin (SEQ ID NO: 3).

In some embodiments, the engineered myocardin protein comprises a sequence at least 85% identical to SEQ ID NO: 14. In some embodiments, the engineered myocardin protein consists of sequence identical to SEQ ID NO: 14. In some embodiments, the engineered myocardin protein comprises a deletion of amino acids from about 439 to about 763 of the native mycocardin (SEQ ID NO: 3).

In some embodiments, the engineered myocardin protein comprises a sequence at least 85% identical to SEQ ID NO: 15. In some embodiments, the engineered myocardin protein consists of sequence identical to SEQ ID NO: 15. In some embodiments, the engineered myocardin protein comprises a deletion of amino acids from about 560 to about 763 of the native mycocardin (SEQ ID NO: 3).

In some embodiments, the engineered myocardin protein comprises a sequence at least 85% identical to SEQ ID NO: 16. In some embodiments, the engineered myocardin protein consists of sequence identical to SEQ ID NO: 16. In some embodiments, the engineered myocardin protein is a functional engineered myocardin protein.

In some embodiments, the functional engineered myocardin protein is expressed at at least 10% of the level of native MYOCD in the same expression system. In some embodiments, the functional engineered myocardin protein is capable of inducing increased expression of at least one marker of cardiomycote phenotype either (a) when expressed in human cardiac fibroblasts with MEF2C and TBX5 or TBX5 in the presence of a TGFβ inhibitor, optionally SB431542, and a Wnt inhibitor, optionally XAV939, or (b) when expressed in human cardiac fibroblasts with ASCL1.

In some embodiments, the polynucleotide is operatively linked to a promoter. In some embodiments, the polynucleotide comprises a MEF2C polynucleotide and a TBX5 polynucleotide.

In some embodiments, the polynucleotide comprises an TBX5 polynucleotide. In some embodiments, the polynucleotide comprises an ASCL1 polynucleotide. In some embodiments, the polynucleotide is flanked by inverted terminal repeats (ITRs) or the polynucleotide is flanked by long terminal repeats (LTRs).

In another aspect, the disclosure provides a recombinant virus comprising any of the polynucleotides of the disclosure. In an embodiment, the recombinant virus is a recombinant adeno-associated virus (rAAV). In some embodiments, the recombinant virus is a lentivirus.

In another aspect, the disclosure provides a population of cells comprising any of the polynucleotides of the disclosure.

In some embodiments, the percentage of cells in the population that exhibit calcium transients (CaT) in an in vitro CaT assay is at least 2-fold greater than the percentage of cells in a control population of cells not comprising the polynucleotide in the same in vitro CaT assay.

In another aspect, the disclosure provides an induced cardiomyocyte (iCM), wherein the iCM comprises any of the polynucleotides of the disclosure.

In another aspect, the disclosure provides a pharmaceutical composition comprising any of the polynucleotides of the disclosure and a non-viral delivery system.

In another aspect, the disclosure provides a pharmaceutical composition comprising any of the recombinant viruses of the disclosure.

In another aspect, the disclosure provides a method of generating an induced cardiomyocyte (iCM), comprising contacting a mammalian fibroblast with a polynucleotide of the disclosure, a recombinant virus of the disclosure, or pharmaceutical composition of the disclosure.

In another aspect, the disclosure provides a method of treating a heart condition in a subject, comprising administering a pharmaceutical composition of the disclosure.

In some embodiments, the recombinant virus is administered via intracardiac catheterization. In some embodiments, the recombinant virus is administered via intracardiac injection. In another aspect, the disclosure provides a recombinant adeno-associated virus (rAAV), comprising an expression cassette (as depicted in FIG. 13B or FIG. 13C), wherein the expression cassette comprises in 5' to 3' order a 5' inverted terminal repeat (ITR), a CAG promoter, an SV40 intron, a polynucleotide encoding one or more proteins, a short polyadenylation signal, and a 3' ITR, and wherein the polynucleotide encoding one or more proteins comprises in 5' to 3' order a polynucleotide encoding MyΔ3, a polynucleotide encoding a P2A linker, and a polynucleotide encoding ASCL1.

In some embodiments, the expression cassette comprises a WPRE. In some embodiments, the MyΔ3 comprises SEQ ID NO: 16. In some embodiments, the 2A linker comprises ATNFSLLKQAGDVEENPGP (SEQ ID NO: 23). In some embodiments, the ASCL1 comprises SEQ ID NO: 1. In some embodiments, the rAAV comprises a polynucleotide at least 95% identical to SEQ ID NO: 35 (MyΔ3A AAV).

In another aspect, the disclosure provides a pharmaceutical composition comprises a rAAV of the disclosure.

In another aspect, the disclosure provides a method of treating a heart condition in a subject, comprising administering a pharmaceutical composition of the disclosure.

These aspects and other features and advantages of the invention are described below in more detail. Those skilled in the art will recognize, or be able to ascertain using no more than routine experimentation, many equivalents to the specific embodiments of the invention described herein. Such equivalents are intended to be encompassed by the following disclosure and claims.

BRIEF DESCRIPTION OF FIGURES

FIG. 1A shows a schematic of the screening strategy for activators of MyMT- or MyMT+SB/XAV mediated human cardiac reprogramming in a human cardiac fibroblast (HCF) cell line. My: MYOCD, M: MEF2C, T: TBX5, SB: SB431542, XAV: XAV-939. FIG. 1B shows six enhancers (ASCL1, DLX3, DLX6, GATA2. GATA5 and MYF6) of human cardiac reprogramming identified from the screen. The graph shows the fold change of α-actinin positive cells from each reprogramming combination relative to the activity of MyMT+SB/XAV. FIG. 1C shows cardiac gene expression analysis for reprogrammed cells. Adult human cardiac fibroblasts (AHCFs) were infected with retroviruses that encoded different reprogramming factors as indicated in the graph. Reprogrammed cells were cultured for 3 weeks. The transcript levels of cardiac marker genes (MYH6, TNNT2, TNNC1, NPPA, TNNI3 and RYR2) were determined by q-PCR.

FIG. 2A-FIG. 2D illustrate ASCL1 and MYF6 enhance cardiac reprogramming in both adult human and pig cardiac fibroblasts. FIG. 2A and FIG. 2B show representative immunocytochemistry images (FIG. 2A) and analyses (FIG. 2B) of reprogrammed adult human cardiac fibroblasts (APCFs) 3 weeks post-infection with indicated retroviruses. Two cardiac proteins α-actinin (upper row) and cTnT (lower row) were used as markers to quantify reprogramming efficiency. The red fluorescent signal is indicative of protein expression in both cases. DAPI was used to stain nuclei (blue). FIG. 2C and FIG. 2D show representative immunocytochemistry images (FIG. 2C) and analyses (FIG. 2D) of reprogrammed adult pig cardiac fibroblasts (AHPFs) 3 weeks post-infection with indicated retroviruses. Two cardiac proteins α-actinin (upper row, red) and cTnT (lower row, red) were used as markers to qualify reprogramming efficiency. DAPI of the nucelei staining is shown (blue).

FIG. 3A-FIG. 3D show representative immunocytochemistry images (FIG. 3A-3D) and analyses (FIG. 3E) to show dose responses of reprogramming factors. AHCFs were infected with indicated retroviruses and were cultured for 3 weeks before immunostaining. Two cardiac proteins α-actinin (upper row, red) and cTnT (lower row, red) were used as markers to qualify reprogramming efficiency. DAPI (blue).

FIG. 4A-FIG. 4B show representative immunocytochemistry images (FIG. 4A) and analyses (FIG. 4B) to determine the optimal combination of two-in-one polycistronic vectors for cardiac reprogramming. AHCFs were infected with indicated retroviruses and were cultured for 3 weeks before immunostaining. Two cardiac proteins α-actinin (up, red) and cTnT (down, red) were used as markers to qualify reprogramming efficiency. DAPI (blue). FIG. 4C shows cardiac gene expression analysis for reprogrammed cells by different combination of two-in-one polycistronic vectors. AHCFs were infected with indicated retroviruses and were cultured for 3 weeks before RNA extraction. The transcript levels of cardiac markers were determined by q-PCR.

FIG. 5A-FIG. 5B show representative immunocytochemistry images (FIG. 5A) and analyses (FIG. 5B) of AHCFs 3 weeks post-infection with GFP, My+A+M+T or My+A retroviruses to show that My+A are enough to induce cardiac reprogramming in human fibroblasts. α-actinin (up, red), cTnT (down, red), DAPI (blue). FIG. 5C-FIG. 5D show representative immunocytochemistry images (FIG. 5C) and analyses (FIG. 5D) of AHCFs 3 weeks post-infection with GFP, My+A+ M+T, My–P2A–A and A–P2A–My retroviruses to show that a single polycistronic vector is enough to induce cardiac reprogramming in human fibroblasts. α-actinin (up, red), cTnT (down, red), DAPI (blue).

FIG. 6A-FIG. 6B show representative immunocytochemistry analyses (FIG. 6A) and images (FIG. 6B) of AHCFs 3 weeks post-infection with GFP and 24 different four-in-one polycistronic retroviruses. α-actinin (up, red), cTnT (down, red), DAPI (blue). FIG. 6C shows a factor position score matrix showing different reprogramming factors prefer different positions in the four-in-one polycistronic vector.

FIG. 7A shows a schematic of an in vivo study of different reprogramming cocktails to repair mouse heart after myocardial infarction. Mice were subjected to myocardial infarction (MI) ligation followed by intramyocardial injection of GFP, ASCL1, MyMT, MyMTA or MyA retroviruses. Reprogramming factors were in a separate virus. Cardiac function was evaluated at various time points by echocardiography. FIG. 7B-FIG. 7D show ejection fraction (FIG. 7B), end systolic volume (FIG. 7C), and end diastolic volume (FIG. 7D), of the left ventricle as quantified by echocardiography at various time points shown. MyMT, MyMTA or MyA improved cardiac function after MI. (n=11-13 for each group. n.s. $p>0.05$; *$p<0.05$; $p<0.01$; *$p<0.001$; ****$p<0.0001$).

FIG. 8A shows the design of a non-integrating lentiviral (NIL) construct encoding native myocardin (MYOCD) and Achaete-scute homolog 1 (ASCL1) proteins. FIG. 8B shows the design of an AAV construct encoding native MYOCD and ASCL1 proteins. FIG. 8C shows expression of MYOCD from the NIL construct compared to expression from a monocistronic NIL construct encoding MYOCD alone. FIG. 8D shows expression of MYOCD from the AAV construct compared to expression from a monocistronic AAV construct encoding MYOCD alone. FIG. 8E shows percentage of α-actinin positive cells after transduction with bicistronic AAV or NIL.

FIG. 13A shows MyA ΔWPRE short A. FIG. 13B shows MyΔ3A ΔWPRE short A. FIG. 13C shows MyΔ3A WPRE short A.

FIG. 17A shows a schematic of the construct design for bicistronic AAV5:MyΔ3A. FIG. 17B shows that bicistronic AAV5: MyΔ3/A improves ejection fraction in a mouse model of myocardial infarction (MI). Mice MI model was generated by ligation of the left anterior descending (LAD) artery. AAV5:GFP or AAV5: MyΔ3/A (delivered in a single viral vector in which MyΔ3 and ASCL1 transcripts were driven from separate promoters (CAG and SCP)) at a dose of $1.2 \times 10^{11}$ genome copies (GC) was intramyocardially injected to animals minutes after the ligation procedure. Cardiac function (ejection fraction) was evaluated by echocardiography at 2, 4 and 7 weeks post-MI. Imaging revealed that mice injected with AAV5:MyΔ3A showed a statistically significant improvement in ejection fraction compared to the mice injected with AAV5:GFP at 4 and 7 weeks post-MI. (n=6-13 for each group. **p<0.01).

FIG. 18A shows a schematic of the construct design for monocistronic AAV5:MyΔ3A. AAV5: MyΔ3A improves ejection fraction in a rat model of myocardial infarction (MI). Hank's Balanced Salt Solution (HBSS) or AAV5:MyΔ3A at dose $1.2 \times 10^{11}$ GC (MyΔ3 and ASCL1 were expressed from a single transcript driven by the CAG promoter with the coding sequences separated by a P2A peptide) was delivered by intramyocardial injection immediately after permanent coronary ligation. Heart function was followed up by echocardiography every two weeks until 8 weeks post-MI. Imaging revealed cardiac function (ejection fraction) in rats injected with vehicle (HBSS) continued to decline after MI. Rats injected with AAV5: MyΔ3A showed a statistically significant improvement in ejection fraction 4-8 weeks post-MI. (n=8 for each group. *p<0.05 ***p<0.001).

FIG. 19A shows heart function in treated (AAV5:MyΔ3A) and vehicle control (HBSS) groups assessed by echocardiography every two weeks until 10 weeks post-MI. Echocardiography revealed that cardiac function in rats injected with vehicle (HBSS) continued to decline after MI. AAV5:MyΔ3A halted this decline in heart function. FIG. 19B shows that AAV5:MyΔ3A treatment caused a statistically significant improvement in ejection fraction 6-10 weeks post-MI compared to animals with vehicle. (n=10 for each group. *p<0.05 **p<0.01).

DETAILED DESCRIPTION

Figure 1A:
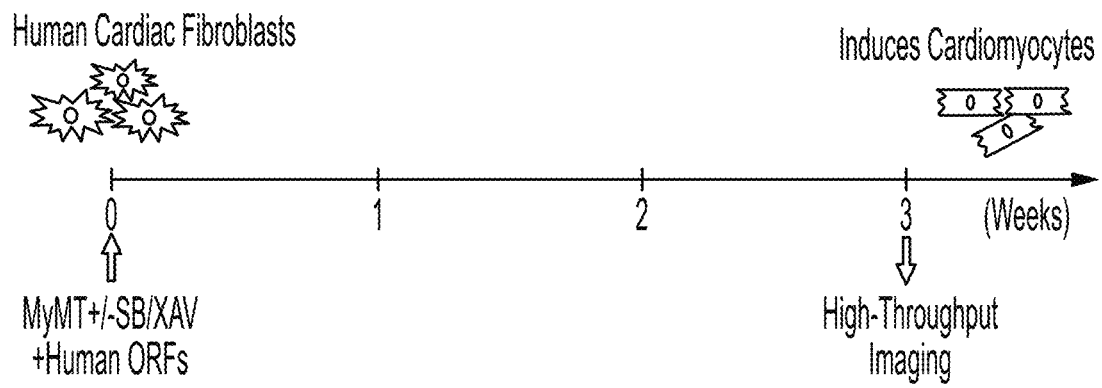
FIG. 1A-FIG. 1C illustrate identification of enhancers of human cardiac reprogramming from a human ORF cDNA screen.

There remains a long-felt and unmet need for compositions and methods suited for, without limitation, generating induced cardiomyocyte cells; direct reprogramming of cardiac fibroblasts into cardiomyocytes, preferably in vivo; treatment of various forms of heart failure, preferably dilated cardiomyopathy; and treatment of heart injury, such as MI. The present disclosure provides such compositions and methods, and more.

The present disclosure provides methods and compositions relation to the generation of induced cardiomyocyte (iCM) cells (in vivo, in vitro, or ex vivo) by reprogramming other cell types. In particular, the present inventors have discovered that differentiated cells, for example, fibroblasts, can be reprogrammed into cardiomyocytes by expression of Achaete-scute homolog 1 (ASCL1) and/or Myogenic Factor 6 (MYF6). ASCL1 is known primarily for its role in nervous system, neuronal, and neuroendocrine development. Mao et al. Functional and Physical Interactions between Mammalian Achaete-Scute Homolog 1 and Myocyte Enhancer Factor 2A. *J. Bio. Chem.* 271:14371-75 (1996); Borges et al. An achaete-scute homologue essential for neuroendocrine differentiation in the lung. *Nature*. 386 (6627):852-55 (1997). In the context of cellular reprogramming, ASCL1 is known in the art as a factor associated with conversion of nonneuronal cells into functional neurons. Chanda et al. Generation of Induced Neuronal Cells by the Single Reprogramming Factor ASCL1. *Stem Cell Report* 3:282-96 (2014); Wapinski et al. Rapid Chromatin Switch in the Direct Reprogramming of Fibroblasts to Neurons. *Cell Reports* 20:3236-47 (2017); Wapinski et al. Hierarchical mechanisms for transcription factor-mediated reprogramming of fibroblasts to neurons. *Cell* 155:621-35 (2013). Indeed, expression of ASCL1 in conjunction with other reprogramming factors has been used in the art to convert human-induced pluripotent stem cells (hiPSCs) from a cardiomyocyte phenotype to a neuronal (Tuj1+cTnT−) or neuronal-like phenotype (Tuj1+ cTnT+)—a contrary effect of reprogramming cardiomyocytes. Chuang et al. Partial Reprogramming of Pluripotent Stem Cell-Derived Cardiomyocytes into Neurons. *Sci Rep.* 7:44840 (2017). In contrast, the present disclosure provides compositions and methods from generating induced cardiomyocyte (iCM) cells from fibroblasts using ASCL1.

MYF6 is a myogenic factor associated with muscle differentiation. It induces fibroblasts to differentiate into myoblasts, and mutations in MYF6 are associated with congenital muscle disease. There is no suggestion that MYF6 is involved in cardiomyocyte differentiation. In contrast, the present disclosure provides compositions and methods from generating induced cardiomyocyte (iCM) cells using MYF6.

Furthermore, the present disclosure provides polynucleotides encoding engineered myocardin proteins with an internal deletion, engineered myocardin proteins with an internal deletion, and methods of use thereof. The present disclosure provides vectors comprising such polynucleotides and, in some embodiments, one or more additional nucleic acids encoding other proteins. The disclosed polynucleotides are useful, for example, for transduction of mammalian fibroblasts with polycistronic adeno-associated virus (AAV) vectors to generate induced cardiomyocytes. The present disclosure further provides methods and compositions relation to the generation of induced cardiomyocyte (iCM) cells by reprogramming of other cell types. In particular, the present inventors have discovered that differentiated cells, for example, fibroblasts, can be reprogrammed into induced cardiomyocytes by expression of Achaete-scute homolog 1 (ASCL1); that co-expression of myocardin (MYOCD) with ASCL1 is effective for such reprogramming; that engineered myocardin proteins with an internal deletion in some embodiments enhance the function of the vector in gene expression, reprogramming, or other functions, or at least retain the same level of function as vectors with the native myocardin protein. Some embodiments of AAV vectors encoding such an engineered myocardin and ASCL1 are surprisingly improved compared to AAV vector encoding native myocardin and ASCL1. Other disclosed embodiments include, without limitation, retroviral (e.g., lentiviral) vectors, vectors for co-expression of engineered myocardin with other factors in addition to or instead of ASCL1, non-viral delivery of the polynucleotides of the disclosure, in vivo and ex vivo methods of applying these embodiments, and compositions and methods for treatment of heart disease, including methods involving administration of one or more vectors and, in some embodiments, one or more small molecules. The invention is limited only by the claims, and the following detailed description provides diverse embodiments beyond those described in this paragraph.

In an aspect, the disclosure relates to engineered variants of myocardin (MYOCD). MYOCD is a large, polyfunctional transcription factor. In addition to showing that expression of ASCL1 in combination with MYOCD was sufficient to induce a cardiomyocyte phenotype in mammalian fibroblasts with or without other reprogramming factors the present inventors recognized that a viral vector encoding ASCL1 and MYOCD generates induced cardiomyocotes. The disclosure provide viral vectors that encode both MYOCD and ASCL1, including, for example, lentiviral and AAV vectors. The present inventors further recognized that the lentiviral vectors of disclosure, in some embodiments, induced cardiomycotes more effectively that the AAV vectors of the disclosure.

The present inventors also surprisingly find that MYOCD comprising an internal deletion retains the expression and function of myocardin and MYOCD comprising an internal deletion can be used alone or in combination with other reprogramming factors (e.g., for generating cardiomyocytes from fibroblasts); and furthermore that viral vectors comprising such engineered MYOCD were, in some embodiments, as effective or more effective than viral vectors comprising the native MYOCD. The present disclosure therefore also provides various engineered MYOCD polynucleotides, viral vectors, gene delivery systems, and method of use thereof.

I. Definitions

As used herein, the term "functional cardiomyocyte" refers to a differentiated cardiomyocyte that is able to send or receive electrical signals. In some embodiments, a cardiomyocyte is said to be a functional cardiomyocyte if it exhibits electrophysiological properties such as action potentials and/or $Ca^{2+}$ transients.

As used herein, a "differentiated non-cardiac cell" can refer to a cell that is not able to differentiate into all cell types of an adult organism (i.e., is not a pluripotent cell), and which is of a cellular lineage other than a cardiac lineage (e.g., a neuronal lineage or a connective tissue lineage). Differentiated cells include, but are not limited to, multipotent cells, oligopotent cells, unipotent cells, progenitor cells, and terminally differentiated cells. In particular embodiments, a less potent cell is considered "differentiated" in reference to a more potent cell.

As used herein, "protein-coding gene" means, when referring to a component of a vector, a polynucleotide that encodes a protein, other than a gene associated with the function of the vector. For example, the term protein-coding gene would encompass a polynucleotide encoding a human protein, or functional variant thereof, with reprogramming activity. It is intended that the phrase "the vector comprising no other protein-coding gene" in reference to a vector means that the vector comprises a polynucleotide(s) encoding the protein of interest(s) that is listed, but no polynucleotide encoding another protein that has reprogramming activity- such as other proteins known in the art to promote either a pluripotent or a cardiomyocyte phenotype. The phrase "the vector comprising no other protein-coding gene" does not exclude polynucleotides encoding proteins required for function of the vector, which optionally may be present, nor does the phrase exclude polynucleotides that do not encode proteins. Such vectors will include non-coding polynucleotide sequences and may include polynucleotides encoding RNA molecules (such as microRNAs). Conversely, when only certain protein-coding genes are listed, it is implied that other protein-coding genes may additionally be present, such as protein-coding genes that encode proteins that have reprogramming activity.further promote reprogramming.

A "somatic cell" is a cell forming the body of an organism. Somatic cells include cells making up organs, skin, blood, bones and connective tissue in an organism, but not germ cells.

The terms "cardiac pathology" or "cardiac dysfunction" are used interchangeably and refer to any impairment in the heart's pumping function. This includes, for example, impairments in contractility, impairments in the ability to relax (sometimes referred to as diastolic dysfunction), abnormal or improper functioning of the heart's valves, diseases of the heart muscle (sometimes referred to as cardiomyopathies), diseases such as angina pectoris, myocardial ischemia and/or infarction characterized by inadequate blood supply to the heart muscle, infiltrative diseases such as amyloidosis and hemochromatosis, global or regional hypertrophy (such as may occur in some kinds of cardiomyopathy or systemic hypertension), and abnormal communications between chambers of the heart.

As used herein, the term "cardiomyopathy" refers to any disease or dysfunction of the myocardium (heart muscle) in which the heart is abnormally enlarged, thickened and/or stiffened. As a result, the heart muscle's ability to pump blood is usually weakened. The etiology of the disease or disorder may be, for example, inflammatory, metabolic, toxic, infiltrative, fibroplastic, hematological, genetic, or unknown in origin. There are two general types of cardiomyopathies: ischemic (resulting from a lack of oxygen) and non-ischemic.

"Heart failure (HF) is a complex clinical syndrome that can result from any structural or functional cardiovascular disorder causing systemic perfusion inadequate to meet the body's metabolic demands without excessively increasing left ventricular filling pressures. It is characterized by specific symptoms, such as dyspnea and fatigue, and signs, such as fluid retention. As used herein, "chronic heart failure" or "congestive heart failure" or "CHF" refer, interchangeably, to an ongoing or persistent forms of heart failure. Common risk factors for CHF include old age, diabetes, high blood pressure and being overweight. CHF is broadly classified according to the systolic function of the left ventricle as HF with reduced or preserved ejection fraction (HFrEF and HFpEF). The term "heart failure" does not mean that the heart has stopped or is failing completely, but that it is weaker than is normal in a healthy person. In some cases, the condition can be mild, causing symptoms that may only be noticeable when exercising, in others, the condition may be more severe, causing symptoms that may be life-threatening, even while at rest. The most common symptoms of chronic heart failure include shortness of breath, tiredness, swelling of the legs and ankles, chest pain and a cough. In some embodiments, the methods of the disclosure decrease, prevent, or ameliorate one or more symptoms of CHF (e.g., HFrEF) in a subject suffering from or at risk for CHF (e.g., HFrEF). In some embodiments, the disclosure provides methods of treating CHF and conditions that can lead to CHF.

As used herein "acute heart failure" or "decompensated heart failure" refer, interchangeably, to a syndrome of the worsening of signs and symptoms reflecting an inability of the heart to pump blood at a rate commensurate to the needs of the body at normal filling pressure. AHF typically develops gradually over the course of days to weeks and then decompensates requiring urgent or emergent therapy due to the severity of these signs or symptoms. AHF may be the result of a primary disturbance in the systolic or diastolic function of the heart or of abnormal venous or arterial vasoconstriction, but generally represents an interaction of multiple factors, including volume overload. The majority of patients with AHF have decompensation of chronic heart failure (CHF) and consequently much of the discussion of the pathophysiology, presentation, and diagnosis of CHF is directly relevant to an understanding of AHF. In other cases, AHF results from an insult to the heart or an event that impairs heart function, such as an acute myocardial infarction, severe hypertension, damage to a heart valve, abnormal heart rhythms, inflammation or infection of the heart, toxins and medications. In some embodiments, the methods of the disclosure decrease, prevent, or ameliorate one or more symptoms of AHF in a subject suffering from or at risk for AHF. In some embodiments, the disclosure provides methods of treating AHF and conditions that can lead to AHF. AHF may be the result of ischemia associated with myocardial infarction.

In some embodiments, the methods of the disclosure (e.g., reprogramming therapy) treat one or more heart conditions (e.g. heart conditions that can lead to acute and chronic heart failure in some subjects). Illustrative conditions treatable according to the methods and compositions of the disclosure include acute myocardial infarction (MI), ischemic heart disease or ischemic cardiomyopathy (CM) (forms of chronic MI), dilated CM, hypertensive CM, familial CM, genetic CM, idiopathic CM, CM resulting from valvular heart disease, medication and toxin-induced CMs, CM due to myocarditis, and peripartum CM. In some embodiments, the compositions and methods disclosure herein treat congenital heart disease. In some embodiments, the methods of the disclosure comprise administering a composition (e.g. a viral vector) to a subject having, exhibiting symptoms of, or at risk for a conditions has progressed to heart failure or has yet to progress to heart failure. Reprogramming could be used either to treat or to prevent heart failure in patients with these conditions. Chronic heart failure due to all of these conditions fall into the general term "heart failure with reduced ejection fraction" (HFrEF).

As used herein, the term "gene of interest" refers to a reprogramming factor or to nucleic acid encoding the reprogramming factor. For example, when the reprogramming factor is a protein, the gene of interest is either—as apparent from context—a protein or the corresponding protein-coding polynucleotide sequence. Introduction, administration, or other use of gene of interest should be understood to refer to any means of increasing the expression of, or increasing the activity of, a gene, gene product, or functional variant of a gene product. Thus, in some embodiments, the disclosure provides methods of generating iCM cells comprising introducing a polynucleotide of interest, e.g. ASCL1 and/or MYF6, as a nucleic acid (e.g. deoxyribonucleotide (DNA) or ribonucleotide (RNA)) into a target cell as a polynucleotide (e.g. deoxyribonucleotide (DNA) or ribonucleotide (RNA)). The polynucleotide may be introduced into a cell in any of the various means known in the art, including without limitation in a viral, non-viral vector, by contacting the cell with naked polynucleotide or polynucleotide in complex with a transfection reagent, or by electroporation. Use of a gene of interest as a nucleic acid may also include indirect alteration of the expression or activity of the gene of interest, such as gene-editing of the locus encoding the endogenous gene, expression of transcription or regulatory factors, contacting cells with a small-molecule activator of the gene of interest, or use of gene-editing methods, including DNA- or RNA-based methods, to alter the expression or activity of the gene of interest as a nucleic acid. In some embodiments, the methods of the disclosure include de-repressing transcription of a gene of interest by editing regulatory regions (e.g. enhancers or promoters), altering splice sites, removing or inserting microRNA recognition sites, administering an antagomir to repress a microRNA, administering a microRNA mimetic, or any other various means of modulating expression or activity of the gene of interest.

As used herein, "gene product" means the product of expression of a polynucleotide sequence. For example, a protein-coding sequence is expressed by translation of the sequence into a protein gene product, or a RNA-coding sequence is expression by transcription of the DNA sequence into the corresponding RNA.

As used herein, the term "totipotent" means the ability of a cell to form all cell lineages of an organism. For example, in mammals, only the zygote and the first cleavage stage blastomeres are totipotent.

As used herein, the term "pluripotent" means the ability of a cell to form all lineages of the body or soma. For example, embryonic stem cells are a type of pluripotent stem cells that are able to form cells from each of the three germs layers, the ectoderm, the mesoderm, and the endoderm. Pluripotent cells can be recognized by their expression of markers such as Nanog and Rex1.

As used herein, the term "multipotent" refers to the ability of an adult stem cell to form multiple cell types of one lineage. For example, hematopoietic stem cells are capable of forming all cells of the blood cell lineage, e.g., lymphoid and myeloid cells.

As used herein, the term "oligopotent" refers to the ability of an adult stem cell to differentiate into only a few different cell types. For example, lymphoid or myeloid stem cells are capable of forming cells of either the lymphoid or myeloid lineages, respectively.

As used herein, the term "unipotent" means the ability of a cell to form a single cell type. For example, spermatogonial stem cells are only capable of forming sperm cells.

As used herein, the terms "subject" or "patient" refers to any animal, such as a domesticated animal, a zoo animal, or a human. The "subject" or "patient" can be a mammal like a dog, cat, horse, livestock, a zoo animal, or a human. The subject or patient can also be any domesticated animal such as a bird, a pet, or a farm animal. Specific examples of "subjects" and "patients" include, but are not limited to, individuals with a cardiac disease or disorder, and individuals with cardiac disorder-related characteristics or symptoms.

The practice of the present disclosure will employ, unless otherwise indicated, conventional techniques of tissue culture, immunology, molecular biology, cell biology and recombinant DNA, which are within the skill of the art. See, e.g., Sambrook and Russell eds. (2001) Molecular Cloning: A Laboratory Manual, $3^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, $5^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; IRL Press (1986) Immobilized Cells and Enzymes; Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, $3^{rd}$ edition (2002) Cold Spring Harbor Laboratory Press; Sohail (2004) Gene Silencing by RNA Interference: Technology and Application (CRC Press); Sell (2013) Stem Cells Handbook.

Unless the context indicates otherwise, it is specifically intended that the various features of the invention described herein can be used in any combination. Moreover, the disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

It must be noted that as used herein and in the appended claims, the singular forms "a", "an", and "the" include plural referents unless the context clearly dictates otherwise. Thus, for example, reference to "a cardiomyocyte" includes a plurality of cardiomyocytes.

Also as used herein, "and/or" refers to and encompasses any and all possible combinations of one or more of the associated listed items, as well as the lack of combinations when interpreted in the alternative ("or").

"Administration," "administering" and the like, when used in connection with a composition of the invention refer both to direct administration, which may be administration to non-cardiomyocytes in vitro, administration to non-cardiomyocytes in vivo, administration to a subject by a medical professional or by self-administration by the subject and/or to indirect administration, which may be the act of prescribing a composition of the invention. When used herein in reference to a cell, it refers to introducing a composition to the cell. Typically, an effective amount is administered, which amount can be determined by one of skill in the art. Any method of administration may be used. Small molecules may be administered to the cells by, for example, addition of the small molecules to the cell culture media or injection in vivo to the site of cardiac injury. Administration to a subject can be achieved by, for example, intravascular injection, intramyocardial delivery, and the like.

As used herein the term "cardiac cell" refers to any cell present in the heart that provides a cardiac function, such as heart contraction or blood supply, or otherwise serves to maintain the structure of the heart. Cardiac cells as used herein encompass cells that exist in the epicardium, myocardium or endocardium of the heart. Cardiac cells also include, for example, cardiac muscle cells or cardiomyocytes, and cells of the cardiac vasculatures, such as cells of a coronary artery or vein. Other non-limiting examples of cardiac cells include epithelial cells, endothelial cells, fibroblasts, cardiac stem or progenitor cells, cardiac conducting cells and cardiac pacemaking cells that constitute the cardiac muscle, blood vessels and cardiac cell supporting structure. Cardiac cells may be derived from stem cells, including, for example, embryonic stem cells or induced pluripotent stem cells.

The term "cardiomyocyte" or "cardiomyocytes" as used herein refers to sarcomere-containing striated muscle cells, naturally found in the mammalian heart, as opposed to skeletal muscle cells. Cardiomyocytes are characterized by the expression of specialized molecules e.g., proteins like myosin heavy chain, myosin light chain, cardiac α-actinin. The term "cardiomyocyte" as used herein is an umbrella term comprising any cardiomyocyte subpopulation or cardiomyocyte subtype, e.g., atrial, ventricular and pacemaker cardiomyocytes.

The term "cardiomyocyte-like cells" is intended to mean cells sharing features with cardiomyocytes, but which may not share all features. For example, a cardiomyocyte-like cell may differ from a cardiomyocyte in expression of certain cardiac genes.

The term "culture" or "cell culture" means the maintenance of cells in an artificial, in vitro environment. A "cell culture system" is used herein to refer to culture conditions in which a population of cells may be grown as monolayers or in suspension. "Culture medium" is used herein to refer to a nutrient solution for the culturing, growth, or proliferation of cells. Culture medium may be characterized by functional properties such as, but not limited to, the ability to maintain cells in a particular state (e.g., a pluripotent state, a quiescent state, etc.), or to mature cells, such as, in some embodiments, to promote the differentiation of progenitor cells into cells of a particular lineage (e.g., a cardiomyocyte).

As used herein, the term "expression" or "express" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample.

As used herein, an "expression cassette" is a DNA polynycleotide comprising one or more polynucleotide encoding protein(s) or nucleic acid(s) that is configured to express the polynucleotide in a host cell. Typically, expression of the polynucleotide(s) is placed under the control of certain regulatory elements, including constitutive or inducible promoters, tissue-specific regulatory elements, and enhancers. Such polynucleotides are said to be "operably linked to" or "operatively linked to" the regulatory elements (e.g., a promoter).

The term "induced cardiomyocyte" or the abbreviation "iCM" refers to a non-cardiomyocyte (and its progeny) that has been transformed into a cardiomyocyte (and/or cardiomyocyte-like cell). The methods of the present disclosure can be used in conjunction with any methods now known or later discovered for generating induced cardiomyocytes, for example, to enhance other techniques.

The term "non-cardiomyocyte" as used herein refers to any cell or population of cells in a cell preparation not fulfilling the criteria of a "cardiomyocyte" as defined and used herein. Non-limiting examples of non-cardiomyocytes include somatic cells, cardiac fibroblasts, non-cardiac fibroblasts, cardiac progenitor cells, and stem cells.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The terms "regenerate," "regeneration" and the like as used herein in the context of injured cardiac tissue shall be given their ordinary meanings and shall also refer to the process of growing and/or developing new cardiac tissue in a heart or cardiac tissue that has been injured, for example, injured due to ischemia, infarction, reperfusion, or other disease. In some embodiments, cardiac tissue regeneration comprises generation of cardiomyocytes.

As used herein, the term "reprogramming" or "transdifferentiation" refers to the generation of a cell of a certain lineage (e.g., a cardiac cell) from a different type of cell (e.g., a fibroblast cell) without an intermediate process of de-differentiating the cell into a cell exhibiting pluripotent stem cell characteristics. As used herein "reprogramming" includes transdifferentiation, dedifferentiation and the like.

As used herein, "reprogramming activity" refers to the ability of a protein or polynucleotide having reprogramming activity to induce or to promote reprogramming of a cell into a cardiomyocyte or cardiomyocyte-like cell when it is introduced into or expressed by the cell, alone or in combination with other proteins or polynucleotides having reprogramming activity. For example, a first protein has reprogramming activity if expression of the first protein in a cell with no other factors induces or promotes reprogramming of the cell; but the first protein also has reprogramming activity, as the term is used herein, if the first protein promotes reprogramming in combination with a second protein—that is, when both the first protein and the second protein are expressed together.

As used herein, the term "reprogramming efficiency" refers to the number of cells in a sample that are successfully reprogrammed to cardiomyocytes relative to the total number of cells in the sample.

The term "reprogramming factor" as used herein includes a factor that is introduced for expression in a cell to assist in the reprogramming of the cell into an induced cardiomyocyte. Reprogramming factors include proteins and nucleic acids (e.g., RNAs such as microRNAs, siRNA, or shRNAs).

The term "stem cells" refer to cells that have the capacity to self-renew and to generate differentiated progeny. The term "pluripotent stem cells" refers to stem cells that can give rise to cells of all three germ layers (endoderm, mesoderm and ectoderm), but do not have the capacity to give rise to a complete organism.

"Treatment," "treating," and "treat" are defined as acting upon a disease, disorder, or condition with an agent to reduce or ameliorate harmful or any other undesired effects of the disease, disorder, condition and/or their symptoms.

As used herein, the term "effective amount" and the like refers to an amount that is sufficient to induce a desired physiologic outcome (e.g., reprogramming of a cell or treatment of a disease). An effective amount can be administered in one or more administrations, applications or dosages. Such delivery is dependent on a number of variables including the time period which the individual dosage unit is to be used, the bioavailability of the composition, the route of administration, etc. It is understood, however, that specific amounts of the compositions (e.g., reprogramming factors) for any particular subject depends upon a variety of factors including the activity of the specific agent employed, the age, body weight, general health, sex, and diet of the subject, the time of administration, the rate of excretion, the composition combination, severity of the particular disease being treated and form of administration.

As used herein, the term "equivalents thereof" in reference to a polypeptide or nucleic acid sequence refers to a polypeptide or nucleic acid that differs from a reference polypeptide or nucleic acid sequence, but retains essential properties (e.g., biological activity). A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, deletions, additions, fusions and truncations in the polypeptide encoded by the reference sequence. Generally, differences are limited so that the sequences of the reference polypeptide and the variant are closely similar overall and, in many regions, identical.

The term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, or cell does not require "isolation" to distinguish it from its naturally occurring counterpart.

As used herein, the term "nucleic acid" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

The terms "polypeptide," "peptide," and "protein," are used interchangeably herein and refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues, immunologically tagged proteins, and the like.

As used herein, the word "polynucleotide" preceded by a gene name (for example, "MYOCD polynucleotide") refers to a polynucleotide sequence encoding the corresponding protein (for example, a "MYOCD protein").

As used herein, the word "protein" preceded by a gene name (for example, "MYOCD protein") refers to either the native protein or a functional variant thereof. A "native protein" is a protein encoded by a genomic copy of a gene of an organism, preferably the organism for which the vector is intended (e.g., a human, a rodent, a primate, or an animal of veterinary interest), in any of the gene's functional isoforms or functional allelic variations.

As used herein, a "functional variant" or "variant" of a protein is a variant with any number of amino acid substitutions, insertions, truncations, or internal deletions that retains the functional attributes of the protein, including, e.g., the protein's ability to induce, in combination with other factors, the reprogramming of cells into cardiomyocytes. Functional variants can be identified computationally, such as variants having only conservative substitutions, or experimentally using in vitro or in vivo assays.

As used herein, a "codon variant" of a polynucleotide sequence is polynucleotide sequence that encodes the same protein as a reference polynucleotide sequence having one or more synonymous codon substitutions. Selection of synonymous codons is within the skill of those in the art, the coding as the genetic code being known. Codon optimization is a know technical that can be performed using a variety of computational tools (such the GENSMART™ Codon Optimization tool available at www.genscript.com). Generally codon optimization is used to increase the expression of protein in a heterologous system, for instance when a human coding sequence is expressed in a bacterial system. The term "codon variant" is intended to encompass both sequences that are optimized in this manner and sequences that are optimized for other purposes, such as removal of CpG islands and/or cryptic start sites.

As used herein, the term "progenitor cell" refers to a cell that is committed to differentiate into a specific type of cell or to form a specific type of tissue. A progenitor cell, like a stem cell, can further differentiate into one or more kinds of cells, but is more mature than a stem cell such that it has a more limited/restricted differentiation capacity.

The term "vector" refers to a macromolecule or complex of molecules comprising a polynucleotide or protein to be delivered to a host cell, either in vitro or in vivo. A vector can be a modified RNA, a lipid nanoparticle (encapsulating either DNA or RNA), a transposon, an adeno-associated virus (AAV) vector, an adenovirus, a retrovirus, an integrating lentiviral vector (LVV), or a non-integrating LVV. Thus, as used herein "vectors" include naked polynucleotides used for transformation (e.g. plasmids) as well as any other composition used to deliver a polynucleotide to a cell, included vectors capable of transducing cells and vectors useful for transfection of cells. "Vector systems" refers to combinations of one, two, three, or more vectors used to delivery one, two, three, or more polynucleotides. For example, in some embodiments, two viral vectors (e.g. two AAV vectors) may be used to delivery two polynucleotides or three viral vectors (e.g. two AAV vectors) may be used to delivery three polynucleotides. For example one AAV may encode the MYOCD or a variant thereof and another AAV may encode ASCL1 or a variant thereof. Alternatively, multiple vectors may be used to delivery a single polynucleotide through post-transfection recombination. Dual vector systems for delivery of large genes are described, for example, in McClements et al. *Yale J. Biol. Med.* 90:611-23 (2017), which is incorporated herein by reference in its entirety.

As used herein, the term "viral vector" refers either to a nucleic acid molecule that includes virus-derived nucleic acid elements that typically facilitate transfer of the nucleic acid molecule or integration into the genome of a cell or to a viral particle that mediates nucleic acid transfer. Viral particles will typically include various viral components and sometimes also cell components in addition to nucleic acid(s).

The term "genetic modification" refers to a permanent or transient genetic change induced in a cell following introduction of new nucleic acid (i.e., nucleic acid exogenous to the cell). Genetic change can be accomplished by incorporation of the new nucleic acid into the genome of the cardiac cell, or by transient or stable maintenance of the new nucleic acid as an extrachromosomal element. Where the cell is a eukaryotic cell, a permanent genetic change can be achieved by introduction of the nucleic acid into the genome of the cell. Suitable methods of genetic modification include viral infection, transfection, conjugation, protoplast fusion, electroporation, particle gun technology, calcium phosphate precipitation, direct microinjection, and the like.

The term "stem cells" refer to cells that have the capacity to self-renew and to generate differentiated progeny. The term "pluripotent stem cells" refers to stem cells that can give rise to cells of all three germ layers (endoderm, mesoderm and ectoderm), but do not have the capacity to give rise to a complete organism. In some embodiments, the compositions for inducing cardiomycocyte phenotype can be used on a population of cells to induce reprogramming. In other embodiments, the compositions induce a cardiomyocyte phenotype.

The term "induced pluripotent stem cells" shall be given its ordinary meaning and shall also refer to differentiated mammalian somatic cells (e.g., adult somatic cells, such as skin) that have been reprogrammed to exhibit at least one characteristic of pluripotency. See, for example, Takahashi et al. (2007) Cell 131(5):861-872, Kim et al. (2011) Proc. Natl. Acad. Sci. 108(19): 7838-7843, Sell (2013) Stem Cells Handbook.

Unless stated otherwise, the abbreviations used throughout the specification have the following meanings: AHCF, adult human cardiac fibroblast; APCF, adult pig cardiac fibroblast; a-MHC-GFP, alpha-myosin heavy chain green fluorescence protein; CAG, CMV early enhancer/chicken beta actin (promoter); CF, cardiac fibroblast; cm, centimeter; CO, cardiac output; EF, ejection fraction; FACS, fluorescence activated cell sorting; GFP, green fluorescence protein; GMT, Gata4, Mef2c and Tbx5; GMTc, Gata4, Mef2c, Tbx5, TGF-βi, WNTi; GO, gene ontology; HCF, human cardiac fibroblast; iCM, induced cardiomyocyte; LAD, left anterior descending (artery); kg, kilogram; μg, microgram; μl, microliter; mg, milligram; ml, milliliter; MI, myocardial infarction; msec, millisecond; min, minute; MyAMT, Myocardin, Ascl1, Mef2c and Tbx5; MyΔ, Myocardin and Ascl1; MyMT, Myocardin, Mef2c and Tbx5; MyMTc, Myocardin, Mef2c, Tbx5, TGF-βi, WNTi; MRI, magnetic resonance imaging; PBS, phosphate buffered saline; PBST, phosphate buffered saline, triton; PFA, paraformaldehyde; qPCR, quantitative polymerase chain reaction; qRT-PCR, quantitative reverse transcriptase polymerase chain reaction; RNA, ribonucleic acid; RNA-seq, RNA sequencing; RT-PCR, reverse transcriptase polymerase chain reaction; sec, second; SV, stroke volume; TGF-β, transforming growth factor beta; TGF-βi, transforming growth factor beta inhibitor; WNT, wingless-Int; WNTi, wingless-Int inhibitor; YFP, yellow fluorescence protein; SCP, super core promoter; 4F, Gata4, Mef2c, TBX5, and Myocardin; 4Fc, Gata4, Mef2c, TBX5, and Myocardin+TGF-βi and WNTi; 7F, Gata4, Mef2c, and Tbx5, Esrrg, Myocardin, Zfpm2, and Mesp1; 7Fc, Gata4, Mef2c, and Tbx5, Esrrg, Myocardin, Zfpm2, and Mesp1+ TGF-βi and WNTi.

The detailed description of the disclosure is divided into various sections only for the reader's convenience and disclosure found in any section may be combined with that in another section. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

II. Reprogramming Factors

In some embodiments, the present disclosure provides reprogramming factors and compositions thereof that are capable of modulating the expression of one or more genes such as polynucleotides or proteins of interest. The present inventors have surprisingly discovered that differentiated cells can be reprogrammed into induced cardiomyocyte (iCM) cells using one or more reprogramming factors that modulate the expression of one or more genes such as polynucleotides or proteins of interest, such as Achaete-scute homolog 1 (ASCL1), Myogenic Factor 6 (MYF6), Myocardin (MYOCD), myocyte-specific enhancer factor 2C (MEF2C), and/or T-box transcription factor 5 (TBX5). In some embodiments, the one or more reprogramming factors are provided as a polynucleotide (e.g., an RNA, an mRNA, or a DNA polynucleotide) that encode one or more genes such as polynucleotides or proteins of interest. In some embodiments, the one or more reprogramming factors are provided as a protein.

In some embodiments, the reprogramming factors are microRNAs or microRNA antagonists, siRNAs, or small molecules that are capable of increasing the expression of one or more genes such as polynucleotides or proteins of interest of interest. In some embodiments, expression of a gene of interest is decreased by expression of a microRNA or a microRNA antagonist that targets a microRNA target site in the transcript from which a gene of interest is expressed. Alternatively, in some embodiments, expression of a gene of interest is increased by expression of a microRNA or a microRNA antagonist. For example, endogenous expression of an Oct4 polypeptide can be indirectly increased by introduction of microRNA-302 (miR-302), or by increased expression of miR-302, which targets a negative regulatory of Oct4. See, e.g., Hu et al., Stem Cells 31(2): 259-68 (2013), which is incorporated herein by reference in its entirety. Hence, miRNA-302 can be an indirect inducer of endogenous Oct polypeptide expression. The miRNA-302 can be introduced alone or with a nucleic acid that encodes the Oct polypeptide.

In some embodiments, the reprogramming factor is a small molecule selected from the group consisting of SB431542, LDN-193189, dexamethasone, LY364947, D4476, myricetin, IWR1, XAV939, docosahexaenoic acid (DHA), S-Nitroso-TV-acetylpenicillamine (SNAP), Hh-Agl.5, alprostadil, cromakalim, MNITMT, A769662, retinoic acid p-hydoxyanlide, decamethonium dibromide, nifedipine, piroxicam, bacitracin, aztreonam, harmalol hydrochloride, amide-C2 (A7), Ph-C12 (CIO), mCF3-C-7 (J5), G856-7272 (A473), 5475707, or any combination thereof.

A. Genes of Interest (Polynucleotides and Proteins of Interest)

In some embodiments, the one or more reprogramming factors provided herein modulate (e.g., increase or decrease) the expression of one or more genes of interest. In some embodiments, the one or more target genes are known to be involved in cardiomyocyte differentiation, proliferation, and/or function. In some embodiments, the one or more target genes are selected from the group consisting of MYOCD, MEF2C, and TBX5. In some embodiments, the one or more target genes have not been previously described to be involved in cardiomyocyte differentiation, proliferation, and/or function, or have been previously described to be involved in the differentiation, proliferation, and/or function of a non-cardiac cell lineage, such as ASCL1. Illustrative gene sequences useful in the compositions and methods of the present disclosure are provided in Table 1. Where more than one isoform of a given gene of interest is known, it will be understood that embodiments of the the present disclosure include compositions and methods that comprise the alternative isoforms of each gene of interest. The compositions and methods of the disclosure are not limited to the disclosed sequences, which are provided for example and illustration and are non-limiting.

In some embodiments, the present disclosure provides a reprogramming factor that modulates the expression of one or more genes of interest selected from ASCL1, MYOCD, MEF2C, and TBX5. In some embodiments, the reprogramming factors disclosed herein modulate the expression of one or more genes of interest selected from ASCL1, MYOCD, MEF2C, AND TBX5, CCNB1, CCND1, CDK1, CDK4, AURKB, OCT4, BAF60C, ESRRG, GATA4, GATA6, HAND2, IRX4, ISLL, MESP1, MESP2, NKX2.5, SRF, TBX20, and ZFPM2.

In some embodiments, the reprogramming factors disclosed herein modulate the expression of one or more genes of interest selected from GATA4, MEF2C, and TBX5 (i.e., GMT). In some embodiments, the reprogramming factors disclosed herein modulate the expression of one or more genes of interest selected from MYOCD, MEF2C, and TBX5 (i.e., MyMT). In some embodiments, the reprogramming factors disclosed herein modulate the expression of one or more genes of interest selected from MYOCD, ASCL1, MEF2C, and TBX5 (i.e., MyAMT). In some embodiments, the reprogramming factors disclosed herein modulate the expression of one or more genes of interest selected from MYOCD and ASCL1 (i.e., MyΔ). In some embodiments, the reprogramming factors disclosed herein modulate the expression of one or more genes of interest selected from GATA4, MEF2C, TBX5, and MYOCD (i.e., 4F). In other embodiments, the reprogramming factors disclosed herein modulate the expression of one or more genes of interest selected from GATA4, MEF2, TBX5, ESRRG, MYOCD, ZFPM2, and MESP1 (i.e., 7F).

In some embodiments, the present disclosure provides a reprogramming factor that modulates the expression of one or more genes of interest selected from ASCL1, MYOCD, MEF2C, TBX5, DLX3, DLX6, GATA2, and GATA5.

TABLE 1

Representative Sequences

| Protein | | Nucleotide (Open Reading Frame) |
|---|---|---|
| ASCL1 | MESSAKMESGGAGOQPQPQPQQPFLPPA ACFFATAAAAAAAAAAAAAQSAQQQQQQ QQQQQQAPQLRPAADGQPSGGGHKSAPK QVKRQRSSSPELMRCKRRLNFSGFGYSL PQQQPAAVARRNERERNRVKLVNLGFAT LREHVPNGAANKKMSKVETLRSAVEYIR ALQQLLDEHDAVSAAFQAGVLSPTISPN YSNDLNSMAGSPVSSYSSDEGSYDPLSP EEQELLDFTNWF (SEQ ID NO: 1) | ATGGAAAGCTCTGCCAAGATGGAGAGCGGCGGCGCCG GCCAGCAGCCCCAGCCGCAGCCCCAGCAGCCCTTCCT GCCGCCCGCAGCCTGTTTCTTTGCCACGGCCGCAGCC GCGGCGGCCGCAGCCGCCGCAGCGGCAGCGCAGAGCG CGCAGCAGCAGCAGCAGCAGCAGCAGCAGCAGCAGCA GGCGCCGCAGCTGAGACCGGCGGCCGACGGCCAGCCC TCAGGGGCGGTCACAAGTCAGCGCCCAAGCAAGTCA AGCGACAGCGCTCGTCTTCGCCCGAACTGATGCGCTG CAAACGCCGGCTCAACTTCAGCGGCTTTGGCTACAGC CTGCCGCAGCAGCAGCCGGCCGCCGTGGCGCGCCGCA ACGAGCGCGAGCGCAACCGCGTCAAGTTGGTCAACCT GGGCTTTGCCACCCTTCGGGAGCACGTCCCCAACGGC GCGGCCAACAAGAAGATGAGTAAGGTGGAGACACTGC GCTCGGCGGTCGAGTACATCCGCGCGCTGCAGCAGCT GCTGGACGAGCATGACGCGGTGAGCGCCGCCTTCCAG GCAGGCGTCCTGTCGCCCACCATCTCCCCCAACTACT CCAACGACTTGAACTCCATGGCCGGCTCGCCGGTCTC ATCCTACTCGTCGGACGAGGGCTCTTACGACCCGCTC AGCCCCGAGGAGCAGGAGCTTCTCGACTTCACCAACT GGTTCTGA (SEQ ID NO: 2) |
| DLX3 | MSGSFDRKLSSILTDISSSLSCHAGSKD SPTLPESSVTDLGYYSAPQHDYYSGQPY GQTVNPYTYHHQFNLNGLAGTGAYSPKS EYTYGASYRQYGAYREQPLPAQDPVSVK EEPEAEVRMVNGKPKKVRKPRTIYSSYQ LAALQRRFQKAQYLALPERAELAAQLGL TQTQVKIWFQNRRSKFKKLYKNGEVPLE HSPNNSDSMACNSPPSPALWDTSSHSTP APARSQLPPPLPYSASPSYLDDPTNSWY HAQNLSGPHLQQQPPQPATLHHASPGPP PNPGAVY (SEQ ID NO: 43) | ATGAGTGGCTCCTTCGATCGCAAGCTCAGCA GCATCCTCACCGACATCTCCAGCTCCCTTAGCTGCCA TGCGGGCTCCAAGGACTCGCCTACCCTGCCCGAGTCT TCTGTCACTGACCTGGGCTACTACAGCGCTCCCCAGC ACGATTACTACTCGGGCCAGCCCTATGGCCAGACGGT GAACCCCTACACCTACCACCACCAATTCAATCTCAAT GGGCTTGCAGGCACGGGCGCTTACTCGCCCAAGTCGG AATATACCTACGGAGCCTCCTACCGGCAATACGGGGC GTATCGGGAGCAGCCGCTGCCAGCCCAGGACCCAGTG TCGGTGAAGGAGGAGCCGGAAGCAGAGGTGCGCATGG TGAATGGGAAGCCCAAGAAGGTCCGAAAGCCGCGTAC GATCTACTCCAGCTACCAGCTGGCCGCCCTGCAGCGC CGCTTCCAGAAGGCCCAGTACCTGGCGCTGCCCGAGC GCGCCGAGCTGGCCGCGCAGCTGGGCCTCACGCAGAC ACAGGTGAAAATCTGGTTCCAGAACCGCCGTTCCAAG TTCAAGAAACTCTACAAGAACGGGGAGGTGCCGCTGG AGCACAGTCCCAATAACAGTGATTCCATGGCCTGCAA CTCACCACCATCACCCGCCCTCTGGGACACCTCTTCC CACTCCACTCCGGCCCCTGCCCGCAGTCAGCTGCCCC CGCCGCTCCCATACAGTGCCTCCCCCAGCTACCTGGA CGACCCCACCAACTCCTGGTATCACGCACAGAACCTG AGTGGACCCCACTTACAGCAGCAGCCGCCTCAGCCAG CCACCCTGCACCATGCCTCTCCCGGGCCCCCGCCCAA CCCTGGGGCTGTGTACTGA (SEQ ID NO: 44) |
| DLX6 | MMTMTTMADGLEGQDSSKSAFMEFGQQQ QQQQQQQQQQQQQQQQPPPPPPPPPQPH SQQSSPAMAGAHYPLHCLHSAAAAAAAG SHHHHHHQHHHHGSPYASGGGNSYNHRS LAAYPYMSHSQHSPYLQSYHNSSAAAQT | ATGATGACCATGACTACGATGGCTGACGGCTTGGAAG GCCAGGACTCGTCCAAATCCGCCTTCATGGAGTTCGG GCAGCAGCAGCAGCAGCAGCAGCAACAGCAGCAGCAG CAGCAGCAGCAACAGCAACAGCCGCGCCGCCGCCGC CGCCGCCGCCGCAGCCGCACTCGCAGCAGAGCTCCCC |

TABLE 1-continued

Representative Sequences

| Protein | Nucleotide (Open Reading Frame) |
|---|---|
| RGDDTDQQKTTVIENGEIRFNGKGKKIR<br>KPRTIYSSLQLQALNHRFQQTQYLALPE<br>RAELAASLGLTQTQVKIWFQNKRSKFKK<br>LLKQGSNPHESDPLQGSAALSPRSPALP<br>PVWDVSASAKGVSMPPNSYMPGYSHWYS<br>SPHQDTMQRPQMM<br>(SEQ ID NO: 45) | GGCCATGGCAGGCGCGCACTACCCTCTGCACTGCCTG<br>CACTCGGCGGCGGCGGCAGCGGCCGGCTCGCACC<br>ACCACCACCACCACCAGCACCACCACCACGGCTCGCC<br>CTACGCGTCGGGCGGAGGGAACTCCTACAACCACCGC<br>TCGCTCGCCGCCTACCCCTACATGAGCCACTCGCAGC<br>ACAGCCCTTACCTCCAGTCCTACCACAACAGCAGCGC<br>AGCCGCCCAGACGCGAGGGGACGACACAGATCAACAA<br>AAAACTACAGTGATTGAAAACGGGGAAATCAGGTTCA<br>ATGGAAAAGGGAAAAAGATTCGGAAGCCTCGGACCAT<br>TTATTCCAGCCTGCAGCTCCAGGCTTTAAACCATCGC<br>TTTCAGCAGACACAGTATCTGGCCCTTCCAGAGAGAG<br>CCGAACTGGCAGCTTCCTTAGGACTGACACAAACACA<br>GGTGAAGATATGGTTTCAGAACAAACGCTCTAAGTTT<br>AAGAAACTGCTGAAGCAGGGCAGTAATCCTCATGAGA<br>GCGACCCCTCCAGGGCTCGGCGGCCCTGTCGCCACG<br>CTCGCCAGCGCTGCCTCCAGTCTGGGACGTTTCTGCC<br>TCGGCCAAGGGTGTCAGTATGCCCCCCAACAGCTACA<br>TGCCTGGCTATTCTCACTGGTACTCCTCTCCACACCA<br>GGACACGATGCAGAGACCACAGATGATGTGA<br>(SEQ ID NO: 46) |
| ESRRG MDSVELCLPESFSLHYEEELLCRMSNKD<br>RHIDSSCSSFIKTEPSSPASLTDSVNHH<br>SPGGSSDASGSYSSTMNGHQNGLDSPPL<br>YPSAPILGGSGPVRKLYDDCSSTIVEDP<br>QTKCEYMLNSMPKRLCLVCGDIASGYHY<br>GVASCEACKAFFKRTIQGNIEYSCPATN<br>ECEITKRRRKSCQACRFMKCLKVGMLKE<br>GVRLDRVRGGRQKYKRRIDAENSPYLNP<br>QLVQPAKKPYNKIVSHLLVAEPEKIYAM<br>PDPTVPDSDIKALTTLCDLADRELVVII<br>GWAKHIPGFSTLSLADQMSLLQSAWMEI<br>LILGVVYRSLSFEDELVYADDYIMDEDQ<br>SKLAGLLDLNNAILQLVKKYKSMKLEKE<br>EFVTLKAIALANSDSMHIEDVEAVQKLQ<br>DVLHEALQDYEAGQHMEDPRRAGKMLMT<br>LPLLRQTSTKAVQHFYNIKLEGKVPMHK<br>LFLEMLEAKV<br>(SEQ ID NO: 47) | ATGGATTCGGTAGAACTTTGCCTTCCTGAATCTTTTT<br>CCCTGCACTACGAGGAAGAGCTTCTCTGCAGAATGTC<br>AAACAAAGATCGACACATTGATTCCAGCTGTTCGTCC<br>TTCATCAAGACGGAACCTTCCAGCCCAGCCTCCCTGA<br>CGGACAGCGTCAACCACCACAGCCCTGGTGGCTCTTC<br>AGACGCCAGTGGGAGCTACAGTTCAACCATGAATGGC<br>CATCAGAACGGACTTGACTCGCCACCTCTCTACCCTT<br>CTGCTCCTATCCTGGGAGGTAGTGGGCCTGTCAGGAA<br>ACTGTATGATGACTGCTCCAGCACCATTGTTGAAGAT<br>CCCCAGACCAAGTGTGAATATATGCTCAACTCGATGC<br>CCAAGAGACTGTGTTTAGTGTGGTGACATCGCTTC<br>TGGGTACCACTATGGGGTAGCATCATGTGAAGCCTGC<br>AAGGCATTCTTCAAGAGGACAATTCAAGGCAATATAG<br>AATACAGCTGCCCTGCCACGAATGAATGTGAAATCAC<br>AAAGCGCAGACGTAAATCCTGCCAGGCTTGCCGCTTC<br>ATGAAGTGTTTAAAAGTGGGCATGCTGAAAGAAGGGG<br>TGCGTCTTGACAGAGTACGTGGAGGTCGGCAGAAGTA<br>CAAGCGCAGGATAGATGCGGAGAACAGCCCATACCTG<br>AACCCTCAGCTGGTTCAGCCAGCCAAAAAGCCATATA<br>ACAAGATTGTCTCACATTTGTTGGTGGCTGAACCGGA<br>GAAGATCTATGCCATGCCTGACCCTACTGTCCCCGAC<br>AGTGACATCAAAGCCCTCACTACACTGTGTGACTTGG<br>CCGACCGAGAGTTGGTGGTTATCATTGGATGGGCGAA<br>GCATATTCCAGGCTTCTCCACGCTGTCCCTGGCGGAC<br>CAGATGAGCCTTCTGCAGAGTGCTTGGATGGAAATTT<br>TGATCCTTGGTGTCGTATACCGGTCTCTTTCGTTTGA<br>GGATGAACTTGTCTATGCAGACGATTATATAATGGAC<br>GAAGACCAGTCCAAATTAGCAGGCCTTCTTGATCTAA<br>ATAATGCTATCCTGCAGCTGGTAAAGAAATACAAGAG<br>CATGAAGCTGGAAAAAGAAGAATTTGTCACCCTCAAA<br>GCTATAGCTCTTGCTAATTCAGACTCCATGCACATAG<br>AAGATGTTGAAGCCGTTCAGAAGCTTCAGGATGTCTT<br>ACATGAAGCGCTGCAGGATTATGAAGCTGGCCAGCAC<br>ATGGAAGACCCTCGTCGAGCTGGCAAGATGCTGATGA<br>CACTGCCACTCCTGAGGCAGACCTCTACCAAGGCCGT<br>GCAGCATTTCTACAACATCAAACTAGAAGGCAAAGTC<br>CCAATGCACAAACTTTTTTTGGAAATGTTGGAGGCCA<br>AGGTCTGA<br>(SEQ ID NO: 48) |
| GATA2 MEVAPEQPRWMAHPAVLNAQHPDSHHPG<br>LAHNYMEPAQLLPPDEVDVFFNHLDSQG<br>NPYYANPAHARARVSYSPAHARLTGGQM<br>CRPHLLHSPGLPWLDGGKAALSAAAAHH<br>HNPWTVSPFSKTPLHPSAAGGPGGPLSV<br>YPGAGGGSGGGSGSSVASLTPTAAHSGS<br>HLFGFPPTPPKEVSPDPSTTGAASPASS<br>SAGGSSAARGEDKDGVKYQVSLTESMKME<br>SGSPLRPGLATMGTQPATHHPIPTYPSY<br>VPAAAHDYSSGLFHPGGFLGGPASSFTP<br>KQRSKARSCSEGRECVNCGATATPLWRR<br>DGTGHYLCNACGLYHKMNGQNRPLIKPK | ATGGAGGTGGCGCCCGAGCAGCCGCGCTGGATGGCGC<br>ACCCGGCCGTGCTGAATGCGCAGCACCCCGACTCACA<br>CCACCCGGGCCTGGCGCACAACTACATGGAACCCGCG<br>CAGCTGCTGCCTCCAGACGAGGTGGACGTCTTCTTCA<br>ATCACCTCGACTCGCAGGGCAACCCCTACTATGCCAA<br>CCCCGCTCACGCGCGGGCGCGCGTCTCCTACAGCCCG<br>GCGCACGCCCGCCTGACCGGAGGCCAGATGTGCCGCC<br>CACACTTGTTGCACAGCCCGGGTTTGCCCTGGCTGGA<br>CGGGGGCAAAGCAGCCCTCTCTGCCGCTGCGGCCCAC<br>CACCACAACCCCTGGACCGTGAGCCCCTTCTCCAAGA<br>CGCCACTGCACCCCTCAGCTGCTGGAGGCCCTGGAGG<br>CCCACTCTCTGTGTACCCAGGGGCTGGGGGTGGGAGC |

TABLE 1-continued

Representative Sequences

| Protein | | Nucleotide (Open Reading Frame) |
|---|---|---|
| | RRLSAARRAGTCCANCQTTTTTLWRRNA NGDPVCNACGLYYKLHNVNRPLTMKKEG IQTRNRKMSNKSKKSKKGAECFEELSKC MQEKSSPFSAAALAGHMAPVGHLPPFSH SGHILPTPTPIHPSSSLSFGHPHPSSMV TAMG (SEQ ID NO: 49) | GGGGGAGGCAGCGGGAGCTCAGTGGCCTCCCTCACCC CTACAGCAGCCCACTCTGGCTCCCACCTTTTCGGCTT CCCACCCACGCCACCCAAAGAAGTGTCTCCTGACCCT AGCACCACGGGGGCTGCGTCTCCAGCCTCATCTTCCG CGGGGGGTAGTGCAGCCCGAGGAGAGGACAAGGACGG CGTCAAGTACCAGGTGTCACTGACGGAGAGCATGAAG ATGGAAAGTGGCAGTCCCCTGCGCCCAGGCCTAGCTA CTATGGGCACCCAGCCTGCTACACACCACCCCATCCC CACCTACCCCTCCTATGTGCCGGCGGCTGCCCACGAC TACAGCAGCGGACTCTTCCACCCCGGAGGCTTCCTGG GGGGACCGGCCTCCAGCTTCACCCCTAAGCAGCGCAG CAAGGCTCGTTCCTGTTCAGAAGGCCGGGAGTGTGTC AACTGTGGGGCCACAGCCACCCCTCTCTGGCGGCGGG ACGGCACCGGCCACTACCTGTGCAATGCCTGTGGCCT CTACCACAAGATGAATGGGCAGAACCGACCACTCATC AAGCCCAAGCGAAGACTGTCGGCCGCCAGAAGAGCCG GCACCTGTTGTGCAAATTGTCAGACGACAACCACCAC CTTATGGCGCCGAAACGCCAACGGGACCCTGTCTGC AACGCCTGTGGCCTCTACTACAAGCTGCACAATGTTA ACAGGCCACTGACCATGAAGAAGGAAGGGATCCAGAC TCGGAACCGGAAGATGTCCAACAAGTCCAAGAAGAGC AAGAAAGGGGCGGAGTGCTTCGAGGAGCTGTCAAAGT GCATGCAGGAGAAGTCATCCCCCTTCAGTGCAGCTGC CCTGGCTGGACACATGGCACCTGTGGGCCACCTCCCG CCCTTCAGCCACTCCGGACACATCCTGCCCACTCCGA CGCCCATCCACCCCTCCTCCAGCCTCTCCTTCGGCCA CCCCCACCCGTCCAGCATGGTGACCGCCATGGGCTAG (SEQ ID NO: 50) |
| GATA4 | MYQSLAMAANHGPPPGAYEAGGPGAFMH GAGAASSPVYVPTPRVPSSVLGLSYLQG GGAGSASGGASGGSSGGAASGAGPGTQQ GSPGWSQAGADGAAYTPPPVSPRFSFPG TTGSLAAAAAAAAAREAAAYSSGGGAAG AGLAGREQYGRAGFAGSYSSPYPAYMAD VGASWAAAAAASAGPFDSPVLHSLPGRA NPAARHPNLVDMEDDESEGRECVNCGAM STPLWRRDGTGHYLCNACGLYHKMNGIN RPLIKPQRRLSASRRVGLSCANCQTTTT TLWRRNAEGEPVCNACGLYMKLHGVPRP LAMRKEGIQTRKRKPKNLNKSKTPAAPS GSESLPPASGASSNSSNATTSSSEEMRP IKTEPGLSSHYGHSSSVSQTFSVSAMSG HGPSIHPVLSALKLSPQGYASPVSQSPQ TSSKQDSWNSLVLADSHGDIITA (SEQ ID NO: 51) | ATGTATCAGAGCTTGGCCATGGCCGCCAACCACGGGC CGCCCCCCGGTGCCTACGAGGCGGGCGGCCCCGGCGC CTTCATGCACGGCGCGGGCGCCGCGTCCTCGCCAGTC TACGTGCCCACACCGCGGGTGCCCTCCTCCGTGCTGG GCCTGTCCTACCTCCAGGGCGGAGGCGCGGGCTCTGC GTCCGGAGGCGCCTCGGGCGGCAGCTCCGGTGGGGCC GCGTCTGGTGCGGGGCCCGGGACCCAGCAGGGCAGCC CGGGATGGAGCCAGGCGGGAGCCGACGGAGCCGCTTA CACCCCGCCGCCGGTGTCGCCGCGCTTCTCCTTCCCG GGGACCACCGGGTCCCTGGCGGCGCCGCCGCCGCTG CCGCGGCCCGGGAAGCTGCGGCCTACAGCAGTGGCGG CGGAGCGGCGGGTGCGGGCCTGGCGGGCCGCGAGCAG TACGGGCGCGCCGGCTTCGCGGGCTCCTACTCCAGCC CCTACCCGGCTTACATGGCCGACGTGGGCGCGTCCTG GGCCGCAGCCGCCGCCGCCTCCGCCGGCCCCTTCGAC AGCCCGGTCCTGCACAGCCTGCCCGGCCGGGCCAACC CGGCCGCCCGACACCCCAATCTCGTAGATATGTTTGA CGACTTCTCAGAAGGCAGAGAGTGTGTCAACTGTGGG GCTATGTCCACCCCGCTCTGGAGGCGAGATGGGACGG GTCACTATCTGTGCAACGCCTGCGGCCTCTACCACAA GATGAACGGCATCAACCGGCCGCTCATCAAGCCTCAG CGCCGGCTGTCCGCCTCCCGCCGAGTGGGCCTCTCCT GTGCCAACTGCCAGACCACCACCACCACGCTGTGGCG CCGCAATGCGGAGGGCGAGCCTGTGTGCAATGCCTGC GGCCTCTACATGAAGCTCCACGGGGTCCCCAGGCCTC TTGCAATGCGGAAAGAGGGGATCCAAACCAGAAAACG GAAGCCCAAGAACCTGAATAAATCTAAGACACCAGCA GCTCCTTCAGGCAGTGAGAGCTTCCTCCCGCCAGCG GTGCTTCCAGCAACTCCAGCAACGCCACCACCAGCAG CAGCGAGGAGATGCGTCCCATCAAGACGGAGCCTGGC CTGTCATCTCACTACGGGCACAGCAGCTCCGTGTCCC AGACGTTCTCAGTCAGTGCGATGTCTGGCCATGGGCC CTCCATCCACCCTGTCCTCTCGGCCCTGAAGCTCTCC CCACAAGGCTATGCGTCTCCCGTCAGCCAGTCTCCAC AGACCAGCTCCAAGCAGGACTCTTGGAACAGCCTGGT CTTGGCCGACAGTCACGGGGACATAATCACTGCGTAA (SEQ ID NO: 52) |
| MESP1 | MAQPLCPPLSESWMLSAAWGPTRRPPPS DKDCGRSLVSSPDSWGSTPADSPVASPA RPGTLRDPRAPSVGRRGARSSRLGSGQR QSASEREKLRMRTLARALHELRRELPPS | ATGGCCCAGCCCCTGTGCCCGCCGCTCTCCGAGTCCT GGATGCTCTCTGCGGCCTGGGGCCCAACTCGGCGGCC GCCGCCCTCCGACAAGGACTGCGGCCGCTCCCTCGTC TCGTCCCCAGACTCATGGGGCAGCACCCCAGCCGACA |

TABLE 1-continued

Representative Sequences

| Protein | | Nucleotide (Open Reading Frame) |
|---|---|---|
| | VAPAGQSLTKIETLRLAIRYIGHLSAVL GLSEESLQRRCRQRGDAGSPRGCPLCPD DCPAQMQTRTQAEGQGQGRGLGLVSAVR AGASWGSPPACPGARAAPEPRDPPALFA EAACPEGQAMEPSPPSPLLPGDVLALLE TWMPLSPLEWLPEEPK (SEQ ID NO: 53) | GCCCCGTGGCGAGCCCCGCGCGGCCAGGCACCCTCCG GGACCCCCGCGCCCCCTCCGTAGGTAGGCGCGGCGCG CGCAGCAGCCGCCTGGGCAGCGGGCAGAGGCAGAGCG CCAGTGAGCGGGAGAAACTGCGCATGCGCACGCTGGC CCGCGCCCTGCACGAGCTGCGCCGCTTTCTACCGCCG TCCGTGGCGCCCGCGGGCCAGAGCCTGACCAAGATCG AGACGCTGCGCCTGGCTATCCGCTATATCGGCCACCT GTCGGCCGTGCTAGGCCTCAGCGAGGAGAGTCTCCAG CGCCGGTGCCGGCAGCGCGGTGACGCGGGGTCCCCTC GGGGCTGCCCGCTGTGCCCCGACGACTGCCCCGCGCA GATGCAGACACGGACGCAGGCTGAGGGGCAGGGGCAG GGGCGCGGGCTGGGCCTGGTATCCGCCGTCCGCGCCG GGGCGTCCTGGGGATCCCCGCCTGCCTGCCCCGGAGC CCGAGCTGCACCCGAGCCGCGCGACCCGCCTGCGCTG TTCGCCGAGGCGGCGTGCCCTGAAGGGCAGGCGATGG AGCCAAGCCCACCGTCCCCGCTCCTTCCGGGCGACGT GCTGGCTCTGTTGGAGACCTGGATGCCCCTCTCGCCT CTGGAGTGGCTGCCTGAGGAGCCCAAGTGA (SEQ ID NO: 54) |
| MYF6 | MMMDLFETGSYFFYLDGENVTLQPLEVA EGSPLYPGSDGTLSPCQDQMPPEAGSDS SGEEHVLAPPGLQPPHCPGQCLIWACKT CKRKSAPTDRRKAATLRERRRLKKINEA FEALKRRTVANPNQRLPKVEILRSAISY IERLQDLLHRLDQQEKMQELGVDPFSYR PKQENLEGADFLRTCSSQWPSVSDHSRG LVITAKEGGASIDSSASSSLRCLSSIVD SISSEERKLPCVEEVVEK (SEQ ID NO: 55) | ATGATGATGGACCTTTTTGAAACTGGCTCCTATTTCT TCTACTTGGATGGGGAAAATGTTACTCTGCAGCCATT AGAAGTGGCAGAAGGCTCTCCTTTGTATCCAGGGAGT GATGGTACCTTGTCCCCCTGCCAGGACCAAATGCCCC CGGAAGCGGGGAGCGACAGCAGCGGAGGGAACATGT CCTGGCGCCCCGGGCCTGCAGCCTCCACACTGCCCC GGCCAGTGTCTGATCTGGGCTTGCAAGACCTGCAAGA GAAAATCTGCCCCACTGACCGGCGAAAAGCCGCCAC CCTGCGCGAAAGGAGGAGGCTAAAGAAAATCAACGAG GCCTTCGAGGCACTGAAGCGGCGAACTGTGGCCAACC CAACCAGAGGCTGCCCAAGGTGGAGATTCTGCGGAG CGCCATCAGCTATATTGAGCGGCTGCAGGACCTGCTG CACCGGCTGGATCAGCAGGAGAAGATGCAGGAGCTGG GGGTGGACCCCTTCAGCTACAGACCCAAACAAGAAAA TCTTGAGGGTGCGGATTTCCTGCGCACCTGCAGCTCC CAGTGGCCAAGTGTTTCCGATCATTCCAGGGGGCTCG TGATAACGGCTAAGGAAGGAGGAGCAAGTATTGATTC GTCAGCCTCGAGTAGCCTTCGATGCCTTTCTTCCATC GTGGACAGTATTTCCTCGGAGGAACGCAAACTCCCCT GCGTGGAGGAAGTGGTGGAGAAGTAA (SEQ ID NO: 56) |
| MYOCD | MTLLGSEHSLLIRSKFRSVLQLRLQQRR TQEQLANQGIIPPLKRPAEFHEQRKHLD SDKAKNSLKRKARNRCNSADLVNMHILQ ASTAERSIPTAQMKLKRARLADDLNEKI ALRPGPLELVEKNILPVDSAVKEAIKGN QVSFSKSTDAFAFEEDSSSDGLSPDQTR SEDPQNSAGSPPDAKASDTPSTGSLGTN QDLASGSENDRNDSASQPSHQSDAGKQG LGPPSTPIAVHAAVKSKSLGDSKNRHKK PKDPKPKVKKLKYHQYIPPDQKAEKSPP PMDSAYARLLQQQQLFLQLQILSQQQQQ QQHRFSYLGMHQAQLKEPNEQMVRNPNS SSTPLSNTPLSPVKNSFSGQTGVSSFKP GPLPPNLDDLKVSELRQQLRIRGLPVSG TKTALMDRLRPFQDCSGNPVPNFGDITT VTFPVTPNTLPNYQSSSSTSALSNGFYH FGSTSSSPPISPASSDLSVAGSLPDTEN DASPSFGLHPSPVHVCTEESLMSSLNGG SVPSELDGLDSEKDKMLVEKQKVINELT WKLQQEQRQVEELRMQLQKQKRNNCSEK KPLPFLAASIKQEEAVSSCPFASQVPVK RQSSSSECHPPACEAAQLQPLGNAHCVE SSDQTNVLSSTFLSPQCSPQHSPLGAVK SPQHISLPPSPNNPHELPSSSGAQGEGH RVSSPISSQVCTAQNSGAHDGHPPSFSP HSSSLHPPFSGAQADSSHGAGGNPCPKS PCVQQKMAGLHSSDKVGPKFSIPSPTES KSSSAISEVTQPPSYEDAVKQQMTRSQQ MDELLDVLIESGEMPADAREDHSCLQKV PKIPRSSRSPTAVLTKPSASFEQASSGS QIPFDPYATDSDEHLEVLLNSQSPLGKM SDVTLLKIGSEEPHFDGIMDGFSGKAAE | ATGACACTCCTGGGGTCTGAGCATTCCTTGCTGATTA GGAGCAAGTTCAGATCAGTTTTACAGTTAAGACTTCA ACAAAGAAGGACCCAGGAACAACTGGCTAACCAAGGC ATAATACCACCACTGAAACGTCCAGCTGAATTCCATG AGCAAAGAAAACATTTGGATAGTGACAAGGCTAAAAA TTCCCTGAAGCGCAAAGCCAGAAACAGGTGCAACAGT GCCGACTTGGTTAATATGCACATACTCCAAGCTTCCA CTGCAGAGAGGTCCATTCCAACTGCTCAGATGAAGCT GAAAAGAGCCCGACTCGCCGATGATCTCAATGAAAAA ATTGCTCTACGACCAGGGCCACTGGAGCTGGTGGAAA AAAACATTCTTCCTGTGGATTCTGCTGTGAAAGAAGC CATAAAAGGTAACCAGGTGAGTTTCTCCAAATCCACG GATGCTTTTGCCTTTGAAGAGGACAGCAGCAGCGATG GGCTTTCTCCGGATCAGACTCGAAGTGAAGACCCCCA AAACTCAGCGGGATCCCCGCCAGACGCTAAAGCCTCA GATACCCCTTCGACAGGTTCTCTGGGGACAAACCAGG ATCTTGCTTCTGGCTCAGAAAATGACAGAAATGACTC AGCCTCACAGCCCAGCCACCAGTCAGATGCGGGGAAG CAGGGGCTTGGCCCCCCCAGCACCCCCATAGCCGTGC ATGCTGCTGTAAAGTCCAATCCTTGGGTGACAGTAA GAACCGCCACAAAAGCCCAAGGACCCCAAGCCAAAG GTGAAGAAGCTTAAATATCACCAGTACATTCCCCCAG ACCAGAAGGCAGAGAAGTCCCCTCCACCTATGGACTC AGCCTACGCTCGGCTGCTCCAGCAACAGCAGCTGTTC CTGCAGCTCCAAATCCTCAGCCAGCAGCAGCAGCAGC AGCAACACCGATTCAGCTACCTAGGGATGCACCAAGC TCAGCTTAAGGAACCAAATGAACAGATGGTCAGAAAT CCAAACTCTTCTTCAACGCCACTGAGCAATACCCCCT TGTCTCCTGTCAAAAACAGTTTTTCTGGACAAACTGG TGTCTCTTCTTTCAAACCAGGCCCACTCCCACCTAAC CTGATGATCTGAAGGTCTCTGAATTAAGACAACAGC TTCGAATTCGGGGCTTGCCTGTGTCAGGCACCAAAAC |

TABLE 1-continued

Representative Sequences

| Protein | | Nucleotide (Open Reading Frame) |
|---|---|---|
| | DLFNAHEILPGPLSPMQTQFSPSSVDSN GLQLSFTESPWETMEWLDLTPPNSTPGF SALTTSSPSIFNIDFLDVTDLNLNSSMD LHLQQW (SEQ ID NO: 3) | GGCTCTCATGGACCGGCTTCGACCCTTCCAGGACTGC TCTGGCAACCCAGTGCCGAACTTTGGGGATATAACGA CTGTCACTTTTCCTGTCACACCCAACACGCTGCCCAA TTACCAGTCTTCCTCTTCTACCAGTGCCCTGTCCAAC GGCTTCTACCACTTTGGCAGCACCAGCTCCAGCCCCC CGATCTCCCCAGCCTCCTCTGACCTGTCAGTCGCTGG GTCCCTGCCGGACACCTTCAATGATGCCTCCCCCTCC TTCGGCCTGCACCCGTCCCCAGTCCACGTGTGCACGG AGGAAAGTCTCATGAGCAGCCTGAATGGGGGCTCTGT TCCTTCTGAGCTGGATGGGCTGGACTCCGAGAAGGAC AAGATGCTGGTGGAGAAGCAGAAGGTGATCAATGAAC TCACCTGGAAACTCCAGCAAGAGCAGAGGCAGGTGGA GGAGCTGAGGATGCAGCTTCAGAAGCAGAAAAGGAAT AACTGTTCAGAGAAGAAGCCGCTGCCTTTCCTGGCTG CCTCCATCAAGCAGGAAGAGGCTGTCTCCAGCTGTCC TTTTGCATCCCAAGTACCTGTGAAAAGACAAAGCAGC AGCTCAGAGTGTCACCCACCGGCTTGTGAAGCTGCTC AACTCCAGCCTCTTGGAAATGCTCATTGTGTGGAGTC CTCAGATCAAACCAATGTACTTTCTTCCACATTTCTC AGCCCCCAGTGTTCCCCTCAGCATTCACCGCTGGGGG CTGTGAAAAGCCCACAGCACATCAGTTTGCCCCCATC ACCCAACAACCCTCACTTTCTGCCCTCATCCTCCGGG GCCCAGGGAGAAGGGCACAGGGTCTCCTCGCCCATCA GCAGCCAGGTGTGCACTGCACAGAACTCAGGAGCACA CGATGGCCATCCTCCAAGCTTCTCTCCCCATTCTTCC AGCCTCCACCCGCCCTTCTCTGGAGCCCAAGCAGACA GCAGTCATGGTGCCGGGGGAAACCCTTGTCCCAAAAG CCCATGTGTACAGCAAAAGATGGCTGGTTTACACTCT TCTGATAAGGTGGGGCCAAAGTTTTCAATTCCATCCC CAACTTTTTCTAAGTCAAGTTCAGCAATTTCAGAGGT AACACAGCCTCCATCCTATGAAGATGCCGTAAAGCAG CAAATGACCCGGAGTCAGCAGATGGATGAACTCCTGG ACGTGCTTATTGAAAGCGGAGAAATGCCAGCAGACGC TAGAGAGGATCACTCATGTCTTCAAAAAGTCCCAAAG ATACCCAGATCTTCCCGAAGTCCAACTGCTGTCCTCA CCAAGCCCTCGGCTTCCTTTGAACAAGCCTCTTCAGG CAGCCAGATCCCCTTTGATCCCTATGCCACCGACAGT GATGAGCATCTTGAAGTCTTATTAAATTCCCAGAGCC CCCTAGGAAAGATGAGTGATGTCACCCTTCTAAAAAT TGGGAGCGAAGAGCCTCACTTTGATGGGATAATGGAT GGATTCTCTGGGAAGGCTGCAGAAGACCTCTTCAATG CACATGAGATCTTGCCAGGCCCCCTCTCTCCAATGCA GACACAGTTTTCACCCTCTTCTGTGGACAGCAATGGG CTGCAGTTAAGCTTCACTGAATCTCCCTGGGAAACCA TGGAGTGGCTGGACCTCACTCCGCCAAATTCCACACC AGGCTTTAGCGCCCTCACCACCAGCAGCCCCAGCATC TTCAACATCGATTTCCTGGATGTCACTGATCTCAATT TGAATTCTTCCATGGACCTTCACTTGCAGCAGTGGTA G (SEQ ID NO: 4) |
| MEF2C | MGRKKIQITRIMDERNRQVTFTKRKFGL MKKAYELSVLCDCEIALIIFNSTNKLFQ YASTDMDKVLLKYTEYNEPHESRTNSDI VEALNKKENKGCESPDPDSSYALTPRTE EKYKKINEEFDNMIKSHKIPAVPPPNFE MPVSIPVSSHNSLVYSNPVSSLGNPNLL PLAHPSLQRNSMSPGVTHRPPSAGNTGG LMGGDLTSGAGTSAGNGYGNPRNSPGLL VSPGNLNKNMQAKSPPPMNLGMNNRKPD LRVLIPPGSKNTMPSVNQRINNSQSAQS LATPVVSVATPTLPGQGMGGYPSAISTT YGTEYSLSSADLSSLSGENTASALHLGS VTGWQQQHLHNMPPSALSQLGACTSTHL SQSSNLSLPSTQSLNIKSEPVSPPRDRT TTPSRYPQHTRHEAGRSPVDSLSSCSSS YDGSDREDHRNEFHSPIGLTRPSPDERE SPSVKRMRLSEGWAT (SEQ ID NO: 5) | ATGGGGAGAAAAAGATTCAGATTACGAGGATTATGG ATGAACGTAACAGACAGGTGACATTTACAAAGAGGAA ATTTGGGTTGATGAAGAAGGCTTATGAGCTGAGCGTG CTGTGTGACTGTGAGATTGCGCTGATCATCTTCAACA GCACCAACAAGCTGTTCCAGTATGCCAGCACCGACAT GGACAAAGTGCTTCTCAAGTACACGGAGTACAACGAG CCGCATGAGAGCCGGACAAACTCAGACATCGTGGAGG CATTGAACAAGAAAGAAAACAAAGGCTGTGAAAGCCC CGATCCCGACTCCTCTTATGCACTCACCCCACGCACT GAAGAAAAATACAAAAAAATTAATGAAGAATTTGATA ATATGATCAAGAGTCATAAAATTCCTGCTGTTCCACC TCCCAACTTCGAGATGCCAGTCATCCCAGTGTCA AGCCACAACAGTTTGGTGTACAGCAACCCTGTCAGCT CACTGGGAAACCCCAACCTATTGCCACTGGCTCACCC TTCTCTGCAGAGGAATAGTATGTCTCCTGGTGTAACA CATCGACCTCCAAGTGCAGGTAACACAGGTGGTCTGA TGGGTGGAGACCTCACGTCTGGTGCAGGCACCAGTGC AGGGAACGGGTATGGCAATCCCCGAAACTCACCAGGT CTGCTGGTCTCACCTGGTAACTTGAACAAGAATATGC AAGCAAAATCTCCTCCCCCAATGAATTTAGGAATGAA TAACCGTAAACCAGATCTCCGAGTTCTTATTCCACCA GGCAGCAAGAATACGATGCCATCAGTGAATCAAAGGA TAAATAACTCCCAGTCGGCTCAGTCATTGGCTACCCC AGTGGTTTCCGTAGCAACTCCTACTTTACCAGGACAA GGAATGGGAGGATATCCATCAGCCATTTCAACAACAT |

TABLE 1-continued

Representative Sequences

| Protein | | Nucleotide (Open Reading Frame) |
|---|---|---|
| | | ATGGTACCGAGTACTCTCTGAGTAGTGCAGACCTGTC |
| | | ATCTCTGTCTGGGTTTAACACCGCCAGCGCTCTTCAC |
| | | CTTGGTTCAGTAACTGGCTGGCAACAGCAACACCTAC |
| | | ATAACATGCCACCATCTGCCCTCAGTCAGTTGGGAGC |
| | | TTGCACTAGCACTCATTTATCTCAGAGTTCAAATCTC |
| | | TCCCTGCCTTCTACTCAAAGCCTCAACATCAAGTCAG |
| | | AACCTGTTTCTCCTCCTAGAGACCGTACCACCACCCC |
| | | TTCGAGATACCCACAACACACGCGCCACGAGGCGGGG |
| | | AGATCTCCTGTTGACAGCTTGAGCAGCTGTAGCAGTT |
| | | CGTACGACGGGAGCGACCGAGAGGATCACCGGAACGA |
| | | ATTCCACTCCCCCATTGGACTCACCAGACCTTCGCCG |
| | | GACGAAAGGGAAAGTCCCTCAGTCAAGCGCATGCGAC |
| | | TTTCTGAAGGATGGGCAACATGA |
| | | (SEQ ID NO: 6) |
| TBX5 | MADADEGFGLAHTPLEPDAKDLPCDSKP | ATGGCCGACGCAGACGAGGGCTTTGGCCTGGCGCACA |
| | ESALGAPSKSPSSPQAAFTQQGMEGIKV | CGCCTCTGGAGCCTGACGCAAAAGACCTGCCCTGCGA |
| | FLHERELWLKFHEVGTEMIITKAGRRMF | TTCGAAACCCGAGAGCGCGCTCGGGGCCCCCAGCAAG |
| | PSYKVKVTGLNPKTKYILLMDIVPADDH | TCCCCGTCGTCCCCGCAGGCCGCCTTCACCCAGCAGG |
| | RYKFADNKWSVTGKAEPAMPGRLYVHPD | GCATGGAGGGAATCAAAGTGTTTCTCCATGAAAGAGA |
| | SPATGAHWMRQLVSFQKLKLTNNHLDPF | ACTGTGGCTAAAATTCCACGAAGTGGGCACGGAAATG |
| | GHIILNSMHKYQPRLHIVKADENNGFGS | ATCATAACCAAGGCTGGAAGGCGGATGTTTCCCAGTT |
| | KNTAFCTHVFPETAFIAVTSYQNHKITQ | ACAAAGTGAAGGTGACGGGCCTTAATCCCAAAACGAA |
| | LKIENNPFAKGFRGSDDMELHRMSRMQS | GTACATTCTTCTCATGGACATTGTACCTGCCGACGAT |
| | KEYPVVPRSTVRQKVASNHSPESSESRA | CACAGATACAAATTCGCAGATAATAAATGGTCTGTGA |
| | LSTSSNLGSQYQCENGVSGPSQDLLPPP | CGGGCAAAGCTGAGCCCGCCATGCCTGGCCGCCTGTA |
| | NPYPLPQEHSQIYHCTKRKEEECSTTDH | CGTGCACCCAGACTCCCCCGCCACCGGGGCGCATTGG |
| | PYKKPYMETSPSEEDSFYRSSYPQQQGL | ATGAGGCAGCTCGTCTCCTTCCAGAAACTCAAGCTCA |
| | GASYRTESAQRQACMYASSAPPSEPVPS | CCAACAACCACCTGGACCCCATTTGGGCATATTATTCT |
| | LEDISCNTWPSMPSYSSCTVTTVQPMDR | AAATTCCATGCACAAATACCAGCCTAGATTACACATC |
| | LPYQHFSAHFTSGPLVPRLAGMANHGSP | GTGAAAGCGGATGAAAATAATGGATTTGGCTCAAAAA |
| | QLGEGMFQHQTSVAHQPVVRQCGPQTGL | ATACAGCGTTCTGCACTCACGTCTTTCCTGAGACTGC |
| | QSPGTLQPPEFLYSHGVPRTLSPHQYHS | GTTTATAGCAGTGACTTCCTACCAGAACCACAAGATC |
| | VHGVGMVPEWSDNS | ACGCAATTAAAGATTGAGAATAATCCCTTTGCCAAAG |
| | (SEQ ID NO: 7) | GATTTCGGGGCAGTGATGACATGGAGCTGCACAGAAT |
| | | GTCAAGAATGCAAAGTAAAGAATATCCCGTGGTCCCC |
| | | AGGAGCACCGTGAGGCAAAAAGTGGCCTCCAACCACA |
| | | GTCCTTTCAGCAGCGAGTCTCGAGCTCTCTCCACCTC |
| | | ATCCAATTTGGGGTCCCAATACCAGTGTGAGAATGGT |
| | | GTTTCCGGCCCCTCCCAGGACCTCCTGCCTCCACCCA |
| | | ACCCATACCCACTGCCCCAGGAGCATAGCCAAATTTA |
| | | CCATTGTACCAAGAGGAAAGAGGAAGAATGTTCCACC |
| | | ACAGACCATCCCTATAAGAAGCCCTACATGGAGACAT |
| | | CACCCAGTGAAGAAGATTCCTTCTACCGCTCTAGCTA |
| | | TCCACAGCAGCAGGGCCTGGGTGCCTCCTACAGGACA |
| | | GAGTCGGCACAGCGGCAAGCTTGCATGTATGCCAGCT |
| | | CTGCGCCCCCAGCGAGCCTGTGCCCAGCCTAGAGGA |
| | | CATCAGCTGCAACACGTGGCCAAGCATGCCTTCCTAC |
| | | AGCAGCTGCACCGTCACCACCGTGCAGCCCATGGACA |
| | | GGCTACCCTACCAGCACTTCTCCGCTCACTTCACCTC |
| | | GGGGCCCCTGGTCCCTCGGCTGGCTGGCATGGCCAAC |
| | | CATGGCTCCCCACAGCTGGGAGAGGGAATGTTCCAGC |
| | | ACCAGACCTCCGTGGCCCACCAGCCTGTGGTCAGGCA |
| | | GTGTGGGCCTCAGACTGGCCTGCAGTCCCCTGGCACC |
| | | CTTCAGCCCCTGAGTTCCTCTACTCTCATGGCGTGC |
| | | CAAGGACTCTATCCCCTCATCAGTACCACTCTGTGCA |
| | | CGGAGTTGGCATGGTGCCAGAGTGGAGCGACAATAGC |
| | | TAA |
| | | (SEQ ID NO: 8) |

Engineered Myocardins

Figure 9A:
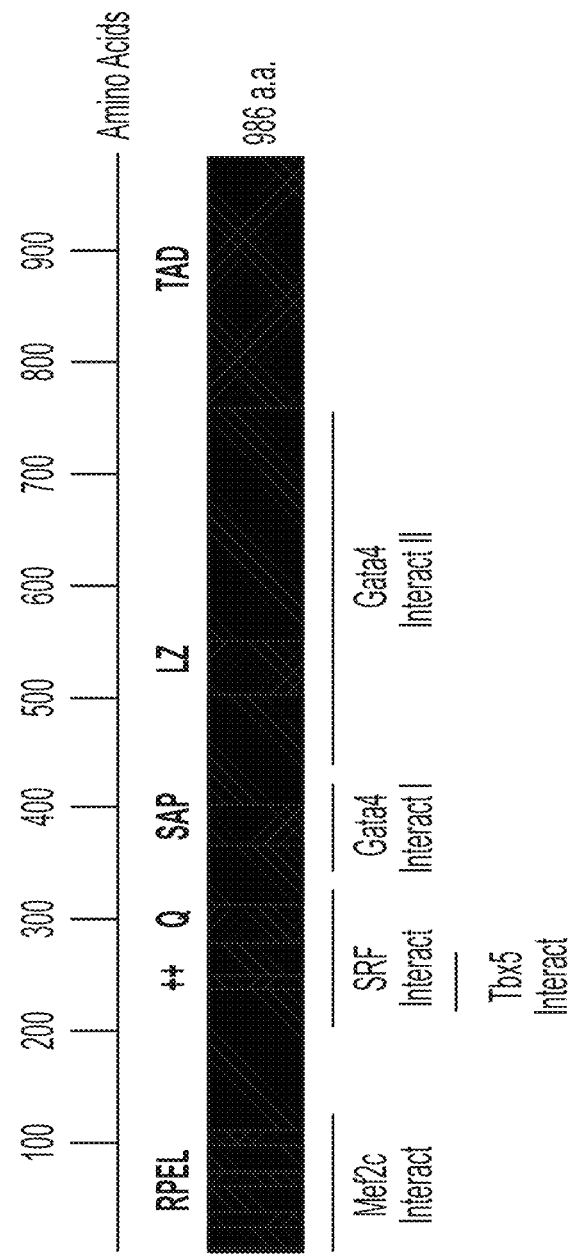
FIG. 9A-FIG. 9D show domain schematics of the native human myocardin (FIG. 1A) and three embodiments of engineered myocardin proteins with internal deletions: MyΔ1 (FIG. 1B), MyΔ2 (FIG. 1C), and MyΔ3 (FIG. 1D).
Figure 9B:
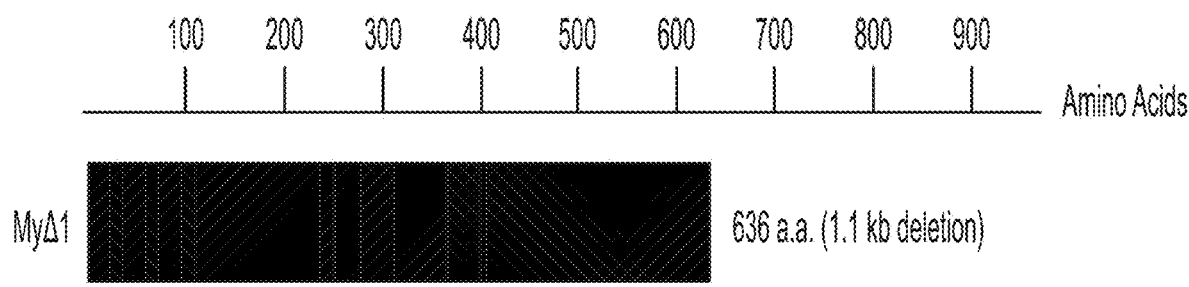
Figure 9C:
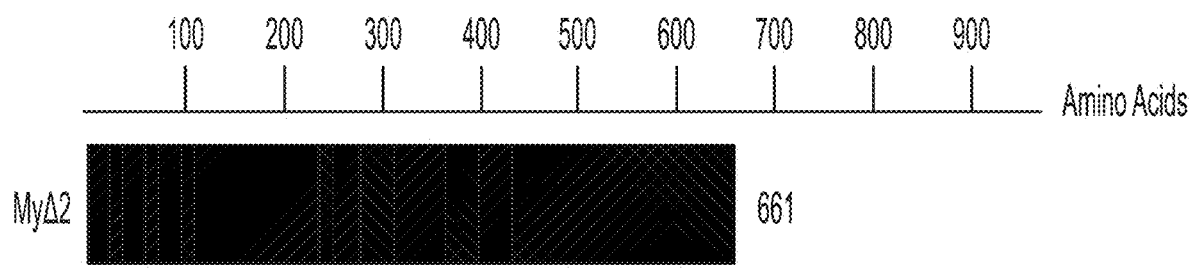
Figure 9D:
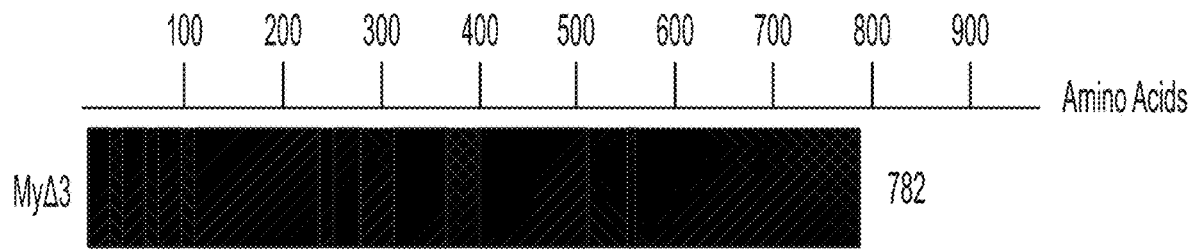

In another aspect, the disclosure relates to engineered variants of myocardin (MYOCD), such as an engineered MYOCD expressed from a smaller open reading frame, as described in U.S. Provisional Pat. Appl. No. 62/788,479. Applicant has found that MYOCD comprising an internal deletion retains the expression and function of mycocardin and MYOCD comprising an internal deletion can be used alone or in combination with other reprogramming factors (e.g., for generating cardiomyocytes from fibroblasts). In some embodiments of the present disclosure, the engineered myocardin protein comprises a deletion of at least 50 amino acids in the region corresponding to amino acids 414-764 of the native mycocardin (FIG. 9A; SEQ ID NO: 3). In some embodiments, the engineered MYOCD is selected from one or three myocardin variants with internal deletions: MyΔ1 having a deletion of residues 414 to 763 (FIG. 9B; SEQ ID NO: 14); MyΔ2 having a deletion of residues 439 to 763 (FIG. 9C; SEQ ID NO: 15); and preferably MyΔ3 having a deletion of residues 560 to 763 (FIG. 9D); SEQ ID NO: 16).

In some embodiments, the MYOCD polynucleotide is an engineered MYOCD polynucleotide. "MYOCD" or "myocardin" refers to either an engineered MYOCD protein or preferably a native MYOCD. In some embodiments, the engineered MYOCD polynucleotide encodes an engineered myocardin protein having a length of at most 500, 550, 600, 650, 700, 750, 800, 850 or any number therebetween of amino acids. In some embodiments, the engineered myocardin protein comprises an SRF interaction domain, an SAP domain, and a TAD domain. In some embodiments, the engineered myocardin protein further comprises a Mef2C internation domain. In some embodiments, the engineered MYOCD polynucleotide encodes an engineered myocardin protein, with a deletion of at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, or 350 amino acids in the region corresponding to amino acids 414-764 of the native myocardin (SEQ ID NO: 3). Various sequences used in the engineering of myocardin are provided in Table 2. In some embodiments, about four N-terminal residues of MYOCD are omitted or altered as inter-species conservation of MYOCD begins at residue 5. In some embodiments, further residues from the N terminus of MYOCD are omitted or altered.

TABLE 2

Sequences Used in Engineering of Myocardin

| | |
|---|---|
| Native MYOCD | MTLLGSEHSLLIRSKFRSVLQLRLQQRRTQEQLANQGIIPPLKRPAEFHEQRKHLDSDKAKNSL KRKARNRCNSADLVNMHILQASTAERSIPTAQMKLKRARLADDLNEKIALRPGPLELVEKNILP VDSAVKEAIKGNQVSFSKSTDAFAFEEDSSSDGLSPDQTRSEDPQNSAGSPPDAKASDTPSTGS LGTNQDLASGSENDRNDSASQPSHQSDAGKQGLGPPSTPIAVHAAVKSKSLGDSKNRHKKPKDP KPKVKKLKYHQYIPPDQKAEKSPPPMDSAYARLLQQQQLFLQLQILSQQQQQQQHRFSYLGMHQ AQLKEPNEQMVRNPNSSSTPLSNTPLSPVKNSFSGQTGVSSFKPGPLPPNLDDLKVSELRQQLR IRGLPVSGTKTALMDRLRPFQDCSGNPVPNFGDITTVTFPVTPNTLPNYQSSSSTSALSNGFYH FGSTSSSPPISPASSDLSVAGSLPDTENDASPSFGLHPSPVHVCTEESLMSSLNGGSVPSELDG LDSEKDKMLVEKQKVINELTWKLQQEQRQVEELRMQLQKQKRNNCSEKKPLPFLAASIKQEEAV SSCPFASQVPVKRQSSSSECHPPACEAAQLQPLGNAHCVESSDQTNVLSSTFLSPQCSPQHSPL GAVKSPQHISLPPSPNNPHELPSSSGAQGEGHRVSSPISSQVCTAQNSGAHDGHPPSFSPHSSS LHPPFSGAQADSSHGAGGNPCPKSPCVQQKMAGLHSSDKVGPKFSIPSPTFSKSSSAISEVTQP PSYEDAVKQQMTRSQQMDELLDVLIESGEMPADAREDHSCLQKVPKIPRSSRSPTAVLTKPSAS FEQASSGSQIPFDPYATDSDEHLEVLLNSQSPLGKMSDVTLLKIGSEEPHFDGIMDGFSGKAAE DLFNAHEILPGPLSPMQTQFSPSSVDSNGLQLSFTESPWETMEWLDLTPPNSTPGFSALTTSSP SIFNIDFLDVTDLNLNSSMDLHLQQW (SEQ ID NO: 3) |
| MYOCD 5-413 | GSEHSLLIRSKFRSVLQLRLQQRRTQEQLANQGIIPPLKRPAEFHEQRKHLDSDKAKNSLKRKA RNRCNSADLVNMHILQASTAERSIPTAQMKLKRARLADDLNEKIALRPGPLELVEKNILPVDSA VKEAIKGNQVSFSKSTDAFAFEEDSSSDGLSPDQTRSEDPQNSAGSPPDAKASDTPSTGSLGTN QDLASGSENDRNDSASQPSHQSDAGKQGLGPPSTPIAVHAAVKSKSLGDSKNRHKKPKDPKPKV KKLKYHQYIPPDQKAEKSPPPMDSAYARLLQQQQLFLQLQILSQQQQQQQHRFSYLGMHQAQLK EPNEQMVRNPNSSSTPLSNTPLSPVKNSFSGQTGVSSFKPGPLPPNLDDLKVSELRQQLRIRGL PVSGTKTALMDRLRPFQDCSGNPVP (SEQ ID NO: 10) |
| MYOCD 764-986 | EVTQPPSYEDAVKQQMTRSQQMDELLDVLIESGEMPADAREDHSCLQKVPKIPRSSRSPTAVLT KPSASFEQASSGSQIPFDPYATDSDEHLEVLLNSQSPLGKMSDVTLLKIGSEEPHFDGIMDGES GKAAEDLFNAHEILPGPLSPMQTQFSPSSVDSNGLQLSFTESPWETMEWLDLTPPNSTPGFSAL TTSSPSIFNIDFLDVTDLNLNSSMDLHLQQW (SEQ ID NO: 11) |
| MYOCD 5-438 | GSEHSLLIRSKFRSVLQLRLQQRRTQEQLANQGIIPPLKRPAEFHEQRKHLDSDKAKNSLKRKA RNRCNSADLVNMHILQASTAERSIPTAQMKLKRARLADDLNEKIALRPGPLELVEKNILPVDSA VKEAIKGNQVSFSKSTDAFAFEEDSSSDGLSPDQTRSEDPQNSAGSPPDAKASDTPSTGSLGTN QDLASGSENDRNDSASQPSHQSDAGKQGLGPPSTPIAVHAAVKSKSLGDSKNRHKKPKDPKPKV KKLKYHQYIPPDQKAEKSPPPMDSAYARLLQQQQLFLQLQILSQQQQQQQHRFSYLGMHQAQLK EPNEQMVRNPNSSSTPLSNTPLSPVKNSFSGQTGVSSFKPGPLPPNLDDLKVSELRQQLRIRGL PVSGTKTALMDRLRPFQDCSGNPVPNFGDITTVTFPVTPNTLPNYQSSSS (SEQ ID NO: 12) |
| MYOCD 1-559 | GSEHSLLIRSKFRSVLQLRLQQRRTQEQLANQGIIPPLKRPAEFHEQRKHLDSDKAKNSLKRKA RNRCNSADLVNMHILQASTAERSIPTAQMKLKRARLADDLNEKIALRPGPLELVEKNILPVDSA VKEAIKGNQVSFSKSTDAFAFEEDSSSDGLSPDQTRSEDPQNSAGSPPDAKASDTPSTGSLGTN QDLASGSENDRNDSASQPSHQSDAGKQGLGPPSTPIAVHAAVKSKSLGDSKNRHKKPKDPKPKV KKLKYHQYIPPDQKAEKSPPPMDSAYARLLQQQQLFLQLQILSQQQQQQQHRFSYLGMHQAQLK EPNEQMVRNPNSSSTPLSNTPLSPVKNSFSGQTGVSSFKPGPLPPNLDDLKVSELRQQLRIRGL PVSGTKTALMDRLRPFQDCSGNPVPNFGDITTVTFPVTPNTLPNYQSSSSTSALSNGFYHFGST SSSPPISPASSDLSVAGSLPDTENDASPSFGLHPSPVHVCTEESLMSSLNGGSVPSELDGLDSE KDKMLVEKQKVINELTWKLQQEQRQVEELRMQLQKQKRNNCSE (SEQ ID NO: 13) |
| MYOCD 1-413, 764-986 (MyΔ1) | MTLLGSEHSLLIRSKFRSVLQLRLQQRRTQEQLANQGIIPPLKRPAEFHEQRKHLDSD KAKNSLKRKARNRCNSADLVNMHILQASTAERSIPTAQMKLKRARLADDLNEKIALRP GPLELVEKNILPVDSAVKEAIKGNQVSESKSTDAFAFEEDSSSDGLSPDQTRSEDPQN SAGSPPDAKASDTPSTGSLGTNQDLASGSENDRNDSASQPSHQSDAGKQGLGPPSTPI AVHAAVKSKSLGDSKNRHKKPKDPKPKVKKLKYHQYIPPDQKAEKSPPPMDSAYARLL QQQQLFLQLQILSQQQQQQQHRFSYLGMHQAQLKEPNEQMVRNPNSSSTPLSNTPLSP VKNSFSGQTGVSSFKPGPLPPNLDDLKVSELRQQLRIRGLPVSGTKTALMDRLRPFQD CSGNPVEVTQPPSYEDAVKQQMTRSQQMDELLDVLIESGEMPADAREDHSCLQKVPK IPRSSRSPTAVLTKPSASFEQASSGSQIPFDPYATDSDEHLEVLLNSQSPLGKMSDVT LLKIGSEEPHEDGIMDGFSGKAAEDLENAHEILPGPLSPMQTQFSPSSVDSNGLQLSF TESPWETMEWLDLTPPNSTPGESALTTSSPSIFNIDELDVTDLNLNSSMDLHLQQW (SEQ ID NO: 14) |

TABLE 2-continued

Sequences Used in Engineering of Myocardin

| | |
|---|---|
| MYOCD 1-438, 764-986 (MyΔ2) | MTLLGSEHSLLIRSKFRSVLQLRLQQRRTQEQLANQGIIPPLKRPAEFHEQRKHLDSD<br>KAKNSLKRKARNRCNSADLVNMHILQASTAERSIPTAQMKLKRARLADDLNEKIALRP<br>GPLELVEKNILPVDSAVKEAIKGNQVSFSKSTDAFAFEEDSSSDGLSPDQTRSEDPQN<br>SAGSPPDAKASDTPSTGSLGTNQDLASGSENDRNDSASQPSHQSDAGKQGLGPPSTPI<br>AVHAAVKSKSLGDSKNRHKKPKDPKPKVKKLKYHQYIPPDQKAEKSPPPMDSAYARLL<br>QQQQLFLQLQILSQQQQQQQHRFSYLGMHQAQLKEPNEQMVRNPNSSSTPLSNTPLSP<br>VKNSFSGQTGVSSFKPGPLPPNLDDLKVSELRQQLRIRGLPVSGTKTALMDRLRPFQD<br>CSGNPVPNFGDITTVTFPVTPNTLPNYQSSSSEVTQPPSYEDAVKQQMTRSQQMDELL<br>DVLIESGEMPADAREDHSCLQKVPKIPRSSRSPTAVLTKPSASFEQASSGSQIPFDPY<br>ATDSDEHLEVLLNSQSPLGKMSDVTLLKIGSEEPHEDGIMDGFSGKAAEDLFNAHEIL<br>PGPLSPMQTQFSPSSVDSNGLQLSFTESPWETMEWLDLTPPNSTPGFSALTTSSPSIF<br>NIDELDVTDLNLNSSMDLHLQQW<br>(SEQ ID NO: 15) |
| MYOCD 1-559, 764-986 (MyΔ3) | MTLLGSEHSLLIRSKFRSVLQLRLQQRRTQEQLANQGIIPPLKRPAEFHEQRKHLDSD<br>KAKNSLKRKARNRCNSADLVNMHILQASTAERSIPTAQMKLKRARLADDLNEKIALRP<br>GPLELVEKNILPVDSAVKEAIKGNQVSFSKSTDAFAFEEDSSSDGLSPDQTRSEDPQN<br>SAGSPPDAKASDTPSTGSLGTNQDLASGSENDRNDSASQPSHQSDAGKQGLGPPSTPI<br>AVHAAVKSKSLGDSKNRHKKPKDPKPKVKKLKYHQYIPPDQKAEKSPPPMDSAYARLL<br>QQQQLFLQLQILSQQQQQQQHRFSYLGMHQAQLKEPNEQMVRNPNSSSTPLSNTPLSP<br>VKNSFSGQTGVSSFKPGPLPPNLDDLKVSELRQQLRIRGLPVSGTKTALMDRLRPFQD<br>CSGNPVPNFGDITTVTFPVTPNTLPNYQSSSSTSALSNGFYHFGSTSSSPPISPASSD<br>LSVAGSLPDTENDASPSFGLHPSPVHVCTEESLMSSLNGGSVPSELDGLDSEKDKMLV<br>EKQKVINELTWKLQQEQRQVEELRMQLQKQKRNNCSEEVTQPPSYEDAVKQQMTRSQQ<br>MDELLDVLIESGEMPADAREDHSCLQKVPKIPRSSRSPTAVLTKPSASFEQASSGSQI<br>PFDPYATDSDEHLEVLLNSQSPLGKMSDVTLLKIGSEEPHEDGIMDGESGKAAEDLEN<br>AHEILPGPLSPMQTQFSPSSVDSNGLQLSFTESPWETMEWLDLTPPNSTPGESALTTS<br>SPSIFNIDFLDVTDLNLNSSMDLHLQQW<br>(SEQ ID NO: 16) |
| Mef2c interaction domain (5-120) | GSEHSLLIRSKFRSVLQLRLQQRRTQEQLANQGIIPPLKRPAEFHEQRKHLDSDKAKNSLKRKA<br>RNRCNSADLVNMHILQASTAERSIPTAQMKLKRARLADDLNEKIALRPGPLE<br>(SEQ ID NO: 17) |
| SRF domain (210-320) | SASQPSHQSDAGKQGLGPPSTPIAVHAAVKSKSLGDSKNRHKKPKDPKPKVKKLKYHQYIPPDQ<br>KAEKSPPPMDSAYARLLQQQQLFLQLQILSQQQQQQQHRFSYLGMHQ<br>(SEQ ID NO: 18) |
| SAP domain (360-413) | SSFKPGPLPPNLDDLKVSELRQQLRIRGLPVSGTKTALMDRLRPFQDCSGNPVP<br>(SEQ ID NO: 19) |
| LZ domain (510-550) | LDGLDSEKDKMLVEKQKVINELTWKLQQEQRQVEELRMQLQ<br>(SEQ ID NO: 20) |
| TAD domain (764-986) | EVTQPPSYEDAVKQQMTRSQQMDELLDVLIESGEMPADAREDHSCLQKVPKIPRSSRSPTAVLT<br>KPSASFEQASSGSQIPFDPYATDSDEHLEVLLNSQSPLGKMSDVTLLKIGSEEPHEDGIMDGES<br>GKAAEDLFNAHEILPGPLSPMQTQFSPSSVDSNGLQLSFTESPWETMEWLDLTPPNSTPGFSAL<br>TTSSPSIFNIDFLDVTDLNLNSSMDLHLQQW<br>(SEQ ID NO: 11) |

In some embodiments, the engineered myocardin protein comprises one or more of an Mef2c interaction domain, an SRF domain, a SAP domain, an LZ domain, and a TAD domain. In some embodiments, the engineered myocardin protein comprises an Mef2c interaction domain, an SRF domain, a SAP domain, an LZ domain, and a TAD domain. In some embodiments, the engineered myocardin protein comprises an Mef2c interaction domain, an SRF domain, a SAP domain, and a TAD domain. In some embodiments, the engineered myocardin protein comprises an SRF domain, a SAP domain, an LZ domain, and a TAD domain. In some embodiments, the engineered myocardin protein comprises an SRF domain, a SAP domain, and a TAD domain.

In some embodiments, the engineered MYOCD is provided as a polynucleotide encoding the engineered MYOCD and, optionally, one or more other proteins of interest. In some embodiments, the polynucleotides are RNA, DNA, or mRNA polynucleotides. In some embodiments, the MYOCD polynucleotide shares identity with any of the isoforms of MYOCD. In some embodiments, the MYOCD polynucleotide encodes an engineered MYOCD protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to a sequence selected from MyΔ1 (SEQ ID NO: 14), MyΔ2 (SEQ ID NO: 15), and MyΔ3 (SEQ ID NO: 16). In some embodiments, the engineered MYOCD protein comprises at least 2, 3, 4, 5, of a Mef2c interaction domain, a SRF domain, a SAP domain, an LZ domain, and a TAD domain. In some embodiments, the Mef2c interaction domain is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 17. In some embodiments, the SRF domain is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 18. In some embodiments, the SAP domain is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 19. In some embodiments, the LZ domain is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 20. In some embodiments, the TAD domain is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 11.

In some embodiments, the engineered myocardin protein comprises two or more fragments of the native MYOCD linked by linkers. In general, a linker refers either to a peptide bond or a polypeptide sequence. In some embodiments other linkers are used, such as any of various chemical linkers used in peptide chemistry known in the art. Reference to a "peptide bond" means that two sequences are joined together to generate a composite sequence without any intervening amino acid residues. For example, MyΔ3 (SEQ ID NO: 16) comprises MYOCD 1-559 (SEQ ID NO: 13) joined by a peptide bond to MYOCD 764-986 (SEQ ID NO: 11). In some embodiments, the linker is any of various polypeptides used as linkers in the art; for example, without limitation, glycine-serine linkers such as G, GG, GGG, GSS, GGS, GGSGGS (SEQ ID NO: 30), GSSGGS (SEQ ID NO: 31), GGSGSS (SEQ ID NO: 32), GGSGGSGGS (SEQ ID NO: 33), GGSGGSGGSGGS (SEQ ID NO: 34). In some embodiments, the linker is a domain of a protein other than MYOCD.

Throughout the disclosure, expression of a polynucleotide may refer to any means known in the art to increase the expression of a gene of interest. In some embodiments, the gene of interest is encoded in the messenger RNA (mRNA). The mRNA may be synthetic or naturally occurring. In some embodiments, the mRNA is chemically modified in various ways known in the art. For example, modified RNAs may be used, such as described in Warren, L. et al. *Cell Stem Cell* 7:618-30 (2010); WO2014081507A1; WO2012019168; WO2012045082; WO2012045075; WO2013052523; WO2013090648; U.S. Pat. No. 9,572,896B2. In some embodiments, expression of the gene of interest is increased by delivery of a polynucleotide to a cell. In some embodiments, the polynucleotide encoding the gene of interest is delivered by a viral or non-viral vector. In some embodiments, the gene of interest is encoded in the DNA polynucleotide, optionally delivered by any viral or non-viral method known in the art. In some embodiments, the disclosure provides methods comprising contacting cells with a lipid nanoparticle comprising a DNA or mRNA encoding a gene of interest. In some embodiments, the methods of the disclosure comprise contacting cells with a virus comprising a DNA or RNA (e.g., a DNA genome, a negative-sense RNA genome, a positive-sense RNA genome, or a double-stranded RNA genome) encoding a gene of interest. In some embodiments, the virus is selected from a retrovirus, adenovirus, AAV, non-integrating lentiviral vector (LVV), and an integrating LVV. In some embodiments, the cells are transfected with a plasmid. In some embodiments, the plasmid comprises a polynucleotide encoding a reprogramming factor. In some embodiments, the plasmid comprises a transposon comprising a reprogramming factor B. Polynucleotides Encoding Proteins of Interest In some embodiments, the reprogramming factors are provided as a polynucleotide encoding the one or more proteins of interest. In some embodiments, the polynucleotides are RNA, DNA, or mRNA polynucleotides. In some embodiments, the polynucleotides comprise a nucleic acid sequence that comprises at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the nucleotide sequence of human ASCL1 (SEQ ID NO: 2) across at least 100, 200, 300, 400, or 500 nucleotides. In some embodiments, the ASCL1 polynucleotide shares identity with any of the isoforms of ASCL1. In some embodiments, the ASCL1 polynucleotide encodes an ASCL1 protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of human ASCL1 (SEQ ID NO: 1).

In some embodiments, the reprogramming factors are provided as a polynucleotide encoding the one or more proteins of interest. In some embodiments, the polynucleotides are RNA, DNA, or mRNA polynucleotides. In some embodiments, the polynucleotides comprise a nucleic acid sequence that comprises at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the nucleotide sequence of human MYF6 (SEQ ID NO: 56) across at least 100, 200, 300, 400, or 500 nucleotides. In some embodiments, the MYF6 polynucleotide shares identity with any of the isoforms of MYF6. In some embodiments, the MYF6 polynucleotide encodes a MYF6 protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of human MYF6 (SEQ ID NO: 55).

In some embodiments, the compositions and methods of the disclosure provide iCM cells comprising, or methods comprising administering, one or more of a myocardin (MYOCD) polynucleotide, a myocyte-specific enhancer factor 2C (MEF2C) polynucleotide, and a T-box transcription factor (TBX5) polynucleotide.

In some embodiments, the compositions and methods of the disclosure provide recombinant viruses comprising, or methods comprising administering, a myocardin (MYOCD) polynucleotide and an ASCL1 polynucleotide. In some embodiments, the compositions and methods of the disclosure provide recombinant viruses comprising, or methods comprising administering, an engineered MYOCD polynucleotide and an ASCL1 polynucleotide.

In some embodiments, the compositions and methods of the disclosure provide iCM cells or recombinant virus or non-viral vectors comprising, or methods comprising administering, an MYOCD polynucleotide. In some embodiments, the MYOCD polynucleotide encodes a MYOCD protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of human MYOCD (SEQ ID NO: 3). In some embodiments, the MYOCD polynucleotide shares at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the nucleotide sequence of human MYOCD (SEQ ID NO: 4) across at least 100, 200, 300, 400, or 500 nucleotides. In some embodiments, the MYOCD polynucleotide shares identity with any of the isoforms of MYOCD.

In some embodiments, the engineered myocardin protein is provided as a polynucleotide encoding the engineered myocardin protein.

In some embodiments, the MYOCD polynucleotide encodes a MYOCD protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of an engineered MYOCD (e.g., SEQ ID NOs: 14).

In some embodiments, the MYOCD polynucleotide encodes a MYOCD protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of an engineered MYOCD (e.g., SEQ ID NOs: 15).

In some embodiments, the MYOCD polynucleotide encodes a MYOCD protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of an engineered MYOCD (e.g., SEQ ID NOs: 16).

In some embodiments, the compositions and methods of the disclosure provide iCM cells or recombinant viruses or non-viral vectors comprising, or methods comprising administering, an MEF2C polynucleotide. In some embodiments, the MEF2C polynucleotide encodes a MEF2C protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of human MEF2C (SEQ ID NO: 5). In some embodiments, the MEF2C polynucleotide shares at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the nucleotide sequence of human MEF2C (SEQ ID NO: 6) across at least 100, 200, 300, 400, or 500 nucleotides. In some embodiments, the MEF2C polynucleotide shares identity with any of the isoforms of MEF2C.

In some embodiments, the compositions and methods of the disclosure provide iCM cells or recombinant viruses or non-viral vectors comprising, or methods comprising administering, an TBX5 polynucleotide. In some embodiments, the TBX5 polynucleotide encodes a TBX5 protein that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the sequence of human TBX5 (SEQ ID NO: 7). In some embodiments, the TBX5 polynucleotide shares at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identity to the nucleotide sequence of human TBX5 (SEQ ID NO: 8) across at least 100, 200, 300, 400, or 500 nucleotides. In some embodiments, the TBX5 polynucleotide shares identity with any of the isoforms of TBX5. The TBX5 polypeptide contains a predicted nuclear localization sequence (NLS), KRKEEECSTTDHPYKKPYME (SEQ ID NO: 9). In some embodiments, the NLS of the polypeptide encoded by the TBX5 polynucleotide is a functional NLS.

In some embodiments, the polynucleotide encoding a protein of interest is a synthetic messenger RNA (mRNA). Synthetic mRNAs provide the genetic information for making proteins of interest and can be chemically modified to avoid triggering an immune response. Zangi et al. (2013) *Nature Biotech* 31:898-907. Since mRNAs do not integrate into the host cell genome, the synthetic mRNA acts for a period of time and then disappears as the cell divides. In some embodiments the synthetic mRNAs are modified, for example, with pseudouridine and/or 5-methyl-cytidine, to reduce innate antiviral response to single-stranded RNA.

In some embodiments, the polynucleotides encoding the one or more proteins of interest may be codon-optimized or otherwise altered so long as the functional activity of the encoded gene is preserved. In some embodiments, the polynucleotides encode a modified or variant of the one or more genes of interest, including truncations, insertions, deletions, or fragments, so long as the functional activity of the encoded gene is preserved.

In some embodiments, the polynucleotides encoding the one or more proteins of interest are comprised in an expression cassette. In some embodiments, the expression cassette comprises one or more polynucleotides encoding one or more genes of interest. For example, in some embodiments, the expression cassette comprises 2, 3, 4, 5, 6, 7, 8, 9, or 10 polynucleotides encoding 2, 3, 4, 5, 6, 7, 8, 9, or 10 genes of interest.

It will be appreciated that where two or more proteins of interest are to be expressed in a cell, one or polynucleotides or expression cassettes can be used. For example, a polycistronic expression cassette can be used wherein one expression cassette can comprise multiple polynucleotides expressing multiple proteins. In some embodiments, the polycistronic expression cassette comprises two or more polynucleotides in a single open reading frame, the polynucleotides linked together by the 2A region of aphthovirus foot-and-mouth disease virus (FMDV) polyprotein, such as described in Donnelly et al. *J. Gen. Virol.* 82:1013-15 (2001) and improvements thereof known in the art. The 2A region produces a ribosomal 'skip' from one codon to the next without the formation of a peptide bond. In some embodiments, the polynucleotide comprises an internal cleavage site, such that two or more peptides are generated by post-translational cleavage.

In some embodiments, multicistronic vectors of the present disclosure comprise a polynucleotide sequence encoding a plurality of polypeptides joined by linkers comprising peptides capable of inducing ribosome skipping or self-cleavage. In some embodiments, the linker comprises a 2A peptide. The term "2A peptide" as used herein refers to a class of ribosome skipping or self-cleaving peptides configured to generate two or more proteins from a single open reading frame. 2A peptides are 18-22 residue-long viral oligopeptides that mediate "cleavage" of polypeptides during translation in eukaryotic cells. "2A peptide" may refer to peptides with various amino acid sequences. In the present disclosure it will be understood that where a lentiviral vector comprises two or more 2A peptides, the 2A peptides may be identical to one another or different. Detailed methodology for design and use of 2A peptides is provided by Szymczak- Workman et al. Design and Construction of 2A Peptide-Linked Multicistronic Vectors. *Cold Spring Harb. Protoc.* 2012 Feb. 1; 2012(2):199-204. In the literature, 2A peptides are often refered to as self-cleaving peptides, but mechanistic studies have shown that the "self-cleavage" observed is actually a consequence of the ribosome skipping the formation of the glycyl-prolyl peptide bond at the C terminus of the 2A peptide. Donnelly et al. *J Gen Virol.* 2001 May; 82(Pt 5):1027-41. The present invention is not bound by theory or limited to ay particular mechanistic understanding of 2A peptide function.

Exemplary 2A peptides include, without limitation, those listed in Table 3.

TABLE 3

Exemplary 2A peptides

| | Source | Nucleotide | Peptide |
|---|---|---|---|
| P2A | porcine teschovirus-1 | GCC ACG AAC TTC TCT CTG TTA AAG CAA GCA GGA GAC GTG GAA GAA AAC CCC GGT CCT (SEQ ID NO: 21) - or - GCT ACT AAC TTC AGC CTG CTG AAG CAG GCT GGA GAC GTG GAG GAG AAC CCT GGA CCT (SEQ ID NO: 22) | ATNFSLLKQAGDVEENPGP (SEQ ID NO: 23) |
| T2A | Thoseaasigna virus | GAG GGC AGA GGA AGT CTG CTA ACA TGC GGT GAC GTC GAG GAG AAT CCT GGA CCT (SEQ ID NO: 24) | EGRGSLLTCGDVEENPGP (SEQ ID NO: 25) |
| E2A | Equine rhinitis A virus (ERAV) | CAG TGT ACT AAT TAT GCT CTC TTG AAA TTG GCT GGA GAT GTT GAG AGC AAC CCT GGA CCT (SEQ ID NO: 26) | QCTNYALLKLAGDCESNPGP (SEQ ID NO: 27) |
| F2A | Foot-and-mouth disease virus (FMDV) | GTG AAA CAG ACT TTG AAT TTT GAC CTT CTC AAG TTG GCG GGA GAC GTG GAG TCC AAC CCT GGA CCT (SEQ ID NO: 28) | VKQTLNFDLLKLAGDVESNPGP (SEQ ID NO: 29) |

Optionally, one or more of the linkers further comprises a sequence encoding the residues Gly-Ser-Gly, which is in some embodiments N-terminal to the 2A peptide. N-terminal to the 2A peptide means that the sequence encoding the residues is upstream to the sequence encoding the 2A peptide. Generally, the Gly-Ser-Gly motif will be immediately N-terminal to the 2A peptide or 1 to 10 other amino acid residues are inserted between the motif and the 2A peptide. In some embodiments, the polynucleotide sequence encoding this motif is GGA AGC GGA. As with any peptide-encoding polynucleotide, the nucleotide sequence may be altered without changing the encoded peptide sequence. Substitution of amino acid residues is within the skill of those in the art, and it will be understood that the term 2A peptide refers to variants of the foregoing that retain the desired skipping/self-cleavage activity but, optionally, have 1, 2, 3, 4, 5, 6, 7, 8, 9, 10 or more substitutions relative to the reference 2A peptide sequence. Exemplary 2A peptides are described in Kim et al. PLOS ONE 6(4): e18556. In some embodiments, two or more different 2A peptides are used in the same construct. Varied 2A peptides have been reported to result in improved expression. See Liu et al. *Sci Rep.* 2017; 7:2193 In some embodiments, the polypeptide comprises a between 1 and 5, or more than 5, Gly or Ser residues N- and/or C-terminal to the 2A peptide (e.g. the P2A peptide). In some embodiments, the polypeptide comprises a Gly-Ser-Gly residues N- and/or C-terminal to the 2A peptide (e.g. the P2A peptide). In some embodiments, the P2A peptide and N-terminal linker comprise SEQ ID NO: 84.

In some embodiments, the disclosure provides an expression cassette comprising, in 5' to 3' order, a promoter, a polynucleotide encoding MYOCD-2A-ASCL1, and a polyadenylation sequence. In some embodiments, the expression cassette comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 35. In some embodiments, the disclosure provides a recombinant AAV (rAAV) comprising the expression cassette, a transfer plasmid comprising the expression cassette, or a rAAV particle comprising the expression cassette. In some embodiments, the rAAV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 35. In some embodiments, the disclosure provides a recombinant lentivirus (rLV) comprising the expression cassette, a transfer plasmid comprising the expression cassette, or a rLV particle comprising the expression cassette. In some embodiments, the rLV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 35.

In some embodiments, the disclosure provides an expression cassette comprising, in 5' to 3' order, a promoter, a polynucleotide encoding MYOCD-2A-MYF6, and a polyadenylation sequence. In some embodiments, the expression cassette comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 36. In some embodiments, the disclosure provides a rAAV comprising the expression cassette, a transfer plasmid comprising the expression cassette, or a rAAV particle comprising the expression cassette. In some embodiments, the rAAV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 36. In some embodiments, the disclosure provides a rLV comprising the expression cassette, a transfer plasmid comprising the expression cassette, or a rLV particle comprising the expression cassette. In some embodiments, the rLV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 36.

In some embodiments, the disclosure provides an expression cassette comprising, in 5' to 3' order, a promoter, a polynucleotide encoding MyΔ3-2A-ASCL1, and a polyadenylation sequence. In some embodiments, the expression cassette comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 37. In some embodiments, the disclosure provides a rAAV comprising the expression cassette, a transfer plasmid comprising the expression cassette, or a rAAV particle comprising the expression cassette. In some embodiments, the rAAV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 37. In some embodiments, the disclosure provides a rLV comprising the expression cassette, a transfer plasmid comprising the expression cassette, or a rLV particle comprising the expression cassette. In some embodiments, the rLV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 37.

In some embodiments, the disclosure provides an expression cassette comprising, in 5' to 3' order, a promoter, a polynucleotide encoding MyΔ3-2A-MYF6, and a polyadenylation sequence. In some embodiments, the expression cassette comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 38. In some embodiments, the disclosure provides a rAAV comprising the expression cassette, a transfer plasmid comprising the expression cassette, or a rAAV particle comprising the expression cassette. In some embodiments, the rAAV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 38. In some embodiments, the disclosure provides a rLV comprising the expression cassette, a transfer plasmid comprising the expression cassette, or a rLV particle comprising the expression cassette. In some embodiments, the rLV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 38.

In some embodiments, the disclosure provides an expression cassette comprising, in 5' to 3' order, a promoter, a polynucleotide encoding ASCL1-2A-MYOCD, and a polyadenylation sequence. In some embodiments, the expression cassette comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 39. In some embodiments, the disclosure provides a rAAV comprising the expression cassette, a transfer plasmid comprising the expression cassette, or a rAAV particle comprising the expression cassette. In some embodiments, the rAAV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 39. In some embodiments, the disclosure provides a rLV comprising the expression cassette, a transfer plasmid comprising the expression cassette, or a rLV particle comprising the expression cassette. In some embodiments, the rLV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 39.

In some embodiments, the disclosure provides an expression cassette comprising, in 5' to 3' order, a promoter, a polynucleotide encoding MYF6-2A-MYOCD, and a polyadenylation sequence. In some embodiments, the expression cassette comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 40. In some embodiments, the disclosure provides a rAAV comprising the expression cassette, a transfer plasmid comprising the expression cassette, or a rAAV particle comprising the expression cassette. In some embodiments, the rAAV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 40. In some embodiments, the disclosure provides a rLV comprising the expression cassette, a transfer plasmid comprising the expression cassette, or a rLV particle comprising the expression cassette. In some embodiments, the rLV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 40.

In some embodiments, the disclosure provides an expression cassette comprising, in 5' to 3' order, a promoter, a polynucleotide encoding ASCL1-2A-MyΔ3, and a polyadenylation sequence. In some embodiments, the expression cassette comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 41. In some embodiments, the disclosure provides a rAAV comprising the expression cassette, a transfer plasmid comprising the expression cassette, or a rAAV particle comprising the expression cassette. In some embodiments, the rAAV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 41. In some embodiments, the disclosure provides a rLV comprising the expression cassette, a transfer plasmid comprising the expression cassette, or a rLV particle comprising the expression cassette. In some embodiments, the rLV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 41.

In some embodiments, the disclosure provides an expression cassette comprising, in 5' to 3' order, a promoter, a polynucleotide encoding MYF6-2A-MyΔ3, and a polyadenylation sequence. In some embodiments, the expression cassette comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 42. In some embodiments, the disclosure provides a rAAV comprising the expression cassette, a transfer plasmid comprising the expression cassette, or a rAAV particle comprising the expression cassette. In some embodiments, the rAAV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 42. In some embodiments, the disclosure provides a rLV comprising the expression cassette, a transfer plasmid comprising the expression cassette, or a rLV particle comprising the expression cassette. In some embodiments, the rLV comprises a polynucleotide at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO: 42.

In some embodiments, the disclosure provides an expression cassette comprising a polynucleotide encoding a protein sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to any one of SEQ ID NOs: 57-64 (i.e., any one of MYOCD-2A-ASCL1, MYOCD-2A-MYF6, MyΔ3-2A-ASCL1, MyΔ3-2A-MYF6, ASCL1-2A-MYOCD, MYF6-2A-MYOCD, ASCL1-2A-MyΔ3, and MYF6-2A-MyΔ3).

III. Vectors

In some embodiments, the reprogramming factors employed to reprogram cells to the cardiac lineage can be introduced into a selected cell or a selected population of cells by a vector. In some embodiments, the vector is a nucleic acid vector, such as a plasmids (e.g., DNA plasmids or RNA plasmids), transposons, cosmids, bacterial or yeast artificial chromosomes, or viral vectors. In some embodiments, the vector is a non-nucleic acid vector, such as a nanoparticle. In some embodiments, the vectors described herein comprise a peptide, such as cell-penetrating peptides or cellular internalization sequences. Cell-penetrating peptides are small peptides that are capable of translocating across plasma membranes. Exemplary cell-penetrating peptides include, but are not limited to, Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynBl, Pep-7, I-IN-1, BGSC (Bis-Guanidinium-Spermidine-Cholesterol, and BGTC (Bis-Guanidinium-Tren-Cholesterol).

Techniques in the field of recombinant genetics can be used for such recombinant expression. Basic texts disclosing general methods of recombinant genetics include Sambrook et al., *Molecular Cloning, A Laboratory Manual* (3rd ed. 2001); Kriegler, Gene *Transfer and Expression: A Laboratory Manual* (1990); and *Current Protocols in Molecular Biology* (Ausubel et al., eds., 1994)). In some embodiments, the vectors do not contain a mammalian origin of replication. In some embodiments, the expression vector is not integrated into the genome and/or is introduced via a vector that does not contain a mammalian origin of replication.

In some cases, the expression vector(s) encodes or comprises, in addition to one or more reprogramming factors, a marker gene that facilitates identification or selection of cells that have been transfected, transduced or infected. Examples of marker genes include, but are not limited to, genes encoding fluorescent proteins, e.g., enhanced green fluorescent protein, Ds-Red (DsRed: Discosoma sp. red fluorescent protein (RFP); Bevis et al. (2002) Nat. Biotechnol. 20(11):83-87), yellow fluorescent protein, mCherry, and cyanofluorescent protein; and genes encoding proteins conferring resistance to a selection agent, e.g., a neomycin resistance gene, a puromycin resistance gene, a blasticidin resistance gene, and the like.

In one embodiment, the expression vector further comprises a suicide gene. Expression of the suicide gene may be regulated by the same or different promoter that expresses at least one proliferation and/or cell cycle reentry factor polypeptide-encoding nucleotide. A suicide gene is one that allows for negative selection of the cells. In the methods described herein, a suicide gene is used as a safety system, allowing the cells expressing the gene to be killed by introduction of a selective agent. This is desirable in case the recombinant gene causes a mutation leading to uncontrolled cell growth. A number of suicide gene systems have been identified, including the herpes simplex virus thymidine kinase (tk or TK) gene, the cytosine deaminase gene, the varicella-zoster virus thymidine kinase gene, the nitroreductase gene, the *Escherichia coli* (*E. coli*) gpt gene, and the *E. coli* Deo gene (also see, for example, Yazawa K, Fisher W E, Brunicardi F C: Current progress in suicide gene therapy for cancer. World J. Surg. (2002) 26(7):783-9). In one embodiment, the suicide gene is the TK gene. In one aspect, the TK gene is a wild-type TK gene. In other aspects, the TK gene is a mutated form of the gene, e.g., sr23tk. Cells expressing the TK protein can be killed using ganciclovir. In another embodiment, the nucleic acid encoding the tetracycline activator protein and the suicide gene are regulated by one promoter.

A. Nucleic Acid Vectors

1. Viral Vectors

Suitable viral vectors include, but are not limited to, viral vectors (e.g. viral vectors based on vaccinia virus; poliovirus; adenovirus (e.g., Li et al. (1994) Invest Opthalmol Vis Sci 35:2543-2549; Borras et al. (1999) Gene Ther 6:515-524; Li and Davidson, (1995) Proc. Natl. Acad. Sci. 92:7700-7704; Sakamoto et al. (1999) Hum Gene Ther 5: 1088-1097; WO 94/12649; WO 93/03769; WO 93/19191; WO 94/28938; WO 95/11984 and WO 95/00655); adeno-associated virus (e.g., Ali et al. (1998) Hum Gene Ther 9(1):81-86, 1998, Flannery et al. (1997) Proc. Natl. Acad. Sci. 94:6916-6921; Bennett et al. (1997) Invest Opthalmol Vis Sci 38:2857-2863; Jomary et al. (1997) Gene Ther 4:683-690; Rolling et al. (1999), Hum Gene Ther 10:641-648; Ali et al. (1996) Hum Mol Genet. 5:591-594; WO 93/09239, Samulski et al. (1989) J. Vir. 63:3822-3828; Mendelson et al. (1988) Virol. 166: 154-165; and Flotte et al. (1993) Proc. Natl. Acad. Sci. 90: 10613-10617; SV40; herpes simplex virus; human immunodeficiency virus (e.g., Miyoshi et al. (1997) Proc. Natl. Acad. Sci. 94: 10319-10323; Takahashi et al. (1999) J Virol 73:7812-7816); a retroviral vector (e.g., Murine-Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. Numerous suitable expression vectors are known to those of skill in the art, and many are commercially available. The following vectors are provided by way of example; for eukaryotic cells: pXT1, pSG5 (Stratagene), pSVK3, pBPV, pMSG, pSVLSV40 (Pharmacia), and pAd (Life Technologies). However, any other vector may be used so long as it is compatible with the cells of the present disclosure.

The ability of certain viruses to infect cells or enter cells via receptor-mediated endocytosis, and express viral genes stably and efficiently have made them attractive candidates for the transfer of foreign nucleic acids into cells (e.g., mammalian cells). Viral vectors can include control sequences such as promoters for expression of the polypeptide of interest. Although many viral vectors integrate into the host cell genome, if desired, the segments that allow such integration can be removed or altered to prevent such integration. Moreover, in some embodiments, the vectors do not contain a mammalian origin of replication. Non-limiting examples of virus vectors are described below that can be used to deliver nucleic acids encoding a transcription factor into a selected cell. In some embodiments, the viral vector is derived from a replication-deficient virus.

In general, other useful viral vectors are based on non-cytopathic eukaryotic viruses in which non-essential genes have been replaced with the polypeptide of interest. Non-cytopathic viruses include certain retroviruses, the life cycle of which involves reverse transcription of genomic viral RNA into DNA with subsequent proviral integration into host cellular DNA. In general, the retroviruses are replication-deficient (e.g., capable of directing synthesis of the desired transcripts, but incapable of manufacturing an infectious particle). Such genetically altered retroviral expression vectors have general utility for the high-efficiency transduction of polynucleotide in vivo.

In some embodiments, a polynucleotide encoding a reprogramming factor can be housed within an infective virus that has been engineered to express a specific binding ligand. The virus particle will thus bind with specificity to the cognate receptors of the target cell and deliver the contents to the cell. In some embodiments, the virus is modified to impart particular viral tropism, e.g., the virus preferentially infects fibroblasts, heart cells, or more particularly cardiac fibroblasts (CFs). For AAV, capsid proteins can be mutated to alter the tropism of the viral vector. For lentivirus, tropism can be modified by using different envelope proteins; this is known as "pseudotyping."

a. Retroviral Vectors

In some embodiments, the viral vector is a retroviral vector. Retroviruses can integrate their genes into the host genome, transfer a large amount of foreign genetic material, infect a broad spectrum of species and cell types, and can be packaged in special cell-lines (Miller et al., *Am. J. Clin. Oncol.*, 15(3):216-221, 1992). In some embodiments, a retroviral vector is altered so that it does not integrate into the host cell genome.

The recombinant retrovirus may comprise a viral polypeptide (e.g., retroviral env) to aid entry into the target cell. Such viral polypeptides are well-established in the art, for example, U.S. Pat. No. 5,449,614. The viral polypeptide may be an amphotropic viral polypeptide, for example, amphotropic env, which aids entry into cells derived from multiple species, including cells outside of the original host species. The viral polypeptide may be a xenotropic viral polypeptide that aids entry into cells outside of the original host species. In some embodiments, the viral polypeptide is an ecotropic viral polypeptide, for example, ecotropic env, which aids entry into cells of the original host species.

Examples of viral polypeptides capable of aiding entry of retroviruses into cells include, but are not limited to: MMLV amphotropic env, MMLV ecotropic env, MMLV xenotropic env, vesicular stomatitis virus-g protein (VSV-g), HIV-1 env, Gibbon Ape Leukemia Virus (GALV) env, RD114, FeLV-C, FeLV-B, MLV 10A1 env gene, and variants thereof, including chimeras. Yee et al. (1994) Methods Cell Biol, Pt A:99-112 (VSV-G); U.S. Pat. No. 5,449,614. In some cases, the viral polypeptide is genetically modified to promote expression or enhanced binding to a receptor.

The retroviral construct may be derived from a range of retroviruses, e.g., MMLV, HIV-1, SIV, FIV, or other retrovirus described herein. The retroviral construct may encode all viral polypeptides necessary for more than one cycle of replication of a specific virus. In some cases, the efficiency of viral entry is improved by the addition of other factors or other viral polypeptides. In other cases, the viral polypeptides encoded by the retroviral construct do not support more than one cycle of replication, e.g., U.S. Pat. No. 6,872,528. In such circumstances, the addition of other factors or other viral polypeptides can help facilitate viral entry. In an exemplary embodiment, the recombinant retrovirus is HIV-1 virus comprising a VSV-g polypeptide, but not comprising a HIV-1 env polypeptide.

The retroviral construct may comprise: a promoter, a multi-cloning site, and/or a resistance gene. Examples of promoters include but are not limited to CMV, SV40, EF1a, β-actin; retroviral LTR promoters, and inducible promoters. The retroviral construct may also comprise a packaging signal (e.g., a packaging signal derived from the MFG vector; a psi packaging signal). Examples of some retroviral constructs known in the art include but are not limited to: pMX, pBabeX or derivatives thereof. Onishi et al. (1996) Experimental Hematology, 24:324-329. In some cases, the retroviral construct is a self-inactivating lentiviral vector (SIN) vector. Miyoshi et al. (1998) J. Virol 72(10):8150-8157. In some cases, the retroviral construct is LL-CG, LS-CG, CL-CG, CS-CG, CLG or MFG. Miyoshi et al. (1998) J. Virol 72(10):8150-8157; Onishi et al. (1996) Experimental Hematology, 24:324-329; Riviere et al. (1995) Proc. Natl. Acad. Sci., 92:6733-6737.

A retroviral vector can be constructed by inserting a nucleic acid (e.g., one encoding a polypeptide of interest or an RNA) into the viral genome in the place of some viral sequences to produce a virus that is replication-defective. To produce virions, a packaging cell line containing the gag, pol, and env genes, but without the LTR and packaging components, is constructed (Mann et al., Cell 33:153-159, 1983). When a recombinant plasmid containing a cDNA, together with the retroviral LTR and packaging sequences is introduced into a special cell line (e.g., by calcium phosphate precipitation), the packaging sequence allows the RNA transcript of the recombinant plasmid to be packaged into viral particles, which are then secreted into the culture media (Nicolas and Rubinstein, In: Vectors: A survey of molecular cloning vectors and their uses, Rodriguez and Denhardt, eds., Stoneham: Butterworth, pp. 494-513, 1988; Temin, In: Gene Transfer, Kucherlapati (ed.), New York: Plenum Press, pp. 149-188, 1986; Mann et al., Cell, 33:153-159, 1983). The media containing the recombinant retroviruses is then collected, optionally concentrated, and used for gene transfer. Retroviral vectors are able to infect a broad variety of cell types. However, integration and stable expression typically involves the division of host cells (Paskind et al., Virology, 67:242-248, 1975).

b. Adenoviral Vectors

In some embodiments, the viral vector is an adenoviral vector. The genetic organization of adenovirus includes an approximate 36 kb, linear, double-stranded DNA virus, which allows substitution of large pieces of adenoviral DNA with foreign sequences up to 7 kb (Grunhaus et al., Seminar in Virology 200(2):535-546, 1992)). Reprogramming factors may be introduced into the cell using adenovirus assisted transfection. Increased transfection efficiencies have been reported in cell systems using adenovirus coupled systems (Kelleher and Vos, Biotechniques, 17(6):1110-7, 1994; Cotten et al., Proc Natl Acad Sci USA, 89(13):6094-6098, 1992; Curiel, Nat Immun, 13(2-3):141-64, 1994.).

c. Adeno-Associated Viral (AAV) Vectors

In some embodiments, the viral vector is an AAV vector. AAV is an attractive vector system as it has a low frequency of integration and it can infect non-dividing cells, thus making it useful for delivery of polynucleotides into mammalian cells, for example, in tissue culture (Muzyczka, Curr Top Microbiol Immunol, 158:97-129, 1992) or in vivo. Details concerning the generation and use of rAAV vectors are described in U.S. Pat. Nos. 5,139,941 and 4,797,368, each incorporated herein by reference in its entirety.

AAV is a replication-deficient parvovirus, the single-stranded DNA genome of which is about 4.7 kb in length including two 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 (1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively; the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). The sequence of the AAV rh.74 genome is provided in U.S. Pat. No. 9,434,928, incorporated herein by reference. Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and pi 9), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA. To generate AAV vectors, the rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection. The AAV vectors of the disclosure include self-complementary, duplexed AAV vectors, synthetic ITRs, and/or AAV vectors with increased packaging compacity. Illustrative methods are provided in U.S. Pat. Nos. 8,784,799; 8,999,678; 9,169,494; 9,447,433; and 9,783,824, each of which is incorporated by reference in its entirety.

AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10, AAV-11, AAV-12, AAV-13 and AAV rh74. Production of pseudotyped rAAV is disclosed in, for example, WO 01/83692. Other types of rAAV variants, for example rAAV with capsid mutations, are also contemplated. See, for example, Marsic et al., Mol. Therapy. 22):1900-09 (2014). The nucleotide sequences of the genomes of various AAV serotypes are known in the art. AAV vectors of the present disclosure include AAV vectors of serotypes AAV1, AAV2, AAV4, AAV5, AAV6, AAV7, AAV8, AAV9, AAV10, AAV39, AAV43, AAV.rh74, and AAV.rh8. Illustrative AAV vectors are provided in U.S. Pat. No. 7,105,345; U.S. Ser. No. 15/782,980; U.S. Pat. Nos. 7,259,151; 6,962,815; 7,718,424; 6,984,517; 7,718,424; 6,156,303; 8,524,446; 7,790,449; 7,906,111; 9,737,618; U.S. application Ser. No. 15/433,322; U.S. Pat. No. 7,198,951, each of which is incorporated by reference in its entirety.

In some embodiments, the AAV expression vector is pseudotyped to enhance targeting. To promote gene transfer and sustain expression in fibroblasts, AAV5, AAV7, and AAV8, may be used. In some cases, the AAV2 geneome is packaged into the capsid of producing pseudotyped vectors AAV2/5, AAV2/7, and AAV2/8 respectively, as described in Balaji et al. *J Surg Res.* 184:691-98 (2013). In some embodiments, an AAV9 may be used to target expression in myofibroblast-like lineages, as described in Piras et al. *Gene Therapy* 23:469-478 (2016). In some embodiments, AAV1, AAV6, or AAV9 is used, and in some embodiments, the AAV is engineered, as described in Asokari et al. *Hum Gene Ther.* 24:906-13 (2013); Pozsgai et al. Mol Ther. 25:855-69 (2017); Kotterman et al. *Nature Reviews Genetics* 15:445-51 (2014); and US20160340393A1 to Schaffer et al. In some embodiments, the viral vector is AAV engineered to increase target cell infectivity as described in US20180066285A1.

In some embodiments, the AAV vectors of the disclosure comprises a modified capsid, in particular as capsid engineered to enhance or promote in vivo or ex vivo transduction of cardiac cells, or more particularly cardiac fibroblasts; or that evade the subject's immune system; or that have improved biodistribrution. Illustrative AAV capsids are provided in U.S. Pat. Nos. 7,867,484; 9,233,131; 10,046,016; WO 2016/133917; WO 2018/222503; and WO 20019/060454, each of which is incorporated by reference in its entirety. In an AAV capsid (or in particular an AAV2 capsid), one or more substitutions at E67, S207, N551, and I698 may be used to increase infectivity towards cardiac fibroblasts. More particularly, the AAV vectors of the disclosue, optionally AAV2-based vectors, may comprise in their capsid proteins one or more substitutions selected from E67A, S207G, V229I, A490T, N551S, A581T, and I698V. In some embodiments, the AAV vectors of the disclosure comprise the AAV-A2 capsid and/or serotype, which is described in WO 2018/222503. In some embodiments, the AAV capsid comprises an insertion in the GH loop of the capsid protein, such as NKIQRTD (SEQ ID NO: 65) or NKTTNKD (SEQ ID NO: 66). It will be appreciated that these substitutions and insertions may be combined together to generate various capsid proteins useful in the present disclosure.

d. Lentiviral Vectors

In some embodiments, the viral vector is a lentiviral vector. Lentiviruses are complex retroviruses, which, in addition to the common retroviral genes gag, pol, and env, contain other genes with regulatory or structural function. Information on lentiviral vectors is available, for example, in Naldini et al., *Science* 272(5259):263-267, 1996; Zufferey et al., *Nat Biotechnol* 15(9):871-875, 1997; Blomer et al., *J Virol.* 71(9):6641-6649, 1997; U.S. Pat. Nos. 6,013,516 and 5,994,136, each of which is incorporated herein by reference in its entirety. Some examples of lentivirus include the Human Immunodeficiency Viruses: HIV-1, HIV-2 and the Simian Immunodeficiency Virus: SIV. Lentiviral vectors have been generated by attenuating the HIV virulence genes, for example, the genes env, vif, vpr, vpu and nef are deleted to make the vector biologically safe. The lentivirus employed can also be replication and/or integration defective.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, which is incorporated herein by reference in its entirety. Those of skill in the art can target the recombinant virus by linkage of the envelope protein with an antibody or a particular ligand for targeting to a receptor of a particular cell type. For example, a target-specific vector can be generated by inserting a nucleic acid segment (including a regulatory region) of interest into the viral vector, along with another gene that encodes a ligand for a receptor on a specific target cell type.

Lentiviral vectors are known in the art, see Naldini et al., (1996 and 1998); Zufferey et al., (1997); Dull et al., 1998, U.S. Pat. Nos. 6,013,516; and 5,994,136 all incorporated herein by reference. In general, these vectors are plasmid-based or virus-based, and are configured to carry the essential sequences for incorporating foreign nucleic acid, for selection and for transfer of the nucleic acid into a host cell. In some cases, a lentiviral vector is introduced into a cell concurrently with one or more lentiviral packaging plasmids, which may include, without limitation, pMD2.G, pRSV-rev, pMDLG-pRRE, and pRRL-GOI. Introduction of a lentiviral vector alone or in combination with lentiviral packaging plasmids into a cell may cause the lentiviral vector to be packaged into a lentiviral particle. In some embodiments, the lentiviral vector is a non-integrating lentiviral (NIL) vector. Illustrative methods for generating NIL vectors, such as the D64V substitution in the integrase gene, are provided in U.S. Pat. No. 8,119,119.

2. Methods of Producing Viral Vectors

In general, a viral vector is produced by introducing a viral DNA or RNA construct into a producer cell. In some cases, the producer cell does not express exogenous genes. In other cases, the producer cell is a "packaging cell" comprising one or more exogenous genes, e.g., genes encoding one or more gag, pol, or env polypeptides and/or one or more retroviral gag, pol, or env polypeptides. The retroviral packaging cell may comprise a gene encoding a viral polypeptide, e.g., VSV-g, that aids entry into target cells. In some cases, the packaging cell comprises genes encoding one or more lentiviral proteins, e.g., gag, pol, env, vpr, vpu, vpx, vif, tat, rev, or nef. In some cases, the packaging cell comprises genes encoding adenovirus proteins such as E1 A or E1 B or other adenoviral proteins. For example, proteins supplied by packaging cells may be retrovirus-derived proteins such as gag, pol, and env; lentivirus-derived proteins such as gag, pol, env, vpr, vpu, vpx, vif, tat, rev, and nef; and adenovirus-derived proteins such as E1 A and E1 B. In many examples, the packaging cells supply proteins derived from a virus that differs from the virus from which the viral vector is derived. Methods of producing recombinant viruses from packaging cells and their uses are well established; see, e.g., U.S. Pat. Nos. 5,834,256; 6,910,434; 5,591,624; 5,817,491; 7,070,994; and 6,995,009.

Packaging cell lines include but are not limited to any easily-transfectable cell line. Packaging cell lines can be based on 293T cells, NIH3T3, COS or HeLa cell lines. Packaging cells are often used to package virus vector plasmids deficient in at least one gene encoding a protein required for virus packaging. Any cells that can supply a protein or polypeptide lacking from the proteins encoded by such viral vectors or plasmids may be used as packaging cells. Examples of packaging cell lines include but are not limited to: Platinum-E (Plat-E), Platinum-A (Plat-A), BOSC 23 (ATCC CRL 11554) and Bing (ATCC CRL 11270). Morita et al. (2000) Gene Therapy 7(12): 1063-1066; Onishi et al. (1996) Experimental Hematology, 24:324-329; U.S. Pat. No. 6,995,009. Commercial packaging lines are also useful, e.g., Ampho-Pak 293 cell line, Eco-Pak 2-293 cell line, RetroPack PT67 cell line, and Retro-X Universal Packaging System (all available from Clontech).

3. Plasmids

Virus vector plasmids (or constructs), include: pMXs, pMxs-IB, pMXs-puro, pMXs-neo (pMXs-IB is a vector carrying the blasticidin-resistant gene instead of the puromycin-resistant gene of pMXs-puro) Kimatura et al. (2003) Experimental Hematology 31: 1007-1014; MFG Riviere et al. (1995) Proc. Natl. Acad. Sci., 92:6733-6737; pBabePuro; Morgenstern et al. (1990) Nucleic Acids Research 18:3587-3596; LL-CG, CL-CG, CS-CG, CLG Miyoshi et al. (1998) J. Vir. 72:8150-8157 and the like as the retrovirus system, and pAdexl Kanegae et al. (1995) Nucleic Acids Research 23:3816-3821 and the like as the adenovirus system. In exemplary embodiments, the retroviral construct comprises blasticidin (e.g., pMXs-IB), puromycin (e.g., pMXs-puro, pBabePuro), or neomycin (e.g., pMXs-neo). Morgenstern et al. (1990) *Nucleic Acids Research* 18:3587-3596.

In some embodiments, the viral vector or plasmid comprises a transposon or a transposable element comprising a polynucleotide encoding a reprogramming factor. Delivery of polnucleotides via DNA transposons, such as piggyBac and Sleeping Beauty, offers advantages in ease of use, ability to delivery larger cargo, speed to clinic, and cost of production. The piggyBac DNA transposon, in particular, offers potential advantages in giving long-term, high-level and stable expression of polynucleotides, and in being significantly less mutagenic, being non-oncogenic and being fully reversible.

4. Direct Translation from Introduced RNA

When the one or more genes of interest are expressed transiently in the selected cells, the gene(s) of interest can be introduced as an RNA molecule, which is translated to protein within the cell's cytoplasm. For example, the protein of interest can be translated from introduced RNA molecules that have the open reading frame (ORF) for the polypeptide flanked by a 5' untranslated region (UTR) containing a translational initiation signal (e.g., a strong Kozak translational initiation signal) and a 3' untranslated region terminating with an oligo(dT) sequence for templated addition of a polyA tail. Such RNA molecules do not have the promoter sequences employed in most expression vectors and expression cassettes. The RNA molecules can be introduced into the selected cells by a variety of techniques, including electroporation or by endocytosis of the RNA complexed with a cationic vehicle. See, e.g., Warren et al., *Cell Stem Cell* 7: 618-30 (2010), incorporated herein by reference in its entirety.

Protein translation can persist for several days, especially when the RNA molecules are stabilized by incorporation of modified ribonucleotides. For example, incorporation of 5-methylcytidine (5mC) for cytidine and/or pseudouridine (psi) for uridine can improve the half-life of the introduced RNA in vivo, and lead to increased protein translation. If high levels of expression are desired, or expression for more than a few days is desired, the RNA can be introduced repeatedly into the selected cells.

The RNA encoding the protein can also include a 5' cap, a nuclear localization signal, or a combination thereof. See, e.g., Warren et al., *Cell Stem Cell* 7: 618-30 (2010).

Such RNA molecules can be made, for example, by in vitro transcription of a template for the polynucleotide of interest using a ribonucleoside blend that includes a 3'-O-Me-m7G(5')ppp(5')G ARCA cap analog, adenosine triphosphate and guanosine triphosphate, 5-methylcytidine triphosphate and pseudouridine triphosphate. The RNA molecules can also be treated with phosphatase to reduce cytotoxicity.

The RNA can be introduced alone or with a microRNA (e.g., for Oct4 expression, miRNA-302), which can be an inducer of endogenous polypeptide expression. The micoRNA functions as a structural RNA that does not encode a protein. Hence, no translation is needed for microRNA to perform its function. The microRNA can be introduced directly into cells, for example, in a delivery vehicle such as a liposome, microvesicle, or exosome. Alternatively, the microRNA can be expressed from an expression cassette or expression vector that has been introduced into a cell or a cell population.

B. Non-Nucleic Acid Vectors

In certain embodiments, the vector comprises lipid particles as described in Kanasty R, Delivery materials for siRNA therapeutics *Nat Mater.* 12(11):967-77 (2013), which is hereby incorporated by reference. In some embodiments, the lipid-based vector is a lipid nanoparticle, which is a lipid particle between about 1 and about 100 nanometers in size.

In some embodiments, the lipid-based vector is a lipid or liposome. Liposomes are artificial spherical vesicles comprising a lipid bilayer.

In some embodiments, the lipid-based vector is a small nucleic acid-lipid particle (SNALP). SNALPs comprise small (less than 200 nm in diameter) lipid-based nanoparticles that encapsulate a nucleic acid. In some embodiments, the SNALP is useful for delivery of an RNA molecule such as siRNA. In some embodiments, SNALP formulations deliver nucleic acids to a particular tissue in a subject, such as the heart.

In some embodiments, the one or more polynucleotides are delivered via polymeric vectors. In some embodiments, the polymeric vector is a polymer or polymerosome. Polymers encompass any long repeating chain of monomers and include, for example, linear polymers, branched polymers, dendrimers, and polysaccharides. Linear polymers comprise a single line of monomers, whereas branched polymers include side chains of monomers. Dendrimers are also branched molecules, which are arranged symmetrically around the core of the molecule. Polysaccharides are polymeric carbohydrate molecules, and are made up of long monosaccharide units linked together. Polymersomes are artificial vesicles made up of synthetic amphiphilic copolymers that form a vesicle membrane, and may have a hollow or aqueous core within the vesicle membrane.

Various polymer-based systems can be adapted as a vehicle for administering DNA or RNA encoding the one or more reprogramming factors. Exemplary polymeric materials include poly(D,L-lactic acid-co-glycolic acid) (PLGA), poly(caprolactone) (PCL), ethylene vinyl acetate polymer (EVA), poly(lactic acid) (PLA), poly(L-lactic acid) (PLLA), poly(glycolic acid) (PGA), poly(L-lactic acid-co-glycolic acid) (PLLGA), poly(D,L-lactide) (PDLA), poly(L-lactide) (PLLA), PLGA-b-poly(ethylene glycol)-PLGA (PLGA-bPEG-PLGA), PLLA-bPEG-PLLA, PLGA-PEG-maleimide (PLGA-PEG-mal), poly(D,L-lactide-co-caprolactone), poly(D,L-lactide-co-caprolactone-co-glycolide), poly(D,L-lactide-co-PEO-co-D,L-lactide), poly(D,L-lactide-co-PPO-co-D,L-lactide), polyalkyl cyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate)(polyacrylic acids), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), trimethylene carbonate, polyvinylpyrrolidone, polyorthoesters, polyphosphazenes, Poly([beta]-amino esters (PBAE), and polyphosphoesters, and blends and/or block copolymers of two or more such polymers. Polymer-based systems may also include Cyclodextrin polymer (CDP)-based nanoparticles such as, for example, CDP-admantane (AD)-PEG conjugates and CDP-AD-PEG-transferrin conjugates.

Exemplary polymeric particle systems for delivery of drugs, including nucleic acids, include those described in U.S. Pat. Nos. 5,543,158, 6,007,845, 6,254,890, 6,998,115, 7,727,969, 7,427,394, 8,323,698, 8,071,082, 8,105,652, US 2008/0268063, US 2009/0298710, US 2010/0303723, US 2011/0027172, US 2011/0065807, US 2012/0156135, US 2014/0093575, WO 2013/090861, each of which are hereby incorporated by reference in its entirety.

In some embodiments, the lipid-based vector comprises a lipid encapsulation system. The lipid encapsulation system can be designed to drive the desired tissue distribution and cellular entry properties, as well as to provide the requisite circulation time and biodegrading character. The lipid encapsulation may involve reverse micelles and/or further comprise polymeric matrices, for example as described in U.S. Pat. No. 8,193,334, which is hereby incorporated by reference. In some embodiments, the particle includes a lipophilic delivery compound to enhance delivery of the particle to tissues, including in a preferential manner. Such compounds are disclosed in US 2013/0158021, which is hereby incorporated by reference in its entirety. Such compounds may generally include lipophilic groups and conjugated amino acids or peptides, including linear or cyclic peptides, and including isomers thereof. In some embodiments, the lipid encapsulation comprises one or more of a phospholipid, cholesterol, polyethylene glycol (PEG)-lipid, and a lipophilic compound.

The particles, whether lipid or polymeric or both, may include additional components useful for enhancing the properties for in vivo nucleic acid delivery (including compounds disclosed in U.S. Pat. No. 8,450,298 and US 2012/0251560, which are each hereby incorporated by reference). The delivery vehicle may accumulate preferentially in certain tissues thereby providing a tissue targeting effect, but in some embodiments, the delivery vehicle further comprises at least one cell-targeting or tissue-targeting ligand. Functionalized particles, including exemplary targeting ligands, are disclosed in US 2010/0303723 and 2012/0156135, which are hereby incorporated by reference in their entireties.

A delivery vehicle can be designed to drive the desired tissue distribution and cellular entry properties of the delivery systems disclosed herein, as well as to provide the requisite circulation time and biodegrading character. For example, lipid particles can employ amino lipids as disclosed in US 2011/0009641, which is hereby incorporated by reference.

The lipid or polymeric particles may have a size (e.g., an average size) in the range of about 50 nm to about 5 µm. In some embodiments, the particles are in the range of about 10 nm to about 100 µm, or about 20 nm to about 50 µm, or about 50 nm to about 5 µm, or about 70 nm to about 500 nm, or about 70 nm to about 200 nm, or about 50 nm to about 100 nm. Particles may be selected so as to avoid rapid clearance by the immune system. Particles may be spherical, or non-spherical in certain embodiments.

C. Promoters and Enhancers

In some embodiments, a nucleic acid encoding a reprogramming factor can be operably linked to a promoter and/or enhancer to facilitate expression of the reprogramming factor. Depending on the host/vector system utilized, any of a number of suitable transcription and translation control elements, including constitutive and inducible promoters, transcription enhancer elements, transcription terminators, etc. may be used in the expression vector (e.g., Bitter et al. (1987) Methods in Enzymology, 153:516-544). Separate promoters and/or enhancers can be employed for each of the polynucleotides.

In some embodiments, the same promoter and/or enhancer is used for two or more polynucleotides in a single open reading frame. Vectors employing this configuration of genetic elements are termed "polycistronic." An example of a polycistronic vector comprises an enhancer and a promoter operatively linked to a single open-reading frame comprising two or more polynucleotides linked by 2A region(s), whereby expression of the open-reading frame result in multiple polypeptides being generated co-translationally. The 2A region is believed to mediate generation of multiple polypeptide sequences through codon skipping; however, the present disclosure relates also to polycistronic vectors that employ post-translational cleavage to generate polypeptides for two or more genes of interest from the same polynucleotide. Illustrative 2A sequences, vectors, and associated methods are provided in US20040265955A1, which is incorporated herein by reference. Other polycistronic vectors of the disclosure employ internal promoter(s), splicing, reinitiation, internal ribosome entry site(s) (IRES), proteolytic cleavable site(s) (e.g. fusagen) and fusion of genes.

Non-limiting examples of suitable eukaryotic promoters (promoters functional in a eukaryotic cell) include CMV, CMV immediate early, HSV thymidine kinase, early and late SV40, long terminal repeats (LTRs) from retrovirus, and mouse metallothionein-I. In some embodiments, promoters that are capable of conferring cardiac-specific expression will be used. Non-limiting examples of suitable cardiac-specific promoters include desmin (Des), alpha-myosin heavy chain (a-MHC), myosin light chain 2 (MLC-2), cardiac troponin T (cTnT) and cardiac troponin C (cTnC). Non-limiting examples of suitable neuron specific promoters include synapsin I (SYN), calcium/calmodulin-dependent protein kinase II, tubulin alpha I, neuron-specific enolase and platelet-derived growth factor beta chain promoters and hybrid promoters by fusing cytomegalovirus enhancer (E) to those neuron-specific promoters.

Examples of suitable promoters for driving expression reprogramming factors include, but are not limited to, retroviral long terminal repeat (LTR) elements; constitutive promoters such as CMV, HSV1-TK, SV40, EF-1a, β-actin, phosphoglycerol kinase (PGK); inducible promoters, such as those containing Tet-operator elements; cardiac-specific promoters, such as desmin (Des), alpha-myosin heavy chain (a-MHC), myosin light chain 2 (MLC-2), cardiac troponin T (cTnT) and cardiac troponin C (cTnC); neural-specific promoters, such as nestin, neuronal nuclei (NeuN), microtubule-associate protein 2 (MAP2), beta III tubulin, neuron-specific enolase (NSE), oligodendrocyte lineage (Olig1/2), and glial fibrillary acidic protein (GFAP); and pancreatic-specific promoters, such as Pax4, Nkx2.2, Ngn3, insulin, glucagon, and somatostatin.

In some embodiments, a polynucleotide is operably linked to a cell type-specific transcriptional regulator element (TRE), where TREs include promoters and enhancers. Suitable TREs include, but are not limited to, TREs derived from the following genes: myosin light chain-2, α-myosin heavy chain, AE3, cardiac troponin C, and cardiac actin. Franz et al. (1997) Cardiovasc. Res. 35:560-566; Robbins et al. (1995) Ann. N. Y. Acad. Sci. 752:492-505; Linn et al. (1995) Circ. Res. 76:584-591; Parmacek et al. (1994) Cell. Biol. 14: 1870-1885; Hunter et al. (1993) Hypertension 22:608-617; and Sartorelli et al. (1992) Proc. Natl. Acad. Sci. USA 89:4047-4051.

The promoter can be one naturally associated with a gene or nucleic acid segment. Similarly, for RNAs (e.g., microRNAs), the promoter can be one naturally associated with a microRNA gene (e.g., an miRNA-302 gene). Such a naturally associated promoter can be referred to as the "natural promoter" and may be obtained by isolating the 5' noncoding sequences located upstream of the coding segment and/or exon. Similarly, an enhancer may be one naturally associated with a nucleic acid sequence. However, the enhancer can be located either downstream or upstream of that sequence.

Alternatively, certain advantages will be gained by positioning the coding nucleic acid segment under the control of a recombinant or heterologous promoter, which refers to a promoter that is not normally associated with a nucleic acid in its natural environment. A recombinant or heterologous enhancer refers also to an enhancer not normally associated with a nucleic acid sequence in its natural environment. Such promoters or enhancers can include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

The promoters employed may be constitutive, inducible, developmentally-specific, tissue-specific, and/or useful under the appropriate conditions to direct high level expression of the nucleic acid segment. For example, the promoter can be a constitutive promoter such as, a CMV promoter, a CMV cytomegalovirus immediate early promoter, a CAG promoter, an EF-1α promoter, a HSV1-TK promoter, an SV40 promoter, a ρ-actin promoter, a PGK promoter, or a combination thereof. Examples of eukaryotic promoters that can be used include, but are not limited to, constitutive promoters, e.g., viral promoters such as CMV, SV40 and RSV promoters, as well as regulatable promoters, e.g., an inducible or repressible promoter such as the tet promoter, the hsp70 promoter and a synthetic promoter regulated by CRE. In some embodiments, the promoter comprises a CAG promoter (i.e. a CMV early enhancer element and chicken beta-actin promoter) (SEQ ID NO: 67). In some embodiments, the expression cassette comprises an SV40 intron (SEQ ID NO: 83). In some embodiments, the promoter comprises a CMV early enhancer element, chicken beta-actin promoter and a CMV intron (SEQ ID NO: 69). In some embodiments, one or more of the polynucleotides encoding a protein of interest is operatively linked to a CAG promoter (SEQ ID NO: 67). In some embodiments, one or more of the polynucleotides encoding a protein of interest is operatively linked to a super core promoter (SCP) (SEQ ID NO: 68), see U.S. Pat. No. 7,968,698. Other examples of promoters that can be employed include a human EF1α elongation factor promoter, a CMV cytomegalovirus immediate early promoter, a CAG chicken albumin promoter, a viral promoter associated with any of the viral vectors described herein, or a promoter that is homologous to any of the promoters described herein (e.g., from another species). In some embodiments, the promoter is a ubiquitous promoter, optionally selected from the group consisting of a CMV, EF1A, EFS, CAG, CBh, SV40, mPGK, hPGK, and UBC promoters. In some embodiments, the promoter is an inducible promoter. In some embodiments, the promoter is fibroblast-specific promoter, optionally selected from the group consisting of COL1A1, COL6A1, FN1 POSTN, COL1A2, MAP2K3, and PPARγ promoters.

In some embodiments, an internal ribosome entry sites (IRES) element can be used to create multigene, or polycistronic, messages. IRES elements are able to bypass the ribosome scanning model of 5'-methylated Cap dependent translation and begin translation at internal sites (Pelletier and Sonenberg, Nature 334(6180):320-325 (1988)). IRES elements from two members of the picornavirus family (polio and encephalomyocarditis) have been described (Pelletier and Sonenberg, Nature 334(6180):320-325 (1988)), as well an IRES from a mammalian message (Macejak & Sarnow, Nature 353:90-94 (1991)). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

In some embodiments, the vectors of the disclosure include one or more polyA signals. Illustrative polyA signals useful in the vectors of the disclosure include the short polyA signal (SEQ ID NO: 74) and the bGH polyA signal (SEQ ID NO: 85).

D. Vector Delivery to Cells

The viral vector may be introduced into a host fibroblast by any method known in the art, including but not limited to: a calcium phosphate method, a lipofection method (e.g., Feigner et al. (1987) Proc. Natl. Acad. Sci. 84:7413-7417), an electroporation method, microinjection, Fugene transfection, nucleofection and the like, and any method described herein.

Examples of procedures include, for example, those described by Stadtfeld and Hochedlinger, Nature Methods 6(5):329-330 (2009); Yusa et al., Nat. Methods 6:363-369 (2009); Woltjen, et al., Nature 458, 766-770 (9 Apr. 2009)). Such methods include, but are not limited to, direct delivery of DNA such as by ex vivo transfection (e.g., Wilson et al., Science, 244:1344-1346, 1989, Nabel & Baltimore, Nature 326:711-713, 1987), optionally with Fugene6 (Roche) or Lipofectamine (Invitrogen); by injection (e.g., U.S. Pat. Nos. 5,994,624, 5,981,274, 5,945,100, 5,780,448, 5,736, 524, 5,702,932, 5,656,610, 5,589,466 and 5,580,859, each incorporated herein by reference), including microinjection (e.g., Harland and Weintraub, J. Cell Biol., 101:1094-1099, 1985; U.S. Pat. No. 5,789,215, incorporated herein by reference in its entirety); by electroporation (e.g., U.S. Pat.

No. 5,384,253, incorporated herein by reference in its entirety, Tur-Kaspa et al., *Mol. Cell Biol.*, 6:716-718, 1986; Potter et al., *Proc. Nat'l Acad. Sci. USA*, 81:7161-7165, 1984); by calcium phosphate precipitation (e.g., Graham & Van Der Eb, *Virology*, 52:456-467, 1973; Chen and Okayama, *Mol. Cell Biol.*, 7(8):2745-2752, 1987; Rippe et al., *Mol. Cell Biol.*, 10:689-695, 1990); by use of DEAE-dextran followed by polyethylene glycol (e.g., Gopal, *Mol. Cell Biol.*, 5:1188-1190, 1985); by direct sonic loading (e.g., Fechheimer et al., *Proc. Nat'l Acad. Sci. USA*, 84:8463-8467, 1987); by liposome-mediated transfection (e.g., Nicolau & Sene, *Biochim. Biophys. Acta*, 721:185-190, 1982, Fraley et al., *Proc. Nat'l Acad. Sci. USA*, 76:3348-3352, 1979; Nicolau et al., *Methods Enzymol.*, 149:157-176, 1987, Wong et al., *Gene*, 10:87-94, 1980, Kaneda et al., *Science*, 243:375-378, 1989, Kato et al., *Biol. Chem.*, 266:3361-3364, 1991), receptor-mediated transfection (e.g., Wu and Wu, *Biochemistry*, 27:887-892, 1988; Wu and Wu, *J. Biol. Chem.*, 262:4429-4432, 1987); by endocytosis of the RNA complexed with a cationic vehicle (Warren et al., *Cell Stem Cell* 7: 618-30 (2010)); and any combination of such methods. Each of the foregoing references is incorporated herein by reference in its entirety.

Various techniques may be employed for introducing nucleic acid molecules of the disclosure into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. Other examples include: N-TER™ Nanoparticle Transfection System by Sigma-Aldrich, FECTOFLY™ transfection reagents for insect cells by Polyplus Transfection, Polyethylenimine "Max" by Polysciences, Inc., Unique, Non-Viral Transfection Tool by Cosmo Bio Co., Ltd., LIPOFECTAMINE™ LTX Transfection Reagent by Invitrogen, SATISFECTION™ Transfection Reagent by Stratagene, LIPOFECTAMINE™ Transfection Reagent by Invitrogen, FUGENE® HD Transfection Reagent by Roche Applied Science, GMP compliant IN VIVO-JETPEI™ transfection reagent by Polyplus Transfection, and Insect GENEJUICE® Transfection Reagent by Novagen.

IV. Reprogramming Factor Compositions

Reprogramming with one or more of ASCL1, MYOCD, MEF2C, and TBX5 can be combined with other reprogramming strategies in some cases with improved results. In some embodiments, the target tissues or starting cells express or are induced to express the Oct4 polypeptide. Target tissues or starting cells can be treated or incubated, respectively, with a reprogramming composition that contains one or more WNT agonists, GSK3 inhibitors, TGF-beta inhibitors, epigenetic modifiers, adenylyl cyclase agonists, Oct-4 expression activators, and any combination thereof. The composition can contain at least two of such agents, or at least three of such agents, or at least four of such agents, or at least five of such agents, or at least six of such agents. For example, the composition can include SB431542 (an ALK4/5/7 inhibitor), CHIR99021 (a GSK3 inhibitor), parnate (an LSD1/KDM1 inhibitor, also called tranylcypromine) and forskolin (an adenylyl cyclase activator).

In certain embodiments, the reprogramming is enhanced by the administration of one or more anti-inflammatory agents, e.g., an anti-inflammatory steroid or a nonsteroidal anti-inflammatory drug (NSAID).

Anti-inflammatory steroids for use in the invention include corticosteroids, and in particular those with glucocorticoid activity, e.g., dexamethasone and prednisone. Nonsteroidal anti-inflammatory drugs (NSAIDs) for use in the invention generally act by blocking the production of prostaglandins that cause inflammation and pain, cyclooxygenase-1 (COX-1) and/or cyclooxygenase-2 (COX-2). Traditional NSAIDs work by blocking both COX-1 and COX-2. The COX-2 selective inhibitors block only the COX-2 enzyme. In certain embodiment, the NSAID is a COX-2 selective inhibitor, e.g., celecoxib (CELEBREX®), rofecoxib (Vioxx), and valdecoxib (B extra). In certain embodiments, the anti-inflammatory is an NSAID prostaglandin inhibitor, e.g., Piroxicam.

To prepare the composition, the vectors and/or the cells are generated, and the vectors or cells are purified as necessary or desired. The vectors, cells, and/or other agents can be suspended in a pharmaceutically acceptable carrier. If the composition contains only compounds, without cells, the composition can be lyophilized. These compounds and cells can be adjusted to an appropriate concentration, and optionally combined with other agents. The absolute weight of a given compound and/or other agent included in a unit dose can vary widely. The dose and the number of administrations can be optimized by those skilled in the art.

For example, about $10^2$-$10^{10}$ vector genomes (vg) may be administered. In some embodiments, the dose be at least about $10^2$ vg, about $10^3$ vg, about $10^4$ vg, about $10^5$ vg, about $10^6$ vg, about $10^7$ vg, about $10^8$ vg, about $10^9$ vg, about $10^{10}$ vg, or more vector genomes. In some embodiments, the dose be about $10^2$ vg, about $10^3$ vg, about $10^4$ vg, about $10^5$ vg, about $10^6$ vg, about $10^7$ vg, about $10^8$ vg, about $10^9$ vg, about $10^{10}$ vg, or more vector genomes.

Daily doses of the compounds can vary as well. Such daily doses can range, for example, from at least about $10^2$ vg/day, about $10^3$ vg/day, about $10^4$ vg/day, about $10^5$ vg/day, about $10^6$ vg/day, about $10^7$ vg/day, about $10^8$ vg/day, about $10^9$ vg/day, about $10^{10}$ vg/day, or more vector genomes per day.

In some embodiments, the method of the disclosure comprise administering a vector or vector system of the disclosure (e.g. an rAAV vector) by intracardiac injection, intramyocardiac injection, intracardiac catheterization, or systemic administration. In some embodiments, the subject (e.g., a human) is treated by administering between about $1\times10^8$ and about $1\times10^{15}$ GC of a vector (e.g., an AAV vector or lentiviral vector) by intracardiac injection, intramyocardiac injection, intracardiac catheterization, or systemic administration. In some embodiments, the subject is treated by administering between about $1\times10^8$ and about $1\times10^{15}$GC, between about $1\times10^8$ and about $1\times10^{15}$ GC, between about $1\times10^9$ and about $1\times10^{14}$ GC, between about $1\times10^{10}$ and about $1\times10^{13}$GC, between about $1\times10^{11}$ and about $1\times10^{12}$GC, or between about $1\times10^{12}$ and about $1\times10^{13}$ GC of vector. In some embodiments, the subject is treated by administering between about $1\times10^8$ and about $1\times10^{10}$ GC, between about $1\times10^9$ and about $1\times10^{11}$ GC, between about $1\times10^{10}$ and about $1\times10^{12}$ GC, between about $1\times10^{11}$ and about $1\times10^{13}$ GC, between about $1\times10^{12}$ and about $1\times10^{14}$ GC, or between about $1\times10^{13}$ and about $1\times10^{15}$ GC of vector. In some embodiments, the subject is treated by administering at least $1\times10^8$, at least about $1\times10^9$, at least about $1\times10^{10}$, at least about $1\times10^{11}$, at least about $1\times10^{12}$, at least about $1\times10^{13}$, or at least about $1\times10^{15}$ GC of vector. In some embodiments, the subject is treated by administering at most $1\times10^8$, at most about $1\times10^9$, at most about $1\times10^{10}$, at most about $1\times10^{11}$, at most about $1\times10^{12}$, at most about $1\times10^{13}$, or at most about $1\times10^{15}$ GC of vector. In some embodiments, the subject (e.g., a human) is treated by administering between about $1\times10^8$ and about $1\times10^{15}$ GC/kg of a vector (e.g., an AAV vector or lentiviral vector) by intracardiac injection or systemically. In some embodiments, the subject is treated by administering between about $1\times10^8$ and about $1\times10^{15}$ GC/kg, between about $1\times10^8$ and about $1\times10^{15}$ GC/kg, between about $1\times10^9$ and about $1\times10^{14}$ GC/kg, between about $1\times10^{10}$ and about $1\times10^{13}$ GC/kg, between about $1\times10^{11}$ and about $1\times10^{12}$ GC/kg, or between about $1\times10^{12}$ and about $1\times10^{13}$ GC/kg of vector. In some embodiments, the subject is treated by administering between about $1\times10^8$ and about $1\times10^{10}$ GC/kg, between about $1\times10^9$ and about $1\times10^{11}$ GC/kg, between about $1\times10^{10}$ and about $1\times10^{12}$ GC/kg, between about $1\times10^{11}$ and about $1\times10^{13}$ GC/kg, between about $1\times10^{12}$ and about $1\times10^{14}$ GC/kg, or between about $1\times10^{13}$ and about $1\times10^{15}$ GC/kg of vector. In some embodiments, the subject is treated by administering at least $1\times10^8$, at least about $1\times10^9$, at least about $1\times10^{10}$, at least about $1\times10^{11}$, at least about $1\times10^{12}$, at least about $1\times10^{13}$, or at least about $1\times10^{15}$ GC/kg of vector. In some embodiments, the subject is treated by administering at most $1\times10^8$, at most about $1\times10^9$, at most about $1\times10^{10}$, at most about $1\times10^{11}$, at most about $1\times10^{12}$, at most about $1\times10^{13}$, or at most about $1\times10^{15}$ GC/kg of vector. It will be appreciated that the amount of vectors and cells for use in treatment will vary not only with the particular carrier selected but also with the route of administration, the nature of the condition being treated and the age and condition of the patient. Ultimately, the attendant health care provider may determine proper dosage. A pharmaceutical composition may be formulated with the appropriate ratio of each compound in a single unit dosage form for administration with or without cells. Cells or vectors can be separately provided and either mixed with a liquid solution of the compound composition, or administered separately.

The compositions can also be formulated for sustained release (for example, using microencapsulation, see WO 94/07529, and/or U.S. Pat. No. 4,962,091). The formulations may, where appropriate, be conveniently presented in discrete unit dosage forms and may be prepared by any of the methods well known to the pharmaceutical arts. Such methods may include the step of mixing the therapeutic agent with liquid carriers, solid matrices, semi-solid carriers, finely divided solid carriers or combinations thereof, and then, if necessary, introducing or shaping the product into the desired delivery system.

One or more suitable unit dosage forms containing the compounds and/or the reprogrammed cells can be administered by a variety of routes including parenteral (including subcutaneous, intravenous, intramuscular and intraperitoneal), intracranial, intraspinal, oral, rectal, dermal, transdermal, intrathoracic, intrapulmonary and intranasal (respiratory) routes.

The vectors or cells of the invention may be prepared in many forms that include aqueous solutions, suspensions, tablets, hard or soft gelatin capsules, and liposomes and other slow-release formulations, such as shaped polymeric gels. Administration of cells often involves parenteral or local administration in an aqueous solution. Similarly, compositions containing cells and/or compounds can be administered in a device, scaffold, or as a sustained release formulation. Different types of formulating procedures are described in U.S. Pat. No. 6,306,434 and in the references contained therein.

Liquid pharmaceutical compositions may be in the form of, for example, aqueous or oily suspensions, solutions, emulsions, syrups or elixirs, dry powders for reconstitution with water or other suitable vehicles before use. Such liquid pharmaceutical compositions may contain conventional additives such as suspending agents, emulsifying agents, non-aqueous vehicles (which may include edible oils), or preservatives.

Vectors and/or cells can be formulated for parenteral administration (e.g., by injection, for example, bolus injection or continuous infusion) and may be presented in unit dosage form in ampoules, prefilled syringes, small volume infusion containers or multi-dose containers with an added preservative. The pharmaceutical compositions can take the form of suspensions, solutions, or emulsions in oily or aqueous vehicles, and can contain formulatory agents such as suspending, stabilizing and/or dispersing agents. Suitable carriers include saline solution, phosphate buffered saline, and other materials commonly used in the art.

The compositions can also contain other ingredients such as agents useful for treatment of cardiac diseases, conditions and injuries, such as, for example, an anticoagulant (e.g., dalteparin (fragmin), danaparoid (organan), enoxaparin (lovenox), heparin, tinzaparin (innohep), and/or warfarin (coumadin)), an antiplatelet agent (e.g., aspirin, ticlopidine, clopidogrel, or dipyridamole), an angiotensin-converting enzyme inhibitor (e.g., Benazepril (Lotensin), Captopril (Capoten), Enalapril (Vasotec), Fosinopril (Monopril), Lisinopril (Prinivil, Zestril), Moexipril (Univasc), Perindopril (Aceon), Quinapril (Accupril), Ramipril (Altace), and/or Trandolapril (Mavik)), angiotensin II receptor blockers (e.g., Candesartan (Atacand), Eprosartan (Teveten), Irbesartan (Avapro), Losartan (Cozaar), Telmisartan (Micardis), and/or Valsartan (Diovan)), a beta blocker (e.g., Acebutolol (Sectral), Atenolol (Tenormin), Betaxolol (Kerlone), Bisoprolol/hydrochlorothiazide (Ziac), Bisoprolol (Zebeta), Carteolol (Cartrol), Metoprolol (Lopressor, Toprol XL), Nadolol (Corgard), Propranolol (Inderal), Sotalol (Betapace), and/or Timolol (Blocadren)), Calcium Channel Blockers (e.g., Amlodipine (Norvasc, Lotrel), Bepridil (Vascor), Diltiazem (Cardizem, Tiazac), Felodipine (Plendil), Nifedipine (Adalat, Procardia), Nimodipine (Nimotop), Nisoldipine (Sular), Verapamil (Calan, Isoptin, Verelan), diuretics (e.g, Amiloride (Midamor), Bumetanide (Bumex), Chlorothiazide (Diuril), Chlorthalidone (Hygroton), Furosemide (Lasix), Hydro-chlorothiazide (Esidrix, Hydrodiuril), Indapamide (Lozol) and/or Spironolactone (Aldactone)), vasodilators (e.g., Isosorbide dinitrate (Isordil), Nesiritide (Natrecor), Hydralazine (Apresoline), Nitrates and/or Minoxidil), statins, nicotinic acid, gemfibrozil, clofibrate, Digoxin, Digitoxin, Lanoxin, or any combination thereof.

Additional agents can also be included such as antibacterial agents, antimicrobial agents, anti-viral agents, biological response modifiers, growth factors; immune modulators, monoclonal antibodies and/or preservatives. The compositions of the invention may also be used in conjunction with other forms of therapy.

The viral vectors and non-viral vectors described herein can be administered to a subject to treat a disease or disorder. Such a composition may be in a single dose, in multiple doses, in a continuous or intermittent manner, depending, for example, upon the recipient's physiological condition, whether the purpose of the administration is in response to traumatic injury or for more sustained therapeutic purposes, and other factors known to skilled practitioners. The administration of the compounds and compositions of the invention may be essentially continuous over a preselected period of time or may be in a series of spaced doses. Both local and systemic administration is contemplated. In some embodiments, localized delivery of a viral or non-viral vector is achieved. In some embodiments, localized delivery of cells and/or vectors is used to generate a population of cells within the heart. In some embodiments, such a localized population operates as "pacemaker cells" for the heart.

Supplementary factors can be included in the compositions and/or in a cell culture media containing any of the cells, compositions, compounds or agents described herein. Examples of such supplementary factors include bone morphogenic protein (BMP)-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, brain derived neurotrophic factor, ciliary neurotrophic factor, cytokine-induced neutrophil chemotactic factor 1, cytokine-induced neutrophil chemotactic factor 2a, cytokine-induced neutrophil chemotactic factor 2p, p endothelial cell growth factor, endothelin 1, epidermal growth factor, epithelial-derived neutrophil attractant, fibroblast growth factor (FGF) 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor (acidic), fibroblast growth factor (basic), growth related protein, growth related protein a, growth related protein p, growth related protein 7, heparin binding epidermal growth factor, hepatocyte growth factor, insulin-like growth factor I, insulin-like growth factor II, insulin-like growth factor binding protein, keratinocyte growth factor, leukemia inhibitory factor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, pre-B cell growth stimulating factor, stem cell factor, transforming growth factor a, transforming growth factor β, transforming growth factor β1, transforming growth factor 01.2, transforming growth factor 132, transforming growth factor β3, latent transforming growth factor β1, transforming growth factor β binding protein I, transforming growth factor β binding protein II, transforming growth factor β binding protein III, and vascular endothelial growth factor.

Exemplary cytokines can be included such as interleukin (IL)-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN), IFN-7, tumor necrosis factor (TNF), TNF1, TNF2, TNF-α, macrophage colony stimulating factor (M-CSF), granulocyte-monocyte colony stimulating factor (GM-CSF), granulocyte colony stimulating factor (G-CSF), megakaryocyte colony stimulating factor (Meg-CSF)-thrombopoietin, stem cell factor, and erythropoietin. Chemokines can also be included such as IP-10 and Stromal Cell-Derived Factor 1α.

Exemplary hormones contemplated for inclusion in the compositions and/or cell culture media described herein can include, but are not limited to, steroid hormones and peptide hormones, such as insulin, somatostatin, growth hormone, hydrocortisone, dexamethasone, 3,3',5-Triiodo-L-thyronine, and L-Thyroxine.

V. Reprogramming Methods

As described herein, target cells (e.g., non-cardiomyocyte cells) can be reprogrammed to the cardiac lineage (e.g., cardiomyocyte lineage) in vitro by incubation of the target cells with the compositions described herein or in vivo by administration of a viral or non-viral vector to target tissues or cells. In some embodiments, the target cells are fibroblast cells. In some embodiments, the target cells are cardiac fibroblast (CF) cells. Non-cardiomyocytes cells can be differentiated into cardiomyocytes cells in vitro or in vivo using any method available to one of skill in the art. For example, see methods described in Ieda et al. (2010) Cell 142:375-386; Christoforou et al. (2013) PLoS ONE 8:e63577; Addis et al. (2013) J. Mol. Cell Cardiol. 60:97-106; Jayawardena et al. (2012) Circ. Res. 110: 1465-1473; Nam Y et al., PNAS USA. 2013; 110:5588-5593; Wada R et al. PNAS USA. 2013; 110: 12667-12672; and Fu J et al., Stem Cell Reports. 2013; 1:235-247. Such methods can therefore be used to generate a population of cardiac progenitor cells or cardiomyocytes that can be transplanted into a subject or used for experimentation.

A. Cells

Cardiomyocytes or cardiac myocytes are the muscle cells that make up the cardiac muscle. Each myocardial cell contains myofibrils, which are long chains of sarcomeres, the contractile units of muscle cells. Cardiomyocytes show striations similar to those on skeletal muscle cells, but unlike multinucleated skeletal cells, they contain only one nucleus. Cardiomyocytes have a high mitochondrial density, which allows them to produce ATP quickly, making them highly resistant to fatigue. Mature cardiomyocytes can express one or more of the following cardiac markers: α-actinin, MLC2v, cMHC, NKX2-5, GATA4, cTNT, cTNI, MEF2c, MLC2a, or any combination thereof. In some embodiments, the mature cardiomyocytes express NKX2-5, MEF2c or a combination thereof. In some embodiments, cardiac progenitor cells express early stage cardiac progenitor markers such as GATA4, ISL1 or a combination thereof.

The non-cardiomyocytes that are induced to cardiomyocytes can be from any of a variety of sources. Cells can be from, e.g., human or non-human mammals. Exemplary non-human mammals include, but are not limited to, mice, rats, cats, dogs, rabbits, guinea pigs, hamsters, sheep, pigs, horses, bovines, and non-human primates. In some embodiments, a cell is from an adult human or non-human mammal. In some embodiments, a cell is from a neonatal human, an adult human, or non-human mammal. In some embodiments, the species of cell and the species of the protein to be expressed are the same. For example, if a mouse cell is used, a mouse ortholog is introduced into the cell. If a human cell is used, a human ortholog is introduced into the cell.

Mammalian non-cardiomyocytes (e.g., human or murine) can be used. In some embodiments, the cardiomyocytes are mammalian cardiomyocytes, and in specific embodiments the non-cardiomyocytes are human cells. In some embodiments, the non-cardiomyocytes can be derived from stem cells (e.g., pluripotent stem cells, induced pluripotent stem cells, reprogrammed cardiac cells or cardiac stem cells) or progenitor cells (e.g., cardiac progenitor cells). Cardiomyocytes can be derived from cardiac or non-cardiac cells. Cardiomyocytes can be from or derived from any of a variety of tissue sources. For example, cardiac fibroblasts, foreskin fibroblast, dermal fibroblasts, lung fibroblasts, etc. The non-cardiomyocytes can be embryonic, fetal, or postnatal (e.g., adult) cells. In preferred embodiments, the non-cardiomyocytes are adult cells.

The non-cardiomyocyte for use in the present invention can be any non-cardiomyocyte cell type known to one of skill in the art. Non-limiting examples of a non-cardiomyocyte include, for example, a somatic cell, a cardiac fibroblast, a non-cardiac fibroblast, a cardiac progenitor cell, and a stem cell. The non-cardiomyocyte can be cardiac cells from the epicardium, myocardium or endocardium of the heart. Non-cardiomyocyte cardiac cells include, for example, smooth muscle and endothelial cells. Other non-limiting examples of cardiac cells include epithelial cells, endothelial cells, fibroblasts, cardiac stem or progenitor cells, cardiac conducting cells and cardiac pacemaking cells that constitute the cardiac muscle, blood vessels and cardiac cell supporting structure. The non-cardiomyocyte can, for example, be selected from one or more of hepatocytes, fibroblasts, endothelial cells, B cells, T cells, dendritic cells, keratinocytes, adipose cells, epithelial cells, epidermal cells, chondrocytes, cumulus cells, neural cells, glial cells, astrocytes, cardiac cells, esophageal cells, skeletal muscle cells, skeletal muscle satellite melanocytes, hematopoietic cells, osteocytes, macrophages, monocytes, mononuclear cells or stem cells including embryonic stem cells, embryonic germ cells, adult brain stem cells, epidermal stem cells, skin stem cells, pancreatic stem cells, kidney stem cells, liver stem cells, breast stem cells, lung stem cells, muscle stem cells, heart stem cells, eye stem cells, bone stem cells, spleen stem cells, immune system stem cells, cord blood stem cells, bone marrow stem cells and peripheral blood stem cells.

Where the cells for reprogramming are a population of non-cardiomyocytes, the population of cells is composed of at least about 30% non-cardiomyocytes, at least about 35% non-cardiomyocytes, at least about 40% non-cardiomyocytes, at least about 45% non-cardiomyocytes, at least about 50% non-cardiomyocytes, at least about 55% non-cardiomyocytes, at least about 60% non-cardiomyocytes, at least about 65% non-cardiomyocytes, at least about 70% non-cardiomyocytes, at least about 75% non-cardiomyocytes, at least about 80% non-cardiomyocytes, at least about 85% non-cardiomyocytes, at least about 90% non-cardiomyocytes, at least about 95% non-cardiomyocytes, at least about 98% non-cardiomyocytes, at least about 99% non-cardiomyocytes, or greater than 99% non-cardiomyocytes.

In some embodiments, the starting cells are adult human cardiac fibroblasts (AHCFs) or adult pig cardiac fibroblasts (APCFs). AHCFs or APCFs can be obtained, for example, by digestion of tissue fragments from the left ventricle of a donor subject. Digestion can be performed with various methods known in the art—for example by subjecting the cells to 10 μg/ml Liberase TH, 10 μg/ml Liberase TM, 1 unit/ml DNase I, and 0.01% Polaxomer for 1 h in 37° C. Various alternative enzymes and digestion procedures are known in the art. The compositions and methods of the disclosure relate to both in vivo and in vitro (ex vivo) applications. The cells to be reprogrammed are referred to as "target cells" or "starting cells." Target cells can be contacted or incubated with the compositions described herein. Such target cells are also referred to as starting cells or collectively as a starting population of cells. A starting population of cells can be derived from various source, and can be heterogeneous or homogeneous. In certain embodiments, the cells to be treated as described herein are adult cells, including any accessible adult cell type(s). In other embodiments, the cells used according to the invention are adult stem cells, progenitor cells, or somatic cells. In still other embodiments, the cells treated with any of the compositions and/or methods described herein include any type of cell from a newborn, including, but not limited to, newborn cord blood, newborn stem cells, progenitor cells, and tissue-derived cells (e.g., somatic cells). Accordingly, a starting population of cells that is reprogrammed by the compositions and/or methods described herein, can be any live somatic cell type.

As illustrated herein, fibroblasts can be reprogrammed to cross lineage boundaries and to be directly converted to another cell type—e.g., a cardiac progenitor cell or a cardiomyocyte cell type. Various cell types from all three germ layers have been shown to be suitable for somatic cell reprogramming by genetic manipulation, including, but not limited to liver and stomach (Aoi et al., *Science* 321(5889): 699-702 (2008); pancreatic β cells (Stadtfeld et al., *Cell Stem Cell* 2: 230-40 (2008); mature B lymphocytes (Hanna et al., *Cell* 133: 250-264 (2008); human dermal fibroblasts (Takahashi et al., *Cell* 131, 861-72 (2007); Yu et al., *Science* 318(5854) (2007); Lowry et al., *Proc Natl Acad Sci USA* 105, 2883-2888 (2008); Aasen et al., *Nat Biotechnol* 26(11): 1276-84 (2008); meningiocytes (Qin et al., *J Biol Chem* 283(48):33730-5 (2008); neural stem cells (DiSteffano et al., *Stem Cells Devel.* 18(5): (2009); and neural progenitor cells (Eminli et al., *Stem Cells* 26(10): 2467-74 (2008). Any such cells can be reprogrammed and/or programmed by use of the compositions and methods described herein.

The cells can be autologous or allogeneic cells (relative to a subject to be treated or who may receive the cells). Cells can be present in the subject or isolated from the subject. Immunosuppressive drugs are commonly used prior to, during, or after cell therapy. Immunosuppresive drugs may also be used prior to, during, or after viral or non-viral vector. In some cases, use of an immunosuppressive drugs may improve treatment outcomes. In some cases, use of an immunosuppressive drugs may diminish side effects of treatment, such as, without limitation, acute graft-versus-host disease, chronic graft-versus-host disease, and post-transplant lymphoproliferative disease. The present disclosure contemplates use of immunosuppressive drugs with any of the methods of treating or preventing a disease or condition of the present disclosure, including, without limitation, methods of the present disclosure in which the lentiviral vector confers resistance to an immunosuppressive drug to transduced cells.

In some embodiments the non-cardiomyocytes are endogenous cells within the subject and the methods of generating induced cardiomyocytes are by in vivo induction. In other embodiments, the non-cardiomyocytes are exogenous and are modified in vitro.

The non-cardiomyocytes can be obtained from a living subject. The cells can be obtained from tissue taken from a living subject. The cells can be obtained from a recently deceased subject who is considered a suitable tissue donor. In some embodiments, the subject is screened for various genetic disorders, viral infections, etc. to determine whether the subject is a suitable source of cells. In general, a cell that is suitable for use in the present invention is non-transformed (e.g., exhibits normal cell proliferation) and is otherwise normal (e.g., exhibits normal karyotype).

Cells can be derived from tissue of a non-embryonic subject, a neonatal infant, a child or an adult. Cells can be derived from neonatal or post-natal tissue collected from a subject within the period from birth, including cesarean birth, to death. For example, the non-cardiomyocytes can be from a subject who is greater than about 10 minutes old, greater than about 1 hour old, greater than about 1 day old, greater than about 1 month old, greater than about 2 months old, greater than about 6 months old, greater than about 1 year old, greater than about 2 years old, greater than about 5 years old, greater than about 10 years old, greater than about 15 years old, greater than about 18 years old, greater than about 25 years old, greater than about 35 years old, >45 years old, >55 years old, >65 years old, >80 years old, <80 years old, <70 years old, <60 years old, <50 years old, <40 years old, <30 years old, <20 years old or <10 years old.

Methods of isolating non-cardiomyocytes cells from tissues are known in the art, and any known method can be used. As a non-limiting example, adult cardiac cells can be obtained from human heart atrial biopsy specimens obtained from patients undergoing cardiac surgery. Cardiac tissue can be minced and digested with collagenase and cardiac stem/progenitor cells expanded in c-kit$^+$ progenitor cell expansion media using the methods of Choi et al. (2013) Transplantation Proceedings 45:420-426. In addition, cardiac fibroblasts can be obtained using the methods of Ieda et al. (2009) Dev. Cell 16(2):233-244. Foreskin fibroblasts can be obtained from foreskin tissue of a male individual. The fibroblasts can be obtained by mincing the foreskin tissue, then dissociating the tissue to single cells. Foreskin cell clumps can be dissociated by any means known in the art including physical de-clumping or enzymatic digestion using, for example, trypsin.

B. In Vitro Reprogramming Methods

The disclosure provides methods for generating cardiomyocytes and/or cardiomyocyte-like cells in vitro. Selected starting cells are treated for a time and under conditions sufficient to convert the starting cells across lineage and/or differentiation boundaries to form cardiac progenitor cells and/or cardiomyocytes. In some embodiments, expression of the gene(s) of interest in the starting cells is initiated for at least 1, 2, 3, 4, 5, 6, 7, 8, 9, or 10 days before treatment with the induced cardiomycocyte cells (iCM cells) described herein. Reprogramming efficiency of the cells can be improved by expression of the genes of interest for at least two days, or at least three days, or at least four days, or at least five days prior to administrations of iCM cells or recombinant viruses or non-viral vectors to the subject. In some embodiments, the starting cells are fibroblast cells. In some embodiments, the starting cells express one or more markers indicative of a differentiated phenotype.

The starting cells can be dispersed in a cell culture medium that contains the reprogramming composition at a density that permits cell expansion. For example, about 1 to $10^{12}$ cells can be contacted with a viral or non-viral vector in a selected cell culture medium, especially when the cells are maintained at a cell density of about 1 to about $10^8$ cells per milliliter, or at a density of about 100 to about $10^7$ cells per milliliter, or at a density of about 1000 to about $10^6$ cells per milliliter. In some embodiments, the methods of the disclosure comprise contacting at least $10^3$ cells, $10^4$ cells, $10^5$ cells, $10^6$ cells, $10^7$ cells, $10^8$ cells, $10^9$ cells, $10^{10}$ cells, $10^{11}$ cells, $10^{12}$ cells, $10^{13}$ cells, $10^{14}$ cells, $10^{15}$ cells, or any number of cells therebetween with viral or non-viral vector(s), thereby inducing expression of the one or more genes of interest.

The time for conversion of starting cells into cardiac progenitor and cardiomyocyte cells can vary. For example, the starting cells can be incubated after treatment with one or more genes of interest until cardiac or cardiomyocyte cell markers are expressed. Such cardiac or cardiomyocyte cell markers can include any of the following markers: α-GATA4, TNNT2, MYH6, RYR2, NKX2-5, MEF2c, ANP, Actinin, MLC2v, cMHC, ISL1, cTNT, cTNI, MLC2a and any combination thereof.

In some embodiments, the induced cardiomycocyte cells are negative for one or more neuronal cells markers. Such neuronal cell markers can include any of the following markers: DCX, TUBB3, MAP2, and ENO2.

Incubation can proceed in any of the compositions described herein, for example, until cardiac progenitor markers are expressed by the starting cells. Such cardiac progenitor markers include Gata4, Tnnt2, Myh6, Ryr2, or a combination thereof. The cardiac progenitor markers such as Gata4, Tnnt2, Myh6, Ryr2, or a combination thereof can be expressed by about 8 days, or by about 9 days, or by about 10 days, or by about 11 days, or by about 12 days, or by about 14 days, or by about 15 days, or by about 16 days, or by about 17 days, or by about 18 days, or by about 19 days, or by about 20 days after starting incubation of cells in the compositions described herein.

Further incubation of the cells can be performed until expression of late stage cardiac progenitor markers such as NKX2-5, MEF2C or a combination thereof occurs. The late stage cardiac progenitor marker such as NKX2-5 and/or MEF2C can be expressed by about 15 days, or by about 16 days, or by about 17 days, or by about 18 days, by about 19 days, or by about 20 days, or by about 21 days, or by about 22 days, or by about 23 days, or by about 24 days, or by about 25 days of incubation of cells using the compositions and methods described herein.

Reprogramming efficiency may be measured as a function of cardiomyocyte markers. Such pluripotency markers include, but are not limited to, the expression of cardiomyocyte marker proteins and mRNA, cardiomyocyte morphology and electrophysiological phenotype. Non-limiting examples of cardiomyocyte markers include, a-sarcoglycan, atrial natriuretic peptide (ANP), bone morphogenetic protein 4 (BMP4), connexin 37, connexin 40, crypto, desmin, GATA4, GATA6, MEF2C, MYH6, myosin heavy chain, NKX2-5, TBX5, and Troponin T. In some aspects, reprogramming efficiency is increased by about 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more higher relative to a control. Non-limiting examples of appropriate controls include a sample that has not been exposed to reprogramming factors.

The expression of various markers specific to cardiomyocytes may be detected by conventional biochemical and immunochemical methods (e.g., enzyme-linked immunosorbent assay, immunohistochemical assay, and the like). Alternatively, expression of a nucleic acid encoding a cardiomyocyte-specific marker can be assessed. Expression of cardiomyocyte-specific marker-encoding nucleic acids in a cell can be confirmed by reverse transcriptase polymerase chain reaction (RT-PCR) or hybridization analysis, molecular biological methods which have been commonly used in the past for amplifying, detecting and analyzing mRNA coding for any marker proteins. Nucleic acid sequences coding for markers specific to cardiomyocytes are known and are available through public databases such as GenBank. Thus, marker-specific sequences needed for use as primers or probes are easily determined.

Cardiomyocytes exhibit some cardiac-specific electrophysiological properties. One electrical characteristic is an action potential, which is a short-lasting event in which the difference of potential between the interior and the exterior of each cardiac cell rises and falls following a consistent trajectory. Another electrophysiological characteristic of cardiomyocytes is the cyclic variations in the cytosolic-free $Ca^{2+}$ concentration, named as $Ca^{2+}$ transients, which are employed in the regulation of the contraction and relaxation of cardiomyocytes. These characteristics can be detected and evaluated to assess whether a population of cells has been reprogrammed into cardiomyocytes.

In some embodiments, the starting cells can be incubated with the reprogramming medium under cell culture conditions for about 1 day to about 30 days, or about 2 days to about 27 days, or about 3 days to about 25 days, or about 4 days to about 23 days, or about 5 days to about 20 days, or about 6 days to about 20 days, or about 10 days to about 20 days.

Cells in the culture media can express a gene of interest particularly during reprogramming. For example, the cells in the culture medium can transiently express the ASCL1 polypeptide. Cells selected for reprogramming do not require expression of heterologous Klf, Sox2, or Myc, and may not be in contact with a Klf, Myc or Sox2 polypeptide. In some embodiments, the expression of other transcription factors such as Myc, Sox2, Klf4 may not be directly or indirectly induced by the culture media.

However, in other embodiments, the cell culture medium can induce expression of endogenous Klf4 polypeptides, Myc polypeptides, Sox2 polypeptides or a combination thereof. For example, expression of endogenous Klf4 polypeptides, Myc polypeptides, and/or Sox2 polypeptides can occur upon exposure to a composition described herein, even when no exogenous Klf4, Myc, and/or Sox2 nucleic acids have been introduced.

1. Culture Conditions

The cells of the present disclosure can be cultured under any conditions known to one of skill in the art. In some embodiments, the cells (e.g., non-cardiomyocytes, cardiomyocytes, and combinations thereof) are cultured in conditions of 1-20% oxygen ($O_2$) and 5% carbon dioxide ($CO_2$). In some embodiments, the cells of the present disclosure are cultured under hypoxic conditions (e.g., in the presence of less than 10% $O_2$). In some embodiments, the cells of the present disclosure are cultured at about 37° C. In some embodiments, the cells of the present disclosure can be cultured at about 37° C., 5% $CO_2$ and 10-20% $O_2$. In some embodiments, the cells are cultured in hypoxic conditions for a period of time. For example, the cells may be cultured under normoxic conditions (~20% $O_2$) for a period of time and then switched to hypoxic conditions, for example ~5% $O_2$.

The advantage of in vitro or ex vivo differentiating of non-cardiomyocytes to cardiomyocytes is the ability to easily identify cells suitable for implantation or for discrimination of cells that are damaged or have not differentiated. In vitro or ex vivo differentiation allows induced cardiomyocytes to be purified or isolated from non-cardiomyocytes that have not differentiated.

After incubation of the starting cells in a reprogramming medium, the cells can then incubated in another media, for example, a maintenance media, an expansion media, or a cardiac induction media that can induce further maturation of the cells.

The base media employed to which the reprogramming agents or induction agents are added can be a convenient cell culture medium. The term "cell culture medium" (also referred to herein as a "culture medium" or "medium") as referred to herein is a medium for culturing cells containing nutrients that maintain cell viability and support proliferation. The cell culture medium can contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are available to those skilled in the art.

Examples of cell culture media that can be employed include MTESR-1® medium (StemCell Technologies, Inc., Vancouver, CA), or ESSENTIAL 8® medium (Life Technologies, Inc.) on a Matrigel substrate (BD Biosciences, NJ) or on a CORNING® Synthemax surface, or in Johansson and Wiles chemically defined media (CDM) supplemented with insulin, transferrin, lipids and polyvinyl alcohol (PVA) as substitute for Bovine Serum Albumin (BSA). Examples of commercially available media also include, but are not limited to, Dulbecco's Modified Eagle's Medium (DMEM), Minimal Essential Medium (MEM), Basal Medium Eagle (BME), RPM1 1640, Ham's F-10, Ham's F-12, a-Minimal Essential Medium (aMEM), Glasgow's Minimal Essential Medium (G-MEM), Iscove's Modified Dulbecco's Medium, or a general purpose media modified for use with pluripotent cells, such as X-VIVO (Lonza) or a hematopoietic base media. In some embodiments, mixtures of two or more cell culture media are used, such as 4 parts Dulbecco's Modified Eagle's Medium (DMEM) to 1 part GIBCO® Media 199. The media may be supplemental with fetal bovine serum (FBS), amino acids, and/or antibotics. In some embodiments, the media is mixed with GIBCO® RPMI 1640 (RPMI)+GIBCO® B-27 Supplement (B27). Growth of cells can be enhanced by additional of rhFGF, rhFGF-10, and rhVEGF (FFV).

The compositions and/or culture media can contain any of the agent(s) or compound(s) described herein in an amount sufficient to induce a cell to express cardiac or cardiomyocyte cell markers. Such cardiac or cardiomyocyte cell markers can include any of the following markers: α-actinin, MLC2v, cMHC, NKX2-5, MEF2c, GATA4, ISL1, cTNT, cTNI, MLC2a and any combination thereof. For example, the culture media can include a TGF-β inhibitor such as SB431542 (e.g., at about 0.1-10 μM), a WNT signaling activator such as CHIR99021 (e.g., at about 3-20 μM), an LSD1/KDM1 inhibitor such as parnate (e.g., at about 0.1-10 μM), and an adenylyl cyclase activator such as forskolin (e.g., at about 3-20 μM).

Incubation can proceed in any of the compositions described herein, for example, until early stage cardiac progenitor markers are expressed by the starting cells. Such early stage cardiac progenitor markers include GATA4, ISL1 or a combination thereof. The early stage cardiac progenitor markers such as GATA4 and/or ISL1 can be expressed by about 6 days, or by about 8 days, or by about 9 days, or by about 10 days, or by about 11 days, or by about 12 days of incubation of cells using the compositions and methods described herein.

The culture media can contain any of the agent(s) or compound(s) described herein in an amount sufficient to reprogram at least 0.001%, or about 0.005%, or about 0.01%, or about 0.02%, or about 0.03% of the cells in a population of cells into a cardiac cell type.

C. In Vivo Reprogramming Methods

In some embodiments, at least one reprogramming factor has been administered to the subject, for example, ASCL1, MYOCD, MEF2C, TBX5, BAF60C, ESRRG, GATA4, GATA6, HAND2, IRX4, ISLL, MEF2C, MESP1, MESP2, NKX2.5, SRF, TBX20, and ZFPM2, or any combination thereof. For example, the subject may be administered a viral or non-viral vector comprising a polynucleotide encoding at least one reprogamming factor. In preferred embodiments, a combination of two or more, and more preferably three or more, of the reprogramming factors are administered to the subject. In some embodiments, one or more of the above listed reprogramming factors is expressly excluded. In other embodiments, the reprogramming factors are selected from the group of ASCL1, MYOCD, MEF2C, TBX5, or any combination thereof. In other embodiments, the reprogramming factors are selected from the group of GATA4, MEF2C, TBX5, MYOCD, or any combination thereof. In specific embodiments, the reprogramming factors are Ascl1 and Myocd (MyA). In specific embodiments, the reprogramming factors are ASCL1, MYOCD, MEF2C and TBX5 (MyAMT). In other some embodiments, the reprogramming factors are GATA4, MEF2C, and TBX5 (GMT). In other specific embodiments, the reprogramming factors are Myocardin, MEF2C, AND TBX5 (i.e., MyMT). In other specific embodiments, the reprogramming factors are GATA4, MEF2C, TBX5, and Myocardin (i.e., 4F). In other embodiments, the reprogramming factors are GATA4, MEF2C, AND TBX5, ESRRG, Myocardin, ZFPM2, and MESP1 (i.e., 7F).

VI. Compositions: Cells and Vectors

The present disclosure provides viral and non-viral vectors. The present disclosure also provides isolated induced cardiomyocytes generated according to the methods of the invention. The induced cardiomyocytes may express at least one cardiac gene at a level higher or a level lower than that found in a naturally occurring cardiomyocyte. The induce cardiomyocyte may be an isolated iCM or a iCM produced in vivo by administration of a composition to the subject.

In some embodiments, the cardiac gene expressed at a higher level than that found in the naturally occurring cardiomyocyte is selected from the group consisting of TNNT2, ACTN2, ATP2A2, MYH6, RYR2, MYH7, and ACTCL. In some embodiments, the cardiac gene expressed at a lower level than that found in the naturally occurring cardiomyocyte is selected from the group consisting of MYBPC3, PIN, MB, LMOD2, MYL2, MYL3, COX6A2, ATP5AL, TTN, TNNI3, PDK4, MYCZ2, CACNALC, SCN5A, MYOCD, and NPPA.

In another aspect, a substantially homogenous population of induced cardiomyocytes generated according to the methods of the invention are provided. In some embodiments, the induced cardiomyocytes of the substantially homogenous population express at least one cardiac gene at a higher level or a lower level than found in a naturally occurring cardiomyocyte.

In some embodiments, the composition comprises a population of isolated induced cardiomyocytes described herein and a carrier, optionally a pharmaceutically acceptable excipient. In some embodiments, the compositions further comprise a stabilizer and/or a preservative.

In some embodiments, the composition comprises a viral or non-viral vector described herein and a carrier, optionally a pharmaceutically acceptable excipient. In some embodiments, the compositions further comprise a stabilizer and/or a preservative.

The composition may comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like.

Parenteral compositions may be prepared using conventional techniques that may include sterile isotonic saline, water, 1,3-butanediol, ethanol, 1,2-propylene glycol, polyglycols mixed with water, Ringer's solution, etc. In one aspect, a coloring agent is added to facilitate locating and properly placing the composition to the intended treatment site.

The composition can include agents that are administered using an implantable device. Suitable implantable devices contemplated by this disclosure include intravascular stents (e.g., self-expandable stents, balloon-expandable stents, and stent-grafts), scaffolds, grafts, and the like. Such implantable devices can be coated on at least one surface, or impregnated, with a composition capable of generating an induced cardiomyocyte. The composition can also include agents that are contained within a reservoir in the implantable device. Where the agents are contained within a reservoir in the implantable device, the reservoir is structured so as to allow the agents to elute from the device. The agents of the composition administered from the implantable device may comprise a WNT inhibitor, the TGF-β inhibitor or both.

Pharmaceutical compositions can be provided in any form amenable to administration. Compositions may include a preservative and/or a stabilizer. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds (QACs), chlorbutanol, 2-ethoxyethanol, and imidurea.

To control tonicity, an aqueous pharmaceutical composition can comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride and calcium chloride.

Compositions may include one or more buffers. Typical buffers include: a phosphate buffer; a Tris buffer; a borate buffer; a succinate buffer; a histidine buffer; or a citrate buffer. Buffers will typically be included at a concentration in the 5-20 mM range. The pH of a composition will generally be between 5 and 8, and more typically between 6 and 8 e.g. between 6.5 and 7.5, or between 7.0 and 7.8.

The composition is preferably sterile. The composition is preferably gluten free. The composition is preferably non-pyrogenic.

The pharmaceutical composition can be administered by any appropriate route, which will be apparent to the skilled person depending on the disease or condition to be treated. Typical routes of administration include oral, intravenous, intra-arterial, intramuscular, subcutaneous, intracranial, intranasal or intraperitoneal.

In some embodiments, a composition comprising cells may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In some embodiments, one or more agents used in the methods of the invention is provided in a controlled release formulation. The term "controlled release formulation" includes sustained release and time-release formulations. Controlled release formulations are well-known in the art. These include excipients that allow for sustained, periodic, pulse, or delayed release of the composition. Controlled release formulations include, without limitation, embedding of the composition (a WNT inhibitor and/or TGF-β inhibitor) into a matrix; enteric coatings; microencapsulation; gels and hydrogels; implants; and any other formulation that allows for controlled release of a composition.

In some embodiments, a reprogrammed population of cells (at various stages of reprogramming) can be frozen at liquid nitrogen temperatures, stored for periods of time, and then thawed for use at a later date. If frozen, a population of reprogrammed cells can be stored in any suitable cryopreservation media, e.g., 10% DMSO, 50% FCS, within 40% RPMI 1640 medium. Once thawed, the cells can be expanded by culturing the cells in an appropriate medium that can contain selected growth factors, vitamins, feeder cells, and other components selected by a person of skill in the art. Viral and non-viral vectors can also be frozen at liquid nitrogen temperatures, or often at higher temperatures, stored for periods of time, and then thawed for use at a later date.

In some embodiments, at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39% of iCM cells are α-actinin positive. In some embodiments, at least 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% of iCM cells are cTnT positive. In some embodiments, at least 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% of iCM cells are α-actinin and cTnT double-positive.

The population of reprogrammed cells generated by the methods described herein can include low percentages of non-cardiac cells (e.g., fibroblasts). For example, a population of reprogrammed cells for use in compositions and for administration to subjects can have less than about 90% non-cardiac cells, less than about 85% non-cardiac cells, less than about 80% non-cardiac cells, less than about 75% non-cardiac cells, less than about 70% non-cardiac cells, less than about 65% non-cardiac cells, less than about 60% non-cardiac cells, less than about 55% non-cardiac cells, less than about 50% non-cardiac cells, less than about 45% non-cardiac cells, less than about 40% non-cardiac cells, less than about 35% non-cardiac cells, less than about 30% non-cardiac cells, less than about 25% non-cardiac cells, less than about 20% non-cardiac cells, less than about 15% non-cardiac cells, less than about 12% non-cardiac cells, less than about 10% non-cardiac cells, less than about 8% non-cardiac cells, less than about 6% non-cardiac cells, less than about 5% non-cardiac cells, less than about 4% non-cardiac cells, less than about 3% non-cardiac cells, less than about 2% non-cardiac cells, or less than about 1% non-cardiac cells of the total cells in the cell population.

Reprogrammed cells can be included in the compositions in varying amounts depending upon the disease or injury to be treated. For example, the compositions can be prepared in liquid form for local or systemic administration containing about $10^3$ to about $10^{12}$ reprogrammed cells, or about $10^4$ to about $10^{10}$ reprogrammed cells, or about $10^5$ to about $10^8$ reprogrammed cells.

One or more of the following types of compounds can also be present in the composition with the cells: a WNT agonist, a GSK3 inhibitor, a TGF-beta signaling inhibitor, an epigenetic modifier, LSD1 inhibitor, an adenylyl cyclase agonist, or any combination thereof. Any of the compounds described herein can be administered with the cells.

The disclosure also provides a kit of parts comprising the above-mentioned agents, compositions or formulations.

VII. Methods of Treatment

The reprogrammed cells and compositions that are described herein can also be employed in a method of treating a subject with a cardiac disease or condition. "Treating" or "treatment of a condition or subject in need thereof" refers to (1) taking steps to obtain beneficial or desired results, including clinical results such as the reduction of symptoms; (2) preventing the disease, for example, causing the clinical symptoms of the disease not to develop in a patient that may be predisposed to the disease, but does not yet experience or display symptoms of the disease; (3) inhibiting the disease, for example, arresting or reducing the development of the disease or its clinical symptoms; (4) relieving the disease, for example, causing regression of the disease or its clinical symptoms; or (5) delaying the disease. For purposes of this invention, beneficial or desired clinical results include, but are not limited to, generating an induced cardiomyocyte and/or promoting myocardial regeneration.

Subjects in need of treatment using the compositions, cells and methods of the present disclosure include, but are not limited to, individuals having a congenital heart defect, individuals suffering from a degenerative muscle disease, individuals suffering from a condition that results in ischemic heart tissue (e.g., individuals with coronary artery disease), and the like. In some examples, a method is useful to treat a degenerative muscle disease or condition (e.g., familial cardiomyopathy, dilated cardiomyopathy, hypertrophic cardiomyopathy, restrictive cardiomyopathy, or coronary artery disease with resultant ischemic cardiomyopathy). In some examples, a subject method is useful to treat individuals having a cardiac or cardiovascular disease or disorder, for example, cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism.

Subjects who are suitable for treatment using the compositions, cells and methods of the present disclosure include individuals (e.g., mammalian subjects, such as humans, non-human primates, domestic mammals, experimental non-human mammalian subjects such as mice, rats, etc.) having a cardiac condition including but limited to a condition that results in ischemic heart tissue (e.g., individuals with coronary artery disease) and the like.

In some examples, an individual suitable for treatment suffers from a cardiac or cardiovascular disease or condition, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism. In some examples, individuals suitable for treatment with a subject method include individuals who have a degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

Subjects in need of treatment using the compositions, cells and methods of the present disclosure include, but are not limited to, individuals having a congenital heart defect, individuals suffering from a degenerative muscle disease, individuals suffering from a condition that results in ischemic heart tissue (e.g., individuals with coronary artery disease), and the like. In some examples, a method is useful to treat a degenerative muscle disease or condition (e.g., familial cardiomyopathy, dilated cardiomyopathy, hypertrophic cardiomyopathy, restrictive cardiomyopathy, or coronary artery disease with resultant ischemic cardiomyopathy). In some examples, a subject method is useful to treat individuals having a cardiac or cardiovascular disease or disorder, for example, cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism.

Subjects who are suitable for treatment using the compositions, cells and methods of the present disclosure include individuals (e.g., mammalian subjects, such as humans, non-human primates, experimental non-human mammalian subjects such as mice, rats, etc.) having a cardiac condition including, but limited to, a condition that results in ischemic heart tissue (e.g., individuals with coronary artery disease) and the like. In some examples, an individual suitable for treatment suffers from a cardiac or cardiovascular disease or condition, e.g., cardiovascular disease, aneurysm, angina, arrhythmia, atherosclerosis, cerebrovascular accident (stroke), cerebrovascular disease, congenital heart disease, congestive heart failure, myocarditis, valve disease coronary, artery disease dilated, diastolic dysfunction, endocarditis, high blood pressure (hypertension), cardiomyopathy, hypertrophic cardiomyopathy, restrictive cardiomyopathy, coronary artery disease with resultant ischemic cardiomyopathy, mitral valve prolapse, myocardial infarction (heart attack), or venous thromboembolism. In some examples, individuals suitable for treatment with a subject method include individuals who have a degenerative muscle disease, e.g., familial cardiomyopathy, dilated cardiomyopathy, hypertrophic cardiomyopathy, restrictive cardiomyopathy, or coronary artery disease with resultant ischemic cardiomyopathy.

Examples of diseases and conditions that can be treated using the reprogrammed cells and/or compositions (containing any of the compounds described herein with or without reprogrammed cells) include any cardiac pathology or cardiac dysfunction. Diseases and conditions that can be treated include those that occur as a consequence of genetic defect, physical injury, environmental insult or conditioning, bad health, obesity and other disease risk.

Ischemic cardiomyopathy is a chronic disorder caused by coronary artery disease (a disease in which there is atherosclerotic narrowing or occlusion of the coronary arteries on the surface of the heart). Coronary artery disease often leads to episodes of cardiac ischemia, in which the heart muscle is not supplied with enough oxygen-rich blood.

Non-ischemic cardiomyopathy is generally classified into three groups based primarily on clinical and pathological characteristics: dilated cardiomyopathy, hypertrophic cardiomyopathy and restrictive and infiltrative cardiomyopathy.

In another embodiment, the cardiac pathology is a genetic disease such as Duchenne muscular dystrophy and Emery Dreiffuss dilated cardiomyopathy.

For example, the cardiac pathology can be selected from the group consisting of congestive heart failure, myocardial infarction, cardiac ischemia, myocarditis and arrhythmia. In some embodiments, the subject is diabetic. In some embodiments, the subject is non-diabetic. In some embodiments, the subject suffers from diabetic cardiomyopathy.

Reprogrammed cells generated as described herein can be employed for tissue reconstitution or regeneration in a human patient or other subjects in need of such treatment. The cells are administered in a manner that permits them to graft or migrate to a diseased or injured tissue site and to reconstitute or regenerate the functionally deficient area. Devices are available that can be adapted for administering cells, for example, to cardiac tissues.

For therapy, recombinant viruses, non-viral vectors, cardiac progenitor cells, cardiomyocytes and/or pharmaceutical compositions can be administered locally or systemically. A reprogrammed population of cells can be introduced by injection, catheter, implantable device, or the like. A population of recombinant viruses or reprogrammed cells can be administered in any physiologically acceptable excipient or carrier that does not adversely affect the cells. For example, the recombinant viruses, non-viral vectors, cardiac progenitor cells, cardiomyocytes and/or pharmaceutical compositions can be administered intravenously or through an intracardiac route (e.g., epicardially or intramyocardially). Methods of administering the recombinant viruses, non-viral vectors, cardiomyocytes and pharmaceutical compositions (e.g., compositions comprising vectors) of the disclosure to subjects, particularly human subjects include injection, implantation, or infusion of the pharmaceutical compositions (e.g., compositions comprising viral vectors) or cells into target sites in the subjects. Injection may include direct muscle injection and infusion may include intravascular infusion. The vectors, pharmaceutical compositions, or cells can be inserted into a delivery device which facilitates introduction by injection or implantation of the pharmaceutical compositions or cells into the subjects. Such delivery devices include tubes, e.g., catheters, for injecting cells and fluids into the body of a recipient subject. The tubes can additionally include a needle, e.g., a syringe, through which the cells of the invention can be introduced into the subject at a desired location. In some embodiments, the pharmaceutical compositions or cells are delivered by microneedle patch as described in, for example, Tang et al. Cardiac cell-integrated microneedle patch for treating myocardial infarction. *Science Advances* 28 Nov. 2018: Vol. 4, no. 11, eaat9365.

The recombinant viruses, non-viral vectors, cardiac progenitor cells and cardiomyocytes can be inserted into such a delivery device, e.g., a syringe, in different forms. A population of recombinant viruses, non-viral vectors, reprogrammed cells can be supplied in the form of a pharmaceutical composition. Such a composition can include an isotonic excipient prepared under sufficiently sterile conditions for human administration. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000. The choice of the cellular excipient and any accompanying constituents of the composition that includes a population of reprogrammed cells can be adapted to optimize administration by the route and/or device employed.

As used herein, the term "solution" includes a carrier or diluent in which the cardiomyocytes and cardiac cells of the invention remain viable or the viral vectors remain biologically active. Carriers and diluents that can be used include saline, aqueous buffer solutions, solvents and/or dispersion media. The use of such carriers and diluents is well known in the art. The solution is preferably sterile and fluid to the extent that easy syringability exists. For transplantation, cardiomyocytes and/or cardiac cells are drawn up into a syringe and administrated to anesthetized transplantation recipients. For direct injection, a needle, syringe, or catheter is inserted into the heart surgically, ideally in a minimally invasive setting. Multiple injections may be made using this procedure.

The cardiac progenitor cells, cardiac cells, and/or cardiomyocytes can also be embedded in a support matrix. A composition that includes a population of reprogrammed cells can also include or be accompanied by one or more other ingredients that facilitate engraftment or functional mobilization of the reprogrammed cells. Suitable ingredients include matrix proteins that support or promote adhesion of the reprogrammed cells, or complementary cell types, such as cardiac pacemaker cells, or cardiac cells at different stages of maturation. In another embodiment, the composition may include physiologically acceptable matrix scaffolds. Such physiologically acceptable matrix scaffolds can be resorbable and/or biodegradable.

A. Methods of Treatment Using Recombinant Viruses

In some aspects, a viral particle of the present disclosure can be used to treat a subject in need thereof. In some embodiments, the recombinant viruses can be administered to the subject in need thereof, where administration into the subject of the recombinant viruses, treats a cardiovascular disease in the subject.

Recombinant viruses may be administered locally or systemically. Recombinant viruses may be engineered to target specific cell types by selecting an appropriate capsid protein or by pseudotyping the virus with a protein from another virus type. To determine the suitability of various therapeutic administration regimens and dosages of viral particle compositions, the recombinant viruses can first be tested in a suitable animal model. At one level, recombinant viruses are assessed for their ability to infect target cells in vivo. Recombinant viruses can also be assessed to ascertain whether they migrate to target tissues, whether they induce an immune response in the host, or to determine an appropriate number, or dosage, of recombinant viruses to be administered. It may be desirable or undesirable for the recombinant viruses to generate an immune response, depending on the disease to be treated. Generally, if repeated administration of a viral particle is required, it will be advantageous if the viral particle is not immunogenic. For testing purposes, viral particle compositions can be administered to immunodeficient animals (such as nude mice, or animals rendered immunodeficient chemically or by irradiation). Target tissues or cells can be harvested after a period of infection and assessed to determine if the tissues or cells have been infected and if the desired phenotype (e.g. induced cardiomyocyte) has been induced in the target tissue or cells.

Recombinant viruses can be administered by various routes, including without limitation direct injection into the heart or cardiac catheterization. Alternatively, the recombinant viruses can be administered systemically such as by intravenous infusion. When direct injection is used, it may be performed either by open-heart surgery or by minimally invasive surgery. In some cases, the recombinant viruses are delivered to the pericardial space by injection or infusion. Injected or infused recombinant viruses can be traced by a variety of methods. For example, recombinant viruses labeled with or expressing a detectable label (such as green fluorescent protein, or beta-galactosidase) can readily be detected. The recombinant viruses may be engineered to cause the target cell to express a marker protein, such as a surface-expressed protein or a fluorescent protein. Alternatively, the infection of target cells with recombinant viruses can be detected by their expression of a cell marker that is not expressed by the animal employed for testing (for example, a human-specific antigen when injecting cells into an experimental animal). The presence and phenotype of the target cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for RNA indicative of a cardiac phenotype.

In some embodiments, the disclosure provides methods of treating myocardial infarction in subject (e.g., a human) in need thereof. In some embodiments, the methods comprise administering an AAV vector encoding MyΔ3 and ASCL1. In some embodiments, the methods comprise administering to the subject an AAV vector comprising a polynucleotide encoding MyΔ3-2A-ASCL1. In some embodiments, the methods comprise administering to the subject an AAV vector comprising a polynucleotide encoding ASCL1-2A-MyΔ3. In some embodiments, the disclosure provides methods of treating myocardial infarction in subject (e.g., a human) in need thereof, comprising administering to the subject an AAV vector comprising a polynucleotide encoding MyΔ3-2A-ASCL1 (AAV:MyΔ3A), wherein the method results in partial, substantial, or complete reversal of heart failure and/or partial, substantial, or complete halt to progression of heart failure and/or partial, substantial, or complete prevention of heart failure in the subject. The AAV vector may be an AAV5 vector. The AAV vector may be a variant of AAV5. The AAV vector may be another AAV vector. The AAV vector may be capable of infection or transduction (e.g., preferential infection or transduction) of non-cardiomyocyte cells (e.g., heart fibroblast cells). In some embodiments, the methods of treatment of the disclosure result in increased left ventricular ejection fraction (LVEF) and/or maintained LVEF in the subject. In some embodiments, the subject suffers from or is at risk for myocardial infarction (MI). In some embodiments, the subject suffers from or is at risk for acute myocardial infarction (AMI). In some embodiments, the subject suffers from or is at risk for acute myocardial infarction (CMI). In some embodiments, the subject suffers from or is at risk for chronic heart failure (e.g., due to MI or AMI or CMI). In some embodiments, the subject suffers from or is at risk for congestive heart failure (e.g., due to MI or AMI or CMI). In various embodiments, the administering step comprises intracardiac or intramyocardial injection, intracoronary catheritization, or systemic administration (e.g., intravenous administration). In some embodiments, AAV delivery of MyΔ3A provides functional benefit in vivo in either or both of acute myocardial infarction (AMI) and chronic myocardial infarction (CMI). In some embodiments, heart failure to due to AMI is partially, substantially or completely reversed. In some embodiments, progression of heart failure due to CMI is partially, substantially or completely halted.

In some embodiments, the administration step comprises administering the AAV vector within about one hour, within about two hours, within about three hours, within about four hours, within about five hours, within about 12 hours, within about 18 hours, or within about 24 hours of a heart attack. In some embodiments, the administration step comprises administering the AAV vector within about one day, within about two days, within about three days, within about four days, within about five days, within about six days, within about seven days, or within about 24 hours of a heart attack. In some embodiments, the administration step comprises administering the AAV vector within about one week, within about two weeks, within about three weeks, or within about four weeks a heart attack.

In an aspect, the disclosure provides a method of treating a heart condition in a subject suffering from or at risk for a heart condition, comprising administering a vector or vector system of the disclosure to the subject. The vector may be a monocistronic, bicistronic, or polycistronic vector. In an embodiment, the disclosure provides a method of promoting, increasing, improving, or sustaining improvement in heart function. In some embodiments, the method increases the number of myocytes in the heart by at least about 5%, at least about 10%, at least about 15%, or at least about 20%. In some embodiments, the heart condition is a myocardiac infarction. In some embodiments, the heart condition is an acute myocardiac infarction. In some embodiments, the heart condition is a heart failure. In some embodiments, the heart condition is a chronic ischemic heart failure. In another aspect, the disclosure provides a kit comprising a vector or vector system of the disclosure, and optionally instructions for use in treating a heart condition.

In another aspect, the disclosure provides method of converting a differentiated non-cardiomycyte cell into a cardiomyocyte, comprising comprising contacting the differentiated cells with a vector or vector system of the disclosure. In some embodiments, the differentiated non-cardiomycyte cell is a differentiated non-cardiomycyte cell. In some embodiments, the differentiated non-cardiomycyte cell is a human differentiated non-cardiomycyte cell. In some embodiments, the differentiated non-cardiomycyte cell is an in vivo differentiated non-cardiomycyte cell. In some embodiments, the differentiated non-cardiomycyte cell is an in vitro differentiated non-cardiomycyte cell. In some embodiments, the differentiated non-cardiomycyte cell is a cardiac cell.

In some embodiments, the methods of the disclosure improve or restore the ejection fraction of the heart. In some embodiments, the improvement comprises at least about 5%, at least about 10%, at least about 20%, at least about 30%, or at least about 40% improvement. In some embodiments, the method comprises increasing the ejection fraction of the heart of the subject to at least about 30%, at least about 40%, at least about 50%, or at least about 60%. In some embodiments, the improvement or restoration of ejection fraction occurs within at most about two, about three, about four, about five, or about six weeks. In some embodiments, the improvement or restoration of ejection fraction occurs within two, three, four, five, or six weeks. In some embodiments, the methods of the disclosure improve or restore the ejection fraction of the heart. In some embodiments, the improvement comprises about 10%, about 20%, about 30%, or about 40% improvement. In some embodiments, the method comprises increasing the ejection fraction of the heart of the subject to about 30%, about 40%, about 50%, or about 60%. In some embodiments, the methods of the disclosure improve or restore the ejection fraction of the heart. In some embodiments, the improvement comprises about 5% to about 10%, about 10% to about 20%, about 20% to about 30%, or about 30% to about 40% improvement. In some embodiments, the method comprises increasing the ejection fraction of the heart of the subject to about 30%, about 40%, about 50%, or about 60%. In some embodiments, the improvement or restoration of ejection fraction occurs within about two, about three, about four, about five, or about six weeks. In some embodiments, the improvement or restoration of ejection fraction occurs within two, three, four, five, or six weeks.

B. Methods of Treatment Using Induced Cardiomyocytes

In some aspects, an induced cardiomyocyte of the present disclosure can be used to treat a subject in need thereof. In some embodiments, the induced cardiomyocytes can be administered to the subject in need thereof, where administration into the subject of the induced cardiomyocytes, treats a cardiovascular disease in the subject.

Many cell types are capable of migrating to an appropriate site for regeneration and differentiation within a subject. To determine the suitability of various therapeutic administration regimens and dosages of cell compositions, the cells can first be tested in a suitable animal model. At one level, cells are assessed for their ability to survive and maintain their phenotype in vivo. Cells can also be assessed to ascertain whether they migrate to diseased or injured sites in vivo, or to determine an appropriate number, or dosage, of cells to be administered. Cell compositions can be administered to immunodeficient animals (such as nude mice, or animals rendered immunodeficient chemically or by irradiation). Tissues can be harvested after a period of regrowth, and assessed as to whether the administered cells or progeny thereof are still present, are alive, and/or have migrated to desired or undesired locations.

Injected cells can be traced by a variety of methods. For example, cells containing or expressing a detectable label (such as green fluorescent protein, or beta-galactosidase) can readily be detected. The cells can be pre-labeled, for example, with BrdU or [$^3$H]-thymidine, or by introduction of an expression cassette that can express green fluorescent protein, or beta-galactosidase. Alternatively, the reprogrammed cells can be detected by their expression of a cell marker that is not expressed by the animal employed for testing (for example, a human-specific antigen when injecting cells into an experimental animal). The presence and phenotype of the administered population of reprogrammed cells can be assessed by fluorescence microscopy (e.g., for green fluorescent protein, or beta-galactosidase), by immunohistochemistry (e.g., using an antibody against a human antigen), by ELISA (using an antibody against a human antigen), or by RT-PCR analysis using primers and hybridization conditions that cause amplification to be specific for RNA indicative of a cardiac phenotype.

C Methods of Treatment Using Reprogramming Factors and Compositions

In other embodiments, a method of treating cardiovascular disease involves administering to the subject in need thereof an effective amount of a reprogramming composition capable of increasing the expression of ASCL1, MYOCD, MEF2C, TBX5, or combinations thereof. In other embodiments, a method of treating cardiovascular disease involves administering to the subject in need thereof an effective amount of a reprogramming composition capable of increasing the expression of ASCL1, MYOCD, MEF2C, TBX5, or combinations thereof.

The invention provides methods of treating a cardiovascular disease comprising administering to a subject in need thereof an effective amount of an induced cardiomyocyte produced by the methods described herein.

In some aspects, an induced cardiomyocyte of the present disclosure can be used to treat a subject in need thereof. In some embodiments, the induced cardiomyocyte can be administered to the subject in need thereof, where administration into the subject of the induced cardiomyocyte, treats a cardiovascular disease in the subject. Thus, in some embodiments, a method of treating cardiovascular disease involves administering to a subject in need thereof a population of induced cardiomyocytes. In other embodiments, a method of treating cardiovascular disease involves administering to the subject in need thereof an effective amount of a composition comprising a WNT inhibitor, a TGF-β inhibitor or both.

In some embodiments, the non-cardiomyocyte is cultured in the presence of the TGF-β inhibitor for about 6 hours, about 12 hours, about 18 hours, about 24 hours, about 30 hours, about 36 hours, about 42 hours, or about 48 hours prior to addition of the WNT inhibitor. In one preferred embodiment, the non-cardiomyocyte is cultured in the presence of the TGF-β inhibitor for about 24 hours prior to addition of the WNT inhibitor.

VIII. Kits

A variety of kits are described herein that include any of the compositions, compounds and/or agents described herein. The kit can include, for example, a culture media in concentrated or non-concentrated form. The kit can include any of the compounds described herein, either mixed together or individually packaged, and in dry or hydrated form. The compounds and/or agents described herein can be packaged separately into discrete vials, bottles or other containers. Alternatively, any of the compounds and/or agents described herein can be packaged together as a single composition, or as two or more compositions that can be used together or separately. The compounds and/or agents described herein can be packaged in appropriate ratios and/or amounts to facilitate conversion of selected cells across differentiation boundaries to form cardiac progenitor cells and/or cardiomyocytes.

The kit can also include an expression cassette, an expression vector, or a combination thereof that includes a polynucleotide segment encoding a protein of interest operably linked to a promoter and other optional regulatory elements. The expression cassette or vector can be provided in dehydrated form or in a ready to use solution.

A kit is described herein for culture of cells in vitro that can include any of the compositions, compounds, expression cassettes, expression vectors, and/or agents described herein, as well as instructions for using those compositions, compounds, expression cassettes, expression vectors, and/or agents.

Some kits can include a cell culture or cell media that includes any of the compositions, compounds and/or agents described herein. The kits can include one or more sterile cell collection devices such as a swab, skin scrapping device, a needle, a syringe, and/or a scalpel. The kits can also include antibodies for detection of cardiac progenitor and/or cardiomyocyte cell markers such as antibodies against any of the following markers: α-actinin, MLC2v, cMHC, NKX2-5, GATA4, ISL1, MEF2C, cTNT, cTNI, MLC2a, and any combination thereof. The antibodies can be labeled so that a detectable signal can be observed when the antibodies form a complex with the cardiac progenitor cell and/or cardiomyocytes cell marker(s).

The instructions can include guidance for introducing a nucleic acid into selected cells (e.g., a selected starting cell or selected cells). Such a nucleic acid can be an RNA, an expression cassette, or an expression vector that encodes a polynucleotide or protein of interest, and culturing the cells for a time and under conditions sufficient to express the polynucleotide or protein of interest. The instructions can also include instructions for converting the cells across differentiation boundaries and into the cardiac lineage using any of the compositions and methods disclosed herein. For example, the instructions can describe amounts of the compositions, compounds and/or agents described herein to add to cell culture media, times sufficient to convert cells to the cardiac lineage, maintenance of appropriate cell densities for optimal conversion, and the like. For example, the instructions can describe procedures for rehydration or dilution of the compositions, compounds and/or agents described herein. When a kit provides a cell culture medium containing some of the compositions, compounds and/or agents described herein, the instructions can describe how to add other compounds and/agents. The instructions can also describe how to convert the selected cells to cardiac progenitor cells or to cardiomyocytes.

The instructions can also describe procedures for detecting cardiac progenitor and/or cardiomyocyte cell markers by use of antibodies against those markers so that the extent of conversion and/or differentiation can be assessed.

Another kit is also described herein that includes any of the compositions, compounds and/or agents described herein for therapeutic treatment of a subject. The kit can include any of the compositions, compounds and/or agents described herein, as well as instructions for administering those compositions, compounds and/or agents. Such instructions can provide the information described throughout this application.

The kit can also include cells. For example, the kit can include chemically induced cardiac progenitor cells and/or cardiomyocytes that have been treated by the compositions and/or methods described herein and that are ready for administration.

The recombinant viruses, non-viral vectors, cells, compositions and/or compounds can be provided within any of the kits in the form of a delivery device. Alternatively a delivery device can be separately included in the kit(s), and the instructions can describe how to assemble the delivery device prior to administration to a subject. The delivery device can provide a scaffold for cell growth and/or a matrix for controlled release of any of the compositions, compounds or agents described herein.

Any of the kits can also include syringes, catheters, scalpels, sterile containers for sample or cell collection, diluents, pharmaceutically acceptable carriers, and the like.

The kits can provide other factors such as any of the supplementary factors or drugs described herein for the compositions in the preceding section or other parts of the application.

ENUMERATED EMBODIMENTS

The invention may be defined by reference to the following enumerated embodiments:

Embodiments Set 1

Clause 1-1. Induced cardiomyocyte (iCM) cells, wherein the cells comprise an ASCL1 polynucleotide.
Clause 1-2. The iCM cells of clause 1-1, wherein the cells comprise a MYOCD polynucleotide, a MEF2C polynucleotide, and a TBX5 polynucleotide.

Clause 1-3. The iCM cells of clause 1-2, wherein the ASCL1 polynucleotide and the MYOCD polynucleotide are expressed from a first polycistronic vector; and wherein the MEF2C polynucleotide and the TBX5 polynucleotide are expressed from a second polycistronic vector.

Clause 1-4. The iCM cells of clause 1-3, wherein the first polycistronic vector and the second polycistronic vector are each independently selected from a lipid nanoparticle, a transposon, an adeno-associated virus (AAV) vector, an adenovirus, a retrovirus, an integrating lentiviral vector (LVV), and a non-integrating LVV.

Clause 1-5. The iCM cells of any of clauses 1-2-4, wherein at least 25% of iCM cells are α-actinin positive.

Clause 1-6. The iCM cells of any of clauses 1-2-5, wherein at least 2% of iCM cells are cTnT positive.

Clause 1-7. The iCM cells of clause 1-1, wherein the cells comprise a polynucleotide encoding MYOCD polypeptide.

Clause 1-8. The iCM cells of clause 1-2, wherein the ASCL1 polynucleotide and the MYOCD polynucleotide are co-translationally expressed from a polycistronic vector.

Clause 1-9. The iCM cells of clause 1-8, wherein the polycistronic vector is a vector comprising a MYOCD-2A-ASCL1 polynucleotide and wherein the vector is selected from a lipid nanoparticle, a transposon, an adeno-associated virus (AAV) vector, an adenovirus, a retrovirus, an integrating lentiviral vector (LVV), and a non-integrating LVV.

Clause 1-10. The iCM cells of any of clauses 1-7-9, wherein at least 25% of iCM cells are α-actinin positive.

Clause 1-11. The iCM cells of any of clauses 1-7-10, wherein at least 5% of iCM cells are cTnT positive.

Clause 1-12. The iCM cells of clause 1-1, wherein the cells are generated from primary adult human cardiac fibroblasts (AHCFs).

Clause 1-13. A method of inducing a cardiomyocyte phenotype in differentiated cells, comprising contacting the differentiated cells with a retroviral expression vector comprising an ASCL1 polynucleotide, thereby generating a population of induced cardiomyocyte (iCM) cells.

Clause 1-14. The method of clause 1-1, wherein the retroviral expression vector comprises a MYOCD polynucleotide.

Clause 1-15. The method of clause 1-14, wherein the ASCL1 polynucleotide and the MYOCD polynucleotide are expressed from a MYOCD-2A-ASCL1 polynucleotide.

Clause 1-16. The method of clause 1-1, wherein the method comprises contacting the source cells with a second retroviral expression vector comprising one or both of a MEF2C polynucleotide and the TBX5 polynucleotide.

Clause 1-17. The method of clause 1-16, wherein the MEF2C polynucleotide and the TBX5 polynucleotide are expressed from a MEF2C-2A-TBX5 polynucleotide or a TBX5-2A-MEF2C polynucleotide.

Clause 1-18. The method of any of clauses 1-13-17, wherein at least 25% of iCM cells are α-actinin positive.

Clause 1-19. The method of any of clauses 1-13-18, wherein at least 5% of iCM cells are cTnT positive.

Clause 1-20. The method of clause 1-13, wherein the differentiated cells comprise primary adult human cardiac fibroblasts (AHCFs).

Clause 1-21. A method of treating a heart condition in a subject, comprising administering one or more nucleic acids encoding an ASCL1 polynucleotide and optionally one or more of a MYOCD polynucleotide, a MEF2C polynucleotide, and a TBX5 polynucleotide into the subject, thereby inducing transdifferentiation of fibroblast cells into induced cardiomyocyte (iCM) cells in the subject in vivo, thereby treating the subject.

Clause 1-22. The method of clause 1-21, wherein the administering step comprises a route of administration selected from direct injection into the heart of the subject, intravenous injection, and delivery into the subject by catheter.

Clause 1-23. The method of clause 1-21, wherein the one or more nucleic acids are provided in one or more retroviral vectors.

Clause 1-24. The method of clause 1-21, wherein the one or more nucleic acids are provided in one or more adeno-associated virus (AAV) vectors.

Clause 1-25. A method of treating a heart condition in a subject, comprising introducing into differentiated cells one or more nucleic acids encoding an ASCL1 polynucleotide and optionally one or more of a MYOCD polynucleotide, a MEF2C polynucleotide, and a TBX5 polynucleotide in cell culture, thereby generating induced cardiomyocyte (iCM) cells ex vivo; and administering the iCM cells to the subject, thereby treating the subject.

Clause 1-26. The method of clause 1-25, wherein the one or more nucleic acids are provided in one or more retroviral vectors.

Clause 1-27. The method of clause 1-25, wherein the one or more nucleic acids are provided in one or more adeno-associated virus (AAV) vectors.

Clause 1-28. The method of clause 1-25, wherein the iCM cells are administered on a biocompatible scaffold.

Clause 1-29. The method of clause 1-25, wherein the differentiated cells comprise primary adult human cardiac fibroblasts (AHCFs).

Clause 1-30. The method of clause 1-29, wherein the AHCFs are autologous cells derived from the subject.

Clause 1-31. The method of clause 1-29, wherein the AHCFs are allogeneic cells derived from a donor other than the subject.

Clause 1-32. A vector, comprising a polynucleotide selected from a MEF2C-2A-TBX5 polynucleotide, a TBX5-2A-MEF2C polynucleotide, and a MYOCD-2A-ASCL1 polynucleotide, wherein the vector is selected from a lipid nanoparticle, a transposon, an adeno-associated virus (AAV) vector, an adenovirus, a retrovirus, an integrating lentiviral vector (LVV), and a non-integrating LVV Embodiments Set 2

Clause 2-1. A vector, comprising, in any 5' to 3' order and on the same or different polynucleotide strands, a MYOCD polynucleotide and either or both of an ASCL1 polynucleotide or a MYF6 polynucleotide; each polynucleotide operatively linked to at least one promoter.

Clause 2-2. The vector of clause 2-1, wherein the vector comprises, in any 5' to 3' order and on the same or different polynucleotide strands, a MYOCD polynucleotide and an ASCL1 polynucleotide.

Clause 2-3. The vector of clause 2-1, wherein the vector comprises, in any 5' to 3' order and on the same or different polynucleotide strands, a MYOCD polynucleotide and a MYF6 polynucleotide.

Clause 2-4. The vector of clause 2-1, wherein the vector comprises, in any 5' to 3' order and on the same or different polynucleotide strands, a MYOCD polynucleotide; either or both of a MEF2C polynucleotide and a TBX5 polynucleotide; and either or both of an ASCL1 polynucleotide and a MYF6 polynucleotide.

Clause 2-5. The vector of clause 2-4, wherein the vector comprises, in any 5' to 3' order and on the same or different polynucleotide strands, a MYOCD polynucleotide, an ASCL1 polynucleotide, a MEF2C polynucleotide, and a TBX5 polynucleotide.

Clause 2-6. The vector of clause 2-4, wherein the vector comprises, in any 5' to 3' order and on the same or different polynucleotide strands, a MYOCD polynucleotide, a MYF6 polynucleotide, a MEF2C polynucleotide, and a TBX5 polynucleotide.

Clause 2-7. The vector of any one of clauses 2-1 to 7, wherein the MYOCD is an engineered myocardin.

Clause 2-8. The vector of any one of clauses 2-1 to 7, wherein the vector comprises no reprogramming factor polynucleotide other than a MYOCD polynucleotide, an ASCL1 polynucleotide, a MYF6 polynucleotide, a MEF2C polynucleotide, or a TBX5 polynucleotide.

Clause 2-9. The vector of any one of clauses 2-1 to 7, wherein the vector comprises no other other protein-coding gene.

Clause 2-10. The vector of any one of clauses 2-1 to 9, wherein the vector is a polycistronic vector.

Clause 2-11. The vector of any one of clauses 2-1 to 10, wherein the vector is selected from a lipid nanoparticle, a transposon, an adeno-associated virus (AAV) vector, an adenovirus, a retrovirus, an integrating lentiviral vector (LVV), and a non-integrating LVV.

Clause 2-12. The vector of any one of clauses 2-1 to 10, wherein the vector is an AAV vector.

Clause 2-13. The vector of any one of clauses 2-1 to 10, wherein the vector is an integrating LVV or a non-integrating LVV.

Clause 2-14. The vector of any one of clauses 2-1 to 13, wherein the vector is capable of reprogramming differentiated cells into induced cardiomyocyte (iCM) cells.

Clause 2-15. The vector of clause 2-14, wherein at least 10%, at least 15%, or at least 20% of iCM cells are α-actinin positive.

Clause 2-16. The vector of clause 2-14 or 15, wherein at least 2%, at least 5%, or at least 8% of iCM cells are cTnT positive.

Clause 2-17. The vector of any one of clauses 2-1 to 16, wherein the ASCL1 polynucleotide, if present, or the MYF6 polynucleotide, if present, and the MYOCD polynucleotide are operatively linked to the same promoter and are co-translationally expressed.

Clause 2-18. The vector of clause 2-2, wherein the vector comprises a MYOCD-2A-ASCL1 polynucleotide or an ASCL1-2A-MYOCD polynucleotide, operatively linked to the same promoter.

Clause 2-19. The vector of clause 2-3, wherein the vector comprises a MYOCD-2A-MYF6 polynucleotide or an ASCL1-2A-MYF6 polynucleotide, operatively linked to the same promoter.

Clause 2-20. The vector of any one of clauses 2-1 to 19, wherein the ASCL1 polynucleotide shares at least 90%, 95%, 96%, 97%, 98%, 99%, or 100% identity to the nucleotide sequence of human ASCL1 (SEQ ID NO: 2).

Clause 2-21. The vector of any one of clauses 2-1 to 19, wherein the MYF6 polynucleotide shares at least 90%, 95%, 96%, 97%, 98%, 99%, or 100% identity to the nucleotide sequence of human MYF6 (SEQ ID NO: 56).

Clause 2-22. A vector system, comprising a first polycistronic vector encoding a MYOCD polynucleotide and either or both of an ASCL1 polynucleotide or a MYF6 polynucleotide; and a second polycistronic vector comprising a MEF2C polynucleotide and a TBX5 polynucleotide.

Clause 2-23. The vector system of clause 2-22, wherein the first polycistronic vector comprises a MYOCD-2A-ASCL1 polynucleotide or an ASCL1-2A-MYOCD polynucleotide.

Clause 2-24. The vector system of clause 2-22, wherein the first polycistronic vector comprises a MYOCD-2A-MYF6 polynucleotide or an ASCL1-2A-MYF6 polynucleotide.

Clause 2-25. The vector system of any one of clauses 2-22 to 24, wherein the first polycistronic vector and the second polycistronic vector are each independently selected from a lipid nanoparticle, a transposon, an adeno-associated virus (AAV) vector, an adenovirus, a retrovirus, an integrating lentiviral vector (LVV), and a non-integrating LVV.

Clause 2-26. The vector system of any one of clauses 2-22 to 25, wherein the ASCL1 polynucleotide shares at least 90%, 95%, 96%, 97%, 98%, 99%, or 100% identity to the nucleotide sequence of human ASCL1 (SEQ ID NO: 2).

Clause 2-27. The vector system of any one of clauses 2-22 to 25, wherein the MYF6 polynucleotide shares at least 90%, 95%, 96%, 97%, 98%, 99%, or 100% identity to the nucleotide sequence of human MYF6 (SEQ ID NO: 56).

Clause 2-28. A method of inducing a cardiomyocyte phenotype in differentiated cells, comprising contacting the differentiated cells with the vector of any one of clauses 2-1 to 21.

Clause 2-29. A method of inducing a cardiomyocyte phenotype in differentiated cells, comprising contacting the differentiated cells with the vector system of any one of clauses 2-22 to 27.

Clause 2-30. The method of clause 2-28 or 29, wherein the differentiated cells are in vitro cells during the contacting step.

Clause 2-31. The method of clause 2-28 or 29, wherein the differentiated cells are in vivo cells in a subject suffering from or at risk for a heart condition.

Clause 2-32. A method of treating a heart condition in a subject suffering from or at risk for a heart condition, comprising contacting the differentiated cells in vitro with the vector of any one of clauses 2-1 to 21 to generate iCM cells, and administering the iCM cells to the subject.

Clause 2-33. A method of treating a heart condition in a subject suffering from or at risk for a heart condition, comprising contacting the differentiated cells in vitro with the vector system of any one of clauses 2-22 to 27 to generate iCM cells, and administering the iCM cells to the subject.

Clause 2-34. A method of treating a heart condition in a subject suffering from or at risk for a heart condition, comprising administering the vector of any one of clauses 2-1 to 21 to the subject.

Clause 2-35. A method of treating a heart condition in a subject suffering from or at risk for a heart condition, comprising administering the vector system of any one of clauses 2-22 to 27 to the subject.

Clause 2-36. A kit comprising the vector of any one of clauses 2-1 to 21, and instructions for use in treating a heart condition.

Clause 2-37. A kit comprising the vector system of any one of clauses 2-22 to 27, and instructions for use in treating a heart condition.

Embodiments Set 3

Clause 3-1. An isolated polynucleotide, comprising an engineered MYOCD polynucleotide encoding an engineered myocardin protein having a length of at most 850 amino acids, wherein the engineered myocardin protein comprises an SRF interaction domain, an SAP domain, and a TAD domain.

Clause 3-2. The polynucleotide of clause 3-1, wherein the engineered myocardin protein comprises an Mef2c interaction domain.

Clause 3-3. The polynucleotide of clause 3-2, wherein:

Clause 3-4. the Mef2c interaction domain shares at least 85% identity to SEQ ID NO: 17, Clause 3-5. the SRF domain shares at least 85% identity to SEQ ID NO: 18, Clause 3-6. the SAP domain shares at least 85% identity to SEQ ID NO: 19, and Clause 3-7. the TAD domain shares at least 85% identity to SEQ ID NO: 11.

Clause 3-8. The polynucleotide of clause 3-1 or 2, wherein the engineered myocardin protein comprises an LZ domain.

Clause 3-9. The polynucleotide of clause 3-4, wherein the LZ domain shares at least 85% identity to SEQ ID NO: 20.

Clause 3-10. The polynucleotide of any of clauses 3-1 to 5, wherein the engineered myocardin protein comprises:

Clause 3-11. a first polypeptide that shares at least 85% identity to residues 5-413 of human myocardin (SEQ ID NO: 10), and Clause 3-12. second polypeptide that shares at least 85% identity to residues 764-986 of human myocardin (SEQ ID NO: 11), Clause 3-13. wherein the first polypeptide and the second polypeptide are linked by a linker comprising a peptide bond or a polypeptide linker of 1-50 amino acid residues.

Clause 3-14. The polynucleotide of any of clauses 3-1 to 5, wherein the engineered myocardin protein comprises:

Clause 3-15. a first polypeptide that shares at least 85% identity to residues 5-438 of human myocardin (SEQ ID NO: 12), and Clause 3-16. second polypeptide that shares at least 85% identity to residues 764-938 of human myocardin (SEQ ID NO: 11), Clause 3-17. wherein the first polypeptide and the second polypeptide are linked by a linker comprising a peptide bond or a polypeptide linker of 1-50 amino acid residues.

Clause 3-18. The polynucleotide of any of clauses 3-1 to 5, wherein the engineered myocardin protein comprises:

Clause 3-19. a first polypeptide that shares at least 85% identity to residues 5-559 of human myocardin (SEQ ID NO: 13), and Clause 3-20. second polypeptide that shares at least 85% identity to residues 764-938 of human myocardin (SEQ ID NO: 11), Clause 3-21. wherein the first polypeptide and the second polypeptide are linked by a linker comprising a peptide bond or a polypeptide linker of 1-50 amino acid residues.

Clause 3-22. The polynucleotide of any of clauses 3-6 to 8, wherein the linker consists of a peptide bond.

Clause 3-23. The polynucleotide of any of clauses 3-6 to 8, wherein the linker is a polypeptide selected from G, GG, GGG, GSG, GSS, GGS, GGSGGS (SEQ ID NO: 30), GSSGGS (SEQ ID NO: 31), GGSGSS (SEQ ID NO: 32), GGSGGSGGS (SEQ ID NO: 33), GGSGGSGGSGGS (SEQ ID NO: 34).

Clause 3-24. The polynucleotide of clause 3-9, wherein the engineered myocardin protein comprises a sequence selected from SEQ ID NOs: 14-16.

Clause 3-25. An isolated polynucleotide, comprising an engineered MYOCD polynucleotide encoding an engineered myocardin protein, wherein the engineered myocardin protein comprises a deletion of at least 50 amino acids in the region corresponding to amino acids 414-764 of the native mycocardin (SEQ ID NO: 3).

Clause 3-26. The polynucleotide of clause 3-12, wherein the engineered myocardin protein comprises a deletion of amino acids from about 414 to about 763 of the native mycocardin (SEQ ID NO: 3).

Clause 3-27. The polynucleotide of clause 3-13, wherein the engineered myocardin protein comprises a sequence at least 85% identical to SEQ ID NO: 14.

Clause 3-28. The polynucleotide of clause 3-14, wherein the engineered myocardin protein consists of sequence identical to SEQ ID NO: 14.

Clause 3-29. The polynucleotide of clause 3-12, wherein the engineered myocardin protein comprises a deletion of amino acids from about 439 to about 763 of the native mycocardin (SEQ ID NO: 3).

Clause 3-30. The polynucleotide of clause 3-16, wherein the engineered myocardin protein comprises a sequence at least 85% identical to SEQ ID NO: 15.

Clause 3-31. The polynucleotide of clause 3-17, wherein the engineered myocardin protein consists of sequence identical to SEQ ID NO: 15.

Clause 3-32. The polynucleotide of clause 3-12, wherein the engineered myocardin protein comprises a deletion of amino acids from about 560 to about 763 of the native mycocardin (SEQ ID NO: 3).

Clause 3-33. The polynucleotide of clause 3-19, wherein the engineered myocardin protein comprises a sequence at least 85% identical to SEQ ID NO: 16.

Clause 3-34. The polynucleotide of clause 3-20, wherein the engineered myocardin protein consists of sequence identical to SEQ ID NO: 16.

Clause 3-35. The polynucleotide of any of clauses 3-1 to 21, wherein the engineered myocardin protein is a functional engineered myocardin protein.

Clause 3-36. The polynucleotide of clause 3-22, wherein the functional engineered myocardin protein is expressed at at least 10% of the level of native MYOCD in the same expression system.

Clause 3-37. The polynucleotide of clause 3-22 or 23, wherein the functional engineered myocardin protein is capable of inducing increased expression of at least one marker of cardiomycote phenotype either (a) when expressed in human cardiac fibroblasts with MEF2C and TBX5 or TBX5 in the presence of a TGFβ inhibitor, optionally SB431542, and a Wnt inhibitor, optionally XAV939, or (b) when expressed in human cardiac fibroblasts with ASCL1.

Clause 3-38. The polynucleotide of any of clause 3-1 to 24, wherein the polynucleotide is operatively linked to a promoter.

Clause 3-39. The polynucleotide of any of clause 3-1 to 25, wherein the polynucleotide comprises a MEF2C polynucleotide and a TBX5 polynucleotide.

Clause 3-40. The polynucleotide of any of clause 3-1 to 25, wherein the polynucleotide comprises an TBX5 polynucleotide.

Clause 3-41. The polynucleotide of any of clause 3-1 to 25, wherein the polynucleotide comprises an ASCL1 polynucleotide.

Clause 3-42. The polynucleotide of any of clause 3-1 to 28, wherein the polynucleotide is flanked by inverted terminal repeats (ITRs) or the polynucleotide is flanked by long terminal repeats (LTRs).

Clause 3-43. A recombinant virus comprising the polynucleotide of any of clauses 3-1 to 42.

Clause 3-44. The recombinant virus of clause 3-30, wherein the recombinant virus is a recombinant adeno-associated virus (rAAV).

Clause 3-45. The recombinant virus of clause 3-30, wherein the recombinant virus is a lentivirus.

Clause 3-46. A population of cells comprising the polynucleotide of any of clause 3-1 to 29.

Clause 3-47. The population of cells of clause 3-46, wherein the percentage of cells in the population that exhibit calcium transients (CaT) in an in vitro CaT assay is at least 2-fold greater than the percentage of cells in a control population of cells not comprising the polynucleotide in the same in vitro CaT assay.

Clause 3-48. An induced cardiomyocyte (iCM), wherein the iCM comprises the polynucleotide of any of clauses 3-1 to 42.

Clause 3-49. A pharmaceutical composition comprising the polynucleotide of any of clauses 3-1 to 42 and a non-viral delivery system.

Clause 3-50. A pharmaceutical composition comprising the recombinant virus of any of clauses 3-43 to 45.

Clause 3-51. A method of generating an induced cardiomyocyte (iCM), comprising contacting a mammalian fibroblast with the polynucleotide of any of clauses 3-1 to 42, the recombinant virus of any of clauses 3-43 to 45, or the pharmaceutical composition of clause 3-49 or clause 3-37.

Clause 3-52. A method of treating a heart condition in a subject, comprising administering the pharmaceutical composition of clause 3-50 to the subject.

Clause 3-53. The method of clause 3-52, wherein the recombinant virus is administered via intracardiac catheterization.

Clause 3-54. The method of clause 3-52, wherein the recombinant virus is administered via intracardiac injection.

Clause 3-55. A recombinant adeno-associated virus (rAAV), comprising an expression cassette (as depicted in FIG. 13B or FIG. 13C), wherein the expression cassette comprises in 5' to 3' order a 5' inverted terminal repeat (ITR), a CAG promoter, an SV40 intron, a polynucleotide encoding one or more proteins, a short polyadenylation signal, and a 3' ITR, and wherein the polynucleotide encoding one or more proteins comprises in 5' to 3' order a polynucleotide encoding MyΔ3, a polynucleotide encoding a P2A linker, and a polynucleotide encoding ASCL1.

Clause 3-56. The rAAV of clause 3-55, wherein the expression cassette comprises a WPRE.

Clause 3-57. The rAAV of clause 3-55 or 56, wherein the MyΔ3 comprises SEQ ID NO: 16.

Clause 3-58. The rAAV of any of clauses 3-55 to 57, wherein the 2A linker comprises ATNFSLLKQAGD-VEENPGP (SEQ ID NO: 23).

Clause 3-59. The rAAV of any of clauses 3-55 to 57, wherein the ASCL1 comprises SEQ ID NO: 1.

Clause 3-60. The rAAV of clause 3-59, wherein the rAAV comprises a polynucleotide at least 95% identical to SEQ ID NO: 35 (MyΔ3A AAV).

Clause 3-61. A pharmaceutical composition comprises the rAAV of any of clauses 3-55 to 60.

Clause 3-62. A method of treating a heart condition in a subject, comprising administering the pharmaceutical composition of clause 3-61 to the subject.

The following non-limiting Examples illustrate some of the experimental work involved in developing the invention.

EXAMPLES

Example 1: Identification of Enhancers of Human Cardiac Reprogramming

Figure 1B:
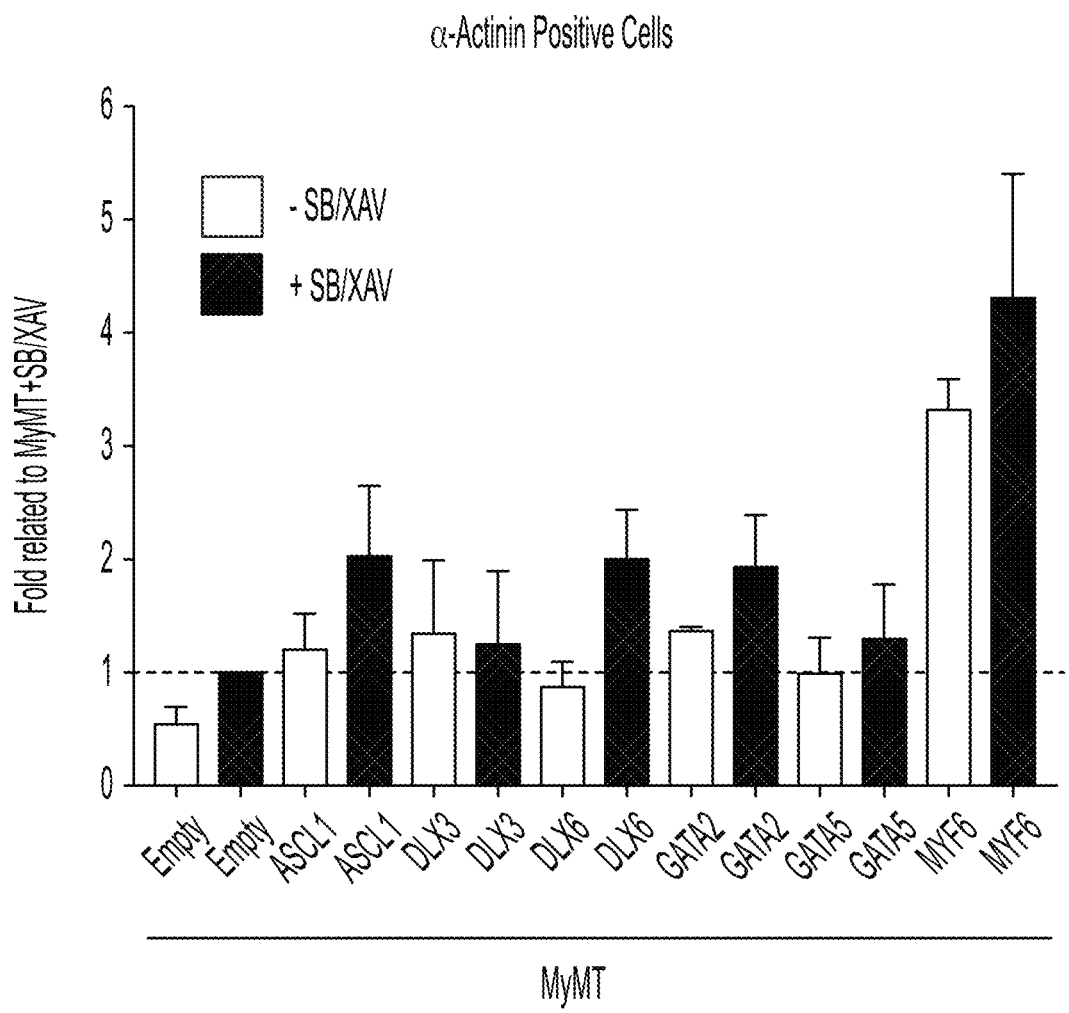
Figure 1C:
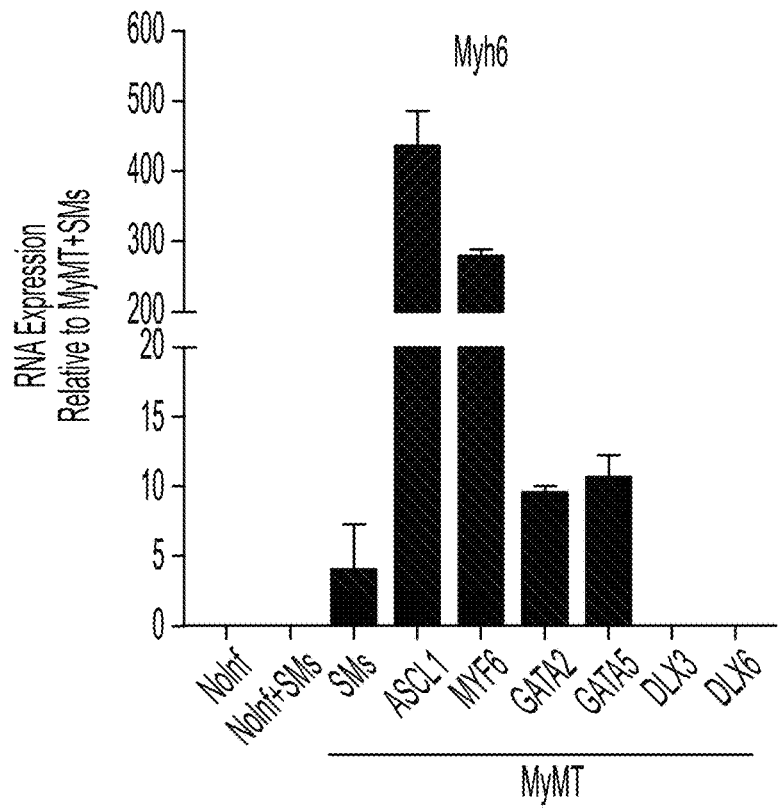
Figure 1C:
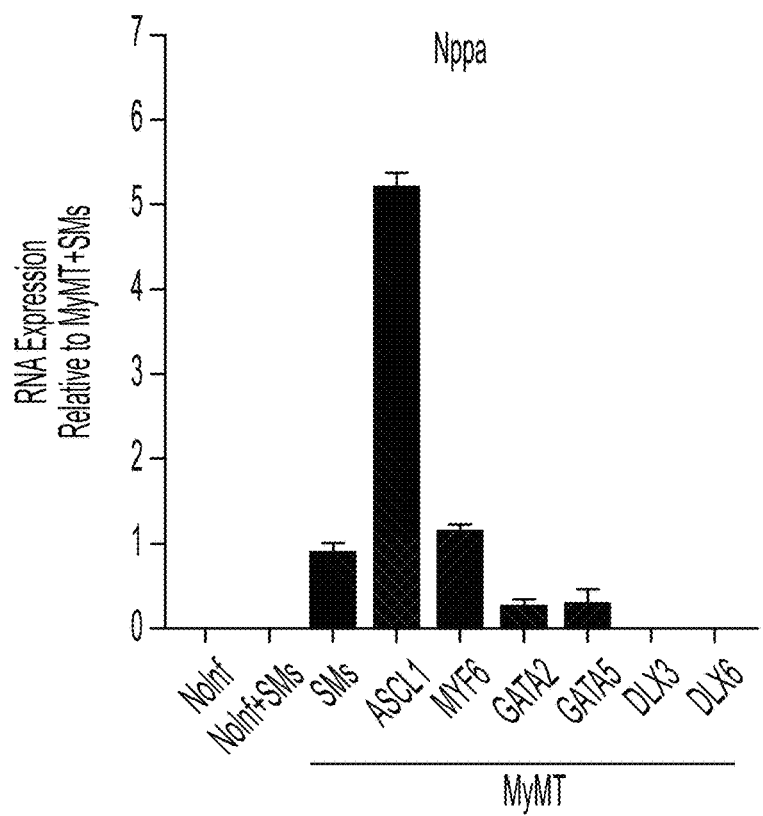
Figure 1C:
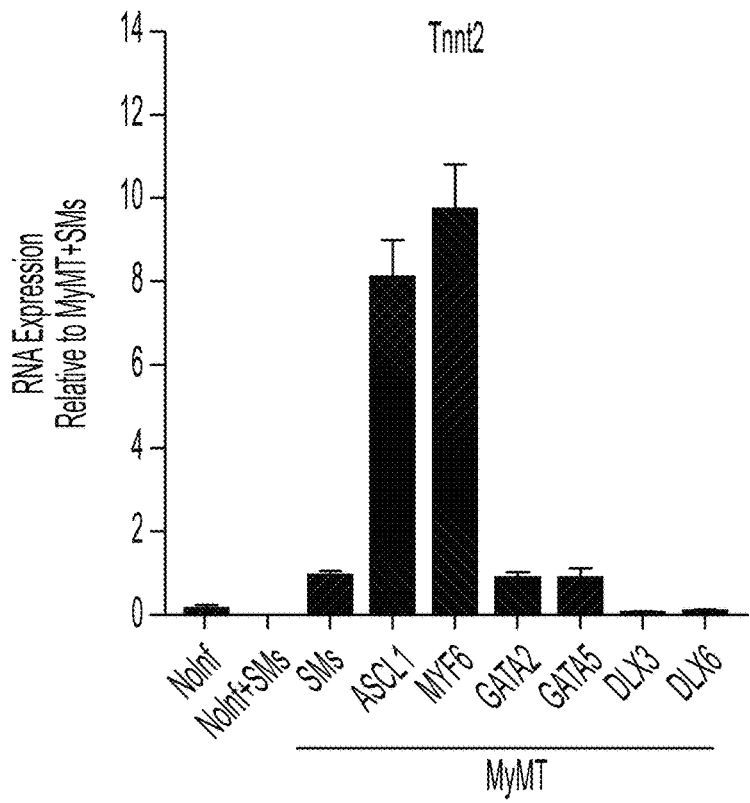
Figure 1C:
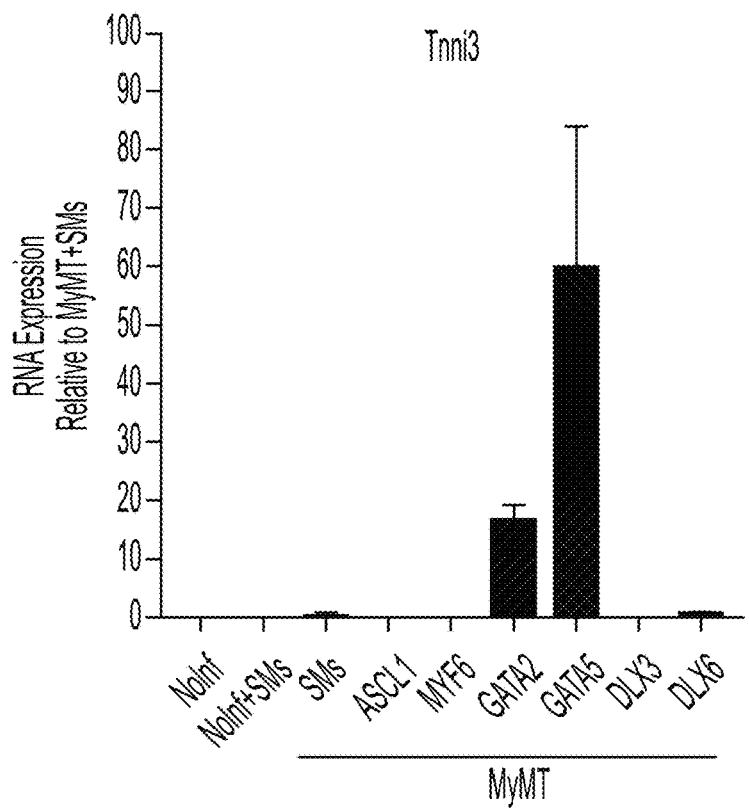
Figure 1C:
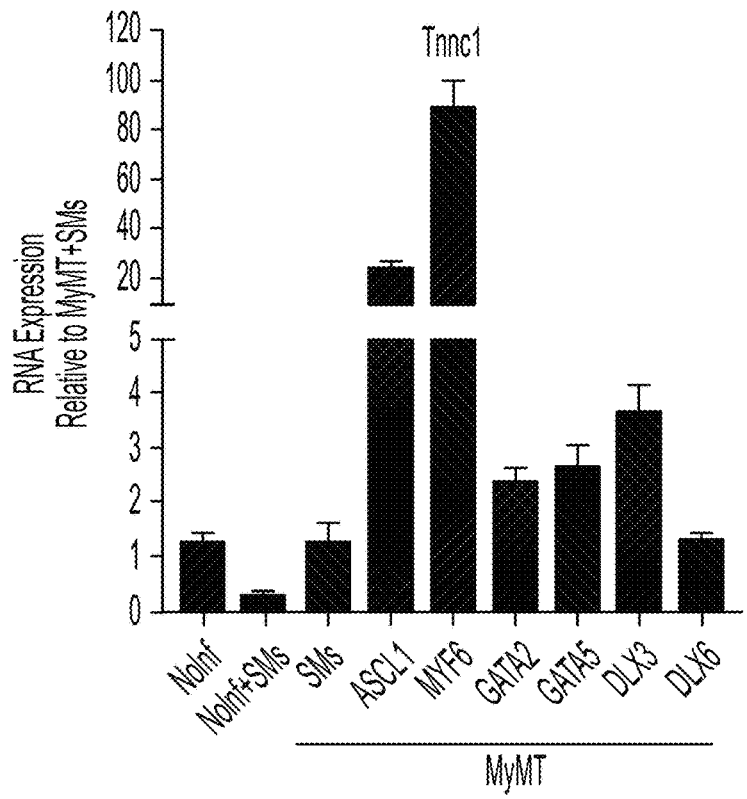
Figure 1C:
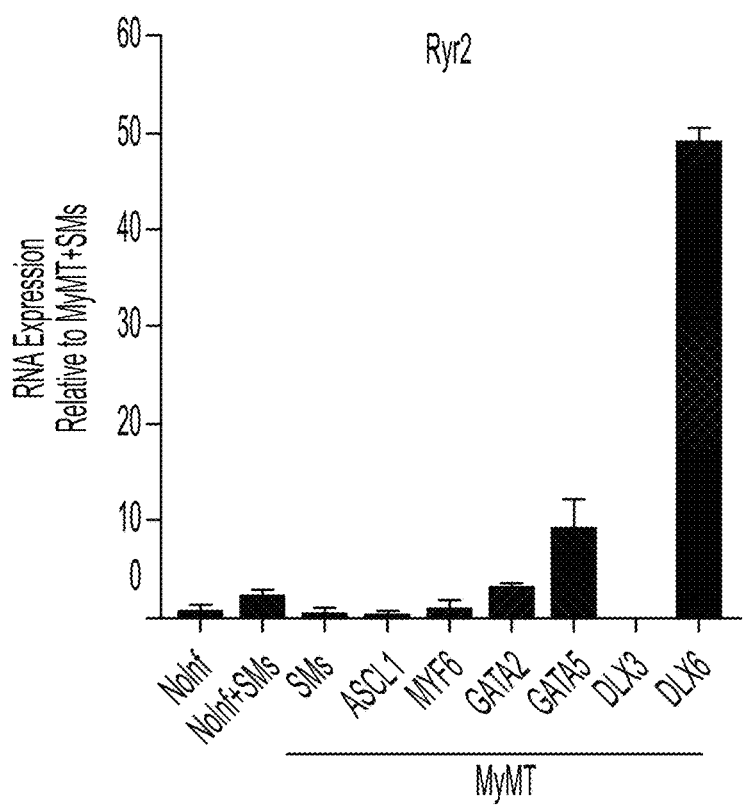

We developed a screening system in which factors that are able to induce human cardiac reprogramming were identified by quantitatively analyzing cardiac marker expression. After three weeks of adding reprogramming factors, a high-throughput cell analyzer system was used to image and quantify cardiac reprogramming efficiency based on cardiac marker α-actinin expression. We used this screening system to screen a retroviral expression library consisting of 1,052 open reading frame (ORF) cDNAs encoding human transcription factors (including nuclear receptors), cytokines, and epigenetic regulators. (Zhou et al., 2017). We added retroviruses encoding individual human ORFs together with MyMT to the HCFs. Positive hits were defined as genes that increase the percentage of α-actinin positive (α-actinin+) cells in combination with either MyMT or MyMT+SB/XAV (FIG. 1A) by a factor of two-fold or greater. The primary screen identified ASCL1, MYF6, DLX3, DLX6, GATA2 and GATA5 as enhancers of human cardiac reprogramming (FIG. 1B). The activity of those six factors were further confirmed by a secondary screen in which additional cardiac markers (MYH6, TNNT2, TNNC1, NPPA, TNNI3 and RYR2) were examined. ASCL1 and MYF6 were identified as the two strongest hits for enhancing cardiac reprogramming from the secondary screen (FIG. 1C).

Example 2: ASCL1 and MYF6 Enhance Human and Pig Cardiac Reprogramming

Because ASCL1 and MYF6 were the two strongest hits for enhancing cardiac reprogramming (FIG. 1C), we focused our attention on ASCL1 and MYF6 in the following studies.

We used primary adult human cardiac fibroblasts (AHCFs) to assess the reprogramming efficiency of adding ASCL1 or MYF6 in combination with different reprogramming factors. Immunocytochemistry showed that addition ASCL1 or MYF6 on top of MyMT generated ~15% α-actinin+, ~50% cTnT+ induced cardiomyocytes (iCMs) after three weeks of reprogramming (FIG. 2A-2B). This reprogramming efficiency is very significant relative to that of MyMT alone. Similar reprogramming efficiency was also achieved using MyMT plus ASCL1 or MYF6 on primary adult pig cardiac fibroblasts (APCFs) (FIGS. 2C&D).

Figure 3A:
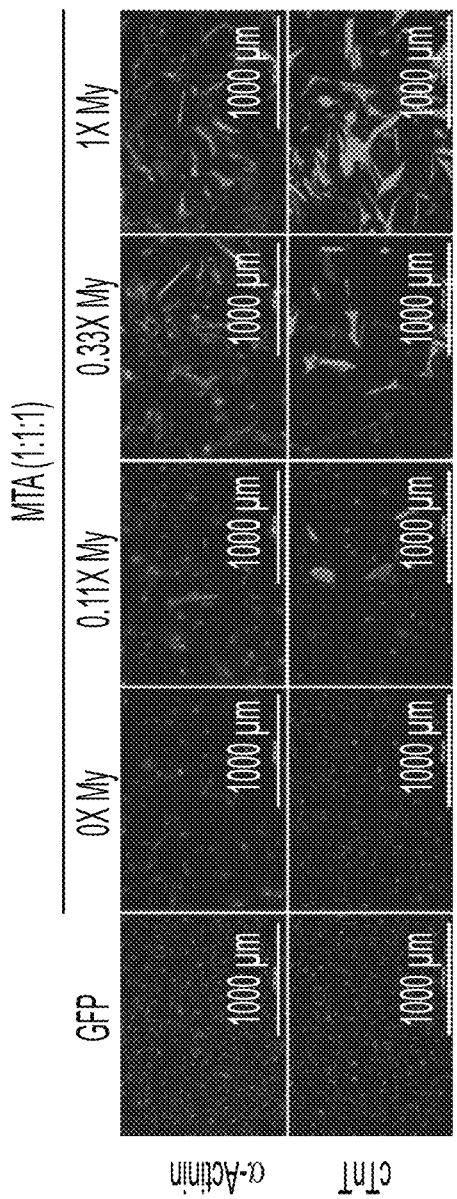
FIG. 3A-FIG. 3E illustrate dose response of reprogramming factors in AHCFs.
Figure 3B:
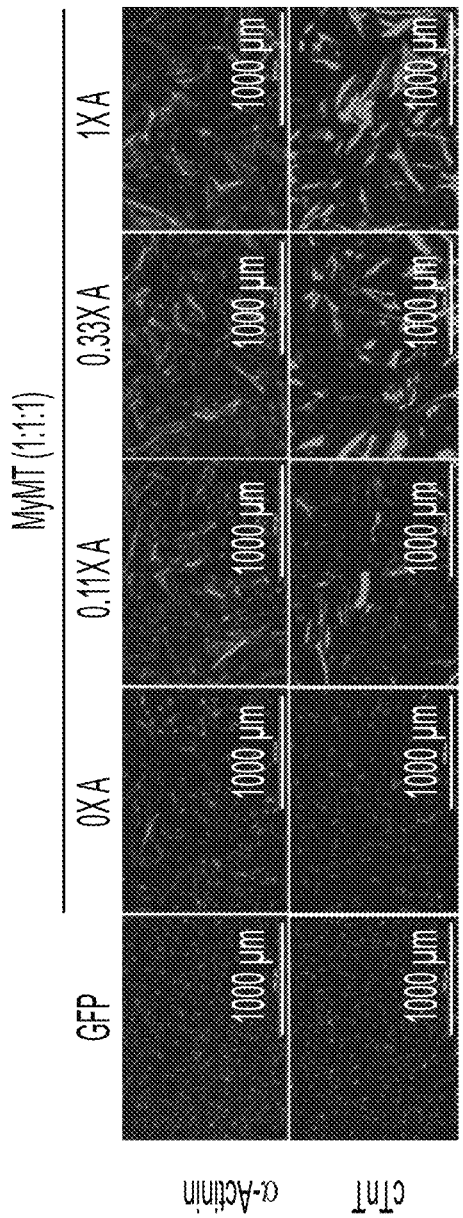
Figure 3C:
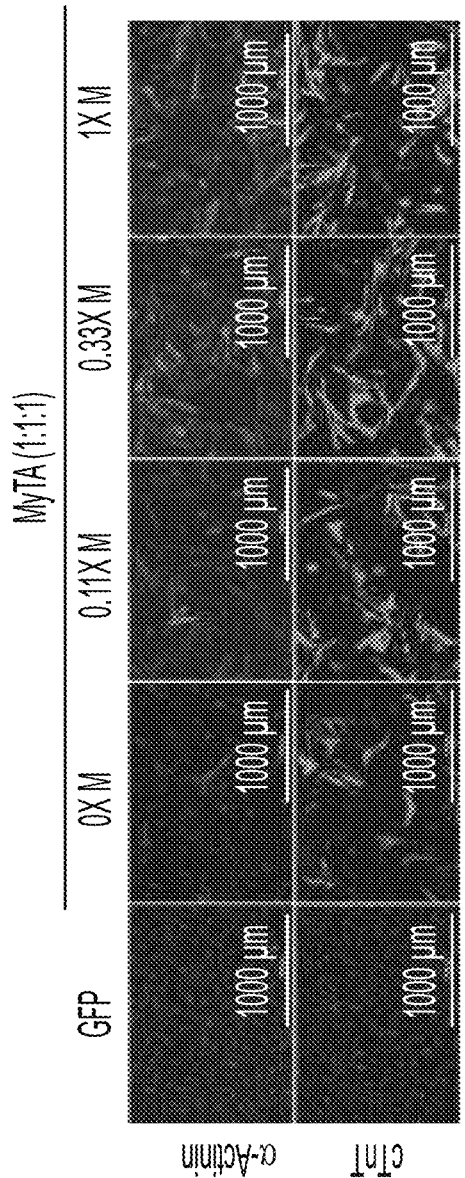
Figure 3D:
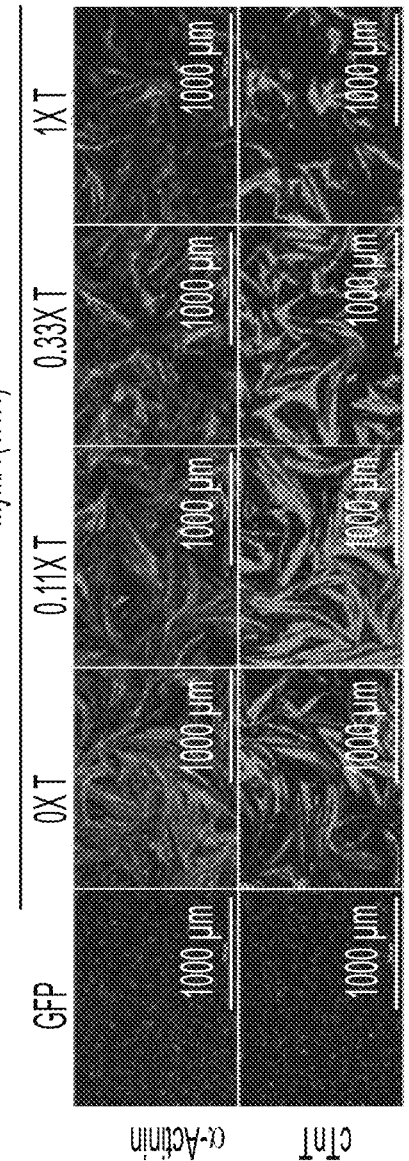
Figure 3E:
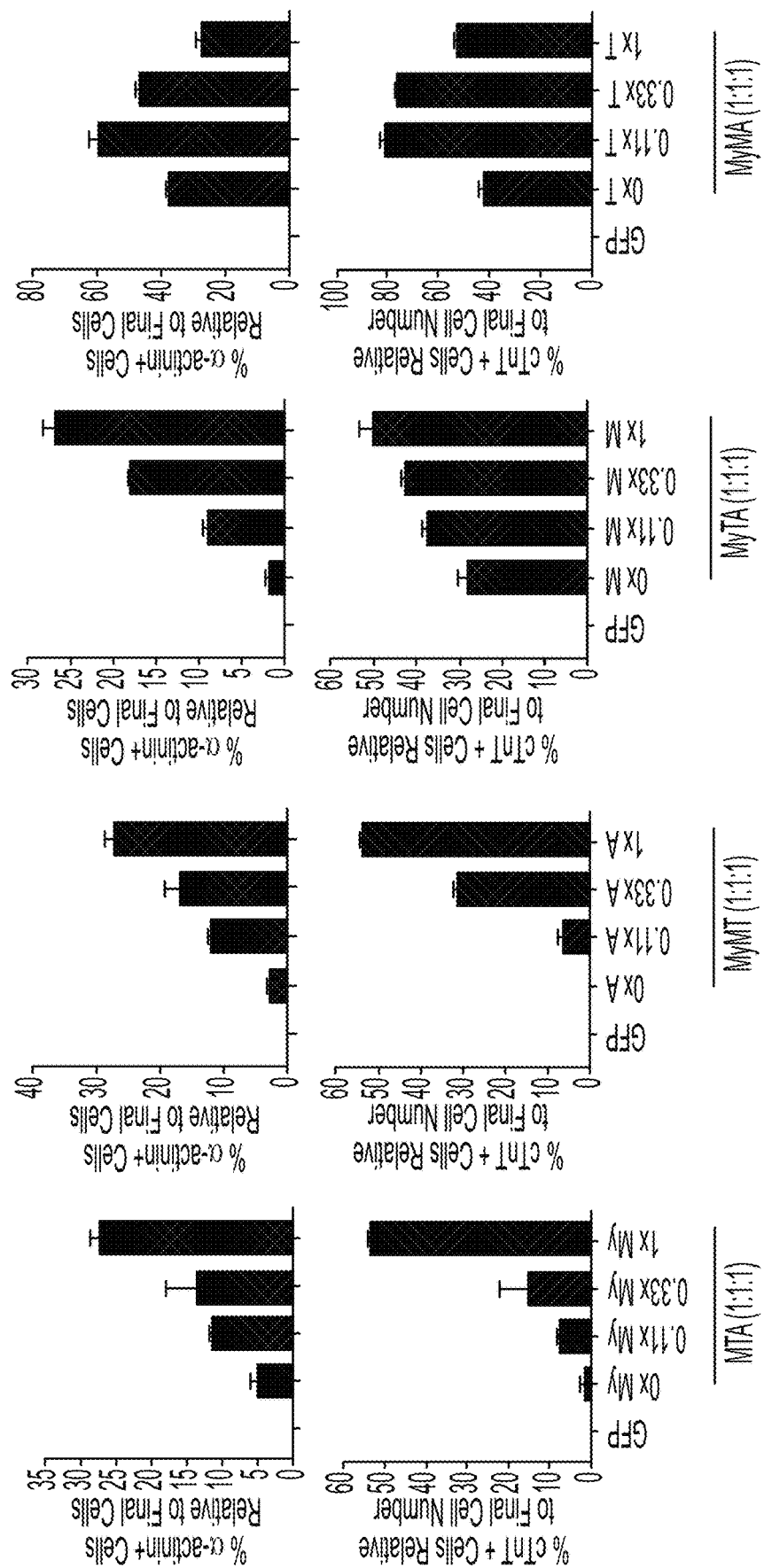

Example 3: Optimal Stoichiometry of Reprogramming Factors Enhances Reprogramming Efficiency It has been shown that the relative ratio (or stoichiometry) of reprogramming factors influence the efficiency and quality of cardiac reprogramming. (Wang et al., 2015). An optimal ratio of reprogramming factors correlated with higher reprogramming efficiency and more mature iCMs. To determine the optimal ratio of MYOCD, ASCL1, MEF2C and TBX5 (MyAMT) for reprogramming, we manipulated the relative levels of My, A, M and T protein expression by mixing various amounts of retrovirus that express one of four reprogramming factors and fixing the ratio of the rest of the three reprogramming factors (FIG. 3A-3E). We transduced AHCFs with those retroviruses cocktails and reprogrammed the cells for three weeks. Cardiac markers α-actinin and cTnT were used to indicate reprogramming efficiency. Immunocytochemistry analysis of reprogrammed AHCFs with antibodies against α-actinin and cTnT showed that cardiac reprogramming efficiency was most sensitive to the expression level of MYOCD and ASCL1. The data indicated that more expression of MYOCD or ASCL1 led to higher levels of reprogramming efficiency. Reprogramming efficiency dropped to almost zero when there was no MYOCD or ASCL1 (FIG. 3A, 3B, 3E). Dosing MEF2C showed a similar pattern of reprogramming efficiency as MYOCD and ASCL1. However, a significant amount of α-actinin+ and cTnT+iCMs can still be detected even without adding MEF2C, indicating cardiac reprogramming is less sensitive to the expression level of MEF2C (FIG. 3C, 3E). Unlike MYOCD, ASCL1 and MEF2C, dosing of TBX5 showed a distinct pattern of reprogramming efficiency, in which the reprogramming efficiency was maximized at a lower level of TBX5 expression (FIGS. 3D&E). Collectively, our results demonstrated that an optimal My, A, M and T stoichiometry, defined by high protein level of MYOCD and ASCL1, medium levels of MEF2C and a low level of TBX5, significantly increases cardiac reprogramming efficiency.

Figure 4A:
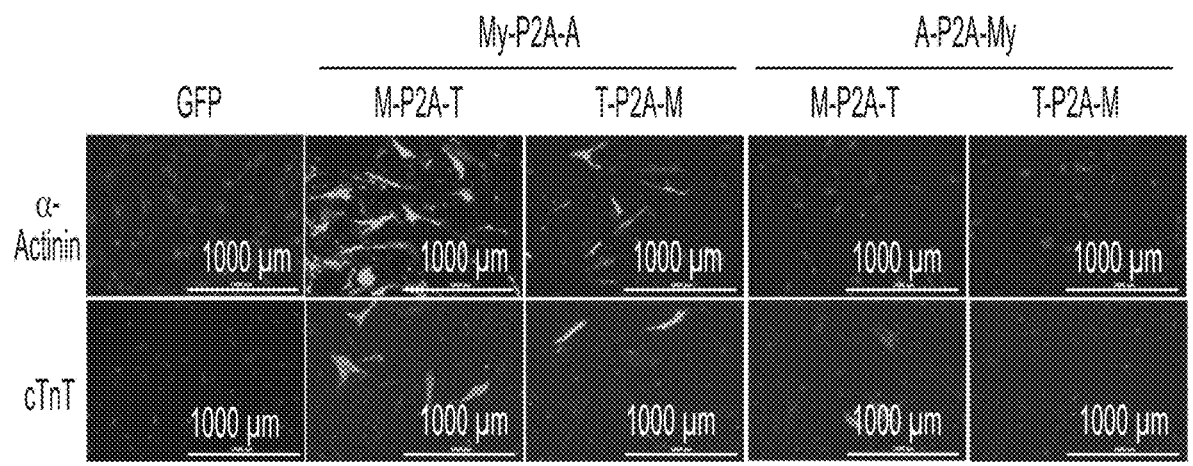
FIG. 4A-FIG. 4C illustrate human cardiac reprogramming by two-in-one polycistronic vectors.
Figure 4B:
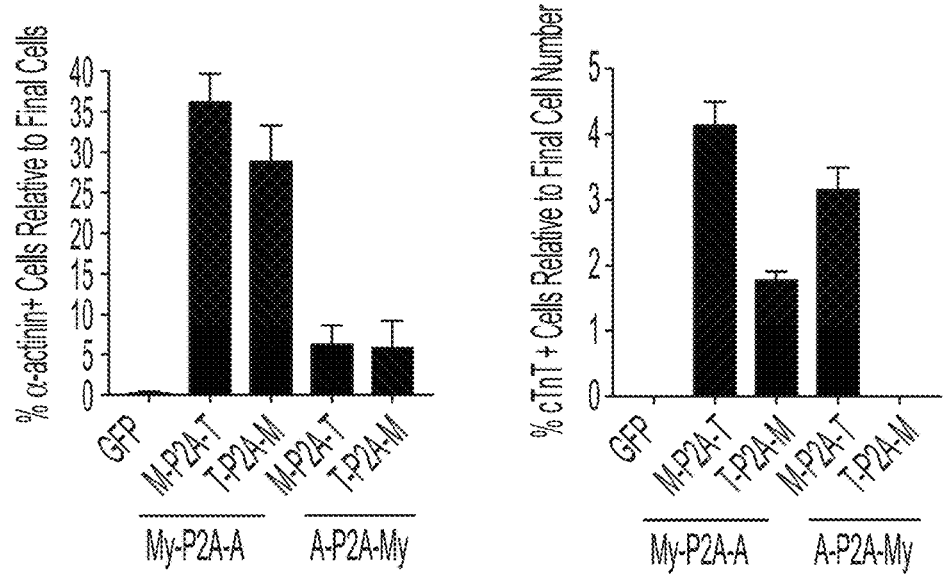
Figure 4C:
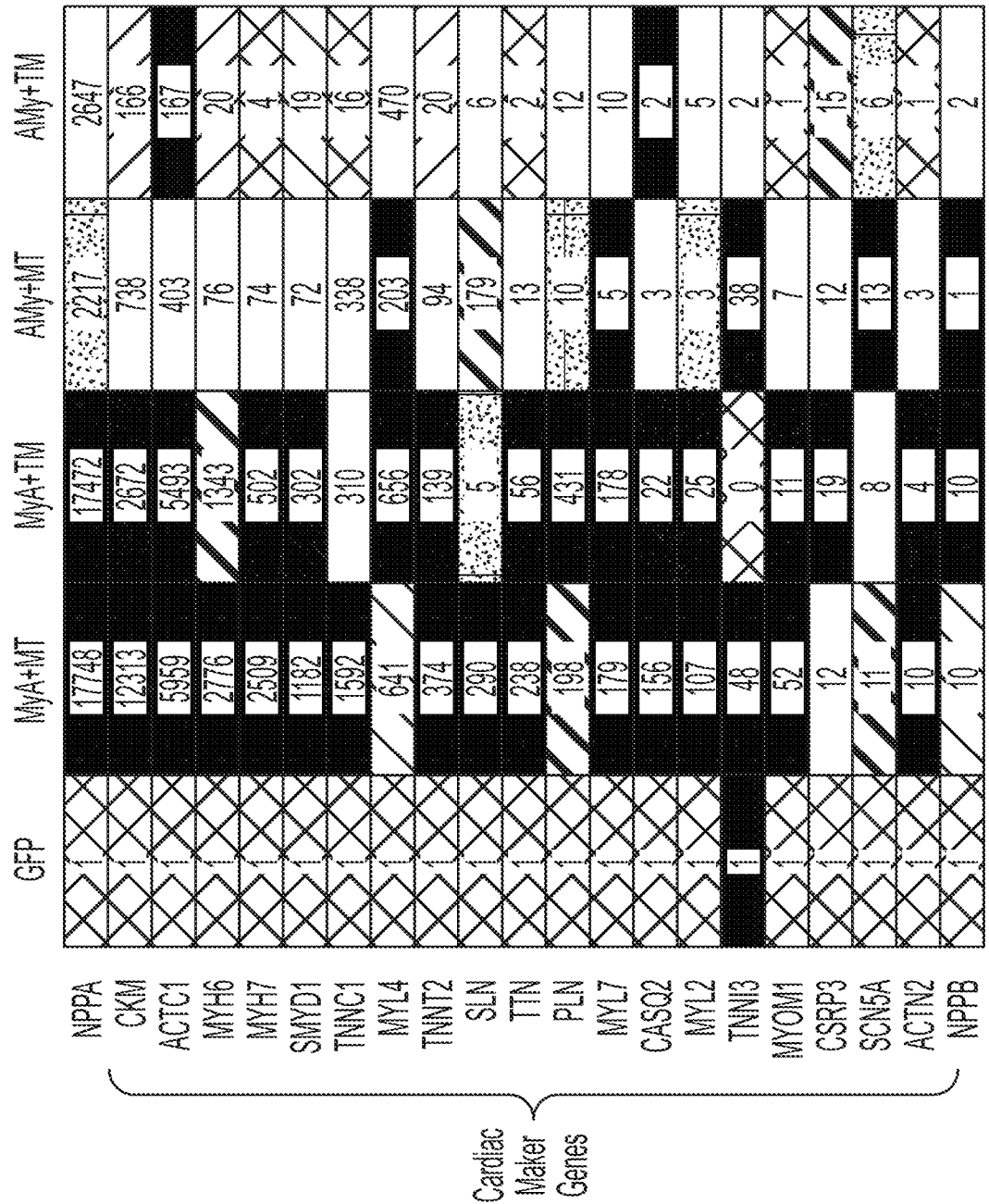

Example 4: Cardiac Reprogramming by Reprogramming Factors in Two-In-One Polycistronic Vectors Gene therapy using separate vectors to express many different genes is not practical for clinical development. AAVs are the most popular gene therapy vectors that have been used in many clinic trails to date [Dunbar, 2018]. However, the packaging capacity of AAVs is only ~4.7 kb, thus, fitting multiple reprogramming factors into the fewest AAV vectors is a major challenge for cardiac reprogramming using AAV. We took advantage of the 2A peptide polycistronic system to put MyAMT reprogramming cocktails into two AAV vectors. Due to the size limitation of AAV and space required for the promoter and other regulatory elements, MYOCD (3.0 kb) can only be paired with ASCL1 (0.7 kb) to fit into one AAV vector, whereas MEF2C (1.4 kb) and TBX5 (1.5 kb) are too large to pair with MYOCD but together can fit into another AAV vector. It has been demonstrated that the order of factors in the 2A polycistronic polynucleotides determined the gene's expression level (Wang et al., 2015). We have demonstrated that the optimal My, A, M and T stoichiometry significantly increases cardiac reprogramming efficiency (FIG. 3A-3E). To achieve the optimal stoichiometry in the 2A polycistronic vectors, we generated all the possible combinations of My+A and M+T with same 2A sequences in a single open reading frame (My-P2A-A, A-P2A-My, M-P2A-T and T-P2A-M). We transduced AHCFs with retroviral combinations that consist of all four possible combinations of polycistronic vectors, including My-P2A-A+M-P2A-T, My-P2A-A+T-P2A-M, A-P2A-My+M-P2A-T and A-P2A-My+T-P2A-M. We analyzed the expression of cardiac markers α-actinin and cTnT by immunocytochemistry after three weeks of reprogramming. We found that the My-P2A-A+M-P2A-T was the optimal combination and generated ~35% of α-actinin+ iCMs and ~4% of cTnT+iCMs (FIG. 4A-4B). Q-PCR analysis of a panel of 21 cardiac markers also demonstrated that My-P2A-A+M-P2A-T is the optimal polycistronic vector combination based on its ability to induce the highest levels of expression of the most cardiac genes (FIG. 4C).

Example 5: Cardiac Reprogramming by a Single Polycistronic Vector

Figure 5A:
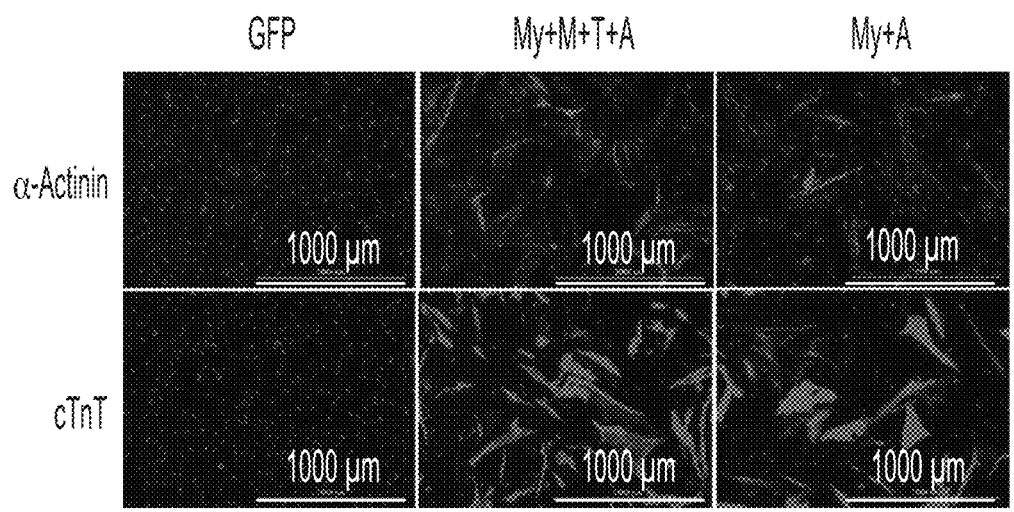
FIG. 5A-FIG. 5D illustrate human cardiac reprogramming by a single polycistronic vector.
Figure 5B:
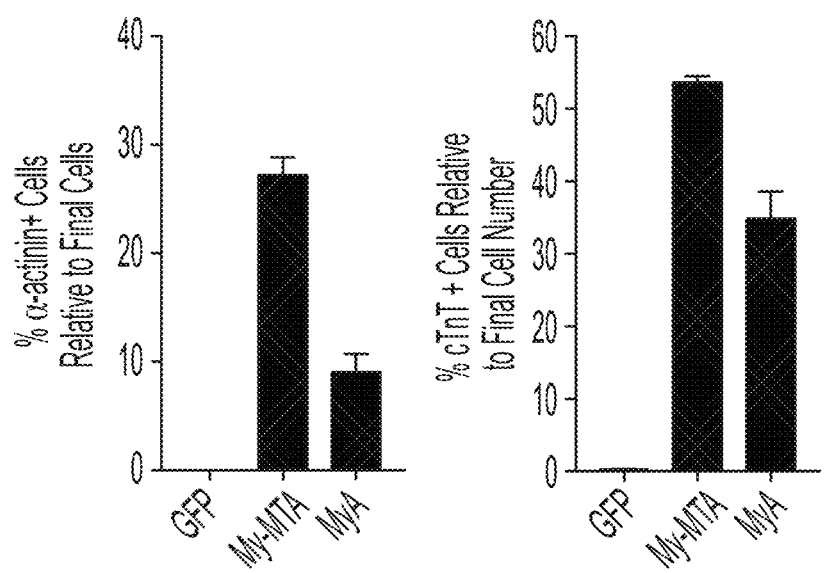
Figure 5C:
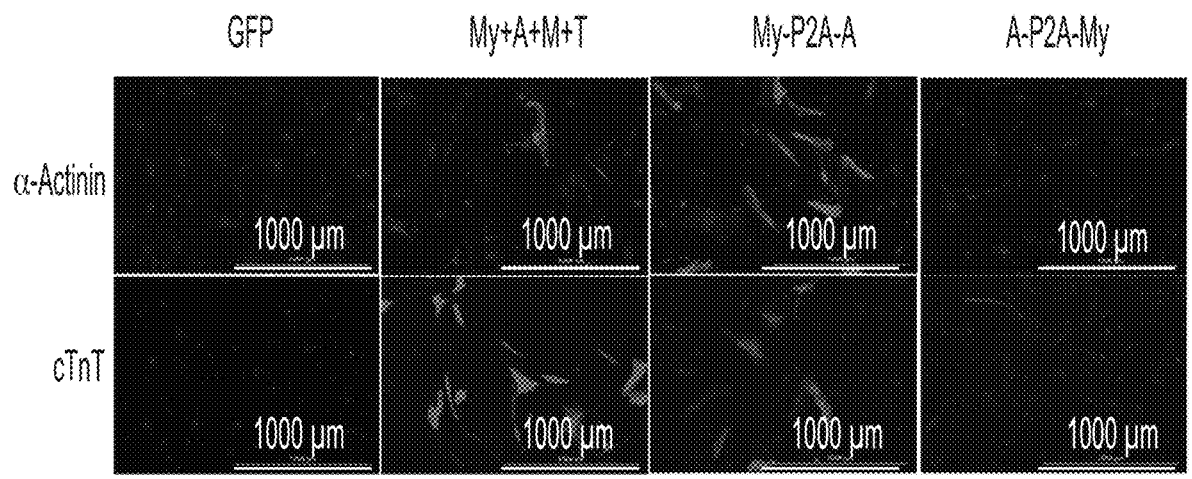
Figure 5D:
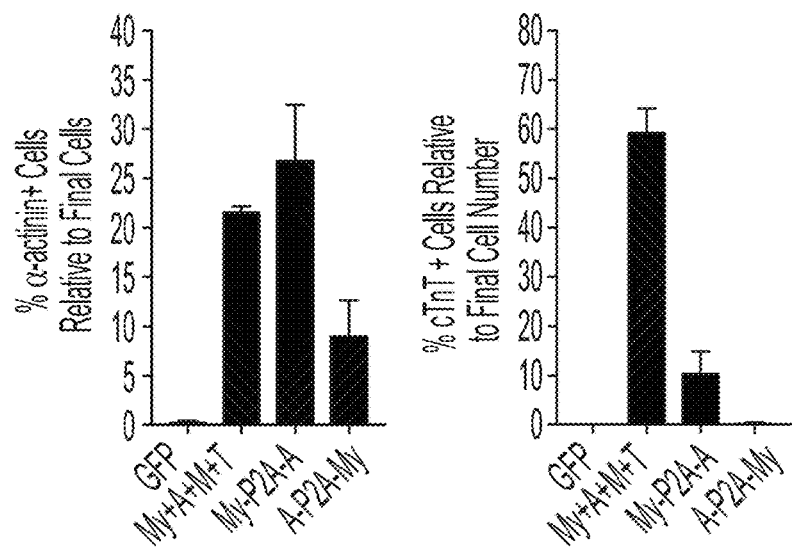

We sought to further simplify the reprogramming vectors by putting all reprogramming factors into a single polycistronic transcription unit. Because our stoichiometry experiment (FIG. 3A-3E) showed that MYOCD and ASCL1 are the most important reprogramming factors in the MyAMT cocktails, and iCMs were generated even without adding MEF2C or TBX5, albeit with lower reprogramming efficiency, we speculated that just MYOCD and ASCL1 (MyA) are able to reprogram AHCFs to iCMs. To test this hypothesis, we transduced MYOCD and ASCL1 retroviruses into AHCFs. Interestingly, ~10% of α-actinin+iCMs and ~30% of cTnT+iCMs were generated by MyA cocktails after three weeks of reprogramming (FIG. 5A-5B). Furthermore, we tested the polycistronic vectors that encode My and A with different orders (My-P2A-A and A-P2A-My), and My-P2A-A showed much better reprogramming efficiency than A-P2A-My (FIG. 5C-5D). Collectively, these data suggest that the MyA combination is able to reprogram human cardiac fibroblasts to iCMs with high efficiency.

Figure 6A:
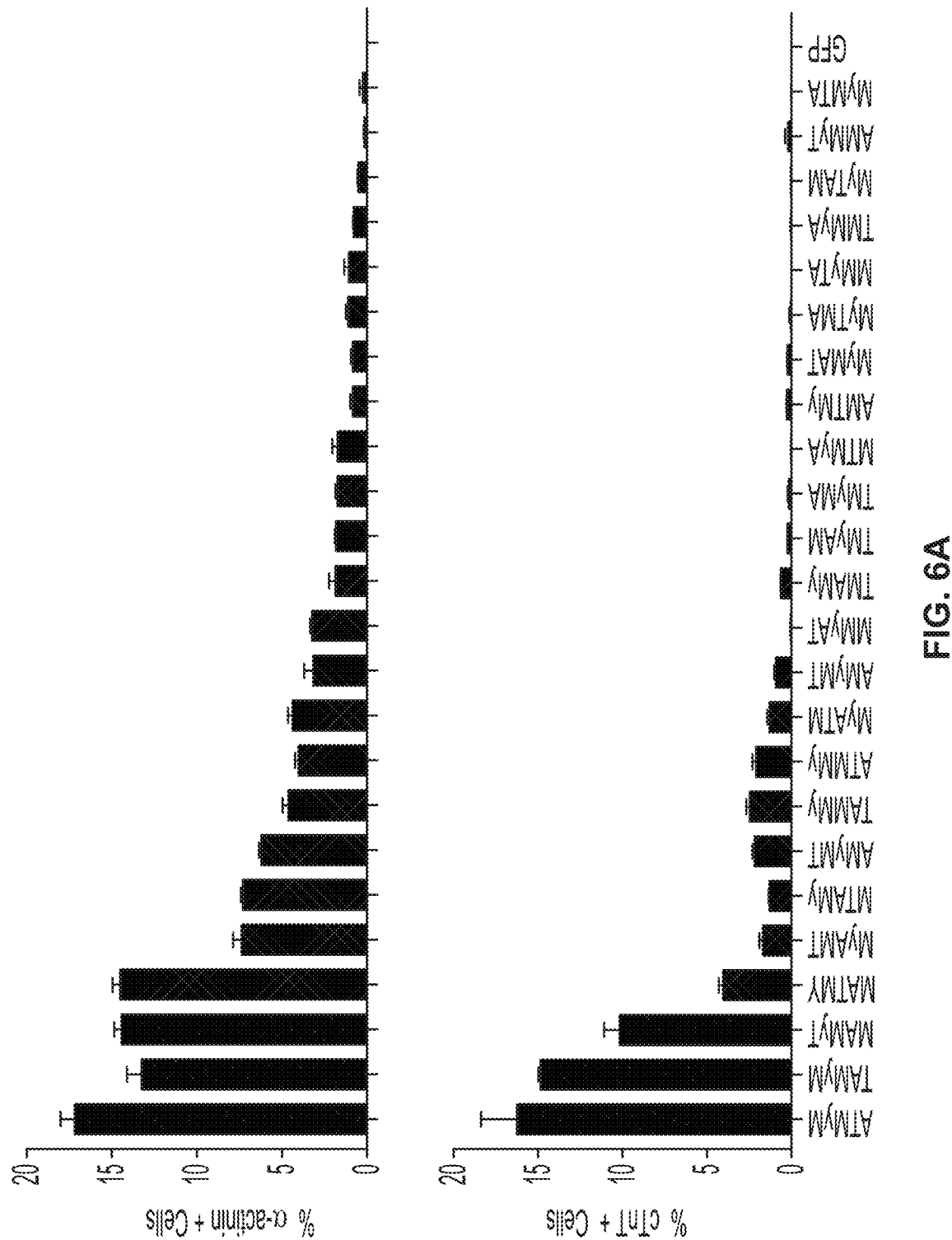
FIG. 6A-FIG. 6C illustrate human cardiac reprogramming by a polycistronic vector expressing four genes.
Figures 6B, 6C:
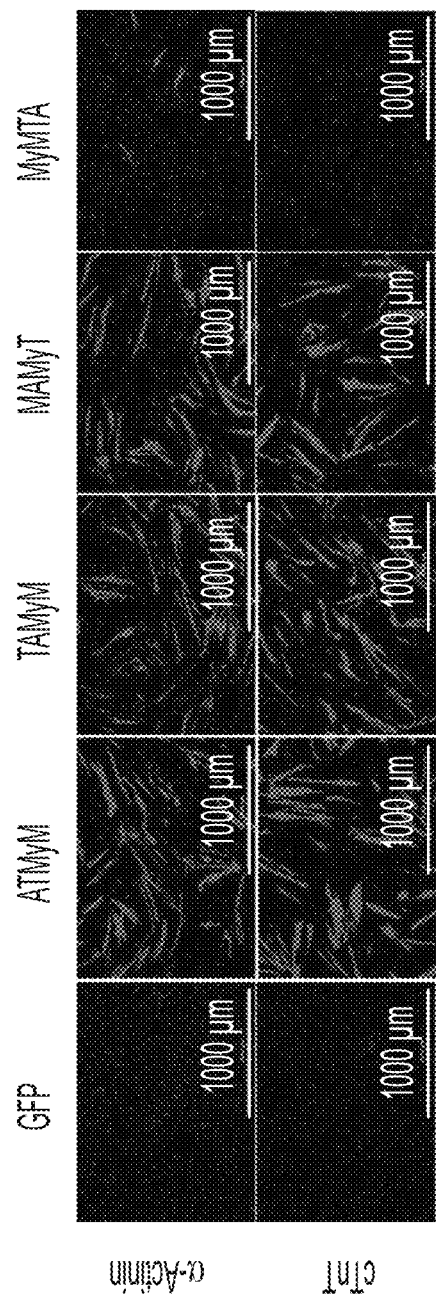

Example 6: Cardiac Reprogramming by a Polycistronic Vector Expressing Four Genes Our data show that the order of reprogramming factors significantly in a polycistronic vector with two factors can influence cardiac reprogramming efficiency (FIG. 3A-3E, FIG. 4A-4C). Since MyAMT showed better reprogramming capacity than MyA (FIG. 4A-4C, FIG. 5A-5D), we sought to further determine the optimal order of four factors, MyAMT, in a single polycistronic polynucleotide. We generated all the possible 24 combinations of My, A, M, T with different translation skipping sequences (P2A, T2A and E2A) in a single polynucleotide. We transduced AHCFs with either GFP or one of 24 combinations of My, A, M, T polycistronic retroviruses and analyzed the expression of cardiac markers α-actinin and cTnT by immunocytochemistry after three weeks of reprogramming. We found that three of 24 polycistronic vectors, A-P2A-T-T2A-My-E2A-M, T-P2A-A-T2A-My-E2A-M and M-P2A-A-T2A-My-E2A-T, are the best combinations which generated ~15% of α-actinin+ iCMs and ~15% of cTnT+iCMs (FIG. 6A-6B). The non-optimized polycistronic vectors, such as My-P2A-M-T2A-T-E2A-A, almost didn't reprogram fibroblasts to iCMs (FIG. 6A-6B), highlighting the importance of stoichiometry of reprogramming factors for cardiac reprogramming. By using factor position score matrix which reflects the average reprogramming efficiency for one particular reprogramming factor in one particular position, we found that MYOCD prefers to be at position 3, ASCL1 prefer to be at position 2, and both MEF2C and TBX5 prefer to be at position 1 or position 4.

Example 7: In Vivo Delivery of Reprogramming Cocktails Promotes Heart Repair

Figure 7A:
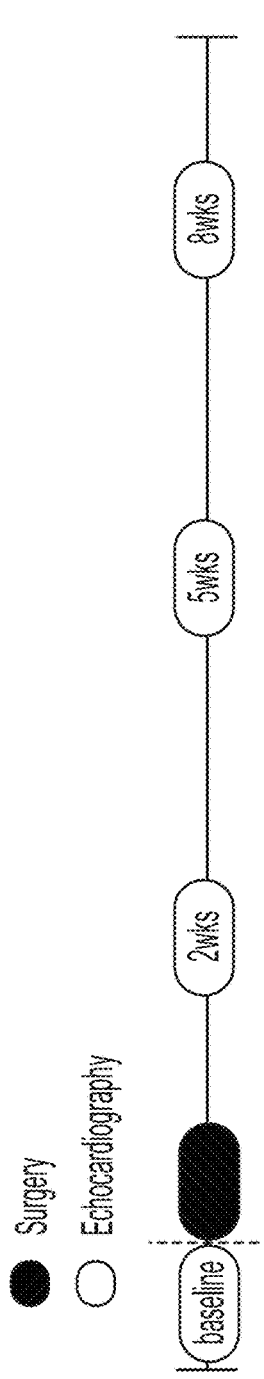
FIG. 7A-FIG. 7D illustrate in vivo delivery of reprogramming cocktails promotes heart repair after myocardial infarction.
Figure 7B:
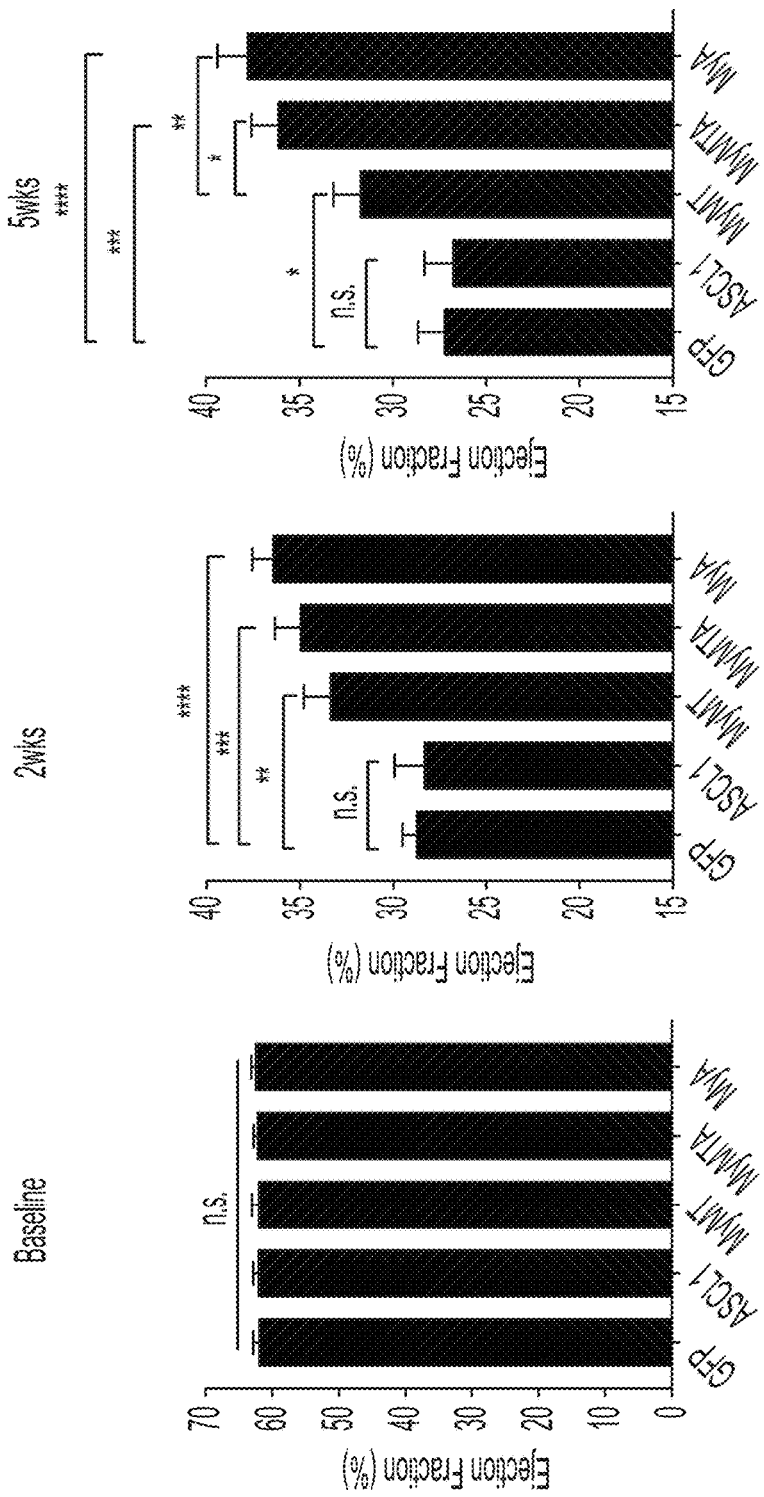
Figure 7C:
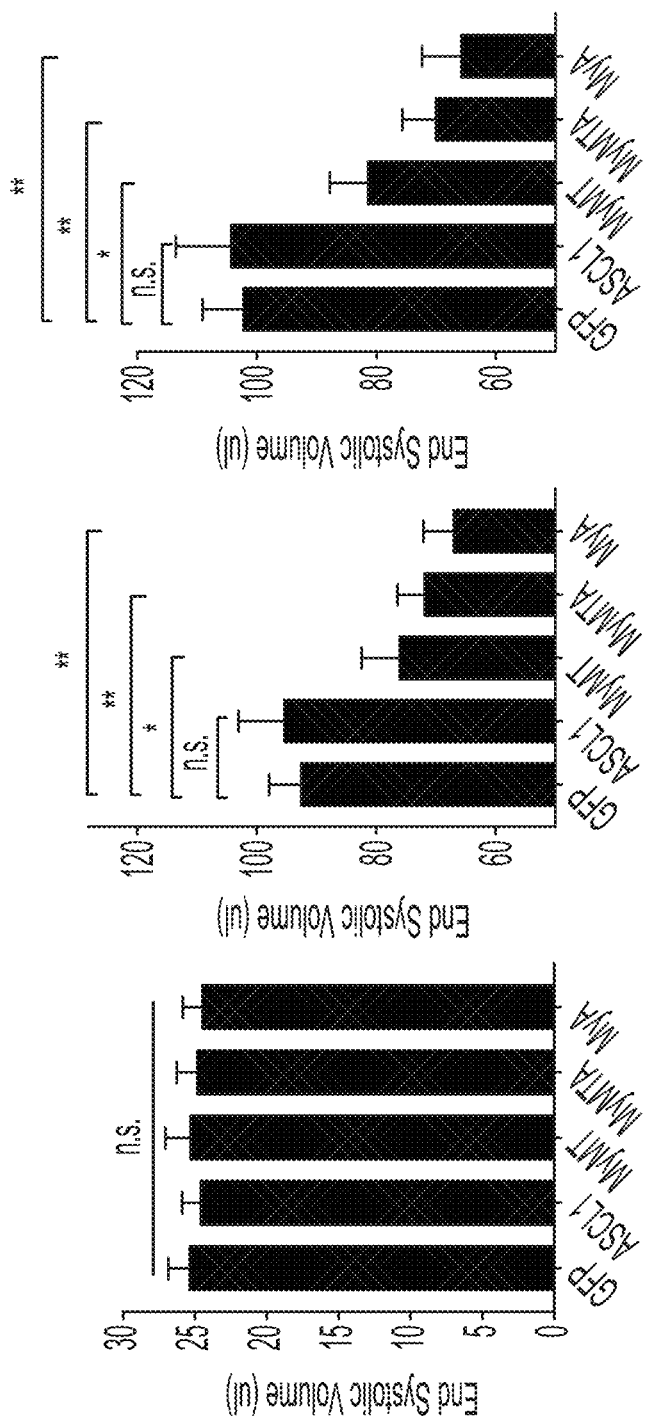
Figure 7D:
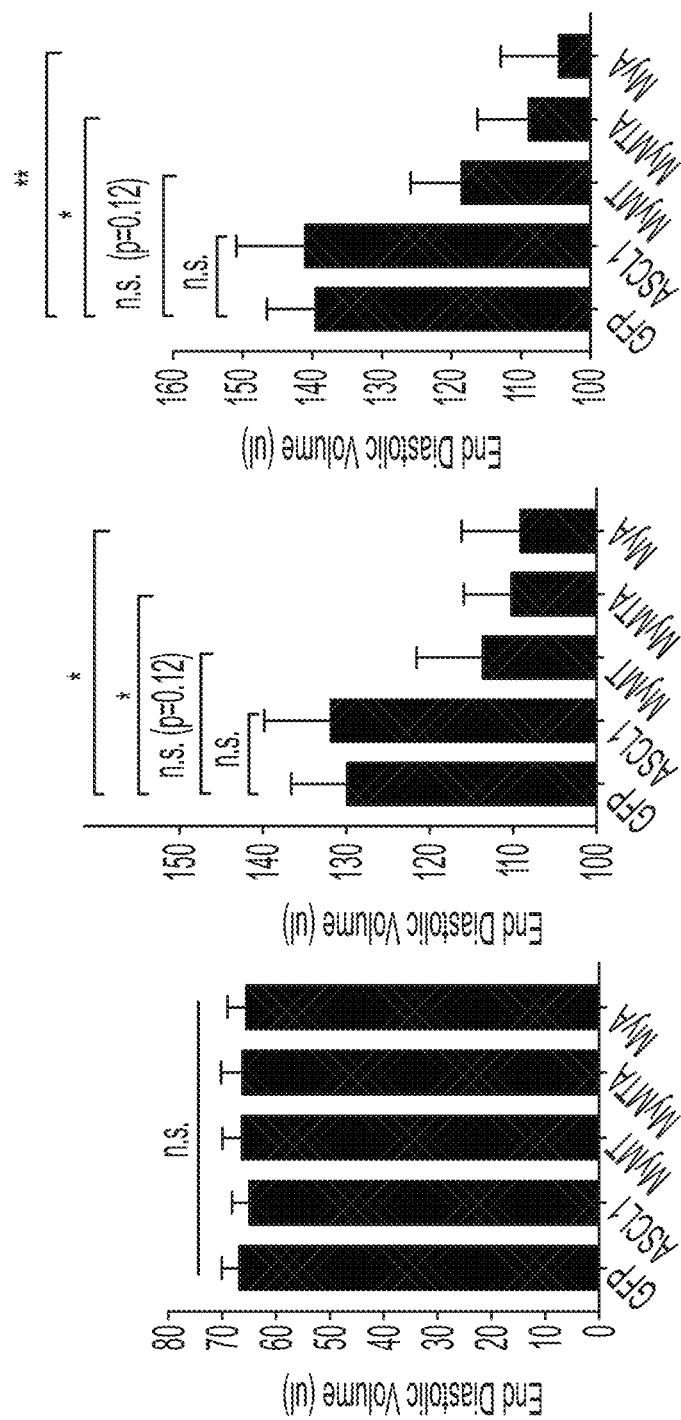

We examined whether forced expression of reprogramming cocktails that we optimized above in non-cardiomyocytes could lead to measurable improvement in the function of injured hearts (FIG. 7A). Mice were subjected to left anterior descending artery (LAD) ligation followed by intramyocardial injection of GFP, ASCL1, MyMT, MyMTA or MyA retroviruses, each encoding a single factor. Cardiac function following MI was assessed in a blinded fashion by ejection fraction (EF), end systolic volume (ESV) and end diastolic volume (EDV) using echocardiography. Before MI surgery, cardiac function of each cohort of mice was equal by assessing EF, ESV and EDV by echocardiography. After MI surgery, cardiac function of GFP-injected mice declined and reached a stable value at two weeks post-MI. In contrast, infection of injured heart with MyMT, MyAMT or MyA retroviruses blunted worsening cardiac function two weeks post-MI. (FIG. 7B-D). The cardiac functional improvement was delayed and less complete with MyMT at five weeks post-MI (FIG. 7B-7D), consistent with the reduced efficiency of this transcription factor combination in reprogramming in vitro (FIG. 2A-2D). Injection of injured heart with ASCL1-expressing vector alone did not have any effect on cardiac function compared with GFP (FIG. 7B-7D). These data suggest MyMT, MyMTA and MyA reprogramming cocktails promote heart repair and adding ASCL1 in combination with Myocardin provides benefit for cardiac functional improvement in vivo.

Materials and Methods

Isolation of primary adult human and pig cardiac fibroblasts. For isolation of adult human cardiac fibroblasts (AHCFs) or adult pig cardiac fibroblasts (APCFs), adult human or pig left ventricules were minced into small pieces and digested in cardiac fibroblast digestion medium (10 μg/ml Liberase TH, 10 μg/ml Liberase TM, 1 unit/ml DNase I, 0.01% Polaxomer) for 1 h in 37° C. After digestion, the cells were filtered through a 70 μM strainer into a 50 mL falcon tube. Cells were pelleted by spinning down for 5 min at 1200×g and placed in fibroblast growth medium. The medium was replaced every two days. Four days later, AHCFs or APCFs were frozen or re-plated for viral transduction.

Retrovirus production. For retrovirus production, PLATINUM-A™ (PLAT-A™) cells from Cell Biolabs, Inc. were seeded into culture dishes (5×10$^4$ cells/cm$^2$) one day before transfection in DMEM supplemented with 10% FBS. Cells reached ~60% confluency on the day of transfection. DNA plasmids (based on the pMXs-ORF vector from Cell Biolabs, Inc.) were transfected into Platinum-A cells using Promega Corp. FUGENE® HD transfection reagent. Forty-eight hours after transfection, viral medium that was filtered through a 0.45-μm filter, and polybrene was added at a concentration of 8 μg/ml.

Cellular reprogramming. For in vitro cardiac reprogramming, AHCFs or APCFs were seeded into culture dishes or plates at a density of 5×10$^3$/cm$^2$ in fibroblast growth medium (day −1). One day after plating cells (day 0), fibroblast growth medium was removed and virus medium was added. One day after viral transduction (day 1), virus medium was replaced by iCM medium that composed of 4 parts Dulbecco's Modified Eagle's Medium (DMEM) and 1 part GIBCO® Media 199, 10% FBS, 1% nonessential amino acids, 1% penicillin/streptomycin, for every two days until day 4. On day 4, medium was changed to 75% iCM media and 25% RPMI+B27. On day 7, medium was changed to 50% iCM and 50% RPMI+B27. On day 11, medium was changed to 25% iCM and 75% RPMI+B27. On day 14, medium was changed to RPMI+B27+FFV (10 ng/ml rhFGF, 15 ng/ml rhFGF-10, and 5 ng/ml rhVEGF) for every day until day 21.

Immunocytochemistry. For immunocytochemistry, cells were fixed in 4% paraformaldehyde for 20 min and permeabilized with 0.1% Triton-X100 at room temperature for 30 min. Cells were washed with PBS three times followed by blocking with 1% bovine serum albumin (BSA) for 1 h. Cells then were incubated with mouse monoclonal anti-cardiac Troponin T (cTnT) antibody (Thermo Scientific, MA5-12960) at 1:200 dilutions or mouse anti-α-actinin antibody (Sigma, A7811) at 1:200 dilutions in 1% BSA for 1 h. After washing with PBS three times, cells were then incubated with donkey anti-mouse Alexa Fluor 594 (Invitrogen, A21203) at 1:200 dilutions in 1% BSA for 1 h. Cells were then imaged and quantified using a cell imaging multi-mode reader, CYTATION™ 5 (BioTek).

Quantitative mRNA measurement. Total RNA was extracted using RNeasy Mini Kit (QIAGEN®) according to vender's protocol. RNAs were retrotranscribed to cDNA using iScript SUPERMIX™ (BIO-RAD®). qPCR was performed using TAQMAN® Gene Expression Master Mix (THERMO SCIENTIFIC®) mRNA levels were normalized by comparison to GAPDH mRNA.

Quantification and statistical analysis. All data are presented as mean with standard error of the mean (SEM) and have n=2-3 per group. P values were calculated with either unpaired/two-way t test or one-way analysis of variance (ANOVA). Statistical analyses were performed using the GRAPHPAD PRISM® 7 software package (GRAPHPAD SOFTWARE™). A P value of <0.05 was considered significant in all cases after corrections were made for multiple pairwise comparisons.

MI surgery, intramyocardial injection of retroviruses and echocardiography. Surgeries were performed on CHARLES RIVER® CD-1 IGS male mice of 9-10 weeks of age. Mice were anesthetized with 2.4% isoflurane/97.6% oxygen and placed in a supine position on a heating pad (37° C.). Animals were intubated with a 20-gauge intravenous catheter and ventilated with a mouse ventilator (MINIVENT™, Harvard Apparatus, Inc.). MI was induced by permanent ligation of the left anterior descending artery (LAD) with a 7-0 prolene suture. Concentrated 10$^{10}$ genome copies (GC) of retrovirus in 20 μl of PBS (concentration=5×10$^{11}$ GC/ml) (GFP, ASCL1, MyMT, MyAMT, or MyA) were injected into the myocardium through an insulin syringe with an incorporated 29 gauge needle (BD). Injection with a full dosage was carried out along the boundary between the infarct zone (IZ) and border zone (BZ) based on the blanched infarct area after coronary artery occlusion. After injection, the chest was closed with sutures and the mouse was allowed to recover with the mouse ventilator and heating pad. All surgical procedures were performed under aseptic conditions. Cardiac function was evaluated by two-dimensional transthoracic echocardiography on conscious mice using a VISUALSONICS™ VEVO® 3100 imaging system. Ejection fraction (EF), end systolic volume (ESV) and end diastolic volume (EDV) were used as indices of cardiac contractile function.

Example 8: Comparison of Lentiviral and Adeno-Associated Viruses Expressing MyA

Figure 8A:
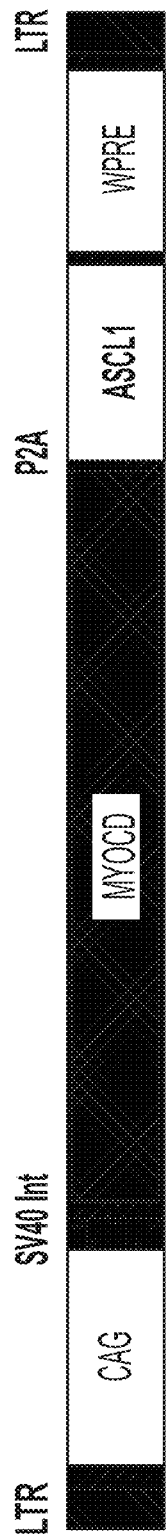
FIG. 8A-FIG. 8E show design and comparative testing of bicistronic expression MyA vectors.

We compared MYOCD expression from lentiviral or AAV vectors encoding MYOCD and a second protein. Polycistronic vectors with MYOCD and ASCL1 were generated in a non-integrating lentivirus (NIL) format using the expression cassette depicted in FIG. 8A. The lentivirus is non-integrating because the integrase included in the plasmid-based packaging system included a mutation to prevent integration of the gene construct into the genome of transduced cells. The same expression construct depicted in FIG. 8A is in some embodiments used to make an integrating lentivirus. In this lentiviral construct, MYOCD-2A-ASCL1 was placed after an SV40 intron ("SV40 Int") under control of a CAG promoter with a WPRE flanked by 5' and 3' long-terminal repeats (LTRs). The 3' LTR operates as a polyadenylation signal in this construct.

An analogous AAV construct (FIG. 8B) was generated by placing the same MYOCD-2A-ASCL1 polynucleotide into an AAV vector, in which the expression cassette is flanked by 5' and 3' inverted terminal repeats (ITR). Due to the packaging limit of the AAV vector, the WPRE was removed and the polyadenylation sequence selected was a short polyA signal ("A") (SEQ ID NO: 75). Control monocistronic constructs with only MYOCD (and not ASCL1) were also made (not shown). The control AAV included a WPRE and used the bGH polyA (SEQ ID NO: 85) in place of the short polyA of the polycistronic AAV.

Cells were transfected with the NIL (FIG. 8C) or AAV vector (FIG. 8D) and analyzed by immunoblotting using antibodies against MYOCD, ASCL1, or the loading control GAPDH. Monocistronic (My) and polycistronic (MyA) NIL vectors expressed MYOCD at the same level (FIG. 8C). MYOCD protein was expressed by cells transduced with monocistronic (M) and polycistronic (MyA) AAVs, but expression of MYOCD protein by the polycistronic MyA AAV vector was lower than expression of MYOCD protein by the polycistronic lentiviral MyA NIL (FIG. 8C), by the monocistronic lentiviral My NIL (FIG. 8C), or by monocistronic adeno-associated virus My AAV (FIG. 8D). A high molecular weight band attributed to uncleaved MYOCD-2A-ASCL1 was observed (black arrow in FIG. 8D).

The ability of AAV MyA or NIL MyA to induce a cardiomyocyte phenotype in transduced cells was assessed by quantative immunofluorescence microscopic detection of α-actinin (FIG. 8E), using the indicated primary antibody and an ALEXA FLUOR® 594 secondary antibody on a BIOTEK CYTATION™ 5 imaging reader, and mRNA was quantitated by quantitative polymerase chain reaction (qPCR) using gene-specific primers for TNNC1, TNNT2, PLN, NPPA, or MYH6 (Table 4).

TABLE 4

Expression of Genetic Markers

| | TNNC1 | TNNT2 | PLN | NPPA | MYH6 |
|---|---|---|---|---|---|
| No Inf | 1.1 | 0.9 | 0.8 | 0.3 | 1.4 |
| No Inf | 0.9 | 1.1 | 1.2 | 3.8 | 0.7 |
| NIL MyA - 1.5 × 10$^9$ GC | 12.3 | 26.8 | 12.1 | 1114.7 | 47.8 |
| NIL MyA - 1.5 × 10$^9$ GC | 11.7 | 23.0 | 9.0 | 963.8 | 16.3 |
| NIL MyA - 5 × 10$^9$ GC | 80.0 | 102.6 | 30.0 | 4405.6 | 64.9 |
| NIL MyA - 5 × 10$^9$ GC | 74.3 | 120.2 | 30.1 | 5436.8 | 64.5 |
| AAV MyA - 5 × 10$^9$ GC | 5.1 | 11.7 | 4.4 | 322.6 | 16.1 |
| AAV MyA - 5 × 10$^9$ GC | 2.4 | 8.9 | 4.2 | 327.4 | 8.4 |
| AAV MyA - 2.5 × 10$^{10}$ GC | 8.0 | 20.0 | 7.2 | 524.4 | 8.6 |
| AAV MyA - 2.5 × 10$^{10}$ GC | 8.2 | 23.3 | 8.8 | 672.5 | 1.6 |

Control samples were not infected (No Inf). Transduction was performed with 1.5×10$^9$, 5×10$^9$, or 2.5×10$^{10}$ genome copies (GC) per 30,000 cells (one well). FIG. 8E shows that NIL MyA (2.5×10$^{10}$ GC not tested) induced α-actinin expression in a greater fraction of cells than AAV MyA (1.5×10$^9$ GC not tested). Table 4 shows that NIL MyA induced higher expression of markers associated with the cardiomyocyte phenotype than AAV MyA.

Example 9: Design and Testing of Engineered Myocardin Proteins with Internal Deletions FIG. 9A shows a domain schematic of wild-type human MYOCD. The N-terminal RPEL domains (RPxxxEL) mediate MEF2C binding. The basic (++) and polyglutamine (Q) motifs are critical for SRF interaction, whereas GATA4 interacts with MYOCD via a domain labeled "Gata4 Interact I" that includes the SAP (SAF-A/B, Acinus and PIAS) domain and also with a second interaction domain labeled "Gata4 Interact II" containing the leucine zipper (LZ). The C-terminus contains a transactivation domain (TAD). The isoform of the native protein expressed in human cardiac tissue is 986 amino acids in length.

To increase the potency of MyA AAV, three myocardin variants with internal deletions were designed and tested in AAV. MyΔ1 has a deletion of residues 414 to 763 (FIG. 9B), which deletes most of the entire second GATA4 interaction domain. MyΔ2 has a deletion of residues 439 to 763 (FIG. 9C), which also deletes most of the entire second GATA4 interaction domain. MyΔ3 has a deletion of residues 560 to 763 (FIG. 9D), which also deletes most of the entire second GATA4 interaction domain but retains the LZ domain.

Figure 10A:
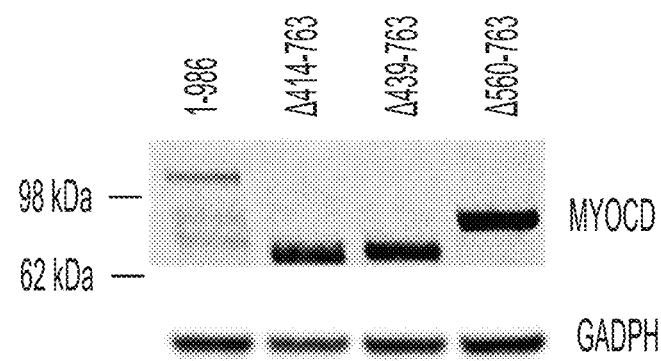
FIG. 10A and FIG. 10B show protein expression (FIG. 10A) and localization (FIG. 10B) of MyΔ1, MyΔ2, and MyΔ3.
Figure 10B:
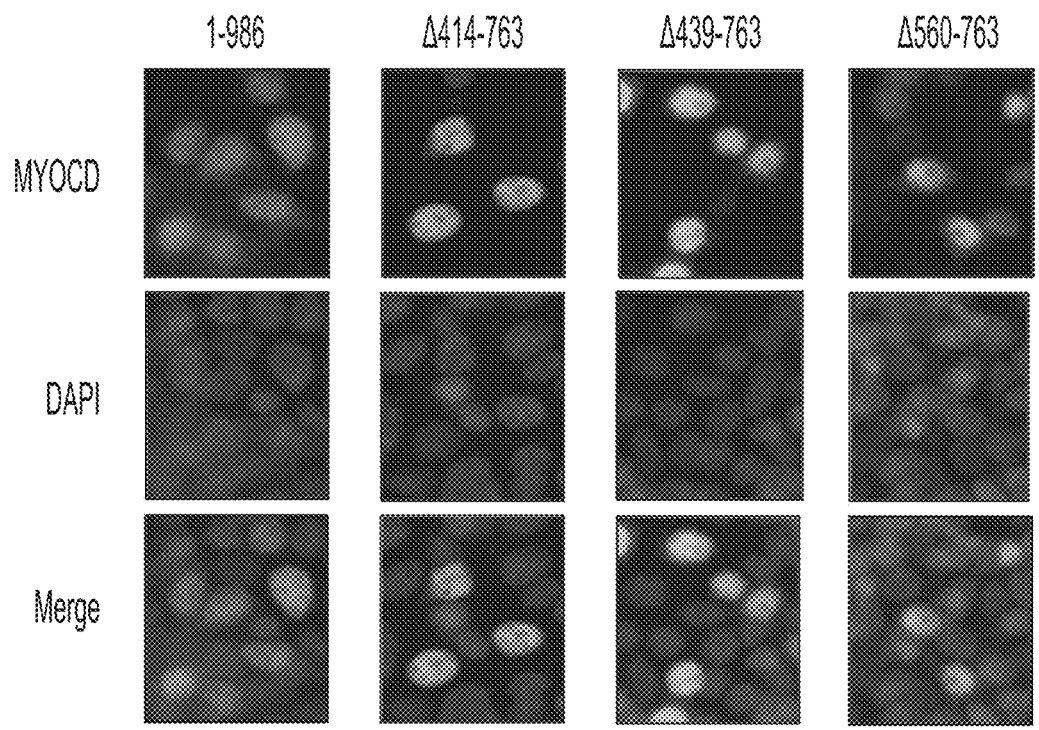

FIG. 10A shows by immunoblot that despite fusing diverse portions of the coding sequence together, the three internal deletion mutants generate stable myocardin protein. Lysates were made from transiently transfected HEK293T cells for 48 hours. FIG. 10B shows immunofluorescence microscopy of native and engineered myocardin proteins. MyΔ1, MyΔ2, and MyΔ3 are each localized to the nucleus of the cell properly, as is the native myocardin protein.

Retroviral vectors encoding native myocardin (MYOCD) or one of three engineered myocardin proteins with an internal deletion (MyΔ1, MyΔ2, or MyΔ3) were generated. Coinfection of a human cardiac fibroblast (HCF) cell line was used to induce expression of MYOCD, MEF2C, and TBX5 (MyMT); MyΔ1, MEF2C, and TBX5 (MyΔ1MT);

MyΔ2, MEF2C, and TBX5 (MyΔ2MT); or MyΔ3, MEF2C, and TBX5 (MyΔ3MT). Coinfection was performed in the presence of two small molecules, TGF-beta inhibitor SB431542 and Wnt inhibitor XAV939, which have been shown to enhance cardiac reprogramming in mouse and human cells (MyMT+SB/XAV) (Mohamed et al., *Circulation*. 135:978-95 (2017); Int'l Patent Appl. No. PCT/US2017/025132).

Calcium transients were assessed as previously described. Qian, L., et al. (2012) Nature 485:593-598. Briefly, isolated myocytes were loaded with Fluo-4 for 30 min at room temperature before being transferred to the superfusion chamber. The loading solution contained a 1:10 mixture of 5 mM Fluo-4 AM in dry DMSO and Powerload™ concentrate (Invitrogen), which was diluted 100-fold into extracellular Tyrode's solution containing suspended myocytes. Calcium transients were evoked by applying voltage pulses at 1 Hz between platinum wires placed on either side of the cell of interest and connected to a field stimulator (IonOptix, Myopacer). Fluo-4 fluorescence transients were recorded via a standard filter set (#49011 ET, Chroma Technology). For each replicate, eight fields of cells were imaged for twenty seconds.

Figure 11:
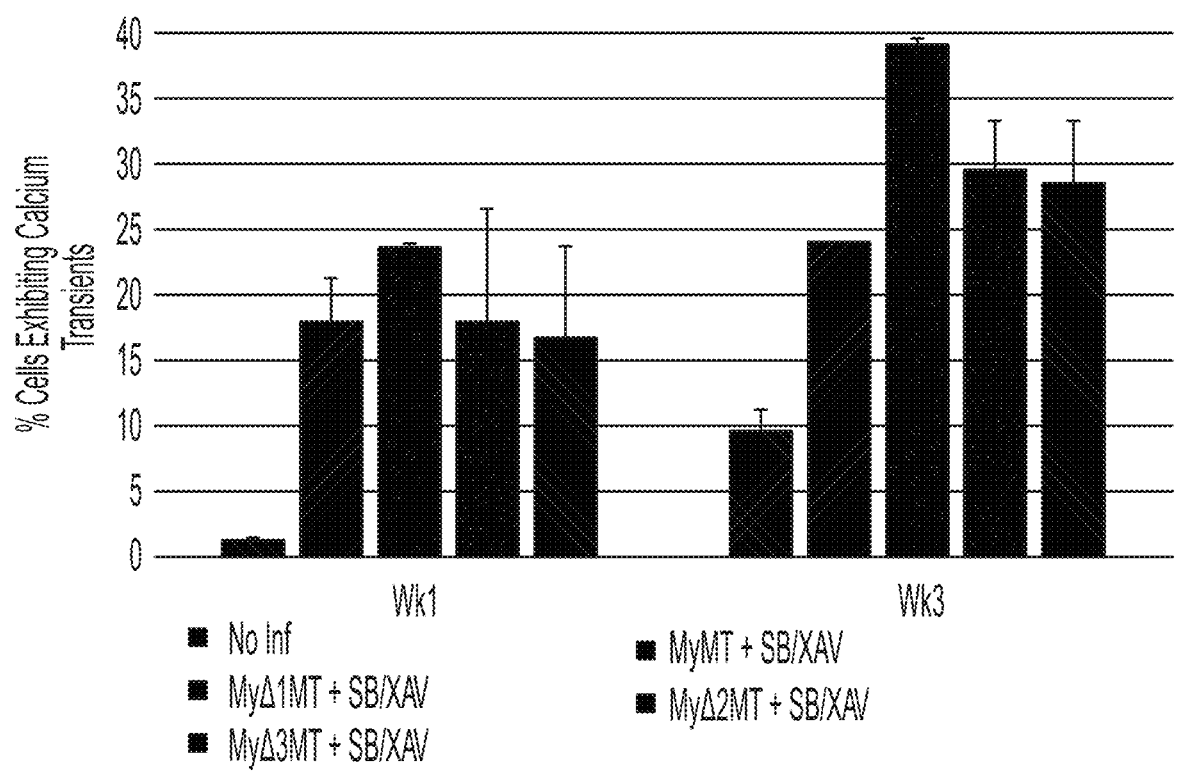
FIG. 11 show calcium transients for cells transduced with MEF2C, TBX5 and native or engineered myocardin in the presence of small molecules SB431542 and XAV939.

FIG. 11 indicates that human cardiac fibroblasts transduced with MEF2C, TBX5 and native or engineered Myocardin all exhibit robust calcium transients after 1 week or 3 weeks of reprogramming. We concluded that MyMT+SB/XAV generated induced cardiomyocytes (iCM) even when native MYOCD is replaced by MyΔ1, MyΔ2, or MyΔ3.

Figure 12A:
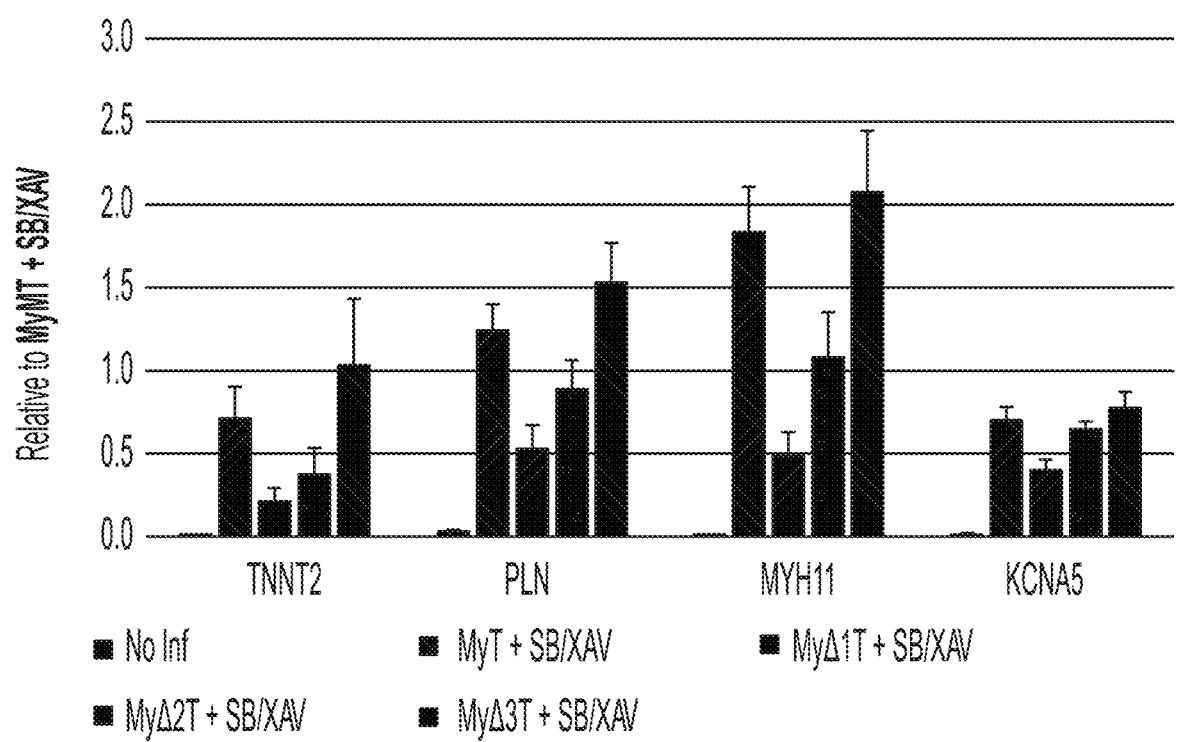
FIG. 12A and FIG. 12B show gene expression by q-PCR (FIG. 12A), and morphology (FIG. 12B) for cells transduced with TBX5 and native or engineered myocardin in the presence of small molecules SB431542 and XAV939.
Figure 12B:
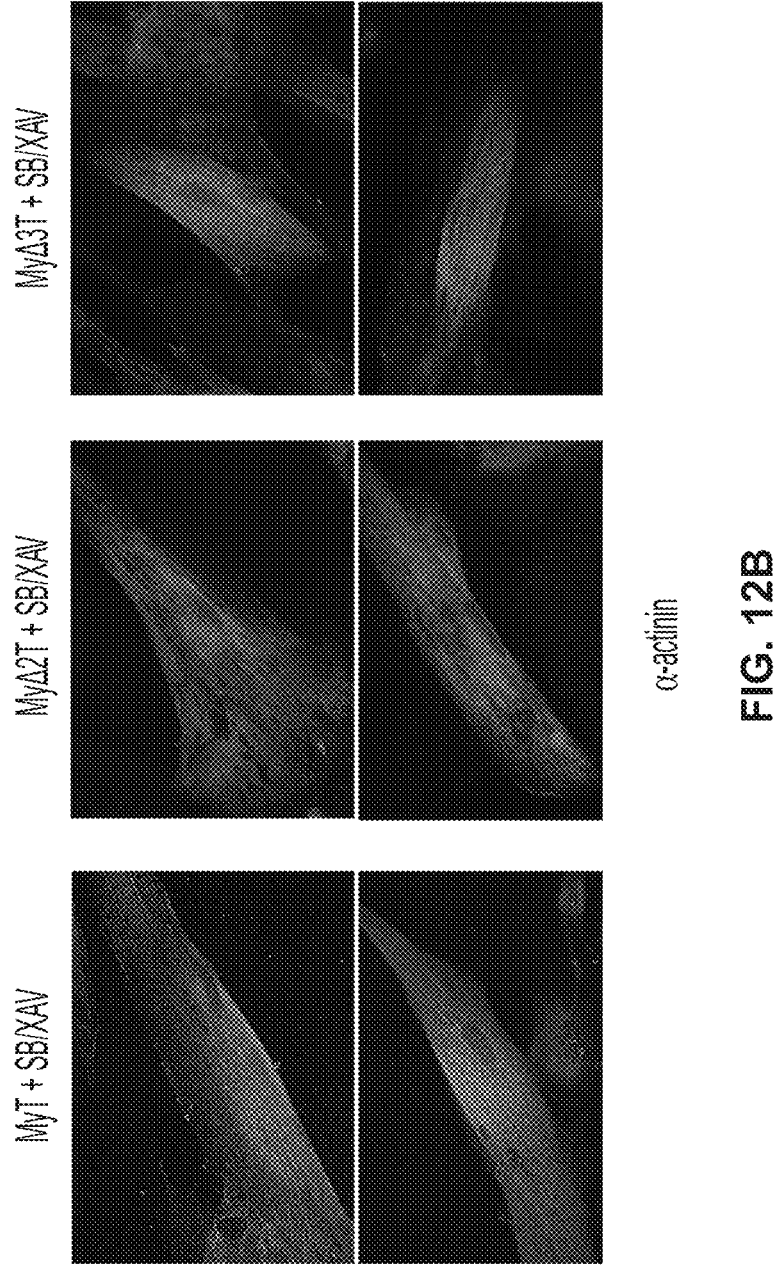

Similar experiments were performed with native or engineered myocardin and TBX5 in the presence of SB431542 and Wnt inhibitor XAV939, but without MEF2C. Coinfection was used to induce expression of MYOCD and TBX5 (MyT), MyΔ1 and TBX5 (MyΔ1T), MyΔ2 and TBX5 (MyΔ2T), or MyΔ3 and TBX5 (MyΔ3T) in the presence of small molecules (+SB/XAV). Expression profiles were measured by qPCR as described in Example 7. FIG. 12A demonstrates that human cardiac fibroblasts transduced with polynucleotides encoding TBX5 and MyΔ3 exhibited a transcriptional profile comparable to those transduced with TBX5 and native MYOCD. FIG. 12B shows immunofluorescence microscopy of cells transduced with MyT or MyΔ3T in the presence of small molecules from the same experiment. Cardiac fibroblasts transduced with TBX5 and native MYOCD, TBX5 and MyΔ2, or TBX5 and MyΔ3 exhibit comparable α-actinin structures.

Example 10: Reprogramming of Human Cardiac Fibroblasts with AAV-Based MyΔ3A

Figure 8B:
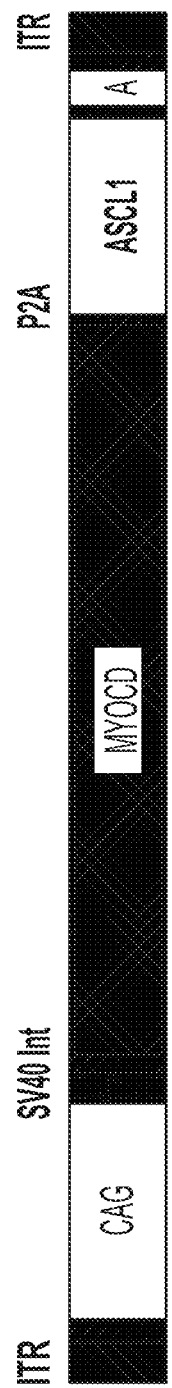
Figure 8C:
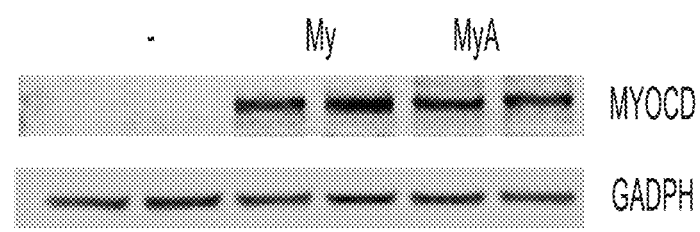
Figure 8D:
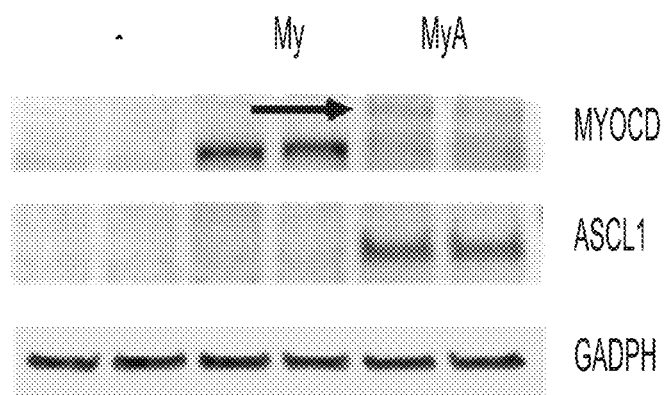
Figure 8E:
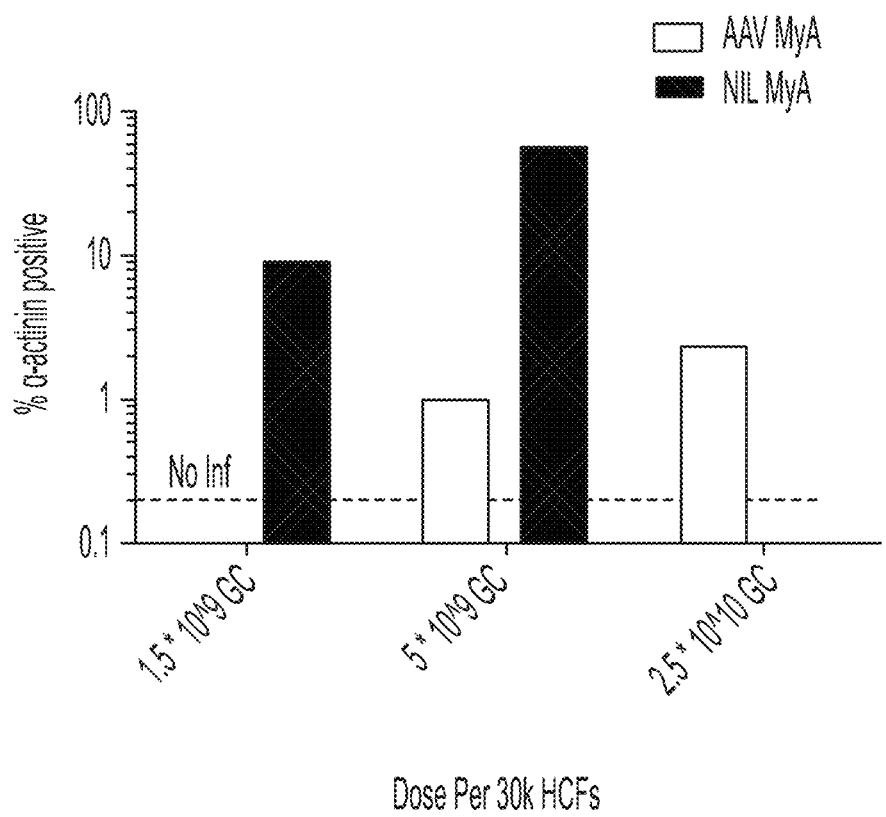
Figure 13A:
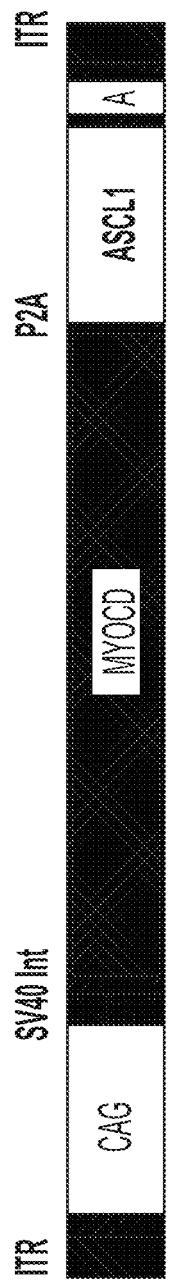
FIGS. 13A-FIG. 13C show design of AAV vectors for expression of native or engineered myocardin proteins with ASCL1.
Figure 13B:
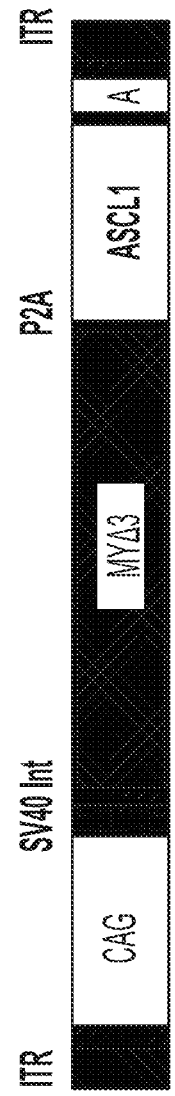
Figure 13C:
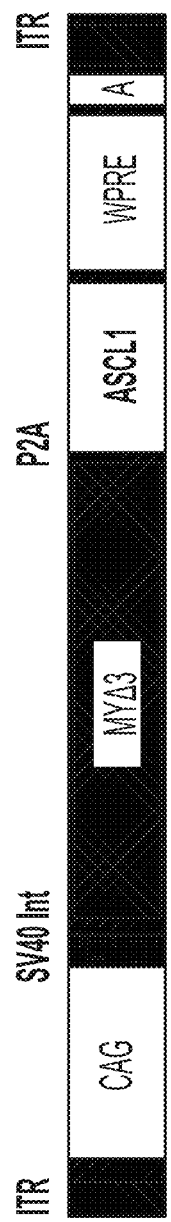

The AAV vector shown in FIG. 8B, which is reproduced as FIG. 13A (MyA ΔWPRE short A) was modified by substitution of native MYOCD with a polynucleotide encoding an engineered myocardin with an internal deletion of residues 560 to 763 (MyΔ3A ΔWPRE short A; FIG. 13B), or this substitution and addition of an WPRE (MyΔ3A WPRE short A; FIG. 13C). Control vectors with native MYOCD, WPRE, and bGH polyA signal (My; not shown); or native MYOCD and short polyA, but no WPRE (My ΔWPRE short A; not shown) were also generated.

Figure 14A:
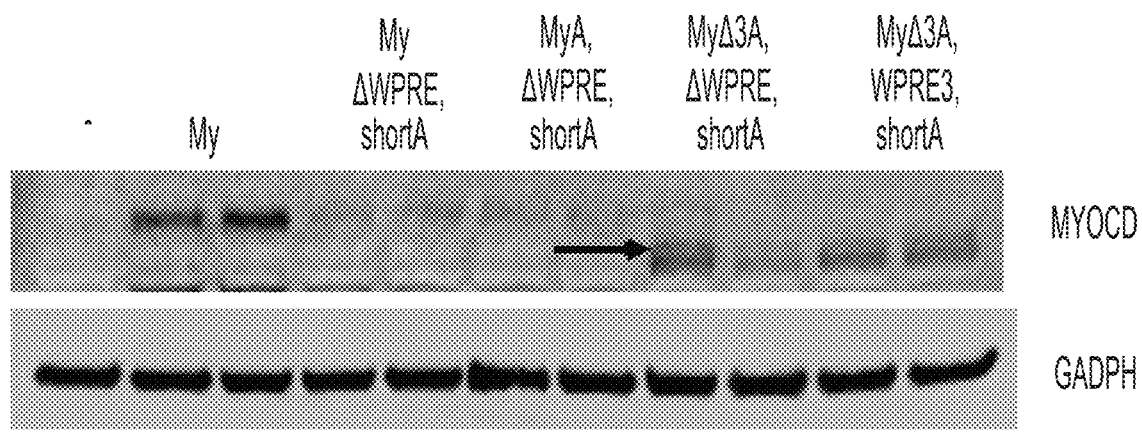
FIGS. 14A-FIG. 14D show testing of bicistronic AAV expression vectors encoding MyΔ3 and ASCL1. Protein expression levels for myocardin (FIG. 14A) and ASCL1 (FIG. 14B) are shown. Percentage of cells expressing markers of cardiac phenotype α-actinin (FIG. 14C) and cTNT (FIG. 14D) are shown.
Figure 14B:
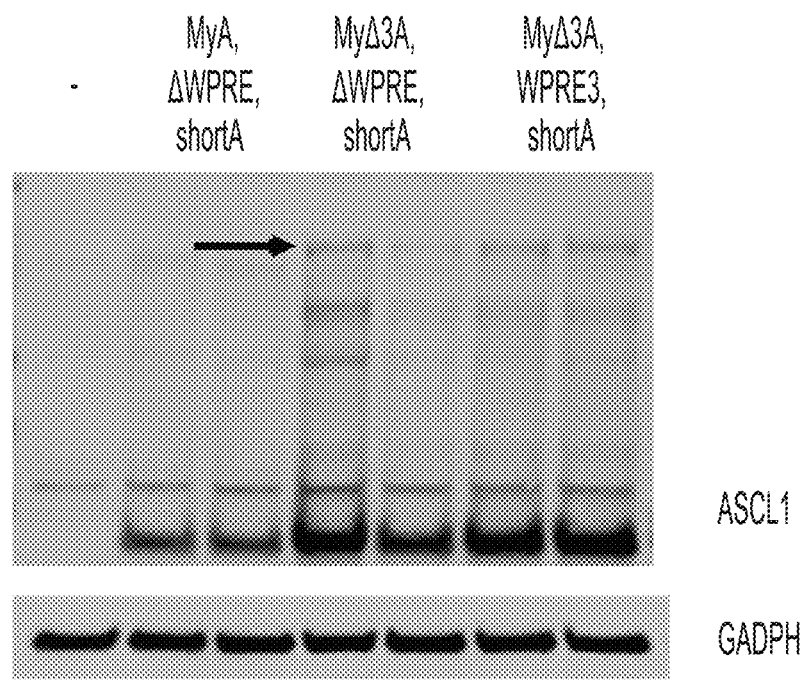

Replacement of wild-type MYOCD with MyΔ3 in the AAV cassette boosted myocardin (FIG. 14A) and ASCL1 (FIG. 14B) protein expression based on immunoblotting with MYOCD or ASCL1-specific antibodies. AAV vector lacking WPRE expressed myocardin protein, though at a lower level than the control vector with WPRE (My compared to My ΔWPRE short A). The engineered mycocardin with internal deletion (MyΔ3A ΔWPRE short A) is expressed at a higher level compared to native MYOCD in vectors lacking WPRE. Addition of a miniature WPRE (WPRE3) to the MyΔ3A AAV construct (MyΔ3A WPRE3 short A) did not have a robust additional effect. A higher molecular weight band corresponding to uncleaved MyΔ3-2A-ASCL1 is also observed (black arrow in FIG. 14A). Replacing native MYOCD with MyΔ3 similarly increases expression of ASCL1 (FIG. 14B). The higher molecular weight band for MyΔ3-2A-ASCL1 is also observed in the immunoblot (black arrow in FIG. 14B).

Native MYOCD plus ASCL1 vector (MyA ΔWPRE short A; now labeled AAV MyΔ) and engineered myocardin plus ASCL1 vector (MyΔ3A ΔWPRE short A; now labeled MyΔ3A) were further tested for their ability to induce a α-actinin+cTnT+ induced cardiomyocyte (iCM) phenotype in the HCF cell line by immunocytochemistry, as described in Example 7. Table 5 demonstrates that MyΔ3A increased expression of various reprogamming factors compared to MyA at various multiplicities of infection (MOI).

TABLE 5

| | Expression of Reprogramming Factors | | | | | | | | |
|---|---|---|---|---|---|---|---|---|---|
| Vector (MOI) | TNNT2 | MYH6 | NPPA | PLN | TNNC1 | ACTC1 | CASQ2 | CSPR3 | MYH7 |
| No Inf | 1.0 | 1.0 | 2.2 | 0.9 | 0.9 | 1.2 | 1.4 | 1.7 | 0.2 |
| No Inf | 1.0 | 1.0 | 0.6 | 1.2 | 1.2 | 0.9 | 0.8 | 2.5 | 1.7 |
| No Inf | 0.8 | 0.9 | 1.8 | 1.0 | 0.9 | 1.0 | 0.9 | 0.2 | 2.7 |
| AAV MyA 10k | 12.5 | 2.6 | 987.0 | 4.6 | 7.0 | 32.0 | 55.2 | 6.1 | 2.3 |
| AAV MyA 10k | 14.0 | 15.7 | 1257.6 | 5.5 | 13.3 | 29.3 | 98.3 | 3.2 | 1.7 |
| AAV MyA 10k | 15.7 | 8.4 | 1085.4 | 6.1 | 13.6 | 41.5 | 66.2 | 1.7 | 0.1 |
| AAV MyA 40k | 21.9 | 13.1 | 4135.0 | 7.2 | 28.4 | 47.4 | 96.9 | 3.7 | 2.5 |
| AAV MyA 40k | 15.8 | 23.7 | 1237.6 | 4.7 | 16.5 | 35.7 | 74.1 | 4.4 | 2.8 |
| AAV MyA 40k | 19.9 | 21.5 | 2996.0 | 6.1 | 14.7 | 42.6 | 105.1 | 4.1 | — |
| AAV MyA 160k | 50.0 | 25.1 | 5979.8 | 12.4 | 45.6 | 132.8 | 206.9 | 4.4 | 4.3 |
| AAV MyA 160k | 46.6 | 19.1 | 7650.1 | 8.6 | 45.3 | 110.7 | 263.8 | 7.0 | 0.2 |
| AAV MyA 160k | 43.6 | 41.9 | 4964.5 | 12.1 | 27.5 | 106.9 | 239.4 | 7.5 | 3.2 |
| AAV MyΔ3A 10k | 94.5 | 147.9 | 14423.4 | 16.7 | 125.0 | 163.9 | 488.8 | 8.2 | 9.2 |
| AAV MyΔ3A 10k | 51.1 | 60.9 | 5759.0 | 10.5 | 56.3 | 101.5 | 277.1 | 8.0 | 7.0 |
| AAV MyΔ3A 10k | 55.0 | 74.4 | 11600.2 | 9.7 | 70.9 | 110.1 | 335.7 | 9.1 | 6.0 |
| AAV MyΔ3A 40k | 112.0 | 164.7 | 26318.9 | 18.9 | 210.4 | 244.7 | 642.5 | 10.5 | 17.3 |
| AAV MyΔ3A 40k | 114.1 | 171.1 | 23530.4 | 20.8 | 153.3 | 241.2 | 658.9 | 13.9 | 8.4 |
| AAV MyΔ3A 40k | 92.0 | 114.2 | 14123.5 | 17.9 | 136.8 | 152.8 | 573.1 | 7.8 | 12.8 |

TABLE 5-continued

Expression of Reprogramming Factors

| Vector (MOI) | TNNT2 | MYH6 | NPPA | PLN | TNNC1 | ACTC1 | CASQ2 | CSPR3 | MYH7 |
|---|---|---|---|---|---|---|---|---|---|
| AAV MyΔ3A 160k | 236.3 | 330.2 | 47673.8 | 31.1 | 308.8 | 380.9 | 1147.3 | 17.4 | 25.7 |
| AAV MyΔ3A 160k | 150.8 | 408.3 | 32839.6 | 27.4 | 254.1 | 457.1 | 1082.5 | 17.8 | 9.4 |
| AAV MyΔ3A 160k | 333.0 | 438.6 | 77995.5 | 48.8 | 523.2 | 785.8 | 1641.8 | 14.1 | 22.2 |

Figure 14C:
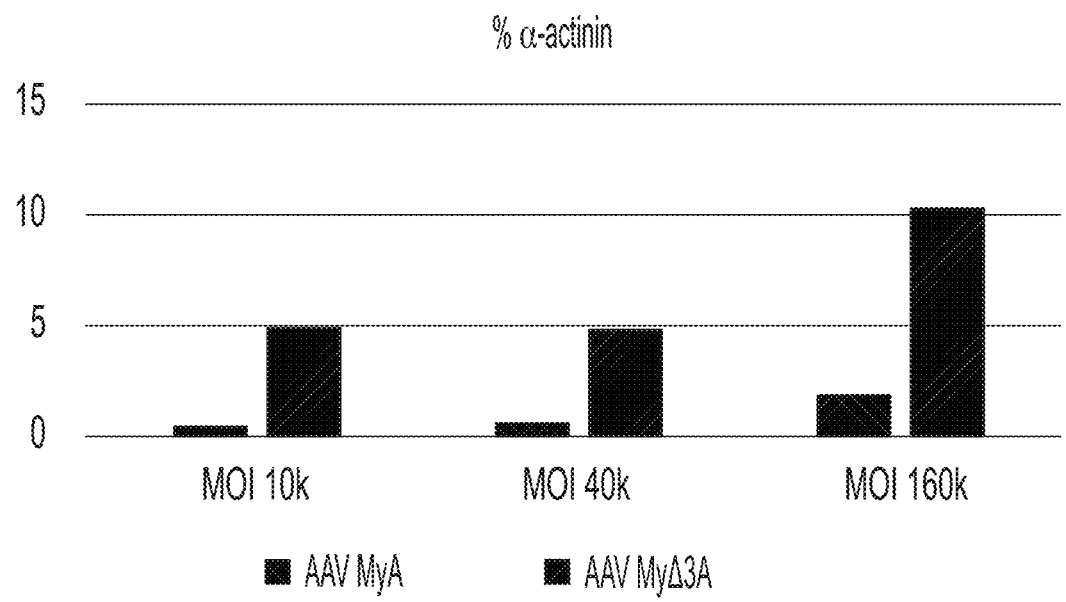
Figure 14D:
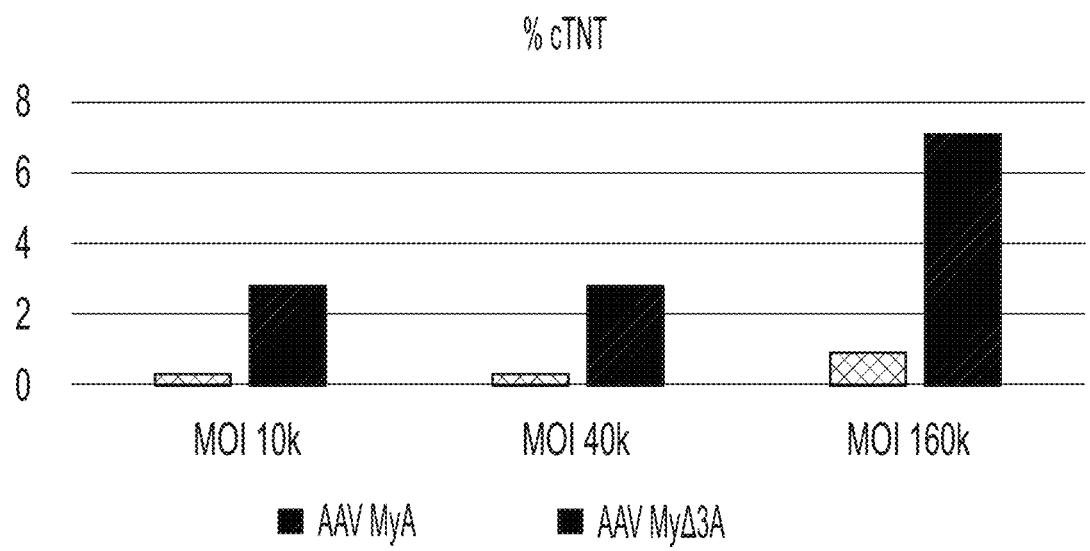

This increased reprogramming factor expression correlated with increased cardiac fibroblast reprogramming capacity of MyΔ3A compared to MyA based on quantitative immunofluorescence measurement of α-actinin+cells (FIG. 14C) or cTnT+cells (FIG. 14D).

Figure 15:
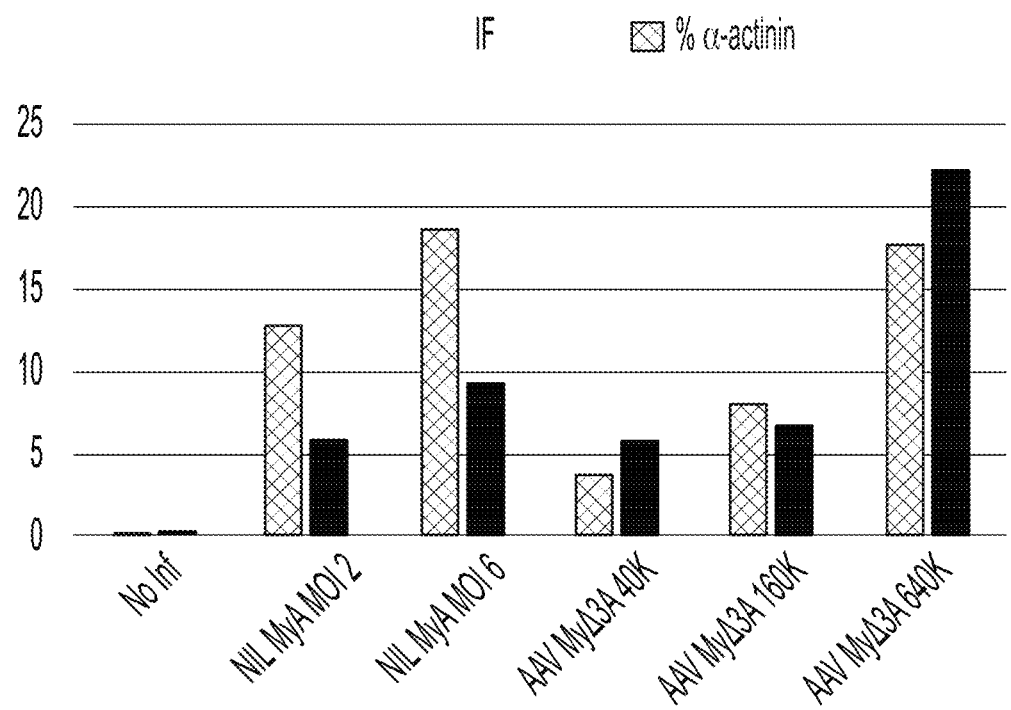
FIG. 15 shows percentage of cells expressing markers of cardiac phenotype α-actinin and cTNT after transduction with bicistonic NIL or AAV vectors.

The enhanced reprogramming capacity of AAV-based reprogramming with MyΔ3A was further validated by head-to-head comparison of AAV to NIL. AAV-based expression of MyΔ3A outperformed NIL-based reprogramming based on immunofluorescent analysis of percentage of α-actinin+ cells or percentage of cTnT+cells (FIG. 15). This contrasts with the lower performance of AAV compared to NIL observed with native MYOCD (FIG. 8E).

Example 11: Reprogramming of Human Cardiac Fibroblasts with AAV-Based MyMyf6

Figure 16A:
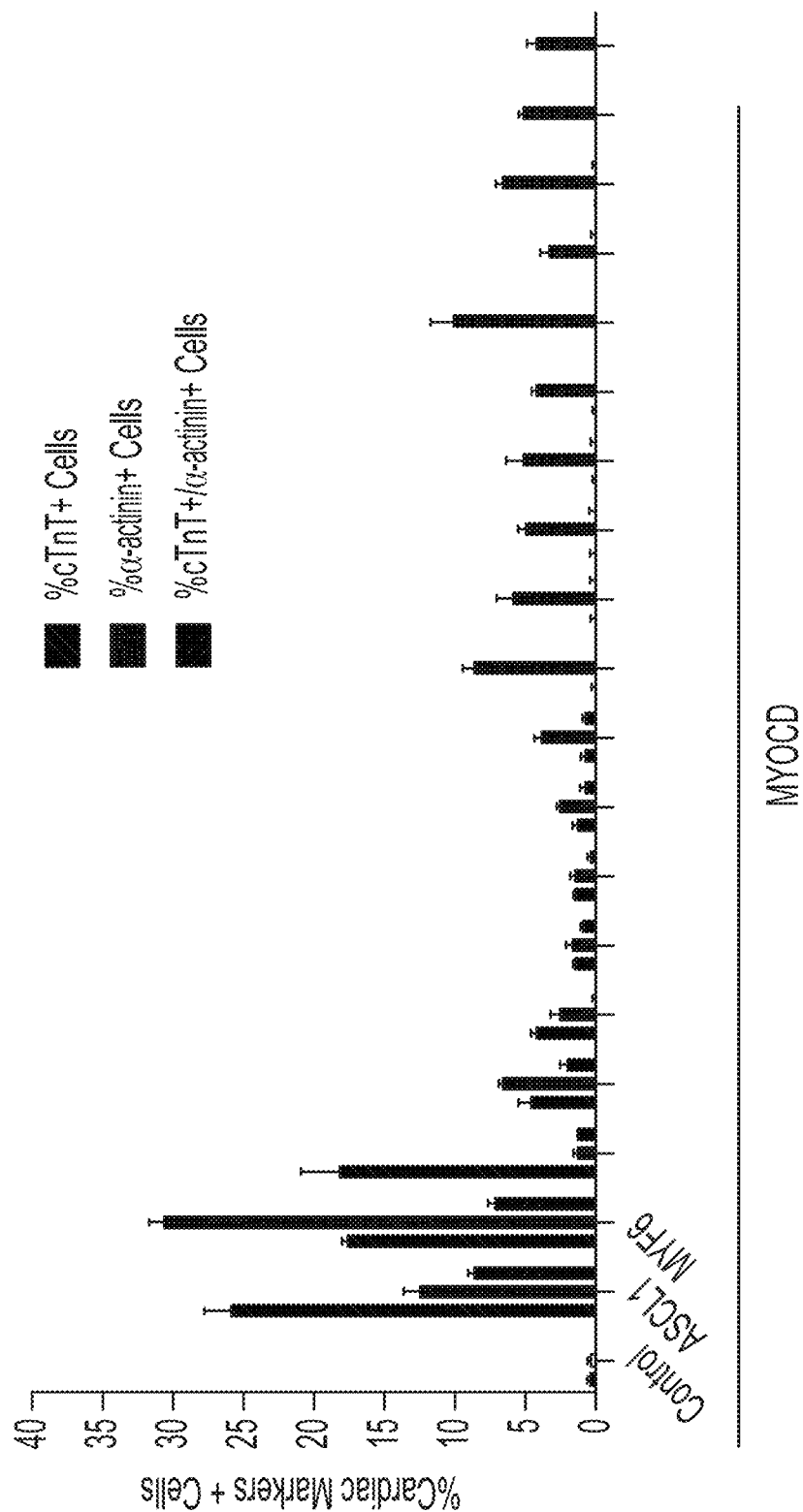
FIGS. 16A-FIG. 16B show testing of MYOCD in combination with ASCL1 and MYF6 for direct reprogramming of human cardiac fibroblasts into cardiomyocytes. MYOCD in combination with either ASCL1 or MYF6 demonstrated robust reprogramming as measured by percentage of cTnT+, α-actinin+, or double positive cells (FIG. 16A). Sixteen other factors showed some but lower reprogramming efficiency. Representative immunofluorescence micrographs are shown in FIG. 16B.
Figure 16B:
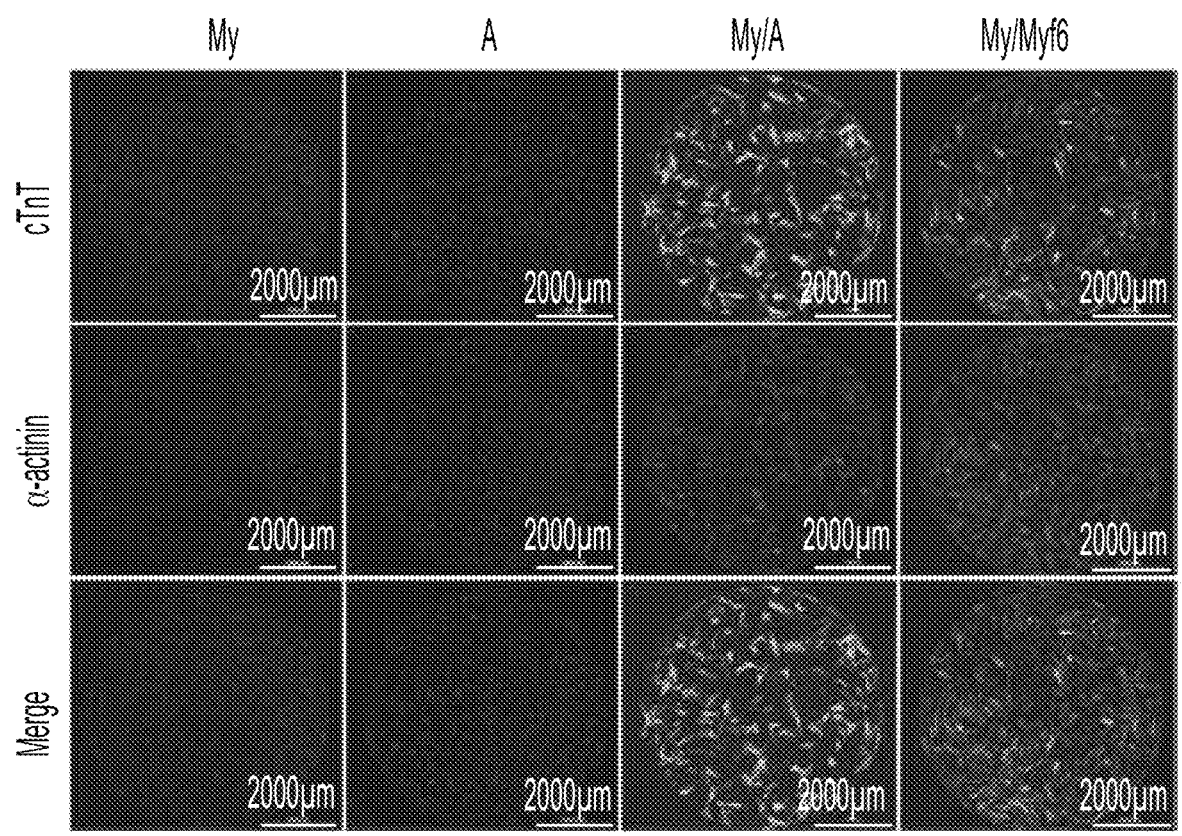

A library of approximately 1,000 human protein-coding genes were screened for reprogramming activity in combination with MYOCD alone by transduction of retroviruses encoding MYOCD and the each of the ~1,000 genes into cardiac fibroblasts. The ~1,000 human protein coding genes were tested for their ability to reprogram human cardiac fibroblasts assayed by expression of cTnT and α-actinin. Results for the best eighteen factors are shown (FIG. 16A). ASCL1 and MYF6 both show robust activity in combination with MYOCD and no other heterologous protein-coding gene. The expression of cTnT and of α-actinin were each quantified by Z-Score. FIG. 16B shows representative immunocytochemistry images of reprogrammed adult human cardiac fibroblasts (AHCFs) two weeks post-infection with retrovirus(es) expressing MYOCD (My); ASCL1 alone (A); MYOCD and ASCL1 (My/A); or MYOCD and MYF6 (My/Myf6). Table 6 shows cardiac gene expression analysis on reprogrammed cells using My/A or My/Myf6 each expressed from a single retroviral vector.

TABLE 6

Expression of Gene Markers

|  | MyA | MyMyf6 |
|---|---|---|
| NPPA | 21000 | 29 |
| ACTC1 | 15000 | 8000 |
| PLN | 1000 | 380 |
| TNNT2 | 160 | 49 |
| CASQ2 | 77 | 30 |
| TNNC1 | 49 | 23 |
| MYH7 | 42 | 96 |
| MYH6 | 26 | 2.3 |
| SCN5A | 24 | 4.0 |
| NPPB | 9.7 | 2.0 |
| ACTN2 | 6.2 | 13 |

AHCFs were infected with retroviruses that encoded MYOCD-2A-ASCL1 (MyA) or MYOCD-2A-MYF6 (My-Myf). Reprogrammed cells were cultured for three weeks. The transcript levels of cardiac marker genes (NPPA, ACTC1, PLN, TNNT2, CAQ2, TNNC1, MYH6, MYH7, SCN5A, NPPB) were determined by q-PCR.

Example 12: Treatment of Myocardial Infarction

Viral vectors for expression of myocardin and ASCL1 were tested in vivo as a treatment for myocardial infarction (MI). Adeno-associated virus (AAV) vectors were constructed by co-transfection of HEK293T cells with a PACG5 plasmid encoding the rep gene of AAV2 and the cap gene of AAV5 and pHelper encoding adenovirus gene E4, E2a and VA along with, individually, each of the three plasmid having a test expression cassette flanked by the inverted terminal repeats (ITRs) of AAV2. This co-transfection generated AAV5 viral particles capable of delivering each of the three expression cassettes. The negative-control expression cassette encoded green fluorescence protein (GFP) under the control of a CAG promoter. Two expression cassettes for mycocardin and ASCL1 were tested. In both tested expression cassettes, the engineered myocardin MyΔ3 was used to reduce the size of the expression cassette.

Figure 17A:
FIGS. 17A-FIG. 17B show in vivo testing of an AAV-delivered myocardin and ASCL1 in a bicistronic format (AAV5:MyΔ3/A).

The first tested expression cassette was a bicistronic expression cassette (FIG. 17A), which placed a polynucleotide (SEQ ID NO: 72) encoding MyΔ3 (SEQ ID NO: 16) under the transcriptional control of a CAG promoter (SEQ ID NO: 67) with an intervening SV40 intron (SEQ ID NO: 73) and a bGH polyA signal (SEQ ID NO: 85). This first expression cassette further included 3' to the MyΔ3 polyA signal, a polynucleotide (SEQ ID NO: 2) encoding ASCL1 (SEQ ID NO: 1) under the transcriptional control of a SCP promoter (SEQ ID NO: 68) and a short polyA signal (SEQ ID NO: 74). No WPRE sequence was used in this construct.

Figure 18A:
FIGS. 18A-FIG. 18B show in vivo testing of an AAV-delivered myocardin and ASCL1 in a monocistronic format (AAV5:MyΔ3A).

The second tested expression cassette was a monocistronic expression cassette (FIG. 18A) similar to that in Example 10, which placed a polynucleotide (SEQ ID NO: 72) encoding MyΔ3 (SEQ ID NO: 16) followed by a polynucleotide sequence (SEQ ID NO: 22) encoding a 2A peptide (SEQ ID NO: 23) and then a polynucleotide (SEQ ID NO: 2) encoding ASCL1 (SEQ ID NO: 1). The complete polynucleotide sequence of this open reading frame is SEQ ID NO: 35, which encodes the polypeptide sequence SEQ ID NO: 57. This second expression cassette placed this MyΔ3-2A-ASCL1 polynucleotide sequence under the transcriptional control of a CAG promoter (SEQ ID NO: 67) with an intervening SV40 intron (SEQ ID NO: 73) and a 3' short polyA signal (SEQ ID NO: 74). No WPRE sequence was used.

As a model for MI, CD-1 mice was generated by ligation of the left anterior descending (LAD) artery, as described in Gao et al. *Cardiovasc Res.* 45:330-38 (2000) (mice); Litwin et al. *Circulation.* 89:345-54 (1994) (rat); and Hood et al. *Cardiovasc Drugs Ther.* 6:233-37 (1992) (dogs). Ligation deprived the heart of oxygen leading to immediate damage to the heart. This damage has been shown to accurately reflect the damage sustained by a human heart during MI. (same citations) In addition, this experimental model is known in the art to be predict of response to treatment for heart failure (e.g. chronic ischemic heart failure).

Figure 17B:
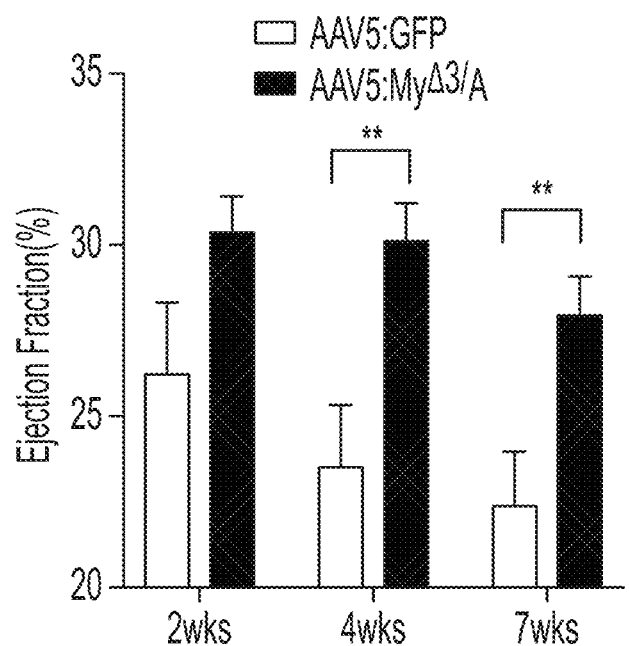

After ligation the heart, the mice were intramyocardially injected with the negative control vector (AAV5:GFP) or the bicistronic vector (labeled AAV5:MyΔ3A) at a dose of $1.2 \times 10^{11}$ genome copies (GC). Systemic administration of a vector, in particular a vector capable of transcytosis (such as, without limitation, AAV8, AAV9, AAVrh10, or selected variants of any known AAV serotype), would be expected to achieve the same result as intracardiac injection, at an adjusted dose (such as by multiplying the dose for intracardiac injection by the weight of the subject in kilograms, or using a dose determined by dosage ranging studies). Cardiac function (ejection fraction) was evaluated by echocardiography at 2, 4 and 7 weeks post-MI. Imaging revealed that mice injected with AAV5:MyΔ3A showed a statistically significant improvement in ejection fraction compared to the mice injected with AAV5:GFP at 4 and 7 weeks post-MI. (n=6-13 for each group. **$p<0.01$). Results are shown in FIG. 17B.

Figure 18B:
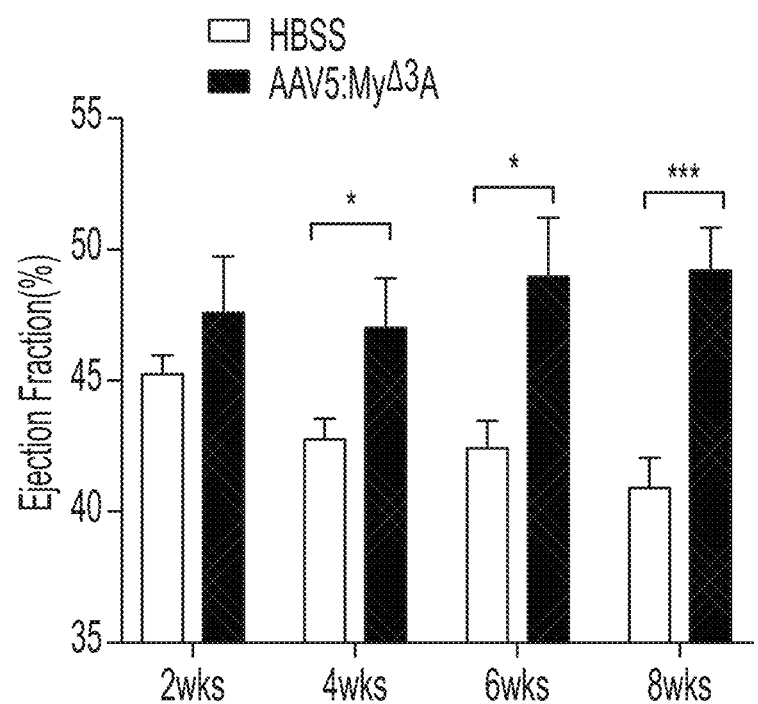

The ligation procedure was repeated on a second cohort of mice. After ligation, the heart was immediately injectioned, intramyocardially, with the vehicle control vector (Hank's Balanced Salt Solution, HBSS) or the monocistronic vector (labeled AAV5:MyΔ3A) again at a dose of $1.2 \times 10^{11}$ genome copies (GC). Heart function was followed up by echocardiography every two weeks until 8 weeks post-MI. Imaging revealed cardiac function (ejection fraction) in rats injected with vehicle (HBSS) continued to decline after MI. Rats injected with AAV5:MyΔ3A showed a statistically significant improvement in ejection fraction 4-8 weeks post-MI. (n=8 for each group. *$p<0.05$ ***$p<0.001$). Results are shown in FIG. 18B. Given that the heart weigh ratio of mice or rats to humans is about 1,000, a dose of between about $10^{13}$ GC to about $10^{14}$ GC is tested for efficacy in humans.

Figure 19B:
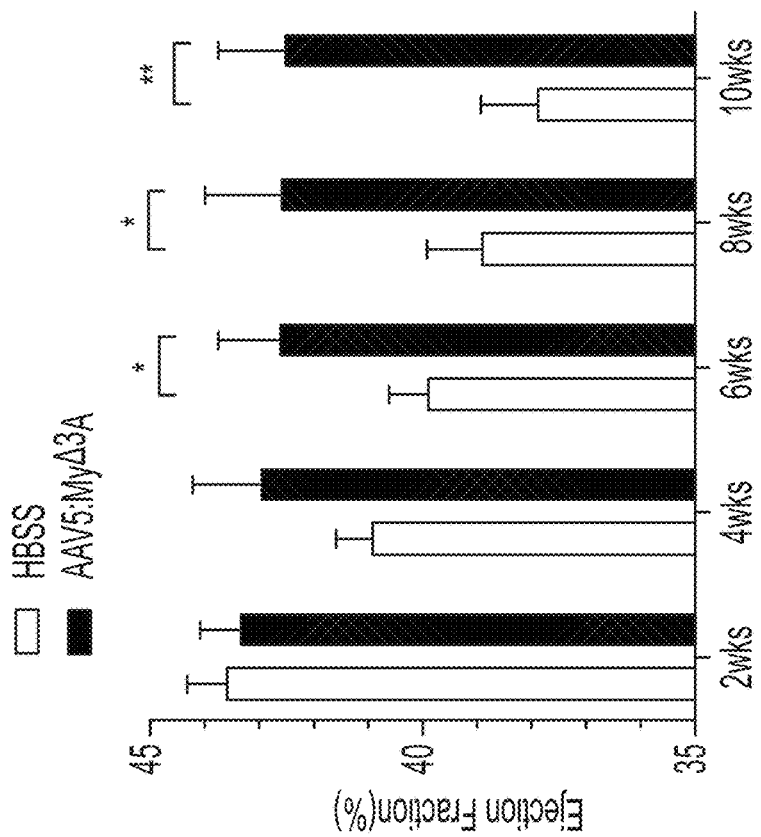
FIGS. 19A-FIG. 19B show in vivo testing of an AAV-delivered myocardin and ASCL1 in a monocistronic format (AAV5:MyΔ3A). AAV5:MyΔ3A improves ejection fraction in a rat model of chronic heart failure due to myocardial infarction (MI). HBSS or AAV5:MyΔ3A at dose $5 \times 10^{11}$ GC (MyΔ3 and ASCL1 transcripts were expressed from a single transcript including a 2A peptide) was delivered by intramyocardial injection at 2 weeks post permanent coronary ligation.
Figure 19A:
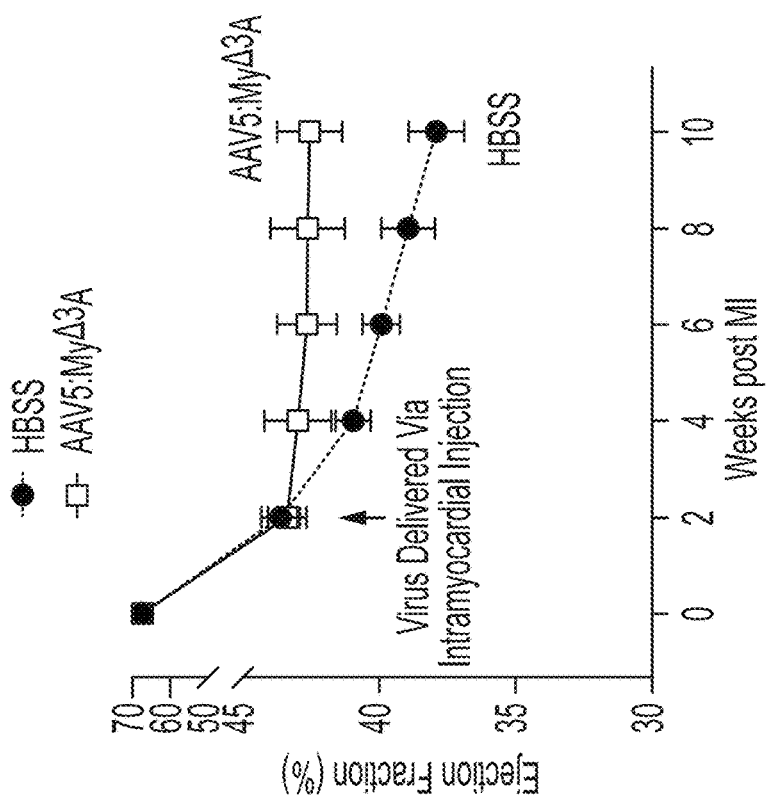

Additional testing was performed in a rat model of chronic myocardial infaction (CMI). The two week time point after LAD ligation for injection of viral vectors was chosen because this is after the phase of fibroblast proliferation post-MI (Fu et al. *J. Clin. Invest.* 128:2127-43 (2018)). FIGS. 19A-FIG. 19B show in vivo testing of an AAV-delivered myocardin and ASCL1 in a monocistronic format (AAV5:MyΔ3A). AAV5:MyΔ3A improves ejection fraction in a rat model of chronic heart failure due to myocardial infarction (MI). HBSS or AAV5:MyΔ3A at dose $5 \times 10^{11}$ GC (MyΔ3 and ASCL1 transcripts were expressed from a single transcript including a 2A peptide) was delivered by intramyocardial injection at 2 weeks post permanent coronary ligation. FIG. 19A shows heart function in treated (AAV5:MyΔ3A) and vehicle control (HBSS) groups assessed by echocardiography every two weeks until 10 weeks post-MI. Echocardiography revealed that cardiac function in rats injected with vehicle (HBSS) continued to decline after MI. AAV5:MyΔ3A halted this decline in heart function. FIG. 19B shows that AAV5:MyΔ3A treatment caused a statistically significant improvement in ejection fraction 6-10 weeks post-MI compared to animals with vehicle. (n=10 for each group. *$p<0.05$ **$p<0.01$).

These data from mice and rats demonstrate that AAV delivery of MyΔ3A can provide functional benefit in vivo in both acute myocardial infarction (AMI) and chronic myocardial infarction (CMI). Heart failure to due to AMI is substantially reversed. Progression of heart failure due to CMI is halted.

What is claimed is:

1. A vector comprising an expression cassette, said expression cassette comprising a myocardin (MYOCD) polynucleotide encoding a MYOCD polypeptide and an Achaete-scute homolog 1 (ASCL1) polynucleotide encoding an ASCL1 polypeptide, wherein said MYOCD polynucleotide and said ASCL1 polynucleotide are each operatively linked to at least one promoter, and wherein the vector is an adeno-associated virus (AAV) vector or a lentiviral vector.

2. The vector of claim 1, wherein the MYOCD polypeptide shares at least 95% identity to the polypeptide sequence set forth in SEQ ID NO: 16.

3. The vector of claim 2, wherein the MYOCD polypeptide comprises the polypeptide sequence set forth in SEQ ID NO: 16.

4. The vector of claim 1, wherein the ASCL1 polypeptide shares 95% identity to the polypeptide sequence set forth in SEQ ID NO: 1.

5. The vector of claim 1, wherein the MYOCD polynucleotide and the ASCL1 polynucleotide are linked via a 2A sequence to form, in 5' to 3' order, a ASCL1-2A-MYCOD polynucleotide, operatively linked to a single promoter.

6. The vector of claim 1, wherein the MYOCD polynucleotide and the ASCL1 polynucleotide are linked via a 2A sequence to form, in 5' to 3' order, a MYOCD-2A-ASCL1 polynucleotide, operatively linked to a single promoter.

7. The vector of claim 6, wherein the MYOCD-2A-ASCL1 polynucleotide encodes a polypeptide sequence that shares at least 95% identity to the polypeptide sequence set forth in SEQ ID NO: 59.

8. The vector of claim 7, wherein the MYOCD-2A-ASCL1 polynucleotide encodes the polypeptide sequence set forth in SEQ ID NO: 59.

9. The vector of claim 1, wherein the vector is an AAV vector.

10. The vector of claim 1, wherein the vector is a lentiviral vector.

11. A method of treating myocardial infarction in a subject in need thereof, comprising administering, by intramyocardial injection, a vector comprising an expression cassette, said expression cassette comprising a myocardin (MYOCD) polynucleotide encoding a MYOCD polypeptide and an Achaete-scute homolog 1 (ASCL1) polynucleotide encoding an ASCL1 polypeptide, wherein said MYOCD polynucleotide and said ASCL1 polynucleotide are each operatively linked to at least one promoter, and wherein the vector is an adeno-associated virus (AAV) vector or a lentiviral vector.

12. The method of claim 11, wherein the method treats one or more symptoms of acute myocardial infarction (AMI) or chronic myocardial infarction (CMI).

13. The method of claim 12, wherein the one or more symptoms comprise a decrease in ejection fraction of the heart of the subject.

14. The method of claim 11, wherein the MYOCD polypeptide shares at least 95% identity to the polypeptide sequence set forth in SEQ ID NO: 16.

15. The method of claim 11, wherein the vector is an AAV vector.

16. The method of claim 11, wherein the vector is a lentiviral vector.

17. The method of claim 11, wherein the MYOCD polynucleotide and the ASCL1 polynucleotide are linked via a 2A sequence to form, in 5' to 3' order, a MYOCD-2A-ASCL1 polynucleotide, operatively linked to a single promoter.

18. The method of claim 11, wherein the expression cassette is flanked by two AAV inverted terminal repeats (ITRs), and wherein the vector is an AAV vector and comprises an AAV capsid.

19. A pharmaceutical composition comprising the vector of claim 1.

20. A kit comprising the vector of claim 1.

21. The method of claim 11, wherein the MYOCD polynucleotide and the ASCL1 polynucleotide are linked via a 2A sequence to form, in 5' to 3' order, a ASCL1-2A-MYCOD polynucleotide, operatively linked to a single promoter.

22. The method of claim 17, wherein the MYOCD-2A-ASCL1 polynucleotide encodes a polypeptide sequence that shares at least 95% identity to the polypeptide sequence set forth in SEQ ID NO: 59.

23. The method of claim 22, wherein the MYOCD-2A-ASCL1 polynucleotide encodes the polypeptide sequence set forth in SEQ ID NO: 59.

24. The method of claim 14, wherein the MYOCD polypeptide comprises the polypeptide sequence set forth in SEQ ID NO: 16.

25. The method of claim 11, wherein the ASCL1 polypeptide shares 95% identity to the polypeptide sequence set forth in SEQ ID NO: 1.

* * * * *

SEQUENCE LISTING

```
<160> NUMBER OF SEQ ID NOS: 84

<210> SEQ ID NO 1
<211> LENGTH: 236
<212> TYPE: PRT
<213> ORGANISM: Homo sapiens

<400> SEQUENCE: 1

Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Ala Pro
    50                  55                  60

Gln Leu Arg Pro Ala Ala Asp Gly Gln Pro Ser Gly Gly Gly His Lys
65                  70                  75                  80

Ser Ala Pro Lys Gln Val Lys Arg Gln Arg Ser Ser Ser Pro Glu Leu
                85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
        115                 120                 125

Asn Arg Val Lys Leu Val Asn Leu Gly Phe Ala Thr Leu Arg Glu His
    130                 135                 140

Val Pro Asn Gly Ala Ala Asn Lys Lys Met Ser Lys Val Glu Thr Leu
```

```
                145                 150                 155                 160
Arg Ser Ala Val Glu Tyr Ile Arg Ala Leu Gln Gln Leu Leu Asp Glu
                    165                 170                 175

His Asp Ala Val Ser Ala Ala Phe Gln Ala Gly Val Leu Ser Pro Thr
            180                 185                 190

Ile Ser Pro Asn Tyr Ser Asn Asp Leu Asn Ser Met Ala Gly Ser Pro
        195                 200                 205

Val Ser Ser Tyr Ser Ser Asp Glu Gly Ser Tyr Asp Pro Leu Ser Pro
    210                 215                 220

Glu Glu Gln Glu Leu Leu Asp Phe Thr Asn Trp Phe
225                 230                 235

<210> SEQ ID NO 2
<211> LENGTH: 711
<212> TYPE: DNA
<213> ORGANISM: Homo sapiens

<400> SEQUENCE: 2
atggaaagct ctgccaagat ggagagcggc ggcgccggcc agcagcccca gccgcagccc      60
cagcagccct tcctgccgcc cgcagcctgt ttctttgcca cggccgcagc cgcggcggcc     120
gcagccgccg cagcggcagc gcagagcgcg cagcagcagc agcagcagca gcagcagcag     180
cagcaggcgc cgcagctgag accggcggcc gacggccagc cctcagggggg cggtcacaag    240 tcagcgccca agcaagtcaa cgacagcgc tcgtcttcgc ccgaactgat gcgctgcaaa     300
cgccggctca acttcagcgg ctttggctac agcctgccgc agcagcagcc ggccgccgtg     360
gcgcgccgca acgagcgcga cgcaaccgc gtcaagttgg tcaacctggg ctttgccacc     420
cttcgggagc acgtccccaa cggcgcggcc aacaagaaga tgagtaaggt ggagacactg     480
cgctcggcgg tcgagtacat ccgcgcgctg cagcagctgc tggacgagca tgacgcggtg     540
agcgccgcct tccaggcagg cgtcctgtcg cccaccatct cccccaacta ctccaacgac     600
ttgaactcca tggccggctc gccggtctca tcctactcgt cggacgaggg ctcttacgac     660
ccgctcagcc ccgaggagca ggagcttctc gacttcacca actggttctg a              711

<210> SEQ ID NO 3
<211> LENGTH: 986
<212> TYPE: PRT
<213> ORGANISM: Homo sapiens

<400> SEQUENCE: 3

Met Thr Leu Leu Gly Ser Glu His Ser Leu Leu Ile Arg Ser Lys Phe
1               5                   10                  15

Arg Ser Val Leu Gln Leu Arg Leu Gln Gln Arg Arg Thr Gln Glu Gln
                20                  25                  30

Leu Ala Asn Gln Gly Ile Ile Pro Pro Leu Lys Arg Pro Ala Glu Phe
            35                  40                  45

His Glu Gln Arg Lys His Leu Asp Ser Asp Lys Ala Lys Asn Ser Leu
        50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
                100                 105                 110

Ala Leu Arg Pro Gly Pro Leu Glu Leu Val Glu Lys Asn Ile Leu Pro
```

```
            115                 120                 125
Val Asp Ser Ala Val Lys Glu Ala Ile Lys Gly Asn Gln Val Ser Phe
            130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
                180                 185                 190

Leu Gly Thr Asn Gln Asp Leu Ala Ser Gly Ser Glu Asn Asp Arg Asn
                195                 200                 205

Asp Ser Ala Ser Gln Pro Ser His Gln Ser Asp Ala Gly Lys Gln Gly
            210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
                260                 265                 270

Gln Lys Ala Glu Lys Ser Pro Pro Met Asp Ser Ala Tyr Ala Arg
            275                 280                 285

Leu Leu Gln Gln Gln Leu Phe Leu Gln Leu Gln Ile Leu Ser Gln
            290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                325                 330                 335

Ser Ser Thr Pro Leu Ser Asn Thr Pro Leu Ser Pro Val Lys Asn Ser
                340                 345                 350

Phe Ser Gly Gln Thr Gly Val Ser Ser Phe Lys Pro Gly Pro Leu Pro
                355                 360                 365

Pro Asn Leu Asp Asp Leu Lys Val Ser Glu Leu Arg Gln Gln Leu Arg
                370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
                405                 410                 415

Asp Ile Thr Thr Val Thr Phe Pro Val Thr Pro Asn Thr Leu Pro Asn
                420                 425                 430

Tyr Gln Ser Ser Ser Thr Ser Ala Leu Ser Asn Gly Phe Tyr His
            435                 440                 445

Phe Gly Ser Thr Ser Ser Pro Pro Ile Ser Pro Ala Ser Ser Asp
            450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
                485                 490                 495

Leu Met Ser Ser Leu Asn Gly Gly Ser Val Pro Ser Glu Leu Asp Gly
                500                 505                 510

Leu Asp Ser Glu Lys Asp Lys Met Leu Val Glu Lys Gln Lys Val Ile
                515                 520                 525

Asn Glu Leu Thr Trp Lys Leu Gln Gln Glu Gln Arg Gln Val Glu Glu
                530                 535                 540
```

```
Leu Arg Met Gln Leu Gln Lys Gln Lys Arg Asn Asn Cys Ser Glu Lys
545                 550                 555                 560

Lys Pro Leu Pro Phe Leu Ala Ala Ser Ile Lys Gln Glu Glu Ala Val
                565                 570                 575

Ser Ser Cys Pro Phe Ala Ser Gln Val Pro Val Lys Arg Gln Ser Ser
            580                 585                 590

Ser Ser Glu Cys His Pro Pro Ala Cys Glu Ala Ala Gln Leu Gln Pro
        595                 600                 605

Leu Gly Asn Ala His Cys Val Glu Ser Ser Asp Gln Thr Asn Val Leu
610                 615                 620

Ser Ser Thr Phe Leu Ser Pro Gln Cys Ser Pro Gln His Ser Pro Leu
625                 630                 635                 640

Gly Ala Val Lys Ser Pro Gln His Ile Ser Leu Pro Pro Ser Pro Asn
                645                 650                 655

Asn Pro His Phe Leu Pro Ser Ser Ser Gly Ala Gln Gly Glu Gly His
            660                 665                 670

Arg Val Ser Ser Pro Ile Ser Ser Gln Val Cys Thr Ala Gln Asn Ser
        675                 680                 685

Gly Ala His Asp Gly His Pro Pro Ser Phe Ser Pro His Ser Ser Ser
690                 695                 700

Leu His Pro Pro Phe Ser Gly Ala Gln Ala Asp Ser Ser His Gly Ala
705                 710                 715                 720

Gly Gly Asn Pro Cys Pro Lys Ser Pro Cys Val Gln Gln Lys Met Ala
                725                 730                 735

Gly Leu His Ser Ser Asp Lys Val Gly Pro Lys Phe Ser Ile Pro Ser
            740                 745                 750

Pro Thr Phe Ser Lys Ser Ser Ala Ile Ser Glu Val Thr Gln Pro
        755                 760                 765

Pro Ser Tyr Glu Asp Ala Val Lys Gln Gln Met Thr Arg Ser Gln Gln
770                 775                 780

Met Asp Glu Leu Leu Asp Val Leu Ile Glu Ser Gly Glu Met Pro Ala
785                 790                 795                 800

Asp Ala Arg Glu Asp His Ser Cys Leu Gln Lys Val Pro Lys Ile Pro
                805                 810                 815

Arg Ser Ser Arg Ser Pro Thr Ala Val Leu Thr Lys Pro Ser Ala Ser
            820                 825                 830

Phe Glu Gln Ala Ser Ser Gly Ser Gln Ile Pro Phe Asp Pro Tyr Ala
        835                 840                 845

Thr Asp Ser Asp Glu His Leu Glu Val Leu Leu Asn Ser Gln Ser Pro
850                 855                 860

Leu Gly Lys Met Ser Asp Val Thr Leu Leu Lys Ile Gly Ser Glu Glu
865                 870                 875                 880

Pro His Phe Asp Gly Ile Met Asp Gly Phe Ser Gly Lys Ala Ala Glu
                885                 890                 895

Asp Leu Phe Asn Ala His Glu Ile Leu Pro Gly Pro Leu Ser Pro Met
            900                 905                 910

Gln Thr Gln Phe Ser Pro Ser Ser Val Asp Ser Asn Gly Leu Gln Leu
        915                 920                 925

Ser Phe Thr Glu Ser Pro Trp Glu Thr Met Glu Trp Leu Asp Leu Thr
930                 935                 940

Pro Pro Asn Ser Thr Pro Gly Phe Ser Ala Leu Thr Thr Ser Ser Pro
945                 950                 955                 960
```

Ser Ile Phe Asn Ile Asp Phe Leu Asp Val Thr Asp Leu Asn Leu Asn
                965                 970                 975

Ser Ser Met Asp Leu His Leu Gln Gln Trp
        980                 985

<210> SEQ ID NO 4
<211> LENGTH: 2961
<212> TYPE: DNA
<213> ORGANISM: Homo sapiens

<400> SEQUENCE: 4

| | | | | | |
|---|---|---|---|---|---|
| atgacactcc | tggggtctga | gcattccttg | ctgattagga | gcaagttcag | atcagtttta | 60 |
| cagttaagac | ttcaacaaag | aaggacccag | gaacaactgg | ctaaccaagg | cataatacca | 120 |
| ccactgaaac | gtccagctga | attccatgag | caaagaaaac | atttggatag | tgacaaggct | 180 |
| aaaaattccc | tgaagcgcaa | agccagaaac | aggtgcaaca | gtgccgactt | ggttaatatg | 240 |
| cacatactcc | aagcttccac | tgcagagagg | tccattccaa | ctgctcagat | gaagctgaaa | 300 |
| agagcccgac | tcgccgatga | tctcaatgaa | aaaattgctc | tacgaccagg | gccactggag | 360 |
| ctggtggaaa | aaacattctt | tcctgtggat | tctgctgtga | agaggccat | aaaaggtaac | 420 |
| caggtgagtt | tctccaaatc | cacgatgct | tttgcctttg | aagaggacag | cagcagcgat | 480 |
| gggctttctc | cggatcagac | tcgaagtgaa | gaccccaaa | actcagcggg | atcccgccca | 540 |
| gacgctaaag | cctcagatac | ccttcgaca | ggttctctgg | ggacaaacca | ggatcttgct | 600 |
| tctggctcag | aaaatgacag | aaatgactca | gcctcacagc | ccagccacca | gtcagatgcg | 660 |
| gggaagcagg | ggcttggccc | cccagcacc | cccatagccg | tgcatgctgc | tgtaaagtcc | 720 |
| aaatccttgg | gtgacagtaa | gaaccgccac | aaaaagccca | aggaccccaa | gccaaggtg | 780 |
| aagaagctta | aatatcacca | gtacattccc | ccagaccaga | aggcagagaa | gtcccctcca | 840 |
| cctatggact | cagcctacgc | tcggctgctc | cagcaacagc | agctgttcct | gcagctccaa | 900 |
| atcctcagcc | agcagcagca | gcagcagcaa | caccgattca | gctacctagg | gatgcaccaa | 960 |
| gctcagctta | aggaaccaaa | tgaacagatg | gtcagaaatc | caaactcttc | ttcaacgcca | 1020 |
| ctgagcaata | ccccttgtc | tcctgtcaaa | aacagttttt | ctggacaaac | tggtgtctct | 1080 |
| tcttcaaac | caggcccact | cccacctaac | ctggatgatc | tgaaggtctc | tgaattaaga | 1140 |
| caacagcttc | gaattcgggg | cttgcctgtg | tcaggcacca | aaacggctct | catgaccgg | 1200 |
| cttcgaccct | tccaggactg | ctctggcaac | ccagtgccga | actttgggga | tataacgact | 1260 |
| gtcacttttc | ctgtcacacc | caacacgctg | cccaattacc | agtcttcctc | ttctaccagt | 1320 |
| gccctgtcca | acggcttcta | ccactttggc | agcaccagct | ccagccccc | gatctcccca | 1380 |
| gcctcctctg | acctgtcagt | cgctgggtcc | ctgccggaca | ccttcaatga | tgcctccccc | 1440 |
| tccttcggcc | tgcacccgtc | cccagtccac | gtgtgcacgg | aggaaagtct | catgagcagc | 1500 |
| ctgaatgggg | gctctgttcc | ttctgagctg | gatgggctgg | actccagaa | ggacaagatg | 1560 |
| ctggtggaga | agcagaaggt | gatcaatgaa | ctcacctgga | actccagca | agagcagagg | 1620 |
| caggtggagg | agctgaggat | gcagcttcag | aagcagaaaa | ggaataactg | ttcagagaag | 1680 |
| aagccgctgc | ctttcctggc | tgcctccatc | aagcaggaag | aggctgtctc | cagctgtcct | 1740 |
| tttgcatccc | aagtacctgt | gaaaagacaa | agcagcagct | cagagtgtca | cccaccggct | 1800 |
| tgtgaagctg | ctcaactcca | gcctcttgga | aatgctcatt | gtgtggagtc | ctcagatcaa | 1860 |
| accaatgtac | tttcttccac | atttctcagc | ccccagtgtt | ccctcagca | ttcaccgctg | 1920 |
| ggggctgtga | aaagcccaca | gcacatcagt | ttgccccat | cacccaacaa | ccctcacttt | 1980 |

-continued

```
ctgccctcat cctccggggc ccagggagaa gggcacaggg tctcctcgcc catcagcagc    2040
caggtgtgca ctgcacagaa ctcaggagca cacgatggcc atcctccaag cttctctccc    2100
cattcttcca gcctccaccc gcccttctct ggagcccaag cagacagcag tcatggtgcc    2160
gggggaaacc cttgtcccaa aagcccatgt gtacagcaaa agatggctgg tttacactct    2220
tctgataagg tggggccaaa gttttcaatt ccatccccaa cttttttctaa gtcaagttca    2280 gcaatttcag aggtaacaca gcctccatcc tatgaagatg ccgtaaagca gcaaatgacc    2340
cggagtcagc agatggatga actcctggac gtgcttattg aaagcggaga atgccagca    2400 gacgctagag aggatcactc atgtcttcaa aaagtcccaa agatacccag atcttcccga    2460
agtccaactg ctgtcctcac caagccctcg gcttcctttg aacaagcctc ttcaggcagc    2520
cagatcccct ttgatcccta tgccaccgac agtgatgagc atcttgaagt cttattaaat    2580
tcccagagcc cctaggaaa gatgagtgat gtcacccttc taaaaattgg gagcgaagag    2640
cctcactttg atgggataat ggatggattc tctgggaagg ctgcagaaga cctcttcaat    2700
gcacatgaga tcttgccagg ccccctctct ccaatgcaga cacagttttc accctcttct    2760
gtggacagca atgggctgca gttaagcttc actgaatctc cctgggaaac catggagtgg    2820
ctggacctca ctccgccaaa ttccacacca ggctttagcg ccctcaccac cagcagcccc    2880
agcatcttca acatcgattt cctggatgtc actgatctca atttgaattc ttccatggac    2940
cttcacttgc agcagtggta g                                              2961
```

<210> SEQ ID NO 5
<211> LENGTH: 463
<212> TYPE: PRT
<213> ORGANISM: Homo sapiens

<400> SEQUENCE: 5

```
Met Gly Arg Lys Lys Ile Gln Ile Thr Arg Ile Met Asp Glu Arg Asn
1               5                   10                  15

Arg Gln Val Thr Phe Thr Lys Arg Lys Phe Gly Leu Met Lys Lys Ala
            20                  25                  30

Tyr Glu Leu Ser Val Leu Cys Asp Cys Glu Ile Ala Leu Ile Ile Phe
        35                  40                  45

Asn Ser Thr Asn Lys Leu Phe Gln Tyr Ala Ser Thr Asp Met Asp Lys
    50                  55                  60

Val Leu Leu Lys Tyr Thr Glu Tyr Asn Glu Pro His Glu Ser Arg Thr
65                  70                  75                  80

Asn Ser Asp Ile Val Glu Ala Leu Asn Lys Lys Glu Asn Lys Gly Cys
                85                  90                  95

Glu Ser Pro Asp Pro Asp Ser Ser Tyr Ala Leu Thr Pro Arg Thr Glu
            100                 105                 110

Glu Lys Tyr Lys Lys Ile Asn Glu Glu Phe Asp Asn Met Ile Lys Ser
        115                 120                 125

His Lys Ile Pro Ala Val Pro Pro Asn Phe Glu Met Pro Val Ser
    130                 135                 140

Ile Pro Val Ser Ser His Asn Ser Leu Val Tyr Ser Asn Pro Val Ser
145                 150                 155                 160

Ser Leu Gly Asn Pro Asn Leu Leu Pro Leu Ala His Pro Ser Leu Gln
                165                 170                 175

Arg Asn Ser Met Ser Pro Gly Val Thr His Arg Pro Pro Ser Ala Gly
            180                 185                 190
```

Asn Thr Gly Gly Leu Met Gly Gly Asp Leu Thr Ser Gly Ala Gly Thr
              195                 200                 205

Ser Ala Gly Asn Gly Tyr Gly Asn Pro Arg Asn Ser Pro Gly Leu Leu
    210                 215                 220

Val Ser Pro Gly Asn Leu Asn Lys Asn Met Gln Ala Lys Ser Pro Pro
225                 230                 235                 240

Pro Met Asn Leu Gly Met Asn Asn Arg Lys Pro Asp Leu Arg Val Leu
                245                 250                 255

Ile Pro Pro Gly Ser Lys Asn Thr Met Pro Ser Val Asn Gln Arg Ile
            260                 265                 270

Asn Asn Ser Gln Ser Ala Gln Ser Leu Ala Thr Pro Val Val Ser Val
        275                 280                 285

Ala Thr Pro Thr Leu Pro Gly Gln Gly Met Gly Gly Tyr Pro Ser Ala
    290                 295                 300

Ile Ser Thr Thr Tyr Gly Thr Glu Tyr Ser Leu Ser Ser Ala Asp Leu
305                 310                 315                 320

Ser Ser Leu Ser Gly Phe Asn Thr Ala Ser Ala Leu His Leu Gly Ser
                325                 330                 335

Val Thr Gly Trp Gln Gln Gln His Leu His Asn Met Pro Pro Ser Ala
            340                 345                 350

Leu Ser Gln Leu Gly Ala Cys Thr Ser Thr His Leu Ser Gln Ser Ser
        355                 360                 365

Asn Leu Ser Leu Pro Ser Thr Gln Ser Leu Asn Ile Lys Ser Glu Pro
    370                 375                 380

Val Ser Pro Pro Arg Asp Arg Thr Thr Thr Pro Ser Arg Tyr Pro Gln
385                 390                 395                 400

His Thr Arg His Glu Ala Gly Arg Ser Pro Val Asp Ser Leu Ser Ser
                405                 410                 415

Cys Ser Ser Ser Tyr Asp Gly Ser Asp Arg Glu Asp His Arg Asn Glu
            420                 425                 430

Phe His Ser Pro Ile Gly Leu Thr Arg Pro Ser Pro Asp Glu Arg Glu
        435                 440                 445

Ser Pro Ser Val Lys Arg Met Arg Leu Ser Glu Gly Trp Ala Thr
    450                 455                 460

<210> SEQ ID NO 6
<211> LENGTH: 1392
<212> TYPE: DNA
<213> ORGANISM: Homo sapiens

<400> SEQUENCE: 6
atggggagaa aaaagattca gattacgagg attatggatg aacgtaacag acaggtgaca      60
tttacaaaga ggaaatttgg gttgatgaag aaggcttatg agctgagcgt gctgtgtgac     120
tgtgagattg cgctgatcat cttcaacagc accaacaagc tgttccagta tgccagcacc     180
gacatggaca aagtgcttct caagtacacg gagtacaacg agccgcatga agccggaca      240 aactcagaca tcgtggaggc attgaacaag aaagaaaaca aggctgtga aagccccgat      300 cccgactcct cttatgcact cacccccacgc actgaagaaa aatacaaaaa aattaatgaa    360
gaatttgata tatgatcaa gagtcataaa attcctgctg ttccacctcc caacttcgag     420
atgccagtct ccatcccagt gtccagccac aacagtttgg tgtacagcaa ccctgtcagc    480
tcactgggaa accccaacct attgccactg gctcacccttc tctgcagag gaatagtatg   540 tctcctggtg taacacatcg acctccaagt gcaggtaaca caggtggtct gatgggtgga    600

-continued

```
gacctcacgt ctggtgcagg caccagtgca gggaacgggt atggcaatcc ccgaaactca    660
ccaggtctgc tggtctcacc tggtaacttg aacaagaata tgcaagcaaa atctcctccc    720
ccaatgaatt taggaatgaa taaccgtaaa ccagatctcc gagttcttat tccaccaggc    780
agcaagaata cgatgccatc agtgaatcaa aggataaata actcccagtc ggctcagtca    840
ttggctaccc cagtggtttc cgtagcaact cctactttac caggacaagg aatgggagga    900
tatccatcag ccatttcaac aacatatggt accgagtact ctctgagtag tgcagacctg    960
tcatctctgt ctgggtttaa caccgccagc gctcttcacc ttggttcagt aactggctgg   1020
caacagcaac acctacataa catgccacca tctgccctca gtcagttggg agcttgcact   1080
agcactcatt tatctcagag ttcaaatctc tccctgcctt ctactcaaag cctcaacatc   1140
aagtcagaac ctgtttctcc tcctagagac cgtaccacca cccttcgag atacccacaa    1200 cacacgcgcc acgaggcggg gagatctcct gttgacagct tgagcagctg tagcagttcg   1260
tacgacggga gcgaccgaga ggatcaccgg aacgaattcc actcccccat tggactcacc   1320
agaccttcgc cggacgaaag ggaaagtccc tcagtcaagc gcatgcgact ttctgaagga   1380
tgggcaacat ga                                                       1392
```

<210> SEQ ID NO 7
<211> LENGTH: 518
<212> TYPE: PRT
<213> ORGANISM: Homo sapiens

<400> SEQUENCE: 7

```
Met Ala Asp Ala Asp Glu Gly Phe Gly Leu Ala His Thr Pro Leu Glu
1               5                   10                  15

Pro Asp Ala Lys Asp Leu Pro Cys Asp Ser Lys Pro Glu Ser Ala Leu
            20                  25                  30

Gly Ala Pro Ser Lys Ser Pro Ser Pro Gln Ala Ala Phe Thr Gln
        35                  40                  45

Gln Gly Met Glu Gly Ile Lys Val Phe Leu His Glu Arg Glu Leu Trp
    50                  55                  60

Leu Lys Phe His Glu Val Gly Thr Glu Met Ile Ile Thr Lys Ala Gly
65                  70                  75                  80

Arg Arg Met Phe Pro Ser Tyr Lys Val Lys Val Thr Gly Leu Asn Pro
                85                  90                  95

Lys Thr Lys Tyr Ile Leu Leu Met Asp Ile Val Pro Ala Asp Asp His
            100                 105                 110

Arg Tyr Lys Phe Ala Asp Asn Lys Trp Ser Val Thr Gly Lys Ala Glu
        115                 120                 125

Pro Ala Met Pro Gly Arg Leu Tyr Val His Pro Asp Ser Pro Ala Thr
    130                 135                 140

Gly Ala His Trp Met Arg Gln Leu Val Ser Phe Gln Lys Leu Lys Leu
145                 150                 155                 160

Thr Asn Asn His Leu Asp Pro Phe Gly His Ile Ile Leu Asn Ser Met
                165                 170                 175

His Lys Tyr Gln Pro Arg Leu His Ile Val Lys Ala Asp Glu Asn Asn
            180                 185                 190

Gly Phe Gly Ser Lys Asn Thr Ala Phe Cys Thr His Val Phe Pro Glu
        195                 200                 205

Thr Ala Phe Ile Ala Val Thr Ser Tyr Gln Asn His Lys Ile Thr Gln
    210                 215                 220

Leu Lys Ile Glu Asn Asn Pro Phe Ala Lys Gly Phe Arg Gly Ser Asp
```

```
                225                 230                 235                 240
Asp Met Glu Leu His Arg Met Ser Arg Met Gln Ser Lys Glu Tyr Pro
                    245                 250                 255
Val Val Pro Arg Ser Thr Val Arg Gln Lys Val Ala Ser Asn His Ser
                260                 265                 270
Pro Phe Ser Ser Glu Ser Arg Ala Leu Ser Thr Ser Ser Asn Leu Gly
            275                 280                 285
Ser Gln Tyr Gln Cys Glu Asn Gly Val Ser Gly Pro Ser Gln Asp Leu
        290                 295                 300
Leu Pro Pro Pro Asn Pro Tyr Pro Leu Pro Gln Glu His Ser Gln Ile
305                 310                 315                 320
Tyr His Cys Thr Lys Arg Lys Glu Glu Glu Cys Ser Thr Thr Asp His
                    325                 330                 335
Pro Tyr Lys Lys Pro Tyr Met Glu Thr Ser Pro Ser Glu Glu Asp Ser
                340                 345                 350
Phe Tyr Arg Ser Ser Tyr Pro Gln Gln Gln Gly Leu Gly Ala Ser Tyr
            355                 360                 365
Arg Thr Glu Ser Ala Gln Arg Gln Ala Cys Met Tyr Ala Ser Ser Ala
        370                 375                 380
Pro Pro Ser Glu Pro Val Pro Ser Leu Glu Asp Ile Ser Cys Asn Thr
385                 390                 395                 400
Trp Pro Ser Met Pro Ser Tyr Ser Ser Cys Thr Val Thr Thr Val Gln
                    405                 410                 415
Pro Met Asp Arg Leu Pro Tyr Gln His Phe Ser Ala His Phe Thr Ser
                420                 425                 430
Gly Pro Leu Val Pro Arg Leu Ala Gly Met Ala Asn His Gly Ser Pro
            435                 440                 445
Gln Leu Gly Glu Gly Met Phe Gln His Gln Thr Ser Val Ala His Gln
        450                 455                 460
Pro Val Val Arg Gln Cys Gly Pro Gln Thr Gly Leu Gln Ser Pro Gly
465                 470                 475                 480
Thr Leu Gln Pro Pro Glu Phe Leu Tyr Ser His Gly Val Pro Arg Thr
                    485                 490                 495
Leu Ser Pro His Gln Tyr His Ser Val His Gly Val Gly Met Val Pro
                500                 505                 510
Glu Trp Ser Asp Asn Ser
            515

<210> SEQ ID NO 8
<211> LENGTH: 1557
<212> TYPE: DNA
<213> ORGANISM: Homo sapiens

<400> SEQUENCE: 8
atggccgacg cagacgaggg ctttggcctg gcgcacacgc tctctggagcc tgacgcaaaa      60 gacctgccct gcgattcgaa acccgagagc gcgctcgggg cccccagcaa gtccccgtcg     120
tccccgcagg ccgccttcac ccagcagggc atggagggaa tcaaagtgtt ctccatgaa      180 agagaactgt ggctaaaatt ccacgaagtg ggcacggaaa tgatcataac caaggctgga     240
aggcggatgt ttcccagtta caagtgaag gtgacgggcc ttaatcccaa acgaagtac      300 attcttctca tggacattgt acctgccgac gatcacagat acaaattcgc agataataaa     360
tggtctgtga cgggcaaagc tgagcccgcc atgcctggcc gctgtacgt gcacccagac     420 tcccccgcca ccggggcgca ttggatgagg cagctcgtct ccttccagaa actcaagctc     480
```

```
accaacaacc acctggaccc atttgggcat attattctaa attccatgca caaataccag    540
cctagattac acatcgtgaa agcggatgaa aataatggat ttggctcaaa aaatacagcg    600
ttctgcactc acgtctttcc tgagactgcg tttatagcag tgacttccta ccagaaccac    660
aagatcacgc aattaaagat tgagaataat ccctttgcca aaggatttcg gggcagtgat    720
gacatggagc tgcacagaat gtcaagaatg caaagtaaag aatatcccgt ggtccccagg    780
agcaccgtga ggcaaaaagt ggcctccaac cacagtcctt tcagcagcga gtctcgagct    840
ctctccacct catccaattt ggggtcccaa taccagtgtg agaatggtgt tccggcccc    900 tcccaggacc tcctgcctcc acccaaccca tacccactgc cccaggagca tagccaaatt    960
taccattgta ccaagaggaa agaggaagaa tgttccacca cagaccatcc ctataagaag   1020
ccctacatgg agacatcacc cagtgaagaa gattccttct accgctctag ctatccacag   1080
cagcagggcc tgggtgcctc ctacaggaca gagtcggcac agcggcaagc ttgcatgtat   1140
gccagctctg cgcccccag cgagcctgtg cccagcctag aggacatcag ctgcaacacg   1200
tggccaagca tgccttccta cagcagctgc accgtcacca ccgtgcagcc catggacagg   1260
ctaccctacc agcacttctc cgctcacttc acctcggggc ccctggtccc tcggctggct   1320
ggcatggcca accatggctc cccacagctg ggagagggaa tgttccagca ccagacctcc   1380
gtggcccacc agcctgtggt caggcagtgt gggcctcaga ctggcctgca gtcccctggc   1440
acccttcagc cccctgagtt cctctactct catggcgtgc caaggactct atcccctcat   1500
cagtaccact ctgtgcacgg agttggcatg gtgccagagt ggagcgacaa tagctaa     1557
```

<210> SEQ ID NO 9
<211> LENGTH: 20
<212> TYPE: PRT
<213> ORGANISM: Unknown
<220> FEATURE:
<223> OTHER INFORMATION: nuclear localization sequence

<400> SEQUENCE: 9

```
Lys Arg Lys Glu Glu Glu Cys Ser Thr Thr Asp His Pro Tyr Lys Lys
1               5                   10                  15

Pro Tyr Met Glu
            20
```

<210> SEQ ID NO 10
<211> LENGTH: 409
<212> TYPE: PRT
<213> ORGANISM: Artificial Sequence
<220> FEATURE:
<223> OTHER INFORMATION: MYOCD 5-413

<400> SEQUENCE: 10

```
Gly Ser Glu His Ser Leu Leu Ile Arg Ser Lys Phe Arg Ser Val Leu
1               5                   10                  15

Gln Leu Arg Leu Gln Gln Arg Arg Thr Gln Glu Gln Leu Ala Asn Gln
            20                  25                  30

Gly Ile Ile Pro Pro Leu Lys Arg Pro Ala Glu Phe His Glu Gln Arg
        35                  40                  45

Lys His Leu Asp Ser Asp Lys Ala Lys Asn Ser Leu Lys Arg Lys Ala
    50                  55                  60

Arg Asn Arg Cys Asn Ser Ala Asp Leu Val Asn Met His Ile Leu Gln
65                  70                  75                  80

Ala Ser Thr Ala Glu Arg Ser Ile Pro Thr Ala Gln Met Lys Leu Lys
```

```
                    85                  90                  95
Arg Ala Arg Leu Ala Asp Asp Leu Asn Glu Lys Ile Ala Leu Arg Pro
            100                 105                 110

Gly Pro Leu Glu Leu Val Glu Lys Asn Ile Leu Pro Val Asp Ser Ala
            115                 120                 125

Val Lys Glu Ala Ile Lys Gly Asn Gln Val Ser Phe Ser Lys Ser Thr
            130                 135                 140

Asp Ala Phe Ala Phe Glu Glu Asp Ser Ser Asp Gly Leu Ser Pro
145                 150                 155                 160

Asp Gln Thr Arg Ser Glu Asp Pro Gln Asn Ser Ala Gly Ser Pro Pro
                165                 170                 175

Asp Ala Lys Ala Ser Asp Thr Pro Ser Thr Gly Ser Leu Gly Thr Asn
            180                 185                 190

Gln Asp Leu Ala Ser Gly Ser Glu Asn Asp Arg Asn Asp Ser Ala Ser
            195                 200                 205

Gln Pro Ser His Gln Ser Asp Ala Gly Lys Gln Gly Leu Gly Pro Pro
    210                 215                 220

Ser Thr Pro Ile Ala Val His Ala Ala Val Lys Ser Lys Ser Leu Gly
225                 230                 235                 240

Asp Ser Lys Asn Arg His Lys Lys Pro Lys Asp Pro Lys Pro Lys Val
                245                 250                 255

Lys Lys Leu Lys Tyr His Gln Tyr Ile Pro Pro Asp Gln Lys Ala Glu
            260                 265                 270

Lys Ser Pro Pro Pro Met Asp Ser Ala Tyr Ala Arg Leu Leu Gln Gln
            275                 280                 285

Gln Gln Leu Phe Leu Gln Leu Gln Ile Leu Ser Gln Gln Gln Gln Gln
    290                 295                 300

Gln Gln His Arg Phe Ser Tyr Leu Gly Met His Gln Ala Gln Leu Lys
305                 310                 315                 320

Glu Pro Asn Glu Gln Met Val Arg Asn Pro Asn Ser Ser Thr Pro
                325                 330                 335

Leu Ser Asn Thr Pro Leu Ser Pro Val Lys Asn Ser Phe Ser Gly Gln
            340                 345                 350

Thr Gly Val Ser Ser Phe Lys Pro Gly Pro Leu Pro Pro Asn Leu Asp
            355                 360                 365

Asp Leu Lys Val Ser Glu Leu Arg Gln Gln Leu Arg Ile Arg Gly Leu
            370                 375                 380

Pro Val Ser Gly Thr Lys Thr Ala Leu Met Asp Arg Leu Arg Pro Phe
385                 390                 395                 400

Gln Asp Cys Ser Gly Asn Pro Val Pro
                405

<210> SEQ ID NO 11
<211> LENGTH: 223
<212> TYPE: PRT
<213> ORGANISM: Artificial Sequence
<220> FEATURE:
<223> OTHER INFORMATION: MYOCD 764-986

<400> SEQUENCE: 11

Glu Val Thr Gln Pro Pro Ser Tyr Glu Asp Ala Val Lys Gln Gln Met
1               5                   10                  15

Thr Arg Ser Gln Gln Met Asp Glu Leu Leu Asp Val Leu Ile Glu Ser
            20                  25                  30

Gly Glu Met Pro Ala Asp Ala Arg Glu Asp His Ser Cys Leu Gln Lys
```

```
                  35                  40                  45

Val Pro Lys Ile Pro Arg Ser Ser Arg Ser Pro Thr Ala Val Leu Thr
 50                  55                  60

Lys Pro Ser Ala Ser Phe Glu Gln Ala Ser Ser Gly Ser Gln Ile Pro
 65                  70                  75                  80

Phe Asp Pro Tyr Ala Thr Asp Ser Asp His Leu Glu Val Leu Leu
                 85                  90                  95

Asn Ser Gln Ser Pro Leu Gly Lys Met Ser Asp Val Thr Leu Leu Lys
                100                 105                 110

Ile Gly Ser Glu Glu Pro His Phe Asp Gly Ile Met Asp Gly Phe Ser
                115                 120                 125

Gly Lys Ala Ala Glu Asp Leu Phe Asn Ala His Glu Ile Leu Pro Gly
            130                 135                 140

Pro Leu Ser Pro Met Gln Thr Gln Phe Ser Pro Ser Val Asp Ser
145                 150                 155                 160

Asn Gly Leu Gln Leu Ser Phe Thr Glu Ser Pro Trp Glu Thr Met Glu
                165                 170                 175

Trp Leu Asp Leu Thr Pro Pro Asn Ser Thr Pro Gly Phe Ser Ala Leu
                180                 185                 190

Thr Thr Ser Ser Pro Ser Ile Phe Asn Ile Asp Phe Leu Asp Val Thr
            195                 200                 205

Asp Leu Asn Leu Asn Ser Ser Met Asp Leu His Leu Gln Gln Trp
210                 215                 220

<210> SEQ ID NO 12
<211> LENGTH: 434
<212> TYPE: PRT
<213> ORGANISM: Artificial Sequence
<220> FEATURE:
<223> OTHER INFORMATION: MYOCD 5-438

<400> SEQUENCE: 12

Gly Ser Glu His Ser Leu Leu Ile Arg Ser Lys Phe Arg Ser Val Leu
 1                   5                  10                  15

Gln Leu Arg Leu Gln Gln Arg Arg Thr Gln Glu Gln Leu Ala Asn Gln
                 20                  25                  30

Gly Ile Ile Pro Pro Leu Lys Arg Pro Ala Glu Phe His Glu Gln Arg
                 35                  40                  45

Lys His Leu Asp Ser Asp Lys Ala Lys Asn Ser Leu Lys Arg Lys Ala
             50                  55                  60

Arg Asn Arg Cys Asn Ser Ala Asp Leu Val Asn Met His Ile Leu Gln
 65                  70                  75                  80

Ala Ser Thr Ala Glu Arg Ser Ile Pro Thr Ala Gln Met Lys Leu Lys
                 85                  90                  95

Arg Ala Arg Leu Ala Asp Asp Leu Asn Glu Lys Ile Ala Leu Arg Pro
                100                 105                 110

Gly Pro Leu Glu Leu Val Glu Lys Asn Ile Leu Pro Val Asp Ser Ala
            115                 120                 125

Val Lys Glu Ala Ile Lys Gly Asn Gln Val Ser Phe Ser Lys Ser Thr
130                 135                 140

Asp Ala Phe Ala Phe Glu Glu Asp Ser Ser Asp Gly Leu Ser Pro
145                 150                 155                 160

Asp Gln Thr Arg Ser Glu Asp Pro Gln Asn Ser Ala Gly Ser Pro Pro
                165                 170                 175

Asp Ala Lys Ala Ser Asp Thr Pro Ser Thr Gly Ser Leu Gly Thr Asn
```

```
                   180                 185                 190

Gln Asp Leu Ala Ser Gly Ser Glu Asn Asp Arg Asn Asp Ser Ala Ser
                195                 200                 205

Gln Pro Ser His Gln Ser Asp Ala Gly Lys Gln Gly Leu Gly Pro Pro
            210                 215                 220

Ser Thr Pro Ile Ala Val His Ala Ala Val Lys Ser Lys Ser Leu Gly
225                 230                 235                 240

Asp Ser Lys Asn Arg His Lys Lys Pro Lys Asp Pro Lys Pro Lys Val
                245                 250                 255

Lys Lys Leu Lys Tyr His Gln Tyr Ile Pro Pro Asp Gln Lys Ala Glu
            260                 265                 270

Lys Ser Pro Pro Pro Met Asp Ser Ala Tyr Ala Arg Leu Leu Gln Gln
        275                 280                 285

Gln Gln Leu Phe Leu Gln Leu Gln Ile Leu Ser Gln Gln Gln Gln Gln
            290                 295                 300

Gln Gln His Arg Phe Ser Tyr Leu Gly Met His Gln Ala Gln Leu Lys
305                 310                 315                 320

Glu Pro Asn Glu Gln Met Val Arg Asn Pro Asn Ser Ser Ser Thr Pro
                325                 330                 335

Leu Ser Asn Thr Pro Leu Ser Pro Val Lys Asn Ser Phe Ser Gly Gln
            340                 345                 350

Thr Gly Val Ser Ser Phe Lys Pro Gly Pro Leu Pro Pro Asn Leu Asp
        355                 360                 365

Asp Leu Lys Val Ser Glu Leu Arg Gln Gln Leu Arg Ile Arg Gly Leu
    370                 375                 380

Pro Val Ser Gly Thr Lys Thr Ala Leu Met Asp Arg Leu Arg Pro Phe
385                 390                 395                 400

Gln Asp Cys Ser Gly Asn Pro Val Pro Asn Phe Gly Asp Ile Thr Thr
                405                 410                 415

Val Thr Phe Pro Val Thr Pro Asn Thr Leu Pro Asn Tyr Gln Ser Ser
            420                 425                 430

Ser Ser

<210> SEQ ID NO 13
<211> LENGTH: 555
<212> TYPE: PRT
<213> ORGANISM: Artificial Sequence
<220> FEATURE:
<223> OTHER INFORMATION: MYOCD 1-559

<400> SEQUENCE: 13

Gly Ser Glu His Ser Leu Leu Ile Arg Ser Lys Phe Arg Ser Val Leu
1               5                   10                  15

Gln Leu Arg Leu Gln Gln Arg Arg Thr Gln Glu Gln Leu Ala Asn Gln
            20                  25                  30

Gly Ile Ile Pro Pro Leu Lys Arg Pro Ala Glu Phe His Glu Gln Arg
        35                  40                  45

Lys His Leu Asp Ser Asp Lys Ala Lys Asn Ser Leu Lys Arg Lys Ala
    50                  55                  60

Arg Asn Arg Cys Asn Ser Ala Asp Leu Val Asn Met His Ile Leu Gln
65                  70                  75                  80

Ala Ser Thr Ala Glu Arg Ser Ile Pro Thr Ala Gln Met Lys Leu Lys
                85                  90                  95

Arg Ala Arg Leu Ala Asp Asp Leu Asn Glu Lys Ile Ala Leu Arg Pro
            100                 105                 110
```

```
Gly Pro Leu Glu Leu Val Glu Lys Asn Ile Leu Pro Val Asp Ser Ala
            115                 120                 125

Val Lys Glu Ala Ile Lys Gly Asn Gln Val Ser Phe Ser Lys Ser Thr
130                 135                 140

Asp Ala Phe Ala Phe Glu Glu Asp Ser Ser Asp Gly Leu Ser Pro
145                 150                 155                 160

Asp Gln Thr Arg Ser Glu Asp Pro Gln Asn Ser Ala Gly Ser Pro Pro
                165                 170                 175

Asp Ala Lys Ala Ser Asp Thr Pro Ser Thr Gly Ser Leu Gly Thr Asn
                180                 185                 190

Gln Asp Leu Ala Ser Gly Ser Glu Asn Asp Arg Asn Asp Ser Ala Ser
            195                 200                 205

Gln Pro Ser His Gln Ser Asp Ala Gly Lys Gln Gly Leu Gly Pro Pro
            210                 215                 220

Ser Thr Pro Ile Ala Val His Ala Ala Val Lys Ser Lys Ser Leu Gly
225                 230                 235                 240

Asp Ser Lys Asn Arg His Lys Lys Pro Lys Asp Pro Lys Pro Lys Val
                245                 250                 255

Lys Lys Leu Lys Tyr His Gln Tyr Ile Pro Pro Asp Gln Lys Ala Glu
            260                 265                 270

Lys Ser Pro Pro Pro Met Asp Ser Ala Tyr Ala Arg Leu Leu Gln Gln
            275                 280                 285

Gln Gln Leu Phe Leu Gln Leu Gln Ile Leu Ser Gln Gln Gln Gln Gln
            290                 295                 300

Gln Gln His Arg Phe Ser Tyr Leu Gly Met His Gln Ala Gln Leu Lys
305                 310                 315                 320

Glu Pro Asn Glu Gln Met Val Arg Asn Pro Asn Ser Ser Ser Thr Pro
                325                 330                 335

Leu Ser Asn Thr Pro Leu Ser Pro Val Lys Asn Ser Phe Ser Gly Gln
                340                 345                 350

Thr Gly Val Ser Ser Phe Lys Pro Gly Pro Leu Pro Pro Asn Leu Asp
            355                 360                 365

Asp Leu Lys Val Ser Glu Leu Arg Gln Gln Leu Arg Ile Arg Gly Leu
            370                 375                 380

Pro Val Ser Gly Thr Lys Thr Ala Leu Met Asp Arg Leu Arg Pro Phe
385                 390                 395                 400

Gln Asp Cys Ser Gly Asn Pro Val Pro Asn Phe Gly Asp Ile Thr Thr
                405                 410                 415

Val Thr Phe Pro Val Thr Pro Asn Thr Leu Pro Asn Tyr Gln Ser Ser
                420                 425                 430

Ser Ser Thr Ser Ala Leu Ser Asn Gly Phe Tyr His Phe Gly Ser Thr
            435                 440                 445

Ser Ser Ser Pro Pro Ile Ser Pro Ala Ser Ser Asp Leu Ser Val Ala
450                 455                 460

Gly Ser Leu Pro Asp Thr Phe Asn Asp Ala Ser Pro Ser Phe Gly Leu
465                 470                 475                 480

His Pro Ser Pro Val His Val Cys Thr Glu Glu Ser Leu Met Ser Ser
                485                 490                 495

Leu Asn Gly Gly Ser Val Pro Ser Glu Leu Asp Gly Leu Asp Ser Glu
                500                 505                 510

Lys Asp Lys Met Leu Val Glu Lys Gln Lys Val Ile Asn Glu Leu Thr
515                 520                 525
```

-continued

```
Trp Lys Leu Gln Gln Glu Gln Arg Gln Val Glu Glu Leu Arg Met Gln
            530                 535                 540

Leu Gln Lys Gln Lys Arg Asn Asn Cys Ser Glu
545                 550                 555

<210> SEQ ID NO 14
<211> LENGTH: 636
<212> TYPE: PRT
<213> ORGANISM: Artificial Sequence
<220> FEATURE:
<223> OTHER INFORMATION: MYOCD 1-413; 764-986 (Mydelta1)

<400> SEQUENCE: 14

Met Thr Leu Leu Gly Ser Glu His Ser Leu Leu Ile Arg Ser Lys Phe
1               5                   10                  15

Arg Ser Val Leu Gln Leu Arg Leu Gln Gln Arg Arg Thr Gln Glu Gln
            20                  25                  30

Leu Ala Asn Gln Gly Ile Ile Pro Pro Leu Lys Arg Pro Ala Glu Phe
            35                  40                  45

His Glu Gln Arg Lys His Leu Asp Ser Asp Lys Ala Lys Asn Ser Leu
    50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
            115                 120                 125

Val Asp Ser Ala Val Lys Glu Ala Ile Lys Gly Asn Gln Val Ser Phe
    130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
            195                 200                 205

Asp Ser Ala Ser Gln Pro Ser His Gln Ser Asp Ala Gly Lys Gln Gly
    210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
            260                 265                 270

Gln Lys Ala Glu Lys Ser Pro Pro Pro Met Asp Ser Ala Tyr Ala Arg
            275                 280                 285

Leu Leu Gln Gln Gln Gln Leu Phe Leu Gln Leu Gln Ile Leu Ser Gln
    290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                325                 330                 335
```

```
Ser Ser Thr Pro Leu Ser Asn Thr Pro Leu Ser Pro Val Lys Asn Ser
            340                 345                 350

Phe Ser Gly Gln Thr Gly Val Ser Ser Phe Lys Pro Gly Pro Leu Pro
        355                 360                 365

Pro Asn Leu Asp Asp Leu Lys Val Ser Glu Leu Arg Gln Gln Leu Arg
    370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Glu Val Thr
                405                 410                 415

Gln Pro Pro Ser Tyr Glu Asp Ala Val Lys Gln Gln Met Thr Arg Ser
            420                 425                 430

Gln Gln Met Asp Glu Leu Leu Asp Val Leu Ile Glu Ser Gly Glu Met
        435                 440                 445

Pro Ala Asp Ala Arg Glu Asp His Ser Cys Leu Gln Lys Val Pro Lys
    450                 455                 460

Ile Pro Arg Ser Ser Arg Ser Pro Thr Ala Val Leu Thr Lys Pro Ser
465                 470                 475                 480

Ala Ser Phe Glu Gln Ala Ser Ser Gly Ser Gln Ile Pro Phe Asp Pro
                485                 490                 495

Tyr Ala Thr Asp Ser Asp Glu His Leu Glu Val Leu Leu Asn Ser Gln
            500                 505                 510

Ser Pro Leu Gly Lys Met Ser Asp Val Thr Leu Leu Lys Ile Gly Ser
        515                 520                 525

Glu Glu Pro His Phe Asp Gly Ile Met Asp Gly Phe Ser Gly Lys Ala
    530                 535                 540

Ala Glu Asp Leu Phe Asn Ala His Glu Ile Leu Pro Gly Pro Leu Ser
545                 550                 555                 560

Pro Met Gln Thr Gln Phe Ser Pro Ser Ser Val Asp Ser Asn Gly Leu
                565                 570                 575

Gln Leu Ser Phe Thr Glu Ser Pro Trp Glu Thr Met Glu Trp Leu Asp
            580                 585                 590

Leu Thr Pro Pro Asn Ser Thr Pro Gly Phe Ser Ala Leu Thr Thr Ser
        595                 600                 605

Ser Pro Ser Ile Phe Asn Ile Asp Phe Leu Asp Val Thr Asp Leu Asn
    610                 615                 620

Leu Asn Ser Ser Met Asp Leu His Leu Gln Gln Trp
625                 630                 635

<210> SEQ ID NO 15
<211> LENGTH: 661
<212> TYPE: PRT
<213> ORGANISM: Artificial Sequence
<220> FEATURE:
<223> OTHER INFORMATION: MYOCD 1-438; 764-986 (Mydelta2)

<400> SEQUENCE: 15

Met Thr Leu Leu Gly Ser Glu His Ser Leu Leu Ile Arg Ser Lys Phe
1               5                   10                  15

Arg Ser Val Leu Gln Leu Arg Leu Gln Gln Arg Arg Thr Gln Glu Gln
            20                  25                  30

Leu Ala Asn Gln Gly Ile Ile Pro Pro Leu Lys Arg Pro Ala Glu Phe
        35                  40                  45

His Glu Gln Arg Lys His Leu Asp Ser Asp Lys Ala Lys Asn Ser Leu
    50                  55                  60
```

```
Lys Arg Lys Ala Arg Asn Arg Cys Asn Ser Ala Asp Leu Val Asn Met
 65                  70                  75                  80

His Ile Leu Gln Ala Ser Thr Ala Glu Arg Ser Ile Pro Thr Ala Gln
                 85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
        115                 120                 125

Val Asp Ser Ala Val Lys Glu Ala Ile Lys Gly Asn Gln Val Ser Phe
    130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
        195                 200                 205

Asp Ser Ala Ser Gln Pro Ser His Gln Ser Asp Ala Gly Lys Gln Gly
    210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
            260                 265                 270

Gln Lys Ala Glu Lys Ser Pro Pro Met Asp Ser Ala Tyr Ala Arg
        275                 280                 285

Leu Leu Gln Gln Gln Gln Leu Phe Leu Gln Leu Gln Ile Leu Ser Gln
    290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                325                 330                 335

Ser Ser Thr Pro Leu Ser Asn Thr Pro Leu Ser Pro Val Lys Asn Ser
            340                 345                 350

Phe Ser Gly Gln Thr Gly Val Ser Phe Lys Pro Gly Pro Leu Pro
        355                 360                 365

Pro Asn Leu Asp Asp Leu Lys Val Ser Glu Leu Arg Gln Gln Leu Arg
    370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
                405                 410                 415

Asp Ile Thr Thr Val Thr Phe Pro Val Thr Pro Asn Thr Leu Pro Asn
            420                 425                 430

Tyr Gln Ser Ser Ser Ser Glu Val Thr Gln Pro Pro Ser Tyr Glu Asp
        435                 440                 445

Ala Val Lys Gln Gln Met Thr Arg Ser Gln Gln Met Asp Glu Leu Leu
    450                 455                 460

Asp Val Leu Ile Glu Ser Gly Glu Met Pro Ala Asp Ala Arg Glu Asp
465                 470                 475                 480

His Ser Cys Leu Gln Lys Val Pro Lys Ile Pro Arg Ser Ser Arg Ser
```

```
                485             490             495
Pro Thr Ala Val Leu Thr Lys Pro Ser Ala Ser Phe Glu Gln Ala Ser
                500             505             510

Ser Gly Ser Gln Ile Pro Phe Asp Pro Tyr Ala Thr Asp Ser Asp Glu
            515             520             525

His Leu Glu Val Leu Leu Asn Ser Gln Ser Pro Leu Gly Lys Met Ser
        530             535             540

Asp Val Thr Leu Leu Lys Ile Gly Ser Glu Pro His Phe Asp Gly
545             550             555             560

Ile Met Asp Gly Phe Ser Gly Lys Ala Ala Glu Asp Leu Phe Asn Ala
                565             570             575

His Glu Ile Leu Pro Gly Pro Leu Ser Pro Met Gln Thr Gln Phe Ser
                580             585             590

Pro Ser Ser Val Asp Ser Asn Gly Leu Gln Leu Ser Phe Thr Glu Ser
            595             600             605

Pro Trp Glu Thr Met Glu Trp Leu Asp Leu Thr Pro Pro Asn Ser Thr
        610             615             620

Pro Gly Phe Ser Ala Leu Thr Thr Ser Ser Pro Ser Ile Phe Asn Ile
625             630             635             640

Asp Phe Leu Asp Val Thr Asp Leu Asn Leu Asn Ser Ser Met Asp Leu
                645             650             655

His Leu Gln Gln Trp
            660

<210> SEQ ID NO 16
<211> LENGTH: 782
<212> TYPE: PRT
<213> ORGANISM: Artificial Sequence
<220> FEATURE:
<223> OTHER INFORMATION: MYOCD 1-559; 764-986 (Mydelta3)

<400> SEQUENCE: 16

Met Thr Leu Leu Gly Ser Glu His Ser Leu Leu Ile Arg Ser Lys Phe
1               5               10              15

Arg Ser Val Leu Gln Leu Arg Leu Gln Gln Arg Arg Thr Gln Glu Gln
            20              25              30

Leu Ala Asn Gln Gly Ile Ile Pro Pro Leu Lys Arg Pro Ala Glu Phe
        35              40              45

His Glu Gln Arg Lys His Leu Asp Ser Asp Lys Ala Lys Asn Ser Leu
    50              55              60

Lys Arg Lys Ala Arg Asn Arg Cys Asn Ser Ala Asp Leu Val Asn Met
65              70              75              80

His Ile Leu Gln Ala Ser Thr Ala Glu Arg Ser Ile Pro Thr Ala Gln
                85              90              95

Met Lys Leu Lys Arg Ala Arg Leu Ala Asp Asp Leu Asn Glu Lys Ile
            100             105             110

Ala Leu Arg Pro Gly Pro Leu Glu Leu Val Glu Lys Asn Ile Leu Pro
        115             120             125

Val Asp Ser Ala Val Lys Glu Ala Ile Lys Gly Asn Gln Val Ser Phe
    130             135             140

Ser Lys Ser Thr Asp Ala Phe Ala Phe Glu Glu Asp Ser Ser Ser Asp
145             150             155             160

Gly Leu Ser Pro Asp Gln Thr Arg Ser Glu Asp Pro Gln Asn Ser Ala
                165             170             175

Gly Ser Pro Pro Asp Ala Lys Ala Ser Asp Thr Pro Ser Thr Gly Ser
```

-continued

```
                180                 185                 190
Leu Gly Thr Asn Gln Asp Leu Ala Ser Gly Ser Glu Asn Asp Arg Asn
                    195                 200                 205

Asp Ser Ala Ser Gln Pro Ser His Gln Ser Asp Ala Gly Lys Gln Gly
210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                    245                 250                 255

Lys Pro Lys Val Lys Lys Leu Lys Tyr His Gln Tyr Ile Pro Pro Asp
                260                 265                 270

Gln Lys Ala Glu Lys Ser Pro Pro Met Asp Ser Ala Tyr Ala Arg
                275                 280                 285

Leu Leu Gln Gln Gln Leu Phe Leu Gln Leu Gln Ile Leu Ser Gln
                290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                    325                 330                 335

Ser Ser Thr Pro Leu Ser Asn Thr Pro Leu Ser Pro Val Lys Asn Ser
                    340                 345                 350

Phe Ser Gly Gln Thr Gly Val Ser Ser Phe Lys Pro Gly Pro Leu Pro
                355                 360                 365

Pro Asn Leu Asp Asp Leu Lys Val Ser Glu Leu Arg Gln Gln Leu Arg
370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
                    405                 410                 415

Asp Ile Thr Thr Val Thr Phe Pro Val Thr Pro Asn Thr Leu Pro Asn
                420                 425                 430

Tyr Gln Ser Ser Ser Ser Thr Ser Ala Leu Ser Asn Gly Phe Tyr His
                435                 440                 445

Phe Gly Ser Thr Ser Ser Ser Pro Pro Ile Ser Pro Ala Ser Ser Asp
450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
                    485                 490                 495

Leu Met Ser Ser Leu Asn Gly Gly Ser Val Pro Ser Glu Leu Asp Gly
                500                 505                 510

Leu Asp Ser Glu Lys Asp Lys Met Leu Val Glu Lys Gln Lys Val Ile
                515                 520                 525

Asn Glu Leu Thr Trp Lys Leu Gln Gln Glu Gln Arg Gln Val Glu Glu
                530                 535                 540

Leu Arg Met Gln Leu Gln Lys Gln Lys Arg Asn Asn Cys Ser Glu Glu
545                 550                 555                 560

Val Thr Gln Pro Pro Ser Tyr Glu Asp Ala Val Lys Gln Gln Met Thr
                    565                 570                 575

Arg Ser Gln Gln Met Asp Glu Leu Leu Asp Val Leu Ile Glu Ser Gly
                580                 585                 590

Glu Met Pro Ala Asp Ala Arg Glu Asp His Ser Cys Leu Gln Lys Val
                595                 600                 605
```

```
Pro Lys Ile Pro Arg Ser Ser Arg Ser Pro Thr Ala Val Leu Thr Lys
    610                 615                 620
Pro Ser Ala Ser Phe Glu Gln Ala Ser Gly Ser Gln Ile Pro Phe
625                 630                 635                 640
Asp Pro Tyr Ala Thr Asp Ser Asp Glu His Leu Glu Val Leu Leu Asn
                645                 650                 655
Ser Gln Ser Pro Leu Gly Lys Met Ser Asp Val Thr Leu Leu Lys Ile
                660                 665                 670
Gly Ser Glu Glu Pro His Phe Asp Gly Ile Met Asp Gly Phe Ser Gly
                675                 680                 685
Lys Ala Ala Glu Asp Leu Phe Asn Ala His Glu Ile Leu Pro Gly Pro
    690                 695                 700
Leu Ser Pro Met Gln Thr Gln Phe Ser Pro Ser Ser Val Asp Ser Asn
705                 710                 715                 720
Gly Leu Gln Leu Ser Phe Thr Glu Ser Pro Trp Glu Thr Met Glu Trp
                725                 730                 735
Leu Asp Leu Thr Pro Pro Asn Ser Thr Pro Gly Phe Ser Ala Leu Thr
                740                 745                 750
Thr Ser Ser Pro Ser Ile Phe Asn Ile Asp Phe Leu Asp Val Thr Asp
                755                 760                 765
Leu Asn Leu Asn Ser Ser Met Asp Leu His Leu Gln Gln Trp
                770                 775                 780

<210> SEQ ID NO 17
<211> LENGTH: 116
<212> TYPE: PRT
<213> ORGANISM: Unknown
<220> FEATURE:
<223> OTHER INFORMATION: Mef2c interaction domain (5-120)

<400> SEQUENCE: 17

Gly Ser Glu His Ser Leu Leu Ile Arg Ser Lys Phe Arg Ser Val Leu
1               5                   10                  15
Gln Leu Arg Leu Gln Gln Arg Arg Thr Gln Glu Gln Leu Ala Asn Gln
                20                  25                  30
Gly Ile Ile Pro Pro Leu Lys Arg Pro Ala Glu Phe His Glu Gln Arg
                35                  40                  45
Lys His Leu Asp Ser Asp Lys Ala Lys Asn Ser Leu Lys Arg Lys Ala
                50                  55                  60
Arg Asn Arg Cys Asn Ser Ala Asp Leu Val Asn Met His Ile Leu Gln
65                  70                  75                  80
Ala Ser Thr Ala Glu Arg Ser Ile Pro Thr Ala Gln Met Lys Leu Lys
                85                  90                  95
Arg Ala Arg Leu Ala Asp Asp Leu Asn Glu Lys Ile Ala Leu Arg Pro
                100                 105                 110
Gly Pro Leu Glu
        115

<210> SEQ ID NO 18
<211> LENGTH: 111
<212> TYPE: PRT
<213> ORGANISM: Unknown
<220> FEATURE:
<223> OTHER INFORMATION: SRF domain (210-320)

<400> SEQUENCE: 18

Ser Ala Ser Gln Pro Ser His Gln Ser Asp Ala Gly Lys Gln Gly Leu
```

```
                1               5                   10                  15
            Gly Pro Pro Ser Thr Pro Ile Ala Val His Ala Ala Val Lys Ser Lys
                            20                  25                  30

Ser Leu Gly Asp Ser Lys Asn Arg His Lys Lys Pro Lys Asp Pro Lys
                        35                  40                  45

Pro Lys Val Lys Lys Leu Lys Tyr His Gln Tyr Ile Pro Pro Asp Gln
                    50                  55                  60

Lys Ala Glu Lys Ser Pro Pro Met Asp Ser Ala Tyr Ala Arg Leu
            65                  70                  75                  80

Leu Gln Gln Gln Gln Leu Phe Leu Gln Leu Gln Ile Leu Ser Gln Gln
                                85                  90                  95

Gln Gln Gln Gln Gln His Arg Phe Ser Tyr Leu Gly Met His Gln
                            100                 105                 110

<210> SEQ ID NO 19
<211> LENGTH: 54
<212> TYPE: PRT
<213> ORGANISM: Unknown
<220> FEATURE:
<223> OTHER INFORMATION: SAP domain (360-413)

<400> SEQUENCE: 19

Ser Ser Phe Lys Pro Gly Pro Leu Pro Pro Asn Leu Asp Asp Leu Lys
1               5                   10                  15

Val Ser Glu Leu Arg Gln Gln Leu Arg Ile Arg Gly Leu Pro Val Ser
                20                  25                  30

Gly Thr Lys Thr Ala Leu Met Asp Arg Leu Arg Pro Phe Gln Asp Cys
            35                  40                  45

Ser Gly Asn Pro Val Pro
        50

<210> SEQ ID NO 20
<211> LENGTH: 41
<212> TYPE: PRT
<213> ORGANISM: Unknown
<220> FEATURE:
<223> OTHER INFORMATION: LZ domain (510-550)

<400> SEQUENCE: 20

Leu Asp Gly Leu Asp Ser Glu Lys Asp Lys Met Leu Val Glu Lys Gln
1               5                   10                  15

Lys Val Ile Asn Glu Leu Thr Trp Lys Leu Gln Gln Glu Gln Arg Gln
                20                  25                  30

Val Glu Glu Leu Arg Met Gln Leu Gln
            35                  40

<210> SEQ ID NO 21
<211> LENGTH: 57
<212> TYPE: DNA
<213> ORGANISM: porcine teschovirus-1

<400> SEQUENCE: 21
gccacgaact tctctctgtt aaagcaagca ggagacgtgg aagaaaaccc cggtcct            57

<210> SEQ ID NO 22
<211> LENGTH: 57
<212> TYPE: DNA
<213> ORGANISM: porcine teschovirus-1

<400> SEQUENCE: 22
```

```
gctactaact tcagcctgct gaagcaggct ggagacgtgg aggagaaccc tggacct        57
```

<210> SEQ ID NO 23
<211> LENGTH: 19
<212> TYPE: PRT
<213> ORGANISM: porcine teschovirus-1

<400> SEQUENCE: 23

```
Ala Thr Asn Phe Ser Leu Leu Lys Gln Ala Gly Asp Val Glu Glu Asn
1               5                   10                  15

Pro Gly Pro
```

<210> SEQ ID NO 24
<211> LENGTH: 54
<212> TYPE: DNA
<213> ORGANISM: Thoseaasigna virus

<400> SEQUENCE: 24

```
gagggcagag gaagtctgct aacatgcggt gacgtcgagg agaatcctgg acct           54
```

<210> SEQ ID NO 25
<211> LENGTH: 18
<212> TYPE: PRT
<213> ORGANISM: Thoseaasigna virus

<400> SEQUENCE: 25

```
Glu Gly Arg Gly Ser Leu Leu Thr Cys Gly Asp Val Glu Glu Asn Pro
1               5                   10                  15

Gly Pro
```

<210> SEQ ID NO 26
<211> LENGTH: 60
<212> TYPE: DNA
<213> ORGANISM: equine rhinitis A virus

<400> SEQUENCE: 26

```
cagtgtacta attatgctct cttgaaattg gctggagatg ttgagagcaa ccctggacct    60
```

<210> SEQ ID NO 27
<211> LENGTH: 20
<212> TYPE: PRT
<213> ORGANISM: equine rhinitis A virus

<400> SEQUENCE: 27

```
Gln Cys Thr Asn Tyr Ala Leu Leu Lys Leu Ala Gly Asp Cys Glu Ser
1               5                   10                  15

Asn Pro Gly Pro
            20
```

<210> SEQ ID NO 28
<211> LENGTH: 66
<212> TYPE: DNA
<213> ORGANISM: foot-and-mouth disease virus

<400> SEQUENCE: 28

```
gtgaaacaga ctttgaattt tgaccttctc aagttggcgg agacgtgga gtccaaccct     60 ggacct                                                                66
```

<210> SEQ ID NO 29
<211> LENGTH: 22
<212> TYPE: PRT
<213> ORGANISM: foot-and-mouth disease virus

```
<400> SEQUENCE: 29

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 30
<211> LENGTH: 6
<212> TYPE: PRT
<213> ORGANISM: Artificial Sequence
<220> FEATURE:
<223> OTHER INFORMATION: Linker

<400> SEQUENCE: 30

Gly Gly Ser Gly Gly Ser
1               5

<210> SEQ ID NO 31
<211> LENGTH: 6
<212> TYPE: PRT
<213> ORGANISM: Artificial Sequence
<220> FEATURE:
<223> OTHER INFORMATION: Linker

<400> SEQUENCE: 31

Gly Ser Ser Gly Gly Ser
1               5

<210> SEQ ID NO 32
<211> LENGTH: 6
<212> TYPE: PRT
<213> ORGANISM: Artificial Sequence
<220> FEATURE:
<223> OTHER INFORMATION: Linker

<400> SEQUENCE: 32

Gly Gly Ser Gly Ser Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Linker

<400> SEQUENCE: 33

Gly Gly Ser Gly Gly Ser Gly Gly Ser
1               5

<210> SEQ ID NO 34
<211> LENGTH: 12
<212> TYPE: PRT
<213> ORGANISM: Artificial Sequence
<220> FEATURE:
<223> OTHER INFORMATION: Linker

<400> SEQUENCE: 34

Gly Gly Ser Gly Gly Ser Gly Gly Ser Gly Gly Ser
1               5                   10

<210> SEQ ID NO 35
<211> LENGTH: 3726
<212> TYPE: DNA
<213> ORGANISM: Artificial Sequence
```

<220> FEATURE:
<223> OTHER INFORMATION: MYOCD-2A-ASCL1

<400> SEQUENCE: 35

```
atgacactcc tggggtctga gcattccttg ctgattagga gcaagttcag atcagtttta     60
cagttaagac ttcaacaaag aaggaccag gaacaactgg ctaaccaagg cataatacca    120
ccactgaaac gtccagctga attccatgag caaagaaaac atttggatag tgacaaggct    180
aaaaattccc tgaagcgcaa agccagaaac aggtgcaaca gtgccgactt ggttaatatg    240
cacatactcc aagcttccac tgcagagagg tccattccaa ctgctcagat gaagctgaaa    300
agagcccgac tcgccgatga tctcaatgaa aaaattgctc tacgaccagg cccactggag    360
ctggtggaaa aaacattct tcctgtggat tctgctgtga agaggccat aaaaggtaac    420
caggtgagtt tctccaaatc cacggatgct tttgcctttg aagaggacag cagcagcgat    480
gggctttctc cggatcagac tcgaagtgaa gacccccaaa actcagcggg atccccgcca    540
gacgctaaag cctcagatac cccttcgaca ggttctctgg ggacaaacca ggatcttgct    600
tctggctcag aaaatgacag aaatgactca gcctcacagc ccagccacca gtcagatgcg    660
gggaagcagg ggcttggccc ccccagcacc cccatagccg tgcatgctgc tgtaaagtcc    720
aaatccttgg gtgacagtaa gaaccgccac aaaaagccca aggaccccaa gccaaaggtg    780
aagaagctta aatatcacca gtacattccc ccagaccaga aggcagagaa gtcccctcca    840
cctatggact cagcctacgc tcggctgctc cagcaacagc agctgttcct gcagctccaa    900
atcctcagcc agcagcagca gcagcagcaa caccgattca gctacctagg gatgcaccaa    960
gctcagctta aggaaccaaa tgaacagatg gtcagaaatc caaactcttc ttcaacgcca   1020
ctgagcaata ccccccttgtc tcctgtcaaa aacagttttt ctggacaaac tggtgtctct   1080
tctttcaaac caggcccact cccacctaac ctggatgatc tgaaggtctc tgaattaaga   1140
caacagcttc gaattcgggg cttgcctgtg tcaggcacca aaacggctct catggaccgg   1200
cttcgaccct tccaggactg ctctggcaac ccagtgccga ctttggggga tataacgact   1260
gtcacttttc ctgtcacacc caacacgctg cccaattacc agtcttcctc ttctaccagt   1320
gccctgtcca acggcttcta ccactttggc agcaccagct ccagccccc gatctcccca   1380
gcctcctctg acctgtcagt cgctgggtcc ctgccggaca ccttcaatga tgcctccccc   1440
tccttcggcc tgcaccccgtc cccagtccac gtgtgcacgg aggaaagtct catgagcagc   1500
ctgaatgggg gctctgttcc ttctgagctg gatgggctgg actccgagaa ggacaagatg   1560
ctggtggaga agcagaaggt gatcaatgaa ctcacctgga aactccagca agagcagagg   1620
caggtggagg agctgaggat gcagcttcag aagcagaaaa ggaataactg ttcagagaag   1680
aagccgctgc ctttcctggc tgcctccatc aagcaggaag aggctgtctc cagctgtcct   1740
tttgcatccc aagtacctgt gaaaagacaa agcagcagct cagagtgtca cccaccggct   1800
tgtgaagctg ctcaactcca gcctcttgga atgctcatt gtgtgagtc ctcagatcaa   1860
accaatgtac tttcttccac atttctcagc ccccagtgtt cccctcagca ttcaccgctg   1920
ggggctgtga aaagcccaca gcacatcagt ttgcccccat cacccaacaa ccctcacttt   1980
ctgcctcat cctccgggc ccaggagaa gggcacaggg tctcctcgcc catcagcagc   2040
caggtgtgca ctgcacagaa ctcaggagca cacgatggcc atcctccaag cttctctccc   2100
cattcttcca gcctccaccc gcccttctct ggagcccaag cagacagcag tcatggtgcc   2160
gggggaaacc cttgtcccaa aagcccatgt gtacagcaaa agatggctgg tttacactct   2220
```

```
tctgataagg tggggccaaa gttttcaatt ccatccccaa ctttttctaa gtcaagttca    2280
gcaatttcag aggtaacaca gcctccatcc tatgaagatg ccgtaaagca gcaaatgacc    2340
cggagtcagc agatggatga actcctggac gtgcttattg aaagcggaga atgccagca    2400 gacgctagag aggatcactc atgtcttcaa aaagtcccaa agatacccag atcttcccga    2460
agtccaactg ctgtcctcac caagccctcg gcttcctttg aacaagcctc ttcaggcagc    2520
cagatcccct tgatcccta tgccaccgac agtgatgagc atcttgaagt cttattaaat    2580
tcccagagcc cctaggaaa gatgagtgat gtcacccttc taaaaattgg gagcgaagag    2640
cctcactttg atgggataat ggatggattc tctgggaagg ctgcagaaga cctcttcaat    2700
gcacatgaga tcttgccagg cccctctct ccaatgcaga cacagttttc accctcttct    2760
gtggacagca atgggctgca gttaagcttc actgaatctc cctgggaaac catggagtgg    2820
ctggacctca ctccgccaaa ttccacacca ggctttagcg ccctcaccac cagcagcccc    2880
agcatcttca acatcgattt cctggatgtc actgatctca atttgaattc ttccatggac    2940
cttcacttgc agcagtgggc cacgaacttc tctctgttaa agcaagcagg agacgtggaa    3000
gaaaaccccg gtcctatgga aagctctgcc aagatggaga gcggcggcgc cggccagcag    3060
ccccagccga agcccagca gcccttcctg ccgcccgcag cctgtttctt tgccacggcc    3120
gcagccgcgg cggccgcagc cgccgcagcg gcagcgcaga gcgcgcagca gcagcagcag    3180
cagcagcagc agcagcagca ggcgccgcag ctgagaccgg cggccgacgg ccagccctca    3240
gggggcggtc acaagtcagc gcccaagcaa gtcaagcgac agcgctcgtc ttcgcccgaa    3300
ctgatgcgct gcaaacgccg gctcaacttc agcggctttg gctacagcct gccgcagcag    3360
cagccggccg ccgtggcgcg ccgcaacgag cgcgagcgca accgcgtcaa gttggtcaac    3420
ctgggctttg ccaccttcg ggagcacgtc cccaacggcg cggccaacaa gaagatgagt    3480
aaggtggaga cactgcgctc ggcggtcgag tacatccgcg cgctgcagca gctgctggac    3540
gagcatgacg cggtgagcgc cgccttccag gcaggcgtcc tgtcgcccac catctccccc    3600
aactactcca acgacttgaa ctccatggcc ggctcgccgg tctcatccta ctcgtcggac    3660
gagggctctt acgacccgct cagccccgag gagcaggagc ttctcgactt caccaactgg    3720
ttctga                                                               3726
```

<210> SEQ ID NO 36
<211> LENGTH: 3744
<212> TYPE: DNA
<213> ORGANISM: Artificial Sequence
<220> FEATURE:
<223> OTHER INFORMATION: MYOCD-2A-MYF6

<400> SEQUENCE: 36

```
atgacactcc tggggtctga gcattccttg ctgattagga gcaagttcag atcagtttta      60
cagttaagac ttcaacaaag aaggacccag gaacaactgg ctaaccaagg cataatacca    120
ccactgaaac gtccagctga attccatgag caaagaaaac atttggatag tgacaaggct    180
aaaaattccc tgaagcgcaa agccagaaac aggtgcaaca gtgccgactt ggttaatatg    240
cacatactcc aagcttccac tgcagagagg tccattccaa ctgctcagat gaagctgaaa    300
agagcccgac tcgccgatga tctcaatgaa aaaattgctc tacgaccagg cccactggag    360
ctggtggaaa aaacattct tcctgtggat tctgctgtga agaggccat aaaaggtaac    420 caggtgagtt tctccaaatc cacgatgct tttgcctttg aagaggacag cagcagcgat    480
gggctttctc cggatcagac tcgaagtgaa gaccccaaa actcagcggg atccccgcca    540
```

```
gacgctaaag cctcagatac cccttcgaca ggttctctgg ggacaaacca ggatcttgct    600
tctggctcag aaaatgacag aaatgactca gcctcacagc ccagccacca gtcagatgcg    660
gggaagcagg ggcttggccc ccccagcacc cccatagccg tgcatgctgc tgtaaagtcc    720
aaatccttgg gtgacagtaa gaaccgccac aaaaagccca aggacccaa gccaaaggtg     780 aagaagctta aatatcacca gtacattccc ccagaccaga aggcagagaa gtcccctcca    840
cctatggact cagcctacgc tcggctgctc cagcaacagc agctgttcct gcagctccaa    900
atcctcagcc agcagcagca gcagcagcaa caccgattca gctacctagg gatgcaccaa    960
gctcagctta aggaaccaaa tgaacagatg gtcagaaatc caaactcttc ttcaacgcca   1020
ctgagcaata ccccttgtc tcctgtcaaa aacagttttt ctggacaaac tggtgtctct    1080
tctttcaaac caggcccact cccacctaac ctggatgatc tgaaggtctc tgaattaaga   1140
caacagcttc gaattcgggg cttgcctgtg tcaggcacca aaacggctct catggaccgg   1200
cttcgaccct tccaggactg ctctggcaac ccagtgccga actttgggga tataacgact   1260 gtcactttc ctgtcacacc caacacgctg cccaattacc agtcttcctc ttctaccagt    1320
gccctgtcca acggcttcta ccactttggc agcaccagct ccagccccc gatctcccca    1380 gcctcctctg acctgtcagt cgctgggtcc ctgccggaca ccttcaatga tgcctccccc   1440
tccttcggcc tgcacccgtc cccagtccac gtgtgcacgg aggaaagtct catgagcagc   1500
ctgaatgggg gctctgttcc ttctgagctg gatgggctgg actccgagaa ggacaagatg   1560
ctggtggaga agcagaaggt gatcaatgaa ctcacctgga aactccagca agagcagagg   1620
caggtggagg agctgaggat gcagcttcag aagcagaaaa ggaataactg ttcagagaag   1680
aagccgctgc cttcctggc tgcctccatc aagcaggaag aggctgtctc cagctgtcct    1740
tttgcatccc aagtacctgt gaaaagacaa agcagcagct cagagtgtca cccaccggct   1800
tgtgaagctg ctcaactcca gcctcttgga aatgctcatt gtgtggagtc ctcagatcaa   1860
accaatgtac tttcttccac atttctcagc ccccagtgtt ccctcagca ttcaccgctg    1920 ggggctgtga aaagcccaca gcacatcagt ttgcccccat cacccaacaa ccctcacttt   1980
ctgccctcat cctccggggc ccagggagaa gggcacaggg tctcctcgcc catcagcagc   2040
caggtgtgca ctgcacagaa ctcaggagca cacgatggcc atcctccaag cttctctccc   2100
cattcttcca gcctccaccc gcccttctct ggagcccaag cagacagcag tcatggtgcc   2160
gggggaaacc cttgtcccaa aagcccatgt gtacagcaaa agatggctgg tttacactct   2220
tctgataagt gggccaaa gttttcaatt ccatccccaa cttttctaa gtcaagttca      2280 gcaatttcag aggtaacaca gcctccatcc tatgaagatg ccgtaaagca gcaaatgacc   2340
cggagtcagc agatggatga actcctggac gtgcttattg aaagcggaga atgccagca    2400 gacgctagag aggatcactc atgtcttcaa aaagtcccaa agatacccag atcttcccga   2460
agtccaactg ctgtcctcac caagcccctcg gcttcctttg aacaagcctc ttcaggcagc   2520
cagatcccct tgatcccta tgccaccgac agtgatgagc atcttgaagt cttattaaat    2580
tcccagagcc ccctaggaaa gatgagtgat gtcaccctc taaaaattgg gagcgaagag    2640
cctcactttg atgggataat ggatggattc tctgggaagg ctgcagaaga cctcttcaat   2700
gcacatgaga tcttgccagg ccccctctct ccaatgcaga cacagttttc accctcttct   2760
gtggacagca atgggctgca gttaagcttc actgaatctc cctgggaaac catggagtgg   2820
ctggacctca ctccgccaaa ttccacacca ggctttagcg ccctcaccac cagcagcccc   2880
```

| | |
|---|---|
| agcatcttca acatcgattt cctggatgtc actgatctca atttgaattc ttccatggac | 2940 |
| cttcacttgc agcagtgggc cacgaacttc tctctgttaa agcaagcagg agacgtggaa | 3000 |
| gaaaaccccg gtcctatgat gatggacctt tttgaaactg gctcctattt cttctacttg | 3060 |
| gatggggaaa atgttactct gcagccatta gaagtggcag aaggctctcc tttgtatcca | 3120 |
| gggagtgatg gtaccttgtc cccctgccag gaccaaatgc ccccggaagc ggggagcgac | 3180 |
| agcagcggag aggaacatgt cctggcgccc cggggcctgc agcctccaca ctgccccggc | 3240 |
| cagtgtctga tctgggcttg caagacctgc aagagaaaat ctgcccccac tgaccggcga | 3300 |
| aaagccgcca ccctgcgcga aggaggagg ctaaagaaaa tcaacgaggc cttcgaggca | 3360 |
| ctgaagcggc gaactgtggc caaccccaac cagaggctgc ccaaggtgga gattctgcgg | 3420 |
| agcgccatca gctatattga gcggctgcag gacctgctgc accggctgga tcagcaggag | 3480 |
| aagatgcagg agctggggt ggacccttc agctacagac ccaaacaaga aaatcttgag | 3540 |
| ggtgcggatt cctgcgcac ctgcagctcc cagtggccaa gtgtttccga tcattccagg | 3600 |
| gggctcgtga taacggctaa ggaaggagga gcaagtattg attcgtcagc ctcgagtagc | 3660 |
| cttcgatgcc tttcttccat cgtggacagt atttcctcgg aggaacgcaa actcccctgc | 3720 |
| gtggaggaag tggtggagaa gtaa | 3744 |

<210> SEQ ID NO 37
<211> LENGTH: 3114
<212> TYPE: DNA
<213> ORGANISM: Artificial Sequence
<220> FEATURE:
<223> OTHER INFORMATION: Mydelta3-2A-ASCL1

<400> SEQUENCE: 37

| | |
|---|---|
| atgacactcc tggggtctga gcattccttg ctgattagga gcaagttcag atcagtttta | 60 |
| cagttaagac ttcaacaaag aaggacccag gaacaactgg ctaaccaagg cataatacca | 120 |
| ccactgaaac gtccagctga attccatgag caaagaaaac atttggatag tgacaaggct | 180 |
| aaaaattccc tgaagcgcaa agccagaaac aggtgcaaca gtgccgactt ggttaatatg | 240 |
| cacatactcc aagcttccac tgcagagagg tccattccaa ctgctcagat gaagctgaaa | 300 |
| agagcccgac tcgccgatga tctcaatgaa aaaattgctc tacgaccagg cccactggag | 360 |
| ctggtggaaa aaacattct tcctgtggat tctgctgtga agaggccat aaaaggtaac | 420 |
| caggtgagtt ctctccaaatc cacgatgct tttgcctttg aagaggacag cagcagcgat | 480 |
| gggctttctc cggatcagac tcgaagtgaa gaccccaaa actcagcggg atccccgcca | 540 |
| gacgctaaag cctcagatac cccttcgaca ggttctctgg gacaaacca ggatcttgct | 600 |
| tctggctcag aaaatgacag aaatgactca gcctcacagc ccagccacca gtcagatgcg | 660 |
| gggaagcagg ggcttggccc ccccagcacc cccatagccg tgcatgctgc tgtaaagtcc | 720 |
| aaatccttgg gtgacagtaa gaaccgccac aaaaagccca aggaccccaa gccaaaggtg | 780 |
| aagaagctta aatatcacca gtacattccc ccagaccaga aggcagagaa gtcccctcca | 840 |
| cctatggact cagcctacgc tcggctgctc cagcaacagc agctgttcct gcagctccaa | 900 |
| atcctcagcc agcagcagca gcagcagcaa caccgattca gctacctagg gatgcaccaa | 960 |
| gctcagctta aggaaccaaa tgaacagatg gtcagaaatc caaactcttc ttcaacgcca | 1020 |
| ctgagcaata cccccttgtc tcctgtcaaa aacagttttt ctggacaaac tggtgtctct | 1080 |
| tctttcaaac caggcccact cccacctaac ctggatgatc tgaaggtctc tgaattaaga | 1140 |
| caacagcttc gaattcgggg cttgcctgtg tcaggcacca aaacggctct catggaccgg | 1200 |

```
cttcgaccct tccaggactg ctctggcaac ccagtgccga actttgggga tataacgact    1260 gtcactttc ctgtcacacc caacacgctg cccaattacc agtcttcctc ttctaccagt    1320
gccctgtcca acggcttcta ccactttggc agcaccagct ccagccccc gatctcccca    1380 gcctcctctg acctgtcagt cgctgggtcc ctgccggaca ccttcaatga tgcctccccc    1440
tccttcggcc tgcacccgtc cccagtccac gtgtgcacgg aggaaagtct catgagcagc    1500
ctgaatgggg gctctgttcc ttctgagctg gatgggctgg actccgagaa ggacaagatg    1560
ctggtggaga agcagaaggt gatcaatgaa ctcacctgga aactccagca agagcagagg    1620
caggtggagg agctgaggat gcagcttcag aagcagaaaa ggaataactg ttcagaggag    1680
gtaacacagc ctccatccta tgaagatgcc gtaaagcagc aaatgacccg gagtcagcag    1740
atggatgaac tcctggacgt gcttattgaa agcggagaaa tgccagcaga cgctagagag    1800
gatcactcat gtcttcaaaa agtcccaaag atacccagat cttcccgaag tccaactgct    1860
gtcctcacca gccctcggc ttcctttgaa caagcctctt caggcagcca gatccccttt    1920
gatccctatg ccaccgacag tgatgagcat cttgaagtct tattaaattc ccagagcccc    1980
ctaggaaaga tgagtgatgt caccccttcta aaaattggga gcgaagagcc tcactttgat    2040
gggataatgg atggattctc tgggaaggct gcagaagacc tcttcaatgc acatgagatc    2100
ttgccaggcc ccctctctcc aatgcagaca cagttttcac cctcttctgt ggacagcaat    2160
gggctgcagt taagcttcac tgaatctccc tgggaaacca tggagtggct ggacctcact    2220
ccgccaaatt ccacaccagg ctttagcgcc ctcaccacca gcagcccag catcttcaac    2280 atcgatttcc tggatgtcac tgatctcaat ttgaattctt ccatggacct tcacttgcag    2340
cagtgggcca cgaacttctc tctgttaaag caagcaggag acgtggaaga aaacccggt    2400 cctatggaaa gctctgccaa gatggagagc ggcggcgccg ccagcagcc ccagccgcag    2460 ccccagcagc ccttcctgcc gcccgcagcc tgtttctttg ccacggccgc agccgcggcg    2520
gccgcagccg ccgcagcggc agcgcagagc gcgcagcagc agcagcagca gcagcagcag    2580
cagcagcagg cgccgcagct gagaccggcg gccgacggcc agccctcagg gggcggtcac    2640
aagtcagcgc ccaagcaagt caagcgacag cgctcgtctt cgcccgaact gatgcgctgc    2700
aaacgccggc tcaacttcag cggctttggc tacagcctgc cgcagcagca gccggccgcc    2760
gtggcgcgcc gcaacgagcg cgagcgcaac cgcgtcaagt tggtcaacct gggctttgcc    2820
acccttcggg agcacgtccc caacggcgcg ccaacaagaa agatgagtaa ggtggagaca    2880
ctgcgctcgg cggtcgagta catccgcgcg ctgcagcagc tgctgacga gcatgacgcg    2940 gtgagcgccg ccttccaggc aggcgtcctg tcgcccacca tctcccccaa ctactccaac    3000
gacttgaact ccatggccgg ctcgccggtc tcatcctact cgtcggacga gggctcttac    3060
gacccgctca gccccgagga gcaggagctt ctcgacttca ccaactggtt ctga    3114
```

<210> SEQ ID NO 38
<211> LENGTH: 3132
<212> TYPE: DNA
<213> ORGANISM: Artificial Sequence
<220> FEATURE:
<223> OTHER INFORMATION: Mydelta3-2A-MYF6

<400> SEQUENCE: 38

```
atgacactcc tggggtctga gcattccttg ctgattagga gcaagttcag atcagttta      60 cagttaagac ttcaacaaag aaggacccag gaacaactgg ctaaccaagg cataatacca     120
```

```
ccactgaaac gtccagctga attccatgag caaagaaaac atttggatag tgacaaggct      180
aaaaattccc tgaagcgcaa agccagaaac aggtgcaaca gtgccgactt ggttaatatg      240
cacatactcc aagcttccac tgcagagagg tccattccaa ctgctcagat gaagctgaaa      300
agagcccgac tcgccgatga tctcaatgaa aaaattgctc tacgaccagg cccactggag      360
ctggtggaaa aaacattct tcctgtggat tctgctgtga agaggccat aaaaggtaac        420
caggtgagtt tctccaaatc cacggatgct tttgcctttg aagaggacag cagcagcgat      480
gggctttctc cggatcagac tcgaagtgaa gaccccccaaa actcagcggg atccccgcca     540
gacgctaaag cctcagatac cccttcgaca ggttctctgg ggacaaacca ggatcttgct      600
tctggctcag aaaatgacag aaatgactca gcctcacagc ccagccacca gtcagatgcg      660
gggaagcagg ggcttggccc cccagcaccc ccatagccg tgcatgctgc tgtaaagtcc       720
aaatccttgg gtgacagtaa gaaccgccac aaaaagccca aggaccccaa gccaaaggtg      780
aagaagctta aatatcacca gtacattccc ccagaccaga aggcagagaa gtcccctcca      840
cctatggact cagcctacgc tcggctgctc cagcaacagc agctgttcct gcagctccaa      900
atcctcagcc agcagcagca gcagcagcaa caccgattca gctacctagg gatgcaccaa     960
gctcagctta aggaaccaaa tgaacagatg gtcagaaatc caaactcttc ttcaacgcca     1020
ctgagcaata cccccttgtc tcctgtcaaa aacagttttt ctggacaaac tggtgtctct     1080
tctttcaaac caggcccact cccacctaac ctggatgatc tgaaggtctc tgaattaaga     1140
caacagcttc gaattcgggg cttgcctgtg tcaggcacca aaacggctct catggaccgg     1200
cttcgaccct tccaggactg ctctggcaac ccagtgccga actttgggga tataacgact     1260
gtcactttc ctgtcacacc caacacgctg cccaattacc agtcttcctc ttctaccagt     1320
gccctgtcca acggcttcta ccactttggc agcaccagct ccagccccc gatctcccca     1380
gcctcctctg acctgtcagt cgctgggtcc ctgccggaca ccttcaatga tgcctccccc     1440
tccttcggcc tgcacccgtc cccagtccac gtgtgcacgg aggaaagtct catgagcagc     1500
ctgaatgggg gctctgttcc ttctgagctg gatgggctgg actccgagaa ggacaagatg     1560
ctggtggaga agcagaaggt gatcaatgaa ctcacctgga aactccagca agagcagagg     1620
caggtggagg agctgaggat gcagcttcag aagcagaaaa ggaataactg ttcagaggag     1680
gtaacacagc ctccatccta tgaagatgcc gtaaagcagc aaatgacccg gagtcagcag     1740
atggatgaac tcctggacgt gcttattgaa agcggagaaa tgccagcaga cgctagagag     1800
gatcactcat gtcttcaaaa agtcccaaag atacccagat cttcccgaag tccaactgct     1860
gtcctcacca agccctcggc ttcctttgaa caagcctctt caggcagcca gatccccttt     1920
gatccctatg ccaccgacag tgatgagcat cttgaagtct tattaaattc ccagagcccc     1980
ctaggaaaga tgagtgatgt caccccttcta aaaattggga gcgaagagcc tcactttgat     2040
gggataatgg atggattctc tgggaaggct gcagaagacc tcttcaatgc acatgagatc     2100
ttgccaggcc ccctctctcc aatgcagaca cagttttcac cctcttctgt ggacagcaat     2160
gggctgcagt taagcttcac tgaatctccc tgggaaacca tggagtggct ggacctcact     2220
ccgccaaatt ccacaccagg ctttagcgcc ctcaccacca gcagcccag catcttcaac     2280
atcgatttcc tggatgtcac tgatctcaat ttgaattctt ccatggacct tcacttgcag     2340
cagtgggcca cgaacttctc tctgttaaag caagcaggag acgtggaaga aaaccccggt     2400
cctatgatga tggaccttttt tgaaactggc tcctatttct ctacttgga tgggaaaat    2460
gttactctgc agccattaga agtggcagaa ggctctcctt tgtatccagg gagtgatggt     2520
```

| | | | | |
|---|---|---|---|---|
| accttgtccc | cctgccagga | ccaaatgccc | ccggaagcgg | ggagcgacag | cagcggagag | 2580 |
| gaacatgtcc | tggcgccccc | gggcctgcag | cctccacact | gccccggcca | gtgtctgatc | 2640 |
| tgggcttgca | agacctgcaa | gagaaaatct | gcccccactg | accggcgaaa | agccgccacc | 2700 |
| ctgcgcgaaa | ggaggaggct | aaagaaaatc | aacgaggcct | cgaggcact | gaagcggcga | 2760 |
| actgtggcca | accccaacca | gaggctgccc | aaggtggaga | ttctgcggag | cgccatcagc | 2820 |
| tatattgagc | ggctgcagga | cctgctgcac | cggctggatc | agcaggagaa | gatgcaggag | 2880 |
| ctgggggtgg | accccttcag | ctacagaccc | aaacaagaaa | atcttgaggg | tgcggatttc | 2940 |
| ctgcgcacct | gcagctccca | gtggccaagt | gtttccgatc | attccagggg | gctcgtgata | 3000 |
| acggctaagg | aaggaggagc | aagtattgat | tcgtcagcct | cgagtagcct | tcgatgcctt | 3060 |
| tcttccatcg | tggacagtat | ttcctcggag | aacgcaaac | tcccctgcgt | ggaggaagtg | 3120 |
| gtggagaagt | aa | | | | | 3132 |

<210> SEQ ID NO 39
<211> LENGTH: 3726
<212> TYPE: DNA
<213> ORGANISM: Artificial Sequence
<220> FEATURE:
<223> OTHER INFORMATION: ASCL1-2A-MYOCD

<400> SEQUENCE: 39

| | | | | |
|---|---|---|---|---|
| atggaaagct | ctgccaagat | ggagagcggc | ggcgccggcc | agcagcccca | gccgcagccc | 60 |
| cagcagcccct | tcctgccgcc | cgcagcctgt | ttctttgcca | cggccgcagc | cgcggcggcc | 120 |
| gcagccgccg | cagcggcagc | gcagagcgcg | cagcagcagc | agcagcagca | gcagcagcag | 180 |
| cagcaggcgc | cgcagctgag | accgcggcc | gacggccagc | cctcaggggg | cggtcacaag | 240 |
| tcagcgccca | agcaagtcaa | gcgacagcgc | tcgtcttcgc | ccgaactgat | gcgctgcaaa | 300 |
| cgccggctca | acttcagcgg | ctttggctac | agcctgccgc | agcagcagcc | ggccgccgtg | 360 |
| gcgcgccgca | acgagcgcga | gcgcaaccgc | gtcaagttgg | tcaacctggg | ctttgccacc | 420 |
| cttcgggagc | acgtcccaa | cggcgcggcc | aacaagaaga | tgagtaaggt | ggagacactg | 480 |
| cgctcggcgg | tcgagtacat | ccgcgcgctg | cagcagctgc | tggacgagca | tgacgcggtg | 540 |
| agcgccgcct | tccaggcagg | cgtcctgtcg | cccaccatct | cccccaacta | ctccaacgac | 600 |
| ttgaactcca | tggccggctc | gccggtctca | tcctactcgt | cggacgaggg | ctcttacgac | 660 |
| ccgctcagcc | ccgaggagca | ggagcttctc | gacttcacca | actggttcgc | cacgaacttc | 720 |
| tctctgttaa | agcaagcagg | agacgtggaa | gaaaacccg | gtcctatgac | actcctgggg | 780 |
| tctgagcatt | ccttgctgat | taggagcaag | ttcagatcag | ttttacagtt | aagacttcaa | 840 |
| caaagaagga | cccaggaaca | actggctaac | caaggcataa | taccaccact | gaaacgtcca | 900 |
| gctgaattcc | atgagcaaag | aaaacatttg | gatagtgaca | aggctaaaaa | ttccctgaag | 960 |
| cgcaaagcca | gaaacaggtg | caacagtgcc | gacttggtta | atatgcacat | actccaagct | 1020 |
| tccactgcag | agaggtccat | tccaactgct | cagatgaagc | tgaaaagagc | ccgactcgcc | 1080 |
| gatgatctca | atgaaaaaat | tgctctacga | ccaggcccac | tggagctggt | ggaaaaaaac | 1140 |
| attcttcctg | tggattctgc | tgtgaaagag | gccataaaag | taaccaggt | gagtttctcc | 1200 |
| aaatccacgg | atgcttttgc | ctttgaagag | gacagcagca | gcgatgggct | ttctccggat | 1260 |
| cagactcgaa | gtgaagaccc | ccaaaactca | gcgggatccc | cgccagacgc | taaagcctca | 1320 |
| gataccccctt | cgacaggttc | tctggggaca | aaccaggatc | ttgcttctgg | ctcagaaaat | 1380 |

```
gacagaaatg actcagcctc acagcccagc caccagtcag atgcggggaa gcaggggctt    1440
ggccccccca gcaccccat agccgtgcat gctgctgtaa agtccaaatc cttgggtgac     1500
agtaagaacc gccacaaaaa gcccaaggac cccaagccaa aggtgaagaa gcttaaatat    1560
caccagtaca ttcccccaga ccagaaggca gagaagtccc ctccacctat ggactcagcc    1620
tacgctcggc tgctccagca acagcagctg ttcctgcagc tccaaatcct cagccagcag    1680
cagcagcagc agcaacaccg attcagctac ctagggatgc accaagctca gcttaaggaa    1740
ccaaatgaac agatggtcag aaatccaaac tcttcttcaa cgccactgag caataccccc    1800
ttgtctcctg tcaaaaacag tttttctgga caaactggtg tctcttcttt caaaccaggc    1860
ccactcccac ctaacctgga tgatctgaag gtctctgaat taagacaaca gcttcgaatt    1920
cggggcttgc ctgtgtcagg caccaaaacg gctctcatgg accggcttcg acccttccag    1980
gactgctctg gcaacccagt gccgaacttt ggggatataa cgactgtcac ttttcctgtc    2040
acacccaaca cgctgcccaa ttaccagtct tcctcttcta ccagtgccct gtccaacggc    2100
ttctaccact ttggcagcac cagctccagc ccccgatct cccagcctc ctctgacctg      2160 tcagtcgctg ggtccctgcc ggacaccttc aatgatgcct cccctcctt cggcctgcac    2220 ccgtccccag tccacgtgtg cacggaggaa agtctcatga gcagcctgaa tggggctct    2280 gttccttctg agctggatgg gctggactcc gagaaggaca agatgctggt ggagaagcag    2340
aaggtgatca atgaactcac ctggaaactc cagcaagagc agaggcaggt ggaggagctg    2400
aggatgcagc ttcagaagca gaaaaggaat aactgttcag agaagaagcc gctgcctttc    2460
ctggctgcct ccatcaagca ggaagaggct gtctccagct gtcctttgc atcccaagta    2520 cctgtgaaaa gacaaagcag cagctcagag tgtcacccac cggcttgtga agctgctcaa    2580
ctccagcctc ttggaaatgc tcattgtgtg gagtcctcag atcaaaccaa tgtactttct    2640
tccacatttc tcagccccca gtgttcccct cagcattcac cgctgggggc tgtgaaaagc    2700
ccacagcaca tcagtttgcc cccatcaccc aacaaccctc actttctgcc ctcatcctcc    2760
ggggcccagg gagaagggca cagggtctcc tcgcccatca gcagccaggt gtgcactgca    2820
cagaactcag gagcacacga tggccatcct ccaagcttct ctccccattc ttccagcctc    2880 caccccgccct tctctggagc ccaagcagac agcagtcatg gtgccggggg aaacccttgt    2940
cccaaaagcc catgtgtaca gcaaaagatg gctggtttac actcttctga taaggtgggg    3000
ccaaagtttt caattccatc cccaactttt tctaagtcaa gttcagcaat ttcagaggta    3060
acacagcctc catcctatga agatgccgta aagcagcaaa tgacccggag tcagcagatg    3120
gatgaactcc tggacgtgct tattgaaagc ggagaaatgc cagcagacgc tagagaggat    3180
cactcatgtc ttcaaaaagt cccaaagata cccagatctt cccgaagtcc aactgctgtc    3240
ctcaccaagc cctcggcttc ctttgaacaa gcctcttcag gcagccagat cccctttgat    3300
ccctatgcca ccgacagtga tgagcatctt gaagtcttat taaattccca gagccccta     3360 ggaaagatga gtgatgtcac ccttctaaaa attgggagcg aagagcctca ctttgatggg    3420
ataatggatg gattctctgg gaaggctgca gaagacctct tcaatgcaca tgagatcttg    3480
ccaggccccc tctctccaat gcagacacag ttttcacccct cttctgtgga cagcaatggg    3540
ctgcagttaa gcttcactga atctccctgg gaaaccatgg agtggctgga cctcactccg    3600
ccaaattcca caccaggctt tagcgccctc accaccagca gccccagcat cttcaacatc    3660
gatttcctgg atgtcactga tctcaatttg aattcttcca tggaccttca cttgcagcag    3720
tggtag                                                              3726
```

<210> SEQ ID NO 40
<211> LENGTH: 3744
<212> TYPE: DNA
<213> ORGANISM: Artificial Sequence
<220> FEATURE:
<223> OTHER INFORMATION: MYF6-2A-MYOCD

<400> SEQUENCE: 40

```
atgatgatgg accttttttga aactggctcc tatttcttct acttggatgg ggaaaatgtt      60
actctgcagc cattagaagt ggcagaaggc tctcctttgt atccagggag tgatggtacc     120
ttgtccccct gccaggacca aatgcccccg aagcgggga gcgacagcag cggagaggaa      180
catgtcctgg cgcccccggg cctgcagcct ccacactgcc ccggccagtg tctgatctgg     240
gcttgcaaga cctgcaagag aaaatctgcc cccactgacc ggcgaaaagc cgccaccctg     300
cgcgaaagga ggaggctaaa gaaaatcaac gaggccttcg aggcactgaa gcggcgaact     360
gtggccaacc ccaaccagag ctgcccaag gtggagattc tgcggagcgc catcagctat      420
attgagcggc tgcaggacct gctgcaccgg ctggatcagc aggagaagat gcaggagctg     480
ggggtggacc cctcagcta cagacccaaa caagaaaatc ttgagggtgc ggatttcctg     540
cgcacctgca gctcccagtg gccaagtgtt tccgatcatt caggggggct cgtgataacg     600
gctaaggaag gaggagcaag tattgattcg tcagcctcga gtagccttcg atgcctttct     660
tccatcgtgg acagtatttc ctcggaggaa cgcaaactcc cctgcgtgga ggaagtggtg     720
gagaaggcca cgaacttctc tctgttaaag caagcaggag acgtggaaga aaaccccggt     780
cctatgacac tcctggggtc tgagcattcc ttgctgatta ggagcaagtt cagatcagtt    840
ttacagttaa gacttcaaca agaaggacc aggaacaac tggctaacca aggcataata      900
ccaccactga acgtccagc tgaattccat gagcaaagaa acatttgga tagtgacaag      960
gctaaaaatt ccctgaagcg caaagccaga acaggtgca acagtgccga cttggttaat    1020
atgcacatac tccaagcttc cactgcagag aggtccattc caactgctca gatgaagctg    1080
aaaagagccc gactcgccga tgatctcaat gaaaaaattg ctctacgacc aggcccactg    1140
gagctggtgg aaaaaaaacat tcttcctgtg gattctgctg tgaaagaggc cataaaaggt    1200
aaccaggtga gtttctccaa atccacggat gcttttgcct ttgaagagga cagcagcagc    1260
gatgggcttt ctccggatca gactcgaagt gaagaccccc aaaactcagc gggatccccg    1320
ccagacgcta agcctcaga tacccctttcg acaggttctc tggggacaaa ccaggatctt    1380
gcttctggct cagaaaatga cagaaatgac tcagcctcac agcccagcca ccagtcagat    1440
gcggggaagc aggggcttgg cccccccagc accccccatag ccgtgcatgc tgctgtaaag    1500
tccaaatcct tgggtgacag taagaaccgc acaaaaagc ccaaggaccc caagccaaag    1560
gtgaagaagc ttaaatatca ccagtacatt cccccagacc agaaggcaga gaagtcccct    1620
ccacctatgg actcagccta cgctcggctg ctccagcaac agcagctgtt cctgcagctc    1680
caaatcctca gccagcagca gcagcagcag caacaccgat tcagctacct agggatgcac    1740
caagctcagc ttaaggaacc aaatgaacag atggtcagaa atccaaactc ttcttcaacg    1800
ccactgagca atacccccctt gtctcctgtc aaaaacagtt tttctggaca aactggtgtc    1860
tcttctttca accaggccc actcccacct aacctggatg atctgaaggt ctctgaatta    1920
agacaacagc ttcgaattcg gggcttgcct gtgtcaggca ccaaaacggc tctcatggac    1980
cggcttcgac ccttccagga ctgctctggc aacccagtgc cgaactttgg ggatataacg    2040
```

```
actgtcacttt tcctgtcac acccaacacg ctgcccaatt accagtcttc ctcttctacc    2100
agtgccctgt ccaacggctt ctaccacttt ggcagcacca gctccagccc ccgatctcc     2160
ccagcctcct ctgacctgtc agtcgctggg tccctgccgg acaccttcaa tgatgcctcc    2220
ccctccttcg gcctgcaccc gtccccagtc cacgtgtgca cggaggaaag tctcatgagc    2280
agcctgaatg ggggctctgt tccttctgag ctggatgggc tggactccga aaggacaag     2340
atgctggtgg agaagcagaa ggtgatcaat gaactcacct ggaaactcca gcaagagcag    2400
aggcaggtgg aggagctgag gatgcagctt cagaagcaga aaaggaataa ctgttcagag    2460
aagaagccgc tgcctttcct ggctgcctcc atcaagcagg aagaggctgt ctccagctgt    2520
ccttttgcat cccaagtacc tgtgaaaaga caaagcagca gctcagagtg tcacccaccg    2580
gcttgtgaag ctgctcaact ccagcctctt ggaaatgctc attgtgtgga gtcctcagat    2640
caaaccaatg tactttcttc acatttctc agccccagt gttccctca gcattcaccg       2700
ctggggctg tgaaaagccc acagcacatc agtttgcccc catcacccaa caaccctcac    2760
tttctgccct catcctccgg ggcccaggga aagggcaca gggtctcctc gcccatcagc    2820
agccaggtgt gcactgcaca gaactcagga gcacacgatg ccatcctcc aagcttctct    2880
ccccattctt ccagcctcca cccgcccttc tctggagccc aagcagacag cagtcatggt   2940
gccgggggaa accttgtcc caaaagccca tgtgtacagc aaaagatggc tggtttacac    3000
tcttctgata aggtggggcc aaagttttca attccatccc aacttttc taagtcaagt     3060
tcagcaattt cagaggtaac acagcctcca tcctatgaag atgccgtaaa gcagcaaatg   3120
acccggagtc agcagatgga tgaactcctg gacgtgctta ttgaaagcgg agaaatgcca   3180
gcagacgcta gagaggatca ctcatgtctt caaaaagtcc caaagatacc cagatcttcc   3240
cgaagtccaa ctgctgtcct caccaagccc tcggcttcct ttgaacaagc ctcttcaggc   3300
agccagatcc cctttgatcc ctatgccacc gacagtgatg agcatcttga agtcttatta   3360
aattcccaga gccccctagg aaagatgagt gatgtcaccc ttctaaaaat tgggagcgaa   3420
gagcctcact ttgatgggat aatggatgga ttctctggga aggctgcaga agacctcttc   3480
aatgcacatg agatcttgcc aggccccctc tctccaatgc agacacagtt ttcaccctct   3540
tctgtggaca gcaatgggct gcagttaagc ttcactgaat ctccctggga aaccatggag   3600
tggctggacc tcactccgcc aaattccaca ccaggcttta gcgccctcac caccagcagc   3660
cccagcatct tcaacatcga tttcctggat gtcactgatc tcaatttgaa ttcttccatg   3720
gaccttcact tgcagcagtg gtag                                          3744
```

<210> SEQ ID NO 41
<211> LENGTH: 3114
<212> TYPE: DNA
<213> ORGANISM: Artificial Sequence
<220> FEATURE:
<223> OTHER INFORMATION: ASCL1-2A-Mydelta3

<400> SEQUENCE: 41

```
atggaaagct ctgccaagat ggagagcggc ggcgccggcc agcagcccca gccgcagccc    60
cagcagccct cctgccgccgc cgcagccgt ttctttgcca cggccgcagc gcggcggcc    120
gcagccgccg cagcggcagc gcagagcgcg cagcagcagc agcagcagca gcagcagcag    180
cagcaggcgc cgcagctgag accgcggcc gacggccagc cctcaggggg cggtcacaag    240
tcagcgccca gcaagtcaa gcgacagcgc tcgtcttcgc ccgaactgat gcgctgcaaa    300
cgccggctca acttcagcgg ctttggctac agcctgccgc agcagcagcc ggccgccgtg    360
```

-continued

```
gcgcgccgca acgagcgcga gcgcaaccgc gtcaagttgg tcaacctggg ctttgccacc    420
cttcgggagc acgtccccaa cggcgcggcc aacaagaaga tgagtaaggt ggagacactg    480
cgctcggcgg tcgagtacat ccgcgcgctg cagcagctgc tggacgagca tgacgcggtg    540
agcgccgcct tccaggcagg cgtcctgtcg cccaccatct cccccaacta ctccaacgac    600
ttgaactcca tggccggctc gccggtctca tcctactcgt cggacgaggg ctcttacgac    660
ccgctcagcc ccgaggagca ggagcttctc gacttcacca actggttcgc cacgaacttc    720
tctctgttaa agcaagcagg agacgtggaa gaaacccccg gtcctatgac actcctgggg    780
tctgagcatt ccttgctgat taggagcaag ttcagatcag ttttacagtt aagacttcaa    840
caaagaagga cccaggaaca actggctaac caaggcataa taccaccact gaaacgtcca    900
gctgaattcc atgagcaaag aaaacatttg gatagtgaca aggctaaaaa ttccctgaag    960
cgcaaagcca gaaacaggtg caacagtgcc gacttggtta atatgcacat actccaagct   1020
tccactgcag agaggtccat tccaactgct cagatgaagc tgaaaagagc ccgactcgcc   1080
gatgatctca atgaaaaaat tgctctacga ccaggcccac tggagctggt ggaaaaaaac   1140
attcttcctg tggattctgc tgtgaaagag gccataaaag gtaaccaggt gagtttctcc   1200
aaatccacgg atgcttttgc ctttgaagag gacagcagca gcgatgggct ttctccggat   1260
cagactcgaa gtgaagaccc ccaaaaactca gcgggatccc cgccagacgc taaagcctca   1320
gatacccctt cgacaggttc tctggggaca aaccaggatc ttgcttctgg ctcagaaaat   1380
gacagaaatg actcagcctc acagcccagc caccagtcag atgcggggaa gcagggcttt   1440 ggcccccccca gcaccccat agccgtgcat gctgctgtaa agtccaaatc cttgggtgac   1500
agtaagaacc gccacaaaaa gcccaaggac cccaagccaa aggtgaagaa gcttaaatat   1560
caccagtaca ttcccccaga ccagaaggca gagaagtccc ctccacctat ggactcagcc   1620
tacgctcggc tgctccagca acagcagctg ttcctgcagc tccaaatcct cagccagcag   1680
cagcagcagc agcaacaccg attcagctac ctagggatgc accaagctca gcttaaggaa   1740
ccaaatgaac agatggtcag aaatccaaac tcttcttcaa cgccactgag caataccccc   1800
ttgtctcctg tcaaaaacag tttttctgga caaactggtg tctcttcttt caaaccaggc   1860
ccactcccac ctaacctgga tgatctgaag gtctctgaat taagacaaca gcttcgaatt   1920
cggggcttgc ctgtgtcagg caccaaaacg gctctcatgg accggcttcg acccttccag   1980
gactgctctg gcaacccagt gccgaacttt ggggatataa cgactgtcac ttttcctgtc   2040
acacccaaca cgctgcccaa ttaccagtct tcctcttcta ccagtgccct gtccaacggc   2100
ttctaccact tggcagcac cagctccagc ccccgatct cccagcctc ctctgacctg   2160 tcagtcgctg ggtccctgcc ggacaccttc aatgatgcct cccctccttt cggcctgcac   2220
ccgtccccag tccacgtgtg cacggaggaa agtctcatga gcagcctgaa tggggctct   2280 gttccttctg agctggatgg gctggactcc gagaaggaca gatgctggt ggagaagcag   2340 aaggtgatca atgaactcac ctggaaactc agcaagagc agaggcaggt ggaggagctg   2400
aggatgcagc ttcagaagca gaaaaggaat aactgttcag aggaggtaac acagcctcca   2460
tcctatgaag atgccgtaaa gcagcaaatg acccggagtc agcagatgga tgaactcctg   2520
gacgtgctta ttgaaagcgg agaaatgcca gcagacgcta gagaggatca ctcatgtctt   2580
caaaaagtcc caaagatacc cagatcttcc cgaagtccaa ctgctgtcct caccaagccc   2640
tcggcttcct ttgaacaagc ctcttcaggc agccagatcc cctttgatcc ctatgccacc   2700
```

| | |
|---|---|
| gacagtgatg agcatcttga agtcttatta aattcccaga gcccctagg aaagatgagt | 2760 |
| gatgtcaccc ttctaaaaat tgggagcgaa gagcctcact ttgatgggat aatggatgga | 2820 |
| ttctctggga aggctgcaga agacctcttc aatgcacatg agatcttgcc aggcccctc | 2880 |
| tctccaatgc agacacagtt ttcaccctct tctgtggaca gcaatgggct gcagttaagc | 2940 |
| ttcactgaat ctccctggga aaccatggag tggctggacc tcactccgcc aaattccaca | 3000 |
| ccaggcttta gcgccctcac caccagcagc cccagcatct tcaacatcga tttcctggat | 3060 |
| gtcactgatc tcaatttgaa ttcttccatg gaccttcact tgcagcagtg gtag | 3114 |

<210> SEQ ID NO 42
<211> LENGTH: 3132
<212> TYPE: DNA
<213> ORGANISM: Artificial Sequence
<220> FEATURE:
<223> OTHER INFORMATION: MYF6-2A-Mydelta3

<400> SEQUENCE: 42

| | |
|---|---|
| atgatgatgg acctttttga aactggctcc tatttcttct acttggatgg ggaaaatgtt | 60 |
| actctgcagc cattagaagt ggcagaaggc tctccttttgt atccagggag tgatggtacc | 120 |
| ttgtcccct gccaggacca aatgcccccg gaagcgggga gcgacagcag cggagaggaa | 180 |
| catgtcctgg cgcccccggg cctgcagcct ccacactgcc ccggccagtg tctgatctgg | 240 |
| gcttgcaaga acctgcaagag aaaatctgcc cccactgacc ggcgaaaagc cgccaccctg | 300 |
| cgcgaaagga ggaggctaaa gaaaatcaac gaggccttcg aggcactgaa gcggcgaact | 360 |
| gtggccaacc ccaaccagag gctgcccaag gtggagattc tgcggagcgc catcagctat | 420 |
| attgagcggc tgcaggacct gctgcaccgg ctggatcagc aggagaagat gcaggagctg | 480 |
| ggggtggacc cctcagcta cagacccaaa caagaaaatc ttgagggtgc ggatttcctg | 540 |
| cgcacctgca gctcccagtg gccaagtgtt tccgatcatt ccaggggggct cgtgataacg | 600 |
| gctaaggaag gaggagcaag tattgattcg tcagcctcga gtagccttcg atgcctttct | 660 |
| tccatcgtgg acagtatttc ctcggaggaa cgcaaactcc cctgcgtgga ggaagtggtg | 720 |
| gagaaggcca cgaacttctc tctgttaaag caagcaggag acgtggaaga aaaccccggt | 780 |
| cctatgacac tcctggggtc tgagcattcc ttgctgatta ggagcaagtt cagatcagtt | 840 |
| ttacagttaa gacttcaaca agaaggacc caggaacaac tggctaacca aggcataata | 900 |
| ccaccactga acgtccagc tgaattccat gagcaaagaa acatttggga tagtgacaag | 960 |
| gctaaaaatt ccctgaagcg caaagccaga acaggtgca acagtgccga cttggttaat | 1020 |
| atgcacatac tccaagcttc cactgcagag aggtccattc caactgctca gatgaagctg | 1080 |
| aaaagagccc gactcgccga tgatctcaat gaaaaaattg ctctacgacc aggcccactg | 1140 |
| gagctggtgg aaaaaaacat tcttcctgtg gattctgctg tgaaagaggc cataaaaggt | 1200 |
| aaccaggtga gtttctccaa atccacggat gcttttgcct ttgaagagga cagcagcagc | 1260 |
| gatgggcttt ctccggatca gactcgaagt gaagaccccc aaaactcagc gggatccccg | 1320 |
| ccagacgcta agcctcaga tacccttcg acaggttctc tggggacaaa ccaggatctt | 1380 |
| gcttctggct cagaaaatga cagaaatgac tcagcctcac agcccagcca ccagtcagat | 1440 |
| gcggggaagc aggggcttgg ccccccagc accccatag ccgtgcatgc tgctgtaaag | 1500 |
| tccaaatcct tgggtgacag taagaaccgc cacaaaaagc ccaaggaccc caagccaaag | 1560 |
| gtgaagaagc ttaaatatca ccagtacatt ccccagacc agaaggcaga gaagtcccct | 1620 |
| ccacctatgg actcagccta cgctcggctg ctccagcaac agcagctgtt cctgcagctc | 1680 |

```
caaatcctca gccagcagca gcagcagcag caacaccgat tcagctacct agggatgcac    1740
caagctcagc ttaaggaacc aaatgaacag atggtcagaa atccaaactc ttcttcaacg    1800
ccactgagca ataccccctt gtctcctgtc aaaaacagtt tttctggaca aactggtgtc    1860
tcttctttca aaccaggccc actcccacct aacctggatg atctgaaggt ctctgaatta    1920
agacaacagc ttcgaattcg gggcttgcct gtgtcaggca ccaaaacggc tctcatggac    1980
cggcttcgac ccttccagga ctgctctggc aacccagtgc cgaactttgg ggatataacg    2040
actgtcactt ttcctgtcac acccaacacg ctgcccaatt accagtcttc ctcttctacc    2100
agtgccctgt ccaacggctt ctaccacttt ggcagcacca gctccagccc ccgatctcc    2160
ccagcctcct ctgacctgtc agtcgctggg tccctgccgg acaccttcaa tgatgcctcc    2220
ccctccttcg gcctgcaccc gtccccagtc acgtgtgca cggaggaaag tctcatgagc    2280
agcctgaatg ggggctctgt tccttctgag ctggatgggc tggactccga aggacaag    2340
atgctggtgg agaagcagaa ggtgatcaat gaactcacct ggaaactcca gcaagagcag    2400
aggcaggtgg aggagctgag gatgcagctt cagaagcaga aaaggaataa ctgttcagag    2460
gaggtaacac agcctccatc ctatgaagat gccgtaaagc agcaaatgac ccggagtcag    2520
cagatggatg aactcctgga cgtgcttatt gaaagcggag aaatgccagc agacgctaga    2580
gaggatcact catgtcttca aaaagtccca aagataccca gatcttcccg aagtccaact    2640
gctgtcctca ccaagccctc ggcttccttt gaacaagcct cttcaggcag ccagatcccc    2700
tttgatccct atgccaccga cagtgatgag catcttgaag tcttattaaa ttcccagagc    2760
cccctaggaa agatgagtga tgtcacccct ctaaaaattg ggagcgaaga gcctcacttt    2820
gatgggataa tggatggatt ctctgggaag gctgcagaag acctcttcaa tgcacatgag    2880
atcttgccag gcccccctctc tccaatgcag acacagtttt caccctcttc tgtggacagc    2940
aatgggctgc agttaagctt cactgaatct ccctgggaaa ccatggagtg gctggacctc    3000
actccgccaa attccacacc aggctttagc gccctcacca ccagcagccc cagcatcttc    3060
aacatcgatt tcctggatgt cactgatctc aatttgaatt cttccatgga ccttcacttg    3120
cagcagtggt ag                                                       3132

<210> SEQ ID NO 43
<211> LENGTH: 287
<212> TYPE: PRT
<213> ORGANISM: Homo sapiens

<400> SEQUENCE: 43

Met Ser Gly Ser Phe Asp Arg Lys Leu Ser Ser Ile Leu Thr Asp Ile
1               5                   10                  15

Ser Ser Ser Leu Ser Cys His Ala Gly Ser Lys Asp Ser Pro Thr Leu
            20                  25                  30

Pro Glu Ser Ser Val Thr Asp Leu Gly Tyr Tyr Ser Ala Pro Gln His
        35                  40                  45

Asp Tyr Tyr Ser Gly Gln Pro Tyr Gly Gln Thr Val Asn Pro Tyr Thr
    50                  55                  60

Tyr His His Gln Phe Asn Leu Asn Gly Leu Ala Gly Thr Gly Ala Tyr
65                  70                  75                  80

Ser Pro Lys Ser Glu Tyr Thr Tyr Gly Ala Ser Tyr Arg Gln Tyr Gly
                85                  90                  95

Ala Tyr Arg Glu Gln Pro Leu Pro Ala Gln Asp Pro Val Ser Val Lys
            100                 105                 110
```

```
Glu Pro Glu Ala Glu Val Arg Met Val Asn Gly Lys Pro Lys Lys
    115                 120                 125
Val Arg Lys Pro Arg Thr Ile Tyr Ser Ser Tyr Gln Leu Ala Ala Leu
130                 135                 140
Gln Arg Arg Phe Gln Lys Ala Gln Tyr Leu Ala Leu Pro Glu Arg Ala
145                 150                 155                 160
Glu Leu Ala Ala Gln Leu Gly Leu Thr Gln Thr Gln Val Lys Ile Trp
                165                 170                 175
Phe Gln Asn Arg Arg Ser Lys Phe Lys Lys Leu Tyr Lys Asn Gly Glu
            180                 185                 190
Val Pro Leu Glu His Ser Pro Asn Asn Ser Asp Ser Met Ala Cys Asn
        195                 200                 205
Ser Pro Pro Ser Pro Ala Leu Trp Asp Thr Ser Ser His Ser Thr Pro
    210                 215                 220
Ala Pro Ala Arg Ser Gln Leu Pro Pro Leu Pro Tyr Ser Ala Ser
225                 230                 235                 240
Pro Ser Tyr Leu Asp Asp Pro Thr Asn Ser Trp Tyr His Ala Gln Asn
                245                 250                 255
Leu Ser Gly Pro His Leu Gln Gln Gln Pro Gln Pro Ala Thr Leu
            260                 265                 270
His His Ala Ser Pro Gly Pro Pro Asn Pro Gly Ala Val Tyr
        275                 280                 285

<210> SEQ ID NO 44
<211> LENGTH: 864
<212> TYPE: DNA
<213> ORGANISM: Homo sapiens

<400> SEQUENCE: 44
atgagtggct ccttcgatcg caagctcagc agcatcctca ccgacatctc cagctccctt      60
agctgccatg cgggctccaa ggactcgcct accctgcccg agtcttctgt cactgacctg     120
ggctactaca gcgctcccca gcacgattac tactcgggcc agccctatgg ccagacggtg     180 aaccectaca cctaccacca ccaattcaat ctcaatgggc ttgcaggcac gggcgcttac     240
tcgcccaagt cggaatatac ctacggagcc tcctaccggc aatacggggc gtatcgggag     300
cagccgctgc agcccagga cccagtgtcg gtgaaggagg agccggaagc agaggtgcgc     360
atggtgaatg ggaagcccaa gaaggtccga aagccgcgta cgatctactc cagctaccag     420
ctggccgccc tgcagcgccg cttccagaag gcccagtacc tggcgctgcc cgagcgcgcc     480
gagctggccg cgcagctggg cctcacgcag acacaggtga aaatctggtt ccagaaccgc     540
cgttccaagt tcaagaaact ctacaagaac ggggaggtgc cgctggagca cagtcccaat     600
aacagtgatt ccatggcctg caactcacca ccatcacccg ccctctggga cacctcttcc     660
cactccactc cggcccctgc cgcagtcag ctgcccccgc cgctcccata cagtgcctcc     720
cccagctacc tggacgaccc caccaactcc tggtatcacg cacagaacct gagtggaccc     780
cacttacagc agcagccgcc tcagccagcc accctgcacc atgcctctcc cgggcccccg     840
cccaaccctg gggctgtgta ctga                                             864

<210> SEQ ID NO 45
<211> LENGTH: 293
<212> TYPE: PRT
<213> ORGANISM: Homo sapiens

<400> SEQUENCE: 45
```

Met Met Thr Met Thr Thr Met Ala Asp Gly Leu Glu Gly Gln Asp Ser
1               5                   10                  15

Ser Lys Ser Ala Phe Met Glu Phe Gly Gln Gln Gln Gln Gln Gln Gln
            20                  25                  30

Gln Gln Gln Gln Gln Gln Gln Gln Gln Gln Gln Pro Pro Pro
        35                  40                  45

Pro Pro Pro Pro Pro Gln Pro His Ser Gln Gln Ser Ser Pro Ala Met
50                  55                  60

Ala Gly Ala His Tyr Pro Leu His Cys Leu His Ser Ala Ala Ala Ala
65              70                  75                  80

Ala Ala Ala Gly Ser His His His His His Gln His His His
            85                  90                  95

Gly Ser Pro Tyr Ala Ser Gly Gly Asn Ser Tyr Asn His Arg Ser
            100                 105                 110

Leu Ala Ala Tyr Pro Tyr Met Ser His Ser Gln His Ser Pro Tyr Leu
            115                 120                 125

Gln Ser Tyr His Asn Ser Ser Ala Ala Gln Thr Arg Gly Asp Asp
        130                 135                 140

Thr Asp Gln Gln Lys Thr Thr Val Ile Glu Asn Gly Glu Ile Arg Phe
145                 150                 155                 160

Asn Gly Lys Gly Lys Lys Ile Arg Lys Pro Arg Thr Ile Tyr Ser Ser
                165                 170                 175

Leu Gln Leu Gln Ala Leu Asn His Arg Phe Gln Gln Thr Gln Tyr Leu
            180                 185                 190

Ala Leu Pro Glu Arg Ala Glu Leu Ala Ala Ser Leu Gly Leu Thr Gln
            195                 200                 205

Thr Gln Val Lys Ile Trp Phe Gln Asn Lys Arg Ser Lys Phe Lys Lys
210                 215                 220

Leu Leu Lys Gln Gly Ser Asn Pro His Glu Ser Asp Pro Leu Gln Gly
225                 230                 235                 240

Ser Ala Ala Leu Ser Pro Arg Ser Pro Ala Leu Pro Pro Val Trp Asp
                245                 250                 255

Val Ser Ala Ser Ala Lys Gly Val Ser Met Pro Asn Ser Tyr Met
            260                 265                 270

Pro Gly Tyr Ser His Trp Tyr Ser Ser Pro His Gln Asp Thr Met Gln
            275                 280                 285

Arg Pro Gln Met Met
        290

<210> SEQ ID NO 46
<211> LENGTH: 882
<212> TYPE: DNA
<213> ORGANISM: Homo sapiens

<400> SEQUENCE: 46
atgatgacca tgactacgat ggctgacggc ttggaaggcc aggactcgtc caaatccgcc    60
ttcatggagt tcgggcagca gcagcagcag cagcagcaac agcagcagca gcagcagcag   120
caacagcaac agccgccgcc gccgccgccg ccgccgccgc agccgcactc gcagcagagc   180
tccccggcca tggcaggcgc gcactaccct ctgcactgcc tgcactcggc ggcggcggcg   240
gcagcggccg gctcgcacca ccaccaccac caccagcacc accaccacgg ctcgccctac   300
gcgtcgggcg gagggaactc ctacaaccac cgctcgctcg ccgcctaccc ctacatgagc   360
cactcgcagc acagccctta cctccagtcc taccacaaca gcagcgcagc cgcccagacg   420

```
cgaggggacg acacagatca acaaaaaact acagtgattg aaaacgggga aatcaggttc    480
aatggaaaag ggaaaaagat tcggaagcct cggaccattt attccagcct gcagctccag    540
gctttaaacc atcgctttca gcagacacag tatctggccc ttccagagag agccgaactg    600
gcagcttcct taggactgac acaaacacag gtgaagatat ggtttcagaa caaacgctct    660
aagtttaaga aactgctgaa gcagggcagt aatcctcatg agagcgaccc cctccagggc    720
tcggcggccc tgtcgccacg ctcgccagcg ctgcctccag tctgggacgt ttctgcctcg    780
gccaagggtg tcagtatgcc ccccaacagc tacatgcctg gctattctca ctggtactcc    840
tctccacacc aggacacgat gcagagacca cagatgatgt ga                      882
```

<210> SEQ ID NO 47
<211> LENGTH: 458
<212> TYPE: PRT
<213> ORGANISM: Homo sapiens

<400> SEQUENCE: 47

```
Met Asp Ser Val Glu Leu Cys Leu Pro Glu Ser Phe Ser Leu His Tyr
1               5                   10                  15

Glu Glu Glu Leu Leu Cys Arg Met Ser Asn Lys Asp Arg His Ile Asp
            20                  25                  30

Ser Ser Cys Ser Ser Phe Ile Lys Thr Glu Pro Ser Ser Pro Ala Ser
        35                  40                  45

Leu Thr Asp Ser Val Asn His His Ser Pro Gly Gly Ser Ser Asp Ala
    50                  55                  60

Ser Gly Ser Tyr Ser Ser Thr Met Asn Gly His Gln Asn Gly Leu Asp
65                  70                  75                  80

Ser Pro Pro Leu Tyr Pro Ser Ala Pro Ile Leu Gly Gly Ser Gly Pro
                85                  90                  95

Val Arg Lys Leu Tyr Asp Asp Cys Ser Ser Thr Ile Val Glu Asp Pro
            100                 105                 110

Gln Thr Lys Cys Glu Tyr Met Leu Asn Ser Met Pro Lys Arg Leu Cys
        115                 120                 125

Leu Val Cys Gly Asp Ile Ala Ser Gly Tyr His Tyr Gly Val Ala Ser
    130                 135                 140

Cys Glu Ala Cys Lys Ala Phe Phe Lys Arg Thr Ile Gln Gly Asn Ile
145                 150                 155                 160

Glu Tyr Ser Cys Pro Ala Thr Asn Glu Cys Glu Ile Thr Lys Arg Arg
                165                 170                 175

Arg Lys Ser Cys Gln Ala Cys Arg Phe Met Lys Cys Leu Lys Val Gly
            180                 185                 190

Met Leu Lys Glu Gly Val Arg Leu Asp Arg Val Arg Gly Gly Arg Gln
        195                 200                 205

Lys Tyr Lys Arg Arg Ile Asp Ala Glu Asn Ser Pro Tyr Leu Asn Pro
    210                 215                 220

Gln Leu Val Gln Pro Ala Lys Lys Pro Tyr Asn Lys Ile Val Ser His
225                 230                 235                 240

Leu Leu Val Ala Glu Pro Glu Lys Ile Tyr Ala Met Pro Asp Pro Thr
                245                 250                 255

Val Pro Asp Ser Asp Ile Lys Ala Leu Thr Thr Leu Cys Asp Leu Ala
            260                 265                 270

Asp Arg Glu Leu Val Val Ile Ile Gly Trp Ala Lys His Ile Pro Gly
        275                 280                 285
```

```
Phe Ser Thr Leu Ser Leu Ala Asp Gln Met Ser Leu Leu Gln Ser Ala
        290                 295                 300

Trp Met Glu Ile Leu Ile Leu Gly Val Val Tyr Arg Ser Leu Ser Phe
305                 310                 315                 320

Glu Asp Glu Leu Val Tyr Ala Asp Asp Tyr Ile Met Asp Glu Asp Gln
                325                 330                 335

Ser Lys Leu Ala Gly Leu Leu Asp Leu Asn Asn Ala Ile Leu Gln Leu
            340                 345                 350

Val Lys Lys Tyr Lys Ser Met Lys Leu Glu Lys Glu Glu Phe Val Thr
        355                 360                 365

Leu Lys Ala Ile Ala Leu Ala Asn Ser Asp Ser Met His Ile Glu Asp
370                 375                 380

Val Glu Ala Val Gln Lys Leu Gln Asp Val Leu His Glu Ala Leu Gln
385                 390                 395                 400

Asp Tyr Glu Ala Gly Gln His Met Glu Asp Pro Arg Arg Ala Gly Lys
                405                 410                 415

Met Leu Met Thr Leu Pro Leu Leu Arg Gln Thr Ser Thr Lys Ala Val
            420                 425                 430

Gln His Phe Tyr Asn Ile Lys Leu Glu Gly Lys Val Pro Met His Lys
        435                 440                 445

Leu Phe Leu Glu Met Leu Glu Ala Lys Val
450                 455
```

<210> SEQ ID NO 48
<211> LENGTH: 1377
<212> TYPE: DNA
<213> ORGANISM: Homo sapiens

<400> SEQUENCE: 48

```
atggattcgg tagaactttg ccttcctgaa tcttttttccc tgcactacga ggaagagctt      60
ctctgcagaa tgtcaaacaa agatcgacac attgattcca gctgttcgtc cttcatcaag     120
acggaacctt ccagcccagc ctccctgacg acagcgtca accaccacag ccctggtggc      180
tcttcagacg ccagtgggag ctacagttca accatgaatg ccatcagaa cggacttgac      240
tcgccacctc tctaccccttc tgctcctatc ctggaggta gtgggcctgt caggaaactg      300
tatgatgact gctccagcac cattgttgaa gatccccaga ccaagtgtga atacatgctc      360
aactcgatgc caagagact gtgtttagtg tgtggtgaca tcgcttctgg gtaccactat      420
ggggtagcat catgtgaagc ctgcaaggca ttcttcaaga ggacaattca aggcaatata      480
gaatacagct gccctgccac gaatgaatgt gaaatcacaa agcgcagacg taatcctgc      540
caggcttgcc gcttcatgaa gtgtttaaaa gtgggcatgc tgaaagaagg ggtgcgtctt      600
gacagagtac gtggaggtcg gcagaagtac aagcgcagga tagatgcgga aacagcccca      660
tacctgaacc ctcagctggt tcagccagcc aaaaagccat ataacaagat tgtctcacat      720
ttgttggtgg ctgaaccgga agatctat gccatgcctg accctactgt ccccgacagt      780
gacatcaaag ccctcactac actgtgtgac ttggccgacc gagagttggt ggttatcatt      840
ggatgggcga agcatattcc aggcttctcc acgctgtccc tggcggacca gatgagcctt      900
ctgcagagtg cttggatgga aattttgatc cttggtgtcg tataccggtc tctttcgttt     960
gaggatgaac ttgtctatgc agacgattat ataatggacg aagaccagtc caaattagca    1020
ggccttcttg atctaaataa tgctatcctg cagctggtaa agaaatacaa gagcatgaag    1080
ctggaaaaag aagaatttgt cacccctcaaa gctatagctc ttgctaattc agactccatg    1140
```

-continued

```
cacatagaag atgttgaagc cgttcagaag cttcaggatg tcttacatga agcgctgcag    1200
gattatgaag ctggccagca catggaagac cctcgtcgag ctggcaagat gctgatgaca    1260
ctgccactcc tgaggcagac ctctaccaag gccgtgcagc atttctacaa catcaaacta    1320
gaaggcaaag tcccaatgca caaactttt ttggaaatgt tggaggccaa ggtctga        1377

<210> SEQ ID NO 49
<211> LENGTH: 480
<212> TYPE: PRT
<213> ORGANISM: Homo sapiens

<400> SEQUENCE: 49

Met Glu Val Ala Pro Glu Gln Pro Arg Trp Met Ala His Pro Ala Val
1               5                   10                  15

Leu Asn Ala Gln His Pro Asp Ser His His Pro Gly Leu Ala His Asn
            20                  25                  30

Tyr Met Glu Pro Ala Gln Leu Leu Pro Pro Asp Glu Val Asp Val Phe
        35                  40                  45

Phe Asn His Leu Asp Ser Gln Gly Asn Pro Tyr Tyr Ala Asn Pro Ala
    50                  55                  60

His Ala Arg Ala Arg Val Ser Tyr Ser Pro Ala His Ala Arg Leu Thr
65                  70                  75                  80

Gly Gly Gln Met Cys Arg Pro His Leu Leu His Ser Pro Gly Leu Pro
                85                  90                  95

Trp Leu Asp Gly Gly Lys Ala Ala Leu Ser Ala Ala Ala His His
            100                 105                 110

His Asn Pro Trp Thr Val Ser Pro Phe Ser Lys Thr Pro Leu His Pro
            115                 120                 125

Ser Ala Ala Gly Gly Pro Gly Gly Pro Leu Ser Val Tyr Pro Gly Ala
        130                 135                 140

Gly Gly Gly Ser Gly Gly Ser Gly Ser Ser Val Ala Ser Leu Thr
145                 150                 155                 160

Pro Thr Ala Ala His Ser Gly Ser His Leu Phe Gly Phe Pro Pro Thr
                165                 170                 175

Pro Pro Lys Glu Val Ser Pro Asp Pro Ser Thr Thr Gly Ala Ala Ser
            180                 185                 190

Pro Ala Ser Ser Ser Ala Gly Gly Ser Ala Ala Arg Gly Glu Asp Lys
        195                 200                 205

Asp Gly Val Lys Tyr Gln Val Ser Leu Thr Glu Ser Met Lys Met Glu
    210                 215                 220

Ser Gly Ser Pro Leu Arg Pro Gly Leu Ala Thr Met Gly Thr Gln Pro
225                 230                 235                 240

Ala Thr His His Pro Ile Pro Thr Tyr Pro Ser Tyr Val Pro Ala Ala
                245                 250                 255

Ala His Asp Tyr Ser Ser Gly Leu Phe His Pro Gly Gly Phe Leu Gly
            260                 265                 270

Gly Pro Ala Ser Ser Phe Thr Pro Lys Gln Arg Ser Lys Ala Arg Ser
        275                 280                 285

Cys Ser Glu Gly Arg Glu Cys Val Asn Cys Gly Ala Thr Ala Thr Pro
    290                 295                 300

Leu Trp Arg Arg Asp Gly Thr Gly His Tyr Leu Cys Asn Ala Cys Gly
305                 310                 315                 320

Leu Tyr His Lys Met Asn Gly Gln Asn Arg Pro Leu Ile Lys Pro Lys
                325                 330                 335
```

```
Arg Arg Leu Ser Ala Ala Arg Arg Ala Gly Thr Cys Cys Ala Asn Cys
            340                 345                 350

Gln Thr Thr Thr Thr Thr Leu Trp Arg Arg Asn Ala Asn Gly Asp Pro
        355                 360                 365

Val Cys Asn Ala Cys Gly Leu Tyr Tyr Lys Leu His Asn Val Asn Arg
    370                 375                 380

Pro Leu Thr Met Lys Lys Glu Gly Ile Gln Thr Arg Asn Arg Lys Met
385                 390                 395                 400

Ser Asn Lys Ser Lys Lys Ser Lys Lys Gly Ala Glu Cys Phe Glu Glu
                405                 410                 415

Leu Ser Lys Cys Met Gln Glu Lys Ser Ser Pro Phe Ser Ala Ala Ala
            420                 425                 430

Leu Ala Gly His Met Ala Pro Val Gly His Leu Pro Pro Phe Ser His
            435                 440                 445

Ser Gly His Ile Leu Pro Thr Pro Thr Pro Ile His Pro Ser Ser Ser
        450                 455                 460

Leu Ser Phe Gly His Pro His Pro Ser Ser Met Val Thr Ala Met Gly
465                 470                 475                 480
```

<210> SEQ ID NO 50
<211> LENGTH: 1443
<212> TYPE: DNA
<213> ORGANISM: Homo sapiens

<400> SEQUENCE: 50

| | | |
|---|---|---|
| atggaggtgg cgcccgagca gccgcgctgg atggcgcacc cggccgtgct gaatgcgcag | 60 |
| caccccgact cacaccaccc gggcctggcg cacaactaca tggaacccgc gcagctgctg | 120 |
| cctccagacg aggtggacgt cttcttcaat cacctcgact cgcagggcaa ccctactat | 180 |
| gccaaccccg ctcacgcgcg ggcgcgcgtc tcctacagcc ccgcgcacgc ccgcctgacc | 240 |
| ggaggccaga tgtgccgccc acacttgttg cacagcccgg gtttgccctg ctggacggg | 300 |
| ggcaaagcag ccctctctgc cgctgcggcc caccaccaca ccccctggac cgtgagcccc | 360 |
| ttctccaaga cgccactgca ccccctcagct gctggaggcc ctggaggccc actctctgtg | 420 |
| tacccagggg ctgggggtgg gagcggggga ggcagcggga gctcagtggc ctccctcacc | 480 |
| cctacagcag cccactctgg ctcccaccct ttcggcttcc cacccacgcc acccaaagaa | 540 |
| gtgtctcctg accctagcac cacggggggct gcgtctccag cctcatcttc gcgggggggt | 600 |
| agtgcagccc gaggagagga caaggacggc gtcaagtacc aggtgtcact gacggagagc | 660 |
| atgaagatgg aaagtggcag tcccctgcgc ccaggcctag ctactatggg cacccagcct | 720 |
| gctacacacc accccatccc cacctacccc tcctatgtgc cggcggctgc ccacgactac | 780 |
| agcagcggac tcttccaccc cggaggcttc ctgggggggac cggcctccag cttcacccct | 840 |
| aagcagcgca gcaaggctcg ttcctgttca gaaggccggg agtgtgtcaa ctgtggggcc | 900 |
| acagccaccc ctctctggcg gcgggacggc accggccact acctgtgcaa tgcctgtggc | 960 |
| ctctaccaca agatgaatgg gcagaaccga ccactcatca gcccaagcg aagactgtcg | 1020 |
| gccgccagaa gagccggcac ctgttgtgca aattgtcaga cgacaaccac caccttatgg | 1080 |
| cgccgaaacg ccaacgggga ccctgtctgc aacgcctgtg gcctctacta caagctgcac | 1140 |
| aatgttaaca ggccactgac catgaagaag gaagggatcc agactcggaa ccggaagatg | 1200 |
| tccaacaagt ccaagaagag caagaaaggg cggagtgctc tcgaggagct gtcaaagtgc | 1260 |
| atgcaggaga agtcatcccc cttcagtgca gctgccctgg ctggacacat ggcacctgtg | 1320 |

```
ggccacctcc cgcccttcag ccactccgga cacatcctgc ccactccgac gcccatccac    1380
ccctcctcca gcctctcctt cggccacccc cacccgtcca gcatggtgac cgccatgggc    1440
tag                                                                  1443
```

<210> SEQ ID NO 51
<211> LENGTH: 443
<212> TYPE: PRT
<213> ORGANISM: Homo sapiens

<400> SEQUENCE: 51

```
Met Tyr Gln Ser Leu Ala Met Ala Ala Asn His Gly Pro Pro Gly
1               5                   10                  15

Ala Tyr Glu Ala Gly Gly Pro Gly Ala Phe Met His Gly Ala Gly Ala
            20                  25                  30

Ala Ser Ser Pro Val Tyr Val Pro Thr Pro Arg Val Pro Ser Ser Val
        35                  40                  45

Leu Gly Leu Ser Tyr Leu Gln Gly Gly Ala Gly Ser Ala Ser Gly
    50                  55                  60

Gly Ala Ser Gly Gly Ser Ser Gly Gly Ala Ala Ser Gly Ala Gly Pro
65                  70                  75                  80

Gly Thr Gln Gln Gly Ser Pro Gly Trp Ser Gln Ala Gly Ala Asp Gly
                85                  90                  95

Ala Ala Tyr Thr Pro Pro Pro Val Ser Pro Arg Phe Ser Phe Pro Gly
            100                 105                 110

Thr Thr Gly Ser Leu Ala Ala Ala Ala Ala Ala Ala Ala Arg Glu
        115                 120                 125

Ala Ala Ala Tyr Ser Ser Gly Gly Gly Ala Ala Gly Ala Gly Leu Ala
        130                 135                 140

Gly Arg Glu Gln Tyr Gly Arg Ala Gly Phe Ala Gly Ser Tyr Ser Ser
145                 150                 155                 160

Pro Tyr Pro Ala Tyr Met Ala Asp Val Gly Ala Ser Trp Ala Ala Ala
                165                 170                 175

Ala Ala Ala Ser Ala Gly Pro Phe Asp Ser Pro Val Leu His Ser Leu
            180                 185                 190

Pro Gly Arg Ala Asn Pro Ala Ala Arg His Pro Asn Leu Val Asp Met
        195                 200                 205

Phe Asp Asp Phe Ser Glu Gly Arg Glu Cys Val Asn Cys Gly Ala Met
210                 215                 220

Ser Thr Pro Leu Trp Arg Arg Asp Gly Thr Gly His Tyr Leu Cys Asn
225                 230                 235                 240

Ala Cys Gly Leu Tyr His Lys Met Asn Gly Ile Asn Arg Pro Leu Ile
                245                 250                 255

Lys Pro Gln Arg Arg Leu Ser Ala Arg Arg Val Gly Leu Ser Cys
            260                 265                 270

Ala Asn Cys Gln Thr Thr Thr Thr Leu Trp Arg Arg Asn Ala Glu
        275                 280                 285

Gly Glu Pro Val Cys Asn Ala Cys Gly Leu Tyr Met Lys Leu His Gly
    290                 295                 300

Val Pro Arg Pro Leu Ala Met Arg Lys Glu Gly Ile Gln Thr Arg Lys
305                 310                 315                 320

Arg Lys Pro Lys Asn Leu Asn Lys Ser Lys Thr Pro Ala Ala Pro Ser
                325                 330                 335

Gly Ser Glu Ser Leu Pro Pro Ala Ser Gly Ala Ser Ser Asn Ser Ser
            340                 345                 350
```

```
Asn Ala Thr Thr Ser Ser Glu Glu Met Arg Pro Ile Lys Thr Glu
            355                 360                 365

Pro Gly Leu Ser Ser His Tyr Gly His Ser Ser Val Ser Gln Thr
        370                 375                 380

Phe Ser Val Ser Ala Met Ser Gly His Gly Pro Ser Ile His Pro Val
385                 390                 395                 400

Leu Ser Ala Leu Lys Leu Ser Pro Gln Gly Tyr Ala Ser Pro Val Ser
                405                 410                 415

Gln Ser Pro Gln Thr Ser Ser Lys Gln Asp Ser Trp Asn Ser Leu Val
            420                 425                 430

Leu Ala Asp Ser His Gly Asp Ile Ile Thr Ala
            435                 440

<210> SEQ ID NO 52
<211> LENGTH: 1332
<212> TYPE: DNA
<213> ORGANISM: Homo sapiens

<400> SEQUENCE: 52
atgtatcaga gcttggccat ggccgccaac cacgggccgc ccccggtgc ctacgaggcg      60 ggcggccccg gcgccttcat gcacggcgcg ggcgccgcgt cctcgccagt ctacgtgccc    120
acaccgcggg tgccctcctc cgtgctgggc ctgtcctacc tccagggcgg aggcgcgggc    180
tctgcgtccg gaggcgcctc gggcggcagc tccggtgggg ccgcgtctgg tgcggggccc    240
gggacccagc agggcagccc gggatggagc caggcgggag ccgacggagc cgcttacacc    300
ccgccgccgg tgtcgccgcg cttctccttc ccggggacca ccgggtccct ggcggccgcc    360
gccgccgctg ccgcggcccg ggaagctgcg gcctacagca gtggcggcgg agcggcgggt    420
gcgggcctgg cgggccgcga gcagtacggg cgcgccggct tcgcgggctc ctactccagc    480
ccctacccgg cttacatggc cgacgtgggc cgtcctgggg ccgcagccgc cgccgcctcc    540
gccggcccct tcgacagccc ggtcctgcac agcctgcccg gccgggccaa ccggccgccg    600 cgacaccccca atctcgtaga tatgtttgac gacttctcag aaggcagaga gtgtgtcaac    660
tgtggggcta tgtccacccc gctctggagg cgagatggga cgggtcacta tctgtgcaac    720
gcctgcggcc tctaccacaa gatgaacggc atcaaccggc cgctcatcaa gcctcagcgc    780
cggctgtccg cctcccgccg agtgggcctc tcctgtgcca actgccagac caccaccacc    840
acgctgtggc ccgcaatgc ggagggcgag cctgtgtgca atgcctgcgg cctctacatg    900
aagctccacg ggtccccag gcctcttgca atgcggaaag aggggatcca aaccagaaaa    960
cggaagccca gaacctgaa taaatctaag acaccagcag ctccttcagg cagtgagagc   1020
cttcctcccg ccagcggtgc ttccagcaac tccagcaacg ccaccaccag cagcagcgag   1080
gagatgcgtc ccatcaagac ggagcctggc ctgtcatctc actacgggca cagcagctcc   1140
gtgtcccaga cgttctcagt cagtgcgatg tctggccatg gccctccat ccaccctgtc   1200 ctctcggccc tgaagctctc cccacaaggc tatgcgtctc ccgtcagcca gtctccacag   1260
accagctcca gcaggactc ttggaacagc ctggtcttgg ccgacagtca cggggacata   1320
atcactgcgt aa                                                      1332

<210> SEQ ID NO 53
<211> LENGTH: 268
<212> TYPE: PRT
<213> ORGANISM: Homo sapiens
```

-continued

<400> SEQUENCE: 53

Met Ala Gln Pro Leu Cys Pro Pro Leu Ser Glu Ser Trp Met Leu Ser
1               5                   10                  15

Ala Ala Trp Gly Pro Thr Arg Arg Pro Pro Ser Asp Lys Asp Cys
            20                  25                  30

Gly Arg Ser Leu Val Ser Ser Pro Asp Ser Trp Gly Ser Thr Pro Ala
        35                  40                  45

Asp Ser Pro Val Ala Ser Pro Ala Arg Pro Gly Thr Leu Arg Asp Pro
    50                  55                  60

Arg Ala Pro Ser Val Gly Arg Gly Ala Arg Ser Ser Arg Leu Gly
65              70                  75                  80

Ser Gly Gln Arg Gln Ser Ala Ser Glu Arg Glu Lys Leu Arg Met Arg
                85                  90                  95

Thr Leu Ala Arg Ala Leu His Glu Leu Arg Arg Phe Leu Pro Pro Ser
            100                 105                 110

Val Ala Pro Ala Gly Gln Ser Leu Thr Lys Ile Glu Thr Leu Arg Leu
        115                 120                 125

Ala Ile Arg Tyr Ile Gly His Leu Ser Ala Val Leu Gly Leu Ser Glu
    130                 135                 140

Glu Ser Leu Gln Arg Arg Cys Arg Gln Arg Gly Asp Ala Gly Ser Pro
145                 150                 155                 160

Arg Gly Cys Pro Leu Cys Pro Asp Asp Cys Pro Ala Gln Met Gln Thr
                165                 170                 175

Arg Thr Gln Ala Glu Gly Gln Gly Gln Gly Arg Gly Leu Gly Leu Val
            180                 185                 190

Ser Ala Val Arg Ala Gly Ala Ser Trp Gly Ser Pro Pro Ala Cys Pro
        195                 200                 205

Gly Ala Arg Ala Ala Pro Glu Pro Arg Asp Pro Pro Ala Leu Phe Ala
    210                 215                 220

Glu Ala Ala Cys Pro Glu Gly Gln Ala Met Glu Pro Ser Pro Ser
225                 230                 235                 240

Pro Leu Leu Pro Gly Asp Val Leu Ala Leu Leu Glu Thr Trp Met Pro
                245                 250                 255

Leu Ser Pro Leu Glu Trp Leu Pro Glu Glu Pro Lys
            260                 265

<210> SEQ ID NO 54
<211> LENGTH: 807
<212> TYPE: DNA
<213> ORGANISM: Homo sapiens

<400> SEQUENCE: 54
atggcccagc ccctgtgccc gccgctctcc gagtcctgga tgctctctgc ggcctggggc      60
ccaactcggc ggccgccgcc ctccgacaag gactgcggcc gctccctcgt ctcgtcccca     120
gactcatggg gcagcacccc agccgacagc cccgtggcga gcccgcgcg ccaggcacc      180 ctccgggacc cccgcgcccc ctccgtaggt aggcgcggcg cgcgcagcag ccgcctgggc     240
agcgggcaga ggcagagcgc cagtgagcgg gagaaactgc gcatgcgcac gctggcccgc     300
gccctgcacg agctgcgccg ctttctaccg ccgtccgtgg cgcccgcggg ccagagcctg     360
accaagatcg agacgctgcg cctggctatc cgctatatcg gccacctgtc ggccgtgcta     420
ggcctcagcg aggagagtct ccagcgccgg tgcggcagc gcggtgacgc ggggtcccct     480
cggggctgcc cgctgtgccc cgacgactgc cccgcgcaga tgcagacacg gacgcaggct     540

```
gaggggcagg ggcaggggcg cgggctgggc ctggtatccg ccgtccgcgc cggggcgtcc      600
tggggatccc cgcctgcctg ccccggagcc cgagctgcac ccgagccgcg cgacccgcct      660
gcgctgttcg ccgaggcggc gtgccctgaa gggcaggcga tggagccaag cccaccgtcc      720
ccgctccttc cgggcgacgt gctggctctg ttggagacct ggatgcccct ctcgcctctg      780
gagtggctgc ctgaggagcc caagtga                                          807
```

<210> SEQ ID NO 55
<211> LENGTH: 242
<212> TYPE: PRT
<213> ORGANISM: Homo sapiens

<400> SEQUENCE: 55

```
Met Met Met Asp Leu Phe Glu Thr Gly Ser Tyr Phe Phe Tyr Leu Asp
1               5                   10                  15

Gly Glu Asn Val Thr Leu Gln Pro Leu Glu Val Ala Glu Gly Ser Pro
            20                  25                  30

Leu Tyr Pro Gly Ser Asp Gly Thr Leu Ser Pro Cys Gln Asp Gln Met
        35                  40                  45

Pro Pro Glu Ala Gly Ser Asp Ser Ser Gly Glu Glu His Val Leu Ala
    50                  55                  60

Pro Pro Gly Leu Gln Pro Pro His Cys Pro Gly Gln Cys Leu Ile Trp
65                  70                  75                  80

Ala Cys Lys Thr Cys Lys Arg Lys Ser Ala Pro Thr Asp Arg Arg Lys
                85                  90                  95

Ala Ala Thr Leu Arg Glu Arg Arg Arg Leu Lys Lys Ile Asn Glu Ala
            100                 105                 110

Phe Glu Ala Leu Lys Arg Arg Thr Val Ala Asn Pro Asn Gln Arg Leu
        115                 120                 125

Pro Lys Val Glu Ile Leu Arg Ser Ala Ile Ser Tyr Ile Glu Arg Leu
    130                 135                 140

Gln Asp Leu Leu His Arg Leu Asp Gln Gln Glu Lys Met Gln Glu Leu
145                 150                 155                 160

Gly Val Asp Pro Phe Ser Tyr Arg Pro Lys Gln Glu Asn Leu Glu Gly
                165                 170                 175

Ala Asp Phe Leu Arg Thr Cys Ser Ser Gln Trp Pro Ser Val Ser Asp
            180                 185                 190

His Ser Arg Gly Leu Val Ile Thr Ala Lys Glu Gly Gly Ala Ser Ile
        195                 200                 205

Asp Ser Ser Ala Ser Ser Ser Leu Arg Cys Leu Ser Ser Ile Val Asp
    210                 215                 220

Ser Ile Ser Ser Glu Glu Arg Lys Leu Pro Cys Val Glu Glu Val Val
225                 230                 235                 240

Glu Lys
```

<210> SEQ ID NO 56
<211> LENGTH: 729
<212> TYPE: DNA
<213> ORGANISM: Homo sapiens

<400> SEQUENCE: 56

```
atgatgatgg acctttttga aactggctcc tatttcttct acttggatgg ggaaaatgtt      60
actctgcagc cattagaagt ggcagaaggc tctccttttgt atccagggag tgatggtacc     120
ttgtccccct gccaggacca aatgccccg gaagcgggga gcgacagcag cggagaggaa       180
```

```
catgtcctgg cgcccccggg cctgcagcct ccacactgcc ccggccagtg tctgatctgg      240
gcttgcaaga cctgcaagag aaaatctgcc cccactgacc ggcgaaaagc cgccaccctg      300
cgcgaaagga ggaggctaaa gaaaatcaac gaggccttcg aggcactgaa gcggcgaact      360
gtggccaacc ccaaccagag gctgcccaag gtggagattc tgcggagcgc catcagctat      420
attgagcggc tgcaggacct gctgcaccgg ctggatcagc aggagaagat gcaggagctg      480
ggggtggacc ccttcagcta cagacccaaa caagaaaatc ttgagggtgc ggatttcctg      540
cgcacctgca gctcccagtg gccaagtgtt tccgatcatt ccagggggct cgtgataacg      600
gctaaggaag gaggagcaag tattgattcg tcagcctcga gtagccttcg atgcctttct      660
tccatcgtgg acagtatttc ctcggaggaa cgcaaactcc cctgcgtgga ggaagtggtg      720
gagaagtaa                                                               729
```

<210> SEQ ID NO 57
<211> LENGTH: 1241
<212> TYPE: PRT
<213> ORGANISM: Artificial Sequence
<220> FEATURE:
<223> OTHER INFORMATION: MYOCD-2A-ASCL1

<400> SEQUENCE: 57

```
Met Thr Leu Leu Gly Ser Glu His Ser Leu Leu Ile Arg Ser Lys Phe
1               5                   10                  15

Arg Ser Val Leu Gln Leu Arg Leu Gln Gln Arg Thr Gln Glu Gln
            20                  25                  30

Leu Ala Asn Gln Gly Ile Ile Pro Pro Leu Lys Arg Pro Ala Glu Phe
        35                  40                  45

His Glu Gln Arg Lys His Leu Asp Ser Asp Lys Ala Lys Asn Ser Leu
    50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
        115                 120                 125

Val Asp Ser Ala Val Lys Glu Ala Ile Lys Gly Asn Gln Val Ser Phe
    130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
        195                 200                 205

Asp Ser Ala Ser Gln Pro Ser His Gln Ser Asp Ala Gly Lys Gln Gly
    210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
```

```
            260                 265                 270
Gln Lys Ala Glu Lys Ser Pro Pro Met Asp Ser Ala Tyr Ala Arg
        275                 280                 285

Leu Leu Gln Gln Gln Leu Phe Leu Gln Leu Gln Ile Leu Ser Gln
        290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
            325                 330                 335

Ser Ser Thr Pro Leu Ser Asn Thr Pro Leu Ser Pro Val Lys Asn Ser
            340                 345                 350

Phe Ser Gly Gln Thr Gly Val Ser Ser Phe Lys Pro Gly Pro Leu Pro
        355                 360                 365

Pro Asn Leu Asp Asp Leu Lys Val Ser Glu Leu Arg Gln Gln Leu Arg
        370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
                405                 410                 415

Asp Ile Thr Thr Val Thr Phe Pro Val Thr Pro Asn Thr Leu Pro Asn
            420                 425                 430

Tyr Gln Ser Ser Ser Thr Ser Ala Leu Ser Asn Gly Phe Tyr His
        435                 440                 445

Phe Gly Ser Thr Ser Ser Pro Pro Ile Ser Pro Ala Ser Ser Asp
        450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
                485                 490                 495

Leu Met Ser Ser Leu Asn Gly Gly Ser Val Pro Ser Glu Leu Asp Gly
            500                 505                 510

Leu Asp Ser Glu Lys Asp Lys Met Leu Val Glu Lys Gln Lys Val Ile
        515                 520                 525

Asn Glu Leu Thr Trp Lys Leu Gln Gln Glu Gln Arg Gln Val Glu Glu
        530                 535                 540

Leu Arg Met Gln Leu Gln Lys Gln Lys Arg Asn Asn Cys Ser Glu Lys
545                 550                 555                 560

Lys Pro Leu Pro Phe Leu Ala Ala Ser Ile Lys Gln Glu Glu Ala Val
                565                 570                 575

Ser Ser Cys Pro Phe Ala Ser Gln Val Pro Val Lys Arg Gln Ser Ser
            580                 585                 590

Ser Ser Glu Cys His Pro Pro Ala Cys Glu Ala Ala Gln Leu Gln Pro
        595                 600                 605

Leu Gly Asn Ala His Cys Val Glu Ser Ser Asp Gln Thr Asn Val Leu
        610                 615                 620

Ser Ser Thr Phe Leu Ser Pro Gln Cys Ser Pro Gln His Ser Pro Leu
625                 630                 635                 640

Gly Ala Val Lys Ser Pro Gln His Ile Ser Leu Pro Pro Ser Pro Asn
                645                 650                 655

Asn Pro His Phe Leu Pro Ser Ser Ser Gly Ala Gln Gly Glu Gly His
            660                 665                 670

Arg Val Ser Ser Pro Ile Ser Ser Gln Val Cys Thr Ala Gln Asn Ser
        675                 680                 685
```

```
Gly Ala His Asp Gly His Pro Pro Ser Phe Ser Pro His Ser Ser Ser
        690             695             700

Leu His Pro Pro Phe Ser Gly Ala Gln Ala Asp Ser Ser His Gly Ala
705             710             715                         720

Gly Gly Asn Pro Cys Pro Lys Ser Pro Cys Val Gln Gln Lys Met Ala
            725             730                     735

Gly Leu His Ser Ser Asp Lys Val Gly Pro Lys Phe Ser Ile Pro Ser
            740             745             750

Pro Thr Phe Ser Lys Ser Ser Ser Ala Ile Ser Glu Val Thr Gln Pro
        755             760             765

Pro Ser Tyr Glu Asp Ala Val Lys Gln Gln Met Thr Arg Ser Gln Gln
770             775             780

Met Asp Glu Leu Leu Asp Val Leu Ile Glu Ser Gly Glu Met Pro Ala
785             790             795             800

Asp Ala Arg Glu Asp His Ser Cys Leu Gln Lys Val Pro Lys Ile Pro
                805             810             815

Arg Ser Ser Arg Ser Pro Thr Ala Val Leu Thr Lys Pro Ser Ala Ser
            820             825             830

Phe Glu Gln Ala Ser Ser Gly Ser Gln Ile Pro Phe Asp Pro Tyr Ala
        835             840             845

Thr Asp Ser Asp Glu His Leu Glu Val Leu Leu Asn Ser Gln Ser Pro
850             855             860

Leu Gly Lys Met Ser Asp Val Thr Leu Leu Lys Ile Gly Ser Glu Glu
865             870             875             880

Pro His Phe Asp Gly Ile Met Asp Gly Phe Ser Gly Lys Ala Ala Glu
            885             890             895

Asp Leu Phe Asn Ala His Glu Ile Leu Pro Gly Pro Leu Ser Pro Met
            900             905             910

Gln Thr Gln Phe Ser Pro Ser Ser Val Asp Ser Asn Gly Leu Gln Leu
        915             920             925

Ser Phe Thr Glu Ser Pro Trp Glu Thr Met Glu Trp Leu Asp Leu Thr
        930             935             940

Pro Pro Asn Ser Thr Pro Gly Phe Ser Ala Leu Thr Thr Ser Ser Pro
945             950             955             960

Ser Ile Phe Asn Ile Asp Phe Leu Asp Val Thr Asp Leu Asn Leu Asn
            965             970             975

Ser Ser Met Asp Leu His Leu Gln Gln Trp Ala Thr Asn Phe Ser Leu
            980             985             990

Leu Lys Gln Ala Gly Asp Val Glu  Glu Asn Pro Gly Pro  Met Glu Ser
        995             1000            1005

Ser Ala Lys Met Glu Ser Gly  Gly Ala Gly Gln Gln  Pro Gln Pro
        1010            1015            1020

Gln Pro  Gln Gln Pro Phe Leu  Pro Pro Ala Ala Cys  Phe Phe Ala
    1025            1030            1035

Thr Ala  Ala Ala Ala Ala Ala  Ala Ala Ala Ala  Ala Ala Gln
    1040            1045            1050

Ser Ala  Gln Gln Gln Gln Gln  Gln Gln Gln Gln  Gln Gln Ala
    1055            1060            1065

Pro Gln  Leu Arg Pro Ala Ala  Asp Gly Gln Pro  Ser Gly Gly Gly
    1070            1075            1080

His Lys  Ser Ala Pro Lys Gln  Val Lys Arg Gln Arg  Ser Ser Ser
    1085            1090            1095
```

```
Pro Glu Leu Met Arg Cys Lys Arg Arg Leu Asn Phe Ser Gly Phe
    1100                1105                1110

Gly Tyr Ser Leu Pro Gln Gln Gln Pro Ala Ala Val Ala Arg Arg
    1115                1120                1125

Asn Glu Arg Glu Arg Asn Arg Val Lys Leu Val Asn Leu Gly Phe
    1130                1135                1140

Ala Thr Leu Arg Glu His Val Pro Asn Gly Ala Ala Asn Lys Lys
    1145                1150                1155

Met Ser Lys Val Glu Thr Leu Arg Ser Ala Val Glu Tyr Ile Arg
    1160                1165                1170

Ala Leu Gln Gln Leu Leu Asp Glu His Asp Ala Val Ser Ala Ala
    1175                1180                1185

Phe Gln Ala Gly Val Leu Ser Pro Thr Ile Ser Pro Asn Tyr Ser
    1190                1195                1200

Asn Asp Leu Asn Ser Met Ala Gly Ser Pro Val Ser Ser Tyr Ser
    1205                1210                1215

Ser Asp Glu Gly Ser Tyr Asp Pro Leu Ser Pro Glu Glu Gln Glu
    1220                1225                1230

Leu Leu Asp Phe Thr Asn Trp Phe
    1235                1240

<210> SEQ ID NO 58
<211> LENGTH: 1247
<212> TYPE: PRT
<213> ORGANISM: Artificial Sequence
<220> FEATURE:
<223> OTHER INFORMATION: MYOCD-2A-MYF6

<400> SEQUENCE: 58

Met Thr Leu Leu Gly Ser Glu His Ser Leu Leu Ile Arg Ser Lys Phe
1               5                   10                  15

Arg Ser Val Leu Gln Leu Arg Leu Gln Gln Arg Arg Thr Gln Glu Gln
                20                  25                  30

Leu Ala Asn Gln Gly Ile Ile Pro Pro Leu Lys Arg Pro Ala Glu Phe
            35                  40                  45

His Glu Gln Arg Lys His Leu Asp Ser Asp Lys Ala Lys Asn Ser Leu
        50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
                100                 105                 110

Ala Leu Arg Pro Gly Pro Leu Glu Leu Val Glu Lys Asn Ile Leu Pro
            115                 120                 125

Val Asp Ser Ala Val Lys Glu Ala Ile Lys Gly Asn Gln Val Ser Phe
        130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
        195                 200                 205
```

```
Asp Ser Ala Ser Gln Pro Ser His Gln Ser Asp Ala Gly Lys Gln Gly
    210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
                260                 265                 270

Gln Lys Ala Glu Lys Ser Pro Pro Met Asp Ser Ala Tyr Ala Arg
                275                 280                 285

Leu Leu Gln Gln Gln Leu Phe Leu Gln Leu Gln Ile Leu Ser Gln
            290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                325                 330                 335

Ser Ser Thr Pro Leu Ser Asn Thr Pro Leu Ser Pro Val Lys Asn Ser
                340                 345                 350

Phe Ser Gly Gln Thr Gly Val Ser Ser Phe Lys Pro Gly Pro Leu Pro
            355                 360                 365

Pro Asn Leu Asp Asp Leu Lys Val Ser Glu Leu Arg Gln Gln Leu Arg
370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
                405                 410                 415

Asp Ile Thr Thr Val Thr Phe Pro Val Thr Pro Asn Thr Leu Pro Asn
                420                 425                 430

Tyr Gln Ser Ser Ser Thr Ser Ala Leu Ser Asn Gly Phe Tyr His
            435                 440                 445

Phe Gly Ser Thr Ser Ser Pro Pro Ile Ser Pro Ala Ser Ser Asp
450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
                485                 490                 495

Leu Met Ser Ser Leu Asn Gly Gly Ser Val Pro Ser Glu Leu Asp Gly
                500                 505                 510

Leu Asp Ser Glu Lys Asp Lys Met Leu Val Glu Lys Gln Lys Val Ile
                515                 520                 525

Asn Glu Leu Thr Trp Lys Leu Gln Gln Glu Gln Arg Gln Val Glu Glu
                530                 535                 540

Leu Arg Met Gln Leu Gln Lys Gln Lys Arg Asn Asn Cys Ser Glu Lys
545                 550                 555                 560

Lys Pro Leu Pro Phe Leu Ala Ala Ser Ile Lys Gln Glu Glu Ala Val
                565                 570                 575

Ser Ser Cys Pro Phe Ala Ser Gln Val Pro Val Lys Arg Gln Ser Ser
                580                 585                 590

Ser Ser Glu Cys His Pro Pro Ala Cys Glu Ala Ala Gln Leu Gln Pro
            595                 600                 605

Leu Gly Asn Ala His Cys Val Glu Ser Ser Asp Gln Thr Asn Val Leu
            610                 615                 620

Ser Ser Thr Phe Leu Ser Pro Gln Cys Ser Pro Gln His Ser Pro Leu
```

-continued

```
            625                 630                 635                 640
        Gly Ala Val Lys Ser Pro Gln His Ile Ser Leu Pro Pro Ser Pro Asn
                        645                 650                 655
        Asn Pro His Phe Leu Pro Ser Ser Gly Ala Gln Gly Glu Gly His
                    660                 665                 670
        Arg Val Ser Ser Pro Ile Ser Ser Gln Val Cys Thr Ala Gln Asn Ser
                    675                 680                 685
        Gly Ala His Asp Gly His Pro Pro Ser Phe Ser Pro His Ser Ser
            690                 695                 700
        Leu His Pro Pro Phe Ser Gly Ala Gln Ala Asp Ser Ser His Gly Ala
        705                 710                 715                 720
        Gly Gly Asn Pro Cys Pro Lys Ser Pro Cys Val Gln Lys Met Ala
                        725                 730                 735
        Gly Leu His Ser Ser Asp Lys Val Gly Pro Lys Phe Ser Ile Pro Ser
                    740                 745                 750
        Pro Thr Phe Ser Lys Ser Ser Ser Ala Ile Ser Glu Val Thr Gln Pro
                    755                 760                 765
        Pro Ser Tyr Glu Asp Ala Val Lys Gln Gln Met Thr Arg Ser Gln Gln
                    770                 775                 780
        Met Asp Glu Leu Leu Asp Val Leu Ile Glu Ser Gly Glu Met Pro Ala
        785                 790                 795                 800
        Asp Ala Arg Glu Asp His Ser Cys Leu Gln Lys Val Pro Lys Ile Pro
                        805                 810                 815
        Arg Ser Ser Arg Ser Pro Thr Ala Val Leu Thr Lys Pro Ser Ala Ser
                    820                 825                 830
        Phe Glu Gln Ala Ser Ser Gly Ser Gln Ile Pro Phe Asp Pro Tyr Ala
                    835                 840                 845
        Thr Asp Ser Asp Glu His Leu Glu Val Leu Leu Asn Ser Gln Ser Pro
                    850                 855                 860
        Leu Gly Lys Met Ser Asp Val Thr Leu Leu Lys Ile Gly Ser Glu Glu
        865                 870                 875                 880
        Pro His Phe Asp Gly Ile Met Asp Gly Phe Ser Gly Lys Ala Ala Glu
                        885                 890                 895
        Asp Leu Phe Asn Ala His Glu Ile Leu Pro Gly Pro Leu Ser Pro Met
                    900                 905                 910
        Gln Thr Gln Phe Ser Pro Ser Ser Val Asp Ser Asn Gly Leu Gln Leu
                    915                 920                 925
        Ser Phe Thr Glu Ser Pro Trp Glu Thr Met Glu Trp Leu Asp Leu Thr
            930                 935                 940
        Pro Pro Asn Ser Thr Pro Gly Phe Ser Ala Leu Thr Thr Ser Ser Pro
        945                 950                 955                 960
        Ser Ile Phe Asn Ile Asp Phe Leu Asp Val Thr Asp Leu Asn Leu Asn
                        965                 970                 975
        Ser Ser Met Asp Leu His Leu Gln Gln Trp Ala Thr Asn Phe Ser Leu
                    980                 985                 990
        Leu Lys Gln Ala Gly Asp Val Glu  Glu Asn Pro Gly Pro  Met Met Met
                    995                 1000                1005
        Asp Leu  Phe Glu Thr Gly Ser  Tyr Phe Phe Tyr Leu  Asp Gly Glu
            1010                1015                1020
        Asn Val  Thr Leu Gln Pro Leu  Glu Val Ala Glu Gly  Ser Pro Leu
            1025                1030                1035
        Tyr Pro  Gly Ser Asp Gly Thr  Leu Ser Pro Cys Gln  Asp Gln Met
            1040                1045                1050
```

```
Pro Pro Glu Ala Gly Ser Asp Ser Ser Gly Glu Glu His Val Leu
    1055                1060                1065

Ala Pro Pro Gly Leu Gln Pro Pro His Cys Pro Gly Gln Cys Leu
    1070                1075                1080

Ile Trp Ala Cys Lys Thr Cys Lys Arg Lys Ser Ala Pro Thr Asp
    1085                1090                1095

Arg Arg Lys Ala Ala Thr Leu Arg Glu Arg Arg Leu Lys Lys
    1100                1105                1110

Ile Asn Glu Ala Phe Glu Ala Leu Lys Arg Arg Thr Val Ala Asn
    1115                1120                1125

Pro Asn Gln Arg Leu Pro Lys Val Glu Ile Leu Arg Ser Ala Ile
    1130                1135                1140

Ser Tyr Ile Glu Arg Leu Gln Asp Leu Leu His Arg Leu Asp Gln
    1145                1150                1155

Gln Glu Lys Met Gln Glu Leu Gly Val Asp Pro Phe Ser Tyr Arg
    1160                1165                1170

Pro Lys Gln Glu Asn Leu Glu Gly Ala Asp Phe Leu Arg Thr Cys
    1175                1180                1185

Ser Ser Gln Trp Pro Ser Val Ser Asp His Ser Arg Gly Leu Val
    1190                1195                1200

Ile Thr Ala Lys Glu Gly Gly Ala Ser Ile Asp Ser Ser Ala Ser
    1205                1210                1215

Ser Ser Leu Arg Cys Leu Ser Ser Ile Val Asp Ser Ile Ser Ser
    1220                1225                1230

Glu Glu Arg Lys Leu Pro Cys Val Glu Glu Val Val Glu Lys
    1235                1240                1245

<210> SEQ ID NO 59
<211> LENGTH: 1037
<212> TYPE: PRT
<213> ORGANISM: Artificial Sequence
<220> FEATURE:
<223> OTHER INFORMATION: Mydelta3-2A-ASCL1

<400> SEQUENCE: 59

Met Thr Leu Leu Gly Ser Glu His Ser Leu Leu Ile Arg Ser Lys Phe
1               5                   10                  15

Arg Ser Val Leu Gln Leu Arg Leu Gln Gln Arg Arg Thr Gln Glu Gln
                20                  25                  30

Leu Ala Asn Gln Gly Ile Ile Pro Pro Leu Lys Arg Pro Ala Glu Phe
            35                  40                  45

His Glu Gln Arg Lys His Leu Asp Ser Asp Lys Ala Lys Asn Ser Leu
        50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
                100                 105                 110

Ala Leu Arg Pro Gly Pro Leu Glu Leu Val Glu Lys Asn Ile Leu Pro
            115                 120                 125

Val Asp Ser Ala Val Lys Glu Ala Ile Lys Gly Asn Gln Val Ser Phe
        130                 135                 140

Ser Lys Ser Thr Asp Ala Phe Ala Phe Glu Glu Asp Ser Ser Ser Asp
145                 150                 155                 160
```

-continued

Gly Leu Ser Pro Asp Gln Thr Arg Ser Glu Asp Pro Gln Asn Ser Ala
            165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
            195                 200                 205

Asp Ser Ala Ser Gln Pro Ser His Gln Ser Asp Ala Gly Lys Gln Gly
            210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
            245                 250                 255

Lys Pro Lys Val Lys Lys Leu Lys Tyr His Gln Tyr Ile Pro Pro Asp
            260                 265                 270

Gln Lys Ala Glu Lys Ser Pro Pro Met Asp Ser Ala Tyr Ala Arg
            275                 280                 285

Leu Leu Gln Gln Gln Gln Leu Phe Leu Gln Leu Gln Ile Leu Ser Gln
            290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
            325                 330                 335

Ser Ser Thr Pro Leu Ser Asn Thr Pro Leu Ser Pro Val Lys Asn Ser
            340                 345                 350

Phe Ser Gly Gln Thr Gly Val Ser Phe Lys Pro Gly Pro Leu Pro
            355                 360                 365

Pro Asn Leu Asp Asp Leu Lys Val Ser Glu Leu Arg Gln Gln Leu Arg
            370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
            405                 410                 415

Asp Ile Thr Thr Val Thr Phe Pro Val Thr Pro Asn Thr Leu Pro Asn
            420                 425                 430

Tyr Gln Ser Ser Ser Ser Thr Ser Ala Leu Ser Asn Gly Phe Tyr His
            435                 440                 445

Phe Gly Ser Thr Ser Ser Ser Pro Pro Ile Ser Pro Ala Ser Ser Asp
            450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
            485                 490                 495

Leu Met Ser Ser Leu Asn Gly Gly Ser Val Pro Ser Glu Leu Asp Gly
            500                 505                 510

Leu Asp Ser Glu Lys Asp Lys Met Leu Val Glu Lys Gln Lys Val Ile
            515                 520                 525

Asn Glu Leu Thr Trp Lys Leu Gln Gln Glu Gln Arg Gln Val Glu Glu
            530                 535                 540

Leu Arg Met Gln Leu Gln Lys Gln Lys Arg Asn Asn Cys Ser Glu Glu
545                 550                 555                 560

Val Thr Gln Pro Pro Ser Tyr Glu Asp Ala Val Lys Gln Gln Met Thr
            565                 570                 575

```
Arg Ser Gln Gln Met Asp Glu Leu Leu Asp Val Leu Ile Glu Ser Gly
            580                 585                 590
Glu Met Pro Ala Asp Ala Arg Glu Asp His Ser Cys Leu Gln Lys Val
            595                 600                 605
Pro Lys Ile Pro Arg Ser Ser Arg Ser Pro Thr Ala Val Leu Thr Lys
            610                 615                 620
Pro Ser Ala Ser Phe Glu Gln Ala Ser Ser Gly Ser Gln Ile Pro Phe
625                 630                 635                 640
Asp Pro Tyr Ala Thr Asp Ser Asp Glu His Leu Glu Val Leu Leu Asn
            645                 650                 655
Ser Gln Ser Pro Leu Gly Lys Met Ser Asp Val Thr Leu Leu Lys Ile
            660                 665                 670
Gly Ser Glu Glu Pro His Phe Asp Gly Ile Met Asp Gly Phe Ser Gly
            675                 680                 685
Lys Ala Ala Glu Asp Leu Phe Asn Ala His Glu Ile Leu Pro Gly Pro
            690                 695                 700
Leu Ser Pro Met Gln Thr Gln Phe Ser Pro Ser Ser Val Asp Ser Asn
705                 710                 715                 720
Gly Leu Gln Leu Ser Phe Thr Glu Ser Pro Trp Glu Thr Met Glu Trp
            725                 730                 735
Leu Asp Leu Thr Pro Pro Asn Ser Thr Pro Gly Phe Ser Ala Leu Thr
            740                 745                 750
Thr Ser Ser Pro Ser Ile Phe Asn Ile Asp Phe Leu Asp Val Thr Asp
            755                 760                 765
Leu Asn Leu Asn Ser Ser Met Asp Leu His Leu Gln Gln Trp Ala Thr
            770                 775                 780
Asn Phe Ser Leu Leu Lys Gln Ala Gly Asp Val Glu Glu Asn Pro Gly
785                 790                 795                 800
Pro Met Glu Ser Ser Ala Lys Met Glu Ser Gly Gly Ala Gly Gln Gln
            805                 810                 815
Pro Gln Pro Gln Pro Gln Pro Phe Leu Pro Pro Ala Ala Cys Phe
            820                 825                 830
Phe Ala Thr Ala Ala Ala Ala Ala Ala Ala Ala Ala Ala Ala Ala
            835                 840                 845
Gln Ser Ala Gln Gln Gln Gln Gln Gln Gln Gln Gln Gln Gln Ala
850                 855                 860
Pro Gln Leu Arg Pro Ala Ala Asp Gly Gln Pro Ser Gly Gly Gly His
865                 870                 875                 880
Lys Ser Ala Pro Lys Gln Val Lys Arg Gln Arg Ser Ser Pro Glu
            885                 890                 895
Leu Met Arg Cys Lys Arg Arg Leu Asn Phe Ser Gly Phe Gly Tyr Ser
            900                 905                 910
Leu Pro Gln Gln Gln Pro Ala Ala Val Ala Arg Arg Asn Glu Arg Glu
            915                 920                 925
Arg Asn Arg Val Lys Leu Val Asn Leu Gly Phe Ala Thr Leu Arg Glu
            930                 935                 940
His Val Pro Asn Gly Ala Ala Asn Lys Lys Met Ser Lys Val Glu Thr
945                 950                 955                 960
Leu Arg Ser Ala Val Glu Tyr Ile Arg Ala Leu Gln Gln Leu Leu Asp
            965                 970                 975
Glu His Asp Ala Val Ser Ala Ala Phe Gln Ala Gly Val Leu Ser Pro
            980                 985                 990
Thr Ile Ser Pro Asn Tyr Ser Asn  Asp Leu Asn Ser Met  Ala Gly Ser
```

-continued

```
                995                1000               1005
        Pro Val Ser Ser Tyr Ser Ser Asp Glu Gly Ser Tyr Asp Pro Leu
            1010               1015               1020

Ser Pro Glu Glu Gln Glu Leu Leu Asp Phe Thr Asn Trp Phe
            1025               1030               1035

<210> SEQ ID NO 60
<211> LENGTH: 1043
<212> TYPE: PRT
<213> ORGANISM: Artificial Sequence
<220> FEATURE:
<223> OTHER INFORMATION: Mydelta3-2A-MYF6

<400> SEQUENCE: 60

Met Thr Leu Leu Gly Ser Glu His Ser Leu Leu Ile Arg Ser Lys Phe
1               5                   10                  15

Arg Ser Val Leu Gln Leu Arg Leu Gln Gln Arg Arg Thr Gln Glu Gln
            20                  25                  30

Leu Ala Asn Gln Gly Ile Ile Pro Pro Leu Lys Arg Pro Ala Glu Phe
        35                  40                  45

His Glu Gln Arg Lys His Leu Asp Ser Asp Lys Ala Lys Asn Ser Leu
    50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95

Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
        115                 120                 125

Val Asp Ser Ala Val Lys Glu Ala Ile Lys Gly Asn Gln Val Ser Phe
130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
            180                 185                 190

Leu Gly Thr Asn Gln Asp Leu Ala Ser Gly Ser Glu Asn Asp Arg Asn
        195                 200                 205

Asp Ser Ala Ser Gln Pro Ser His Gln Ser Asp Ala Gly Lys Gln Gly
    210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
            260                 265                 270

Gln Lys Ala Glu Lys Ser Pro Pro Met Asp Ser Ala Tyr Ala Arg
        275                 280                 285

Leu Leu Gln Gln Gln Gln Leu Phe Leu Gln Leu Gln Ile Leu Ser Gln
    290                 295                 300

Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
```

-continued

```
                    325                 330                 335
    Ser Ser Thr Pro Leu Ser Asn Thr Pro Leu Ser Pro Val Lys Asn Ser
                340                 345                 350

Phe Ser Gly Gln Thr Gly Val Ser Ser Phe Lys Pro Gly Pro Leu Pro
                355                 360                 365

Pro Asn Leu Asp Asp Leu Lys Val Ser Glu Leu Arg Gln Gln Leu Arg
                370                 375                 380

Ile Arg Gly Leu Pro Val Ser Gly Thr Lys Thr Ala Leu Met Asp Arg
    385                 390                 395                 400

Leu Arg Pro Phe Gln Asp Cys Ser Gly Asn Pro Val Pro Asn Phe Gly
                    405                 410                 415

Asp Ile Thr Thr Val Thr Phe Pro Val Thr Pro Asn Thr Leu Pro Asn
                420                 425                 430

Tyr Gln Ser Ser Ser Thr Ser Ala Leu Ser Asn Gly Phe Tyr His
                435                 440                 445

Phe Gly Ser Thr Ser Ser Pro Pro Ile Ser Pro Ala Ser Ser Asp
                450                 455                 460

Leu Ser Val Ala Gly Ser Leu Pro Asp Thr Phe Asn Asp Ala Ser Pro
    465                 470                 475                 480

Ser Phe Gly Leu His Pro Ser Pro Val His Val Cys Thr Glu Glu Ser
                    485                 490                 495

Leu Met Ser Ser Leu Asn Gly Gly Ser Val Pro Ser Glu Leu Asp Gly
                500                 505                 510

Leu Asp Ser Glu Lys Asp Lys Met Leu Val Glu Lys Gln Lys Val Ile
                515                 520                 525

Asn Glu Leu Thr Trp Lys Leu Gln Gln Glu Gln Arg Gln Val Glu Glu
                530                 535                 540

Leu Arg Met Gln Leu Gln Lys Gln Lys Arg Asn Asn Cys Ser Glu Glu
    545                 550                 555                 560

Val Thr Gln Pro Pro Ser Tyr Glu Asp Ala Val Lys Gln Gln Met Thr
                    565                 570                 575

Arg Ser Gln Gln Met Asp Glu Leu Leu Asp Val Leu Ile Glu Ser Gly
                580                 585                 590

Glu Met Pro Ala Asp Ala Arg Glu Asp His Ser Cys Leu Gln Lys Val
                595                 600                 605

Pro Lys Ile Pro Arg Ser Ser Arg Ser Pro Thr Ala Val Leu Thr Lys
                610                 615                 620

Pro Ser Ala Ser Phe Glu Gln Ala Ser Ser Gly Ser Gln Ile Pro Phe
    625                 630                 635                 640

Asp Pro Tyr Ala Thr Asp Ser Asp Glu His Leu Glu Val Leu Leu Asn
                    645                 650                 655

Ser Gln Ser Pro Leu Gly Lys Met Ser Asp Val Thr Leu Leu Lys Ile
                660                 665                 670

Gly Ser Glu Glu Pro His Phe Asp Gly Ile Met Asp Gly Phe Ser Gly
                675                 680                 685

Lys Ala Ala Glu Asp Leu Phe Asn Ala His Glu Ile Leu Pro Gly Pro
    690                 695                 700

Leu Ser Pro Met Gln Thr Gln Phe Ser Pro Ser Ser Val Asp Ser Asn
    705                 710                 715                 720

Gly Leu Gln Leu Ser Phe Thr Glu Ser Pro Trp Glu Thr Met Glu Trp
                    725                 730                 735

Leu Asp Leu Thr Pro Pro Asn Ser Thr Pro Gly Phe Ser Ala Leu Thr
                740                 745                 750
```

```
Thr Ser Ser Pro Ser Ile Phe Asn Ile Asp Phe Leu Asp Val Thr Asp
            755                 760                 765

Leu Asn Leu Asn Ser Ser Met Asp Leu His Leu Gln Gln Trp Ala Thr
        770                 775                 780

Asn Phe Ser Leu Leu Lys Gln Ala Gly Asp Val Glu Glu Asn Pro Gly
785                 790                 795                 800

Pro Met Met Met Asp Leu Phe Glu Thr Gly Ser Tyr Phe Phe Tyr Leu
                805                 810                 815

Asp Gly Glu Asn Val Thr Leu Gln Pro Leu Glu Val Ala Glu Gly Ser
            820                 825                 830

Pro Leu Tyr Pro Gly Ser Asp Gly Thr Leu Ser Pro Cys Gln Asp Gln
        835                 840                 845

Met Pro Pro Glu Ala Gly Ser Asp Ser Ser Gly Glu Glu His Val Leu
    850                 855                 860

Ala Pro Pro Gly Leu Gln Pro Pro His Cys Pro Gly Gln Cys Leu Ile
865                 870                 875                 880

Trp Ala Cys Lys Thr Cys Lys Arg Lys Ser Ala Pro Thr Asp Arg Arg
                885                 890                 895

Lys Ala Ala Thr Leu Arg Glu Arg Arg Arg Leu Lys Lys Ile Asn Glu
            900                 905                 910

Ala Phe Glu Ala Leu Lys Arg Arg Thr Val Ala Asn Pro Asn Gln Arg
        915                 920                 925

Leu Pro Lys Val Glu Ile Leu Arg Ser Ala Ile Ser Tyr Ile Glu Arg
    930                 935                 940

Leu Gln Asp Leu Leu His Arg Leu Asp Gln Gln Glu Lys Met Gln Glu
945                 950                 955                 960

Leu Gly Val Asp Pro Phe Ser Tyr Arg Pro Lys Gln Glu Asn Leu Glu
                965                 970                 975

Gly Ala Asp Phe Leu Arg Thr Cys Ser Ser Gln Trp Pro Ser Val Ser
            980                 985                 990

Asp His Ser Arg Gly Leu Val Ile Thr Ala Lys Glu Gly Gly Ala Ser
        995                 1000                1005

Ile Asp Ser Ser Ala Ser Ser Leu Arg Cys Leu Ser Ser Ile
    1010                1015                1020

Val Asp Ser Ile Ser Ser Glu Glu Arg Lys Leu Pro Cys Val Glu
    1025                1030                1035

Glu Val Val Glu Lys
    1040

<210> SEQ ID NO 61
<211> LENGTH: 1241
<212> TYPE: PRT
<213> ORGANISM: Artificial Sequence
<220> FEATURE:
<223> OTHER INFORMATION: ASCL1-2A-MYOCD

<400> SEQUENCE: 61

Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Ala Pro
    50                  55                  60
```

```
Gln Leu Arg Pro Ala Ala Asp Gly Gln Pro Ser Gly Gly His Lys
 65                  70                  75                  80

Ser Ala Pro Lys Gln Val Lys Arg Gln Ser Ser Pro Glu Leu
                 85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
                115                 120                 125

Asn Arg Val Lys Leu Val Asn Leu Gly Phe Ala Thr Leu Arg Glu His
        130                 135                 140

Val Pro Asn Gly Ala Ala Asn Lys Lys Met Ser Lys Val Glu Thr Leu
145                 150                 155                 160

Arg Ser Ala Val Glu Tyr Ile Arg Ala Leu Gln Gln Leu Leu Asp Glu
                165                 170                 175

His Asp Ala Val Ser Ala Ala Phe Gln Ala Gly Val Leu Ser Pro Thr
            180                 185                 190

Ile Ser Pro Asn Tyr Ser Asn Asp Leu Asn Ser Met Ala Gly Ser Pro
        195                 200                 205

Val Ser Ser Tyr Ser Ser Asp Glu Gly Ser Tyr Asp Pro Leu Ser Pro
210                 215                 220

Glu Glu Gln Glu Leu Leu Asp Phe Thr Asn Trp Phe Ala Thr Asn Phe
225                 230                 235                 240

Ser Leu Leu Lys Gln Ala Gly Asp Val Glu Glu Asn Pro Gly Pro Met
                245                 250                 255

Thr Leu Leu Gly Ser Glu His Ser Leu Leu Ile Arg Ser Lys Phe Arg
            260                 265                 270

Ser Val Leu Gln Leu Arg Leu Gln Gln Arg Arg Thr Gln Glu Gln Leu
        275                 280                 285

Ala Asn Gln Gly Ile Ile Pro Pro Leu Lys Arg Pro Ala Glu Phe His
        290                 295                 300

Glu Gln Arg Lys His Leu Asp Ser Asp Lys Ala Lys Asn Ser Leu Lys
305                 310                 315                 320

Arg Lys Ala Arg Asn Arg Cys Asn Ser Ala Asp Leu Val Asn Met His
                325                 330                 335

Ile Leu Gln Ala Ser Thr Ala Glu Arg Ser Ile Pro Thr Ala Gln Met
            340                 345                 350

Lys Leu Lys Arg Ala Arg Leu Ala Asp Asp Leu Asn Glu Lys Ile Ala
        355                 360                 365

Leu Arg Pro Gly Pro Leu Glu Leu Val Glu Lys Asn Ile Leu Pro Val
        370                 375                 380

Asp Ser Ala Val Lys Glu Ala Ile Lys Gly Asn Gln Val Ser Phe Ser
385                 390                 395                 400

Lys Ser Thr Asp Ala Phe Ala Phe Glu Glu Asp Ser Ser Ser Asp Gly
                405                 410                 415

Leu Ser Pro Asp Gln Thr Arg Ser Glu Asp Pro Gln Asn Ser Ala Gly
            420                 425                 430

Ser Pro Pro Asp Ala Lys Ala Ser Asp Thr Pro Ser Thr Gly Ser Leu
        435                 440                 445

Gly Thr Asn Gln Asp Leu Ala Ser Gly Ser Glu Asn Asp Arg Asn Asp
        450                 455                 460

Ser Ala Ser Gln Pro Ser His Gln Ser Asp Ala Gly Lys Gln Gly Leu
465                 470                 475                 480
```

```
Gly Pro Pro Ser Thr Pro Ile Ala Val His Ala Ala Val Lys Ser Lys
                485                 490                 495

Ser Leu Gly Asp Ser Lys Asn Arg His Lys Pro Lys Asp Pro Lys
        500                 505                 510

Pro Lys Val Lys Lys Leu Lys Tyr His Gln Tyr Ile Pro Pro Asp Gln
        515                 520                 525

Lys Ala Glu Lys Ser Pro Pro Met Asp Ser Ala Tyr Ala Arg Leu
530                 535                 540

Leu Gln Gln Gln Gln Leu Phe Leu Gln Leu Gln Ile Leu Ser Gln Gln
545                 550                 555                 560

Gln Gln Gln Gln Gln His Arg Phe Ser Tyr Leu Gly Met His Gln Ala
                565                 570                 575

Gln Leu Lys Glu Pro Asn Glu Gln Met Val Arg Asn Pro Asn Ser Ser
            580                 585                 590

Ser Thr Pro Leu Ser Asn Thr Pro Leu Ser Pro Val Lys Asn Ser Phe
        595                 600                 605

Ser Gly Gln Thr Gly Val Ser Ser Phe Lys Pro Gly Pro Leu Pro Pro
    610                 615                 620

Asn Leu Asp Asp Leu Lys Val Ser Glu Leu Arg Gln Gln Leu Arg Ile
625                 630                 635                 640

Arg Gly Leu Pro Val Ser Gly Thr Lys Thr Ala Leu Met Asp Arg Leu
                645                 650                 655

Arg Pro Phe Gln Asp Cys Ser Gly Asn Pro Val Pro Asn Phe Gly Asp
            660                 665                 670

Ile Thr Thr Val Thr Phe Pro Val Thr Pro Asn Thr Leu Pro Asn Tyr
        675                 680                 685

Gln Ser Ser Ser Ser Thr Ser Ala Leu Ser Asn Gly Phe Tyr His Phe
    690                 695                 700

Gly Ser Thr Ser Ser Ser Pro Pro Ile Ser Pro Ala Ser Ser Asp Leu
705                 710                 715                 720

Ser Val Ala Gly Ser Leu Pro Asp Thr Phe Asn Asp Ala Ser Pro Ser
                725                 730                 735

Phe Gly Leu His Pro Ser Pro Val His Val Cys Thr Glu Glu Ser Leu
            740                 745                 750

Met Ser Ser Leu Asn Gly Gly Ser Val Pro Ser Glu Leu Asp Gly Leu
        755                 760                 765

Asp Ser Glu Lys Asp Lys Met Leu Val Glu Lys Gln Lys Val Ile Asn
    770                 775                 780

Glu Leu Thr Trp Lys Leu Gln Gln Glu Gln Arg Gln Val Glu Glu Leu
785                 790                 795                 800

Arg Met Gln Leu Gln Lys Gln Lys Arg Asn Asn Cys Ser Glu Lys Lys
                805                 810                 815

Pro Leu Pro Phe Leu Ala Ala Ser Ile Lys Gln Glu Glu Ala Val Ser
            820                 825                 830

Ser Cys Pro Phe Ala Ser Gln Val Pro Val Lys Arg Gln Ser Ser Ser
        835                 840                 845

Ser Glu Cys His Pro Pro Ala Cys Glu Ala Ala Gln Leu Gln Pro Leu
    850                 855                 860

Gly Asn Ala His Cys Val Glu Ser Ser Asp Gln Thr Asn Val Leu Ser
865                 870                 875                 880

Ser Thr Phe Leu Ser Pro Gln Cys Ser Pro Gln His Ser Pro Leu Gly
                885                 890                 895

Ala Val Lys Ser Pro Gln His Ile Ser Leu Pro Pro Ser Pro Asn Asn
```

```
                    900             905             910
Pro His Phe Leu Pro Ser Ser Ser Gly Ala Gln Gly Glu Gly His Arg
            915                 920             925

Val Ser Ser Pro Ile Ser Ser Gln Val Cys Thr Ala Gln Asn Ser Gly
        930                 935             940

Ala His Asp Gly His Pro Ser Phe Ser Pro His Ser Ser Ser Leu
945                 950             955                 960

His Pro Pro Phe Ser Gly Ala Gln Ala Asp Ser Ser His Gly Ala Gly
            965                 970             975

Gly Asn Pro Cys Pro Lys Ser Pro Cys Val Gln Gln Lys Met Ala Gly
            980                 985             990

Leu His Ser Ser Asp Lys Val Gly Pro Lys Phe Ser Ile Pro Ser Pro
        995                 1000            1005

Thr Phe Ser Lys Ser Ser Ser Ala Ile Ser Glu Val Thr Gln Pro
    1010                1015                1020

Pro Ser Tyr Glu Asp Ala Val Lys Gln Gln Met Thr Arg Ser Gln
    1025                1030                1035

Gln Met Asp Glu Leu Leu Asp Val Leu Ile Glu Ser Gly Glu Met
    1040                1045                1050

Pro Ala Asp Ala Arg Glu Asp His Ser Cys Leu Gln Lys Val Pro
    1055                1060                1065

Lys Ile Pro Arg Ser Ser Arg Ser Pro Thr Ala Val Leu Thr Lys
    1070                1075                1080

Pro Ser Ala Ser Phe Glu Gln Ala Ser Ser Gly Ser Gln Ile Pro
    1085                1090                1095

Phe Asp Pro Tyr Ala Thr Asp Ser Asp Glu His Leu Glu Val Leu
    1100                1105                1110

Leu Asn Ser Gln Ser Pro Leu Gly Lys Met Ser Asp Val Thr Leu
    1115                1120                1125

Leu Lys Ile Gly Ser Glu Glu Pro His Phe Asp Gly Ile Met Asp
    1130                1135                1140

Gly Phe Ser Gly Lys Ala Ala Glu Asp Leu Phe Asn Ala His Glu
    1145                1150                1155

Ile Leu Pro Gly Pro Leu Ser Pro Met Gln Thr Gln Phe Ser Pro
    1160                1165                1170

Ser Ser Val Asp Ser Asn Gly Leu Gln Leu Ser Phe Thr Glu Ser
    1175                1180                1185

Pro Trp Glu Thr Met Glu Trp Leu Asp Leu Thr Pro Pro Asn Ser
    1190                1195                1200

Thr Pro Gly Phe Ser Ala Leu Thr Thr Ser Ser Pro Ser Ile Phe
    1205                1210                1215

Asn Ile Asp Phe Leu Asp Val Thr Asp Leu Asn Leu Asn Ser Ser
    1220                1225                1230

Met Asp Leu His Leu Gln Gln Trp
    1235                1240

<210> SEQ ID NO 62
<211> LENGTH: 1247
<212> TYPE: PRT
<213> ORGANISM: Artificial Sequence
<220> FEATURE:
<223> OTHER INFORMATION: MYF6-2A-MYOCD

<400> SEQUENCE: 62

Met Met Met Asp Leu Phe Glu Thr Gly Ser Tyr Phe Phe Tyr Leu Asp
```

```
1               5                   10                  15
Gly Glu Asn Val Thr Leu Gln Pro Leu Glu Val Ala Glu Gly Ser Pro
                20                  25                  30

Leu Tyr Pro Gly Ser Asp Gly Thr Leu Ser Pro Cys Gln Asp Gln Met
            35                  40                  45

Pro Pro Glu Ala Gly Ser Asp Ser Ser Gly Glu Glu His Val Leu Ala
50                      55                  60

Pro Pro Gly Leu Gln Pro Pro His Cys Pro Gly Gln Cys Leu Ile Trp
65                  70                  75                  80

Ala Cys Lys Thr Cys Lys Arg Lys Ser Ala Pro Thr Asp Arg Arg Lys
                85                  90                  95

Ala Ala Thr Leu Arg Glu Arg Arg Leu Lys Lys Ile Asn Glu Ala
                    100                 105                 110

Phe Glu Ala Leu Lys Arg Arg Thr Val Ala Asn Pro Asn Gln Arg Leu
                115                 120                 125

Pro Lys Val Glu Ile Leu Arg Ser Ala Ile Ser Tyr Ile Glu Arg Leu
            130                 135                 140

Gln Asp Leu Leu His Arg Leu Asp Gln Gln Glu Lys Met Gln Glu Leu
145                 150                 155                 160

Gly Val Asp Pro Phe Ser Tyr Arg Pro Lys Gln Glu Asn Leu Glu Gly
                165                 170                 175

Ala Asp Phe Leu Arg Thr Cys Ser Ser Gln Trp Pro Ser Val Ser Asp
                180                 185                 190

His Ser Arg Gly Leu Val Ile Thr Ala Lys Glu Gly Gly Ala Ser Ile
            195                 200                 205

Asp Ser Ser Ala Ser Ser Ser Leu Arg Cys Leu Ser Ser Ile Val Asp
    210                 215                 220

Ser Ile Ser Ser Glu Glu Arg Lys Leu Pro Cys Val Glu Glu Val Val
225                 230                 235                 240

Glu Lys Ala Thr Asn Phe Ser Leu Leu Lys Gln Ala Gly Asp Val Glu
                245                 250                 255

Glu Asn Pro Gly Pro Met Thr Leu Leu Gly Ser Glu His Ser Leu Leu
                260                 265                 270

Ile Arg Ser Lys Phe Arg Ser Val Leu Gln Leu Arg Leu Gln Gln Arg
            275                 280                 285

Arg Thr Gln Glu Gln Leu Ala Asn Gln Gly Ile Ile Pro Pro Leu Lys
            290                 295                 300

Arg Pro Ala Glu Phe His Glu Gln Arg Lys His Leu Asp Ser Asp Lys
305                 310                 315                 320

Ala Lys Asn Ser Leu Lys Arg Lys Ala Arg Asn Arg Cys Asn Ser Ala
                325                 330                 335

Asp Leu Val Asn Met His Ile Leu Gln Ala Ser Thr Ala Glu Arg Ser
                340                 345                 350

Ile Pro Thr Ala Gln Met Lys Leu Lys Arg Ala Arg Leu Ala Asp Asp
                355                 360                 365

Leu Asn Glu Lys Ile Ala Leu Arg Pro Gly Pro Leu Glu Leu Val Glu
            370                 375                 380

Lys Asn Ile Leu Pro Val Asp Ser Ala Val Lys Glu Ala Ile Lys Gly
385                 390                 395                 400

Asn Gln Val Ser Phe Ser Lys Ser Thr Asp Ala Phe Ala Phe Glu Glu
                405                 410                 415

Asp Ser Ser Ser Asp Gly Leu Ser Pro Asp Gln Thr Arg Ser Glu Asp
            420                 425                 430
```

```
Pro Gln Asn Ser Ala Gly Ser Pro Asp Ala Lys Ala Ser Asp Thr
        435                 440                 445
Pro Ser Thr Gly Ser Leu Gly Thr Asn Gln Asp Leu Ala Ser Gly Ser
    450                 455                 460
Glu Asn Asp Arg Asn Asp Ser Ala Ser Gln Pro Ser His Gln Ser Asp
465                 470                 475                 480
Ala Gly Lys Gln Gly Leu Gly Pro Pro Ser Thr Pro Ile Ala Val His
                485                 490                 495
Ala Ala Val Lys Ser Lys Ser Leu Gly Asp Ser Lys Asn Arg His Lys
            500                 505                 510
Lys Pro Lys Asp Pro Lys Pro Lys Val Lys Lys Leu Lys Tyr His Gln
        515                 520                 525
Tyr Ile Pro Pro Asp Gln Lys Ala Glu Lys Ser Pro Pro Pro Met Asp
    530                 535                 540
Ser Ala Tyr Ala Arg Leu Leu Gln Gln Gln Gln Leu Phe Leu Gln Leu
545                 550                 555                 560
Gln Ile Leu Ser Gln Gln Gln Gln Gln Gln His Arg Phe Ser Tyr
                565                 570                 575
Leu Gly Met His Gln Ala Gln Leu Lys Glu Pro Asn Glu Gln Met Val
            580                 585                 590
Arg Asn Pro Asn Ser Ser Ser Thr Pro Leu Ser Asn Thr Pro Leu Ser
        595                 600                 605
Pro Val Lys Asn Ser Phe Ser Gly Gln Thr Gly Val Ser Ser Phe Lys
    610                 615                 620
Pro Gly Pro Leu Pro Pro Asn Leu Asp Asp Leu Lys Val Ser Glu Leu
625                 630                 635                 640
Arg Gln Gln Leu Arg Ile Arg Gly Leu Pro Val Ser Gly Thr Lys Thr
                645                 650                 655
Ala Leu Met Asp Arg Leu Arg Pro Phe Gln Asp Cys Ser Gly Asn Pro
            660                 665                 670
Val Pro Asn Phe Gly Asp Ile Thr Thr Val Thr Phe Pro Val Thr Pro
        675                 680                 685
Asn Thr Leu Pro Asn Tyr Gln Ser Ser Ser Thr Ser Ala Leu Ser
    690                 695                 700
Asn Gly Phe Tyr His Phe Gly Ser Thr Ser Ser Ser Pro Pro Ile Ser
705                 710                 715                 720
Pro Ala Ser Ser Asp Leu Ser Val Ala Gly Ser Leu Pro Asp Thr Phe
                725                 730                 735
Asn Asp Ala Ser Pro Ser Phe Gly Leu His Pro Ser Pro Val His Val
            740                 745                 750
Cys Thr Glu Glu Ser Leu Met Ser Ser Leu Asn Gly Gly Ser Val Pro
        755                 760                 765
Ser Glu Leu Asp Gly Leu Asp Ser Glu Lys Asp Lys Met Leu Val Glu
    770                 775                 780
Lys Gln Lys Val Ile Asn Glu Leu Thr Trp Lys Leu Gln Gln Glu Gln
785                 790                 795                 800
Arg Gln Val Glu Glu Leu Arg Met Gln Leu Gln Lys Gln Lys Arg Asn
                805                 810                 815
Asn Cys Ser Glu Lys Lys Pro Leu Pro Phe Leu Ala Ala Ser Ile Lys
            820                 825                 830
Gln Glu Glu Ala Val Ser Ser Cys Pro Phe Ala Ser Gln Val Pro Val
        835                 840                 845
```

```
Lys Arg Gln Ser Ser Ser Ser Glu Cys His Pro Pro Ala Cys Glu Ala
850                 855                 860

Ala Gln Leu Gln Pro Leu Gly Asn Ala His Cys Val Glu Ser Ser Asp
865                 870                 875                 880

Gln Thr Asn Val Leu Ser Ser Thr Phe Leu Ser Pro Gln Cys Ser Pro
                885                 890                 895

Gln His Ser Pro Leu Gly Ala Val Lys Ser Pro Gln His Ile Ser Leu
            900                 905                 910

Pro Pro Ser Pro Asn Asn Pro His Phe Leu Pro Ser Ser Gly Ala
        915                 920                 925

Gln Gly Glu Gly His Arg Val Ser Ser Pro Ile Ser Ser Gln Val Cys
930                 935                 940

Thr Ala Gln Asn Ser Gly Ala His Asp Gly His Pro Pro Ser Phe Ser
945                 950                 955                 960

Pro His Ser Ser Ser Leu His Pro Pro Phe Ser Gly Ala Gln Ala Asp
                965                 970                 975

Ser Ser His Gly Ala Gly Gly Asn Pro Cys Pro Lys Ser Pro Cys Val
            980                 985                 990

Gln Gln Lys Met Ala Gly Leu His Ser Ser Asp Lys Val Gly Pro Lys
            995                 1000                1005

Phe Ser Ile Pro Ser Pro Thr Phe Ser Lys Ser Ser Ser Ala Ile
1010                1015                1020

Ser Glu Val Thr Gln Pro Pro Ser Tyr Glu Asp Ala Val Lys Gln
1025                1030                1035

Gln Met Thr Arg Ser Gln Gln Met Asp Glu Leu Leu Asp Val Leu
1040                1045                1050

Ile Glu Ser Gly Glu Met Pro Ala Asp Ala Arg Glu Asp His Ser
1055                1060                1065

Cys Leu Gln Lys Val Pro Lys Ile Pro Arg Ser Ser Arg Ser Pro
1070                1075                1080

Thr Ala Val Leu Thr Lys Pro Ser Ala Ser Phe Glu Gln Ala Ser
1085                1090                1095

Ser Gly Ser Gln Ile Pro Phe Asp Pro Tyr Ala Thr Asp Ser Asp
1100                1105                1110

Glu His Leu Glu Val Leu Leu Asn Ser Gln Ser Pro Leu Gly Lys
1115                1120                1125

Met Ser Asp Val Thr Leu Leu Lys Ile Gly Ser Glu Glu Pro His
1130                1135                1140

Phe Asp Gly Ile Met Asp Gly Phe Ser Gly Lys Ala Ala Glu Asp
1145                1150                1155

Leu Phe Asn Ala His Glu Ile Leu Pro Gly Pro Leu Ser Pro Met
1160                1165                1170

Gln Thr Gln Phe Ser Pro Ser Ser Val Asp Ser Asn Gly Leu Gln
1175                1180                1185

Leu Ser Phe Thr Glu Ser Pro Trp Glu Thr Met Glu Trp Leu Asp
1190                1195                1200

Leu Thr Pro Pro Asn Ser Thr Pro Gly Phe Ser Ala Leu Thr Thr
1205                1210                1215

Ser Ser Pro Ser Ile Phe Asn Ile Asp Phe Leu Asp Val Thr Asp
1220                1225                1230

Leu Asn Leu Asn Ser Ser Met Asp Leu His Leu Gln Gln Trp
1235                1240                1245
```

<210> SEQ ID NO 63
<211> LENGTH: 1037
<212> TYPE: PRT
<213> ORGANISM: Artificial Sequence
<220> FEATURE:
<223> OTHER INFORMATION: ASCL1-2A-Mydelta3

<400> SEQUENCE: 63

```
Met Glu Ser Ser Ala Lys Met Glu Ser Gly Gly Ala Gly Gln Gln Pro
1               5                   10                  15

Gln Pro Gln Pro Gln Gln Pro Phe Leu Pro Pro Ala Ala Cys Phe Phe
            20                  25                  30

Ala Thr Ala Ala Ala Ala Ala Ala Ala Ala Ala Ala Ala Ala Ala Gln
        35                  40                  45

Ser Ala Gln Gln Gln Gln Gln Gln Gln Gln Gln Gln Gln Gln Ala Pro
    50                  55                  60

Gln Leu Arg Pro Ala Ala Asp Gly Gln Pro Ser Gly Gly Gly His Lys
65                  70                  75                  80

Ser Ala Pro Lys Gln Val Lys Arg Gln Arg Ser Ser Ser Pro Glu Leu
                85                  90                  95

Met Arg Cys Lys Arg Arg Leu Asn Phe Ser Gly Phe Gly Tyr Ser Leu
            100                 105                 110

Pro Gln Gln Gln Pro Ala Ala Val Ala Arg Arg Asn Glu Arg Glu Arg
        115                 120                 125

Asn Arg Val Lys Leu Val Asn Leu Gly Phe Ala Thr Leu Arg Glu His
    130                 135                 140

Val Pro Asn Gly Ala Ala Asn Lys Lys Met Ser Lys Val Glu Thr Leu
145                 150                 155                 160

Arg Ser Ala Val Glu Tyr Ile Arg Ala Leu Gln Gln Leu Leu Asp Glu
                165                 170                 175

His Asp Ala Val Ser Ala Ala Phe Gln Ala Gly Val Leu Ser Pro Thr
            180                 185                 190

Ile Ser Pro Asn Tyr Ser Asn Asp Leu Asn Ser Met Ala Gly Ser Pro
        195                 200                 205

Val Ser Ser Tyr Ser Ser Asp Glu Gly Ser Tyr Asp Pro Leu Ser Pro
    210                 215                 220

Glu Glu Gln Glu Leu Leu Asp Phe Thr Asn Trp Phe Ala Thr Asn Phe
225                 230                 235                 240

Ser Leu Leu Lys Gln Ala Gly Asp Val Glu Glu Asn Pro Gly Pro Met
                245                 250                 255

Thr Leu Leu Gly Ser Glu His Ser Leu Leu Ile Arg Ser Lys Phe Arg
            260                 265                 270

Ser Val Leu Gln Leu Arg Leu Gln Gln Arg Arg Thr Gln Glu Gln Leu
        275                 280                 285

Ala Asn Gln Gly Ile Ile Pro Pro Leu Lys Arg Pro Ala Glu Phe His
    290                 295                 300

Glu Gln Arg Lys His Leu Asp Ser Asp Lys Ala Lys Asn Ser Leu Lys
305                 310                 315                 320

Arg Lys Ala Arg Asn Arg Cys Asn Ser Ala Asp Leu Val Asn Met His
                325                 330                 335

Ile Leu Gln Ala Ser Thr Ala Glu Arg Ser Ile Pro Thr Ala Gln Met
            340                 345                 350

Lys Leu Lys Arg Ala Arg Leu Ala Asp Asp Leu Asn Glu Lys Ile Ala
        355                 360                 365

Leu Arg Pro Gly Pro Leu Glu Leu Val Glu Lys Asn Ile Leu Pro Val
```

```
            370                 375                 380
Asp Ser Ala Val Lys Glu Ala Ile Lys Gly Asn Gln Val Ser Phe Ser
385                 390                 395                 400

Lys Ser Thr Asp Ala Phe Ala Phe Glu Glu Asp Ser Ser Ser Asp Gly
                405                 410                 415

Leu Ser Pro Asp Gln Thr Arg Ser Glu Asp Pro Gln Asn Ser Ala Gly
                420                 425                 430

Ser Pro Pro Asp Ala Lys Ala Ser Asp Thr Pro Ser Thr Gly Ser Leu
                435                 440                 445

Gly Thr Asn Gln Asp Leu Ala Ser Gly Ser Glu Asn Asp Arg Asn Asp
            450                 455                 460

Ser Ala Ser Gln Pro Ser His Gln Ser Asp Ala Gly Lys Gln Gly Leu
465                 470                 475                 480

Gly Pro Pro Ser Thr Pro Ile Ala Val His Ala Ala Val Lys Ser Lys
                485                 490                 495

Ser Leu Gly Asp Ser Lys Asn Arg His Lys Lys Pro Lys Asp Pro Lys
                500                 505                 510

Pro Lys Val Lys Lys Leu Lys Tyr His Gln Tyr Ile Pro Pro Asp Gln
                515                 520                 525

Lys Ala Glu Lys Ser Pro Pro Met Asp Ser Ala Tyr Ala Arg Leu
530                 535                 540

Leu Gln Gln Gln Leu Phe Leu Gln Leu Gln Ile Leu Ser Gln Gln
545                 550                 555                 560

Gln Gln Gln Gln Gln His Arg Phe Ser Tyr Leu Gly Met His Gln Ala
                565                 570                 575

Gln Leu Lys Glu Pro Asn Glu Gln Met Val Arg Asn Pro Asn Ser Ser
            580                 585                 590

Ser Thr Pro Leu Ser Asn Thr Pro Leu Ser Pro Val Lys Asn Ser Phe
            595                 600                 605

Ser Gly Gln Thr Gly Val Ser Ser Phe Lys Pro Gly Pro Leu Pro Pro
            610                 615                 620

Asn Leu Asp Asp Leu Lys Val Ser Glu Leu Arg Gln Gln Leu Arg Ile
625                 630                 635                 640

Arg Gly Leu Pro Val Ser Gly Thr Lys Thr Ala Leu Met Asp Arg Leu
                645                 650                 655

Arg Pro Phe Gln Asp Cys Ser Gly Asn Pro Val Pro Asn Phe Gly Asp
                660                 665                 670

Ile Thr Thr Val Thr Phe Pro Val Thr Pro Asn Thr Leu Pro Asn Tyr
                675                 680                 685

Gln Ser Ser Ser Thr Ser Ala Leu Ser Asn Gly Phe Tyr His Phe
690                 695                 700

Gly Ser Thr Ser Ser Pro Pro Ile Ser Pro Ala Ser Ser Asp Leu
705                 710                 715                 720

Ser Val Ala Gly Ser Leu Pro Asp Thr Phe Asn Asp Ala Ser Pro Ser
                725                 730                 735

Phe Gly Leu His Pro Ser Pro Val His Val Cys Thr Glu Glu Ser Leu
                740                 745                 750

Met Ser Ser Leu Asn Gly Gly Ser Val Pro Ser Glu Leu Asp Gly Leu
                755                 760                 765

Asp Ser Glu Lys Asp Lys Met Leu Val Glu Lys Gln Lys Val Ile Asn
                770                 775                 780

Glu Leu Thr Trp Lys Leu Gln Gln Glu Gln Arg Gln Val Glu Glu Leu
785                 790                 795                 800
```

Arg Met Gln Leu Gln Lys Gln Lys Arg Asn Asn Cys Ser Glu Glu Val
            805                 810                 815

Thr Gln Pro Pro Ser Tyr Glu Asp Ala Val Lys Gln Gln Met Thr Arg
            820                 825                 830

Ser Gln Gln Met Asp Glu Leu Leu Asp Val Leu Ile Glu Ser Gly Glu
            835                 840                 845

Met Pro Ala Asp Ala Arg Glu Asp His Ser Cys Leu Gln Lys Val Pro
850                 855                 860

Lys Ile Pro Arg Ser Arg Ser Pro Thr Ala Val Leu Thr Lys Pro
865                 870                 875                 880

Ser Ala Ser Phe Glu Gln Ala Ser Gly Ser Gln Ile Pro Phe Asp
            885                 890                 895

Pro Tyr Ala Thr Asp Ser Asp Glu His Leu Glu Val Leu Leu Asn Ser
            900                 905                 910

Gln Ser Pro Leu Gly Lys Met Ser Asp Val Thr Leu Leu Lys Ile Gly
            915                 920                 925

Ser Glu Glu Pro His Phe Asp Gly Ile Met Asp Gly Phe Ser Gly Lys
            930                 935                 940

Ala Ala Glu Asp Leu Phe Asn Ala His Glu Ile Leu Pro Gly Pro Leu
945                 950                 955                 960

Ser Pro Met Gln Thr Gln Phe Ser Pro Ser Ser Val Asp Ser Asn Gly
            965                 970                 975

Leu Gln Leu Ser Phe Thr Glu Ser Pro Trp Glu Thr Met Glu Trp Leu
            980                 985                 990

Asp Leu Thr Pro Pro Asn Ser Thr Pro Gly Phe Ser Ala Leu Thr Thr
            995                 1000                1005

Ser Ser  Pro Ser Ile Phe Asn  Ile Asp Phe Leu Asp  Val Thr Asp
    1010                1015                1020

Leu Asn  Leu Asn Ser Ser Met  Asp Leu His Leu Gln  Gln Trp
    1025                1030                1035

<210> SEQ ID NO 64
<211> LENGTH: 1043
<212> TYPE: PRT
<213> ORGANISM: Artificial Sequence
<220> FEATURE:
<223> OTHER INFORMATION: MYF6-2A-Mydelta3

<400> SEQUENCE: 64

Met Met Met Asp Leu Phe Glu Thr Gly Ser Tyr Phe Phe Tyr Leu Asp
1               5                   10                  15

Gly Glu Asn Val Thr Leu Gln Pro Leu Glu Val Ala Glu Gly Ser Pro
            20                  25                  30

Leu Tyr Pro Gly Ser Asp Gly Thr Leu Ser Pro Cys Gln Asp Gln Met
            35                  40                  45

Pro Pro Glu Ala Gly Ser Asp Ser Ser Gly Glu Glu His Val Leu Ala
        50                  55                  60

Pro Pro Gly Leu Gln Pro Pro His Cys Pro Gly Gln Cys Leu Ile Trp
65                  70                  75                  80

Ala Cys Lys Thr Cys Lys Arg Lys Ser Ala Pro Thr Asp Arg Arg Lys
                85                  90                  95

Ala Ala Thr Leu Arg Glu Arg Arg Arg Leu Lys Lys Ile Asn Glu Ala
            100                 105                 110

Phe Glu Ala Leu Lys Arg Arg Thr Val Ala Asn Pro Asn Gln Arg Leu
            115                 120                 125

```
Pro Lys Val Glu Ile Leu Arg Ser Ala Ile Ser Tyr Ile Glu Arg Leu
    130                 135                 140

Gln Asp Leu Leu His Arg Leu Asp Gln Gln Glu Lys Met Gln Glu Leu
145                 150                 155                 160

Gly Val Asp Pro Phe Ser Tyr Arg Pro Lys Gln Glu Asn Leu Glu Gly
                165                 170                 175

Ala Asp Phe Leu Arg Thr Cys Ser Ser Gln Trp Pro Ser Val Ser Asp
            180                 185                 190

His Ser Arg Gly Leu Val Ile Thr Ala Lys Glu Gly Ala Ser Ile
        195                 200                 205

Asp Ser Ser Ala Ser Ser Leu Arg Cys Leu Ser Ser Ile Val Asp
    210                 215                 220

Ser Ile Ser Ser Glu Glu Arg Lys Leu Pro Cys Val Glu Val Val
225                 230                 235                 240

Glu Lys Ala Thr Asn Phe Ser Leu Leu Lys Gln Ala Gly Asp Val Glu
                245                 250                 255

Glu Asn Pro Gly Pro Met Thr Leu Leu Gly Ser Glu His Ser Leu Leu
            260                 265                 270

Ile Arg Ser Lys Phe Arg Ser Val Leu Gln Leu Arg Leu Gln Gln Arg
        275                 280                 285

Arg Thr Gln Glu Gln Leu Ala Asn Gln Gly Ile Ile Pro Pro Leu Lys
290                 295                 300

Arg Pro Ala Glu Phe His Glu Gln Arg Lys His Leu Asp Ser Asp Lys
305                 310                 315                 320

Ala Lys Asn Ser Leu Lys Arg Lys Ala Arg Asn Arg Cys Asn Ser Ala
                325                 330                 335

Asp Leu Val Asn Met His Ile Leu Gln Ala Ser Thr Ala Glu Arg Ser
            340                 345                 350

Ile Pro Thr Ala Gln Met Lys Leu Lys Arg Ala Arg Leu Ala Asp Asp
        355                 360                 365

Leu Asn Glu Lys Ile Ala Leu Arg Pro Gly Pro Leu Glu Leu Val Glu
370                 375                 380

Lys Asn Ile Leu Pro Val Asp Ser Ala Val Lys Glu Ala Ile Lys Gly
385                 390                 395                 400

Asn Gln Val Ser Phe Ser Lys Ser Thr Asp Ala Phe Ala Phe Glu Glu
                405                 410                 415

Asp Ser Ser Ser Asp Gly Leu Ser Pro Asp Gln Thr Arg Ser Glu Asp
            420                 425                 430

Pro Gln Asn Ser Ala Gly Ser Pro Asp Ala Lys Ala Ser Asp Thr
        435                 440                 445

Pro Ser Thr Gly Ser Leu Gly Thr Asn Gln Asp Leu Ala Ser Gly Ser
450                 455                 460

Glu Asn Asp Arg Asn Asp Ser Ala Ser Gln Pro Ser His Gln Ser Asp
465                 470                 475                 480

Ala Gly Lys Gln Gly Leu Gly Pro Pro Ser Thr Pro Ile Ala Val His
                485                 490                 495

Ala Ala Val Lys Ser Lys Ser Leu Gly Asp Ser Lys Asn Arg His Lys
            500                 505                 510

Lys Pro Lys Asp Pro Lys Pro Lys Val Lys Lys Leu Lys Tyr His Gln
        515                 520                 525

Tyr Ile Pro Pro Asp Gln Lys Ala Glu Lys Ser Pro Pro Pro Met Asp
530                 535                 540
```

```
Ser Ala Tyr Ala Arg Leu Leu Gln Gln Gln Leu Phe Leu Gln Leu
545                 550                 555                 560

Gln Ile Leu Ser Gln Gln Gln Gln Gln His Arg Phe Ser Tyr
            565                 570                 575

Leu Gly Met His Gln Ala Gln Leu Lys Glu Pro Asn Glu Gln Met Val
                580                 585                 590

Arg Asn Pro Asn Ser Ser Thr Pro Leu Ser Asn Thr Pro Leu Ser
        595                 600                 605

Pro Val Lys Asn Ser Phe Ser Gly Gln Thr Gly Val Ser Ser Phe Lys
        610                 615                 620

Pro Gly Pro Leu Pro Pro Asn Leu Asp Asp Leu Lys Val Ser Glu Leu
625                 630                 635                 640

Arg Gln Gln Leu Arg Ile Arg Gly Leu Pro Val Ser Gly Thr Lys Thr
                645                 650                 655

Ala Leu Met Asp Arg Leu Arg Pro Phe Gln Asp Cys Ser Gly Asn Pro
            660                 665                 670

Val Pro Asn Phe Gly Asp Ile Thr Thr Val Thr Phe Pro Val Thr Pro
        675                 680                 685

Asn Thr Leu Pro Asn Tyr Gln Ser Ser Ser Thr Ser Ala Leu Ser
        690                 695                 700

Asn Gly Phe Tyr His Phe Gly Ser Thr Ser Ser Ser Pro Pro Ile Ser
705                 710                 715                 720

Pro Ala Ser Ser Asp Leu Ser Val Ala Gly Ser Leu Pro Asp Thr Phe
                725                 730                 735

Asn Asp Ala Ser Pro Ser Phe Gly Leu His Pro Ser Pro Val His Val
            740                 745                 750

Cys Thr Glu Glu Ser Leu Met Ser Ser Leu Asn Gly Gly Ser Val Pro
            755                 760                 765

Ser Glu Leu Asp Gly Leu Asp Ser Glu Lys Asp Lys Met Leu Val Glu
            770                 775                 780

Lys Gln Lys Val Ile Asn Glu Leu Thr Trp Lys Leu Gln Gln Glu Gln
785                 790                 795                 800

Arg Gln Val Glu Glu Leu Arg Met Gln Leu Gln Lys Gln Lys Arg Asn
                805                 810                 815

Asn Cys Ser Glu Glu Val Thr Gln Pro Pro Ser Tyr Glu Asp Ala Val
            820                 825                 830

Lys Gln Gln Met Thr Arg Ser Gln Gln Met Asp Glu Leu Leu Asp Val
            835                 840                 845

Leu Ile Glu Ser Gly Glu Met Pro Ala Asp Ala Arg Glu Asp His Ser
850                 855                 860

Cys Leu Gln Lys Val Pro Lys Ile Pro Arg Ser Ser Arg Ser Pro Thr
865                 870                 875                 880

Ala Val Leu Thr Lys Pro Ser Ala Ser Phe Glu Gln Ala Ser Ser Gly
                885                 890                 895

Ser Gln Ile Pro Phe Asp Pro Tyr Ala Thr Asp Ser Asp Glu His Leu
            900                 905                 910

Glu Val Leu Leu Asn Ser Gln Ser Pro Leu Gly Lys Met Ser Asp Val
            915                 920                 925

Thr Leu Leu Lys Ile Gly Ser Glu Glu Pro His Phe Asp Gly Ile Met
            930                 935                 940

Asp Gly Phe Ser Gly Lys Ala Ala Glu Asp Leu Phe Asn Ala His Glu
945                 950                 955                 960

Ile Leu Pro Gly Pro Leu Ser Pro Met Gln Thr Gln Phe Ser Pro Ser
```

```
                    965                 970                 975
Ser Val Asp Ser Asn Gly Leu Gln Leu Ser Phe Thr Glu Ser Pro Trp
            980                 985                 990

Glu Thr Met Glu Trp Leu Asp Leu  Thr Pro Pro Asn Ser  Thr Pro Gly
        995                 1000                1005

Phe Ser  Ala Leu Thr Thr Ser  Ser Pro Ser Ile Phe  Asn Ile Asp
    1010                1015                1020

Phe Leu  Asp Val Thr Asp Leu  Asn Leu Asn Ser Ser  Met Asp Leu
    1025                1030                1035

His Leu  Gln Gln Trp
    1040

<210> SEQ ID NO 65
<211> LENGTH: 7
<212> TYPE: PRT
<213> ORGANISM: Artificial Sequence
<220> FEATURE:
<223> OTHER INFORMATION: Made in Lab - AAV capsid insert

<400> SEQUENCE: 65

Asn Lys Ile Gln Arg Thr Asp
1               5

<210> SEQ ID NO 66
<211> LENGTH: 7
<212> TYPE: PRT
<213> ORGANISM: Artificial Sequence
<220> FEATURE:
<223> OTHER INFORMATION: Made in Lab - AAV capsid insert

<400> SEQUENCE: 66

Asn Lys Thr Thr Asn Lys Asp
1               5

<210> SEQ ID NO 67
<211> LENGTH: 615
<212> TYPE: DNA
<213> ORGANISM: Artificial Sequence
<220> FEATURE:
<223> OTHER INFORMATION: Made in Lab - CAG promoter

<400> SEQUENCE: 67
ataacttacg gtaaatggcc cgcctggctg accgcccaac gacccccgcc cattgacgtc      60
aataatgacg tatgttccca tagtaacgcc aatagggact ttccattgac gtcaatgggt     120
ggagtattta cggtaaactg cccacttggc agtacatcaa gtgtatcata tgccaagtac     180
gccccctatt gacgtcaatg acggtaaatg gcccgcctgg cattatgccc agtacatgac     240
cttatgggac tttcctactt ggcagtacat ctactcgagg ccacgttctg cttcactctc     300
cccatctccc cccccteeee accccceaatt ttgtatttat ttattttttta attatttttgt     360 gcagcgatgg gggcgggggg ggggggggggg cgcgcgccag gcggggcggg gcggggcgag     420
gggcggggcg gggcgaggcg gagaggtgcg gcggcagcca atcagagcgg cgcgctccga     480
aagtttcctt ttatggcgag gcggcggcgg cggcggccct ataaaaagcg aagcgcgcgg     540
cgggcgggag cgggatcagc caccgcggtg gcggcctaga gtcgacgagg aactgaaaaa     600
ccagaaagtt aactg                                                      615

<210> SEQ ID NO 68
<211> LENGTH: 81
<212> TYPE: DNA
```

<213> ORGANISM: Artificial Sequence
<220> FEATURE:
<223> OTHER INFORMATION: Made in Lab - SCP promoter

<400> SEQUENCE: 68

```
gtacttatat aaggggggtgg gggcgcgttc gtcctcagtc gcgatcgaac actcgagccg    60
agcagacgtg cctacggacc g                                              81
```

<210> SEQ ID NO 69
<211> LENGTH: 96
<212> TYPE: DNA
<213> ORGANISM: Human betaherpesvirus 5

<400> SEQUENCE: 69

```
gtaagtaccg cctatagact ctataggcac accccttttgg ctcttatgca tgctgacaga   60
ctaacagact gttcctttcc tgggtctttt ctgcag                              96
```

<210> SEQ ID NO 70
<211> LENGTH: 724
<212> TYPE: PRT
<213> ORGANISM: Adeno-associated virus 5

<400> SEQUENCE: 70

```
Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
```

```
                260             265             270
Phe Asp Phe Asn Arg Phe His Ser His Trp Ser Pro Arg Asp Trp Gln
            275                 280             285
Arg Leu Ile Asn Asn Tyr Trp Gly Phe Arg Pro Arg Ser Leu Arg Val
        290              295            300
Lys Ile Phe Asn Ile Gln Val Lys Glu Val Thr Val Gln Asp Ser Thr
305             310              315                 320
Thr Thr Ile Ala Asn Asn Leu Thr Ser Thr Val Gln Val Phe Thr Asp
                325             330                 335
Asp Asp Tyr Gln Leu Pro Tyr Val Val Gly Asn Gly Thr Glu Gly Cys
            340             345             350
Leu Pro Ala Phe Pro Pro Gln Val Phe Thr Leu Pro Gln Tyr Gly Tyr
        355             360             365
Ala Thr Leu Asn Arg Asp Asn Thr Glu Asn Pro Thr Glu Arg Ser Ser
    370             375             380
Phe Phe Cys Leu Glu Tyr Phe Pro Ser Lys Met Leu Arg Thr Gly Asn
385             390             395             400
Asn Phe Glu Phe Thr Tyr Asn Phe Glu Glu Val Pro Phe His Ser Ser
            405             410             415
Phe Ala Pro Ser Gln Asn Leu Phe Lys Leu Ala Asn Pro Leu Val Asp
                420             425             430
Gln Tyr Leu Tyr Arg Phe Val Ser Thr Asn Asn Thr Gly Gly Val Gln
            435             440             445
Phe Asn Lys Asn Leu Ala Gly Arg Tyr Ala Asn Thr Tyr Lys Asn Trp
450             455             460
Phe Pro Gly Pro Met Gly Arg Thr Gln Gly Trp Asn Leu Gly Ser Gly
465             470             475             480
Val Asn Arg Ala Ser Val Ser Ala Phe Ala Thr Thr Asn Arg Met Glu
                485             490             495
Leu Glu Gly Ala Ser Tyr Gln Val Pro Pro Gln Pro Asn Gly Met Thr
            500             505             510
Asn Asn Leu Gln Gly Ser Asn Thr Tyr Ala Leu Glu Asn Thr Met Ile
            515             520             525
Phe Asn Ser Gln Pro Ala Asn Pro Gly Thr Thr Ala Thr Tyr Leu Glu
        530             535             540
Gly Asn Met Leu Ile Thr Ser Glu Ser Glu Thr Gln Pro Val Asn Arg
545             550             555             560
Val Ala Tyr Asn Val Gly Gly Gln Met Ala Thr Asn Asn Gln Ser Ser
                565             570             575
Thr Thr Ala Pro Ala Thr Gly Thr Tyr Asn Leu Gln Glu Ile Val Pro
            580             585             590
Gly Ser Val Trp Met Glu Arg Asp Val Tyr Leu Gln Gly Pro Ile Trp
            595             600             605
Ala Lys Ile Pro Glu Thr Gly Ala His Phe His Pro Ser Pro Ala Met
        610             615             620
Gly Gly Phe Gly Leu Lys His Pro Pro Met Met Leu Ile Lys Asn
625             630             635             640
Thr Pro Val Pro Gly Asn Ile Thr Ser Phe Ser Asp Val Pro Val Ser
            645             650             655
Ser Phe Ile Thr Gln Tyr Ser Thr Gly Gln Val Thr Val Glu Met Glu
            660             665             670
Trp Glu Leu Lys Lys Glu Asn Ser Lys Arg Trp Asn Pro Glu Ile Gln
        675             680             685
```

Tyr Thr Asn Asn Tyr Asn Asp Pro Gln Phe Val Asp Phe Ala Pro Asp
            690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 71
<211> LENGTH: 2175
<212> TYPE: DNA
<213> ORGANISM: Adeno-associated virus 5

<400> SEQUENCE: 71

```
atgtcttttg ttgatcaccc tccagattgg ttggaagaag ttggtgaagg tcttcgcgag      60
tttttgggcc ttgaagcggg cccaccgaaa ccaaaaccca atcagcagca tcaagatcaa     120
gcccgtggtc ttgtgctgcc tggttataac tatctcggac ccggaaacgg tctcgatcga     180
ggagagcctg tcaacagggc agacgaggtc gcgcgagagc acgacatctc gtacaacgag     240
cagcttgagg cgggagacaa ccccctacctc aagtacaacc acgcggacgc cgagtttcag     300
gagaagctcg ccgacgacac atccttcggg ggaaacctcg gaaaggcagt ctttcaggcc     360
aagaaaaggg ttctcgaacc ttttggcctg gttgaagagg gtgctaagac ggcccctacc     420
ggaaagcgga tagacgacca ctttccaaaa agaaagaagg ctcggaccga agaggactcc     480
aagccttcca cctcgtcaga cgccgaagct ggacccagcg atcccagca gctgcaaatc     540
ccagcccaac cagcctcaag tttgggagct gatacaatgt ctgcgggagg tggcggccca     600
ttgggcgaca taaccaagg tgccgatgga gtgggcaatg cctcgggaga ttggcattgc     660
gattccacgt ggatggggga cagagtcgtc accaagtcca cccgaacctg ggtgctgccc     720
agctacaaca ccaccagta ccgagagatc aaaagcggct ccgtcgacgg aagcaacgcc     780
aacgcctact ttggatacag caccccctgg gggtactttg actttaaccg cttccacagc     840
cactggagcc ccgagactg gcaaagactc atcaacaact actggggctt cagacccccgg     900
tccctcagag tcaaaatctt caacattcaa gtcaaagagg tcacggtgca ggactccacc     960
accaccatcg ccaacaacct cacctccacc gtccaagtgt ttacggacga cgactaccag    1020
ctgcccctacg tcgtcggcaa cgggaccgag ggatgcctgc cggccttccc tcgcaggtc    1080
tttacgctgc cgcagtacgg ttacgcgacg ctgaaccgcg acaacacaga aaatccccac    1140
gagaggagca gcttcttctg cctagagtac tttcccagca agatgctgag aacgggcaac    1200
aactttgagt ttacctacaa ctttgaggag gtgcccttcc actccagctt cgctcccagt    1260
cagaacctct tcaagctggc caacccgctg gtggaccagt acttgtaccg cttcgtgagc    1320
acaaataaca ctggcggagt ccagttcaac aagaacctgg ccgggagata cgccaacacc    1380
tacaaaaact ggttcccggg gcccatgggc cgaacccagg ctggaacct gggctccggg    1440
gtcaaccgcg ccagtgtcag cgccttcgcc acgaccaata ggatggagct cgagggcgcg    1500
agttaccagg tgcccccgca gccgaacggc atgaccaaca cctccagggg cagcaacacc    1560
tatgccctgg agaacactat gatcttcaac agccagccgg cgaacccggg caccaccgcc    1620
acgtacctcg agggcaacat gctcatcacc agcgagagcg agacgcagcc ggtgaaccgc    1680
gtggcgtaca acgtcggcgg gcagatggcc accaacaacc agagctccac cactgccccc    1740
gcgaccggca cgtacaacct ccaggaaatc gtgcccggca gcgtgtggat ggagagggac    1800
gtgtacctcc aaggacccat ctgggccaag atcccagaga cggggcgca ctttcacccc    1860
```

-continued

| | |
|---|---|
| tctccggcca tgggcggatt cggactcaaa cacccaccgc ccatgatgct catcaagaac | 1920 |
| acgcctgtgc ccggaaatat caccagcttc tcggacgtgc ccgtcagcag cttcatcacc | 1980 |
| cagtacagca ccgggcaggt caccgtggag atggagtggg agctcaagaa ggaaaactcc | 2040 |
| aagaggtgga acccagagat ccagtacaca aacaactaca cgaccccca gtttgtggac | 2100 |
| tttgccccgg acagcaccgg ggaatacaga accaccagac ctatcggaac ccgatacctt | 2160 |
| acccgacccc tttaa | 2175 |

<210> SEQ ID NO 72
<211> LENGTH: 2346
<212> TYPE: DNA
<213> ORGANISM: Artificial Sequence
<220> FEATURE:
<223> OTHER INFORMATION: Made in Lab - MyDeta3 polynucleotide

<400> SEQUENCE: 72

| | |
|---|---|
| atgacactcc tggggtctga gcattccttg ctgattagga gcaagttcag atcagtttta | 60 |
| cagttaagac ttcaacaaag aaggaccag gaacaactgg ctaaccaagg cataatacca | 120 |
| ccactgaaac gtccagctga attccatgag caaagaaaac atttggatag tgacaaggct | 180 |
| aaaaattccc tgaagcgcaa agccagaaac aggtgcaaca gtgccgactt ggttaatatg | 240 |
| cacatactcc aagcttccac tgcagagagg tccattccaa ctgctcagat gaagctgaaa | 300 |
| agagcccgac tcgccgatga tctcaatgaa aaaattgctc tacgaccagg cccactggag | 360 |
| ctggtggaaa aaacattct tcctgtggat tctgctgtga agaggccat aaaaggtaac | 420 |
| caggtgagtt tctccaaatc cacgatgct tttgccttg aagaggacag cagcagcgat | 480 |
| gggctttctc cggatcagac tcgaagtgaa gacccccaaa actcagcggg atccccgcca | 540 |
| gacgctaaag cctcagatac cccttcgaca ggttctctgg ggacaaacca ggatcttgct | 600 |
| tctggctcag aaaatgacag aaatgactca gcctcacagc ccagccacca gtcagatgcg | 660 |
| gggaagcagg ggcttggccc ccccagcacc cccatagccg tgcatgctgc tgtaaagtcc | 720 |
| aaatccttgg gtgacagtaa gaaccgccac aaaaagccca aggaccccaa gccaaaggtg | 780 |
| aagaagctta aatatcacca gtacattccc ccagaccaga aggcagagaa gtcccctcca | 840 |
| cctatggact cagcctacgc tcggctgctc cagcaacagc agctgttcct gcagctccaa | 900 |
| atcctcagcc agcagcagca gcagcagcaa caccgattca gctacctagg gatgcaccaa | 960 |
| gctcagctta aggaaccaaa tgaacagatg gtcagaaatc caaactcttc ttcaacgcca | 1020 |
| ctgagcaata ccccccttgtc tcctgtcaaa aacagttttt ctggacaaac tggtgtctct | 1080 |
| tctttcaaac caggcccact cccacctaac ctggatgatc tgaaggtctc tgaattaaga | 1140 |
| caacagcttc gaattcgggg cttgcctgtg tcaggcacca aaacggctct catggaccgg | 1200 |
| cttcgaccct tccaggactg ctctggcaac ccagtgccga actttgggga tataacgact | 1260 |
| gtcacttttc ctgtcacacc caacacgctg cccaattacc agtcttcctc ttctaccagt | 1320 |
| gccctgtcca acggcttcta ccactttggc agcaccagct ccagcccccc gatctcccca | 1380 |
| gcctcctctg acctgtcagt cgctgggtcc ctgccggaca ccttcaatga tgcctccccc | 1440 |
| tccttcggcc tgcacccgtc cccagtccac gtgtgcacgg aggaaagtct catgagcagc | 1500 |
| ctgaatgggg gctctgttcc ttctgagctg atgggctgg actccagaa ggacaagatg | 1560 |
| ctggtggaga agcagaaggt gatcaatgaa ctcacctgga aactccagca agagcagagg | 1620 |
| caggtggagg agctgaggat gcagcttcag aagcagaaaa ggaataactg ttcagaggag | 1680 |
| gtaacacagc ctccatccta tgaagatgcc gtaaagcagc aaatgacccg gagtcagcag | 1740 |

```
atggatgaac tcctggacgt gcttattgaa agcggagaaa tgccagcaga cgctagagag    1800
gatcactcat gtcttcaaaa agtcccaaag atacccagat cttcccgaag tccaactgct    1860
gtcctcacca agccctcggc ttcctttgaa caagcctctt caggcagcca gatccccttt    1920
gatccctatg ccaccgacag tgatgagcat cttgaagtct tattaaattc ccagagcccc    1980
ctaggaaaga tgagtgatgt caccttcta aaaattggga gcgaagagcc tcactttgat     2040
gggataatgg atggattctc tgggaaggct gcagaagacc tcttcaatgc acatgagatc    2100
ttgccaggcc ccctctctcc aatgcagaca cagttttcac cctcttctgt ggacagcaat    2160
gggctgcagt taagcttcac tgaatctccc tgggaaacca tggagtggct ggacctcact    2220
ccgccaaatt ccacaccagg ctttagcgcc ctcaccacca gcagcccag catcttcaac     2280 atcgatttcc tggatgtcac tgatctcaat ttgaattctt ccatggacct tcacttgcag    2340
cagtgg                                                               2346
```

```
<210> SEQ ID NO 73
<211> LENGTH: 97
<212> TYPE: DNA
<213> ORGANISM: Simian virus 40

<400> SEQUENCE: 73
gtaagtttag tcttttgtc tttatttca ggtcccggat ccggtggtgg tgcaaatcaa      60
agaactgctc ctcagtggat gttgccttta cttctag                             97

<210> SEQ ID NO 74
<211> LENGTH: 49
<212> TYPE: DNA
<213> ORGANISM: Artificial Sequence
<220> FEATURE:
<223> OTHER INFORMATION: Made in Lab - PolyA signal sequence

<400> SEQUENCE: 74
aataaaagat ctttattttc attagatctg tgtgttggtt ttttgtgtg                49

<210> SEQ ID NO 75
<211> LENGTH: 589
<212> TYPE: DNA
<213> ORGANISM: Woodchuck hepatitis virus

<400> SEQUENCE: 75
aatcaacctc tggattacaa aatttgtgaa agattgactg gtattcttaa ctatgttgct    60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggcccgttg tcaggcaacg tggcgtggtg tgcactgtgt ttgctgacgc aaccccact    240 ggttggggca ttgccaccac ctgtcagctc ctttccggga cttttcgctttt ccctccct    300 attgccacgg cggaactcat cgccgcctgc cttgcccgct gctggacagg gctcggctg    360 ttgggcactg acaattccgt ggtgttgtcg gggaaatcat cgtcctttcc ttggctgctc    420
gcctgtgttg ccacctggat tctgcgcggg acgtccttct gctacgtccc ttcggccctc    480
aatccagcgg accttccttc ccgcggcctg ctgccggctc tgcggcctct tccgcgtctt    540
cgccttcgcc ctcagacgag tcggatctcc ctttgggccg cctccccgc                589

<210> SEQ ID NO 76
<211> LENGTH: 130
<212> TYPE: DNA
```

<213> ORGANISM: Adeno-associated virus 2

<400> SEQUENCE: 76

```
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct                                                          130
```

<210> SEQ ID NO 77
<211> LENGTH: 4376
<212> TYPE: DNA
<213> ORGANISM: Artificial Sequence
<220> FEATURE:
<223> OTHER INFORMATION: Made in Lab - Bicistronic AAV5-MyDeta3A
      expression cassette

<400> SEQUENCE: 77

```
tgtagttaat gattaacccg ccatgctact tatctacgta gccatgctct aggaagatcg    60
gaattcgccc ttaagcataa cttacggtaa atggcccgcc tggctgaccg cccaacgacc   120
cccgcccatt gacgtcaata atgacgtatg ttcccatagt aacgccaata gggactttcc   180
attgacgtca atgggtggag tatttacggt aaactgccca cttggcagta catcaagtgt   240
atcatatgcc aagtacgccc cctattgacg tcaatgacgg taaatggccc gcctggcatt   300
atgcccagta catgacctta tgggactttc ctacttggca gtacatctac tcgaggccac   360
gttctgcttc actctcccca tctccccccc ctccccaccc ccaattttgt atttatttat   420
tttttaatta ttttgtgcag cgatggggc ggggggggg gggggcgcg cgccaggcgg   480
ggcggggcgg ggcgagggc ggggcgggc gaggcggaga ggtgcggcgg cagccaatca   540
gagcggcgcg ctccgaaagt tcctttttat ggcgaggcgg cggcggcggc ggccctataa   600
aaagcgaagc gcgcggcggg cgggagcggg atcagccacc gcggtggcgg cctagagtcg   660
acgaggaact gaaaaaccag aaagttaact ggtaagttta gtcttttgt cttttatttc    720
aggtcccgga tccggtggtg gtgcaaatca agaactgct cctcagtgga tgttgccttt   780
acttctaggc ctgtacgaa gtgttacttc tgctctaaaa gctgcggaat tgtacccgcg   840
gccgatccaa tcgatgccac catgacactc ctggggtctg agcattcctt gctgattagg   900
agcaagttca gatcagtttt acagttaaga cttcaacaaa gaaggaccca ggaacaactg   960
gctaaccaag gcataatacc accactgaaa cgtccagctg aattccatga gcaaagaaaa  1020
catttggata tgacaaggc taaaaattcc ctgaagcgca agccagaaa caggtgcaac  1080
agtgccgact tggttaatat gcacatactc caagcttcca ctgcagagag gtccattcca  1140
actgctcaga tgaagctgaa aagagcccga ctcgccgatg atctcaatga aaaaattgct  1200
ctacgaccag gcccactgga gctggtgaa aaaacattc ttcctgtgga ttctgctgtg  1260
aaagaggcca taaaggtaa ccaggtgagt ttctccaaat ccacggatgc ttttgccttt  1320
gaagaggaca gcagcagcga tgggctttct ccggatcaga ctcgaagtga agaccccaa  1380
aactcagcgg gatccccgcc agacgctaaa gcctcagata ccccttcgac aggttctctg  1440
gggacaaacc aggatcttgc ttctggctca gaaaatgaca gaaatgactc agcctcacag  1500
cccagccacc agtcagatgc ggggaagcag gggcttggcc cccccagcac ccccatagcc  1560
gtgcatgctg ctgtaaagtc caaatccttg ggtgacagta agaaccgcca caaaagccc  1620
aaggaccca agccaaggt gaagaagctt aaatatcacc agtacattcc cccagaccag  1680
aaggcagaga agtcccctcc acctatggac tcagcctacg ctcggctgct ccagcaacag  1740
```

| | |
|---|---|
| cagctgttcc tgcagctcca atcctcagc cagcagcagc agcagcagca acaccgattc | 1800 |
| agctacctag ggatgcacca agctcagctt aaggaaccaa atgaacagat ggtcagaaat | 1860 |
| ccaaactctt cttcaacgcc actgagcaat accccttgt ctcctgtcaa aaacagtttt | 1920 |
| tctggacaaa ctggtgtctc ttctttcaaa ccaggcccac tcccacctaa cctggatgat | 1980 |
| ctgaaggtct ctgaattaag acaacagctt cgaattcggg gcttgcctgt gtcaggcacc | 2040 |
| aaaacggctc tcatggaccg gcttcgaccc ttccaggact gctctggcaa cccagtgccg | 2100 |
| aactttgggg atataacgac tgtcactttt cctgtcacac caacacgct gcccaattac | 2160 |
| cagtcttcct cttctaccag tgccctgtcc aacggcttct accactttgg cagcaccagc | 2220 |
| tccagccccc cgatctcccc agcctcctct gacctgtcag tcgctgggtc cctgccggac | 2280 |
| accttcaatg atgcctcccc ctccttcggc ctgcacccgt ccccagtcca cgtgtgcacg | 2340 |
| gaggaaagtc tcatgagcag cctgaatggg ggctctgttc cttctgagct ggatgggctg | 2400 |
| gactccgaga aggacaagat gctggtggag aagcagaagg tgatcaatga actcacctgg | 2460 |
| aaactccagc aagagcagag gcaggtgag gagctgagga tgcagcttca gaagcagaaa | 2520 |
| aggaataact gttcagagga ggtaacacag cctccatcct atgaagatgc cgtaaagcag | 2580 |
| caaatgaccc ggagtcagca gatggatgaa ctcctggacg tgcttattga aagcggagaa | 2640 |
| atgccagcag acgctagaga ggatcactca tgtcttcaaa aagtcccaaa gatacccaga | 2700 |
| tcttcccgaa gtccaactgc tgtcctcacc aagccctcgg cttcctttga caagcctct | 2760 |
| tcaggcagcc agatccccctt tgatccctat gccaccgaca gtgatgagca tcttgaagtc | 2820 |
| ttattaaatt cccagagccc cctaggaaag atgagtgatg tcacccttct aaaaattggg | 2880 |
| agcgaagagc ctcactttga tgggataatg gatggattct ctgggaaggc tgcagaagac | 2940 |
| ctcttcaatg cacatgagat cttgccaggc cccctctctc caatgcagac acagttttca | 3000 |
| ccctcttctg tggacagcaa tgggctgcag ttaagcttca ctgaatctcc ctgggaaacc | 3060 |
| atggagtggc tggacctcac tccgccaaat tccacaccag gctttagcgc cctcaccacc | 3120 |
| agcagcccca gcatcttcaa catcgatttc ctggatgtca ctgatctcaa tttgaattct | 3180 |
| tccatggacc ttcacttgca gcagtggtga gatctgcctc gactgtgcct tctagttgcc | 3240 |
| agccatctgt tgtttgcccc tcccccgtgc cttccttgac cctggaaggt gccactccca | 3300 |
| ctgtcctttc ctaataaaat gaggaaattg catcgcattg tctgagtagg tgtcattcta | 3360 |
| ttctgggggg tggggtgggg caggacagca aggggagga ttgggaagac aatagcaggc | 3420 |
| atgctgggga cctaggtact tatataaggg ggtgggggcg cgttcgtcct cagtcgcgat | 3480 |
| cgaacactcg agccgagcag acgtgcctac ggaccgatgg aaagctctgc caagatggag | 3540 |
| agcggcggcg ccggccagca gccccagccg cagcccagc agcccttcct gccgcccgca | 3600 |
| gcctgtttct ttgccacggc cgcagccgcg gcggccgcag ccgccgcagc ggcagcgcag | 3660 |
| agcgcgcagc agcagcagca gcagcagcag cagcagcagc aggcgccgca gctgagaccg | 3720 |
| gcggccgacg gccagccctc aggggcggt cacaagtcag cgcccaagca agtcaagcga | 3780 |
| cagcgctcgt cttcgcccga actgatgcgc tgcaaacgcc ggctcaactt cagcggcttt | 3840 |
| ggctacagcc tgccgcagca gcagccgcc gcgtggcgc gccgcaacga gcgcgagcgc | 3900 |
| aaccgcgtca agttggtcaa cctgggcttt gccaccttc gggagcacgt ccccaacggc | 3960 |
| gcggccaaca agaagatgag taaggtggag acactgcgct cggcggtcga gtacatccgc | 4020 |
| gcgctgcagc agctgctgga cgagcatgac gcggtgagcg ccgccttcca ggcaggcgtc | 4080 |
| ctgtcgccca ccatctcccc caactactcc aacgacttga actccatggc cggctcgccg | 4140 |

| | |
|---|---:|
| gtctcatcct actcgtcgga cgagggctct tacgacccgc tcagccccga ggagcaggag | 4200 |
| cttctcgact tcaccaactg gttctagaag cttaataaaa gatctttatt ttcattagat | 4260 |
| ctgtgtgttg gttttttgtg tgctggggac tcgagttaag ggcgaattcc cgattaggat | 4320 |
| cttcctagag catggctacg tagataagta gcatggcggg ttaatcatta actaca | 4376 |

<210> SEQ ID NO 78
<211> LENGTH: 4636
<212> TYPE: DNA
<213> ORGANISM: Artificial Sequence
<220> FEATURE:
<223> OTHER INFORMATION: Made in Lab - Bicistronic AAV5-MyDeta3A
    expression cassette

<400> SEQUENCE: 78

| | |
|---|---:|
| ctgcgcgctc gctcgctcac tgaggccgcc cgggcaaagc ccgggcgtcg ggcgaccttt | 60 |
| ggtcgcccgg cctcagtgag cgagcgagcg cgcagagagg gagtggccaa ctccatcact | 120 |
| aggggttcct tgtagttaat gattaacccg ccatgctact tatctacgta gccatgctct | 180 |
| aggaagatcg gaattcgccc ttaagcataa cttacggtaa atggcccgcc tggctgaccg | 240 |
| cccaacgacc cccgcccatt gacgtcaata atgacgtatg ttcccatagt aacgccaata | 300 |
| gggactttcc attgacgtca atgggtggag tatttacggt aaactgccca cttggcagta | 360 |
| catcaagtgt atcatatgcc aagtacgccc cctattgacg tcaatgacgg taaatggccc | 420 |
| gcctggcatt atgcccagta catgacctta tgggactttc ctacttggca gtacatctac | 480 |
| tcgaggccac gttctgcttc actctcccca tctcccccc ctcccaccc caatttgt | 540 |
| atttatttat ttttaatta ttttgtgcag cgatggggc ggggggggg gggggcgcg | 600 |
| cgccaggcgg ggcggggcgg ggcgagggc gggcgggc gaggcggaga ggtgcggcgg | 660 |
| cagccaatca gagcggcgcg ctccgaaagt ttcctttat ggcgaggcgg cggcggcggc | 720 |
| ggccctataa aaagcgaagc gcgcggcggg cgggagcggg atcagccacc gcggtggcgg | 780 |
| cctagagtcg acgaggaact gaaaaaccag aaagttaact ggtaagttta gtcttttgt | 840 |
| cttttatttc aggtcccgga tccggtggtg gtgcaaatca agaactgct cctcagtgga | 900 |
| tgttgccttt acttctaggc ctgtacggaa gtgttacttc tgctctaaaa gctgcggaat | 960 |
| tgtacccgcg gccgatccaa tcgatgccac catgacactc ctggggtctg agcattcctt | 1020 |
| gctgattagg agcaagttca gatcagtttt acagttaaga cttcaacaaa gaaggaccca | 1080 |
| ggaacaactg gctaaccaag gcataatacc accactgaaa cgtccagctg aattccatga | 1140 |
| gcaaagaaaa catttggata gtgacaaggc taaaaattcc ctgaagcgca aagccagaaa | 1200 |
| caggtgcaac agtgccgact tggttaatat gcacatactc caagcttcca ctgcagagag | 1260 |
| gtccattcca actgctcaga tgaagctgaa agagcccga ctcgccgatg atctcaatga | 1320 |
| aaaaattgct ctacgaccag gcccactgga gctggtggaa aaaacattc ttcctgtgga | 1380 |
| ttctgctgtg aaagaggcca taaaaggtaa ccaggtgagt ttctccaaat ccacggatgc | 1440 |
| ttttgccttt gaagaggaca gcagcagcga tgggctttct ccggatcaga ctcgaagtga | 1500 |
| agacccccaa aactcagcgg gatccccgcc agacgctaaa gcctcagata ccccttcgac | 1560 |
| aggttctctg gggacaaacc aggatcttgc ttctggctca gaaaatgaca gaaatgactc | 1620 |
| agcctcacag cccagccacc agtcagatgc ggggaagcag gggcttggcc cccagcac | 1680 |
| ccccatagcc gtgcatgctg ctgtaaagtc caaatccttg ggtgacagta agaaccgcca | 1740 |
| caaaaagccc aaggacccca gccaaaggt gaagaagctt aaatatcacc agtacattcc | 1800 |

```
cccagaccag aaggcagaga agtcccctcc acctatggac tcagcctacg ctcggctgct   1860
ccagcaacag cagctgttcc tgcagctcca atcctcagc cagcagcagc agcagcagca    1920
acaccgattc agctacctag ggatgcacca agctcagctt aaggaaccaa atgaacagat   1980
ggtcagaaat ccaaactctt cttcaacgcc actgagcaat accccttgt ctcctgtcaa    2040 aaacagtttt tctggacaaa ctggtgtctc ttctttcaaa ccaggcccac tcccacctaa   2100
cctggatgat ctgaaggtct ctgaattaag acaacagctt cgaattcggg gcttgcctgt   2160
gtcaggcacc aaaacggctc tcatggaccg gcttcgaccc ttccaggact gctctggcaa   2220
cccagtgccg aactttgggg atataacgac tgtcactttt cctgtcacac caacacgct   2280 gcccaattac cagtcttcct cttctaccag tgccctgtcc aacggcttct accactttgg   2340
cagcaccagc tccagccccc cgatctcccc agcctcctct gacctgtcag tcgctgggtc   2400
cctgccggac accttcaatg atgcctcccc ctccttcggc ctgcacccgt ccccagtcca   2460
cgtgtgcacg gaggaaagtc tcatgagcag cctgaatggg ggctctgttc cttctgagct   2520
ggatgggctg gactccgaga aggacaagat gctggtggag aagcagaagg tgatcaatga   2580
actcacctgg aaactccagc aagagcgag gcaggtggag gagctgagga tgcagcttca    2640
gaagcagaaa aggaataact gttcagagga ggtaacacag cctccatcct atgaagatgc   2700
cgtaaagcag caaatgaccc ggagtcagca gatggatgaa ctcctggacg tgcttattga   2760
aagcggagaa atgccagcag acgctagaga ggatcactca tgtcttcaaa aagtcccaaa   2820
gatacccaga tcttcccgaa gtccaactgc tgtcctcacc aagccctcgg cttcctttga   2880
acaagcctct tcaggcagcc agatcccctt tgatccctat gccaccgaca gtgatgagca   2940
tcttgaagtc ttattaaatt cccagagccc cctaggaaag atgagtgatg tcacccttct   3000
aaaaattggg agcgaagagc ctcactttga tgggataatg gatggattct ctgggaaggc   3060
tgcagaagac ctcttcaatg cacatgagat cttgccaggc cccctctctc caatgcagac   3120
acagttttca ccctcttctg tggacagcaa tgggctgcag ttaagcttca ctgaatctcc   3180
ctggaaaacc atggagtggc tggacctcac tccgccaaat tccacaccag gctttagcgc   3240
cctcaccacc agcagcccca gcatcttcaa catcgatttc ctggatgtca ctgatctcaa   3300
tttgaattct tccatggacc ttcacttgca gcagtggtga gatctgcctc gactgtgcct   3360
tctagttgcc agccatctgt tgtttgcccc tccccgtgc cttccttgac cctggaaggt    3420
gccactccca ctgtcctttc ctaataaaat gaggaaattg catcgcattg tctgagtagg   3480
tgtcattcta ttctgggggg tggggtgggg caggacagca aggggagga ttgggaagac    3540 aatagcaggc atgctgggga cctaggtact tatataaggg ggtgggggcg cgttcgtcct   3600
cagtcgcgat cgaacactcg agccgagcag acgtgcctac ggaccgatgg aaagctctgc   3660
caagatggag agcggcggcg ccggccagca gccccagccg cagccccagc agcccttcct   3720
gccgcccgca gcctgtttct ttgccacggc cgcagccgcg gcggccgcag ccgccgcagc   3780
ggcagcgcag agcgcgcagc agcagcagca gcagcagcag cagcagcagc aggcgccgca   3840
gctgagaccg gcggccgacg gccagccctc aggggcggt cacaagtcag cgcccaagca    3900
agtcaagcga cagcgctcgt cttcgcccga actgatgcgc tgcaaacgcc ggctcaactt   3960
cagcggcttt ggctacagcc tgccgcagca gcagcggcc gccgtggcgc gccgcaacga    4020
gcgcgagcgc aaccgcgtca gttggtcaa cctgggcttt gccacccttc gggagcacgt    4080
ccccaacggc gcggccaaca agaagatgag taaggtggag acactgcgct cggcggtcga   4140
```

| | |
|---|---|
| gtacatccgc gcgctgcagc agctgctgga cgagcatgac gcggtgagcg ccgccttcca | 4200 |
| ggcaggcgtc ctgtcgccca ccatctcccc caactactcc aacgacttga actccatggc | 4260 |
| cggctcgccg gtctcatcct actcgtcgga cgagggctct tacgacccgc tcagccccga | 4320 |
| ggagcaggag cttctcgact tcaccaactg gttctagaag cttaataaaa gatctttatt | 4380 |
| ttcattagat ctgtgtgttg gttttttgtg tgctggggac tcgagttaag ggcgaattcc | 4440 |
| cgattaggat cttcctagag catggctacg tagataagta gcatggcggg ttaatcatta | 4500 |
| actacaagga acccctagtg atggagttgg ccactccctc tctgcgcgct cgctcgctca | 4560 |
| ctgaggccgg gcgaccaaag gtcgcccgac gcccgggctt tgcccgggcg gcctcagtga | 4620 |
| gcgagcgagc gcgcag | 4636 |

<210> SEQ ID NO 79
<211> LENGTH: 7447
<212> TYPE: DNA
<213> ORGANISM: Artificial Sequence
<220> FEATURE:
<223> OTHER INFORMATION: Made in Lab - Bicistronic AAV5-MyDeta3A
      transfer plasmid

<400> SEQUENCE: 79

| | |
|---|---|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccagattta | 240 |
| attaaggctg cgcgctcgct cgctcactga ggccgcccgg gcaaagcccg ggcgtcgggc | 300 |
| gacctttggt cgcccggcct cagtgagcga gcgagcgcgc agagagggag tggccaactc | 360 |
| catcactagg ggttccttgt agttaatgat taacccgcca tgctacttat ctacgtagcc | 420 |
| atgctctagg aagatcggaa ttcgccctta agcataactt acggtaaatg gcccgcctgg | 480 |
| ctgaccgccc aacgaccccc gcccattgac gtcaataatg acgtatgttc ccatagtaac | 540 |
| gccaataggg actttccatt gacgtcaatg ggtggagtat ttacggtaaa ctgcccactt | 600 |
| ggcagtacat caagtgtatc atatgccaag tacgccccct attgacgtca atgacggtaa | 660 |
| atggcccgcc tggcattatg cccagtacat gaccttatgg gactttccta cttggcagta | 720 |
| catctactcg aggccacgtt ctgcttcact ctccccatct cccccccctc cccacccccca | 780 |
| attttgtatt tatttatttt ttaattattt tgtgcagcga tggggcgggg ggggggggg | 840 |
| gggcgcgcgc caggcgggc ggggcgggc gaggggcggg gcgggcgag gcggagaggt | 900 |
| gcggcggcag ccaatcagag cggcgcgctc cgaaagtttc cttttatggc gaggcggcgg | 960 |
| cggcggcggc cctataaaaa gcgaagcgcg cggcgggcgg gagcgggatc agccaccgcg | 1020 |
| gtggcggcct agagtcgacg aggaactgaa aaccagaaa gttaactggt aagtttagtc | 1080 |
| tttttgtctt ttatttcagg tcccggatcc ggtggtggtg caaatcaaag aactgctcct | 1140 |
| cagtggatgt tgcctttact tctaggcctg tacggaagtg ttacttctgc tctaaaagct | 1200 |
| gcggaattgt acccgcggcc gatccaatcg atgccaccat gacactcctg ggtctgagc | 1260 |
| attccttgct gattaggagc aagttcgat cagttttaca gttaagactt caacaaagaa | 1320 |
| ggacccagga caactggct aaccaaggca taataccacc actgaaacgt ccagctgaat | 1380 |
| tccatgagca agaaaacat ttggatagtg acaaggctaa aaattccctg aagcgcaaag | 1440 |
| ccagaaacag gtgcaacagt gccgacttgg ttaatatgca catactccaa gcttccactg | 1500 |

```
cagagaggtc cattccaact gctcagatga agctgaaaag agcccgactc gccgatgatc    1560
tcaatgaaaa aattgctcta cgaccaggcc cactggagct ggtggaaaaa aacattcttc    1620
ctgtggattc tgctgtgaaa gaggccataa aaggtaacca ggtgagtttc tccaaatcca    1680
cggatgcttt tgcctttgaa gaggacagca gcagcgatgg gctttctccg gatcagactc    1740
gaagtgaaga cccccaaaac tcagcgggat ccccgccaga cgctaaagcc tcagataccc    1800
cttcgacagg ttctctgggg acaaaccagg atcttgcttc tggctcagaa aatgacagaa    1860
atgactcagc ctcacagccc agccaccagt cagatgcggg gaagcagggg cttggccccc    1920
ccagcacccc catagccgtg catgctgctg taaagtccaa atccttgggt gacagtaaga    1980
accgccacaa aaagcccaag gaccccaagc caaaggtgaa gaagcttaaa tatcaccagt    2040
acattccccc agaccagaag gcagagaagt cccctccacc tatggactca gcctacgctc    2100
ggctgctcca gcaacagcag ctgttcctgc agctccaaat cctcagccag cagcagcagc    2160
agcagcaaca ccgattcagc tacctaggga tgcaccaagc tcagcttaag gaaccaaatg    2220
aacagatggt cagaaatcca aactcttctt caacgccact gagcaatacc cccttgtctc    2280
ctgtcaaaaa cagttttttct ggacaaactg gtgtctcttc tttcaaacca ggcccactcc    2340
cacctaacct ggatgatctg aaggtctctg aattaagaca acagcttcga attcggggct    2400
tgcctgtgtc aggcaccaaa acggctctca tggaccggct tcgacccttc caggactgct    2460
ctggcaaccc agtgccgaac tttggggata taacgactgt cacttttcct gtcacaccca    2520
acacgctgcc caattaccag tcttcctctt ctaccagtgc cctgtccaac ggcttctacc    2580
actttggcag caccagctcc agcccccccga tctccccagc ctcctctgac ctgtcagtcg    2640
ctgggtccct gccggacacc ttcaatgatg cctccccctc cttcggcctg cacccgtccc    2700
cagtccacgt gtgcacggag gaaagtctca tgagcagcct gaatggggc tctgttcctt    2760
ctgagctgga tgggctggac tccgagaagg acaagatgct ggtggagaag cagaaggtga    2820
tcaatgaact cacctggaaa ctccagcaag agcagaggca ggtggaggag ctgaggatgc    2880
agcttcagaa gcagaaaagg aataactgtt cagaggaggt aacacagcct ccatcctatg    2940
aagatgccgt aaagcagcaa atgacccgga gtcagcagat ggatgaactc ctggacgtgc    3000
ttattgaaag cggagaaatg ccagcagacg ctagagagga tcactcatgt cttcaaaaag    3060
tcccaaagat acccagatct tcccgaagtc caactgctgt cctcaccaag ccctcggctt    3120
cctttgaaca agcctcttca ggcagccaga tccccttgta tccctatgcc accgacagtg    3180
atgagcatct tgaagtctta ttaaattccc agagcccccct aggaaagatg agtgatgtca    3240
cccttctaaa aattgggagc gaagagcctc actttgatgg gataatggat ggattctctg    3300
ggaaggctgc agaagacctc ttcaatgcac atgagatctt gccaggcccc ctctctccaa    3360
tgcagacaca gttttcaccc tcttctgtgg acagcaatgg gctgcagtta agcttcactg    3420
aatctccctg ggaaaccatg gagtggctgg acctcactcc gccaaattcc acaccaggct    3480
ttagcgccct caccaccagc agcccagca tcttcaacat cgatttcctg gatgtcactg    3540
atctcaattt gaattcttcc atggaccttc acttgcagca gtggtgagat ctgcctcgac    3600
tgtgccttct agttgccagc catctgttgt ttgcccctcc ccgtgccttc cttgaccctt    3660
ggaaggtgcc actcccactg tcctttccta ataaaatgag gaaattgcat cgcattgtct    3720
gagtaggtgt cattctattc tggggggtgg ggtggggcag gacagcaagg gggaggattg    3780
ggaagacaat agcaggcatg ctggggacct aggtacttat ataaggggt gggggcgcgt    3840
tcgtcctcag tcgcgatcga acactcgagc cgagcagacg tgcctacgga ccgatggaaa    3900
```

```
gctctgccaa gatggagagc ggcggcgccg ccagcagcc ccagccgcag ccccagcagc   3960
ccttcctgcc gcccgcagcc tgtttctttg ccacggccgc agccgcggcg gccgcagccg   4020
ccgcagcggc agcgcagagc gcgcagcagc agcagcagca gcagcagcag cagcagcagg   4080
cgccgcagct gagaccggcg gccgacggcc agccctcagg gggcggtcac aagtcagcgc   4140
ccaagcaagt caagcgacag cgctcgtctt cgcccgaact gatgcgctgc aaacgccggc   4200
tcaacttcag cggctttggc tacagcctgc cgcagcagca gccggccgcc gtggcgcgcc   4260
gcaacgagcg cgagcgcaac cgcgtcaagt tggtcaacct gggctttgcc acccttcggg   4320
agcacgtccc caacggcgcg gccaacaaga agatgagtaa ggtggagaca ctgcgctcgg   4380
cggtcgagta catccgcgcg ctgcagcagc tgctggacga gcatgacgcg gtgagcgccg   4440
ccttccaggc aggcgtcctg tcgcccacca tctcccccaa ctactccaac gacttgaact   4500
ccatggccgg ctcgccggtc tcatcctact cgtcggacga gggctcttac gacccgctca   4560
gccccgagga gcaggagctt ctcgacttca ccaactggtt ctagaagctt aataaaagat   4620
ctttattttc attagatctg tgtgttggtt ttttgtgtgc tggggactcg agttaagggc   4680
gaattcccga ttaggatctt cctagagcat ggctacgtag ataagtagca tggcgggtta   4740
atcattaact acaaggaacc cctagtgatg gagttggcca ctccctctct gcgcgctcgc   4800
tcgctcactg aggccgggcg accaaaggtc gcccgacgcc cgggctttgc ccgggcggcc   4860
tcagtgagcg agcgagcgcg cagccttaat taacctaatt cactggccgt cgttttacaa   4920
cgtcgtgact gggaaaaccc tggcgttacc caacttaatc gccttgcagc acatcccccct   4980 ttcgccagct ggcgtaatag cgaagaggcc cgcaccgatc gcccttccca acagttgcgc   5040
agcctgaatg gcgaatggga cgcgccctgt agcggcgcat taagcgcggc gggtgtggtg   5100
gttacgcgca gcgtgaccgc tacacttgcc agcgccctag cgcccgctcc tttcgctttc   5160
ttcccttcct ttctcgccac gttcgccggc tttccccgtc aagctctaaa tcggggggctc   5220 cctttagggt tccgatttag tgctttacgg cacctcgacc ccaaaaaact tgattagggt   5280
gatggttcac gtagtgggcc atcgccccga tagacggttt ttcgcccttt gacgctggag   5340
ttcacgttcc tcaatagtgg actcttgttc caaactggaa caacactcaa ccctatctcg   5400
gtctattctt ttgatttata agggatttt ccgatttcgg cctattggtt aaaaaatgag   5460
ctgatttaac aaaaatttaa cgcgaatttt aacaaaatat taacgtttat aatttcaggt   5520
ggcatctttc ggggaaatgt gcgcggaacc cctatttgtt tatttttcta aatacattca   5580
aatatgtatc cgctcatgag acaataaccc tgataaatgc ttcaataata ttgaaaaagg   5640
aagagtatga gtattcaaca tttccgtgtc gcccttattc cctttttgc ggcattttgc   5700 cttcctgttt tgctcaccc agaaacgctg gtgaaagtaa aagatgctga agatcagttg   5760
ggtgcacgag tgggttacat cgaactggat ctcaatagtg gtaagatcct tgagagtttt   5820
cgccccgaag aacgttttcc aatgatgagc acttttaaag ttctgctatg tggcgcggta   5880
ttatcccgta ttgacgccgg gcaagagcaa ctcggtcgcc gcatacacta ttctcagaat   5940
gacttggttg agtactcacc agtcacagaa aagcatctta cggatggcat gacagtaaga   6000
gaattatgca gtgctgccat aaccatgagt gataacactg cggccaactt acttctgaca   6060
acgatcggag gaccgaagga gctaaccgct tttttgcaca acatggggga tcatgtaact   6120
cgccttgatc gttgggaacc ggagctgaat gaagccatac caaacgacga gcgtgacacc   6180
acgatgcctg tagtaatggt aacaacgttg cgcaaactat taactggcga actacttact   6240
```

| | |
|---|---|
| ctagcttccc ggcaacaatt aatagactgg atggaggcgg ataaagttgc aggaccactt | 6300 |
| ctgcgctcgg cccttccggc tggctggttt attgctgata atctggagc cggtgagcgt | 6360 |
| gggtctcgcg gtatcattgc agcactgggg ccagatggta agccctcccg tatcgtagtt | 6420 |
| atctacacga cggggagtca ggcaactatg gatgaacgaa atagacagat cgctgagata | 6480 |
| ggtgcctcac tgattaagca ttggtaactg tcagaccaag tttactcata tatactttag | 6540 |
| attgatttaa aacttcattt ttaatttaaa aggatctagg tgaagatcct ttttgataat | 6600 |
| ctcatgacca aaatccctta acgtgagttt tcgttccact gagcgtcaga ccccgtagaa | 6660 |
| aagatcaaag gatcttcttg agatcctttt tttctgcgcg taatctgctg cttgcaaaca | 6720 |
| aaaaaccac cgctaccagc ggtggtttgt ttgccggatc aagagctacc aactcttttt | 6780 |
| ccgaaggtaa ctggcttcag cagagcgcag ataccaaata ctgtccttct agtgtagccg | 6840 |
| tagttaggcc accacttcaa gaactctgta gcaccgccta catacctcgc tctgctaatc | 6900 |
| ctgttaccag tggctgctgc cagtggcgat aagtcgtgtc ttaccgggtt ggactcaaga | 6960 |
| cgatagttac cggataaggc gcagcggtcg ggctgaacgg ggggttcgtg cacacagccc | 7020 |
| agcttggagc gaacgaccta caccgaactg agatacctac agcgtgagct atgagaaagc | 7080 |
| gccacgcttc ccgaagggag aaaggcggac aggtatccgg taagcggcag ggtcggaaca | 7140 |
| ggagagcgca cgagggagct tccaggggga aacgcctggt atctttatag tcctgtcggg | 7200 |
| tttcgccacc tctgacttga gcgtcgattt ttgtgatgct cgtcaggggg gcggagccta | 7260 |
| tggaaaaacg ccagcaacgc ggccttttta cggttcctgg ccttttgctg cggttttgct | 7320 |
| cacatgttct ttcctgcgtt atcccctgat tctgtggata accgtattac cgcctttgag | 7380 |
| tgagctgata ccgctcgccg cagccgaacg accgagcgca gcgagtcagt gagcgaggaa | 7440 |
| gcggaag | 7447 |

<210> SEQ ID NO 80
<211> LENGTH: 4150
<212> TYPE: DNA
<213> ORGANISM: Artificial Sequence
<220> FEATURE:
<223> OTHER INFORMATION: Made in Lab - Monocistronic AAV5-MyDeta3A
    expression cassette

<400> SEQUENCE: 80

| | |
|---|---|
| tgtagttaat gattaacccg ccatgctact tatctacgta gccatgctct aggaagatcg | 60 |
| gaattcgccc ttaagcataa cttacggtaa atggcccgcc tggctgaccg cccaacgacc | 120 |
| cccgcccatt gacgtcaata atgacgtatg ttcccatagt aacgccaata gggactttcc | 180 |
| attgacgtca atgggtggag tatttacggt aaactgccca cttggcagta catcaagtgt | 240 |
| atcatatgcc aagtacgccc cctattgacg tcaatgacgg taaatggccc gcctggcatt | 300 |
| atgcccagta catgacctta tgggactttc ctacttggca gtacattact cgaggccacg | 360 |
| ttctgcttca ctctccccat ctccccccc ctccccaccc caatttttgt atttatttat | 420 |
| tttttaatta ttttgtgcag cgatggggc gggggggggg ggggcgcg cgccaggcgg | 480 |
| ggcggggcgg ggcgagggc ggggcgggc gaggcggaga ggtgcggcgg cagccaatca | 540 |
| gagcggcgcg ctccgaaagt ttccttttat ggcgaggcg cggcggcggc ggccctataa | 600 |
| aaagcgaagc gcgcggcggg cgggagcggg atcagccacc gcggtggcgg cctagagtcg | 660 |
| acgaggaact gaaaaccag aaagttaact ggtaagttta gtctttttgt cttttatttc | 720 |
| aggtcccgga tccggtggtg gtgcaaatca aagaactgct cctcagtgga tgttgccttt | 780 |

```
acttctaggc ctgtacggaa gtgttacttc tgctctaaaa gctgcggaat tgtacccgcg    840
gccgatccaa tcgatacaga tctagcggcc gcgccaccat gacactcctg gggtctgagc    900
attccttgct gattaggagc aagttcagat cagttttaca gttaagactt caacaaagaa    960
ggacccagga caactggct aaccaaggca taataccacc actgaaacgt ccagctgaat   1020
tccatgagca agaaaacat ttggatagtg acaaggctaa aaattccctg aagcgcaaag   1080
ccagaaacag gtgcaacagt gccgacttgg ttaatatgca catactccaa gcttccactg   1140
cagagaggtc cattccaact gctcagatga agctgaaaag agcccgactc gccgatgatc   1200
tcaatgaaaa aattgctcta cgaccaggcc cactggagct ggtggaaaaa acattcttc    1260
ctgtggattc tgctgtgaaa gaggccataa aaggtaacca ggtgagtttc tccaaatcca   1320
cggatgcttt tgcctttgaa gaggacagca gcagcgatgg gctttctccg gatcagactc   1380
gaagtgaaga ccccaaaac tcagcgggat ccccgccaga cgctaaagcc tcagataccc    1440
cttcgacagg ttctctgggg acaaaccagg atcttgcttc tggctcagaa aatgacagaa   1500
atgactcagc ctcacagccc agccaccagt cagatgcggg gaagcagggg cttgcccccc   1560
ccagcacccc catagccgtg catgctgctg taaagtccaa atccttgggt gacagtaaga   1620
accgccacaa aaagcccaag gaccccaagc caaaggtgaa gaagcttaaa tatcaccagt   1680
acattccccc agaccagaag gcagagaagt cccctccacc tatggactca gcctacgctc   1740
ggctgctcca gcaacagcag ctgttcctgc agctccaaat cctcagccag cagcagcagc   1800
agcagcaaca ccgattcagc tacctaggga tgcaccaagc tcagcttaag gaaccaaatg   1860
aacagatggt cagaaatcca aactcttctt caacgccact gagcaatacc ccttgtctc    1920
ctgtcaaaaa cagttttct ggacaaactg gtgtctcttc tttcaaacca ggcccactcc    1980
cacctaacct ggatgatctg aaggtctctg aattaagaca acagcttcga attcgggct    2040
tgcctgtgtc aggcaccaaa acggctctca tggaccggct tcgacccttc caggactgct   2100
ctggcaaccc agtgccgaac tttgggata taacgactgt cactttcct gtcacaccca    2160
acacgctgcc caattaccag tcttcctctt ctaccagtgc cctgtccaac ggcttctacc   2220
actttgcag caccagctcc agccccccga tctccccagc ctcctctgac ctgtcagtcg   2280
ctgggtccct gccggacacc ttcaatgatg cctcccccctc cttcggcctg cacccgtccc   2340
cagtccacgt gtgcacggag gaaagtctca tgagcagcct gaatggggc tctgttcctt    2400
ctgagctgga tgggctggac tccgagaagg acaagatgct ggtggagaag cagaaggtga   2460
tcaatgaact cacctggaaa ctccagcaag agcagaggca ggtggaggag ctgaggatgc   2520
agcttcagaa gcagaaaagg aataactgtt cagaggaggt aacacagcct ccatcctatg   2580
aagatgccgt aaagcagcaa atgacccgga gtcagcagat ggatgaactc ctggacgtgc   2640
ttattgaaag cggagaaatg ccagcagacg ctagagagga tcactcatgt cttcaaaaag   2700
tcccaaagat acccagatct ccccgaagtc caactgctgt cctcaccaag ccctcggctt   2760
cctttgaaca agcctcttca ggcagccaga tccccttga tccctatgcc accgacagtg   2820
atgagcatct tgaagtctta ttaaattccc agagccccct aggaaagatg agtgatgtca   2880
cccttctaaa aattgggagc gaagagcctc actttgatgg gataatggat ggattctctg   2940
ggaaggctgc agaagacctc ttcaatgcac atgagatctt gccaggcccc ctctctccaa   3000
tgcagacaca gttttcaccc ctcttctgtgg acagcaatgg gctgcagtta agcttcactg   3060
aatctccctg ggaaaccatg gagtggctgg acctcactcc gccaaattcc acaccaggct   3120
ttagcgccct caccaccagc agccccagca tcttcaacat cgatttcctg gatgtcactg   3180
```

```
atctcaattt gaattcttcc atggaccttc acttgcagca gtggggatct ggagccacga    3240
acttctctct gttaaagcaa gcaggagacg tggaagaaaa ccccggtcct atggaaagct    3300
ctgccaagat ggagagcggc ggcgccggcc agcagcccca gccgcagccc cagcagccct    3360
tcctgccgcc cgcagcctgt ttctttgcca cggccgcagc cgcggcggcc gcagccgccg    3420
cagcggcagc gcagagcgcg cagcagcagc agcagcagca gcagcagcag cagcaggcgc    3480
cgcagctgag accggcggcc gacggccagc cctcaggggg cggtcacaag tcagcgccca    3540
agcaagtcaa gcgacagcgc tcgtcttcgc ccgaactgat gcgctgcaaa cgccggctca    3600
acttcagcgc ctttggctac agcctgccgc agcagcagcc ggccgccgtg gcgcgccgca    3660
acgagcgcga gcgcaaccgc gtcaagttgg tcaacctggg cttttgccacc cttcgggagc    3720 acgtccccaa cggcgcggcc aacaagaaga tgagtaaggt ggagacactg cgctcggcgg    3780
tcgagtacat ccgcgcgctg cagcagctgc tggacgagca tgacgcggtg agcgccgcct    3840
tccaggcagg cgtcctgtcg cccaccatct cccccaacta ctccaacgac ttgaactcca    3900
tggccggctc gccggtctca tcctactcgt cggacgaggg ctcttacgac ccgctcagcc    3960
ccgaggagca ggagcttctc gacttccacc actggttctg aaagcttaat aaaagatctt    4020
tattttcatt agatctgtgt gttggttttt tgtgtgctgg ggactcgagt taagggcgaa    4080
ttcccgatta ggatcttcct agagcatggc tacgtagata agtagcatgg cgggttaatc    4140
attaactaca                                                          4150

<210> SEQ ID NO 81
<211> LENGTH: 4410
<212> TYPE: DNA
<213> ORGANISM: Artificial Sequence
<220> FEATURE:
<223> OTHER INFORMATION: Made in Lab - Monocistronic AAV5-MyDeta3A
      expression cassette

<400> SEQUENCE: 81
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120 agggggttcct tgtagttaat gattaacccg ccatgctact tatctacgta gccatgctct     180
aggaagatcg gaattcgccc ttaagcataa cttacggtaa atggcccgcc tggctgaccg     240
cccaacgacc cccgcccatt gacgtcaata atgacgtatg ttcccatagt aacgccaata     300
gggactttcc attgacgtca atgggtggag tatttacggt aaactgccca cttggcagta     360
catcaagtgt atcatatgcc aagtacgccc cctattgacg tcaatgacgg taaatggccc     420
gcctggcatt atgcccagta catgacctta tgggactttc ctacttggca gtacattact     480
cgaggccacg ttctgcttca ctctccccat ctccccccc ctccccaccc caatttttgt     540
atttatttat tttttaatta ttttgtgcag cgatggggc ggggggggg gggggcgcg     600 cgccaggcgg ggcggggcgg ggcgagggc ggggcgggc gaggcggaga ggtgcggcgg     660
cagccaatca gagcggcgcg ctccgaaagt tccttttat ggcgaggcg cggcggcggc     720 ggccctataa aagcgaagc gcgcggcggg cgggagcggg atcagccacc gcggtggcgg     780
cctagagtcg acgaggaact gaaaaaccag aaagttaact ggtaagttta gtcttttgt     840 ctttttttc aggtcccgga tccggtggtg gtgcaaatca agaactgct cctcagtgga     900 tgttgccttt acttctaggc ctgtacgaa gtgttacttc tgctctaaa gctgcggaat     960 tgtacccgcg gccgatccaa tcgatacaga tctagcggcc gcgccaccat gacactcctg    1020
```

```
gggtctgagc attccttgct gattaggagc aagttcagat cagttttaca gttaagactt    1080
caacaaagaa ggacccagga acaactggct aaccaaggca taataccacc actgaaacgt    1140
ccagctgaat tccatgagca agaaaaacat ttggatagtg acaaggctaa aaattccctg    1200
aagcgcaaag ccagaaacag gtgcaacagt gccgacttgg ttaatatgca catactccaa    1260
gcttccactg cagagaggtc cattccaact gctcagatga agctgaaaag agcccgactc    1320
gccgatgatc tcaatgaaaa aattgctcta cgaccaggcc cactggagct ggtggaaaaa    1380
aacattcttc ctgtggattc tgctgtgaaa gaggccataa aggtaaccca ggtgagtttc    1440
tccaaatcca cggatgcttt tgcctttgaa aggacagca gcagcgatgg gctttctccg    1500
gatcagactc gaagtgaaga ccccaaaac tcagcgggat ccccgccaga cgctaaagcc    1560
tcagataccc cttcgacagg ttctctgggg acaaaccagg atcttgcttc tggctcagaa    1620
aatgacagaa atgactcagc ctcacagccc agccaccagt cagatgcggg gaagcagggg    1680 cttggcccc ccagcacccc catagccgtg catgctgctg taaagtccaa atccttgggt    1740
gacagtaaga accgccacaa aaagcccaag acccaagc caaggtgaa gaagcttaaa     1800 tatcaccagt acattccccc agaccagaag gcagagaagt ccctccacc tatggactca    1860 gcctacgctc ggctgctcca gcaacagcag ctgttcctgc agctccaaat cctcagccag    1920
cagcagcagc agcagcaaca ccgattcagc tacctaggga tgcaccaagc tcagcttaag    1980
gaaccaaatg aacagatggt cagaaatcca aactcttctt caacgccact gagcaatacc    2040
cccttgtctc ctgtcaaaaa cagttttttct ggacaaactg gtgtctcttc tttcaaacca    2100
ggcccactcc cacctaacct ggatgatctg aaggtctctg aattaagaca acagcttcga    2160
attcggggct tgcctgtgtc aggcaccaaa acggctctca tggaccggct tcgacccttc    2220
caggactgct ctggcaaccc agtgccgaac tttggggata taacgactgt cactttttcct    2280 gtcacaccca acacgctgcc caattaccag tcttcctctt ctaccagtgc cctgtccaac    2340
ggcttctacc actttggcag caccagctcc agccccccga tctccccagc ctcctctgac    2400
ctgtcagtcg ctgggtccct gccggacacc ttcaatgatg cctcccctc cttcggcctg    2460 cacccgtccc cagtccacgt gtgcacggag gaaagtctca tgagcagcct gaatgggggc    2520
tctgttcctt ctgagctgga tgggctggac tccgagaagg acaagatgct ggtggagaag    2580
cagaaggtga tcaatgaact cacctggaaa ctccagcaag agcagaggca ggtggaggag    2640
ctgaggatgc agcttcagaa gcagaaaagg aataactgtt cagaggaggt aacacagcct    2700
ccatcctatg aagatgccgt aaagcagcaa atgacccgga gtcagcagat ggatgaactc    2760
ctggacgtgc ttattgaaag cggagaaatg ccagcagacg ctagagagga tcactcatgt    2820
cttcaaaaag tccaaagat acccagatct tcccgaagtc caactgctgt cctcaccaag    2880
ccctcggctt cctttgaaca agcctcttca ggcagccaga tccccttttga tccctatgcc    2940 accgacagtg atgagcatct tgaagtctta ttaaattccc agagcccct aggaaagatg    3000 agtgatgtca cccttctaaa aattgggagc gaagagcctc actttgatgg gataatggat    3060
ggattctctg gaaggctgc agaagacctc ttcaatgcac atgagatctt gccaggcccc    3120
ctctctccaa tgcagacaca gttttcaccc tcttctgtgg acagcaatgg gctgcagtta    3180
agcttcactg aatctccctg ggaaaccatg gagtggctgg acctcactcc gccaaattcc    3240
acaccaggct ttagcgccct caccaccagc agcccagca tcttcaacat cgatttcctg    3300
gatgtcactg atctcaattt gaattcttcc atggaccttc acttgcagca gtgggatct    3360
```

```
ggagccacga acttctctct gttaaagcaa gcaggagacg tggaagaaaa ccccggtcct   3420
atggaaagct ctgccaagat ggagagcggc ggcgccggcc agcagcccca gccgcagccc   3480
cagcagccct tcctgccgcc cgcagcctgt ttctttgcca cggccgcagc cgcggcggcc   3540
gcagccgccg cagcggcagc gcagagcgcg cagcagcagc agcagcagca gcagcagcag   3600
cagcaggcgc cgcagctgag accggcggcc gacggccagc cctcaggggg cggtcacaag   3660
tcagcgccca gcaagtcaa cgacagcgc tcgtcttcgc ccgaactgat gcgctgcaaa    3720
cgccggctca acttcagcgg cttttggctac agcctgccgc agcagcagcc ggccgccgtg   3780
gcgcgccgca acgagcgcga gcgcaaccgc gtcaagttgg tcaacctggg cttttgccacc   3840 cttcgggagc acgtccccaa cggcgcggcc aacaagaaga tgagtaaggt ggagacactg   3900
cgctcggcgg tcgagtacat ccgcgcgctg cagcagctgc tggacgagca tgacgcggtg   3960
agcgccgcct tccaggcagg cgtcctgtcg cccaccatct cccccaacta ctccaacgac   4020
ttgaactcca tggccggctc gccggtctca tcctactcgt cggacgaggg ctcttacgac   4080
ccgctcagcc ccgaggagca ggagcttctc gacttcacca actggttctg aaagcttaat   4140
aaaagatctt tattttcatt agatctgtgt gttggttttt tgtgtgctgg ggactcgagt   4200
taagggcgaa ttcccgatta ggatcttcct agagcatggc tacgtagata agtagcatgg   4260
cgggttaatc attaactaca aggaacccct agtgatggag ttggccactc cctctctgcg   4320
cgctcgctcg ctcactgagg ccgggcgacc aaaggtcgcc cgacgcccgg gctttgcccg   4380
ggcggcctca gtgagcgagc gagcgcgcag                                   4410

<210> SEQ ID NO 82
<211> LENGTH: 7221
<212> TYPE: DNA
<213> ORGANISM: Artificial Sequence
<220> FEATURE:
<223> OTHER INFORMATION: Made in Lab - Monocistronic AAV5-MyDeta3A
      transfer plasmid

<400> SEQUENCE: 82
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccagattta     240
attaaggctg cgcgctcgct cgctcactga ggccgcccgg gcaaagcccg ggcgtcgggc     300
gacctttggt cgcccggcct cagtgagcga gcgagcgcgc agagagggag tggccaactc     360
catcactagg ggttccttgt agttaatgat taacccgcca tgctacttat ctacgtagcc     420
atgctctagg aagatcggaa ttcgccctta agcataactt acggtaaatg gcccgcctgg     480
ctgaccgccc aacgaccccc gcccattgac gtcaataatg acgtatgttc ccatagtaac     540
gccaataggg actttccatt gacgtcaatg ggtggagtat ttacggtaaa ctgcccactt     600
ggcagtacat caagtgtatc atatgccaag tacgccccct attgacgtca atgacggtaa     660
atggcccgcc tggcattatg cccagtacat gaccttatgg gactttccta cttggcagta     720
cattactcga ggccacgttc tgcttcactc tccccatctc cccccccctc cccaccccca     780
attttgtatt tatttatttt ttaattattt tgtgcagcga tgggggcggg gggggggggg     840
gggcgcgcgc caggcggggc ggggcggggc gaggggcggg gcggggcgag gcggagaggt     900
gcggcggcag ccaatcagag cggcgcgctc cgaaagtttc cttttatggc gaggcggcgg     960
```

-continued

| | |
|---|---|
| cggcggcggc cctataaaaa gcgaagcgcg cggcgggcgg gagcgggatc agccaccgcg | 1020 |
| gtggcggcct agagtcgacg aggaactgaa aaaccagaaa gttaactggt aagtttagtc | 1080 |
| tttttgtctt ttatttcagg tcccggatcc ggtggtggtg caaatcaaag aactgctcct | 1140 |
| cagtggatgt tgcctttact tctaggcctg tacggaagtg ttacttctgc tctaaaagct | 1200 |
| gcggaattgt acccgcggcc gatccaatcg atacagatct agcggccgcg ccaccatgac | 1260 |
| actcctgggg tctgagcatt ccttgctgat taggagcaag ttcagatcag ttttacagtt | 1320 |
| aagacttcaa caaagaagga cccaggaaca actggctaac caaggcataa taccaccact | 1380 |
| gaaacgtcca gctgaattcc atgagcaaag aaaacatttg gatagtgaca aggctaaaaa | 1440 |
| ttccctgaag cgcaaagcca gaaacaggtg caacagtgcc gacttggtta atatgcacat | 1500 |
| actccaagct tccactgcag agaggtccat tccaactgct cagatgaagc tgaaaagagc | 1560 |
| ccgactcgcc gatgatctca atgaaaaaat tgctctacga ccaggccac tggagctggt | 1620 |
| ggaaaaaaac attcttcctg tggattctgc tgtgaaagag gccataaaag gtaaccaggt | 1680 |
| gagtttctcc aaatccacgg atgcttttgc ctttgaagag gacagcagca gcgatgggct | 1740 |
| ttctccggat cagactcgaa gtgaagaccc ccaaaactca gcgggatccc cgccagacgc | 1800 |
| taaagcctca gataccccctt cgacaggttc tctgggaca aaccaggatc ttgcttctgg | 1860 |
| ctcagaaaat gacagaaatg actcagcctc acagcccagc caccagtcag atgcggggaa | 1920 |
| gcagggcttt ggcccccca gcaccccat agccgtgcat gctgctgtaa agtccaaatc | 1980 |
| cttgggtgac agtaagaacc gccacaaaaa gcccaaggac cccaagccaa aggtgaagaa | 2040 |
| gcttaaatat caccagtaca ttcccccaga ccagaaggca gagaagtccc ctccaccctat | 2100 |
| ggactcagcc tacgctcggc tgctccagca acagcagctg ttcctgcagc tccaaatcct | 2160 |
| cagccagcag cagcagcagc agcaacaccg attcagctac ctagggatgc accaagctca | 2220 |
| gcttaaggaa ccaaatgaac agatggtcag aaatccaaac tcttcttcaa cgccactgag | 2280 |
| caatacccc ttgtctcctg tcaaaaacag ttttttctgga caaactggtg tctcttcttt | 2340 |
| caaaccaggc ccactcccac ctaacctgga tgatctgaag gtctctgaat taagacaaca | 2400 |
| gcttcgaatt cggggcttgc ctgtgtcagg caccaaaacg gctctcatgg accggcttcg | 2460 |
| acccttccag gactgctctg caacccagt gccgaacttt ggggatataa cgactgtcac | 2520 |
| ttttcctgtc acaccccaaca cgctgcccaa ttaccagtct tcctcttcta ccagtgccct | 2580 |
| gtccaacggc ttctaccact tggcagcac cagctccagc ccccgatct ccccagcctc | 2640 |
| ctctgacctg tcagtcgctg ggtccctgcc ggacaccttc aatgatgcct ccccctcctt | 2700 |
| cggcctgcac ccgtccccag tccacgtgtg cacggaggaa agtctcatga gcagcctgaa | 2760 |
| tgggggctct gttccttctg agctggatgg gctggactcc gagaaggaca gatgctggt | 2820 |
| ggagaagcag aaggtgatca tgaactcac ctggaaactc cagcaagagc agaggcaggt | 2880 |
| ggaggagctg aggatgcagc ttcagaagca gaaaaggaat aactgttcag aggaggtaac | 2940 |
| acagcctcca tcctatgaag atgccgtaaa gcagcaaatg acccgagtc agcagatgga | 3000 |
| tgaactcctg gacgtgctta ttgaaagcgg agaaatgcca gcagacgcta gagaggatca | 3060 |
| ctcatgtctt caaaaagtcc caagatacc cagatcttcc cgaagtccaa ctgctgtcct | 3120 |
| caccaagccc tcggcttcct tgaacaagc ctcttcaggc agccagatcc cctttgatcc | 3180 |
| ctatgccacc gacagtgatg agcatcttga agtcttatta aattcccaga gcccctagg | 3240 |
| aaagatgagt gatgtcaccc ttctaaaaat tgggagcgaa gagcctcact tgatgggat | 3300 |
| aatggatgga ttctctggga aggctgcaga agacctcttc aatgcacatg agatcttgcc | 3360 |

```
aggccccctc tctccaatgc agacacagtt ttcaccctct tctgtggaca gcaatgggct   3420
gcagttaagc ttcactgaat ctccctggga accatggag tggctggacc tcactccgcc    3480
aaattccaca ccaggcttta gcgccctcac caccagcagc cccagcatct tcaacatcga   3540
tttcctggat gtcactgatc tcaatttgaa ttcttccatg gccttcact tgcagcagtg    3600 gggatctgga gccacgaact tctctctgtt aaagcaagca ggagacgtgg aagaaaaccc   3660
cggtcctatg gaaagctctg ccaagatgga gagcggcggc gccggccagc agccccagcc   3720
gcagccccag cagcccttcc tgccgcccgc agcctgtttc tttgccacgg ccgcagccgc   3780
ggcggccgca gccgccgcag cggcagcgca gagcgcgcag cagcagcagc agcagcagca   3840
gcagcagcag caggcgccgc agctgagacc ggcggccgac ggccagccct caggggggcgg  3900 tcacaagtca gcgcccaagc aagtcaagcg acagcgctcg tcttcgcccg aactgatgcg   3960
ctgcaaacgc cggctcaact tcagcggctt tggctacagc ctgccgcagc agcagccggc   4020
cgccgtggcg cgccgcaacg agcgcgagcg caaccgcgtc aagttggtca acctgggctt   4080
tgccacccct cgggagcacg tccccaacgg cgcggccaac aagaagatga gtaaggtgga   4140
gacactgcgc tcggcggtcg agtacatccg cgcgctgcag cagctgctgg acgagcatga   4200
cgcggtgagc gccgccttcc aggcaggcgt cctgtcgccc accatctccc ccaactactc   4260
caacgacttg aactccatgg ccggctcgcc ggtctcatcc tactcgtcgg acgagggctc   4320
ttacgacccg ctcagccccg aggagcagga gcttctcgac ttcaccaact ggttctgaaa   4380
gcttaataaa agatctttat tttcattaga tctgtgtgtt ggttttttgt gtgctgggga   4440
ctcgagttaa gggcgaattc ccgattagga tcttcctaga gcatggctac gtagataagt   4500
agcatggcgg gttaatcatt aactacaagg aaccccctagt gatggagttg gccactccct  4560
ctctgcgcgc tcgctcgctc actgaggccg ggcgaccaaa ggtcgcccga cgcccgggct   4620
ttgcccgggc ggcctcagtg agcgagcgag cgcgcagcct taattaacct aattcactgg   4680
ccgtcgtttt acaacgtcgt gactgggaaa accctggcgt tacccaactt aatcgccttg   4740
cagcacatcc ccctttcgcc agctggcgta atagcgaaga ggcccgcacc gatcgccctt   4800
cccaacagtt gcgcagcctg aatggcgaat gggacgcgcc ctgtagcggc gcattaagcg   4860
cggcgggtgt ggtggttacg cgcagcgtga ccgctacact tgccagcgcc ctagcgcccg   4920
ctcctttcgc tttcttccct ccttttctcg ccacgttcgc cggctttccc cgtcaagctc   4980
taaatcgggg gctcccttta gggttccgat ttagtgcttt acggcacctc gaccccaaaa   5040
aacttgatta gggtgatggt tcacgtagtg gccatcgcc ccgatagacg ttttttcgcc    5100
ctttgacgct ggagttcacg ttcctcaata gtggactctt gttccaaact ggaacaacac   5160
tcaaccctat ctcggtctat tcttttgatt tataagggat ttttccgatt tcggcctatt   5220
ggttaaaaaa tgagctgatt taacaaaaat ttaacgcgaa ttttaacaaa atattaacgt   5280
ttataatttc aggtggcatc tttcggggaa atgtgcgcgg aacccctatt tgtttatttt   5340
tctaaataca ttcaaatatg tatccgctca tgagacaata accctgataa atgcttcaat   5400
aatattgaaa aaggaagagt atgagtattc aacatttccg tgtcgccctt attccctttt   5460
ttgcggcatt ttgccttcct gttttgctc acccagaaac gctggtgaaa gtaaaagatg    5520
ctgaagatca gttgggtgca cgagtgggtt acatcgaact ggatctcaat agtggtaaga   5580
tccttgagag ttttcgcccc gaagaacgtt ttccaatgat gagcactttt aaagttctgc   5640
tatgtggcgc ggtattatcc cgtattgacg ccgggcaaga gcaactcggt cgccgcatac   5700
```

```
actattctca gaatgacttg gttgagtact caccagtcac agaaaagcat cttacggatg    5760
gcatgacagt aagagaatta tgcagtgctg cctaaccat gagtgataac actgcggcca     5820
acttacttct gacaacgatc ggaggaccga aggagctaac cgcttttttg cacaacatgg    5880
gggatcatgt aactcgcctt gatcgttggg aaccggagct gaatgaagcc ataccaaacg    5940
acgagcgtga caccacgatg cctgtagtaa tggtaacaac gttgcgcaaa ctattaactg    6000
gcgaactact tactctagct tcccggcaac aattaataga ctggatggag gcggataaag    6060
ttgcaggacc acttctgcgc tcggcccttc cggctggctg gtttattgct gataaatctg    6120
gagccggtga gcgtgggtct cgcggtatca ttgcagcact ggggccagat ggtaagccct    6180
cccgtatcgt agttatctac acgacgggga gtcaggcaac tatggatgaa cgaaatagac    6240
agatcgctga gataggtgcc tcactgatta agcattggta actgtcagac caagtttact    6300
catatatact ttagattgat ttaaaacttc attttaatt taaaaggatc taggtgaaga     6360
tcctttttga taatctcatg accaaaatcc cttaacgtga gttttcgttc cactgagcgt    6420
cagaccccgt agaaaagatc aaaggatctt cttgagatcc ttttttctg cgcgtaatct     6480 gctgcttgca acaaaaaaa ccaccgctac cagcggtggt ttgtttgccg gatcaagagc     6540
taccaactct ttttccgaag gtaactggct tcagcagagc gcagatacca aatactgtcc    6600
ttctagtgta gccgtagtta ggccaccact tcaagaactc tgtagcaccg cctacatacc    6660
tcgctctgct aatcctgtta ccagtggctg ctgccagtgg cgataagtcg tgtcttaccg    6720
ggttggactc aagacgatag ttaccggata aggcgcagcg gtcgggctga cggggggtt    6780 cgtgcacaca gcccagcttg gagcgaacga cctacaccga actgagatac ctacagcgtg    6840
agctatgaga aagcgccacg cttcccgaag ggagaaaggc ggacaggtat ccggtaagcg    6900
gcagggtcgg aacaggagag cgcacgaggg agcttccagg gggaaacgcc tggtatcttt    6960
atagtcctgt cgggtttcgc cacctctgac ttgagcgtcg attttgtga tgctcgtcag     7020 gggggcggag cctatggaaa aacgccagca acgcggcctt tttacggttc ctggccttt     7080 gctgcggttt tgctcacatg ttctttcctg cgttatcccc tgattctgtg gataaccgta    7140
ttaccgcctt tgagtgagct gataccgctc gccgcagccg aacgaccgag cgcagcgagt    7200
cagtgagcga ggaagcggaa g                                              7221
```

<210> SEQ ID NO 83
<211> LENGTH: 1040
<212> TYPE: PRT
<213> ORGANISM: Artificial Sequence
<220> FEATURE:
<223> OTHER INFORMATION: Made in Lab protein

<400> SEQUENCE: 83

```
Met Thr Leu Leu Gly Ser Glu His Ser Leu Leu Ile Arg Ser Lys Phe
 1               5                  10                  15

Arg Ser Val Leu Gln Leu Arg Leu Gln Gln Arg Arg Thr Gln Glu Gln
            20                  25                  30

Leu Ala Asn Gln Gly Ile Ile Pro Pro Leu Lys Arg Pro Ala Glu Phe
        35                  40                  45

His Glu Gln Arg Lys His Leu Asp Ser Asp Lys Ala Lys Asn Ser Leu
    50                  55                  60

Lys Arg Lys Ala Arg Asn Arg Cys Asn Ser Ala Asp Leu Val Asn Met
65                  70                  75                  80

His Ile Leu Gln Ala Ser Thr Ala Glu Arg Ser Ile Pro Thr Ala Gln
                85                  90                  95
```

```
Met Lys Leu Lys Arg Ala Arg Leu Ala Asp Asp Leu Asn Glu Lys Ile
            100                 105                 110

Ala Leu Arg Pro Gly Pro Leu Glu Leu Val Glu Lys Asn Ile Leu Pro
            115                 120                 125

Val Asp Ser Ala Val Lys Glu Ala Ile Lys Gly Asn Gln Val Ser Phe
130                 135                 140

Ser Lys Ser Thr Asp Ala Phe Ala Phe Glu Glu Asp Ser Ser Ser Asp
145                 150                 155                 160

Gly Leu Ser Pro Asp Gln Thr Arg Ser Glu Asp Pro Gln Asn Ser Ala
                165                 170                 175

Gly Ser Pro Pro Asp Ala Lys Ala Ser Asp Thr Pro Ser Thr Gly Ser
                180                 185                 190

Leu Gly Thr Asn Gln Asp Leu Ala Ser Gly Ser Glu Asn Asp Arg Asn
            195                 200                 205

Asp Ser Ala Ser Gln Pro Ser His Gln Ser Asp Ala Gly Lys Gln Gly
            210                 215                 220

Leu Gly Pro Pro Ser Thr Pro Ile Ala Val His Ala Ala Val Lys Ser
225                 230                 235                 240

Lys Ser Leu Gly Asp Ser Lys Asn Arg His Lys Lys Pro Lys Asp Pro
                245                 250                 255

Lys Pro Lys Val Lys Lys Leu Lys Tyr His Gln Tyr Ile Pro Pro Asp
                260                 265                 270

Gln Lys Ala Glu Lys Ser Pro Pro Met Asp Ser Ala Tyr Ala Arg
                275                 280                 285

Leu Leu Gln Gln Gln Gln Leu Phe Leu Gln Leu Gln Ile Leu Ser Gln
            290                 295                 300

Gln Gln Gln Gln Gln Gln His Arg Phe Ser Tyr Leu Gly Met His Gln
305                 310                 315                 320

Ala Gln Leu Lys Glu Pro Asn Glu Gln Met Val Arg Asn Pro Asn Ser
                325                 330                 335

Ser Ser Thr Pro Leu Ser Asn Thr Pro Leu Ser Pro Val Lys Asn Ser
            340                 345                 350

Phe Ser Gly Gln Thr Gly Val Ser Ser Phe Lys Pro Gly Pro Leu Pro
            355                 360                 365

Pro Asn Leu Asp Asp Leu Lys Val Ser Glu Leu Arg Gln Gln Leu Arg
            370                 375                 380

Ile Arg Gly Leu Pro Val Ser Gly Thr Lys Thr Ala Leu Met Asp Arg
385                 390                 395                 400

Leu Arg Pro Phe Gln Asp Cys Ser Gly Asn Pro Val Pro Asn Phe Gly
            405                 410                 415

Asp Ile Thr Thr Val Thr Phe Pro Val Thr Pro Asn Thr Leu Pro Asn
            420                 425                 430

Tyr Gln Ser Ser Ser Ser Thr Ser Ala Leu Ser Asn Gly Phe Tyr His
            435                 440                 445

Phe Gly Ser Thr Ser Ser Ser Pro Pro Ile Ser Pro Ala Ser Ser Asp
            450                 455                 460

Leu Ser Val Ala Gly Ser Leu Pro Asp Thr Phe Asn Asp Ala Ser Pro
465                 470                 475                 480

Ser Phe Gly Leu His Pro Ser Pro Val His Val Cys Thr Glu Glu Ser
                485                 490                 495

Leu Met Ser Ser Leu Asn Gly Gly Ser Val Pro Ser Glu Leu Asp Gly
            500                 505                 510
```

```
Leu Asp Ser Glu Lys Asp Lys Met Leu Val Glu Lys Gln Lys Val Ile
        515                 520                 525

Asn Glu Leu Thr Trp Lys Leu Gln Gln Glu Gln Arg Gln Val Glu Glu
        530                 535                 540

Leu Arg Met Gln Leu Gln Lys Gln Lys Arg Asn Asn Cys Ser Glu Glu
545                 550                 555                 560

Val Thr Gln Pro Pro Ser Tyr Glu Asp Ala Val Lys Gln Gln Met Thr
                565                 570                 575

Arg Ser Gln Gln Met Asp Glu Leu Leu Asp Val Leu Ile Glu Ser Gly
            580                 585                 590

Glu Met Pro Ala Asp Ala Arg Glu Asp His Ser Cys Leu Gln Lys Val
        595                 600                 605

Pro Lys Ile Pro Arg Ser Ser Arg Ser Pro Thr Ala Val Leu Thr Lys
        610                 615                 620

Pro Ser Ala Ser Phe Glu Gln Ala Ser Ser Gly Ser Gln Ile Pro Phe
625                 630                 635                 640

Asp Pro Tyr Ala Thr Asp Ser Asp Glu His Leu Glu Val Leu Leu Asn
                645                 650                 655

Ser Gln Ser Pro Leu Gly Lys Met Ser Asp Val Thr Leu Leu Lys Ile
            660                 665                 670

Gly Ser Glu Glu Pro His Phe Asp Gly Ile Met Asp Gly Phe Ser Gly
        675                 680                 685

Lys Ala Ala Glu Asp Leu Phe Asn Ala His Glu Ile Leu Pro Gly Pro
        690                 695                 700

Leu Ser Pro Met Gln Thr Gln Phe Ser Pro Ser Ser Val Asp Ser Asn
705                 710                 715                 720

Gly Leu Gln Leu Ser Phe Thr Glu Ser Pro Trp Glu Thr Met Glu Trp
                725                 730                 735

Leu Asp Leu Thr Pro Pro Asn Ser Thr Pro Gly Phe Ser Ala Leu Thr
            740                 745                 750

Thr Ser Ser Pro Ser Ile Phe Asn Ile Asp Phe Leu Asp Val Thr Asp
        755                 760                 765

Leu Asn Leu Asn Ser Ser Met Asp Leu His Leu Gln Gln Trp Gly Ser
770                 775                 780

Gly Ala Thr Asn Phe Ser Leu Leu Lys Gln Ala Gly Asp Val Glu Glu
785                 790                 795                 800

Asn Pro Gly Pro Met Glu Ser Ser Ala Lys Met Glu Ser Gly Gly Ala
                805                 810                 815

Gly Gln Gln Pro Gln Pro Gln Pro Gln Gln Pro Phe Leu Pro Pro Ala
            820                 825                 830

Ala Cys Phe Phe Ala Thr Ala Ala Ala Ala Ala Ala Ala Ala Ala Ala
        835                 840                 845

Ala Ala Ala Gln Ser Ala Gln Gln Gln Gln Gln Gln Gln Gln Gln Gln
        850                 855                 860

Gln Gln Ala Pro Gln Leu Arg Pro Ala Ala Asp Gly Gln Pro Ser Gly
865                 870                 875                 880

Gly Gly His Lys Ser Ala Pro Lys Gln Val Lys Arg Gln Arg Ser Ser
                885                 890                 895

Ser Pro Glu Leu Met Arg Cys Lys Arg Arg Leu Asn Phe Ser Gly Phe
            900                 905                 910

Gly Tyr Ser Leu Pro Gln Gln Gln Pro Ala Ala Val Ala Arg Arg Asn
        915                 920                 925

Glu Arg Glu Arg Asn Arg Val Lys Leu Val Asn Leu Gly Phe Ala Thr
```

```
                930             935             940
Leu Arg Glu His Val Pro Asn Gly Ala Ala Asn Lys Lys Met Ser Lys
945                 950                 955                 960

Val Glu Thr Leu Arg Ser Ala Val Glu Tyr Ile Arg Ala Leu Gln Gln
                965                 970                 975

Leu Leu Asp Glu His Asp Ala Val Ser Ala Ala Phe Gln Ala Gly Val
                980                 985                 990

Leu Ser Pro Thr Ile Ser Pro Asn Tyr Ser Asn Asp Leu Asn Ser Met
                995                 1000                1005

Ala Gly Ser Pro Val Ser Ser Tyr Ser Ser Asp Glu Gly Ser Tyr
        1010                1015                1020

Asp Pro Leu Ser Pro Glu Glu Gln Glu Leu Leu Asp Phe Thr Asn
        1025                1030                1035

Trp Phe
    1040

<210> SEQ ID NO 84
<211> LENGTH: 22
<212> TYPE: PRT
<213> ORGANISM: Artificial Sequence
<220> FEATURE:
<223> OTHER INFORMATION: Made in Lab - GSG-P2A peptide linker

<400> SEQUENCE: 84

Gly Ser Gly Ala Thr Asn Phe Ser Leu Leu Lys Gln Ala Gly Asp Val
1               5                   10                  15

Glu Glu Asn Pro Gly Pro
            20
```